United States Patent
Quattropani et al.

(10) Patent No.: US 12,016,852 B2
(45) Date of Patent: Jun. 25, 2024

(54) PYRROLIDINE GLYCOSIDASE INHIBITORS

(71) Applicant: Asceneuron SA, Lausanne (CH)

(72) Inventors: Anna Quattropani, Rolle (CH); Grant Wishart, Lanarkshire (GB); Santosh S. Kulkarni, Bangalore (IN); Paul Rakesh, Bangalore (IN)

(73) Assignee: Asceneuron SA, Lausanne (CH)

( * ) Notice: Subject to any disclaimer, the term of this patent is extended or adjusted under 35 U.S.C. 154(b) by 311 days.

(21) Appl. No.: 17/269,814

(22) PCT Filed: Aug. 22, 2019

(86) PCT No.: PCT/EP2019/072469
§ 371 (c)(1),
(2) Date: Feb. 19, 2021

(87) PCT Pub. No.: WO2020/039027
PCT Pub. Date: Feb. 27, 2020

(65) Prior Publication Data
US 2021/0213005 A1    Jul. 15, 2021

(30) Foreign Application Priority Data

Aug. 22, 2018   (EP) .................................... 18190164

(51) Int. Cl.
| | |
|---|---|
| *A61K 31/4439* | (2006.01) |
| *A61K 31/4025* | (2006.01) |
| *A61K 31/4155* | (2006.01) |
| *A61K 31/416* | (2006.01) |
| *A61K 31/4196* | (2006.01) |
| *A61K 31/422* | (2006.01) |
| *A61K 31/4245* | (2006.01) |
| *A61K 31/427* | (2006.01) |
| *A61K 31/454* | (2006.01) |
| *A61K 31/4709* | (2006.01) |
| *A61K 31/496* | (2006.01) |
| *A61K 31/497* | (2006.01) |
| *A61K 31/501* | (2006.01) |
| *A61K 31/506* | (2006.01) |
| *A61K 31/5377* | (2006.01) |
| *A61K 31/541* | (2006.01) |
| *C07D 401/14* | (2006.01) |
| *C07D 405/04* | (2006.01) |
| *C07D 405/14* | (2006.01) |
| *C07D 413/14* | (2006.01) |
| *C07D 417/14* | (2006.01) |

(52) U.S. Cl.
CPC ...... *A61K 31/4439* (2013.01); *A61K 31/4025* (2013.01); *A61K 31/4155* (2013.01); *A61K 31/416* (2013.01); *A61K 31/4196* (2013.01); *A61K 31/422* (2013.01); *A61K 31/4245* (2013.01); *A61K 31/427* (2013.01); *A61K 31/454* (2013.01); *A61K 31/4709* (2013.01); *A61K 31/496* (2013.01); *A61K 31/497* (2013.01); *A61K 31/501* (2013.01); *A61K 31/506* (2013.01); *A61K 31/5377* (2013.01); *A61K 31/541* (2013.01); *C07D 401/14* (2013.01); *C07D 405/04* (2013.01); *C07D 405/14* (2013.01); *C07D 413/14* (2013.01); *C07D 417/14* (2013.01)

(58) Field of Classification Search
CPC ............ A61K 31/4025; A61K 31/4155; A61K 31/416; A61K 31/4196; A61K 31/422; A61K 31/4245; A61K 31/427; A61K 31/4439; A61K 31/454; A61K 31/4709; A61K 31/496; A61K 31/497; A61K 31/501; A61K 31/506; A61K 31/5377; A61K 31/541; A61P 25/28; C07D 401/14; C07D 405/04; C07D 405/14; C07D 413/14; C07D 487/04
See application file for complete search history.

(56) References Cited

U.S. PATENT DOCUMENTS

| | | | |
|---|---|---|---|
| 3,299,067 A | 1/1967 | Gilbert et al. | |
| 3,457,263 A | 7/1969 | Regnier et al. | |
| 3,485,757 A | 12/1969 | Shapiro | |
| 3,489,757 A | 1/1970 | Koppe et al. | |

(Continued)

FOREIGN PATENT DOCUMENTS

| | | |
|---|---|---|
| CN | 1791594 A | 6/2006 |
| CN | 103435606 | 12/2013 |

(Continued)

OTHER PUBLICATIONS

Smith, P.W. et al. "New spiropiperidines as potent and selective non-peptide tachykinin NK2 receptor antagonists", J. Med. Chem., vol. 38, pp. 3772-3779, 1995.

Abdel-Magid, A. F. et al. "Reductive Amination of Aldehydes and Ketones with Sodium Triacetoxyborohydride. Studies on Direct and Indirect Reductive Amination Procedures" J. Org. Chem., (1996), 61, pp. 3849-3862.

Albertson, N. F. "Alkylation with Non-ketonic Mannich Bases. Aminothiazoles and Pyrrole" J. Am. Chem. Soc., 1948, 70(2), 669-670.

(Continued)

*Primary Examiner* — Kortney L. Klinkel
*Assistant Examiner* — Padmaja S Rao
(74) *Attorney, Agent, or Firm* — COOLEY LLP

(57) ABSTRACT

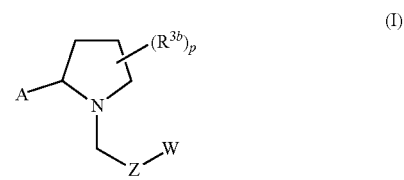

Compounds of formula (I) wherein A, W, $R^{3b}$, Z and p have the meaning according to the claims, can be employed, inter alia, for the treatment of taupathies and Alzheimer's disease.

16 Claims, No Drawings

(56) References Cited

U.S. PATENT DOCUMENTS

| | | |
|---|---|---|
| 4,600,025 A | 7/1986 | Grigg et al. |
| 5,935,974 A | 8/1999 | Rae et al. |
| 7,582,769 B2 | 9/2009 | Murray et al. |
| 7,666,875 B2 | 2/2010 | Gallagher, Jr. et al. |
| 8,008,326 B2 | 8/2011 | Borza et al. |
| 8,952,166 B2 | 2/2015 | Ding et al. |
| 9,120,781 B2 | 9/2015 | Li et al. |
| 10,336,775 B2 | 7/2019 | Quattropani et al. |
| 10,344,021 B2 | 7/2019 | Quattropani et al. |
| 10,556,902 B2 | 2/2020 | Quattropani et al. |
| 10,696,668 B2 | 6/2020 | Quattropani et al. |
| 10,995,090 B2 | 5/2021 | Quattropani et al. |
| 11,046,712 B2 | 6/2021 | Quattropani et al. |
| 11,213,525 B2 | 1/2022 | Quattropani et al. |
| 11,261,183 B2 | 3/2022 | Quattropani et al. |
| 11,591,327 B2 | 2/2023 | Quattropani et al. |
| 11,612,599 B2 | 3/2023 | Quattropani et al. |
| 11,731,972 B2 | 8/2023 | Quattropani et al. |
| 11,795,165 B2 | 10/2023 | Quattropani et al. |
| 2004/0106645 A1 | 6/2004 | Blackburn et al. |
| 2006/0287340 A1 | 12/2006 | Moriya et al. |
| 2008/0300276 A1 | 12/2008 | Borza et al. |
| 2009/0012078 A1 | 1/2009 | Andrews et al. |
| 2009/0163545 A1 | 6/2009 | Goldfarb |
| 2010/0022517 A1 | 1/2010 | Richards et al. |
| 2011/0053982 A1 | 3/2011 | Fay et al. |
| 2011/0060012 A1 | 3/2011 | Meyers et al. |
| 2011/0060019 A1 | 3/2011 | Murray et al. |
| 2012/0208808 A1 | 8/2012 | Buchstaller et al. |
| 2016/0031871 A1 | 2/2016 | Yu et al. |
| 2020/0002326 A1 | 1/2020 | Quattropani et al. |
| 2020/0385375 A1 | 12/2020 | Quattropani et al. |
| 2021/0077488 A1 | 3/2021 | Quattropani et al. |
| 2021/0186958 A1 | 6/2021 | Quattropani et al. |
| 2021/0198250 A1 | 7/2021 | Quattropani et al. |
| 2021/0206766 A1 | 7/2021 | Quattropani et al. |
| 2022/0143042 A1 | 5/2022 | Quattropani et al. |
| 2022/0177470 A1 | 6/2022 | Quattropani et al. |
| 2022/0380358 A1 | 12/2022 | Quattropani et al. |
| 2022/0411440 A1 | 12/2022 | Quattropani et al. |
| 2023/0120169 A1 | 4/2023 | Quattropani et al. |

FOREIGN PATENT DOCUMENTS

| | | |
|---|---|---|
| EP | 2301936 | 3/2011 |
| EP | 2687507 | 1/2014 |
| FR | 1311316 | 12/1962 |
| JP | 2010/270034 | 12/2010 |
| WO | WO1993/021181 | 10/1993 |
| WO | WO1997/043279 | 11/1997 |
| WO | WO1998/046590 | 10/1998 |
| WO | WO99/21850 | 5/1999 |
| WO | WO02/094799 | 11/2002 |
| WO | WO2003/092678 | 11/2003 |
| WO | WO2004/002481 | 1/2004 |
| WO | WO2004/005293 | 1/2004 |
| WO | WO2004/022558 | 3/2004 |
| WO | WO2004/094380 | 11/2004 |
| WO | WO2005/110982 | 11/2005 |
| WO | WO2006/092049 | 9/2006 |
| WO | WO-2007008541 A2 | 1/2007 |
| WO | WO2007/115077 | 10/2007 |
| WO | WO2007/135398 | 11/2007 |
| WO | WO2007/146122 | 12/2007 |
| WO | WO2008/012623 | 1/2008 |
| WO | WO2008/025170 | 3/2008 |
| WO | WO2009/011904 | 1/2009 |
| WO | WO2009/053373 | 4/2009 |
| WO | WO2009/131926 | 10/2009 |
| WO | WO2010/018868 | 2/2010 |
| WO | WO2010/021381 | 2/2010 |
| WO | WO2010/022517 | 3/2010 |
| WO | WO2010/026989 | 3/2010 |
| WO | WO2010/089127 | 8/2010 |
| WO | WO2010/101949 | 9/2010 |
| WO | WO2010/108115 | 9/2010 |
| WO | WO2010/108268 | 9/2010 |
| WO | WO2010/151318 | 12/2010 |
| WO | WO2011/140640 | 11/2011 |
| WO | WO2012/037298 | 3/2012 |
| WO | WO2012/061927 | 5/2012 |
| WO | WO2012/062157 | 5/2012 |
| WO | WO2012/062759 | 5/2012 |
| WO | WO2012/083435 | 6/2012 |
| WO | WO2012/117219 | 9/2012 |
| WO | WO2013/028715 | 2/2013 |
| WO | WO2013/066729 | 5/2013 |
| WO | WO2014/023723 | 2/2014 |
| WO | WO2014/032187 | 3/2014 |
| WO | WO2014/159234 | 10/2014 |
| WO | WO2015/083028 | 6/2015 |
| WO | WO2015/128333 | 9/2015 |
| WO | WO2015/164508 | 10/2015 |
| WO | WO2016/030443 | 3/2016 |
| WO | WO2017/001660 | 1/2017 |
| WO | WO2017/076900 | 5/2017 |
| WO | WO2017/087858 | 5/2017 |
| WO | WO2017/087863 | 5/2017 |
| WO | WO2017/091818 | 6/2017 |
| WO | WO2017/106254 | 6/2017 |
| WO | WO2017/144633 | 8/2017 |
| WO | WO2017/144635 | 8/2017 |
| WO | WO2017/144637 | 8/2017 |
| WO | WO2017/144639 | 8/2017 |
| WO | WO 2017/223243 | 12/2017 |
| WO | WO2018/026371 | 2/2018 |
| WO | WO2018/109198 | 6/2018 |
| WO | WO2018/109202 | 6/2018 |
| WO | WO2018/140299 | 8/2018 |
| WO | WO2018/141984 | 8/2018 |
| WO | WO2018/153507 | 8/2018 |
| WO | WO2018/153508 | 8/2018 |
| WO | WO2018/154133 | 8/2018 |
| WO | WO2018/217558 | 11/2018 |
| WO | WO2020/039028 | 2/2020 |
| WO | WO2020/039029 | 2/2020 |
| WO | WO2020/039030 | 2/2020 |
| WO | WO2020/169804 | 2/2020 |

OTHER PUBLICATIONS

Andres, J. I. et al. "Synthesis, Evaluation, and Radiolabeling of New Potent Positive Allosteric Modulators of the Metabotropic Glutamate Receptor 2 as Potential Tracers for Positron Emission Tomography Imaging" J. Med. Chem., (2012), 55, pp. 8685-8699.

Ansari et al. "The Role of Insulin Resistance and Protein O-GlcNAcylation in Neurodegeneration", Frontiers in Neuroscience, 2019, vol. 13, Article 473, 9 pages.

Aitipamula, S. et al. "Polymorphs, Salts, and Cocrystals: What's in a Name?", Crystal Growth & Design, 12(5), 2012, p. 2147-2152.

Apsunde, T.D. et al. "Microwave-Assisted Iridium-Catalyzed Synthesis of Nicotine and Anabasine Derivatives", Synthesis, vol. 45, No. 15, 2013, pp. 2120-2124.

Aube, J. et al. "Intramolecular Schmidt reaction of alkyl azides", J. Am. Chem. Soc. 1991, vol. 113, No. 23, p. 8965-8966.

Augustine, J. K. et al. "Propylphosphonic anhydride (T3P®): an efficient reagent for the one-pot synthesis of 1,2,4-oxadiazoles, 1,3,4-oxadiazoles, and 1,3,4-thiadiazoles" Tetrahedron, (2009), 65, pp. 9989-9996.

Bastin, R. J. et al. "Salt Selection and Optimisation Procedures for Pharmaceutical New Chemical Entities", Organic Process Research & Development, 2000, 4, 427-435.

Berge, S. M. et al. "Pharmaceutical Salts", Journal of Pharmaceutical Sciences, 1977, 66(1), 1-19.

Biscoe, M. R. et al. "A New Class of Easily Activated Palladium Precatalysts for Facile C—N Cross-Coupling Reactions and Low Temperature Oxidative Addition of Aryl Chlorides", J. Am. Chem. Soc., 2008, 130, 6686-6687.

Bohnert, T. et al. "Plasma Protein Binding: From Discovery to Development", J. Pharmaceutical Sciences, 2013, 102, 2953-2994.

(56) References Cited

OTHER PUBLICATIONS

Bras, N. F. et al. "Glycosidase inhibitors: a patent review (2008-2013)" Expert Opinion on Therapeutic Patents, vol. 24, No. 8, 2014, pp. 857-874.
Bundgaard, H. "Design and Application of Prodrugs", from A Textbook of Drug Design and Development Chapter 5, Harwood Academic Publishers, 1991, 113-191.
Bundgaard, H. "Design of prodrugs: Bioreversible derivatives for various functional groups and chemical entities", Design of Prodrugs, (1985), 1 page.
Calcagno, A. M. "Comparison of Drug Transporter Levels in Normal Colon, Colon Cancer, and Caco-2 Cells: Impact on Drug Disposition and Discovery", Mol. Pharm., 2006, 3(1), 87-93.
CAS Registry (Online) Nos. 948053-91-6; 540512-02-5; 697229-62-2; 346662-52-0; 345992-64-5 (STN database summary sheets) Sep. 26, 2007.
"Chemical Encyclopedia", vol. 4, pp. 990-993, 1988. (Machine translation attached).
Chen, Y. et al. "Discovery of new acetylcholinesterase and butyrylcholinesterase inhibitors through structurebased virtual screening", RSC Advances, 2017, 7(6), 3429-3438.
Chen W. et al. "Redox-Neutral [alpha]-Arylation of Amines", Organic Letters, vol. 16, No. 3, 2014, pp. 730-732.
Chrovian, C. C. et al. "A Dipolar Cycloaddition Reaction To Access 6-Methyl-4,5,6,7-tetrahydro-1H-[1,2,3]triazolo[4,5-c]pyridines Enables the Discovery Synthesis and Preclinical Profiling of a P2X7 Antagonist Clinical Candidate", J. Med. Chem. 2018, 61(1), p. 207-223.
Collet, A. "Resolution of Racemates: Did you say 'Classical?'", Angewandte Chemie International Edition, 1998, 37(23), 3239-3241.
Dai, W. et al. "Highly Chemoselective and Enantioselective Catalytic Oxidation of Heteroaromatic Sulfides via High-Valent Manganese(IV)-Oxo Cation Radical Oxidizing Intermediates", ACS Catalysis, 2017, vol. 7, p. 4890-4895.
Dassanayaka, S. and Jones, S. "O-GlcNAc and the cardiovascular system", Pharmacology & Therapeutics, 2014, 142, 62-71.
Database registry (online) Chemical abstract service, Columbus, Ohio, US; Dec. 6, 2011, "Piperazine, 1-[1-(1,3-benzodioxol-5-yl)ethyl]-4-(5-bromo-6-methoxy-2-pyridinyl)-", Database accession No. 1349611-60-4.
Database Pubchem Compound (Online) NCBI; Jan. 24, 2012, XP002768130, Database accession No. CID 54914491.
Database PubChem Compound (Online) NCBI; May 28, 2009; XP002768131, Database accession No. CID 28798635.
Database PubChem Compound, NCBI; 9. Apr. 2016; XP002768133, Database accession No. CID 118902929.
Database Registry, Chemical Abstracts Service, 2016, CID120907609, 10 pages.
Database Registry, Chemical Abstracts Service, Jan. 11, 2017, XP002768132, Database accession No. 2055841-81-9.
Dorfmueller, H. C et al. "Cell-Penetrant, Nanomolar O-GlcNAcase Inhibitors Selective against Lysosomal Hexosaminidases", Chem. Biol., 2010, 17, 1250-1255.
Dubois, B. et al. "Preclinical Alzheimer's disease: Definition, natural history, and diagnostic criteria", Alzheimers Dement., 2016, 12, 292-323.
Dubois, B. et al. "Advancing research diagnostic criteria for Alzheimer's disease: the IWG-2 criteria", Lancet Neurol., 2014, 13, 614-629.
Dyatkin, A. B. et al. "Determination of the Absolute Configuration of a Key Tricyclic Component of a Novel Vasopressin Receptor Antagonist by Use of Vibrational Circular Dichroism", Chirality, 2002, 14, 215-219.
Ellman, J. A. et al. "N-tert-Butanesulfinyl Imines: Versatile Intermediates for the Asymmetric Synthesis of Amines" Acc. Chem. Res. (2002), 35, pp. 984-995.
Fleury-Bregeot et al. "Suzuki-Miyaura Cross-Coupling of Potassium Alkoxyethyltri-fluoroborates: Access to Aryl/Heteroarylethyloxy Motifs", J. Org. Chem. 2012, vol. 77, No. 22, p. 10399-10408.

Fors, B. P. et al. "A Highly Active Catalyst for Pd-Catalyzed Amination Reactions: Cross-Coupling Reactions Using Aryl Mesylates and the Highly Selective Monoarylation of Primary Amines Using Aryl Chlorides", J. Am. Chem. Soc., 2008, 130, 13552-13554.
Frehel, D. et al. "New synthesis of 5,6,7,8-tetrahydro-4H-thieno[2,3-d]azepine", Journal of Heterocyclic Chemistry, 1985, vol. 22, p. 1011-1016.
Frings, M. et al. "Sulfoximines from a Medicinal Chemist's Perspective: Physicochemical and in vitro Parameters Relevant for Drug Discovery", European Journal of Medicinal Chemistry, 2017, 126, 225-245.
Goho, A. "Tricky Business", Science News, 2004, 166(8), 122-124.
Gong et al. "O-GlcNAcylation: A regulator of tau pathology and neurodegeneration", Alzheimer's & Dementia, 2016, vol. 12, p. 1078-1089.
Golub, T. R. et al. "Molecular Classification of Cancer: Class Discovery and Class Prediction by Gene Expression Monitoring", Science, 1999, 286, 531-537.
Gould, P. L. "Salt selection for basic drugs", International Journal of Pharmaceutics, 1986, 33, 201-217.
Graham, D. L. et al. "Increased O-GlcNAcylation reduces pathological tau without affecting its normal phosphorylation in a mouse model of tauopathy", Neuropharmacology, 2014, 79, 307-313.
Gujjar, R. et al. "Lead Optimization of Aryl and Aralkyl Amine-Based Triazolopyrimidine Inhibitors of Plasmodium falciparum Dihydroorotate Dehydrogenase with Antimalarial Activity in Mice", J. Med. Chem., 2011, 54 (11), 3935-3949.
Haleblian, J.; McCrone, W. "Pharmaceutical Applications of Polymorphism", J. Pharm. Sci., 1969, 58(8), 911-929.
Haleblian, J. "Characterization of Habits and Crystalline Modification of Solids and Their Pharmaceutical Applications", J. Pharm. Sci., 1975, 64(8), 1269-1288.
Hemming, K. "Product Class 6: 1,2,4-Oxadizoles" Science of Synthesis, (2004), 13(6), pp. 127-184.
Hulikal, V. "Deuterium Labeled Compounds in Drug Discovery Process", Abstract, Bioorganics ond Applied Materials Pvt Ltd. (2010), 1 page.
Jakopin, Z. et al. "Recent Advances in the Synthesis of 1,2,4- and 1,3,4-Oxadiazoles" Current Organic Chemistry, (2008), 12(10), pp. 850-898.
Kempson, J. "Name Reactions in Heterocyclic Chemistry II" John Wiley & Sons. Eds. Jie Jack Li and E. J. Corey, (2011), pp. 299-308.
Kim, E. J. et al. "Enzymatic characterization of O-GlcNAcase isoforms using a fluorogenic GlcNAc substrate", Carbohydrate Research, 2006, 341(8), p. 971-982.
Kim, E. J. "Chemical Arsenal for the Study of O-GlcNAc", Molecules, 2011, vol. 16, p. 1987-2022.
Kim et al. "Discovery of β-Arrestin Biased Ligands of 5-HT7R", Journal of Medicinal Chemistry, 2018, vol. 61, p. 7218-7233.
Knapp, S. et al. "An Allosamizoline/ Glucosamine Hybrid NAGase Inhibitor", Synlett, 1997, 5, 435-436.
Lefebvre, T. "Recall sugars, forget Alzheimer's", Nature Chemical Biology, 2012, 8(4), 325-326.
Legros, J. et al. "Applications of Catalytic Asymmetric Sulfide Oxidations to the Syntheses of Biologically Active Sulfoxides", Adv. Synth. Catal., 2005, 347, 19-31.
Liu, X. et al. "Rational Use of Plasma Protein and Tissue Binding Data in Drug Design", J. Med. Chem. 2014, 57, 8238-8248.
Marwaha, A. et al. "Bioisosteric Transformations and Permutations in the Triazolopyrimidine Scaffold to Identify the Minimum Pharmacophore Required for Inhibitory Activity against Plasmodium falciparum Dihydroorotate Dehydrogenase", J. Med. Chem., 2012, 55(17), 7425-7436.
Mariappa, D. et al. "A mutant O-GlcNAcase as a probe to reveal global dynamics of the *Drosophila* O-GlcNAc developmental proteome", Biochem J., 2015, 470(2), 255-262.
Marotta, N. P. et al., "O-GlcNAc modification blocks the aggregation and toxicity of the Parkinson's disease associated protein α-synuclein", Nat. Chem, 2015, 7(11), 913-920.
Masuda, N. et al. "Studies of nonnucleoside HIV-1 reverse transcriptase inhibitors. Part 1: Design and synthesis of thiazolidene-benzenesulfonamides", Bioorg. Med. Chem., 2004, 12, 6171-6182.

(56) References Cited

OTHER PUBLICATIONS

Merchant, R. R. et al. "Regioselective Preparation of Saturated Spirocyclic and Ring- Expanded Fused Pyrazoles", J. Org. Chem. 2014, vol. 79, No. 18, p. 8800-8811.

Micksch, M. et al. "Synthesis of 1,2-Diaryl- and 1-Aryl-2-alkylimidazoles with Sterically Demanding Substituents", Eur J. Org. Chem. 2013, Issue 27, p. 6137-6145.

Miller III et al. "Design of e-pharmacophore models using compound fragments for the trans-sialidase of Trypanosoma cruzi: screening for novel inhibitor scaffolds", Journal of Molecular Graphics and Modelling, vol. 45, 2013, p. 84-97.

Mittur A. "Piribedil: Antiparkinsonian Properties and Potential Clinical Utility in Dopaminergic Disorders" Current Drug Therapy (2011), 6, pp. 17-34.

Moradi-Afrapoli, F. et al. "In vitro α-glucosidase inhibitory activity of phenolic constituents from aerial parts of Polygonum hyrcanicum", DARU Journal of Pharmaceutical Sciences, 2012, 20(1), 37, 6 pages.

Motiwala, H. F. et al. "Remodeling and Enhancing Schmidt Reaction Pathways in Hexafluoroisopropanol", J. Org. Chem. 2016, vol. 81, No. 8, p. 1593-1609.

Nandi, A. et al. "Global Identification of O-GlcNAc-Modified Proteins", Anal. Chem., 2006, 78, 452-458.

Nelson, P. T. et al. "Correlation of Alzheimer Disease Neuropathologic Changes With Cognitive Status: A Review of the Literature", J. Neuropathol. Exp. Neurol., 2012, 71(5), 362-381.

Nettekoven, M. et al. "Synthetic Access to 2-Amido-5-aryl-8-methoxy-triazolopyridine and 2- Amido-5-morpholino-8-methoxy-triazolopyridine Derivatives as Potential Inhibitors of the Adenosine Receptor Subtypes", Synthesis, 2003, 1649-1652.

Obach, R. S. "Prediction of human clearance of twenty-nine drugs from hepatic microsomal intrinsic clearance data: and examination of in vitro half-life approach and nonspecific binding to microsomes", Drug. Metab. Dispos., 1999, 27(11), 1350-1359.

Okamura, H. et al. "Rhodium-Catalyzed Imination of Sulfoxides and Sulfides: Efficient Preparation of N-Unsubstituted Sulfoximines and Sulfilimines", Organic Letters, 2004, 6, 1305-1307.

O'Mahony, G. E. et al. "Synthesis of enantioenriched sulfoxides" Arkivoc, 2011, 1-110.

Orain, D. et al. "Synthesis of Orthogonally Protected 2,6-Diazaspiro[3.5]nonane and 2,6-Diazaspiro[3.4]octane Analogues as Versatile Building Blocks in Medicinal Chemistry", Synlett, 2015, 26(13), 1815-1818.

Papillon, J. P. N. et al. "Discovery of N-[5-(6-Chloro-3-cyano-1-methyl-1H-indol-2-yl)-pyridin-3-ylmethyl]-ethanesulfonamide, a Cortisol-Sparing CYP11B2 Inhibitor that Lowers Aldosterone in Human Subjects", J. Med. Chem., 2015, 58(23), 9382-9394.

Park, M.-J. et al. "High Glucose-induced O-GlcNAcylated Carbohydrate Response Element-binding Protein (ChREBP) Mediates Mesangial Cell Lipogenesis and Fibrosis", J. Biol. Chem., 2014, 289, 13519-13530.

Reddy et al. "Synthesis of Chiral Benzimidazole-Pyrrolidine Derivatives and their Application in Organocatalytic Aldol and Michael Addition Reactions", Synthetic Communications, vol. 37, No. 24, 2007, pp. 4289-4299.

Rouhi, A. M. et al. "The Right Stuff: From Research and Development to the Clinic, Getting Drug Crystals Right is Full of Pitfalls." Chem. Eng. News. (2003):32-35.

Ryan et al. "The O-GlcNAc modification protects against protein misfolding and aggregation in neurodegenerative disease", ACS Chemical Neuroscience, 2019, 17 pages.

SantaCruz, K. et al. "Tau Suppression in a Neurodegenerative Mouse Model Improves Memory Function", Science, 2005, 309, 476-481.

Serajuddin, A. T. M. "Salt formation to improve drug solubility", Advanced Drug Delivery Reviews, 2007, 59(7), 603-616.

Shan, X. et al. "Reduced protein O-glycosylation in the nervous system of the mutant SOD1 transgenic mouse model of amyotrophic lateral sclerosis", Neuroscience Letters, 2012, 516, 296-301.

Shen, Q. et al. "Hydroxycoumarin Derivatives: Novel and Potent a-Glucosidase Inhibitors", J. Med. Chem., 2010, 53(23), 8252-8259.

Shirude, P. et al. "Lead Optimization of 1,4-Azaindoles as Antimycobacterial Agents", J. Med. Chem., 2014, 57(13), 5728-5737.

Sippy, K. B. et al. "Preparation and characterization of N-(3-pyridinyl) spirocyclic diamines as ligands for nicotinic acetylcholine receptors", Bioorganic & Med. Chemistry Letters, 2009, 19(6), 1682-1685.

Skedelj, V. et al. "Discovery of the first inhibitors of bacterial enzyme D-aspartate ligase from Enterococcus faecium ($Asl_{fm}$)", Eur. J. Med. Chem., 2013, 67, 208-220.

Silverman, "Prodrugs and Drug Delivery Systems", The Organic Chemistry of Drug Design and Drug Action, (1992), Chapter 8, p. 352-399.

Song, S. et al. "Efficient and Practical Oxidative Bromination and Iodination of Arenes and Heteroarenes with DMSO and Hydrogen Halide: A Mild Protocol for Late-Stage Functionalization", Org. Lett., 2015, 17(12), 2886-2889.

Sperling, R. A. et al. "Toward defining the preclinical stages of Alzheimer's disease: Recommendations from the National Institute on Aging-Alzheimer's Association workgroups on diagnostic guidelines for Alzheimer's disease", Alzheimers Dement., 2011, 7, 280-292.

Spillantini, M. G.; Goedert, M. "Tau pathology and neurodegeneration", Lancet Neurol., 2013, 12, 609-622.

Tamura, B. K. et al. "Weight Loss in Patients with Alzheimer's Disease" J. Nutrition for the Elderly (2008), 26(3-4), pp. 21-38.

Tan, H. et al. "Rational Screening Approach for Classical Chiral Resolution under Thermodynamic Equilibrium: A Case Study of Diphenyl-Substituted N-Methyl-Piperazine", Organic Process Research and Development, 2011, 15(1), 53-63.

Tanuwidjaja, J. et al. "One-Pot Asymmetric Synthesis of Either Diastereomer of tert-Butanesulfinyl-protected Amines from Ketones", J. Org. Chem. 2007, 72, 626-629.

The U. S. Pharmacopeia 38—National Formulary 35 Chapter 941, Characterization of crystalline and partially crystalline solids by X-ray powder diffraction (XRPD) Official May 1, 2015, 427-431.

Thiel, O. R. et al. "Practical Synthesis of a Vanilloid Receptor-1 Antagonist" J. Org. Chem., (2008), 73(9), pp. 3508-3515.

Trapannone, R. et al. "O-GlcNAc transferase inhibitors: current tools and future challenges", Biochemical Society Transactions, 2016, 44(1), 88-93.

Vasudevan, A. et al. "Identification of aminopiperidine benzamides as MCHrl antagonists", Bioorganic & Medicinal Chemistry Letters, 2005, 15(14), 3412-3416.

Volpe, D. A. "Application of Method Suitability for Drug Permeability Classification", The AAPS Journal, 2010, 12(4), 670-678.

Wall, G. M. "Pharmaceutical Applications of Drug Crystal Studies", Pharm. Manuf., 1986, 3, 32-42.

Wang, Z. et al. "Enrichment and Site Mapping of O-Linked N-Acetylglucosamine by a Combination of Chemical/Enzymatic Tagging, Photochemical Cleavage, and Electron Transfer Dissociation Mass Spectrometry", Mol. Cell Proteomics, 2010, 9(1), 153-160.

Waterman, K. C. "Improved Protocol and Data Analysis for Accelerated Shelf-Life Estimation of Solid Dosage Forms", Pharm. Res., 2007, 24(4), 780-790.

Weinberg, K. et al. "Synthesis and differential functionalisation of pyrrolidine and piperidine based spirodiamine scaffolds", Tetrahedron, 2013, 69(23), 4694-4707.

Wermuth, C. G. et al. "Designing Prodrugs and Bioprecursors I: Carrier Prodrugs", The Practice of Medicinal Chemistry: Chapter 31, Academic Press, 1996, 671-696.

Wiessner et al. "A novel non-carbohydrate o-linked beta-n-acetylglucosaminidase inhibitor increases tau o-glenacylation In vivo", Abstracts of the Annual Meeting of the Society for Neuroscience, Society for Neuroscience, 2013, 43, 2 pages.

Williams, D. R. et al. "Pathological tau burden and distribution distinguishes progressive supranuclear palsy-parkinsonism from Richardson's syndrome", Brain, 2007, 130, 1566-1576.

(56) References Cited

OTHER PUBLICATIONS

Xu, Daqian et al. "The synthesis of chiral tridentate ligands from L-proline and their application in the copper(II)-catalyzed enantioselective Henry reaction", Tetrahedron Asymmetry, vol. 28, No. 7, 2017, p. 954-963.

Hiroshi Yamanaka, Hiroshi Miyazaki and Naomi chi Murakami, Chemical Abstract, "Separation of optical isomers", Japan, Gakkai Shopping Santa, 1989, 21 pages.

Yoshida, M. et al. "Study of biodegradable copoly(L-lactic acid/glycolic acid) formulations with controlled release of Z-100 for application in radiation therapy", Int. J. Pharm., 1995, 115, 61-67.

Youngdale et al. "Synthesis and pharmacological activity of 3-(2-pyrrolidinyl)indoles", Journal of Medicinal Chemistry, vol. 7, Jul. 1, 1964, pp. 415-427.

Yu, Y. J. et al. "One-Pot Synthesis of Spirocyclic or Fused Pyrazoles from Cyclic Ketones: Calcium Carbide as the Carbon Source in Ring Expansion", Org. Chem. 2017, vol. 82, No. 18, p. 9479-9486.

Yuzwa, S. A. et al. "Mapping O-GlcNAc modification sites on tau and generation of a site-specific O-GlcNAc tau antibody", Amino Acids, 2011, 40, 857-868.

Yuzwa, S. A. et al. "A potent mechanism-inspired O-GlcNAcase inhibitor that blocks phosphorylation of tau in vivo", Nat. Chem. Biol., 2008, 4(8), 483-490.

Yuzwa et al. "O-GlcNAc and neurodegeneration: biochemical mechanisms and potential roles in Alzheimer's disease and beyond", Chem. Soc. Review, 2014, 20 pages.

Yuzwa, S. A. et al. "Increasing O-GlcNAc slows neurodegeneration and stabilizes tau against aggregation", Nat. Chem. Biol., 2012, 8(4), 393-399.

Zenzola, M. et al. "Transfer of Electrophilic NH Using Convenient Sources of Ammonia: Direct Synthesis of NH Sulfoximines from Sulfoxides", Angew. Chem. Int. Ed., 2016, 55, 7203-7207.

Zhang, Chen et al. "Nontraditional Reactions of Azomethine Ylides: Decarboxylative Three- Component Couplings of [alpha]-Amino Acids", Journal of the American Chemical Society, vol. 132, No. 6, 2010, pp. 1798-1799.

"Acute Leukemia", Merck Manual (Online Edition), Hematology and Oncology, 6 pages, pp. 1-6, 2013.

Damasio, "Alzheimer's Disease and related dementias", Cecil Textbook of Medicine, 20th Edition, vol. 2, Edited by Bennett and Plum, pp. 1992-1996, 1996.

Gura, "Cancer Models: Systems for identifying new drugs are often faulty", Science, vol. 278, pp. 1041-1042, 1997 (5 pages).

Johnson et al., "Relationships between drug activity in NCI preclinical in vitro and in vivo models and early clinical trials", British Journal of Cancer, vol. 84, No. 10, pp. 1424-1431, 2001.

Layzer, "Degenerative diseases of the nervous system", Cecil Textbook of Medicine, 20th Edition, Section Five, vol. 2, Edited by Bennett and Plum, pp. 2050-2057, 1996.

Pearce et al. "Failure modes in anticancer drug discovery and development", Cancer Drug Design and Discovery Edited by Stephen Neidle, Chapter 18, pp. 424-435, 2008.

Simone "Oncology: Introduction", Cecil Textbook of Medicine, 20th Edition, vol. 1, Edited by Bennett and Plum, pp. 1004-1010, 1996.

Co-pending U.S. Appl. No. 18/570,861, inventors Dirk Beher et al., filed Dec. 15, 2023.

PYRROLIDINE GLYCOSIDASE INHIBITORS

RELATED APPLICATIONS

This application is a U.S. National Phase application, filed under U.S.C. § 371(c), of International Application No. PCT/EP2019/072469, filed Aug. 22, 2019, which claims priority to, and the benefit of, European Application No. 18190164.6, filed Aug. 22, 2018, the contents of each of which are incorporated here in their entirety.

The present invention relates to compounds of formula (I)

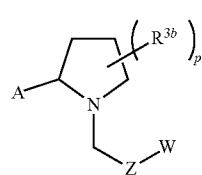

(I)

wherein A, W, $R^{3b}$, Z and p have the meaning according to the claims, and/or physiologically acceptable salts, tautomers, solvates, stereoisomers and derivatives thereof. The compounds of formula (I) can be used as glycosidase inhibitors. Objects of the invention are also pharmaceutical compositions comprising the compounds of formula (I), and the use of the compounds of formula (I) for the treatment of one or more tauopathies and Alzheimer's disease.

A wide range of cellular proteins, both nuclear and cytoplasmic, are post-translationally modified by the addition of the monosaccharide 2-acetamido-2-deoxy-β-D-glucopyranoside (β-N-acetyl glucosamine) which is attached via an O-glycosidic linkage. This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase). A second enzyme, known as O-GlcNAcase, removes this post-translational modification to liberate proteins making the O-GlcNAc-modification a dynamic cycle occurring several times during the lifetime of a protein.

O-GlcNAc-modified proteins regulate a wide range of vital cellular functions including, for example, transcription, proteasomal degradation and cellular signaling. O-GlcNAc is also found on many structural proteins. For example, it has been found on a number of cytoskeletal proteins, including neurofilament proteins, synapsins, synapsin-specific clathrin assembly protein AP-3 and Ankyrin-G. O-GlcNAc modification has been found to be abundant in the brain. It has also been found on proteins clearly implicated in the etiology of several diseases including tauopathies, Alzheimer's disease (AD), synucleinopathies, Parkinson's disease, amyotrophic lateral sclerosis, and cancer. For example, it is well established that AD and a number of related tauopathies including Down's Syndrome, progressive supranuclear palsy (PSP), Pick's disease, corticobasal degeneration (CBD), argyrophilic grain disease (AGD), globular glial tauopathy (GGT), frontotemporal dementia and parkinsonism linked to chromosome-17 (FTLD-17, Niemann-Pick Type C disease are characterized, in part, by the development of neurofibrillary tangles (NFTs). NFTs are also a histopathological hallmark of chronic traumatic encephalopathy that is a consequence of traumatic brain injury. These NFTs are aggregates of paired helical filaments (PHFs) and are composed of an abnormal form of the cytoskeletal protein "tau". Normally, tau stabilizes a key cellular network of microtubules that is essential for distributing proteins and nutrients within neurons. In AD patients, however, tau becomes hyperphosphorylated, disrupting its normal function, forming PHFs and ultimately aggregating to form NFTs. Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups. A clear parallel between NFT levels in the brains of AD patients and the severity of dementia strongly supports a key role for tau dysfunction in AD. The precise causes of this hyperphosphorylation of tau remain elusive. Accordingly, considerable effort has been dedicated toward: a) elucidating the molecular physiological basis of tau hyperphosphorylation; and b) identifying strategies that could limit tau hyperphosphorylation in the hope that these might halt, or even reverse, the progression of tauopathies and Alzheimer's disease. Several lines of evidence suggest that up-regulation of a number of kinases may be involved in hyperphosphorylation of tau, although very recently, an alternative basis for this hyperphosphorylation has been advanced.

In particular, it has recently emerged that phosphate levels of tau are regulated by the levels of O-GlcNAc on tau. The presence of O-GlcNAc on tau has stimulated studies that correlate O-GlcNAc levels with tau phosphorylation levels. The recent interest in this field stems from the observation that O-GlcNAc modification has been found to occur on many proteins at amino acid residues that are also known to be phosphorylated. Consistent with this observation, it has been found that increases in phosphorylation levels result in decreased O-GlcNAc levels and conversely, increased O-GlcNAc levels correlate with decreased phosphorylation levels. This reciprocal relationship between O-GlcNAc and phosphorylation has been termed the "Yin-Yang hypothesis" and has gained strong biochemical support by the recent discovery that the enzyme OGTase forms a functional complex with phosphatases that act to remove phosphate groups from proteins. Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD. Hyperphosphorylated tau in human AD brains has markedly lower levels of O-GlcNAc than are found in healthy human brains. Very recently, it has been shown that O-GlcNAc levels of soluble tau protein from human brains affected with AD are markedly lower than those from healthy brain. Furthermore, PHF from diseased brain was suggested to lack completely any O-GlcNAc modification whatsoever. The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosaminidase inhibitor was used to increase tau O-GlcNAc levels, whereupon it was observed that phosphorylation levels decreased. Moreover, it has been described that the O-GlcNAc modification of tau directly inhibits its aggregation without perturbing the conformational properties of tau monomers. The implication of these collective results is that by maintaining healthy O-GlcNAc levels in AD patients, such as by inhibiting the action of O-GlcNAcase (OGA), one should be able to block hyperphosphorylation of tau and all of the associated effects of tau hyperphosphorylation, including the formation of NFTs and downstream effects. However, because the proper functioning of the lysosomal β-hexosaminidases is critical, any potential therapeutic intervention for the treatment of AD that blocks the action of O-GlcNAcase would have to avoid the concomitant inhibition of both lysosomal hexosaminidases A and B.

Consistent with the known properties of the hexosamine biosynthetic pathway, the enzymatic properties of O-GlcNAc transferase (OGTase), and the reciprocal relationship between O-GlcNAc and phosphorylation, it has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase should compensate for the age-related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention comes from studies showing that when transgenic mice harboring human tau are treated with kinase inhibitors, they do not develop typical motor defects and, in another case, show a decreased level of insoluble tau.

These studies provide a clear link between lowering tau phosphorylation levels and alleviating AD-like behavioral symptoms in a murine model of this disease.

There is evidence indicating that the modification with O-GlcNAc may have a general function in preventing harmful protein aggregation. This has been directly demonstrated for the tau protein and also for the protein alpha-synuclein that is a toxic aggregating protein associated with synucleinopathies, including Parkinson's disease. Two other aggregating proteins that are associated with amyotrophic lateraly sclerosis (Tar DNA binding protein-43 (TDP-43) and superoxide-dismutase I (SOD-1)) and frontotemporal lobar degeneration (TDP-43) are known to carry the O-GlcNAc modification. These results indicate that increasing O-GlcNAcylation with OGA inhibitors could be in general beneficial in diseases associated with protein aggregation.

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animal models of ischemia/reperfusion, trauma hemorrhage, hypervolemic shock and calcium paradox. Moreover, strong evidence indicates that these cardioprotective effects are mediated by elevated levels of protein O-GlcNAc modification. There is also evidence that the O-GlcNAc modification plays a role in a variety of neurodegenerative diseases, including Parkinson's disease and related synucleinopathies, and Huntington's disease.

Humans have three genes encoding enzymes that cleave terminal β-N-acetyl-glucosamine residues from glycoconjugates. The first of these encodes the enzyme O-glycoprotein-2-acetamido-2-deoxy-β-D-glucopyranosidase (O-GlcNAcase). O-GlcNAcase is a member of family 84 of glycoside hydrolases. O-GlcNAcase acts to hydrolyze O-GlcNAc off of serine and threonine residues of post-translationally modified proteins. Consistent with the presence of O-GlcNAc on many intracellular proteins, the enzyme O-GlcNAcase appears to have a role in the etiology of several diseases including type II diabetes, AD and cancer. Although O-GlcNAcase was likely isolated earlier on, about 20 years elapsed before its biochemical role in acting to cleave O-GlcNAc from serine and threonine residues of proteins was understood. More recently O-GlcNAcase has been cloned, partially characterized, and suggested to have additional activity as a histone acetyltransferase.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

Low molecular weight OGA inhibitors are e.g. disclosed in the international applications WO 2008/025170 and WO 2014/032187, which are structurally different from the compounds of the present invention. Further compounds that have some structurally similar elements are disclosed in WO 2016/030443, U.S. Pat. Nos. 3,489,757, 3,299,067, WO 99/21850, WO 2005/110982 and WO 2009/053373. However, these compounds do not show the improved pharmacological properties more closely described below.

Presently, no OGA inhibitor has reached the market. Thus, there is a need for low molecular weight molecules that selectively inhibit OGA and provide improved pharmacological properties that are of high relevance in drug development.

The present invention has the object of providing novel compounds having valuable properties, in particular those which can be used for the preparation of medicaments.

In this regard, plasma protein binding (PPB) is an important differentiating factor in drug development as it determines at least in part the unbound, and thus, likely effective) drug concentrations at pharmacological target site. It is a well-acknowledged paradigm that, in the absence of energy-dependent processes (e.g. transporter-mediated active organ uptake or efflux), once steady state equilibrium has been reached, unbound drug concentration in plasma may be considered equal to unbound drug concentration in the target tissue(s), i.e. only the unbound drug in the tissues is available for binding to the target receptor and can therefore drive the desired pharmacologic activity (Free drug theory (FDT) (Bohnert, T. et al. J. Pharmaceutical Sciences 2013, 102, 2953-2994). As a consequence, high plasma protein binding may also have a negative impact on efficacy since it is the free fraction of drug that is responsible for the pharmacological action.

Plasma protein binding information can be used to estimate the unbound and thus effective concentration of drugs in order to establish pharmacokinetic/pharmacodynamic (PKPD) relationships in animals and humans. The extent of plasma protein binding across species provides important information for PKPD modelling and helps to better understand translational aspects and/or efficacy differences between animal models and humans.

In the present invention, the introduction of a sulfoximine group results in an increased unbound fraction (decreased PPB) for compounds of Formula (I). In addition, the preferred compounds of the invention provide a low variability of fractions unbound across several animal species including humans. As a consequence, free drug concentrations in tissues are increased, directly yielding higher unbound brain concentrations (as measured by cerebrospinal fluid concentrations as surrogate) with similar effects measurable across different species which often greatly improve predictability of human PK and result in lower effective human dose due to the same extent of increase of unbound fractions across species (Liu et al. J. Med. Chem. 2014, 57, 8238).

It has been surprisingly found that the compounds according to the invention and salts thereof have very valuable pharmacological properties. The compounds achieve increased metabolic stability, as e.g. shown in microsome stability assays.

Further, preferred glycosidase inhibitors of formula I provide increased unbound, i.e. free fractions in plasma. Moreover, the preferred compounds according to the invention and salts thereof consistently provide increased free fractions in plasma across species including humans (low inter-species variability), which make them ideal for pharmaceutical development and their application as a drug.

The invention relates to compounds of formula (I)

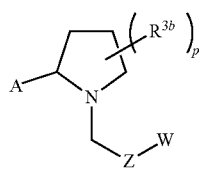

wherein
A denotes one of the following groups:

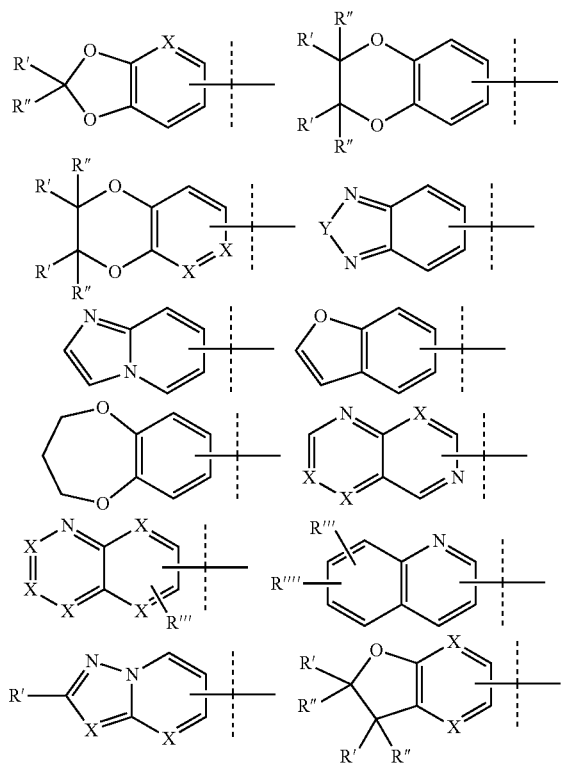

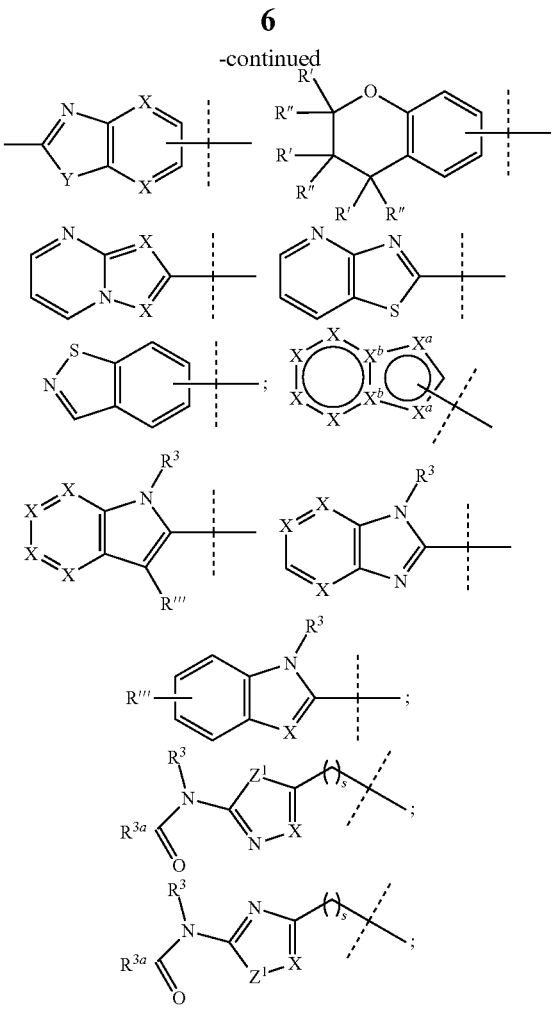

X is N or CR;
$X^a$ is N, $NR^3$, C (in case it is an atom bearing a bond connecting the group to the rest of the molecule) or CR''';
$X^b$ is N or C;
Y is O, S, SO or $SO_2$;
R', R'' denote each independently H, Hal or straight chain or branched alkyl having 1 to 12 carbon atoms;
R''', R'''' independently denote H, Hal, $NR^3R^4$, $CHR^3R^4$, $OR^3$, CN or a straight chain or branched alkyl having 1 to 12 carbon atoms, wherein 1 to 3 $CH_2$-groups may be replaced by a group selected from O, $NR^3$, S, SO, $SO_2$, $S(O)(NR^{3'})$, $N(SO)R^3$, CO, COO, OCO, $CONR^3$, $NR^3CO$,

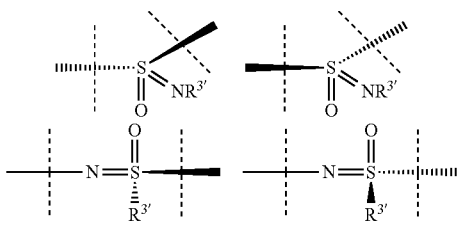

and wherein 1 to 5 hydrogen atoms may be replaced by Hal, $NR^3R^4$ or $NO_2$ or by one of the following groups:

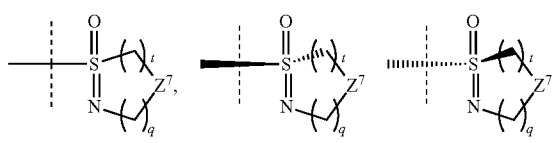

or R", R independently denote one of the following groups:

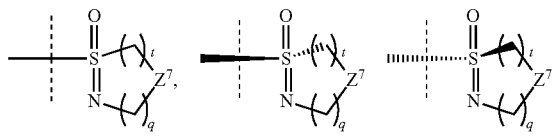

R³, R⁴ denote each independently H or a straight chain or branched alkyl group having 1 to 12 carbon atoms;
$R^{3a}$ denote a straight chain or branched alkyl group having 1 to 12 carbon atoms;
$R^{3b}$ is independently selected from the group consisting of H, Hal and a straight chain or branched alkyl having 1 to 12 carbon atoms, wherein 1 to 3 $CH_2$-groups may be replaced by a group selected from O or $NR^3$, and wherein 1 to 5 hydrogen atoms may be replaced by CN or Hal, such as fluoro; or two $R^{3b}$ substituents are bound to the same carbon atom and form together a cyclopropylidene radical;
W denotes R or Q
Z denotes a six-membered aromatic or saturated ring, optionally containing one or two heteroatoms selected from N, O and S, which ring may be substituted by one or two substituents selected from R', or Z may also denote a single bond if W is Q;
Q denotes one of the following groups:

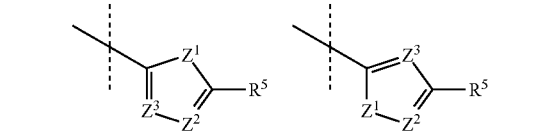

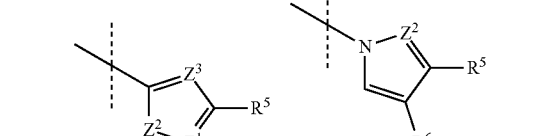

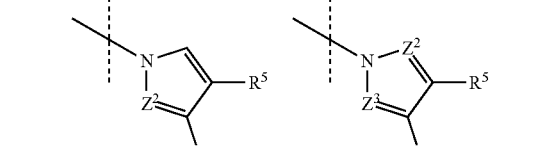

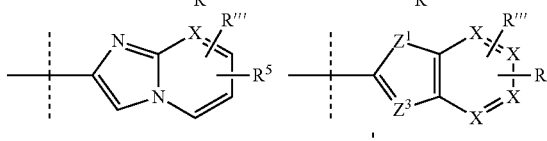

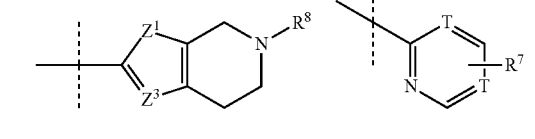

-continued

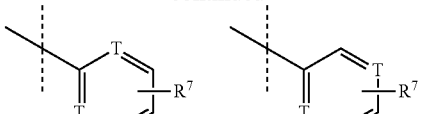

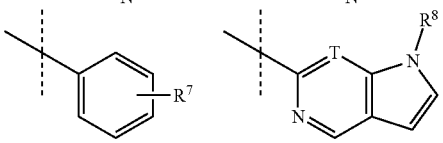

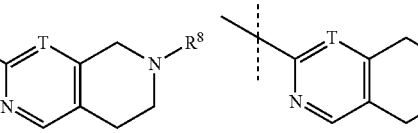

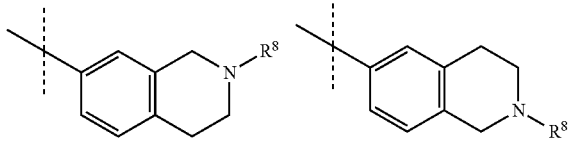

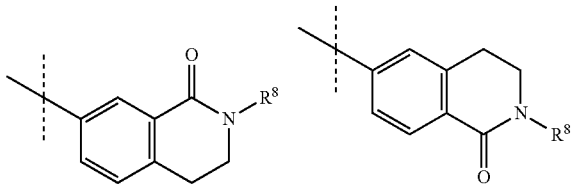

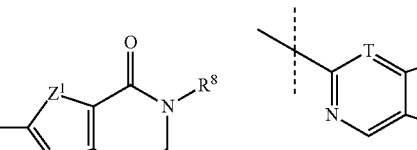

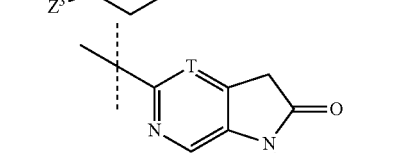

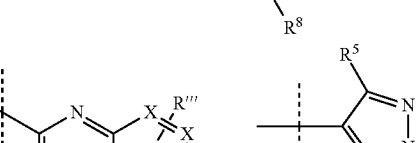

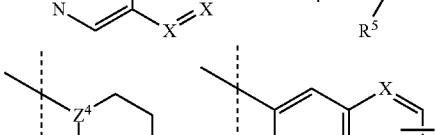

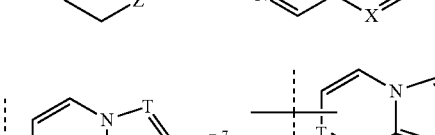

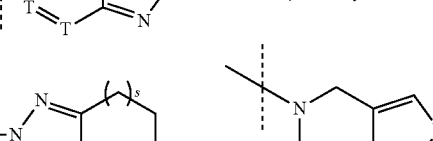

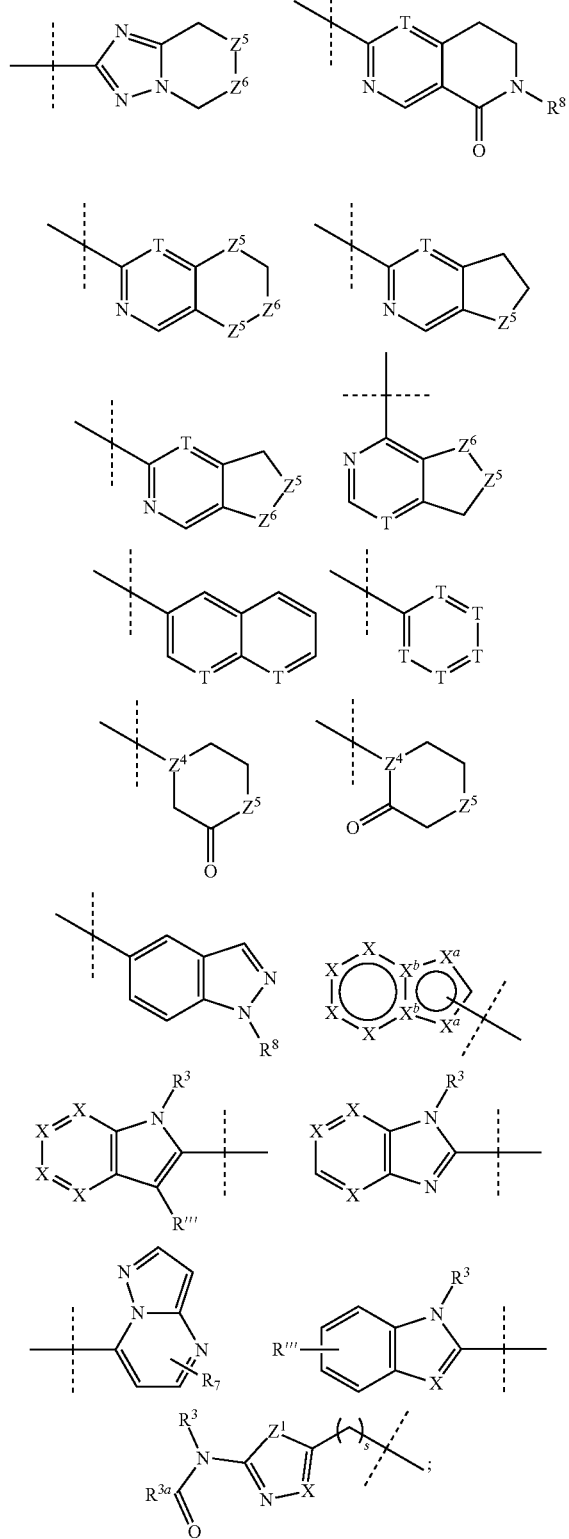

$Z^1$ is S, O, $NR^3$;

$Z^2$, $Z^3$ independently denote $CR^5$, $CR^6$ or N;

$Z^4$ is N, CH, CON, COCH;

$Z^5$ is O, $NR^B$, $CHR^5$, $SO_2$, $S(O)(NR^{3'})$, $N(SO)R^{3'}$,

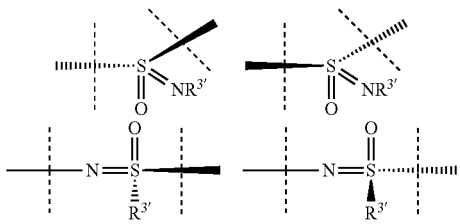

$Z^6$ is $CH_2$, CO, $S(O)(NR^{3'})$, $N(SO)R^{3'}$,

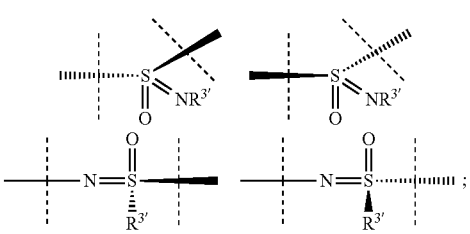

$Z^7$ is $C(R^3)_2$, S, O, $NR^{3'}$;

p denotes 1, 2 or 3;

s denotes 0 or 1;

T is N, CH or $CR^7$;

$R^{3'}$ denotes H or a straight chain or branched alkyl group having 1 to 12 carbon atoms, wherein 1 to 3 $CH_2$-groups may be replaced by a group selected from $SO_2$, CO, O, and wherein 1 to 5 hydrogen atoms may be replaced by Hal;

R, $R^5$, $R^6$, $R^7$ independently denote H, Hal, CN, OH, $NR^3R^4$, $NO_2$ or a straight chain or branched alkyl having 1 to 12 carbon atoms, wherein 1 to 3 $CH_2$-groups may be replaced by a group selected from O, $NR^3$, S, SO, $SO_2$, $S(O)(NR^{3'})$, $N(SO)R^3$, CO, COO, OCO, $CONR^3$, $NR^3CO$

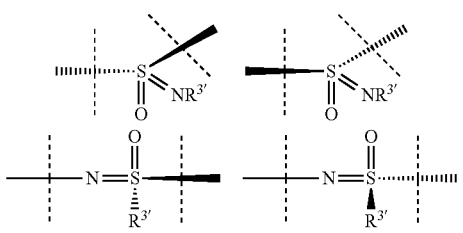

and wherein 1 to 5 hydrogen atoms may be replaced by Hal, $NR^3R^4$, $NO_2$, $OR^3$, Het, Ar, Cyc or by one of the following groups:

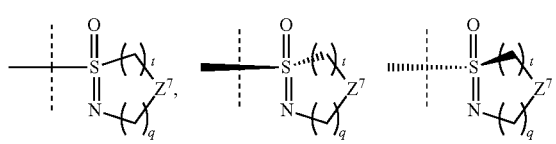

or R, $R^5$, $R^6$, $R^7$ denote Ar, Het or Cyc or one of the following groups:

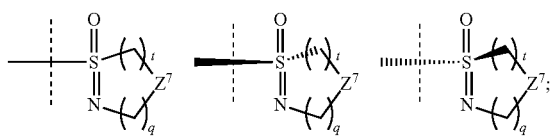

$R^8$ denotes H or straight chain or branched alkyl having 1 to 12 carbon atoms, wherein 1 to 3 $CH_2$-groups may be replaced by a group selected from SO, $SO_2$, S(O)($NR^{3'}$), N(SO)$R^{3'}$, CO, COO, OCO, $CONR^3$, $NR^3CO$, and

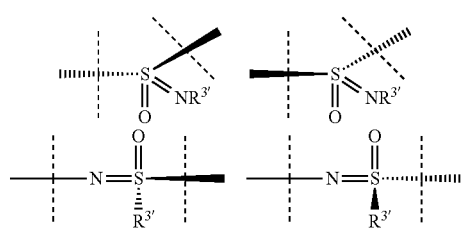

and further wherein 1 to 5 hydrogen atoms may be replaced by CN, $OR^3$, $SR^3$, Hal, $NR^3R^4$, $NO_2$ or by one of the following groups:

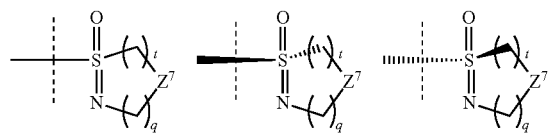

or $R^8$ denotes Ar, Het or Cyc or denotes one of the following groups:

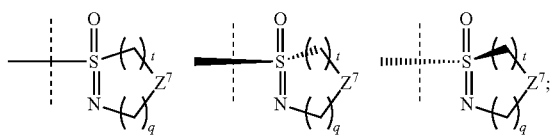

Hal denotes F, Cl, Br or I;
Het denotes a saturated, unsaturated or aromatic ring, being monocyclic or bicyclic or fused-bicyclic and having 3- to 8-members and containing 1 to 4 heteroatoms selected from N, O and S, which may be substituted by 1 to 3 substituents selected from $R^5$, Hal and $OR^3$;
Ar denotes a 6-membered carbocyclic aromatic ring or a fused or non-fused bicylic aromatic ring system, which is optionally substituted by 1 to 3 substituents independently selected from $R^5$, $OR^3$ and Hal;
Cyc denotes a saturated or an unsaturated carbocyclic ring having from 3 to 8 carbon atoms which is optionally substituted by 1 to 3 substituents independently selected from $R^5$ or Hal or OH;
t and q denote independently from one another 0, 1, 2 or 3, with t+q≥1
in its non-racemic form and pharmaceutically usable derivatives, solvates, salts, prodrugs, stereoisomers and tautomers or compounds of formula (I), wherein one or more H atoms may be replaced by D (deuterium).

Specifically, formula (I) includes the following two enantiomers of formula Ia and Ib:

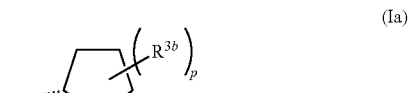

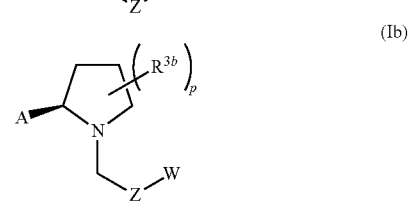

wherein A, W, $R^{3b}$, Z and p have the meaning given above.

The invention also relates to a mixture of, i.e. a composition comprising, compounds Ia and Ib as set out above, having identical groups A, W, $R^{3b}$, Z and p in equal or unequal amounts and to the use thereof as a medicament as discribed herein.

If individual groups and indices, such as T and s, occur more than once in a compound of formula I, they can have the same or different meanings according to the respective definition of that group.

A further preferred compound of formula I is a single enantiopure or enantiomerically enriched diastereoisomer, i.e. a compound wherein the stereogenic center bearing the group A has an S-configuration and any other stereogenic center within the compound has either an S- or an R-configuration.

Preferred compounds of the present invention are preferably used as single isomer in their non-racemic form, i.e. as diasteromerically and enatiomerically pure compounds or their diastereomerically and enaniomerically enriched mixtures of the respective diastereomers and enantiomers. Very preferred are formulae Ib.

In general, compounds of formula I are preferred that contain one ore more preferred groups such as T and indices such as s. Compounds of formula I are the more preferred, the more preferred groups or indices they contain.

If substituents, such as the group $R^8$, are connected to the remainder of the molecule through a heteroatom, the connecting atom in the respective group is preferably a carbon atom or the respective group is H.

The invention also relates to the use of compounds of formula (I), I(a), I(b) as a medicament.

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention. It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by re-crystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

An enantiomerically enriched mixture or a non-racemic form of a compound of formula (I) preferably denotes a compound of formula (I) or related formula having an enantiomeric excess, as measured by methods well known by one skilled in the art, of 10% or more, preferably 50% or more, and more preferably more than 95%. Most preferably an enantiomerically enriched mixture denotes a compound of Formula (I) or related Formulae having an enantiomeric excess of more than 98%.

The nomenclature as used herein for defining compounds, especially the compounds according to the invention, is in general based on the rules of the IUPAC-organization for chemical compounds and especially organic compounds. The compounds of invention have been named according to the standards used in the program AutoNom 2000 or ACD Lab Version 12.01 or Instant JChem Version: 15.12.7.0. The determination of the stereochemistry (S) or (R) is performed using standard rules of the nomenclature well known by one skilled in the art.

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent the expression of such substituent may differ from each other (e.g. methyl and ethyl). It shall be understood accordingly that a multiple substitution by any radical of the invention may involve identical or different radicals. Hence, if individual radicals occur several times within a compound, the radicals can adopt any of the meanings indicated, independently of one another.

The term "alkyl" or "alkyl group" refers to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl. In certain embodiments of the invention, 1 or more, preferable 1 to 3 $CH_2$ groups may be replaced by other divalent groups accoding to the defintions given above and below. In a particular embodiment, an H atom of alkyl may be replaced by Cyc.

In an embodiment of the invention, alkyl denotes unbranched or branched alkyl having 1-10 C atoms, in which 1-7 H atoms may be replaced independently from one another by Hal. A preferred embodiment of alkyl denotes unbranched or branched alkyl having 1-6 C atoms, in which 1-4 atoms may be replaced independently from one another by Hal. In a more preferred embodiment of the invention, alkyl denotes unbranched or branched alkyl having 1-4 C atoms, in which 1-3 H atoms can be replaced independently from one another by Hal, particularly by F and/or Cl. It is most preferred that alkly denotes unbranched or branched alkyl having 1-6 C atoms. Highly preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of alkyl is independently of one another in any radical of the invention.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In an embodiment of the invention, Cyc denotes cycloalkyl having 3-7 C atoms, in which 1-4 H atoms may be replaced independently of one another by Hal. Preferred is $C_3$-$C_7$-cycloalkyl. More preferred is $C_4$-$C_7$-cycloalkyl. Most preferred is $C_5$-$C_7$-cycloalkyl, i.e. cyclopentyl, cyclohexyl or cycloheptyl, highly preferably cyclohexyl. It shall be understood that the respective denotation of Cyc is independently of one another in any radical of the invention.

The term "Ar", "aryl" or "carboaryl" for the purposes of this invention refers to a mono- or polycyclic aromatic hydrocarbon systems having 3 to 14, preferably 3-12, more preferably 4 to 12, most preferably 5 to 10, highly preferably 6 to 8 carbon atoms, which can be optionally substituted. The term "Ar" or "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suited aryl radicals are phenyl, biphenyl, naphthyl, 1-naphthyl, 2-naphthyl and anthracenyl, but likewise indanyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

Ar and aryl are preferably selected from the following group: phenyl, o-, m- or p-tolyl, o-, m- or p-ethylphenyl, o-, m- or p-propylphenyl, o-, m- or p-isopropylphenyl, o-, m- or p-tert. butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethylsulfonamido)-phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Irrespective of further substitutions, Het denotes preferably 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazo-, -1-yl, -4- or -5-yl, 1,2,4-triazo-, -1-yl, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-iso-5i-ndolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo-[3.2.1]octyl or dibenzofuranyl, 1-methyl-1 H-pyrazol-4-yl,

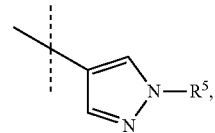

and preferably

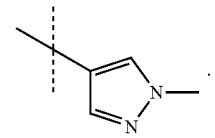

The heterocyclic radicals may also be partially or fully hydrogenated.

Irrespective of further substitutions, Het can thus also denote, preferably, 2,3-dihydro-2-, -3-, -4- or -5-furyl, 2,5-dihydro-2-, -3-, -4- or 5-furyl, tetra-hydro-2- or -3-furyl, 1,3-dioxolan-4-yl, tetrahydro-2or -3-thienyl, 2,3-di-hydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, 2-, 3- or 4-thiomorpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-(-2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-di-hydro-2H-1,5-benzodioxepin-6- or -7-yl, furthermore preferably 2,3-dihydrobenzofuranyl, 2,3-dihydro-2-oxofuranyl, 3,4-dihydro-2-oxo-1 H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes piperidinyl, 4-hydroxypiperidinyl, piperazinyl, 4-methylpiperazinyl, pyrrolidinyl, morpholinyl, dihydro-pyrazolyl, dihydro-pyridyl, dihydropyranyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, particularly when the halogens are substituted on an alkyl (haloalkyl) or alkoxy group (e.g. $CF_3$ and $CF_3O$). It shall be understood that the respective denotation of Hal is independently of one another in any radical of the invention.

A compound of formula I, wherein Z is other than a single bond and T, if present, denotes CH or a group $CR^7$, wherein $R^7$ is Hal, CN or alkyl having 1 to 6 carbon atoms, wherein 1 to 3 H-atoms may be replaced by Hal.

Compounds of formula I are preferred, wherein Z denotes a single bond or one of the following groups:

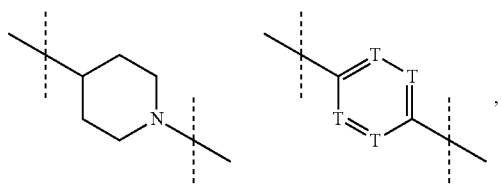

wherein T has the meaning given above and denotes preferably CH or a group $CR^7$, wherein $R^7$ is Hal, CN or alkyl or alkoxy having 1 to 6 carbon atoms, wherein 1 to 3 H-atoms may be replaced by Hal.

Compounds of formula I are especially preferred, wherein Z denotes one of the following goups:

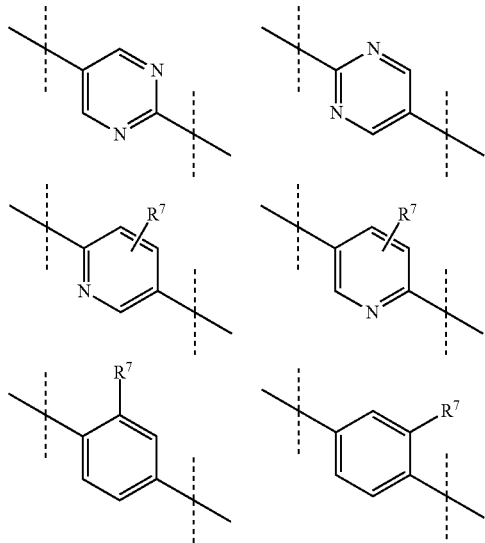

wherein $R^7$ has the meaning given above.

If Z is a single bond, $R^5$, if present, preferably denotes H, Ar, Het or Cyc or one of the following groups:

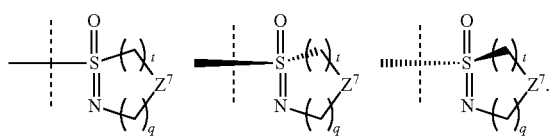

If Z is other than a single bond, $R^5$, if present, is preferably H, Hal, CN, $NR^3R^4$, $NO_2$ or a straight chain or branched alkyl having 1 to 12 carbon atoms, wherein 1 to 3 $CH_2$-groups may be replaced by a group selected from O, $NR^3$, S, SO, $SO_2$, $S(O)(NR^{3'})$, $N(SO)R^{3'}$, CO, COO, OCO, $CONR^3$, $NR^3CO$

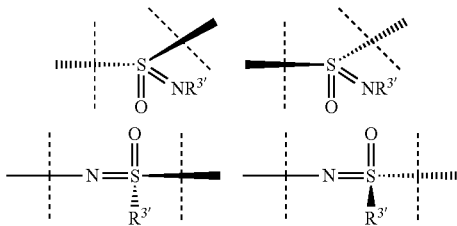

and wherein 1 to 5 hydrogen atoms may be replaced by Hal, $NR^3R^4$, $NO_2$, $OR^3$, Het, Ar, Cyc or by one of the following groups:

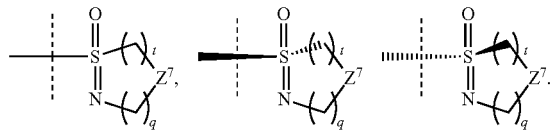

$R^{3'}$ denotes preferably H, methyl, ethyl, 2-hydroxyethyl or 2-methoxyethyl.

Preferably, the group $S(O)(NR^{3'})$ is selected from

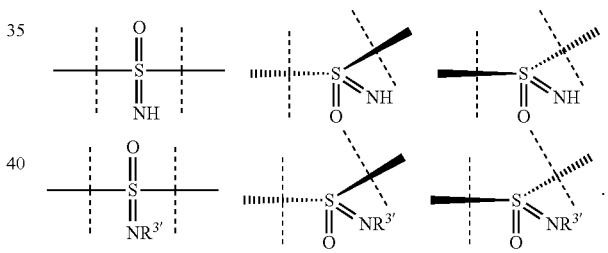

Preferably, the group $N(SO)R^{3'}$ is selected from

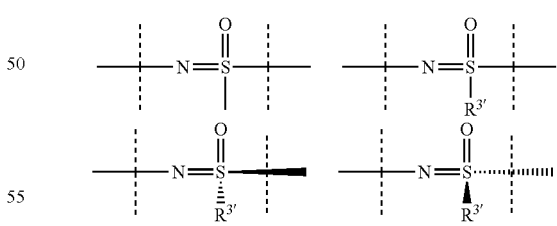

In a preferred embodiment, A is selected from

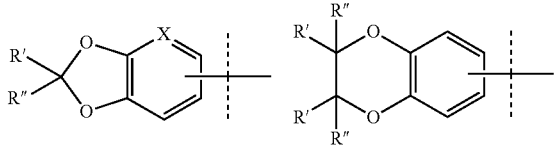

-continued
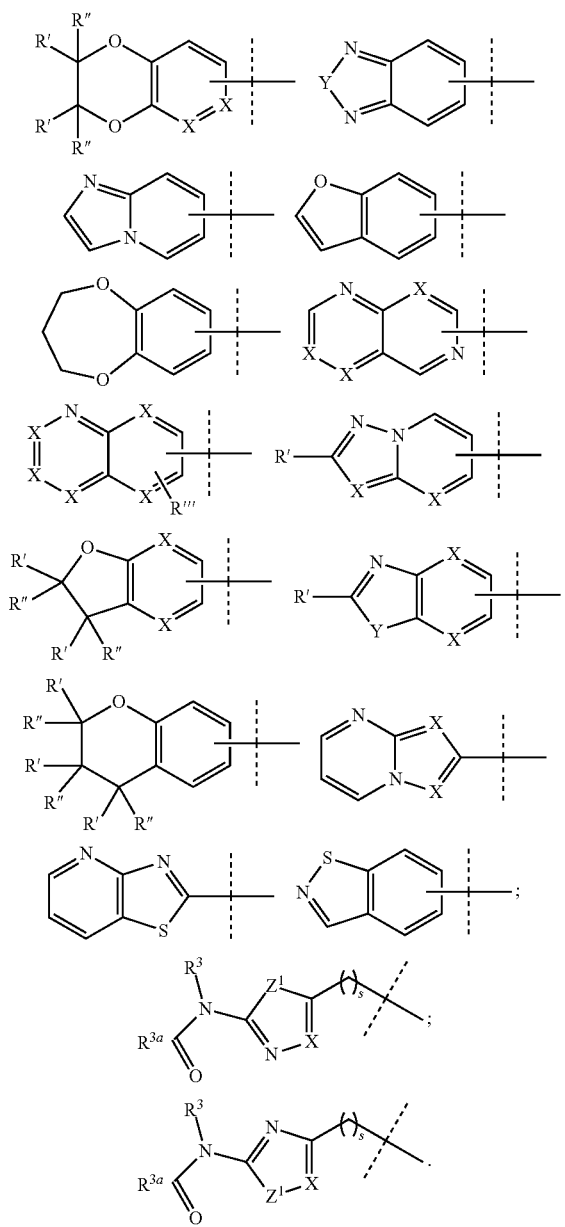
or A is selected from the following groups, wherein at least one X is not CH:
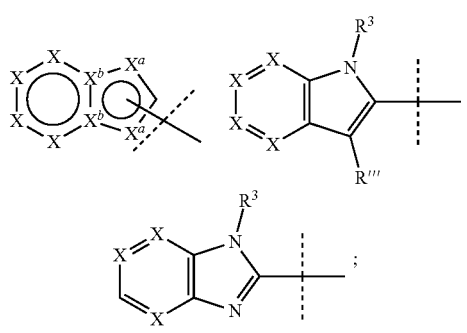
A more preferably denotes one of the following groups:
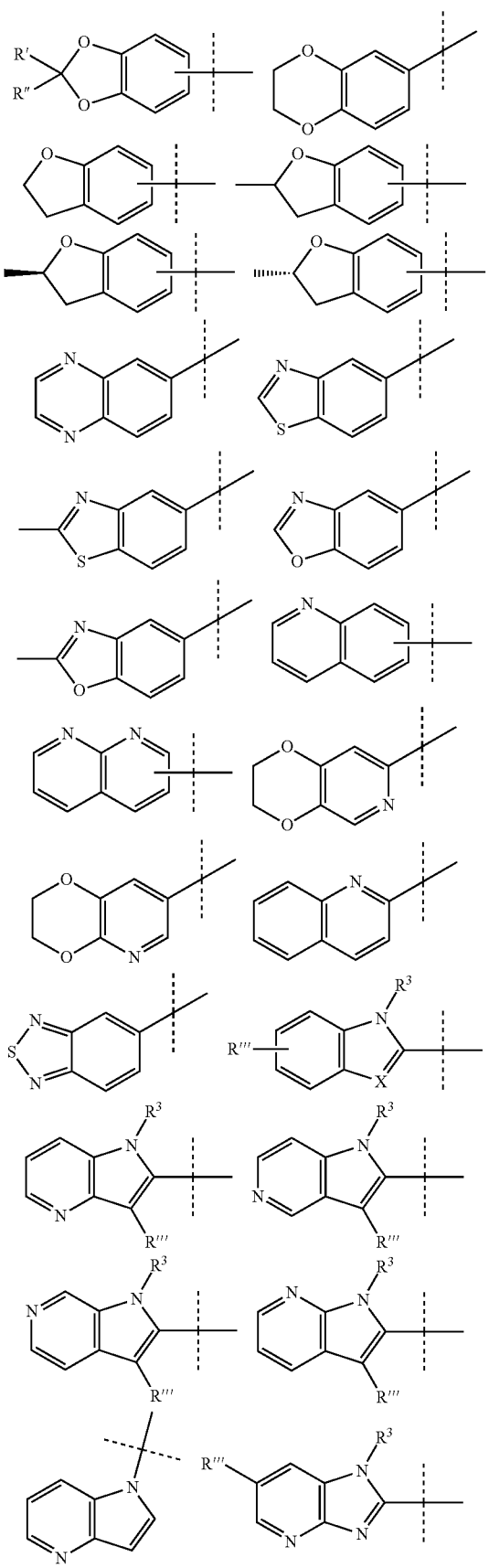

-continued

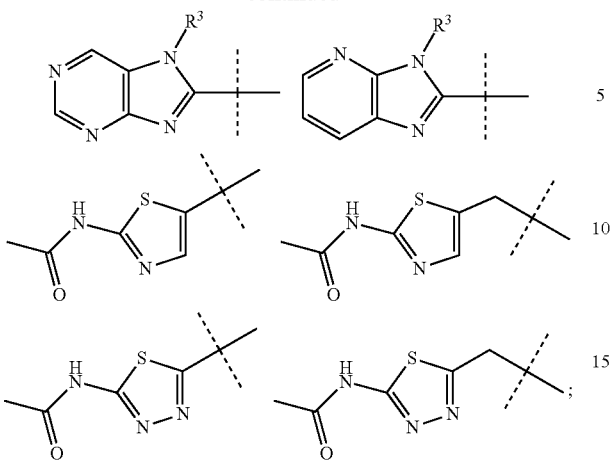

wherein R³, X, R', R" and R''' have the meaning given above.

If A denotes

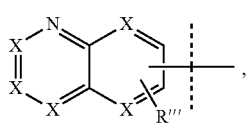

wherein R''' and X have the meaning given above, it is preferably

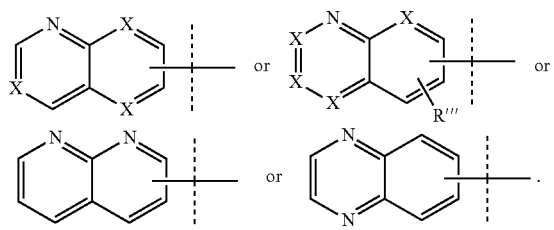

If A denotes

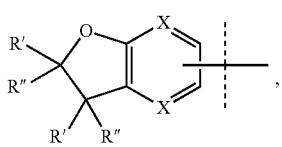

wherein R', R" and X have the meaning given above, it is preferably

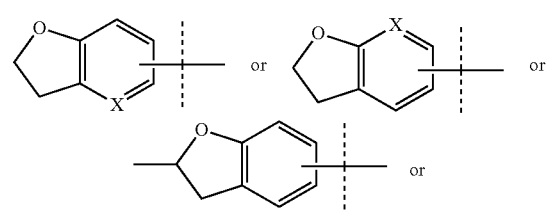

-continued

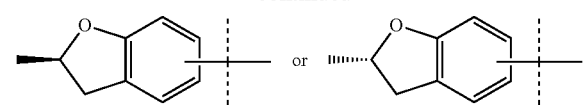

If A denotes

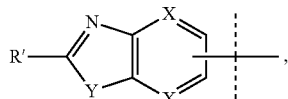

wherein R', X and Y have the meaning given above, it is preferably

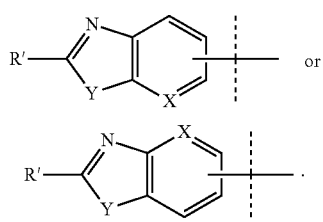

A is especially preferred one of the following groups:

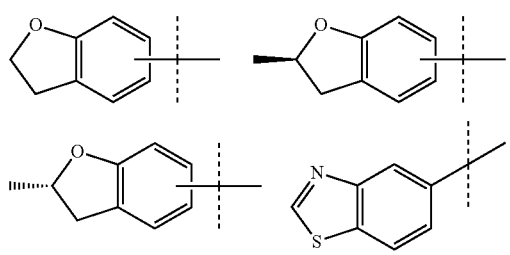

The group Q preferably denotes one of the following groups:

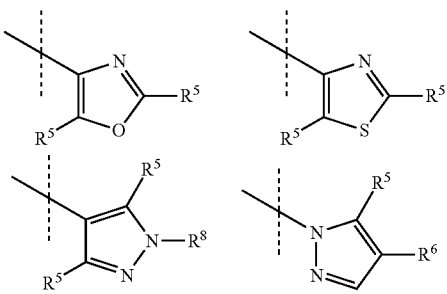

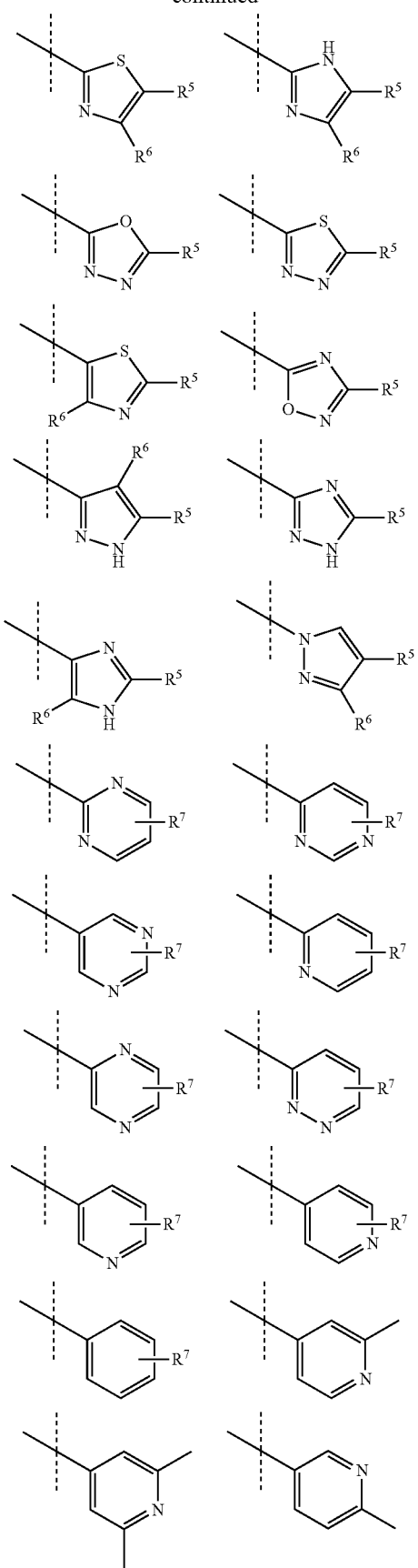
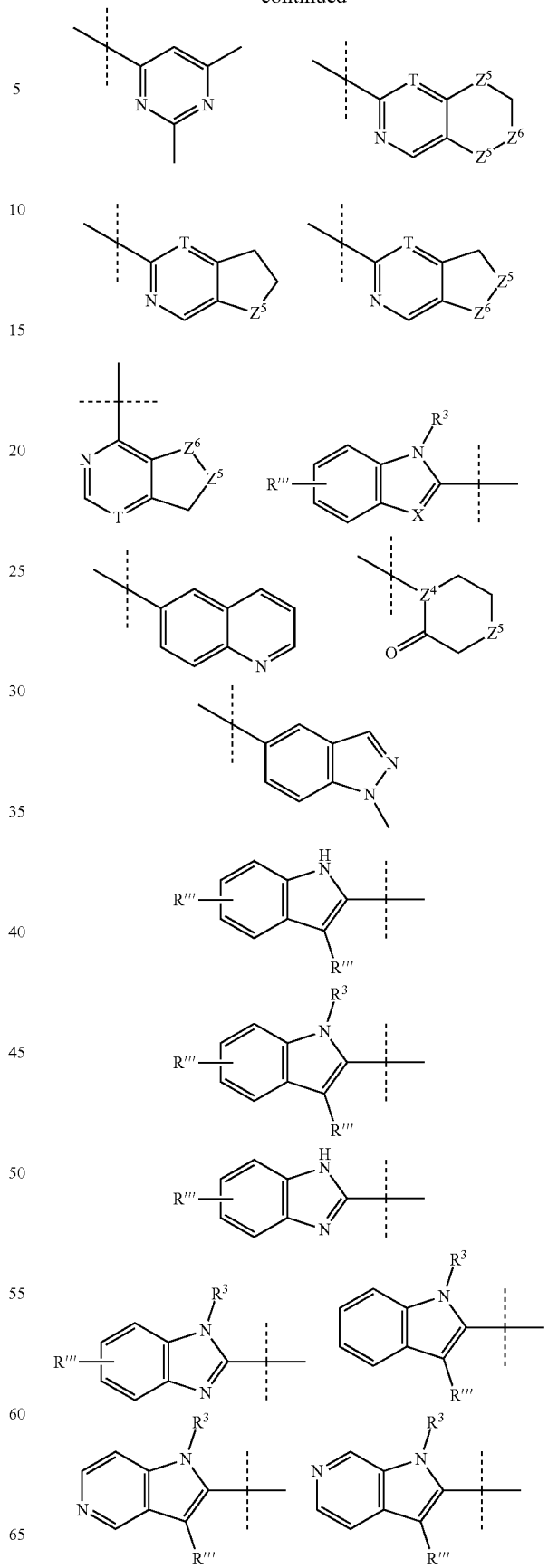

-continued

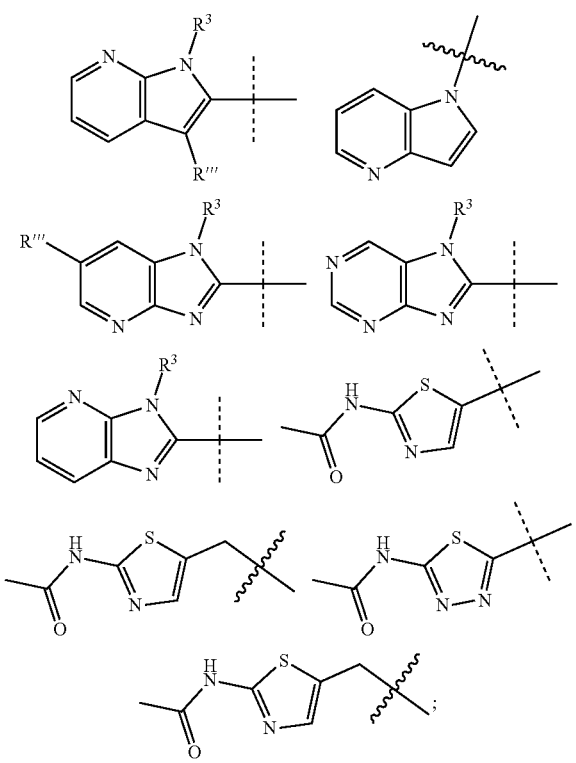

wherein X, R''', R³, T, Z⁵, Z⁶, R⁶ and R⁷ have the meaning given above.

R, R⁵, R⁶, R⁷ and Rare preferably independently H, CN, $SO_2CH_3$, $SO_2CH_2CH_3$, $SO_2CH_2CH_2OH$, $SO_2CH_2CH_2OCH_3$, $S(O)(NR^{3'})CH_3$, $S(O)(NR^{3'})CH_2CH_3$, $S(O)(NR^{3'})CH_2CH_2OH$, $S(O)(NR^{3'})CH_2CH_2OCH_3$, $N(SO)R^{3'}CH_3$, $N(SO)R^{3'}CH_2CH_3$, $N(SO)R^{3'}CH_2CH_2OH$, $N(SO)R^{3'}CH_2CH_2OCH_3$,

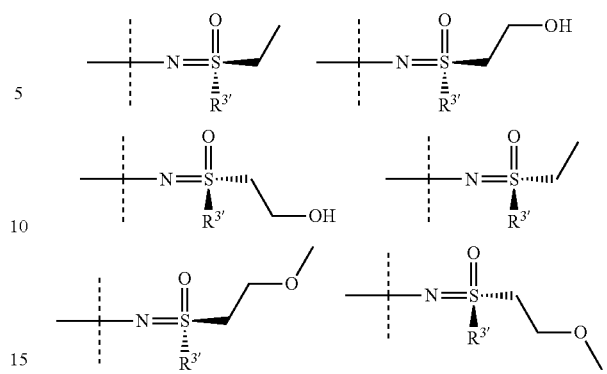

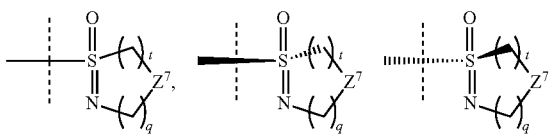

Hal, $NR^3R^4$, $NO_2$, phenyl, benzyl, $CH_2$-pyridyl, O-phenyl, O-pyridyl, 0-pyrimidinyl, O-benzyl, 2-, 3- or 4-hydroxy or methoxyphenyl, alkyl, alkoxy (Oalkyl), hydroxyalkylen, alkoxyalkylen, COOH, COOalkyl, CONHalkyl, $CONH_2$, $CON(CH_3)_2$, NHCOalkyl, $NHCOCH_3$, NHCOphenyl, NHCOpyridyl, $NHCH_2CH_3$, $NHCH_2CH_2CH_3$, $NHCOCH_2CH_2OH$, CO—N-morpholinyl, $CON(CH_3)$ $CH_2CH_2N(CH_3)_2$, CO-1-piperidinyl, CO-4-hydroxy-1-piperidinyl, CO-1-piperazinyl, CO-4-methyl-1-piperazinyl, $CH_2$—N— morpholinyl, $CH_2N(H)COCH_3$, $CH_2N(CH_3)COCH_3$, $CH_2NH_2$, $NH_2$, $CH(OH)CH_3$, $CH(OR^3)CH_3$ or a group selected from

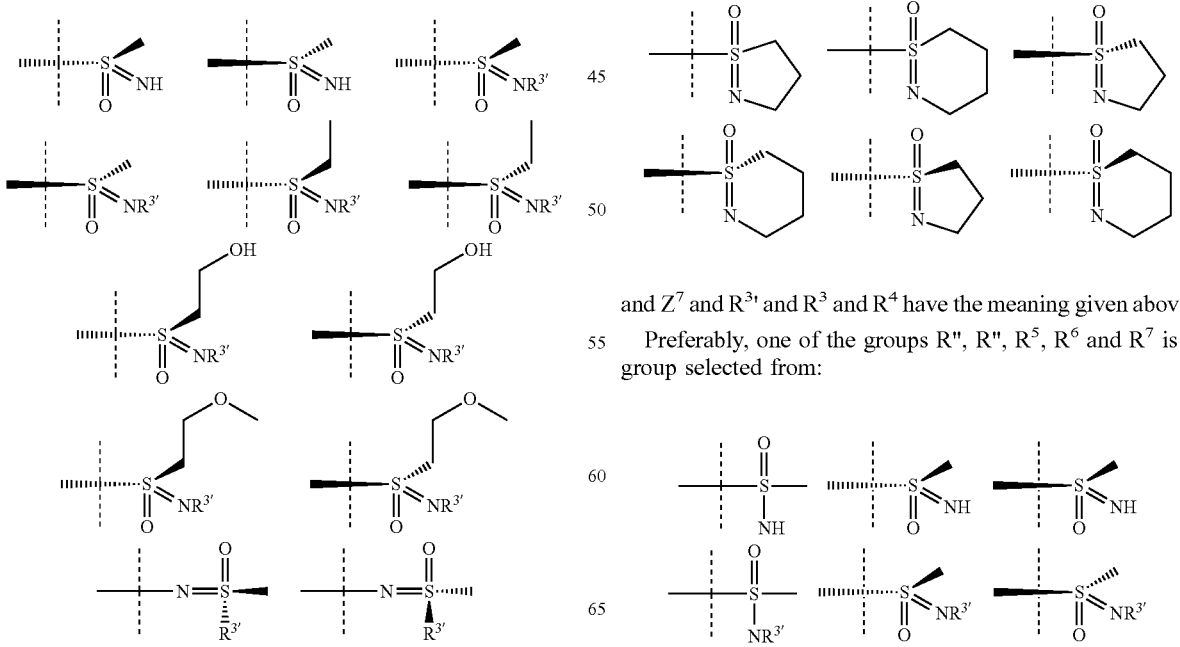

wherein t+q is 2 or 3, preferably a group selected from

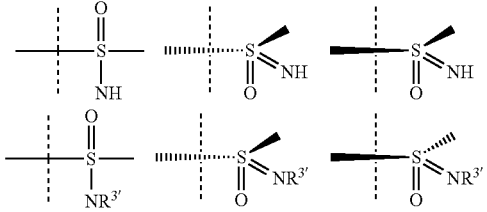

and Z⁷ and $R^{3'}$ and R³ and R⁴ have the meaning given above.

Preferably, one of the groups R", R''', R⁵, R⁶ and R⁷ is a group selected from:

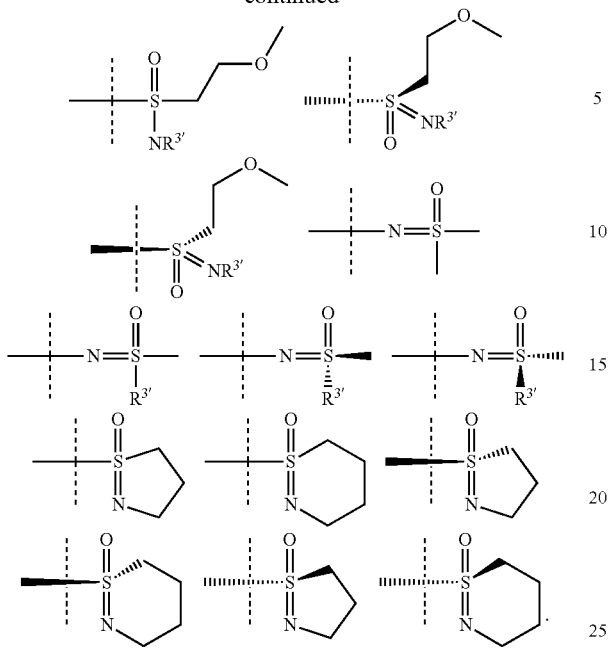

Preferred are compounds of formua I, wherein only one of the groups R''', R'''', $R^5$, $R^6$ and $R^7$ contains a group $S(O)(NR^{3'})$, $N(SO)R^{3'}$, $R^{3'}$ $R^{3'}$,

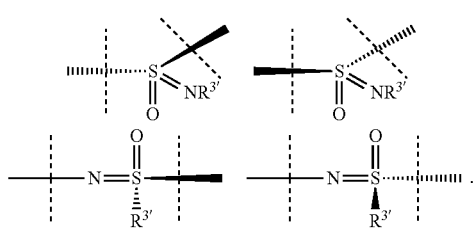

More preferred are compounds of formua I, wherein one of the groups $R^5$, $R^6$ and $R^7$ contains the group $S(O)(NH)$, $S(O)(NR^{3'})$ or $N(SO)R^{3'}$,

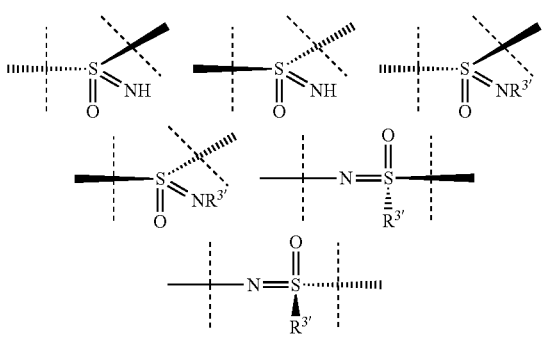

while the others of these groups denote H or methyl.

$R^8$ is preferably a group selected from H, COalkyl or alkyl or hydroxyl alkyl. More preferably, $R^8$ is H, COmethyl or methyl, $CON(SO)R^{3'}CH_3$, $CON(SO)R^{3'}CH_2CH_3$, $CON(SO)R^{3'}CH_2CH_2OH$, $CON(SO)R^{3'}CH_2CH_2OCH_3$, $S(O)(NH)CH_3$, $S(O)(NR^{3'})CH_3$, $S(O)(NR^{3'})CH_2CH_3$, $S(O)(NR^{3'})CH_2CH_2OH$, $S(O)(NR^{3'})CH_2CH_2OCH_3$,

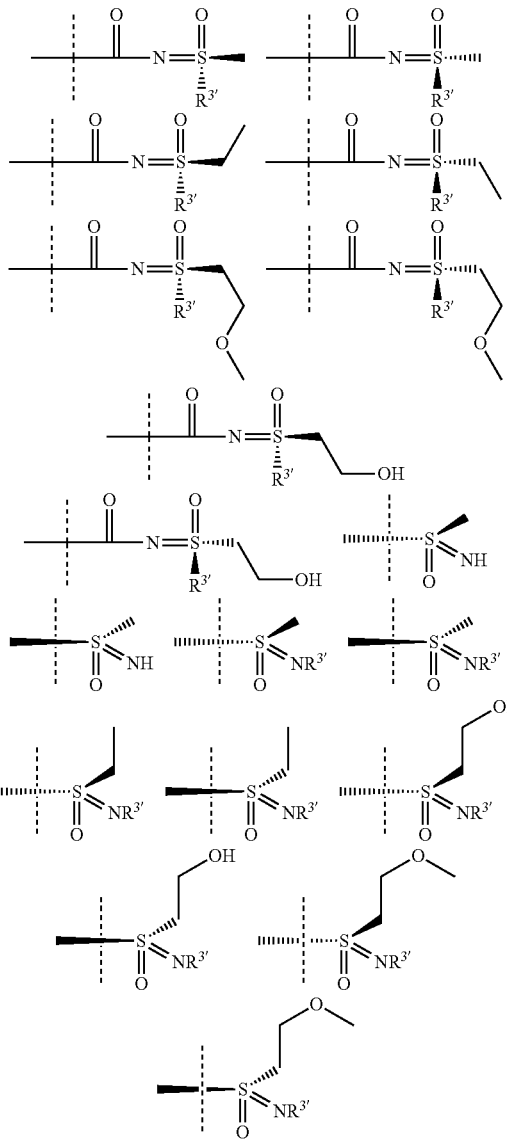

more preferably wherein $R^{3'}$ is H or methyl.

X denotes preferably N or CH.

Y is preferably O or S.

R', R" denote each independently preferably H, methyl or ethyl. More preferred are compounds of formula I, wherein both R', R" are simultaneously H or wherein one of the groups is H and the other group is a straight chain or branched alkyl having 1 to 12 carbon atoms, more preferably methyl or ethyl.

T is preferably N or CH, most preferably N.

$Z^1$ is preferably S or NH.

$Z^2$, $Z^3$ preferabyl denote independently CH or N.

$Z^4$ is preferably N or CH.

$Z^5$ is preferably $NR^8$, $CHR^5$, $S(O)(NR^{3'})$, $N(SO)R^3$, more preferably

$Z^6$ is preferably $CH_2$, CO, $SO_2$ or

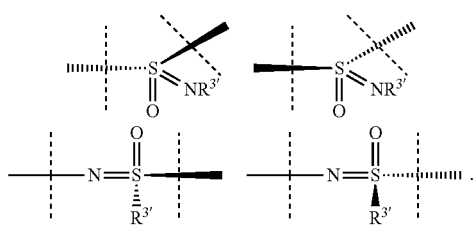

$Z^7$ is preferably $CH_2$, S, O, NH. If $Z^7$ is S, O, $NR^{3'}$, t and q are each 1 or one of t and q is 1 while the other denotes 2.

Most preferably, t and q simultaneously denote 1.
Compounds of formula I are further preferred, wherein
A is preferably selected from one of the following groups:

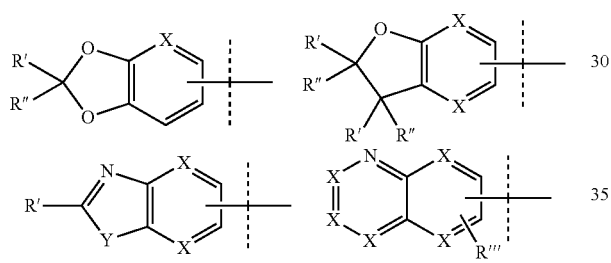

and
the group Q is preferably selected from one of the following groups:

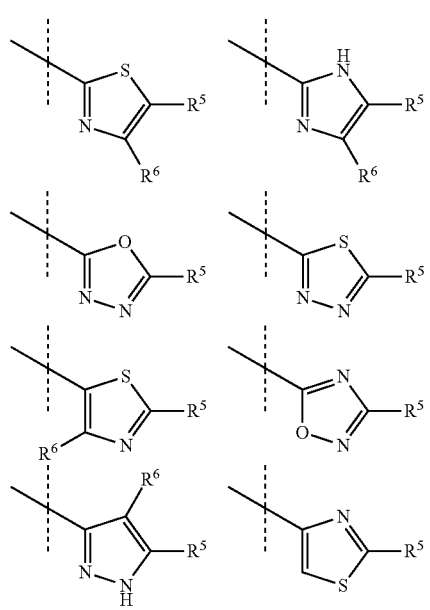

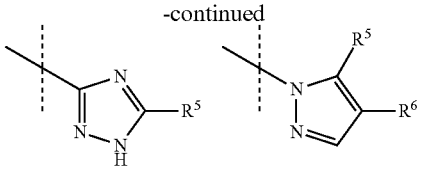
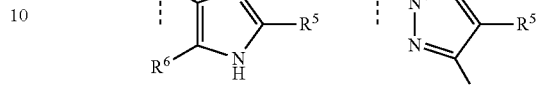
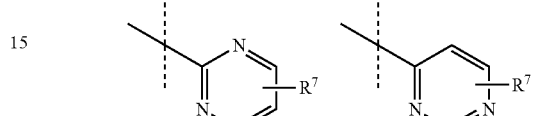
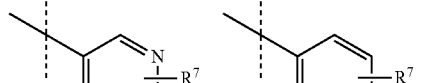
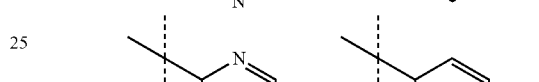
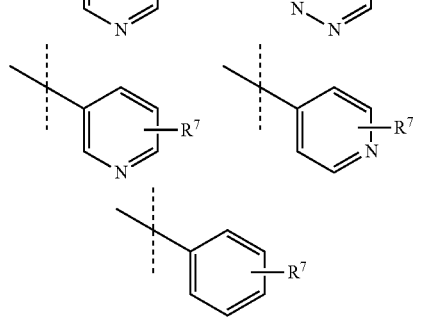

wherein $R^5$, $R^6$, $R^7$ are as defined above,
and pharmaceutically usable derivatives, solvates, salts, prodrugs, tautomers, enantiomers, racemates and stereoisomers thereof, including mixtures thereof in all ratios and compounds of formula I, wherein one or more H atoms may be replaced by D (deuterium).

Compounds according to the invention are preferred, wherein Z is other than a single bond and T, if present, denotes CH or a group $CR^7$, wherein $R^7$ is Hal, CN or alkyl having 1 to 6 carbon atoms, wherein 1 to 3 H-atoms may be replaced by Hal.

Compounds according to the invention are especially preferred, wherein $R^{3b}$ denotes H.

In an especially preferred embodiment, the invention also relates to compounds of formula (Ix) and their use according to the present invention:

(Ix)

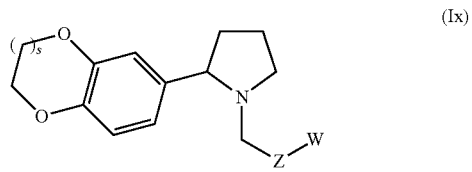

wherein
  s is as defined above;
  Z preferably denotes a six-membered aromatic or saturated ring, optionally containing one or two heteroatoms selected from N, O and S, which ring may be substituted by one or two substituents selected from R⁷;
and
  Q as group preferably denotes one of the following groups:
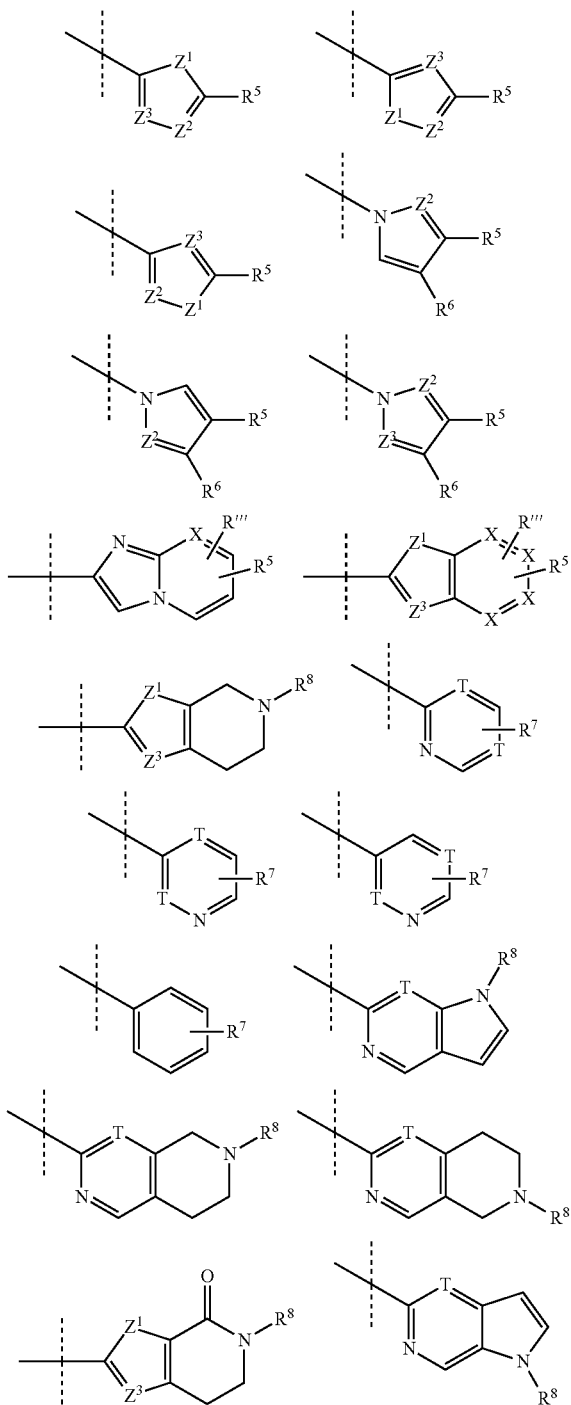
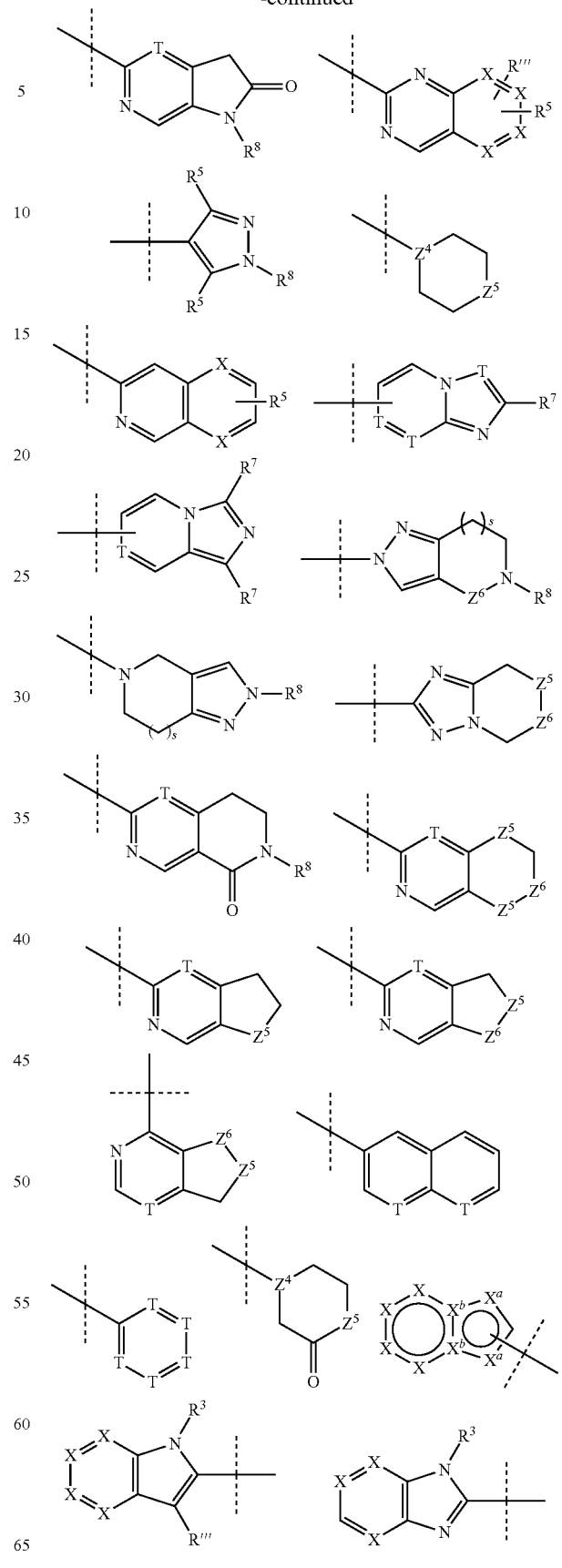

In preferred embodiments of the invention, the group

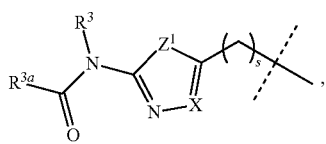

more specifically denotes one of the following groups:

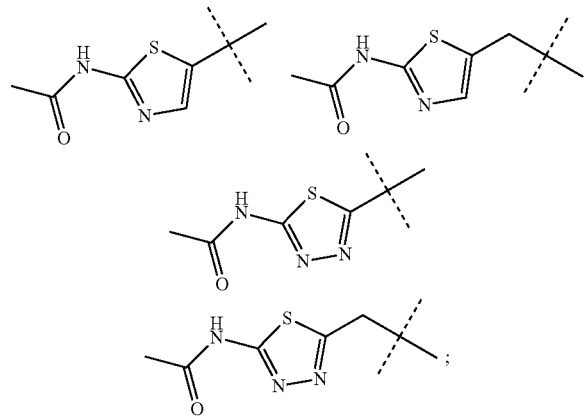

In a further especially preferred embodiment, the invention also relates to compounds of formula (Iy) and their use according to the present invention:

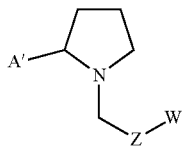

(Iy)

wherein
Z, and W have the meaning given above, and
A' preferably denotes one of the following groups:

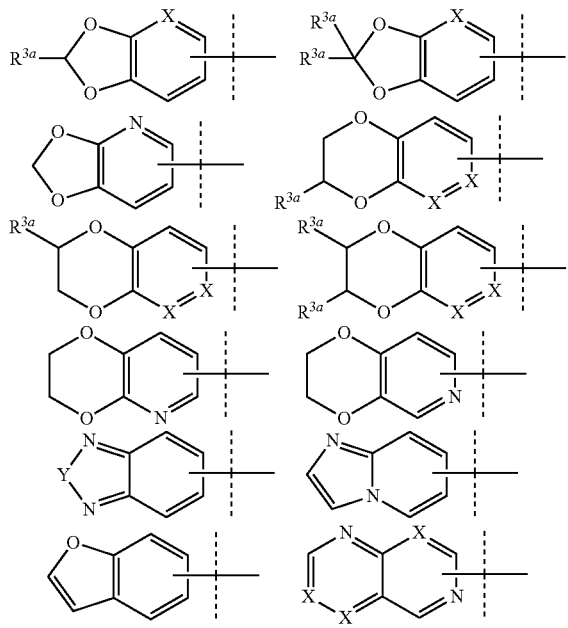

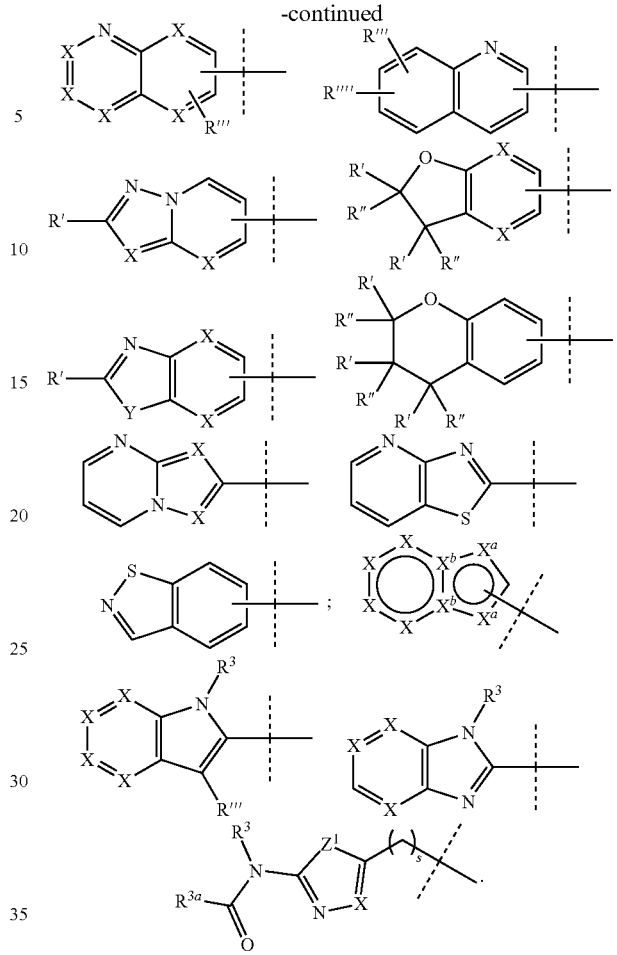

Throughout the specification and claims, the individual groups such as COO, CONR$^3$,

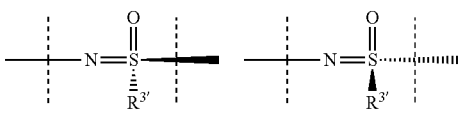

can be attached through any of the linking atoms to the rest of the compound of formula I, i.e. a respective part of the compound of fomula I may be attached to the right or left or lower of upper side of the individual group as presented in the specification.

Accordingly, the subject-matter of the invention relates to compounds of formula (I) as medicament, in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means that the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

Particularly highly preferred embodiments are those compounds of formula (I) listed in Table 1 and/or physiologically acceptable salts thereof.

TABLE 1

| | | | | |
|---|---|---|---|---|
| | Compounds of formulae (I). OGA enzyme inhibition assay: | | | |
| No | Structure | Optical rotation | Configuration specification | OGA IC50 |
| 1 | | | Racemic | + |
| 2 | | | Second elution on Chiracel OJ-H (250 X 4.6) mm, 5 μm, 20 mM, 0.5% Isopropyl amine in IPA, Rt 5.35, The enantiomeric purity is 100%. | + |
| 3 | | | Racemic | + |
| 4 | | | Racemic | +++ |
| 5 | | | Racemic | +++ |
| 6 | | $[\alpha]^{26}_D$ = −0.55, c 0.11 (MeOH). | Second elution on Chiralcel ODH (250 X 4.6) mm, 5 μm, 20 mM, IPA, Rt 4.11, The enantiomeric purity is 99.35%. | ++++ |

TABLE 1-continued

Compounds of formulae (I). OGA enzyme inhibition assay:

| No | Structure | Optical rotation | Configuration specification | OGA IC50 |
|---|---|---|---|---|
| 7 | 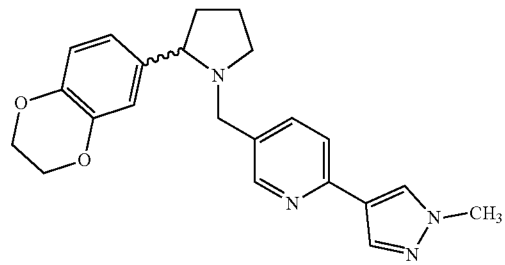 [SMILES: Cn1cc(-c2ccc(CN3CCCC3c3ccc4c(c3)OCCO4)cn2)cn1] | $[\alpha]^{26}_D$ = 11.18, c 0.17 (MeOH). | Second elution on Chiralpak OXH (250 X 4.6) mm, 5 μm, 20 mM, 0.55 IPA in methanol, Rt 3.84, The enantiomeric purity is 99.48% | +++ |
| 8 | 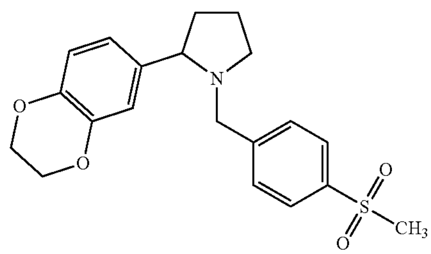 [SMILES: CS(=O)(=O)c1ccc(CN2CCCC2c2ccc3c(c2)OCCO3)cc1] | | Racemic | ++ |
| 9 | 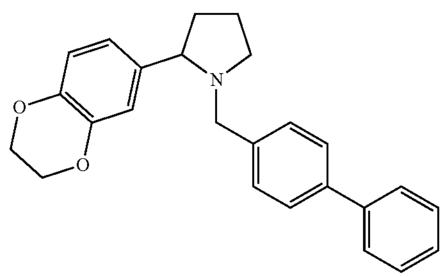 [SMILES: c1ccc(-c2ccc(CN3CCCC3c3ccc4c(c3)OCCO4)cc2)cc1] | | Racemic | ++ |
| 10 | 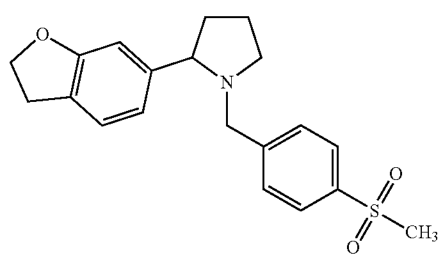 | | Racemic | ++ |
| 11 | 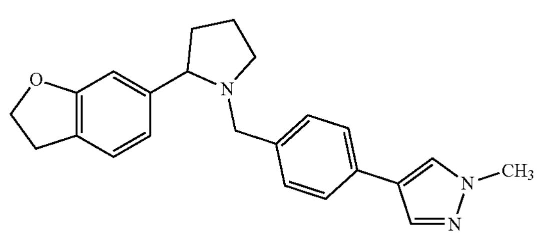 | | Racemic | ++++ |

TABLE 1-continued

Compounds of formulae (I). OGA enzyme inhibition assay:

| No | Structure | Optical rotation | Configuration specification | OGA IC50 |
|---|---|---|---|---|
| 12 | 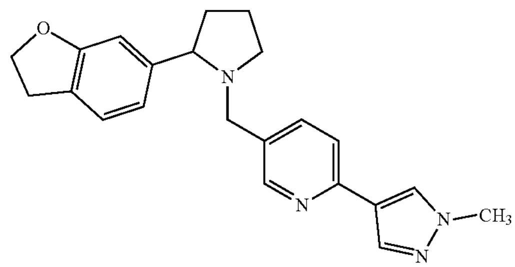 [SMILES: Cn1cc(-c2ccc(CN3CCCC3c3ccc4c(c3)OCC4)cn2)cn1] | | Racemic | +++ |
| 13 | 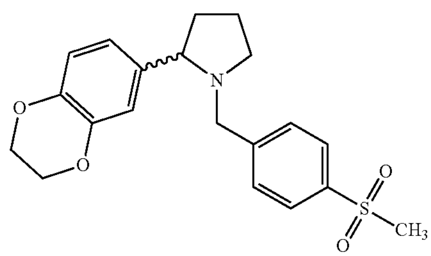 [SMILES: CS(=O)(=O)c1ccc(CN2CCCC2c2ccc3c(c2)OCCO3)cc1] | | First elution on Chiralcel OJH (250 X 4.6) mm, 5 μm, 20 mM, MeOH, Rt 6.84, The enantiomeric purity is 98.1%. | ++ |
| 14 | 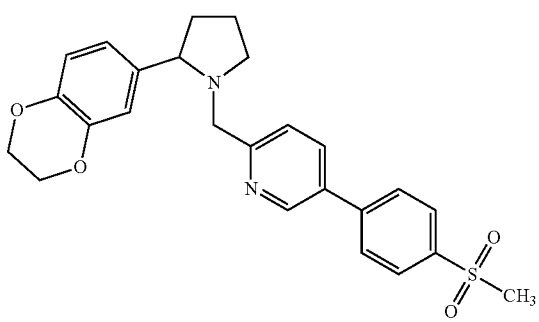 [SMILES: CS(=O)(=O)c1ccc(-c2ccc(CN3CCCC3c3ccc4c(c3)OCCO4)nc2)cc1] | | Racemic | ++ |
| 15 | 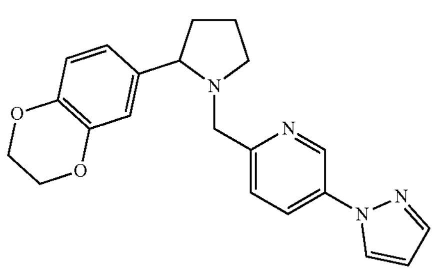 [SMILES: c1cnn(-c2ccc(CN3CCCC3c3ccc4c(c3)OCCO4)nc2)c1] | | Racemic | + |
| 16 | 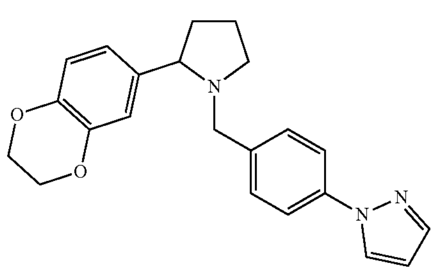 [SMILES: c1cnn(-c2ccc(CN3CCCC3c3ccc4c(c3)OCCO4)cc2)c1] | | Racemic | +++ |

TABLE 1-continued

Compounds of formulae (I). OGA enzyme inhibition assay:

| No | Structure | Optical rotation | Configuration specification | OGA IC50 |
|---|---|---|---|---|
| 17 | 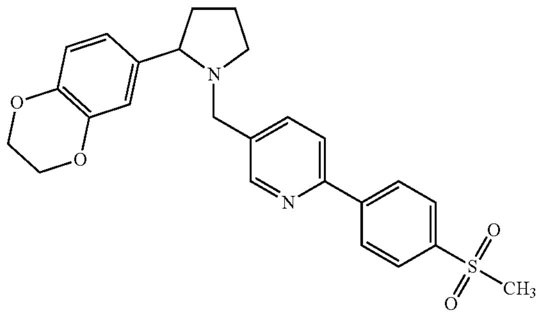 [SMILES: CS(=O)(=O)c1ccc(-c2ccc(CN3CCCC3c3ccc4c(c3)OCCO4)cn2)cc1] | | Racemic | ++ |
| 18 | 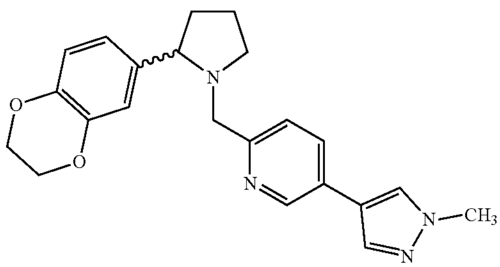 [SMILES: Cn1cc(-c2ccc(CN3CCCC3c3ccc4c(c3)OCCO4)nc2)cn1] | | First elution on YMC Cellulose-SB (250 X 4.6) mm, 5 μm, 20 mM, 0.5% isopropylamine in isopropylalcohol, Rt 2.57, The enantiomeric purity is 100.00%. | + |
| 19 | 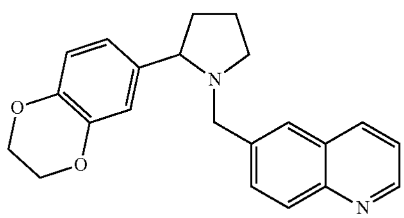 [SMILES: c1cnc2ccc(CN3CCCC3c3ccc4c(c3)OCCO4)cc2c1] | | Racemic | ++ |
| 20 | 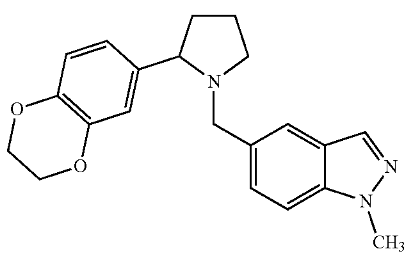 [SMILES: Cn1ncc2cc(CN3CCCC3c3ccc4c(c3)OCCO4)ccc21] | | Racemic | ++ |
| 21 | 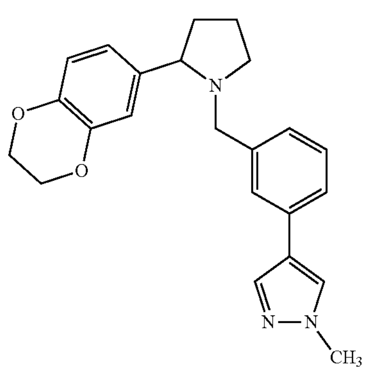 [SMILES: Cn1cc(-c2cccc(CN3CCCC3c3ccc4c(c3)OCCO4)c2)cn1] | | Racemic | ++ |

TABLE 1-continued

Compounds of formulae (I). OGA enzyme inhibition assay:

| No | Structure | Optical rotation | Configuration specification | OGA IC50 |
|---|---|---|---|---|
| 22 | 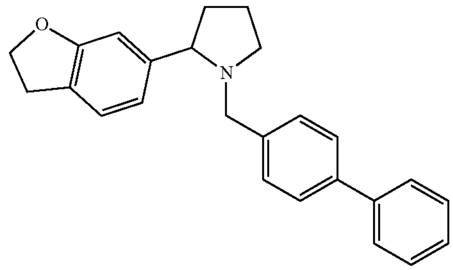 [SMILES: c1ccc(-c2ccc(CN3CCCC3c3ccc4c(c3)OCC4)cc2)cc1] | | Racemic | ++ |
| 23 | 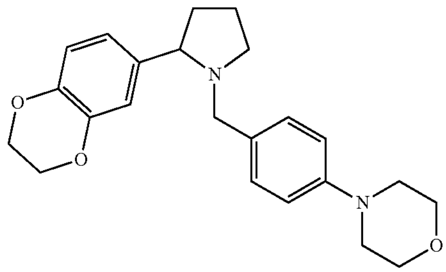 [SMILES: c1cc(N2CCOCC2)ccc1CN1CCCC1c1ccc2c(c1)OCCO2] | | Racemic | ++ |
| 24 | 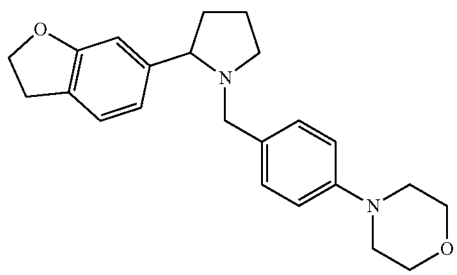 [SMILES: c1cc(N2CCOCC2)ccc1CN1CCCC1c1ccc2c(c1)OCC2] | | Racemic | ++ |
| 25 | 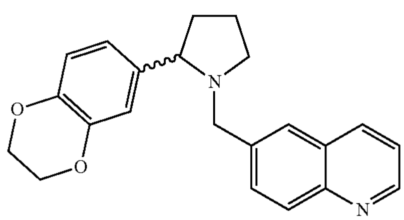 [SMILES: c1cnc2ccc(CN3CCCC3c3ccc4c(c3)OCCO4)cc2c1] | $[\alpha]^{26}_D =$ 14.86, c 0.074 (MeOH). | First elution on YMC Amylose-SA (250 X 4.6) mm, 5 µm, 20 mM, 0.5% isopropylamine in MeOH, Rt 2.96, The enantiomeric purity is 100.00%. | +++ |
| 26 | 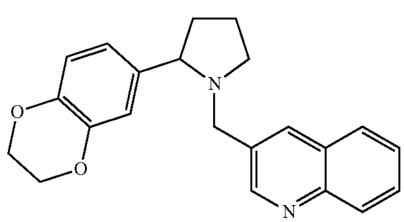 [SMILES: c1ccc2ncc(CN3CCCC3c3ccc4c(c3)OCCO4)cc2c1] | | Racemic | ++ |
| 27 | 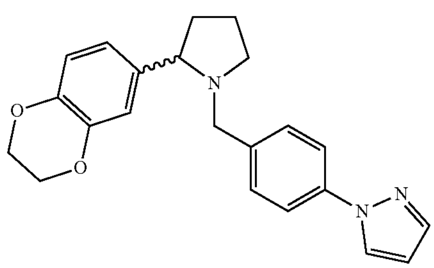 [SMILES: c1cnn(-c2ccc(CN3CCCC3c3ccc4c(c3)OCCO4)cc2)c1] | $[\alpha]^{26}_D =$ −3.00, c 0.18 (MeOH). | First elution on YMC Amylose-SA (250 X 4.6) mm, 5 µm, 20 mM, 0.5% isopropylamine in MeOH, Rt 2.14, The enantiomeric purity is 100.00% | +++ |

TABLE 1-continued

Compounds of formulae (I). OGA enzyme inhibition assay:

| No | Structure | Optical rotation | Configuration specification | OGA IC50 |
|----|-----------|------------------|-----------------------------|----------|
| 28 | 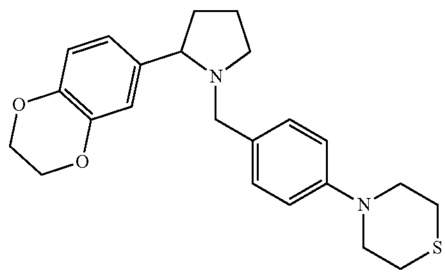 [SMILES: c1cc(N2CCSCC2)ccc1CN1CCCC1c1ccc2c(c1)OCCO2] | | Racemic | ++ |
| 29 | 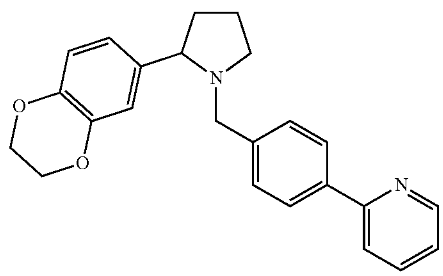 | | Racemic | ++ |
| 30 | 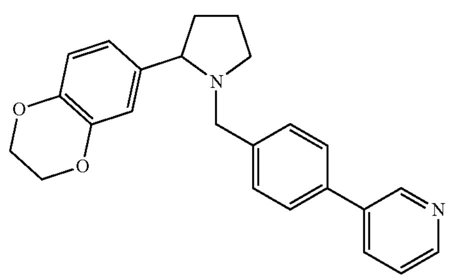 | | Racemic | +++ |
| 31 | 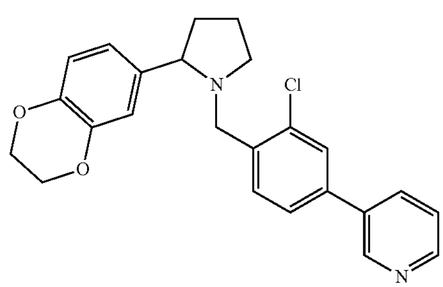 [SMILES: Clc1cc(-c2cccnc2)ccc1CN1CCCC1c1ccc2c(c1)OCCO2] | | Racemic | ++ |
| 32 | 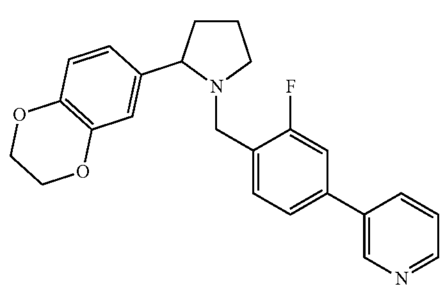 [SMILES: Fc1cc(-c2cccnc2)ccc1CN1CCCC1c1ccc2c(c1)OCCO2] | | Racemic | +++ |

TABLE 1-continued

Compounds of formulae (I). OGA enzyme inhibition assay:

| No | Structure | Optical rotation | Configuration specification | OGA IC50 |
|---|---|---|---|---|
| 33 | 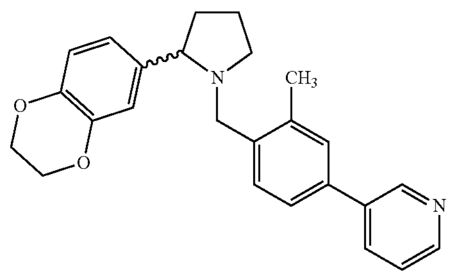 [SMILES: Cc1cc(-c2cccnc2)ccc1CN1CCCC1c1ccc2c(c1)OCCO2] | $[\alpha]^{26}_D =$ 10.35, c 0.85 (MeOH). | Second elution on Chiralcel OJ-H (250 X 4.6) mm, 5 μm, 20 mM, 0.5% isopropylamine in isopropylalcohol, Rt 3.06 min, The enantiomeric purity is 99.08%. | +++ |
| 34 | 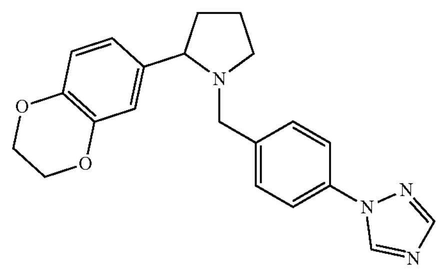 [SMILES: c1ncn(-c2ccc(CN3CCCC3c3ccc4c(c3)OCCO4)cc2)n1] | | Racemic | +++ |
| 35 | 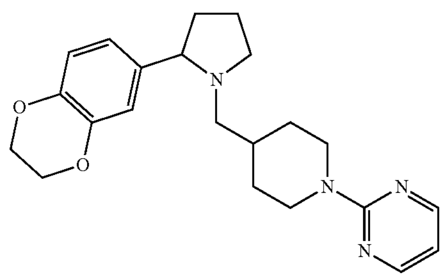 | | Racemic | ++ |
| 36 | 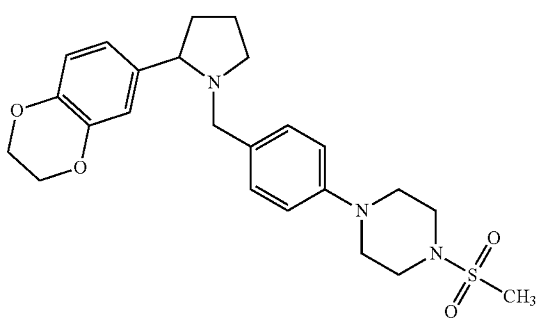 [SMILES: CS(=O)(=O)N1CCN(c2ccc(CN3CCCC3c3ccc4c(c3)OCCO4)cc2)CC1] | | Racemic | ++ |
| 37 | 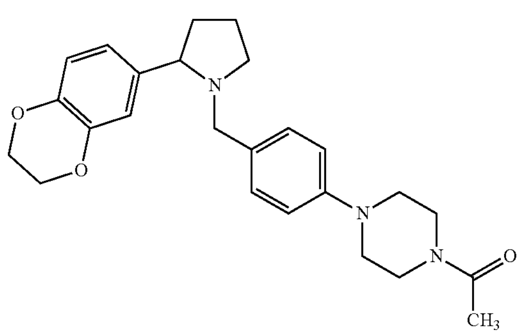 | | Racemic | ++ |

TABLE 1-continued

Compounds of formulae (I). OGA enzyme inhibition assay:

| No | Structure | Optical rotation | Configuration specification | OGA IC50 |
|---|---|---|---|---|
| 38 | 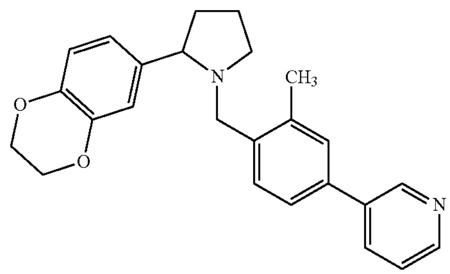 [SMILES: Cc1cc(-c2cccnc2)ccc1CN1CCCC1c1ccc2c(c1)OCCO2] | | Racemic | +++ |
| 39 | 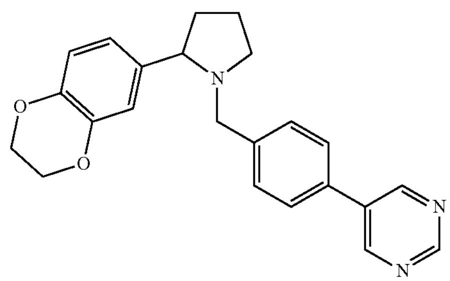 [SMILES: c1ncc(-c2ccc(CN3CCCC3c3ccc4c(c3)OCCO4)cc2)cn1] | | Racemic | +++ |
| 40 | 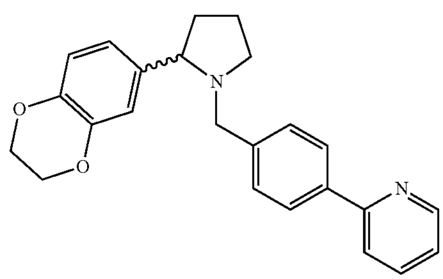 | $[\alpha]^{26}_D$ = 9.23, c 0.55 (MeOH). | Second elution on Chiralcel OD-H (250 X 4.6) mm, 5 μm, 20 mM, 0.5% isopropylamine in methanol, Rt 5.64 min, The enantiomeric purity is 99.01%. | +++ |
| 41 | 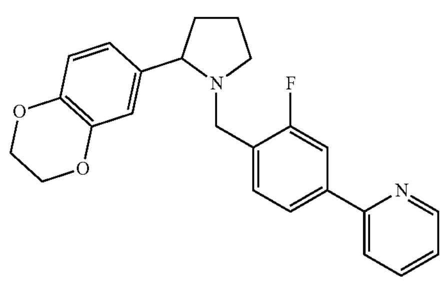 [SMILES: Fc1cc(-c2ccccn2)ccc1CN1CCCC1c1ccc2c(c1)OCCO2] | | Racemic | ++ |
| 42 | 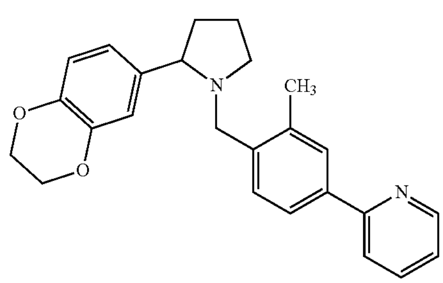 | | Racemic | ++ |

TABLE 1-continued

Compounds of formulae (I). OGA enzyme inhibition assay:

| No | Structure | Optical rotation | Configuration specification | OGA IC50 |
|---|---|---|---|---|
| 43 | 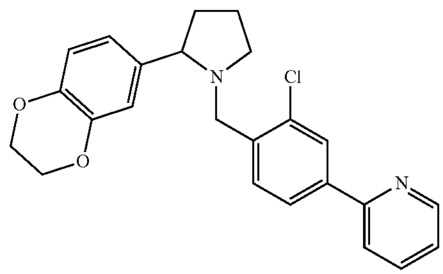 [SMILES: Clc1cc(-c2ccccn2)ccc1CN1CCCC1c1ccc2c(c1)OCCO2] | | Racemic | + |
| 44 | 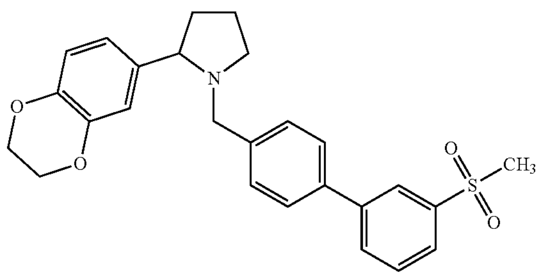 | | Racemic | ++ |
| 45 | 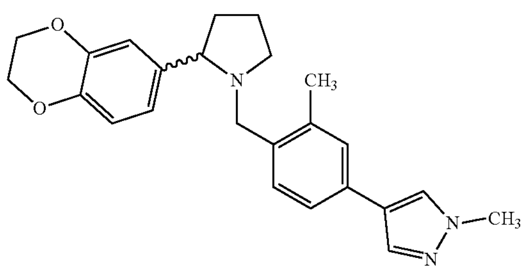 | | Racemic | +++ |
| 46 | 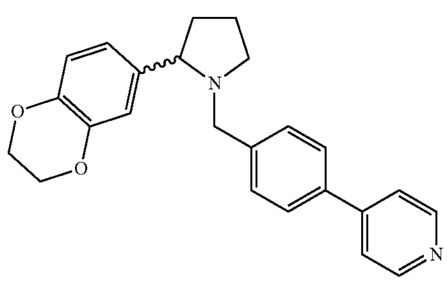 [SMILES: c1cc(-c2ccc(CN3CCCC3c3ccc4c(c3)OCCO4)cc2)ccn1] | | Racemic | ++ |
| 47 | 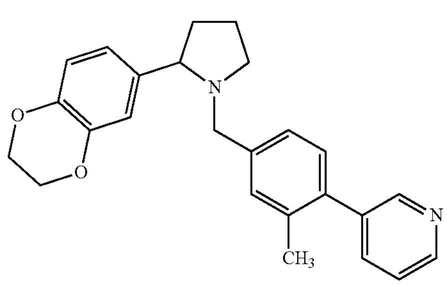 [SMILES: Cc1cc(CN2CCCC2c2ccc3c(c2)OCCO3)ccc1-c1cccnc1] | | Racemic | ++ |

TABLE 1-continued

Compounds of formulae (I). OGA enzyme inhibition assay:

| No | Structure | Optical rotation | Configuration specification | OGA IC50 |
|---|---|---|---|---|
| 48 | 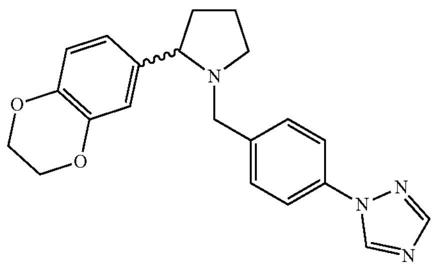 [SMILES: c1ncn(-c2ccc(CN3CCCC3c3ccc4c(c3)OCCO4)cc2)n1] | | Second elution on Chiralcel OJ-H (250 X 30) mm, 5 μm, IPA, Rt 3.79, The enantiomeric purity is 100.00% | +++ |
| 49 | 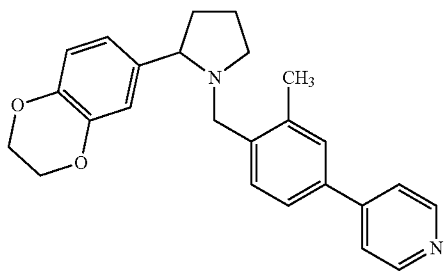 [SMILES: Cc1cc(-c2ccncc2)ccc1CN1CCCC1c1ccc2c(c1)OCCO2] | | Racemic | ++ |
| 50 | 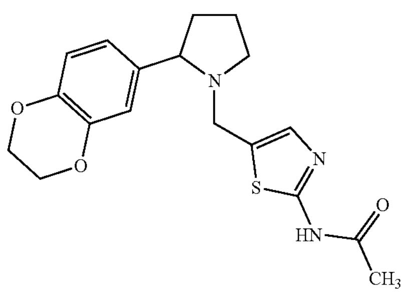 [SMILES: CC(=O)Nc1ncc(CN2CCCC2c2ccc3c(c2)OCCO3)s1] | | Racemic | ++ |
| 51 | 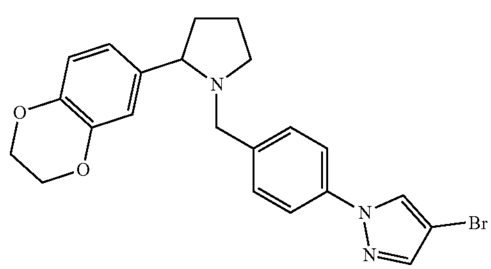 | | Racemic | +++ |
| 52 | 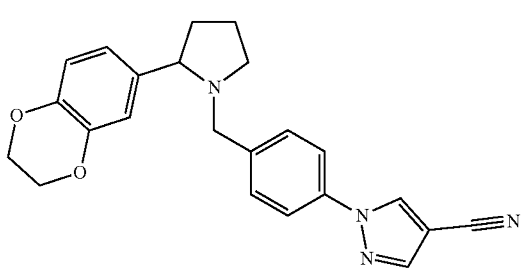 [SMILES: N#Cc1cnn(-c2ccc(CN3CCCC3c3ccc4c(c3)OCCO4)cc2)c1] | | Racemic | +++ |

TABLE 1-continued

Compounds of formulae (I). OGA enzyme inhibition assay:

| No | Structure | Optical rotation | Configuration specification | OGA IC50 |
|---|---|---|---|---|
| 53 | 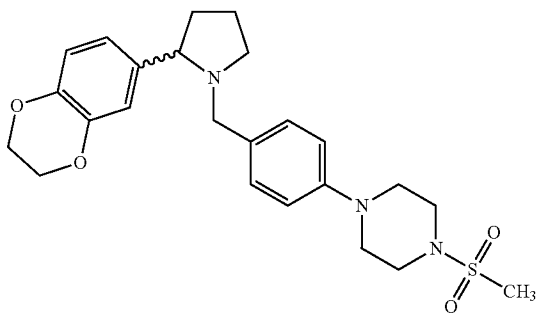 [SMILES: CS(=O)(=O)N1CCN(c2ccc(CN3CCCC3c3ccc4c(c3)OCCO4)cc2)CC1] | | First elution on Lux A1 (250 X 4.6) mm, 5 μm, 0.5% isopropylamine in isopropylalcohol, Rt 3.06, The enantiomeric purity is 100.00%. | +++ |
| 54 | 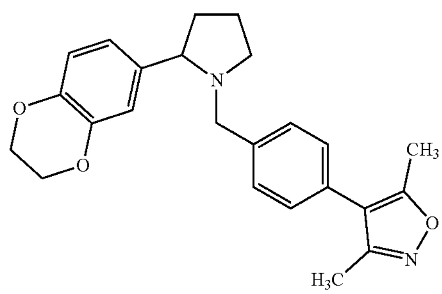 [SMILES: Cc1noc(C)c1-c1ccc(CN2CCCC2c2ccc3c(c2)OCCO3)cc1] | | Racemic | + |
| 55 | 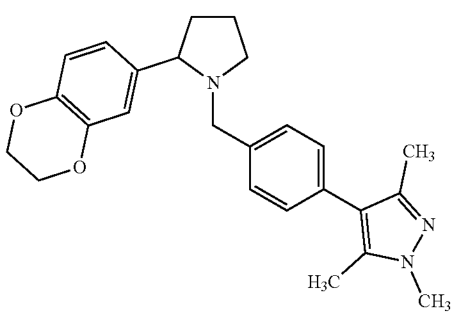 | | Racemic | + |
| 56 | 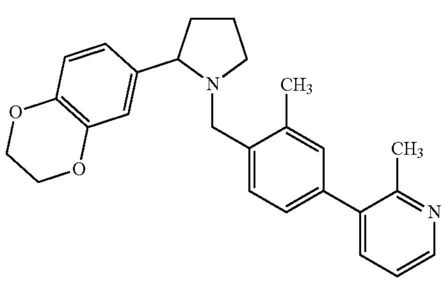 [SMILES: Cc1cc(-c2cccnc2C)ccc1CN1CCCC1c1ccc2c(c1)OCCO2] | | Racemic | ++ |
| 57 | 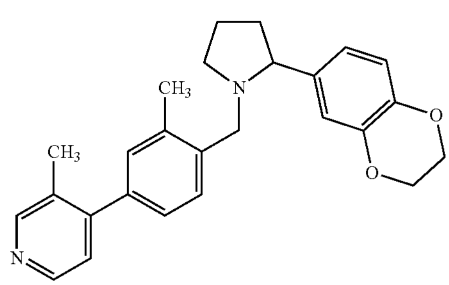 [SMILES: Cc1cc(-c2ccncc2C)ccc1CN1CCCC1c1ccc2c(c1)OCCO2] | | Racemic | ++ |

TABLE 1-continued

Compounds of formulae (I). OGA enzyme inhibition assay:

| No | Structure | Optical rotation | Configuration specification | OGA IC50 |
|---|---|---|---|---|
| 58 | 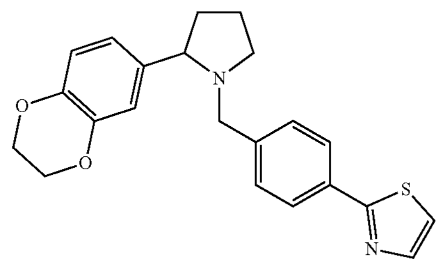 [SMILES: c1csc(-c2ccc(CN3CCCC3c3ccc4c(c3)OCCO4)cc2)n1] | | Racemic | +++ |
| 59 | 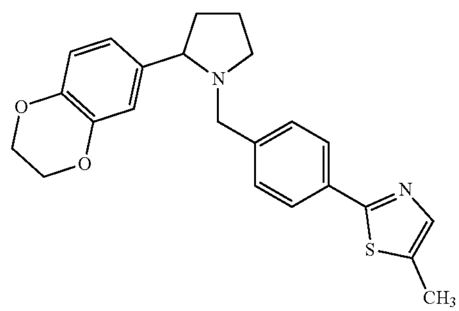 [SMILES: Cc1cnc(-c2ccc(CN3CCCC3c3ccc4c(c3)OCCO4)cc2)s1] | | Racemic | ++ |
| 60 | 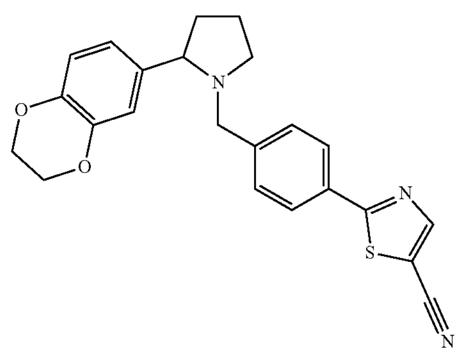 [SMILES: N#Cc1cnc(-c2ccc(CN3CCCC3c3ccc4c(c3)OCCO4)cc2)s1] | | Racemic | +++ |
| 61 | 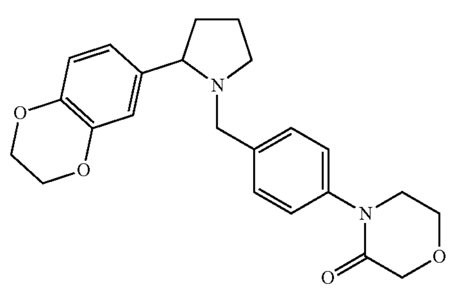 | | Racemic | ++ |
| 62 | 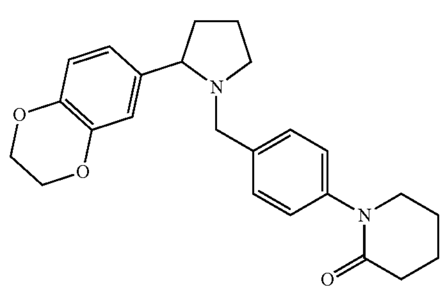 | | Racemic | ++ |

TABLE 1-continued

Compounds of formulae (I). OGA enzyme inhibition assay:

| No | Structure | Optical rotation | Configuration specification | OGA IC50 |
|---|---|---|---|---|
| 63 | 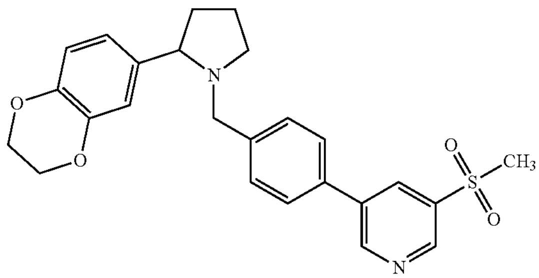 | | Racemic | +++ |
| 64 | 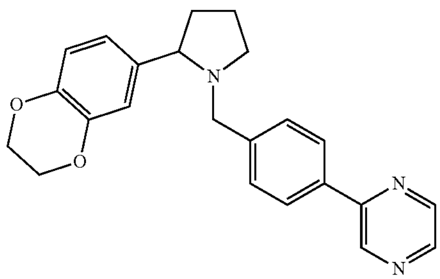 | | Racemic | +++ |
| 65 | 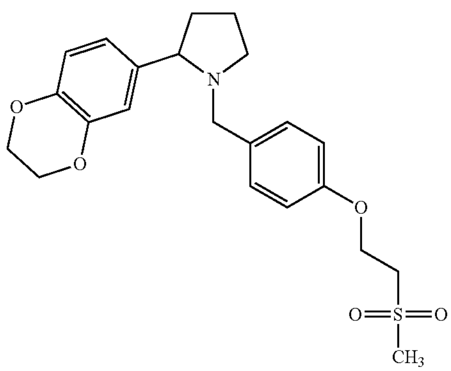 | | Racemic | + |
| 66 | 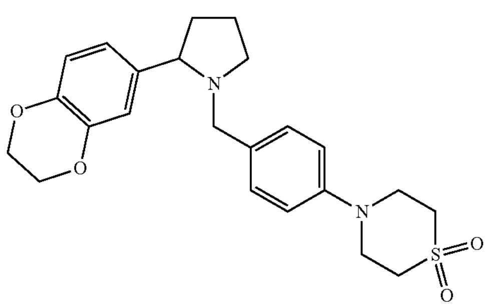 [SMILES: O=S1(=O)CCN(c2ccc(CN3CCCC3c3ccc4c(c3)OCCO4)cc2)CC1] | | Racemic | ++ |
| 67 | 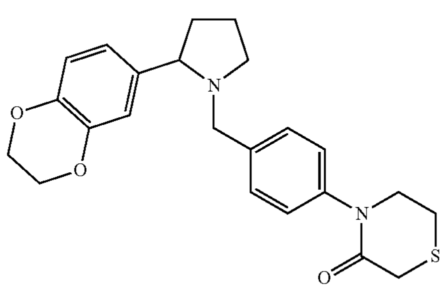 [SMILES: O=C1CSCCN1c1ccc(CN2CCCC2c2ccc3c(c2)OCCO3)cc1] | | Racemic | ++ |

TABLE 1-continued

Compounds of formulae (I). OGA enzyme inhibition assay:

| No | Structure | Optical rotation | Configuration specification | OGA IC50 |
|---|---|---|---|---|
| 68 | 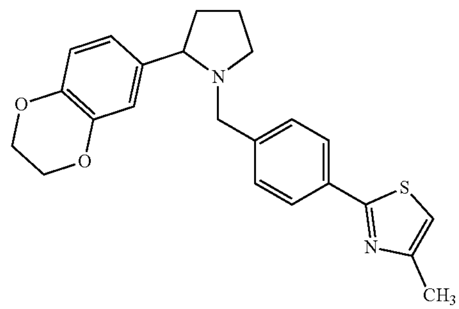 [SMILES: Cc1csc(-c2ccc(CN3CCCC3c3ccc4c(c3)OCCO4)cc2)n1] | | Racemic | ++ |
| 69 | 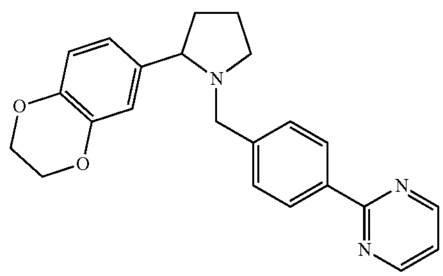 | | Racemic | +++ |
| 70 | 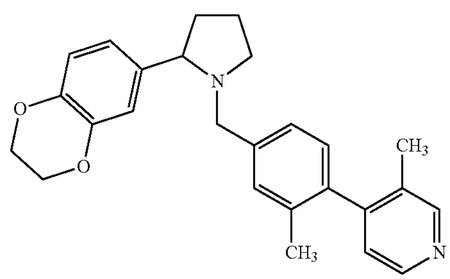 [SMILES: Cc1cnccc1-c1ccc(CN2CCCC2c2ccc3c(c2)OCCO3)cc1C] | | Racemic | + |
| 71 | 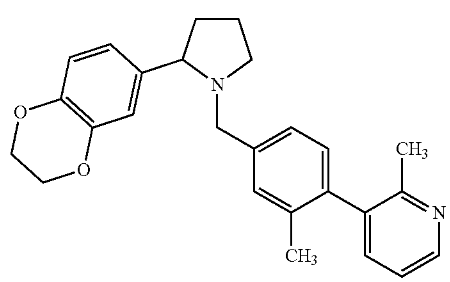 [SMILES: Cc1cc(CN2CCCC2c2ccc3c(c2)OCCO3)ccc1-c1cccnc1C] | | Racemic | ++ |
| 72 | 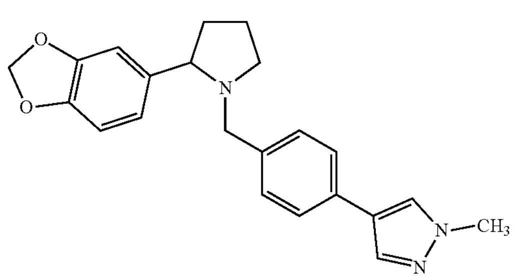 | | Racemic | ++ |

TABLE 1-continued

Compounds of formulae (I). OGA enzyme inhibition assay:

| No | Structure | Optical rotation | Configuration specification | OGA IC50 |
|----|-----------|------------------|----------------------------|----------|
| 73 | 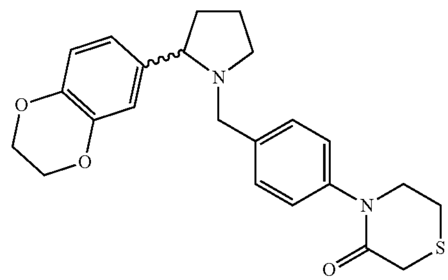 [SMILES: O=C1CSCCN1c1ccc(CN2CCCC2c2ccc3c(c2)OCCO3)cc1] | | First elution on Chiralcel OJ-H (250 X 4.6) mm, 5 μm, 0.5% Isopropylamine in Methanol, Rt 3.20 min, The enantiomeric purity is 100.00%. | ++ |
| 74 | 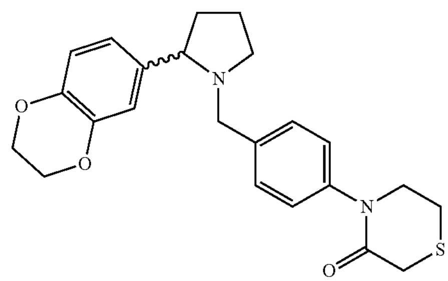 [SMILES: O=C1CSCCN1c1ccc(CN2CCCC2c2ccc3c(c2)OCCO3)cc1] | | Second elution on Chiralcel OJ-H (250 X 4.6) mm, 5 μm, 0.5% Isopropylamine in Methanol, Rt 3.53 min, The enantiomeric purity is 96.01%. | + |
| 75 | 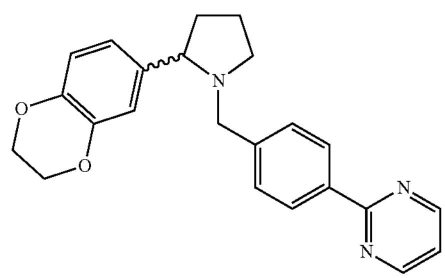 [SMILES: c1cnc(-c2ccc(CN3CCCC3c3ccc4c(c3)OCCO4)cc2)nc1] | | First elution on Lux A1 (250 X 4.6) mm, 5 μm, isopropylalcohol, Rt 3.96 min, The enantiomeric purity is 100.00%. | +++ |
| 76 | 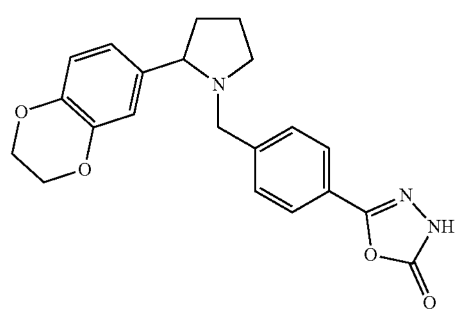 [SMILES: O=c1[nH]nc(-c2ccc(CN3CCCC3c3ccc4c(c3)OCCO4)cc2)o1] | | Racemic | ++ |
| 77 | 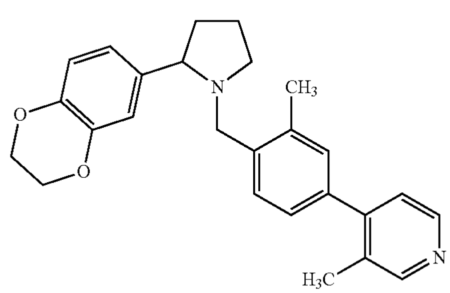 | | | |

TABLE 1-continued
| | | Compounds of formulae (I). OGA enzyme inhibition assay: | | |
|---|---|---|---|---|
| No | Structure | Optical rotation | Configuration specification | OGA IC50 |
| 78 | 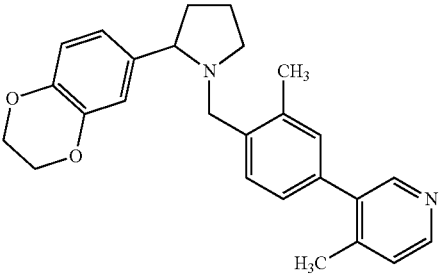 [SMILES: Cc1cc(-c2cnccc2C)ccc1CN1CCCC1c1ccc2c(c1)OCCO2] | | | |
| 79 | 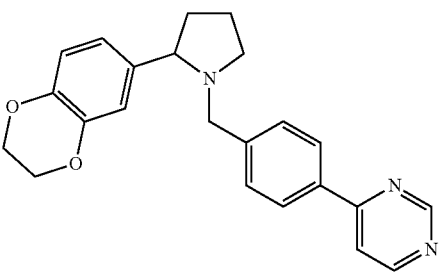 [SMILES: c1cc(-c2ccc(CN3CCCC3c3ccc4c(c3)OCCO4)cc2)ncn1] | | | |
| 80 | 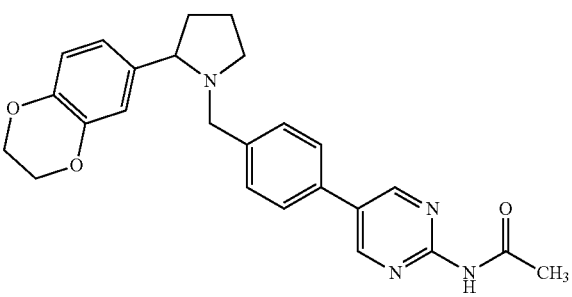 [SMILES: CC(=O)Nc1ncc(-c2ccc(CN3CCCC3c3ccc4c(c3)OCCO4)cc2)cn1] | | | |
| 81 | 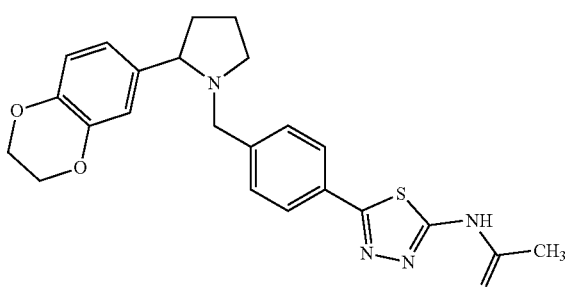 | | | |
| 82 | 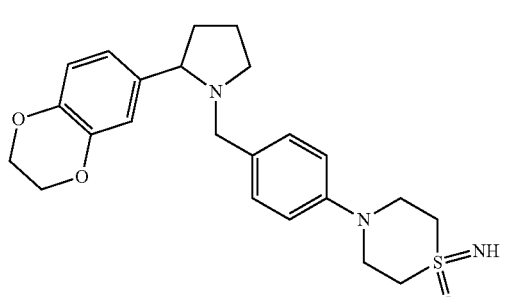 | | | |

TABLE 1-continued

Compounds of formulae (I). OGA enzyme inhibition assay:

| No | Structure | Optical rotation | Configuration specification | OGA IC50 |
|----|-----------|------------------|----------------------------|----------|
| 83 | 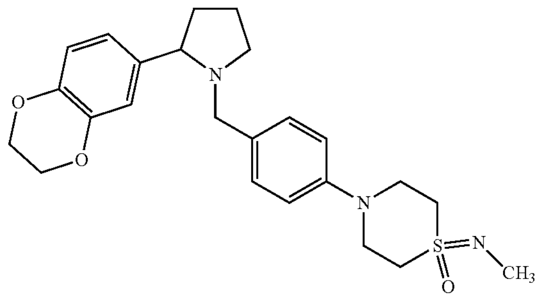 [SMILES: CN=S1(=O)CCN(c2ccc(CN3CCCC3c3ccc4c(c3)OCCO4)cc2)CC1] | | | |
| 84 | 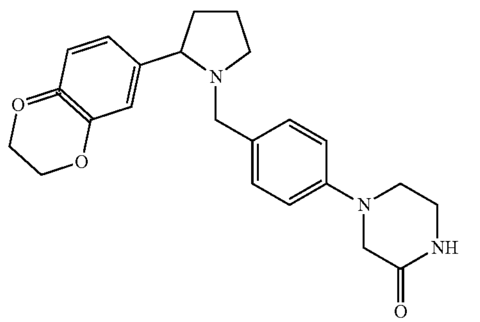 | | | |
| 85 | 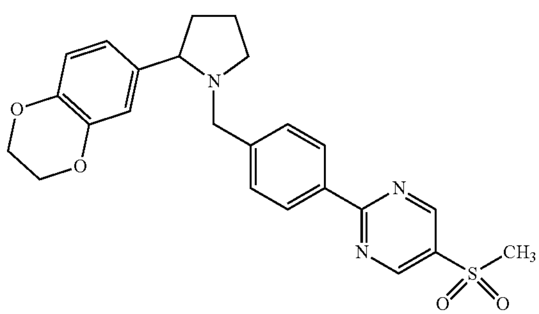 | | | |
| 86 | 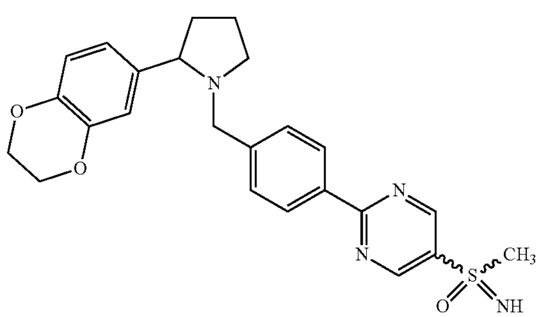 | | | |
| 87 | 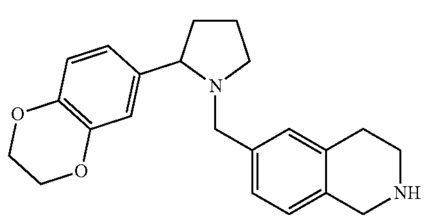 | | | |

TABLE 1-continued

Compounds of formulae (I). OGA enzyme inhibition assay:

| No | Structure | Optical rotation | Configuration specification | OGA IC50 |
|---|---|---|---|---|
| 88 | 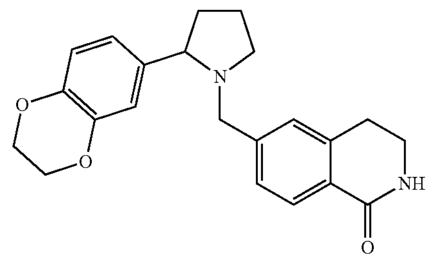 | | | |
| 89 | 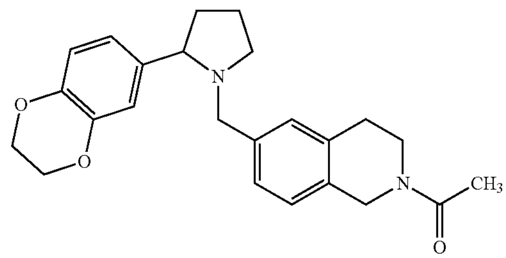 [SMILES: CC(=O)N1CCc2cc(CN3CCCC3c3ccc4c(c3)OCCO4)ccc2C1] | | | |
| 90 | 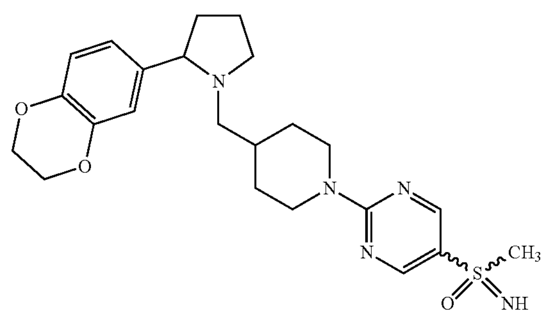 | | | |
| 91 | 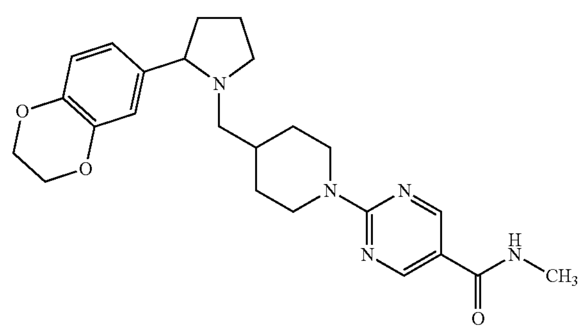 | | | |
| 92 | 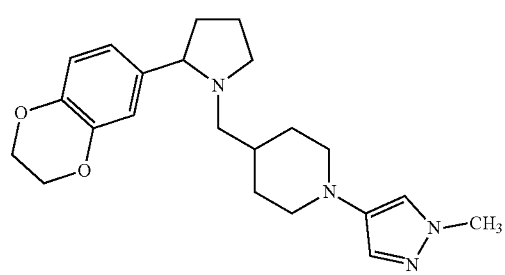 | | | |

TABLE 1-continued

Compounds of formulae (I). OGA enzyme inhibition assay:

| No | Structure | Optical rotation | Configuration specification | OGA IC50 |
|---|---|---|---|---|
| 93 | 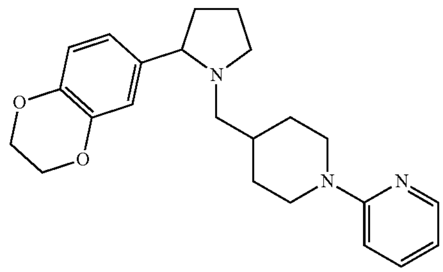 | | | |
| 94 | 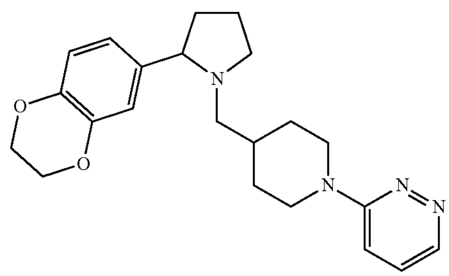 | | | |
| 95 | 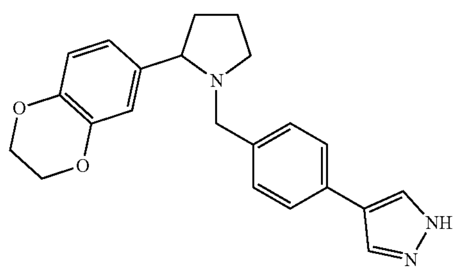 | | | |
| 96 | 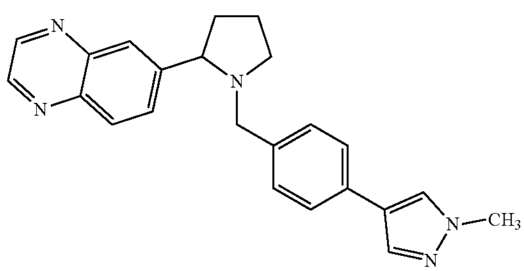 [SMILES: Cn1cc(-c2ccc(CN3CCCC3c3ccc4nccnc4c3)cc2)cn1] | | | |
| 97 | 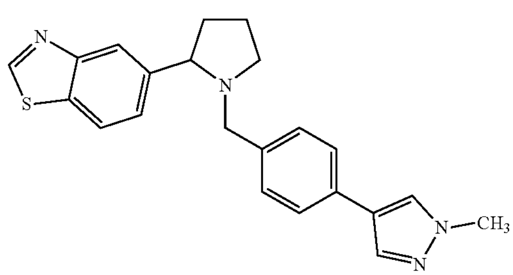 | | | |

TABLE 1-continued

Compounds of formulae (I). OGA enzyme inhibition assay:

| No | Structure | Optical rotation | Configuration specification | OGA IC50 |
|---|---|---|---|---|
| 98 | 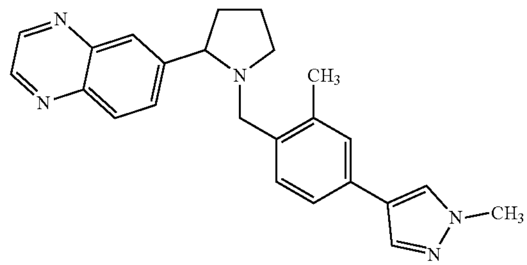 [SMILES: Cc1cc(-c2cnn(C)c2)ccc1CN1CCCC1c1ccc2nccnc2c1] | | | |
| 99 | 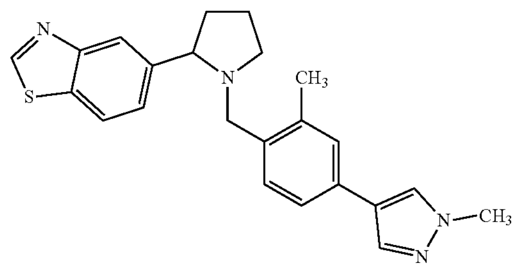 [SMILES: Cc1cc(-c2cnn(C)c2)ccc1CN1CCCC1c1ccc2scnc2c1] | | | |
| 100 | 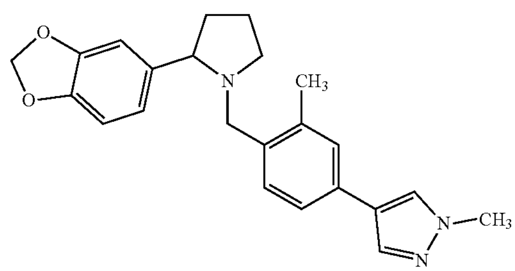 [SMILES: Cc1cc(-c2cnn(C)c2)ccc1CN1CCCC1c1ccc2c(c1)OCO2] | | | |
| 101 | 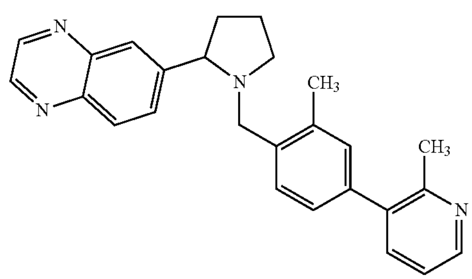 [SMILES: Cc1cc(-c2cccnc2C)ccc1CN1CCCC1c1ccc2nccnc2c1] | | | |
| 102 | 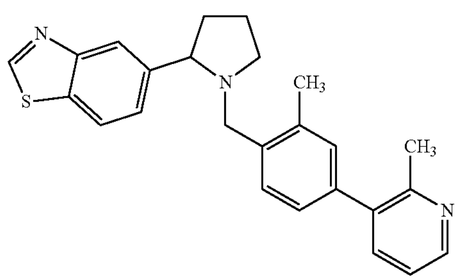 [SMILES: Cc1cc(-c2cccnc2C)ccc1CN1CCCC1c1ccc2scnc2c1] | | | |

TABLE 1-continued

Compounds of formulae (I). OGA enzyme inhibition assay:

| No | Structure | Optical rotation | Configuration specification | OGA IC50 |
|----|-----------|------------------|-----------------------------|----------|
| 103 | 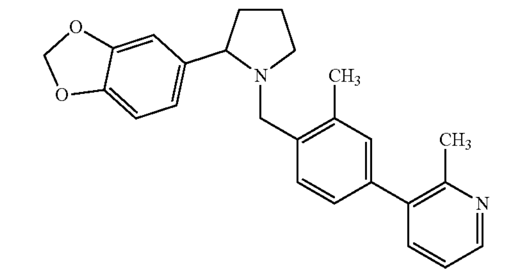 [SMILES: Cc1cc(-c2cccnc2C)ccc1CN1CCCC1c1ccc2c(c1)OCO2] | | | |
| 104 | 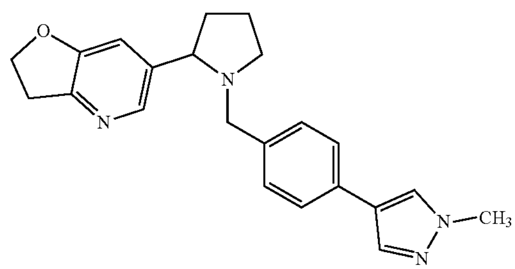 [SMILES: Cn1cc(-c2ccc(CN3CCCC3c3cnc4c(c3)OCC4)cc2)cn1] | | | |
| 105 | 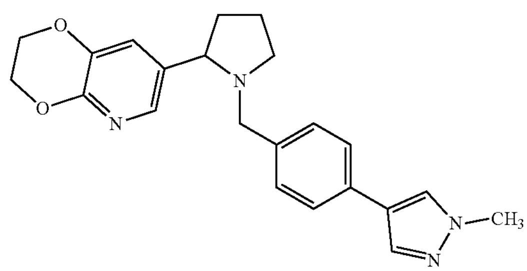 [SMILES: Cn1cc(-c2ccc(CN3CCCC3c3cnc4c(c3)OCCO4)cc2)cn1] | | | |
| 106 | 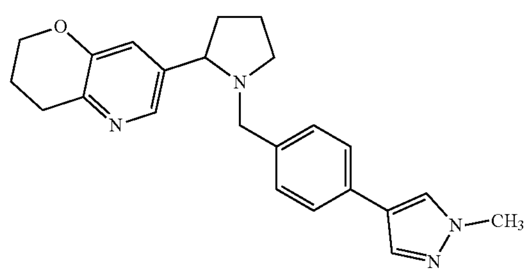 [SMILES: Cn1cc(-c2ccc(CN3CCCC3c3cnc4c(c3)OCCC4)cc2)cn1] | | | |
| 107 | 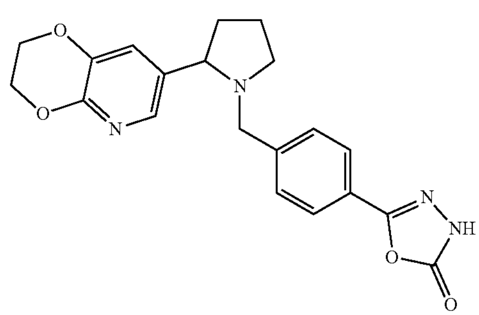 [SMILES: O=c1[nH]nc(-c2ccc(CN3CCCC3c3cnc4c(c3)OCCO4)cc2)o1] | | | |

TABLE 1-continued

| | | Compounds of formulae (I). OGA enzyme inhibition assay: | | | |
|---|---|---|---|---|---|
| No | Structure | | Optical rotation | Configuration specification | OGA IC50 |
| 108 | | | | | |
| 109 | | | | | |
| 110 | | | | | |
| 111 | | | | | |
| 112 | | | | | |

TABLE 1-continued

Compounds of formulae (I). OGA enzyme inhibition assay:

| No | Structure | Optical rotation | Configuration specification | OGA IC50 |
|---|---|---|---|---|
| 113 | 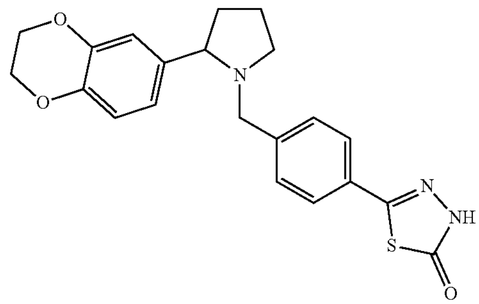 [SMILES: O=c1[nH]nc(-c2ccc(CN3CCCC3c3ccc4c(c3)OCCO4)cc2)s1] | | | |
| 114 | 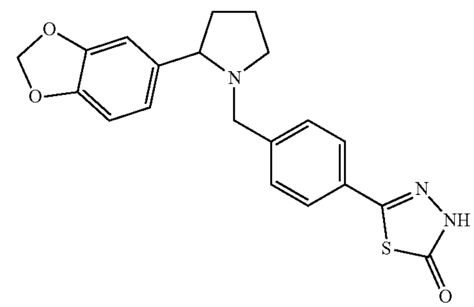 [SMILES: O=c1[nH]nc(-c2ccc(CN3CCCC3c3ccc4c(c3)OCO4)cc2)s1] | | | |
| 115 | 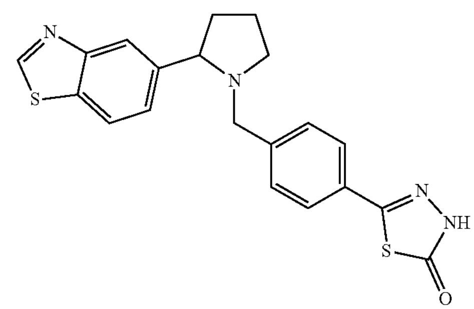 [SMILES: O=c1[nH]nc(-c2ccc(CN3CCCC3c3ccc4scnc4c3)cc2)s1] | | | |
| 116 | 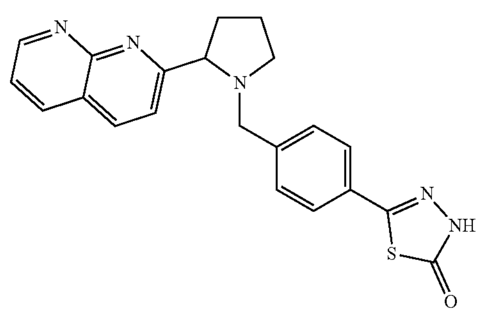 [SMILES: O=c1[nH]nc(-c2ccc(CN3CCCC3c3ccc4cccnc4n3)cc2)s1] | | | |
| 117 | 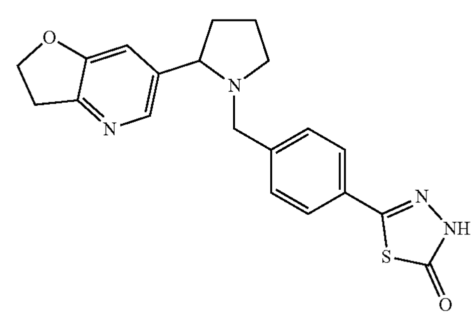 [SMILES: O=c1[nH]nc(-c2ccc(CN3CCCC3c3cnc4c(c3)OCC4)cc2)s1] | | | |

TABLE 1-continued

Compounds of formulae (I). OGA enzyme inhibition assay:

| No | Structure | Optical rotation | Configuration specification | OGA IC50 |
|----|-----------|------------------|----------------------------|----------|
| 118 | 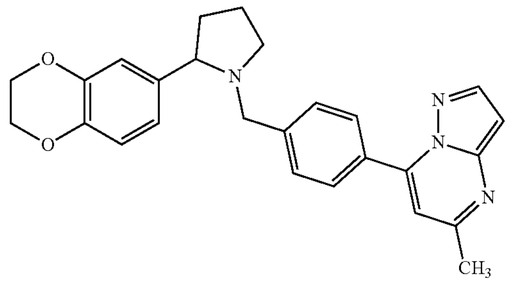 [SMILES: Cc1cc(-c2ccc(CN3CCCC3c3ccc4c(c3)OCCO4)cc2)n2nccc2n1] | | | |
| 119 | 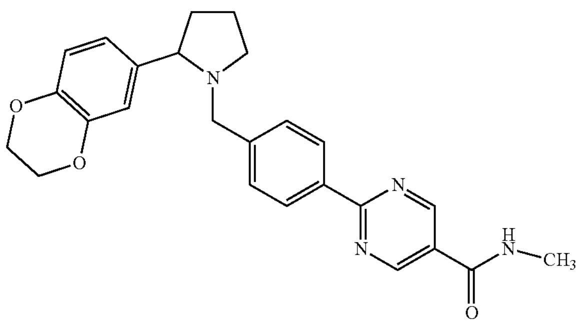 [SMILES: CNC(=O)c1cnc(-c2ccc(CN3CCCC3c3ccc4c(c3)OCCO4)cc2)nc1] | | | |
| 120 | 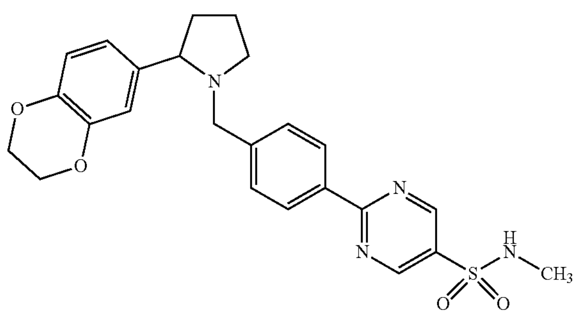 | | | |
| 121 | 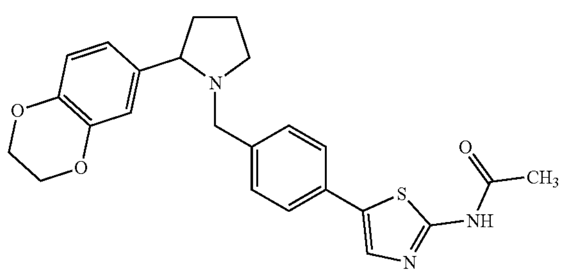 [SMILES: CC(=O)Nc1ncc(-c2ccc(CN3CCCC3c3ccc4c(c3)OCCO4)cc2)s1] | | | |
| 122 | 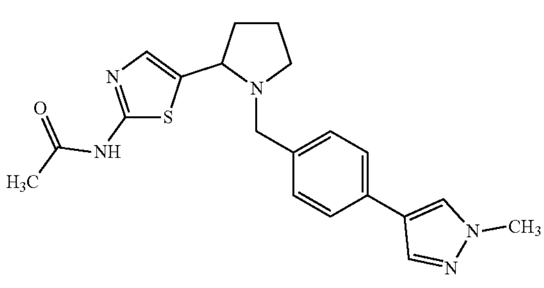 [SMILES: CC(=O)Nc1ncc(C2CCCN2Cc2ccc(-c3cnn(C)c3)cc2)s1] | | | |

TABLE 1-continued
Compounds of formulae (I). OGA enzyme inhibition assay:
| No | Structure | Optical rotation | Configuration specification | OGA IC50 |
|----|-----------|------------------|------------------------------|----------|
| 123 | 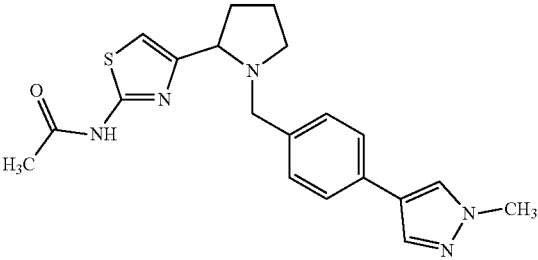 | | | |
| 124 | 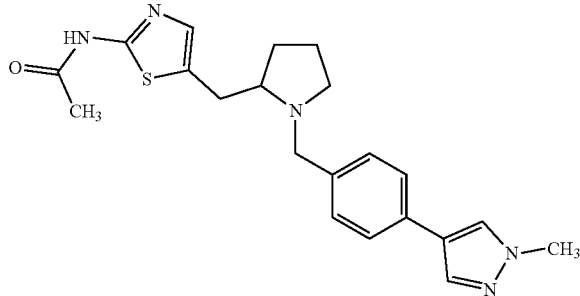 | | | |
| 125 | 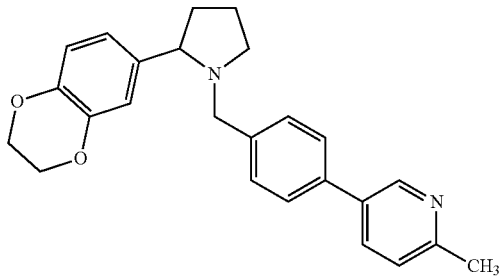 [SMILES: Cc1ccc(-c2ccc(CN3CCCC3c3ccc4c(c3)OCCO4)cc2)cn1] | | | |
| 126 | 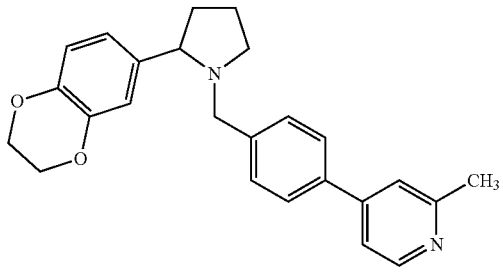 | | | |
| 127 | 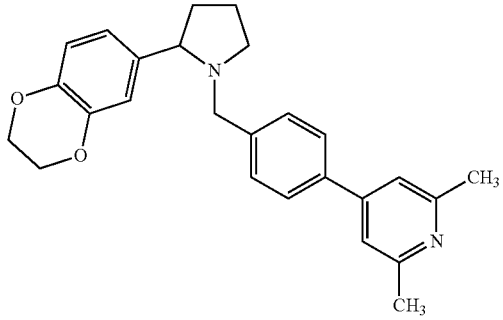 [SMILES: Cc1cc(-c2ccc(CN3CCCC3c3ccc4c(c3)OCCO4)cc2)cc(C)n1] | | | |

TABLE 1-continued
Compounds of formulae (I). OGA enzyme inhibition assay:
| No | Structure | Optical rotation | Configuration specification | OGA IC50 |
|---|---|---|---|---|
| 128 | 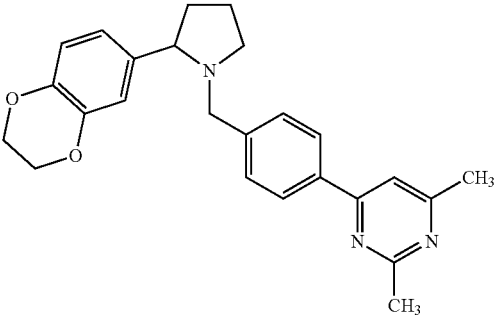 [SMILES: Cc1cc(-c2ccc(CN3CCCC3c3ccc4c(c3)OCCO4)cc2)nc(C)n1] | | | |
| 129 | 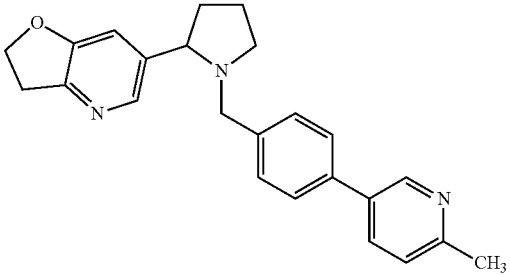 | | | |
| 130 | 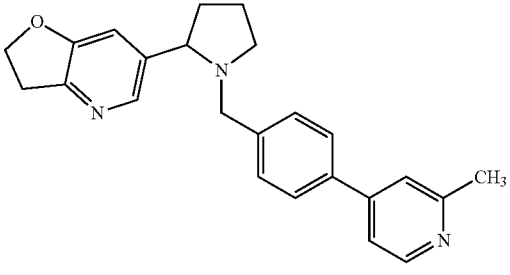 | | | |
| 131 | 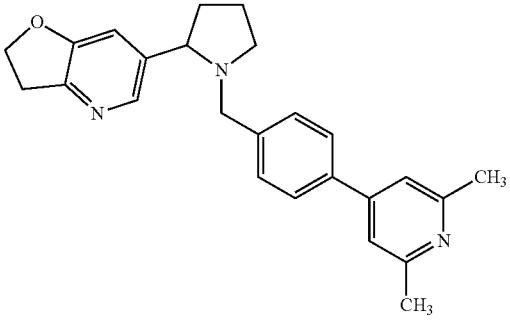 [SMILES: Cc1cc(-c2ccc(CN3CCCC3c3cnc4c(c3)OCC4)cc2)cc(C)n1] | | | |
| 132 | 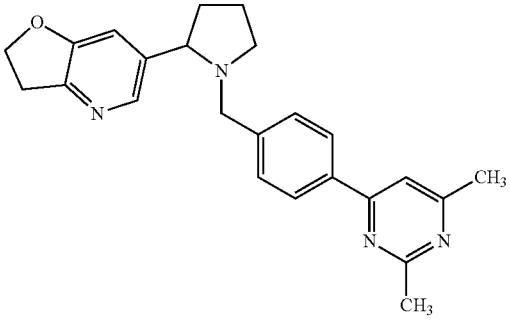 [SMILES: Cc1cc(-c2ccc(CN3CCCC3c3cnc4c(c3)OCC4)cc2)nc(C)n1] | | | |

TABLE 1-continued

Compounds of formulae (I). OGA enzyme inhibition assay:

| No | Structure | Optical rotation | Configuration specification | OGA IC50 |
|---|---|---|---|---|
| 133 | 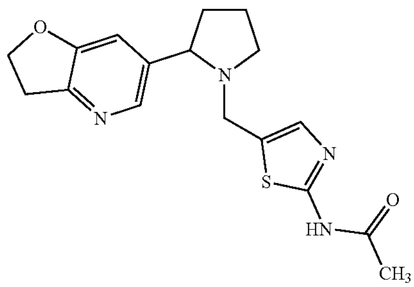 [SMILES: CC(=O)Nc1ncc(CN2CCCC2c2cnc3c(c2)OCC3)s1] | | | |
| 134 | 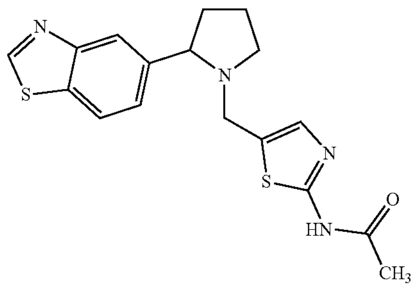 [SMILES: CC(=O)Nc1ncc(CN2CCCC2c2ccc3scnc3c2)s1] | | | |
| 135 | 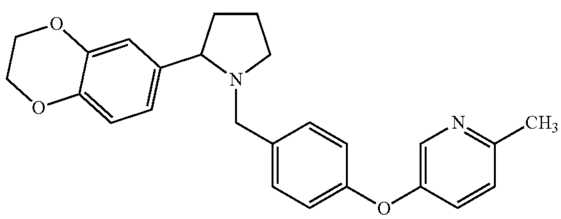 [SMILES: Cc1ccc(Oc2ccc(CN3CCCC3c3ccc4c(c3)OCCO4)cc2)cn1] | | | |
| 136 | 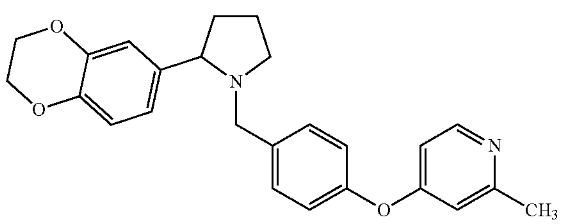 [SMILES: Cc1cc(Oc2ccc(CN3CCCC3c3ccc4c(c3)OCCO4)cc2)ccn1] | | | |
| 137 | 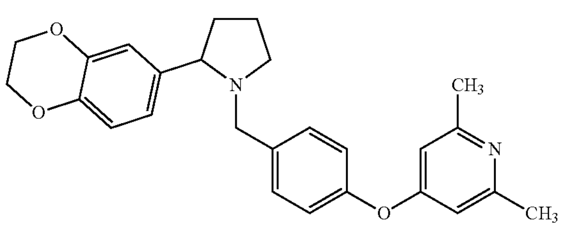 [SMILES: Cc1cc(Oc2ccc(CN3CCCC3c3ccc4c(c3)OCCO4)cc2)cc(C)n1] | | | |
| 138 | 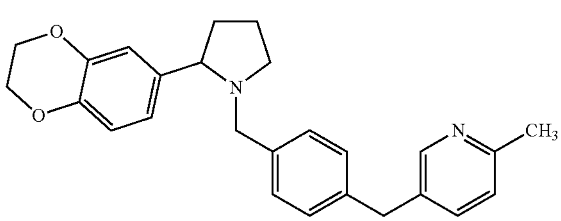 [SMILES: Cc1ccc(Cc2ccc(CN3CCCC3c3ccc4c(c3)OCCO4)cc2)cn1] | | | |

TABLE 1-continued

Compounds of formulae (I). OGA enzyme inhibition assay:

| No | Structure | Optical rotation | Configuration specification | OGA IC50 |
|---|---|---|---|---|
| 139 | 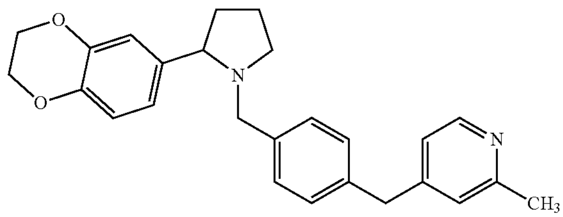 [SMILES: Cc1cc(Cc2ccc(CN3CCCC3c3ccc4c(c3)OCCO4)cc2)ccn1] | | | |
| 140 | 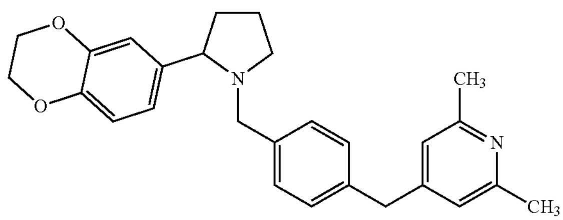 [SMILES: Cc1cc(Cc2ccc(CN3CCCC3c3ccc4c(c3)OCCO4)cc2)cc(C)n1] | | | |
| 141 | 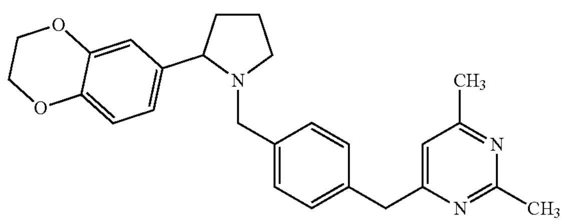 [SMILES: Cc1cc(Cc2ccc(CN3CCCC3c3ccc4c(c3)OCCO4)cc2)nc(C)n1] | | | |
| 142 | 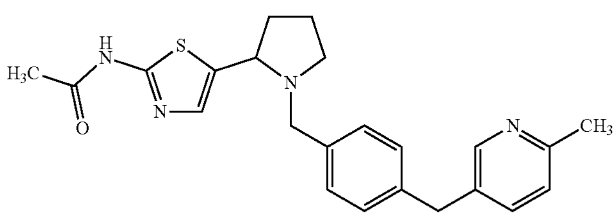 [SMILES: CC(=O)Nc1ncc(C2CCCN2Cc2ccc(Cc3ccc(C)nc3)cc2)s1] | | | |
| 143 | 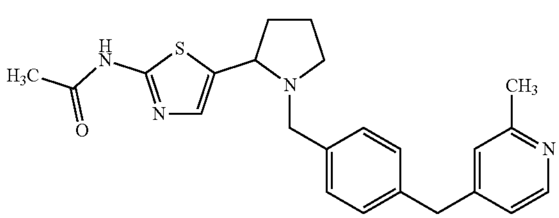 [SMILES: CC(=O)Nc1ncc(C2CCCN2Cc2ccc(Cc3ccnc(C)c3)cc2)s1] | | | |
| 144 | 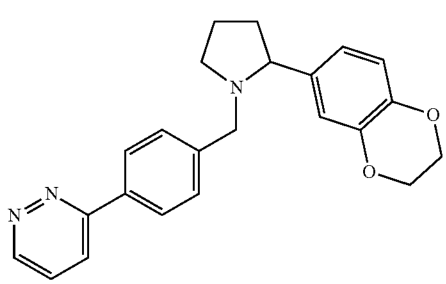 [SMILES: c1cnnc(-c2ccc(CN3CCCC3c3ccc4c(c3)OCCO4)cc2)c1] | | Racemic | +++ |

TABLE 1-continued

Compounds of formulae (I). OGA enzyme inhibition assay:

| No | Structure | Optical rotation | Configuration specification | OGA IC50 |
|---|---|---|---|---|
| 145 | 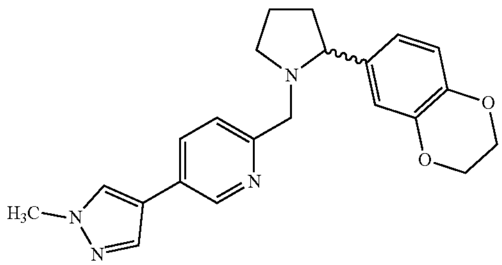 [SMILES: Cn1cc(-c2ccc(CN3CCCC3c3ccc4c(c3)OCCO4)nc2)cn1] | | Second elution on YMC Cellulose-SB (250 X 4.6) mm, 5 μm, 20 mM, 0.5% isopropylamine in isopropylalcohol, Rt 3.75, The enantiomeric purity is 99.73%. | ++ |
| 146 | 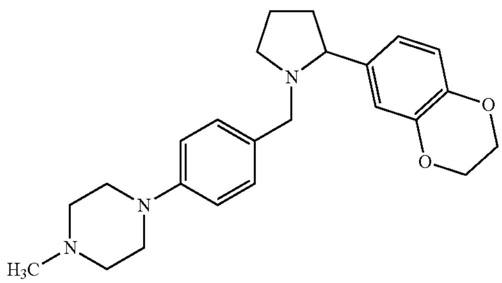 [SMILES: CN1CCN(c2ccc(CN3CCCC3c3ccc4c(c3)OCCO4)cc2)CC1] | | Racemic | + |
| 147 | 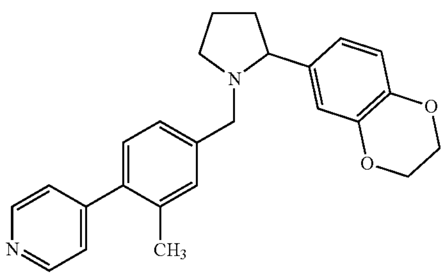 [SMILES: Cc1cc(CN2CCCC2c2ccc3c(c2)OCCO3)ccc1-c1ccncc1] | | Racemic | + |
| 148 | 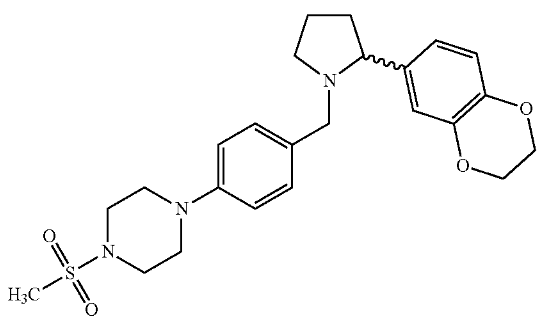 [SMILES: CS(=O)(=O)N1CCN(c2ccc(CN3CCCC3c3ccc4c(c3)OCCO4)cc2)CC1] | | Second elution on Lux A1 (250 X 4.6) mm, 5 μm, 0.5% isopropylamine in isopropylalcohol, Rt 3.61. Enantiomeric purity is 99.19% | + |
| 149 | 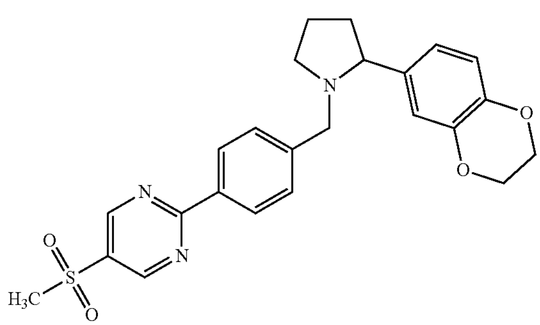 [SMILES: CS(=O)(=O)c1cnc(-c2ccc(CN3CCCC3c3ccc4c(c3)OCCO4)cc2)nc1] | | Racemic | +++ |

TABLE 1-continued

Compounds of formulae (I). OGA enzyme inhibition assay:

| No | Structure | Optical rotation | Configuration specification | OGA IC50 |
|----|-----------|------------------|------------------------------|----------|
| 150 | 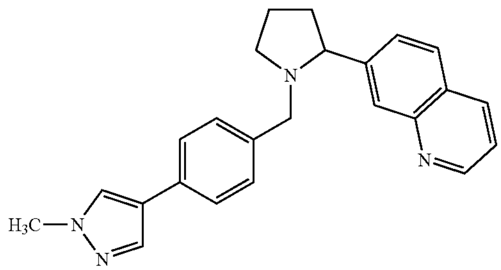 [SMILES: Cn1cc(-c2ccc(CN3CCCC3c3ccc4cccnc4c3)cc2)cn1] | | Racemic | +++ |
| 151 | 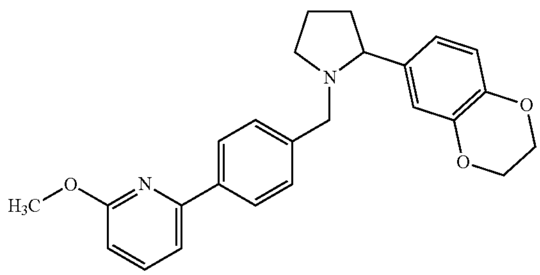 [SMILES: COc1cccc(-c2ccc(CN3CCCC3c3ccc4c(c3)OCCO4)cc2)n1] | | Racemic | ++ |
| 152 | 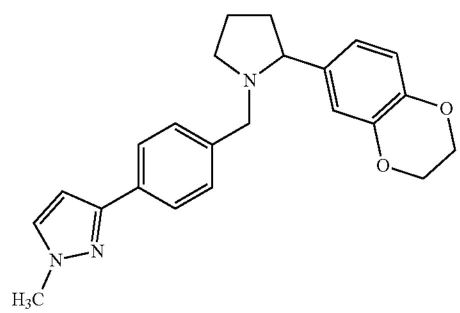 [SMILES: Cn1ccc(-c2ccc(CN3CCCC3c3ccc4c(c3)OCCO4)cc2)n1] | | Racemic | ++ |
| 153 | 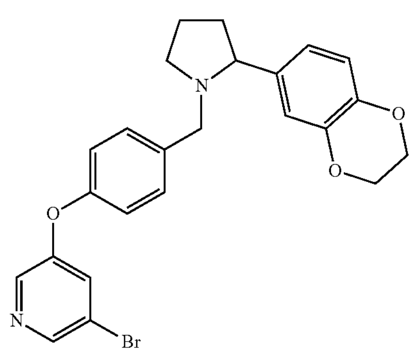 [SMILES: Brc1cncc(Oc2ccc(CN3CCCC3c3ccc4c(c3)OCCO4)cc2)c1] | | Racemic | ++ |

TABLE 1-continued

Compounds of formulae (I). OGA enzyme inhibition assay:

| No | Structure | Optical rotation | Configuration specification | OGA IC50 |
|---|---|---|---|---|
| 154 | 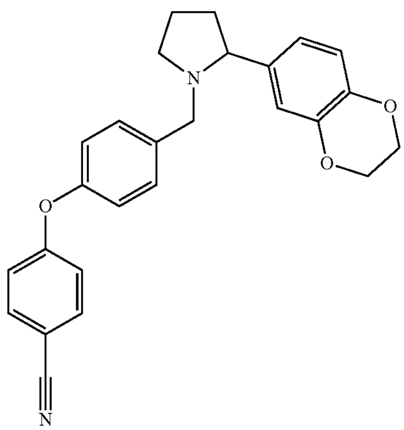 [SMILES: N#Cc1ccc(Oc2ccc(CN3CCCC3c3ccc4c(c3)OCCO4)cc2)cc1] | | Racemic | ++ |
| 155 | 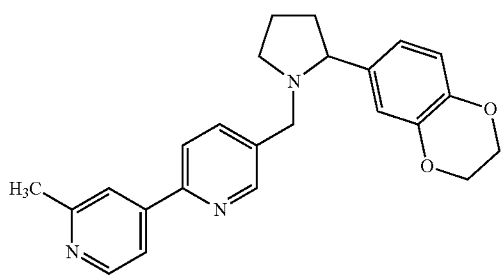 [SMILES: Cc1cc(-c2ccc(CN3CCCC3c3ccc4c(c3)OCCO4)cn2)ccn1] | | Racemic | ++ |
| 156 | 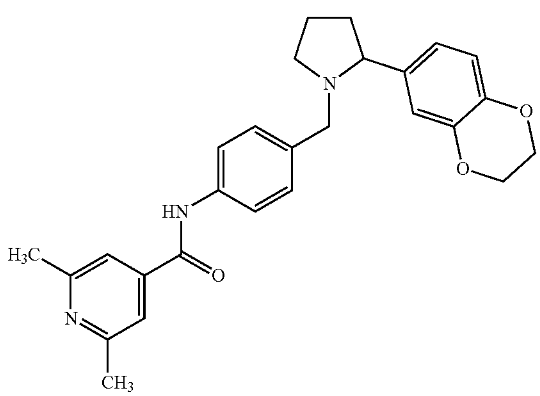 [SMILES: Cc1cc(C(=O)Nc2ccc(CN3CCCC3c3ccc4c(c3)OCCO4)cc2)cc(C)n1] | | Racemic | ++ |
| 157 | 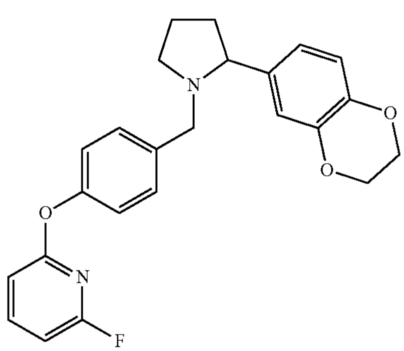 [SMILES: Fc1cccc(Oc2ccc(CN3CCCC3c3ccc4c(c3)OCCO4)cc2)n1] | | Racemic | ++ |

TABLE 1-continued

Compounds of formulae (I). OGA enzyme inhibition assay:

| No | Structure | Optical rotation | Configuration specification | OGA IC50 |
|---|---|---|---|---|
| 158 | 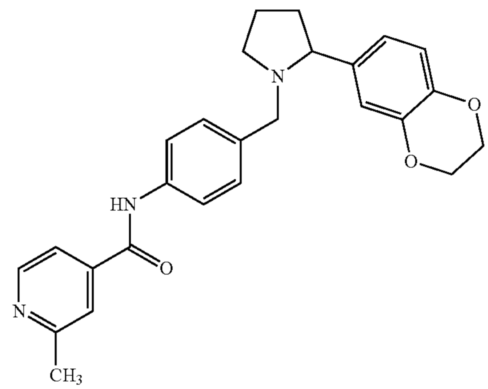 [SMILES: Cc1cc(C(=O)Nc2ccc(CN3CCCC3c3ccc4c(c3)OCCO4)cc2)ccn1] | | Racemic | ++ |
| 159 | 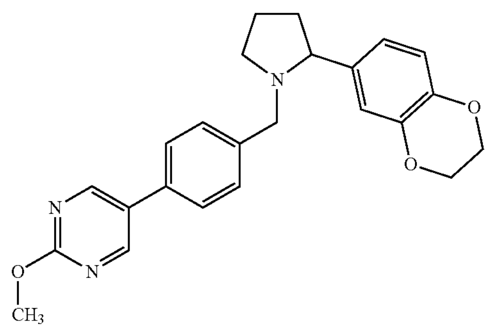 [SMILES: COc1ncc(-c2ccc(CN3CCCC3c3ccc4c(c3)OCCO4)cc2)cn1] | | Racemic | ++++ |
| 160 | 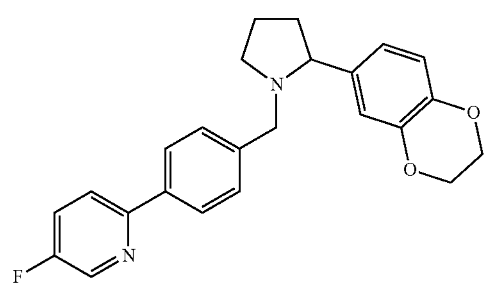 [SMILES: Fc1ccc(-c2ccc(CN3CCCC3c3ccc4c(c3)OCCO4)cc2)nc1] | | Racemic | +++ |
| 161 | 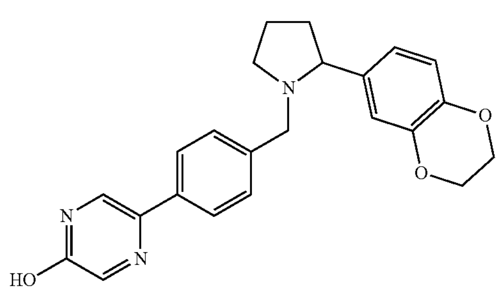 [SMILES: Oc1cnc(-c2ccc(CN3CCCC3c3ccc4c(c3)OCCO4)cc2)cn1] | | Racemic | ++++ |

Activity range of the compounds of Formula (I) is the following:
+ 1 to 10 μM
++ 0.2 to 1 μM
+++ 0.2 to 0.05 μM
++++ below 0.05 μM Further preferred compounds of the invention are the following:
| Structure |
|---|
| 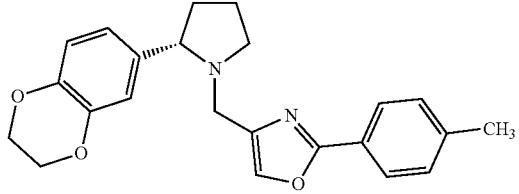 [SMILES: Cc1ccc(-c2nc(CN3CCC[C@H]3c3ccc4c(c3)OCCO4)co2)cc1] |
| 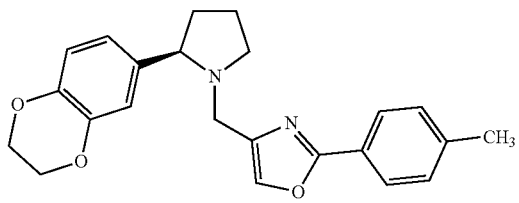 [SMILES: Cc1ccc(-c2nc(CN3CCC[C@@H]3c3ccc4c(c3)OCCO4)co2)cc1] |
| 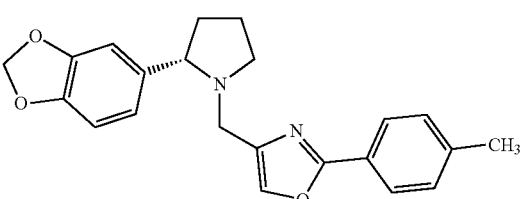 |
| 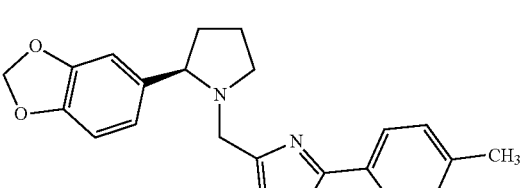 |
| 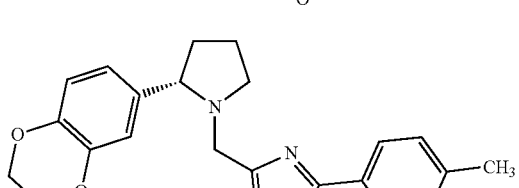 |
| 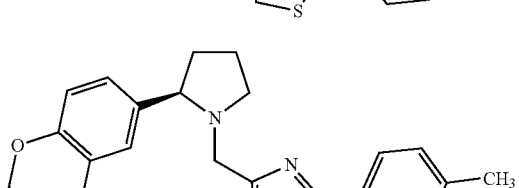 |
| 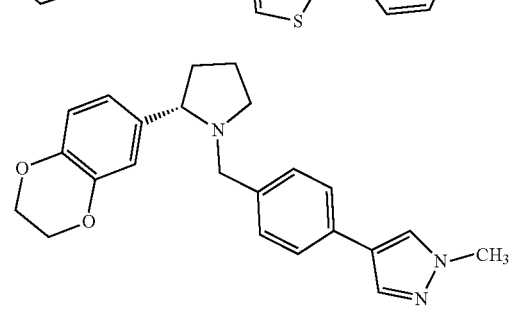 |
-continued
| Structure |
|---|
| 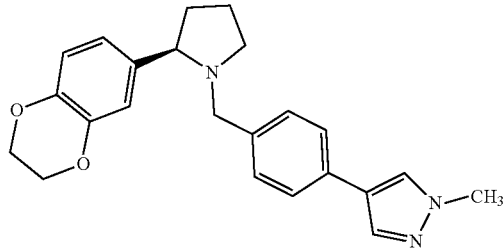 [SMILES: Cn1cc(-c2ccc(CN3CCC[C@@H]3c3ccc4c(c3)OCCO4)cc2)cn1] |
| 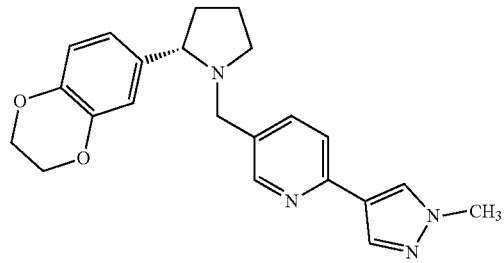 |
| 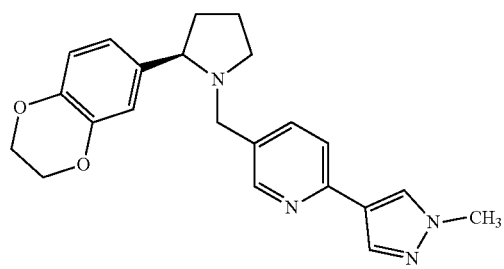 [SMILES: Cn1cc(-c2ccc(CN3CCC[C@@H]3c3ccc4c(c3)OCCO4)cn2)cn1] |
| 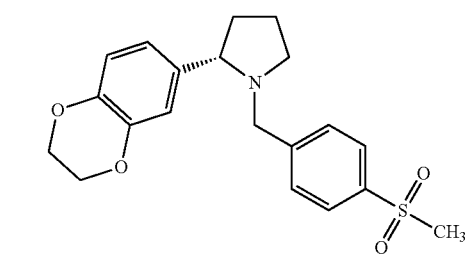 [SMILES: CS(=O)(=O)c1ccc(CN2CCC[C@H]2c2ccc3c(c2)OCCO3)cc1] |
| 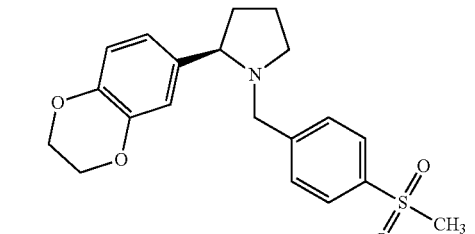 |
| 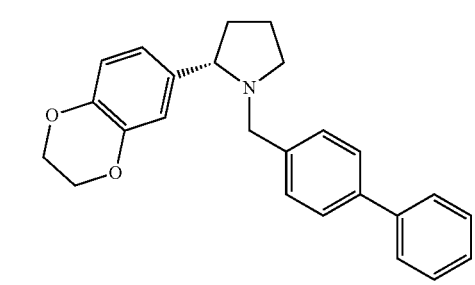 |

| 101 -continued | 102 -continued |
|---|---|
| Structure | Structure |
| 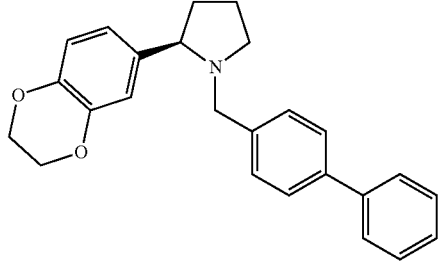 [SMILES: c1ccc(-c2ccc(CN3CCC[C@@H]3c3ccc4c(c3)OCCO4)cc2)cc1] | 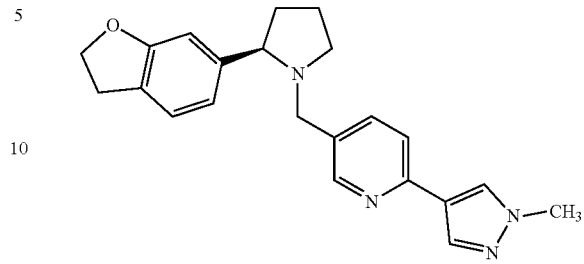 |
| 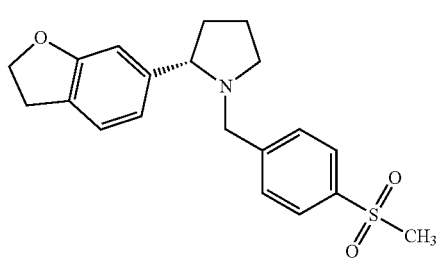 [SMILES: CS(=O)(=O)c1ccc(CN2CCC[C@H]2c2ccc3c(c2)OCC3)cc1] | 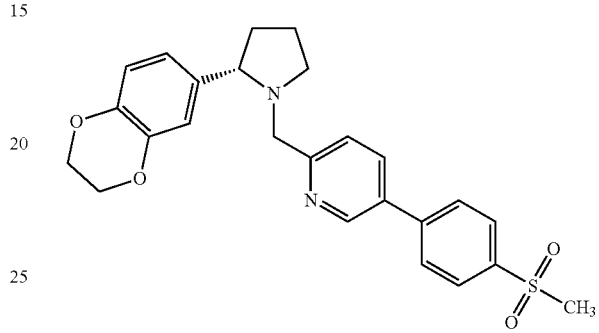 |
| 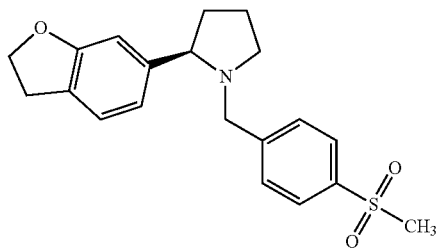 [SMILES: CS(=O)(=O)c1ccc(CN2CCC[C@@H]2c2ccc3c(c2)OCC3)cc1] | 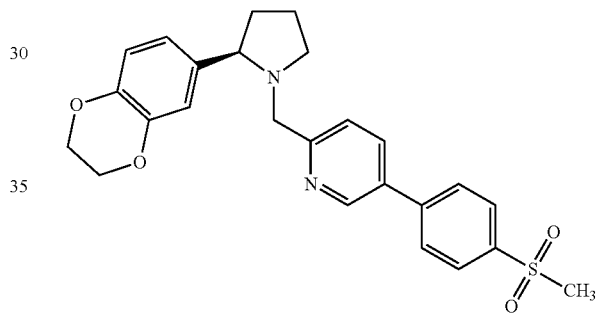 |
| 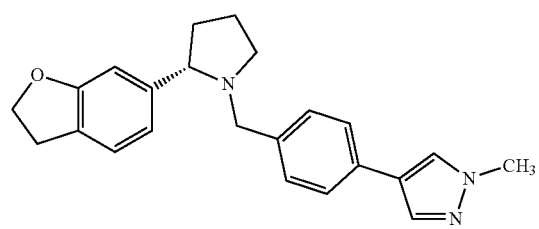 [SMILES: Cn1cc(-c2ccc(CN3CCC[C@H]3c3ccc4c(c3)OCC4)cc2)cn1] | 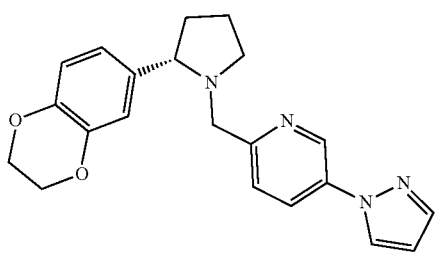 [SMILES: c1cnn(-c2ccc(CN3CCC[C@H]3c3ccc4c(c3)OCCO4)nc2)c1] |
| 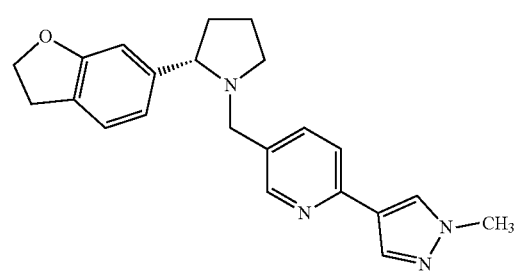 | 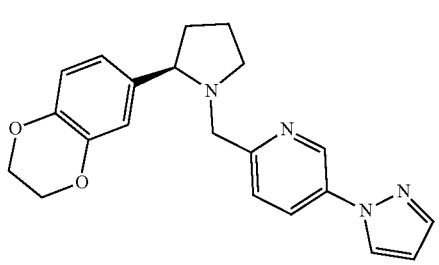 [SMILES: c1cnn(-c2ccc(CN3CCC[C@@H]3c3ccc4c(c3)OCCO4)nc2)c1] |

| 103 -continued | 104 -continued |
|---|---|
| Structure | Structure |
| 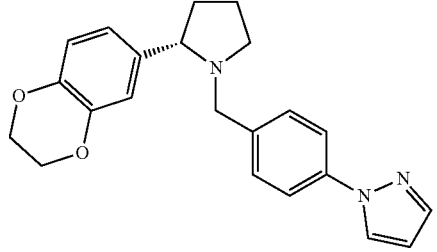 [SMILES: c1cnn(-c2ccc(CN3CCC[C@H]3c3ccc4c(c3)OCCO4)cc2)c1] | 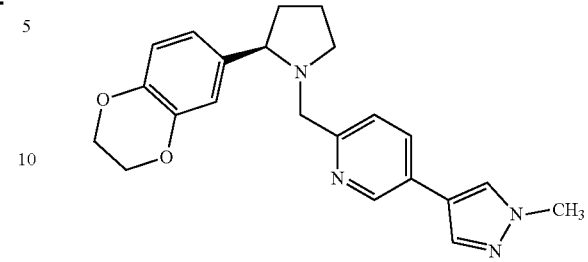 |
| 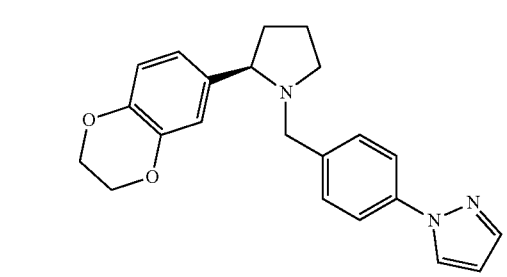 [SMILES: c1cnn(-c2ccc(CN3CCC[C@@H]3c3ccc4c(c3)OCCO4)cc2)c1] | 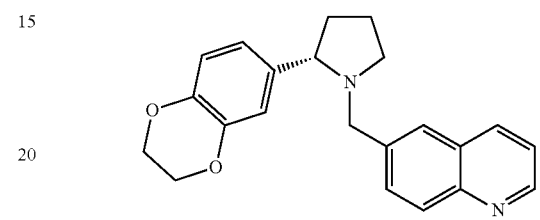 |
| 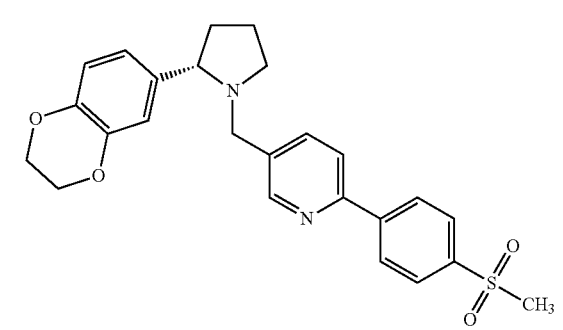 | 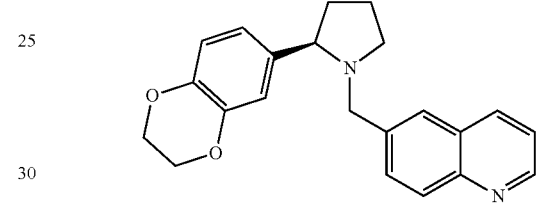 |
| 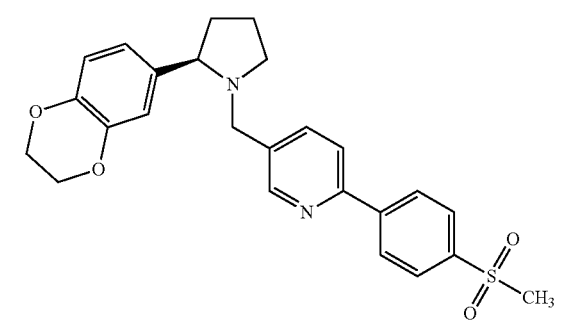 [SMILES: CS(=O)(=O)c1ccc(-c2ccc(CN3CCC[C@@H]3c3ccc4c(c3)OCCO4)cn2)cc1] | 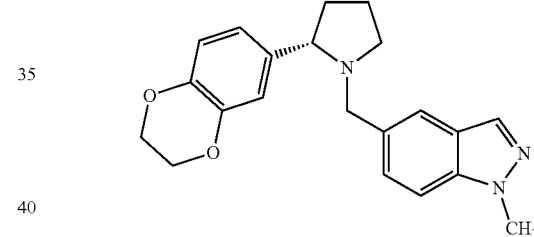 |
| 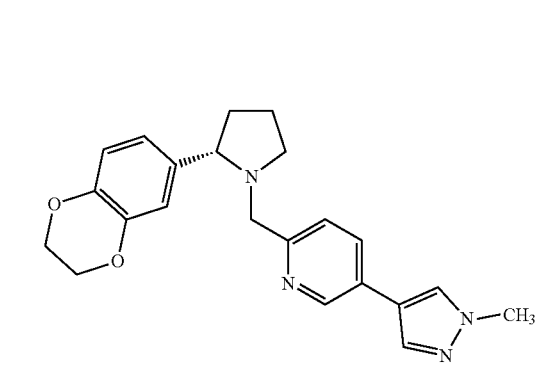 [SMILES: Cn1cc(-c2ccc(CN3CCC[C@H]3c3ccc4c(c3)OCCO4)nc2)cn1] | 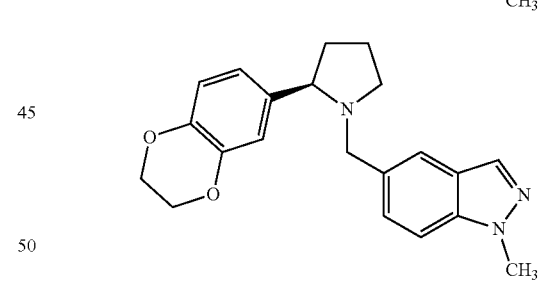 |
| | 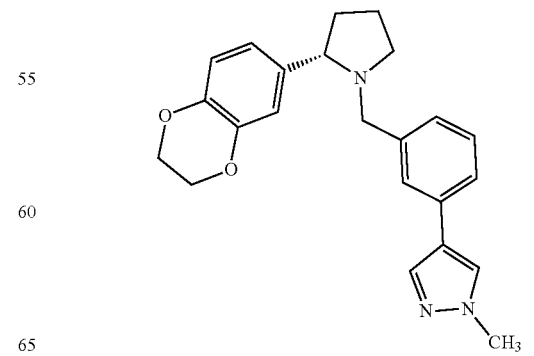 |

| 105 -continued | 106 -continued |
|---|---|
| Structure | Structure |
| 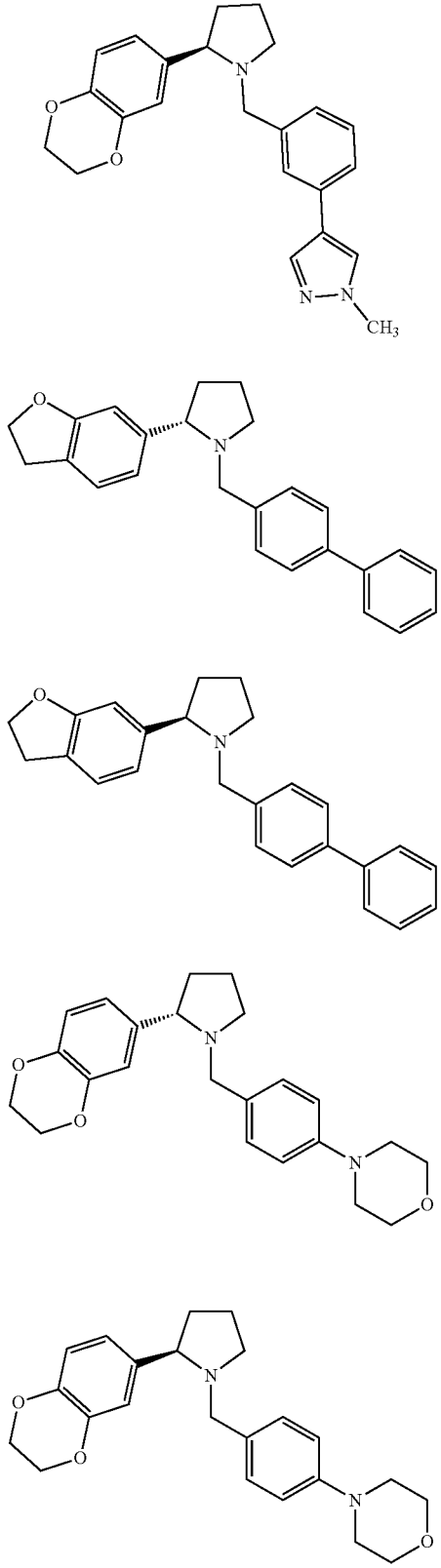 | 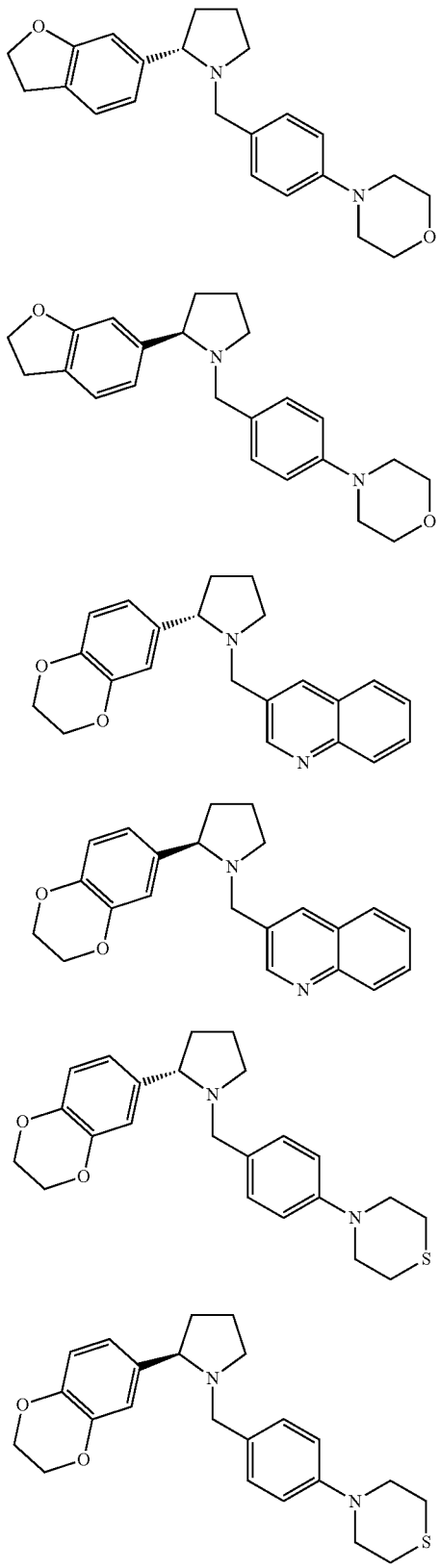 |

| 107 -continued | 108 -continued |
|---|---|
| Structure | Structure |
| 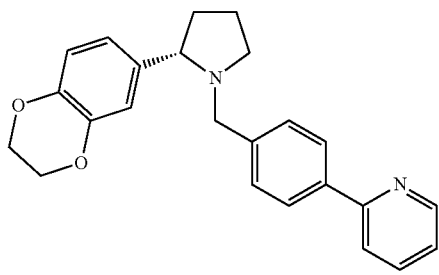 | 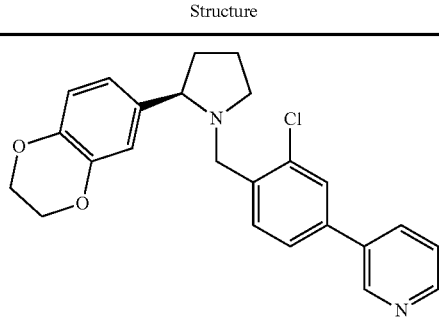 |
| 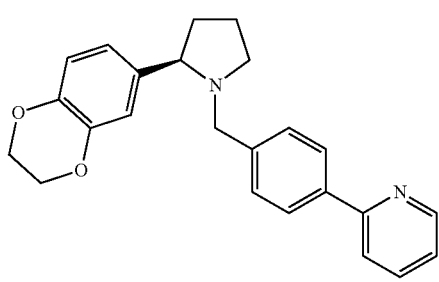 | 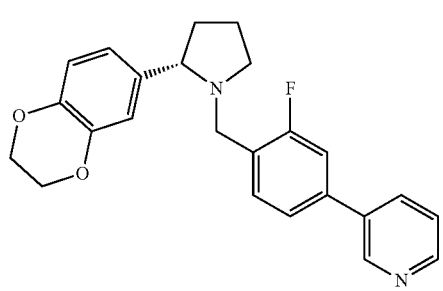 |
| 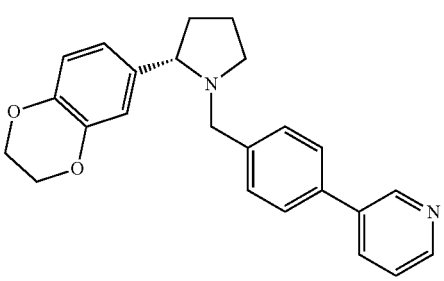 [SMILES: c1cncc(-c2ccc(CN3CCC[C@H]3c3ccc4c(c3)OCCO4)cc2)c1] | 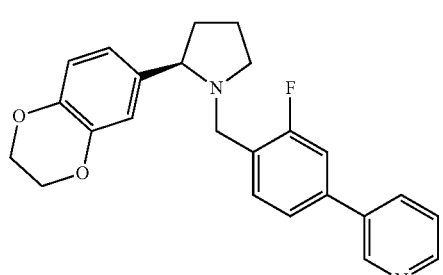 |
| 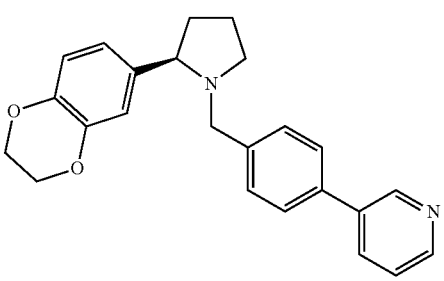 [SMILES: c1cncc(-c2ccc(CN3CCC[C@@H]3c3ccc4c(c3)OCCO4)cc2)c1] | 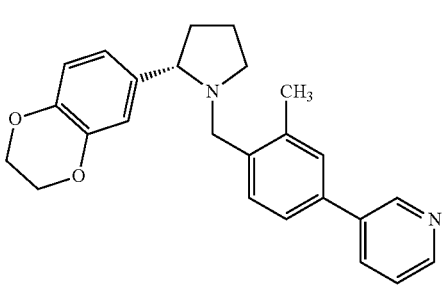 |
| 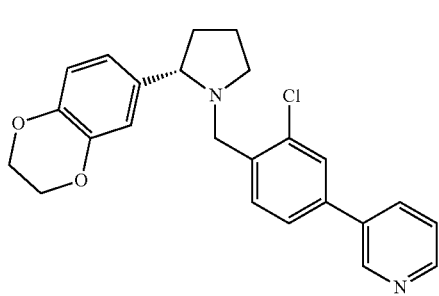 [SMILES: Clc1cc(-c2cccnc2)ccc1CN1CCC[C@H]1c1ccc2c(c1)OCCO2] | 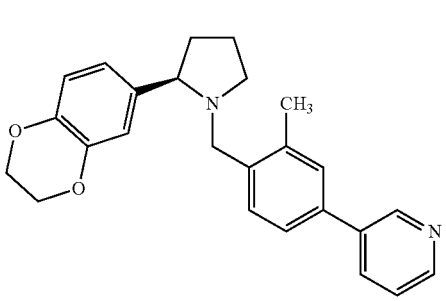 [SMILES: Cc1cc(-c2cccnc2)ccc1CN1CCC[C@@H]1c1ccc2c(c1)OCCO2] |

| 109 -continued | 110 -continued |
|---|---|
| Structure | Structure |
| 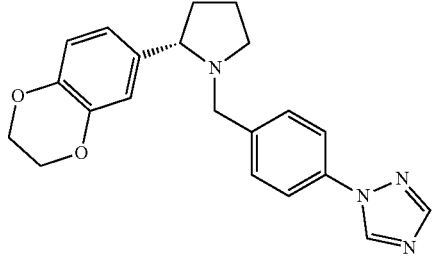 | 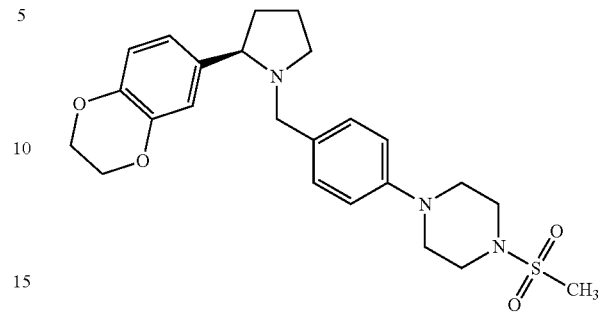 |
| 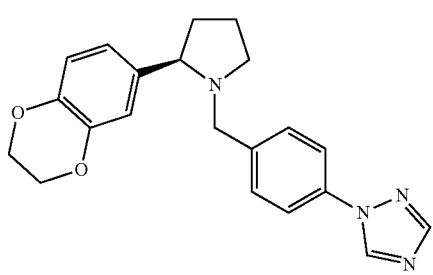 [SMILES: c1ncn(-c2ccc(CN3CCC[C@@H]3c3ccc4c(c3)OCCO4)cc2)n1] | 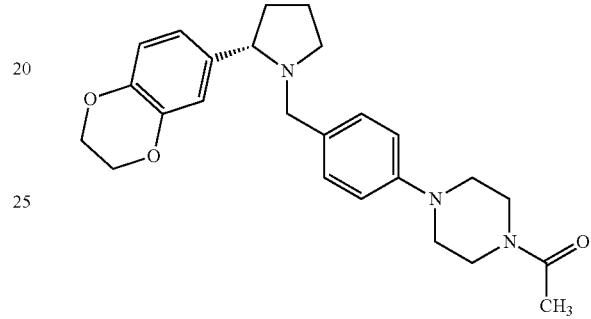 |
| 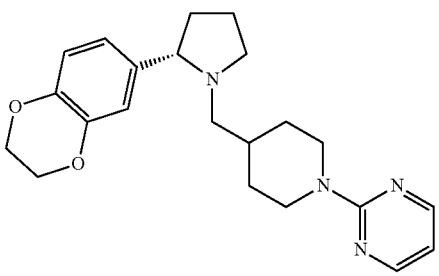 [SMILES: c1cnc(N2CCC(CN3CCC[C@H]3c3ccc4c(c3)OCCO4)CC2)nc1] | 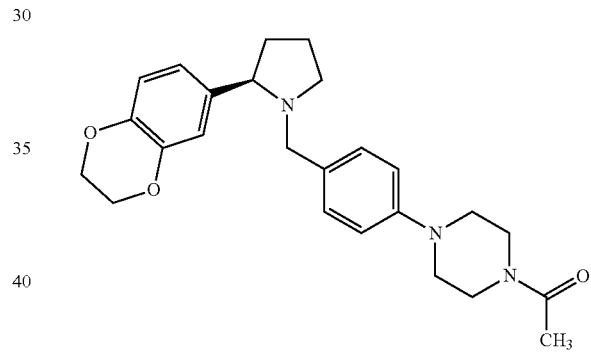 |
| 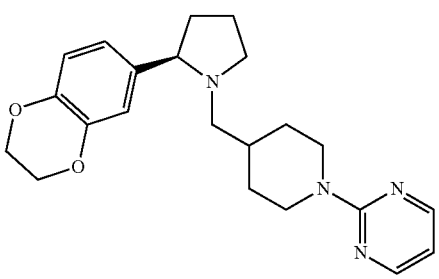 [SMILES: c1cnc(N2CCC(CN3CCC[C@@H]3c3ccc4c(c3)OCCO4)CC2)nc1] | 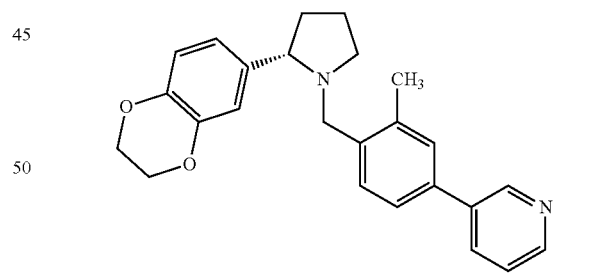 |
| 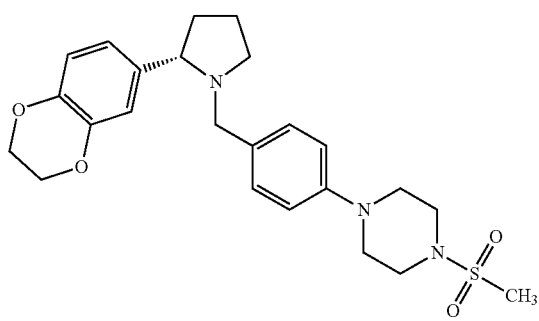 [SMILES: CS(=O)(=O)N1CCN(c2ccc(CN3CCC[C@H]3c3ccc4c(c3)OCCO4)cc2)CC1] | 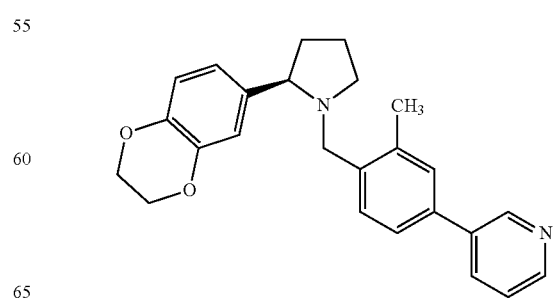 |

| 111 -continued Structure | 112 -continued Structure |
|---|---|
| 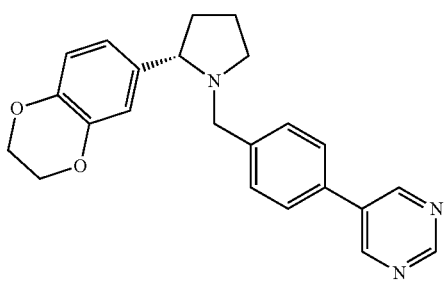 [SMILES: c1ncc(-c2ccc(CN3CCC[C@H]3c3ccc4c(c3)OCCO4)cc2)cn1] | 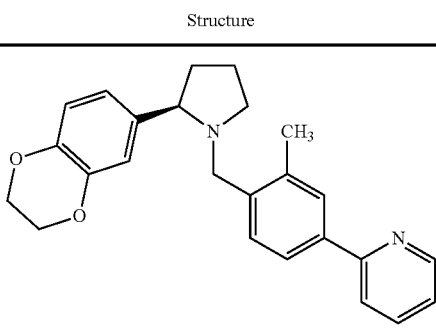 |
| 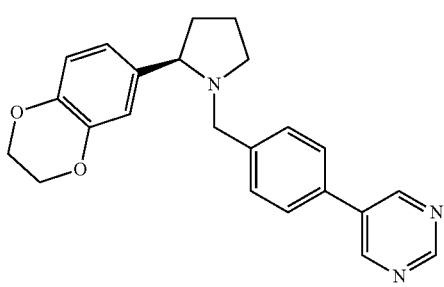 | 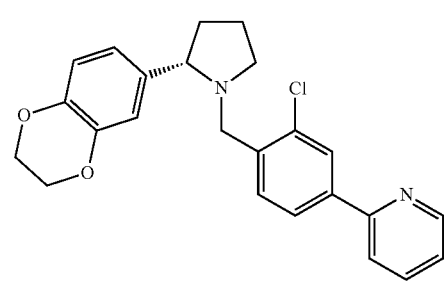 |
| 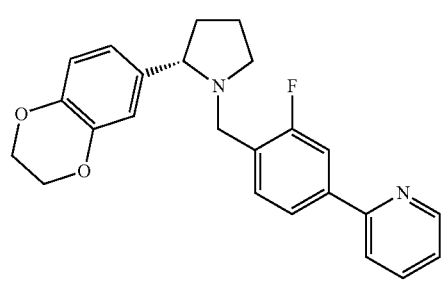 | 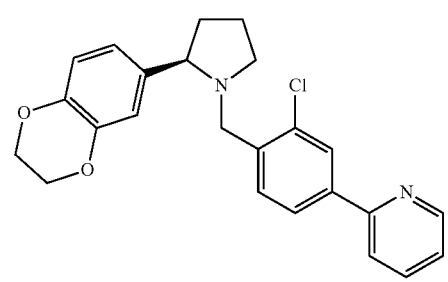 |
| 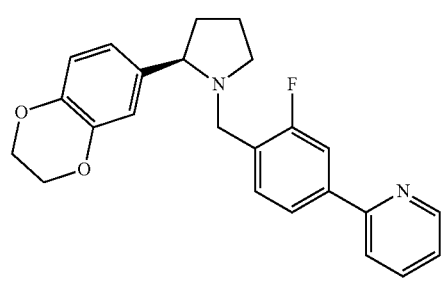 [SMILES: Fc1cc(-c2ccccn2)ccc1CN1CCC[C@@H]1c1ccc2c(c1)OCCO2] | 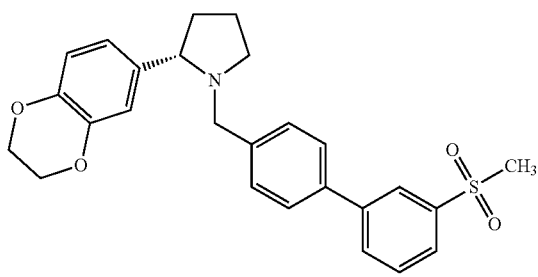 |
| 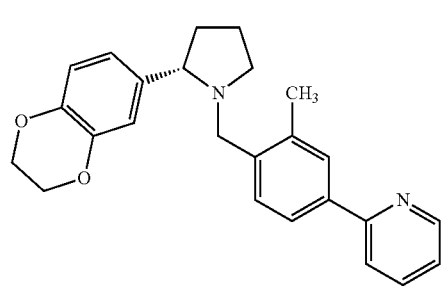 [SMILES: Cc1cc(-c2ccccn2)ccc1CN1CCC[C@H]1c1ccc2c(c1)OCCO2] | 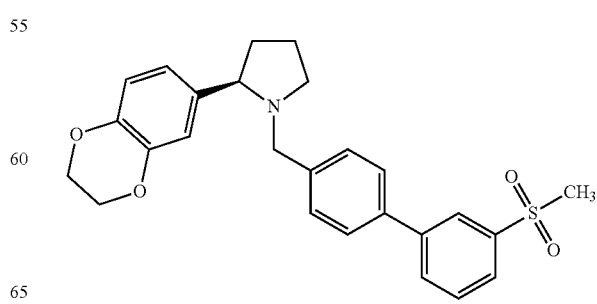 |

| 113 -continued | | 114 -continued | |
|---|---|---|---|
| Structure | | Structure | |
| 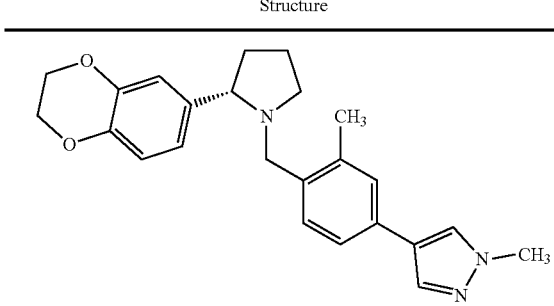 | | 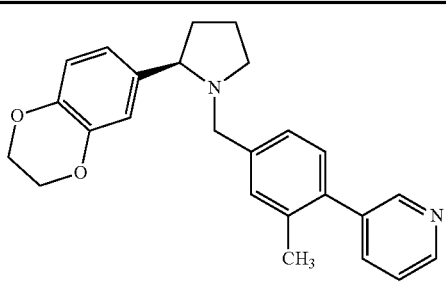 | |
| 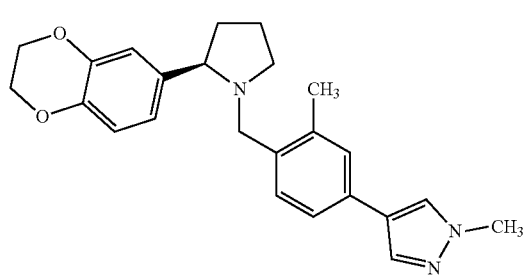 [SMILES: Cc1cc(-c2cnn(C)c2)ccc1CN1CCC[C@@H]1c1ccc2c(c1)OCCO2] | | 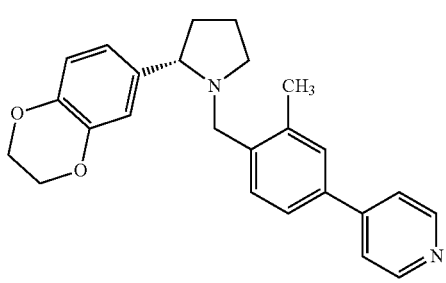 | |
| 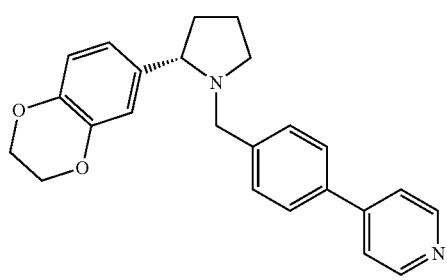 [SMILES: c1cc(-c2ccc(CN3CCC[C@H]3c3ccc4c(c3)OCCO4)cc2)ccn1] | | 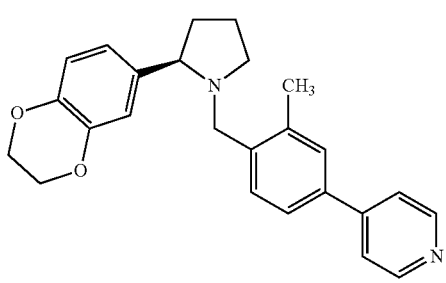 | |
| 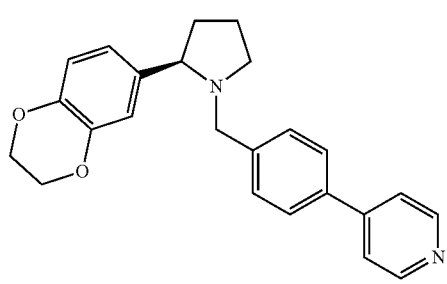 [SMILES: c1cc(-c2ccc(CN3CCC[C@@H]3c3ccc4c(c3)OCCO4)cc2)ccn1] | | 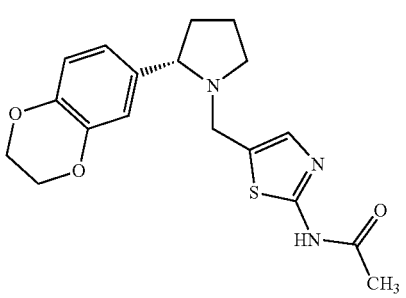 | |
| 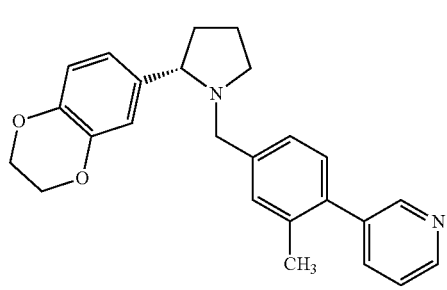 | | 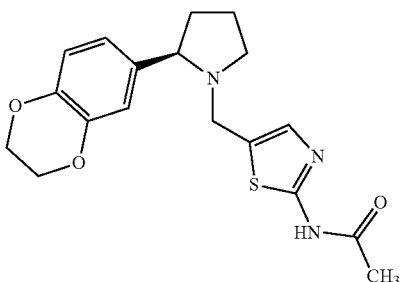 | |

| Structure | | Structure |
|---|---|---|
| 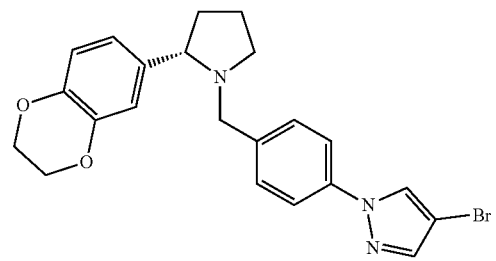 [SMILES: Brc1cnn(-c2ccc(CN3CCC[C@H]3c3ccc4c(c3)OCCO4)cc2)c1] | | 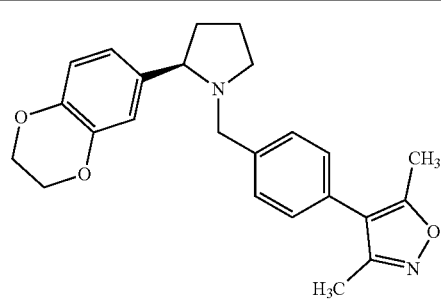 |
| 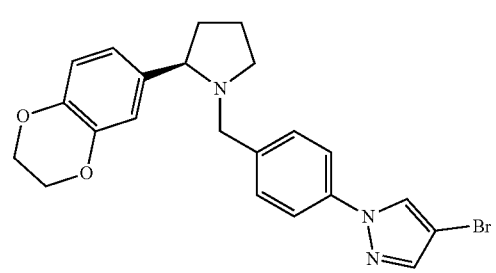 [SMILES: Brc1cnn(-c2ccc(CN3CCC[C@@H]3c3ccc4c(c3)OCCO4)cc2)c1] | | 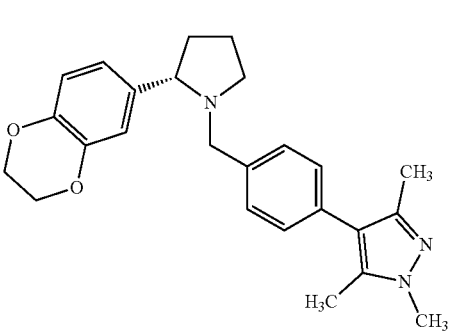 |
| 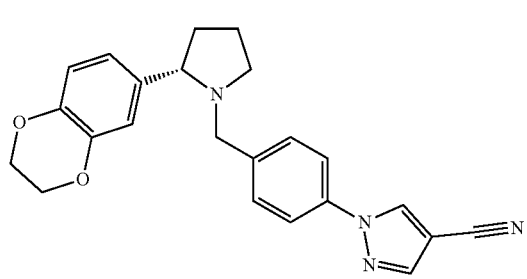 [SMILES: N#Cc1cnn(-c2ccc(CN3CCC[C@H]3c3ccc4c(c3)OCCO4)cc2)c1] | | 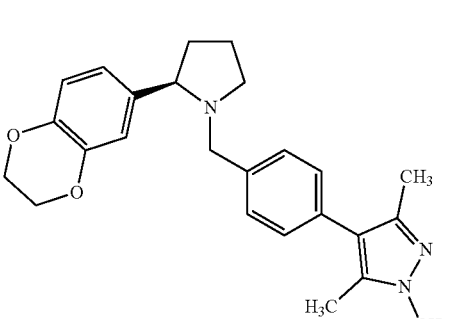 [SMILES: Cc1noc(C)c1-c1ccc(CN2CCC[C@@H]2c2ccc3c(c2)OCCO3)cc1] |
| 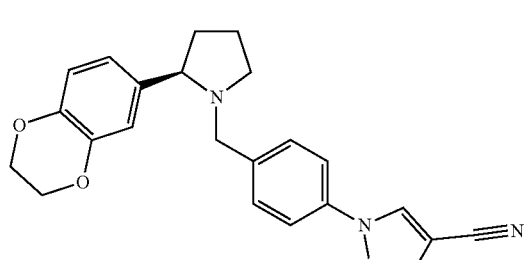 | | 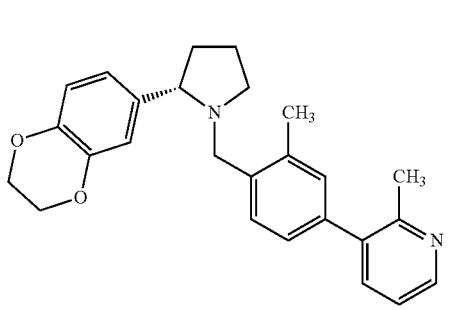 [SMILES: Cc1cc(-c2cccnc2C)ccc1CN1CCC[C@H]1c1ccc2c(c1)OCCO2] |
| 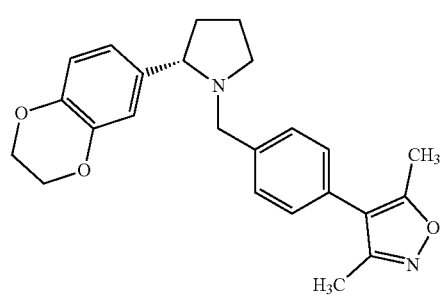 | | 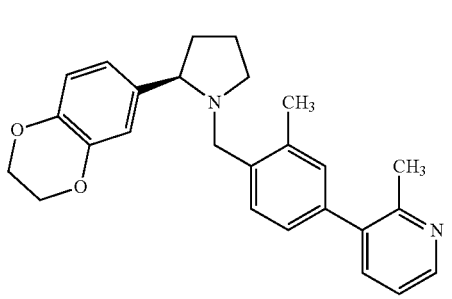 [SMILES: Cc1cc(-c2cccnc2C)ccc1CN1CCC[C@@H]1c1ccc2c(c1)OCCO2] |

| 117 -continued | 118 -continued |
|---|---|
| Structure | Structure |
| 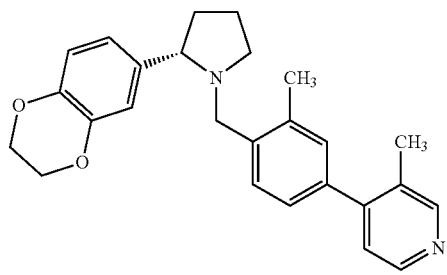 [SMILES: Cc1cc(-c2ccncc2C)ccc1CN1CCC[C@H]1c1ccc2c(c1)OCCO2] | 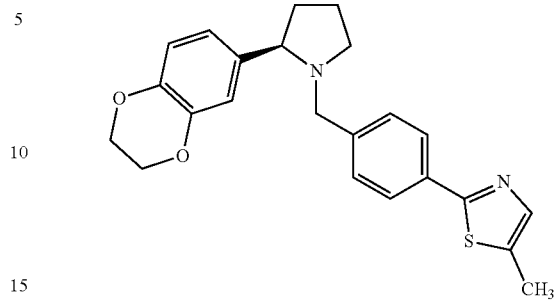 |
| 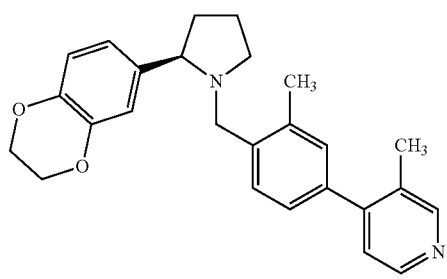 [SMILES: Cc1cc(-c2ccncc2C)ccc1CN1CCC[C@@H]1c1ccc2c(c1)OCCO2] | 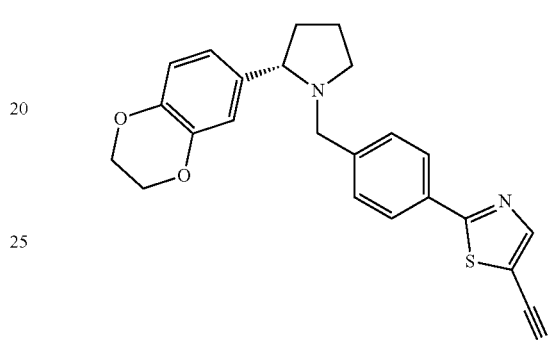 |
| 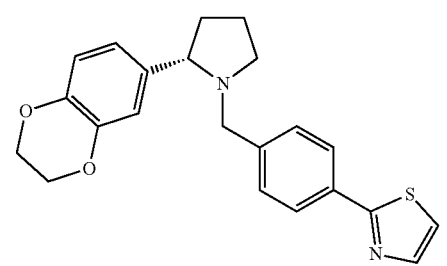 | 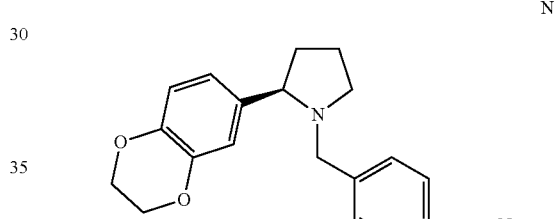 |
| 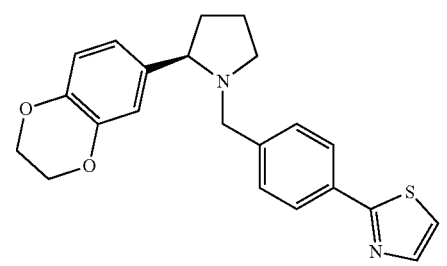 [SMILES: c1csc(-c2ccc(CN3CCC[C@@H]3c3ccc4c(c3)OCCO4)cc2)n1] | 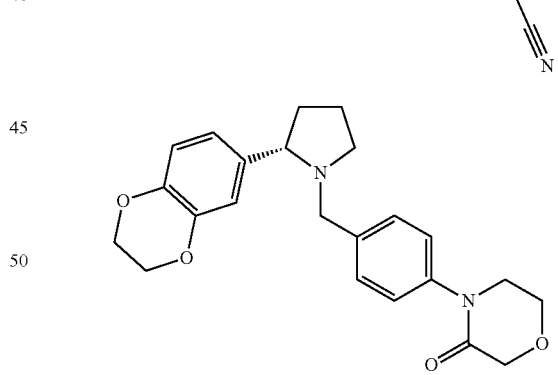 |
| 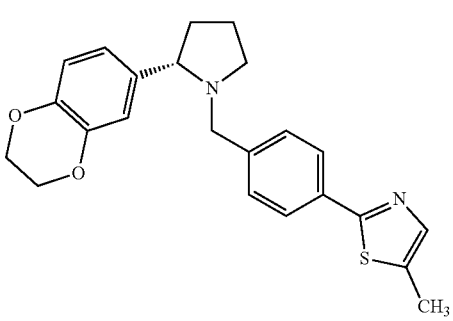 [SMILES: Cc1cnc(-c2ccc(CN3CCC[C@H]3c3ccc4c(c3)OCCO4)cc2)s1] | 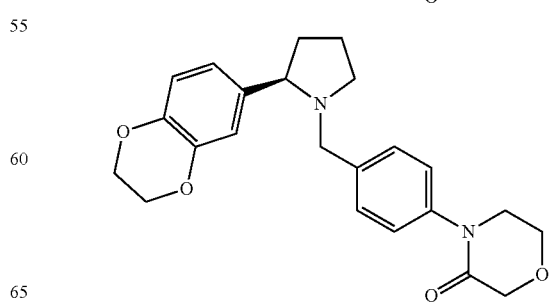 |

| 119 -continued | 120 -continued |
|---|---|
| Structure | Structure |
| 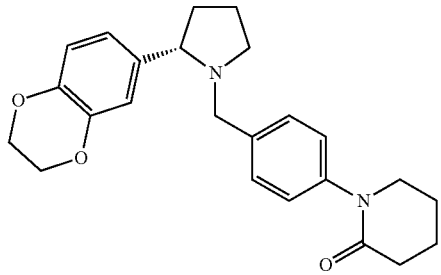 [SMILES: O=C1CCCCN1c1ccc(CN2CCC[C@H]2c2ccc3c(c2)OCCO3)cc1] | 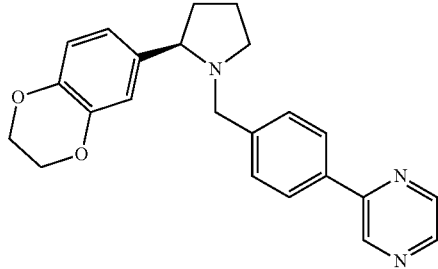 |
| 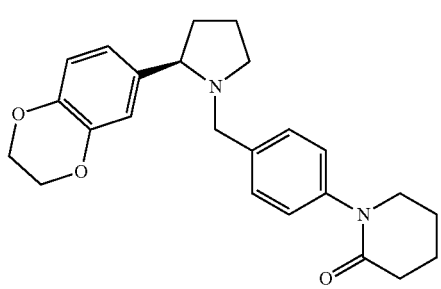 [SMILES: O=C1CCCCN1c1ccc(CN2CCC[C@@H]2c2ccc3c(c2)OCCO3)cc1] | 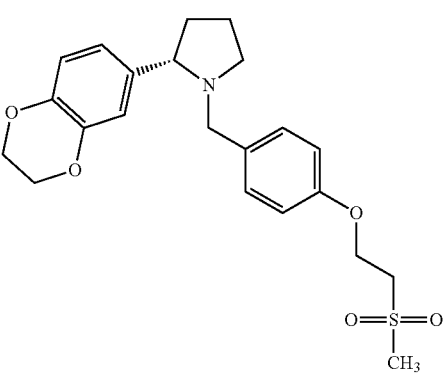 |
| 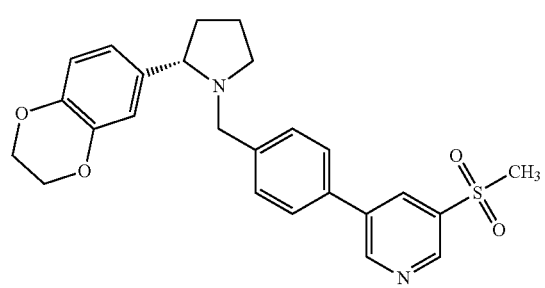 [SMILES: CS(=O)(=O)c1cncc(-c2ccc(CN3CCC[C@H]3c3ccc4c(c3)OCCO4)cc2)c1] | 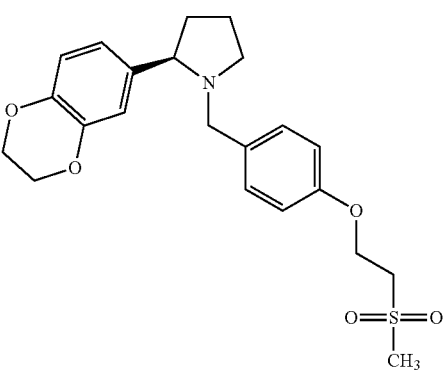 |
| 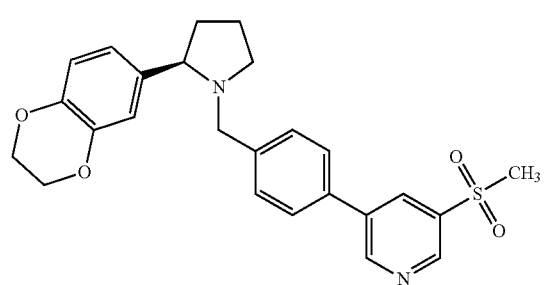 [SMILES: CS(=O)(=O)c1cncc(-c2ccc(CN3CCC[C@@H]3c3ccc4c(c3)OCCO4)cc2)c1] | |
| 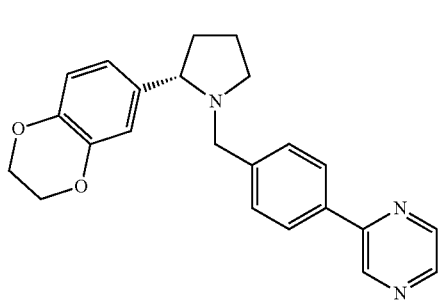 [SMILES: c1cnc(-c2ccc(CN3CCC[C@H]3c3ccc4c(c3)OCCO4)cc2)cn1] | 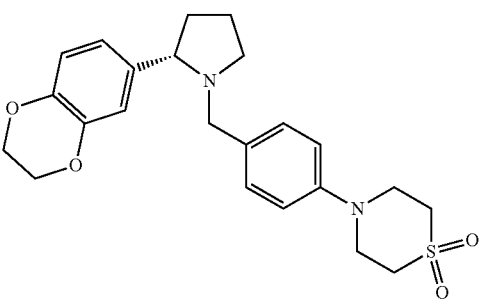 |

121
-continued
Structure
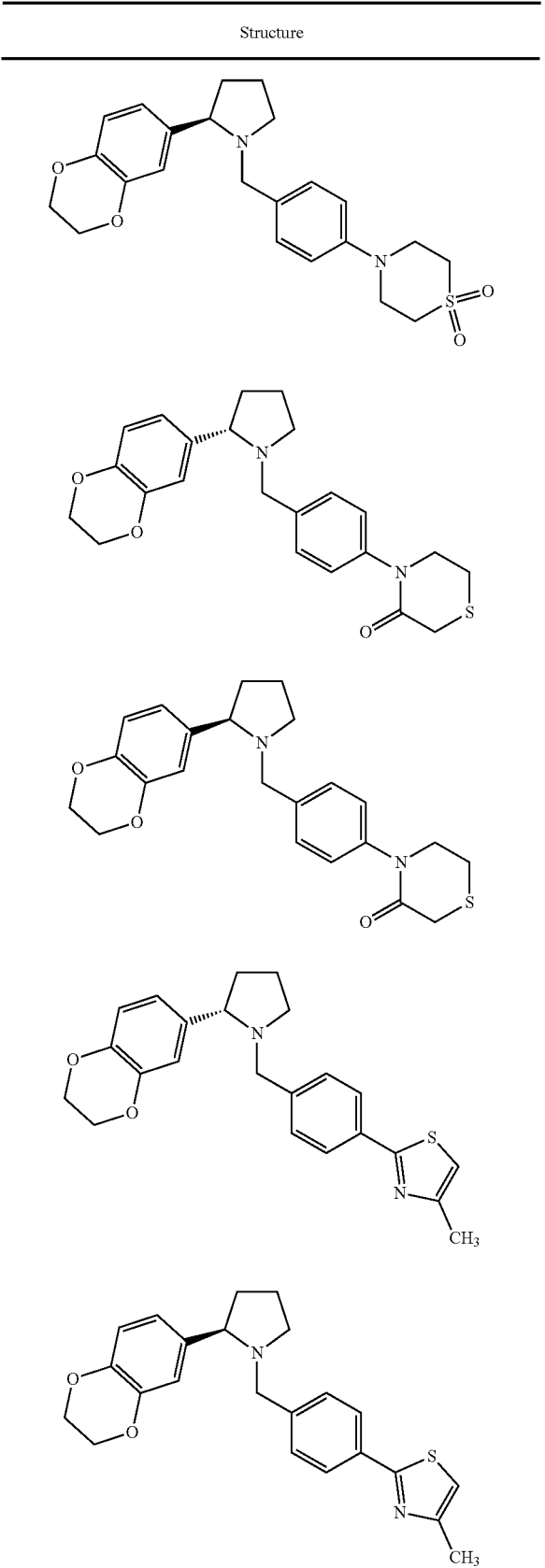
122
-continued
Structure
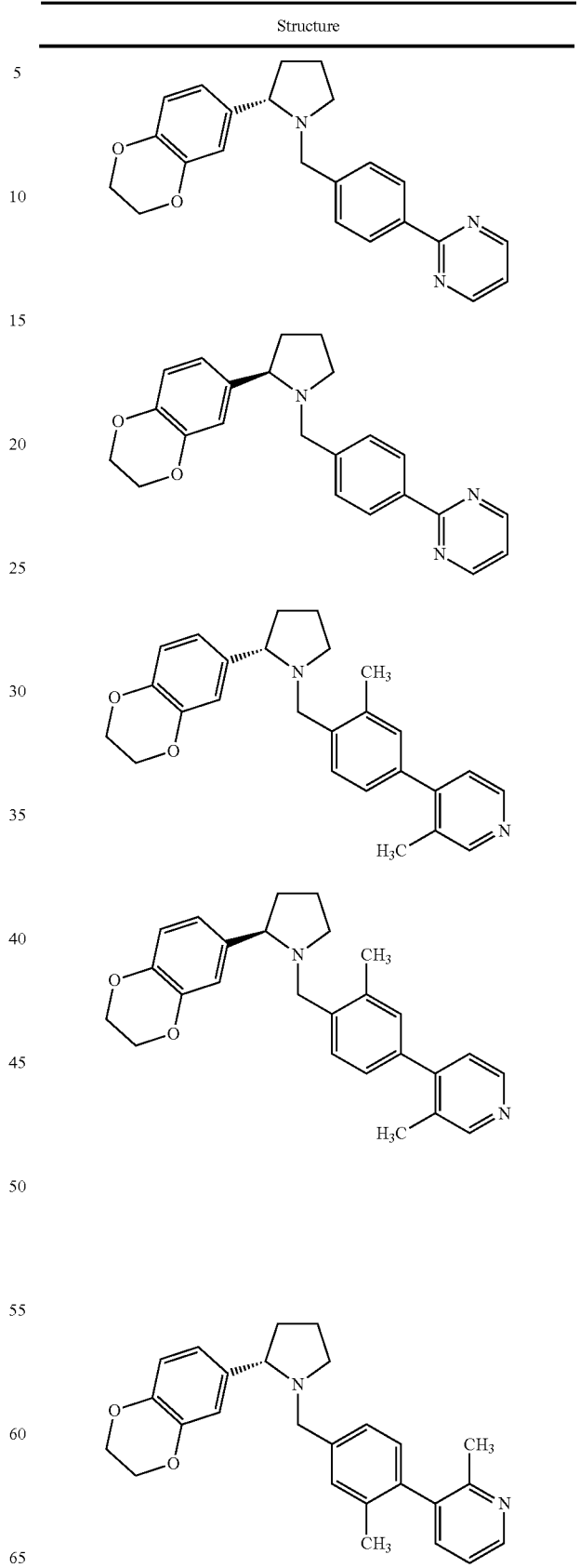

| 123 -continued Structure | 124 -continued Structure |
|---|---|
| 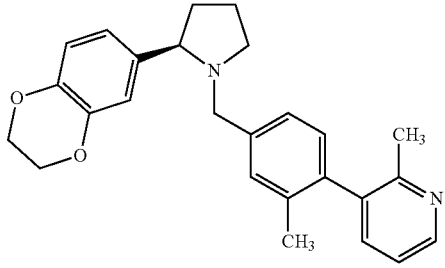 [SMILES: Cc1cc(CN2CCC[C@@H]2c2ccc3c(c2)OCCO3)ccc1-c1cccnc1C] | 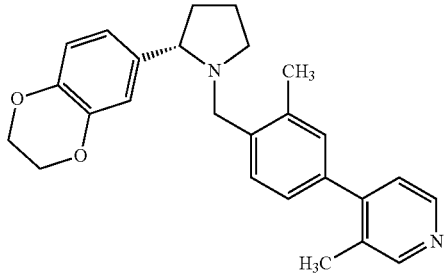 |
| 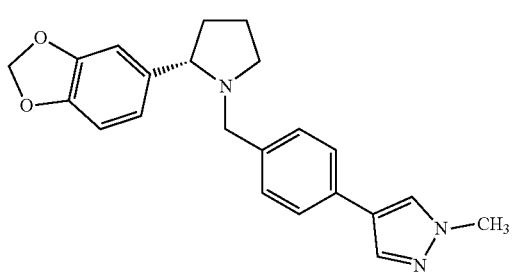 [SMILES: Cn1cc(-c2ccc(CN3CCC[C@H]3c3ccc4c(c3)OCO4)cc2)cn1] | 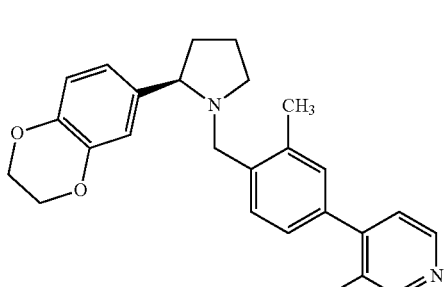 |
| 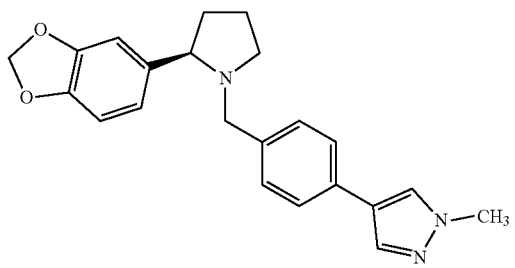 [SMILES: Cn1cc(-c2ccc(CN3CCC[C@@H]3c3ccc4c(c3)OCO4)cc2)cn1] | 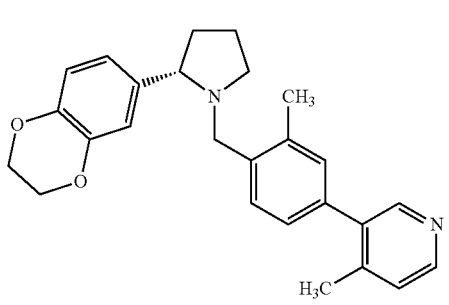 |
| 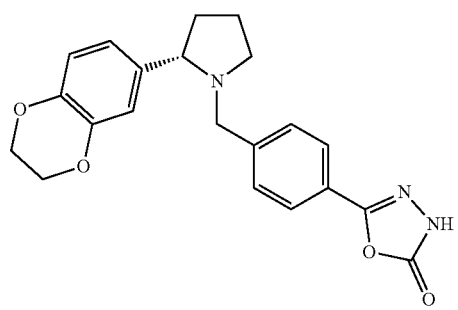 [SMILES: O=c1[nH]nc(-c2ccc(CN3CCC[C@H]3c3ccc4c(c3)OCCO4)cc2)o1] | 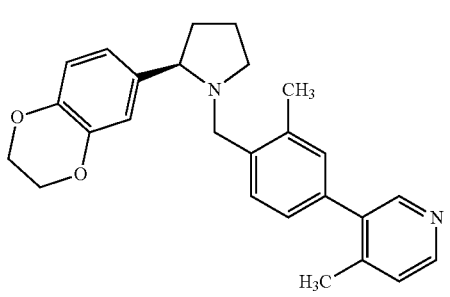 [SMILES: Cc1cc(-c2cnccc2C)ccc1CN1CCC[C@@H]1c1ccc2c(c1)OCCO2] |
|  | 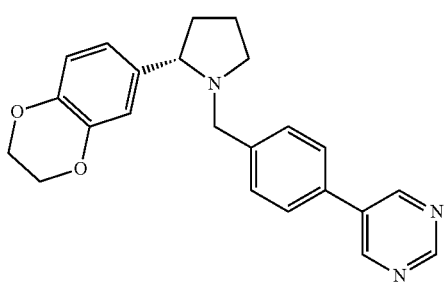 |

| 125 -continued | 126 -continued |
|---|---|
| Structure | Structure |
| 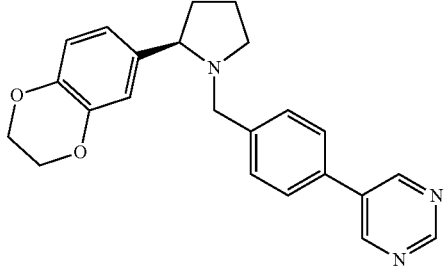 [SMILES: c1ncc(-c2ccc(CN3CCC[C@@H]3c3ccc4c(c3)OCCO4)cc2)cn1] | 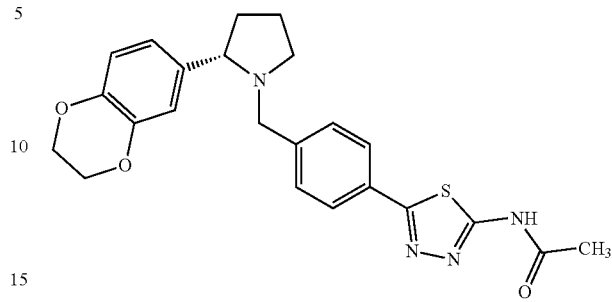 |
| 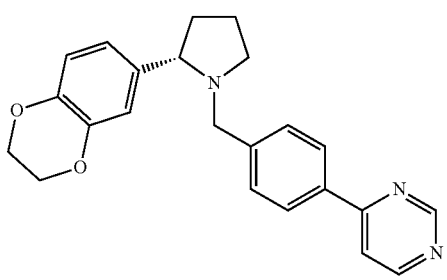 | 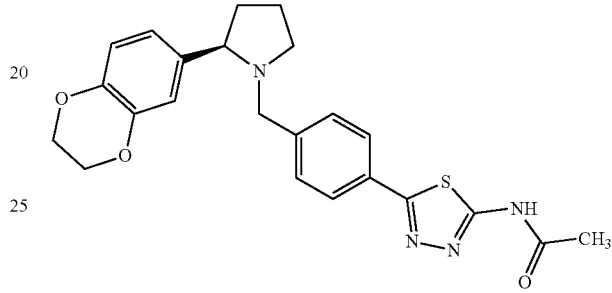 |
| 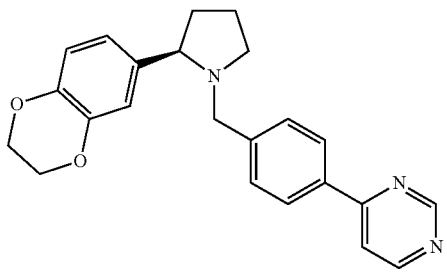 [SMILES: c1cc(-c2ccc(CN3CCC[C@@H]3c3ccc4c(c3)OCCO4)cc2)ncn1] | 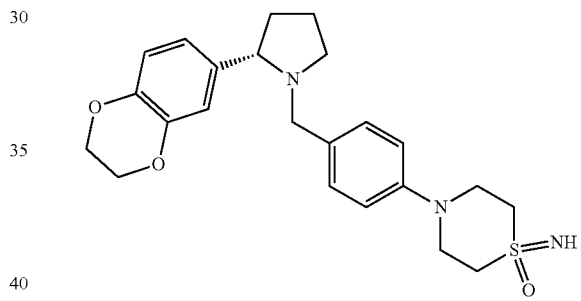 |
| 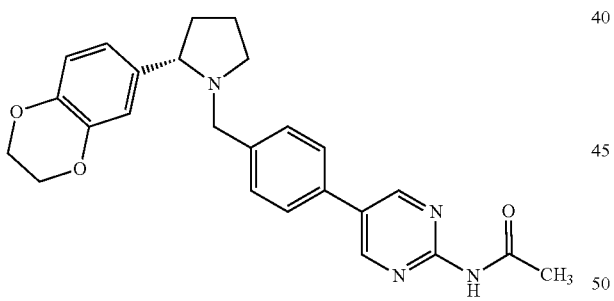 | |
| 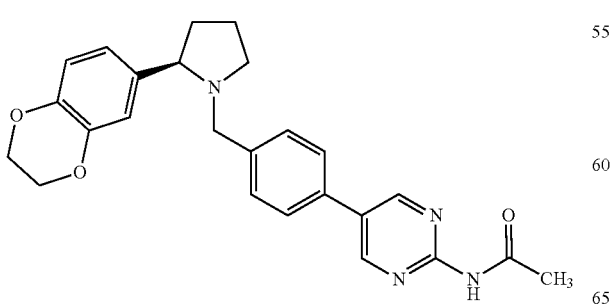 | |

| 127 -continued | 128 -continued |
|---|---|
| Structure | Structure |
| 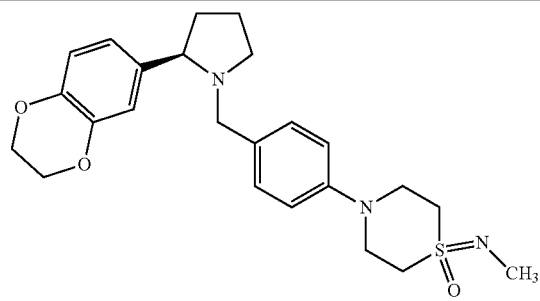 [SMILES: CN=S1(=O)CCN(c2ccc(CN3CCC[C@@H]3c3ccc4c(c3)OCCO4)cc2)CC1] | 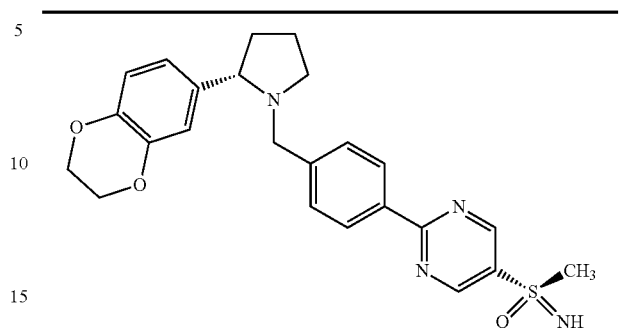 |
| 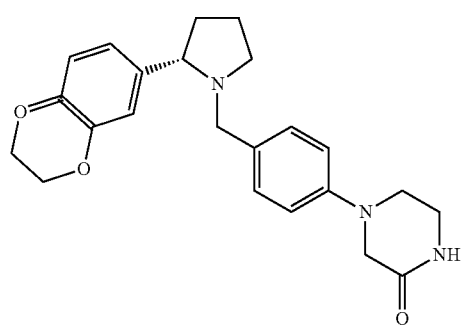 | 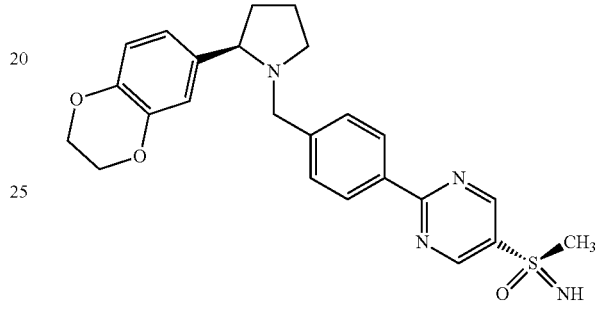 |
| 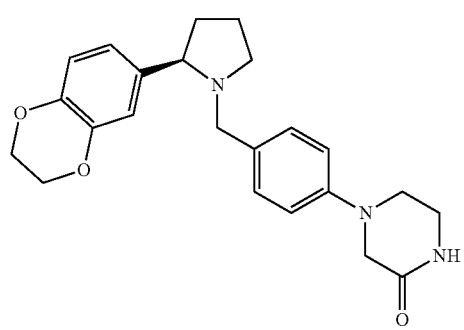 [SMILES: O=C1CN(c2ccc(CN3CCC[C@@H]3c3ccc4c(c3)OCCO4)cc2)CCN1] | 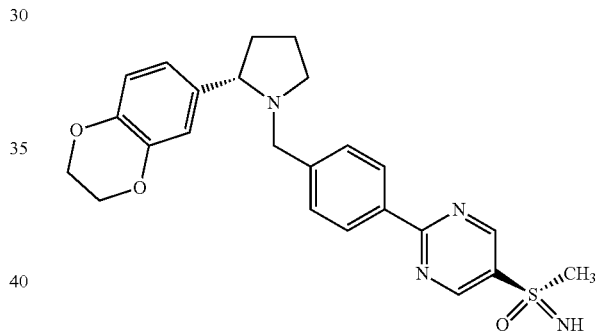 |
| 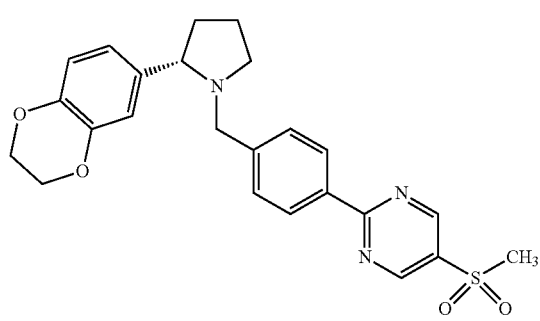 [SMILES: CS(=O)(=O)c1cnc(-c2ccc(CN3CCC[C@H]3c3ccc4c(c3)OCCO4)cc2)nc1] | 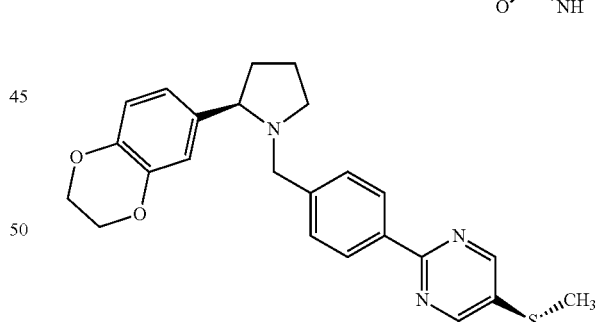 |
| 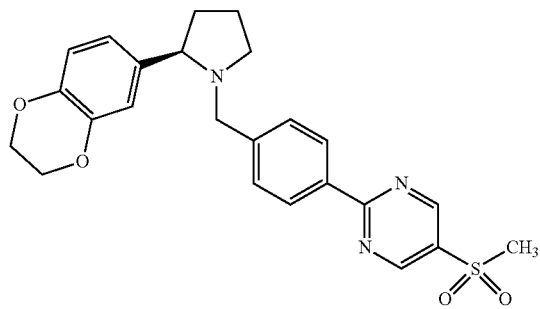 [SMILES: CS(=O)(=O)c1cnc(-c2ccc(CN3CCC[C@@H]3c3ccc4c(c3)OCCO4)cc2)nc1] | 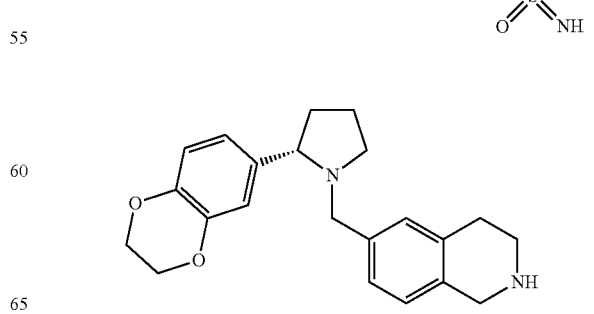 |

| 129 -continued | 130 -continued |
|---|---|
| Structure | Structure |
| 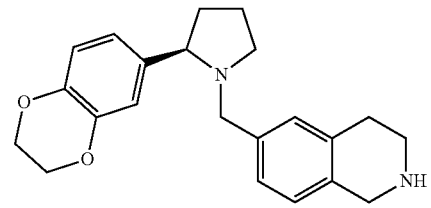 [SMILES: c1cc2c(cc1CN1CCC[C@@H]1c1ccc3c(c1)OCCO3)CCNC2] | 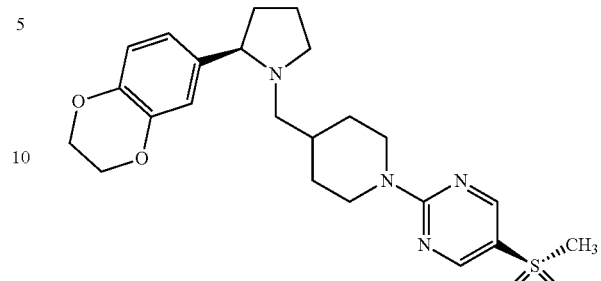 |
| 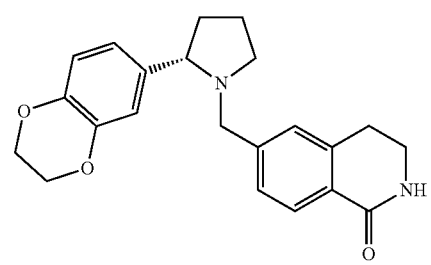 [SMILES: O=C1NCCc2cc(CN3CCC[C@H]3c3ccc4c(c3)OCCO4)ccc21] | 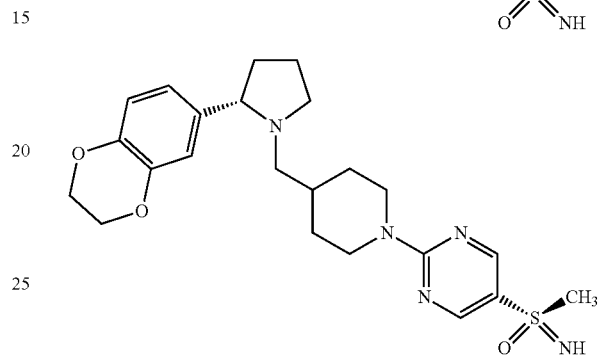 |
| 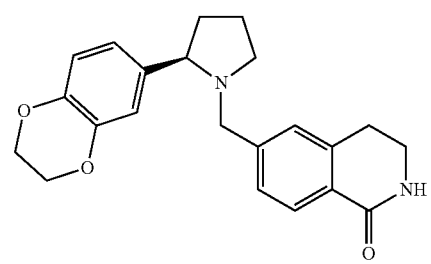 [SMILES: O=C1NCCc2cc(CN3CCC[C@@H]3c3ccc4c(c3)OCCO4)ccc21] | 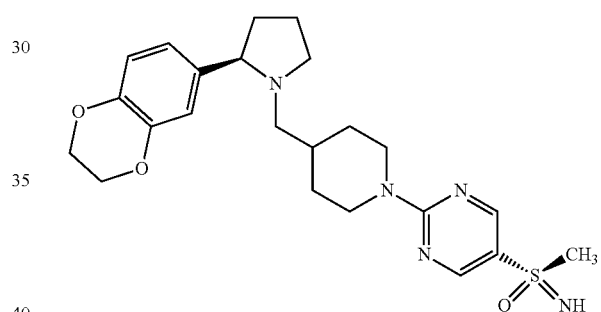 |
| 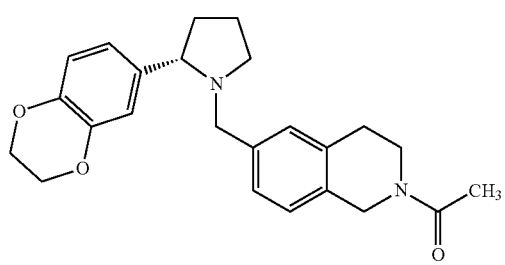 [SMILES: CC(=O)N1CCc2cc(CN3CCC[C@H]3c3ccc4c(c3)OCCO4)ccc2C1] | 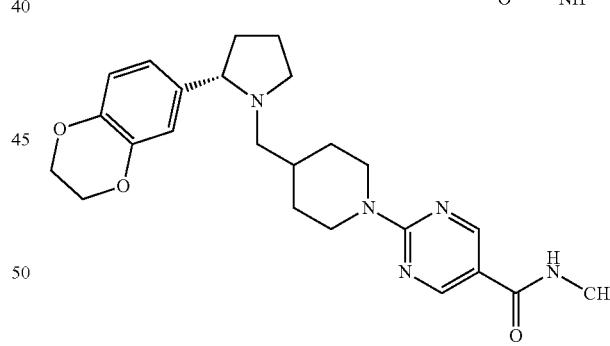 |
| 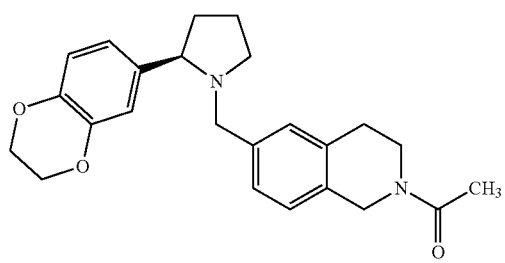 [SMILES: CC(=O)N1CCc2cc(CN3CCC[C@@H]3c3ccc4c(c3)OCCO4)ccc2C1] |  |
| 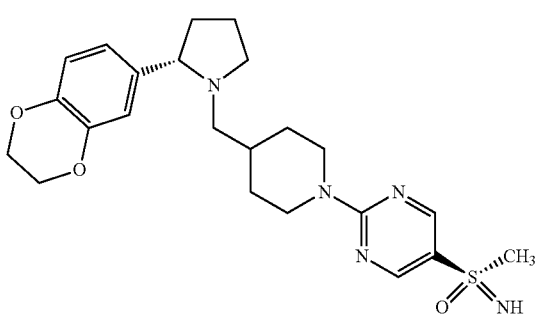 [SMILES: C[S@](=N)(=O)c1cnc(N2CCC(CN3CCC[C@H]3c3ccc4c(c3)OCCO4)CC2)nc1] | |

| 131 -continued | 132 -continued |
|---|---|
| Structure | Structure |
| 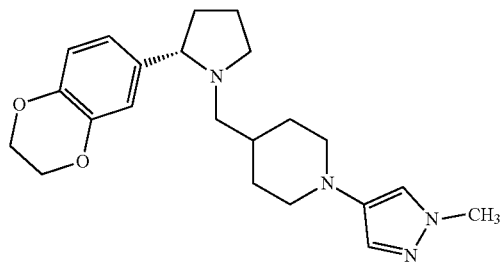 | 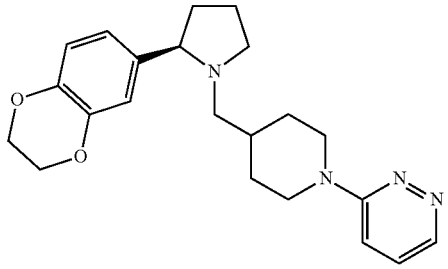 |
| 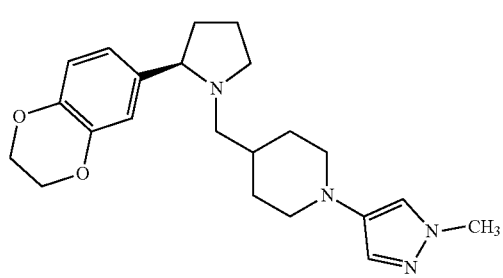 [SMILES: Cn1cc(N2CCC(CN3CCC[C@@H]3c3ccc4c(c3)OCCO4)CC2)cn1] | 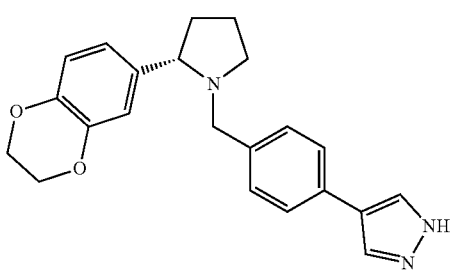 [SMILES: c1cc(-c2cn[nH]c2)ccc1CN1CCC[C@H]1c1ccc2c(c1)OCCO2] |
| 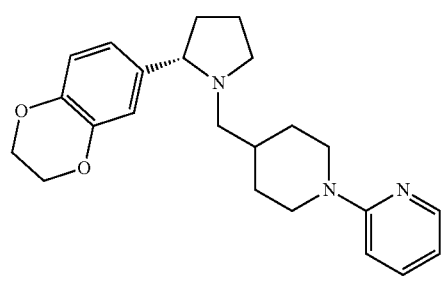 | 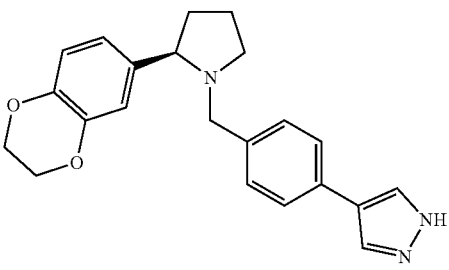 [SMILES: c1cc(-c2cn[nH]c2)ccc1CN1CCC[C@@H]1c1ccc2c(c1)OCCO2] |
| 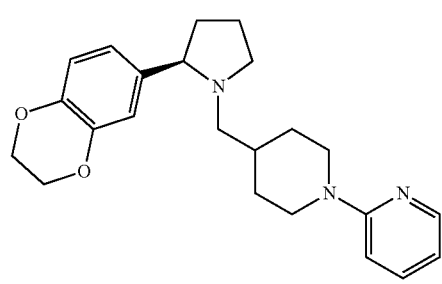 | 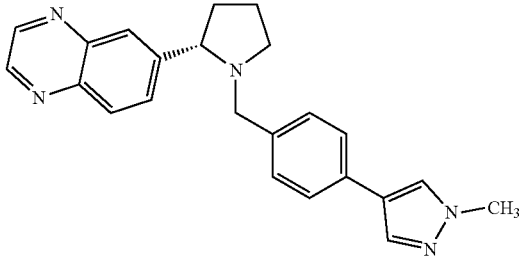 [SMILES: Cn1cc(-c2ccc(CN3CCC[C@H]3c3ccc4nccnc4c3)cc2)cn1] |
| 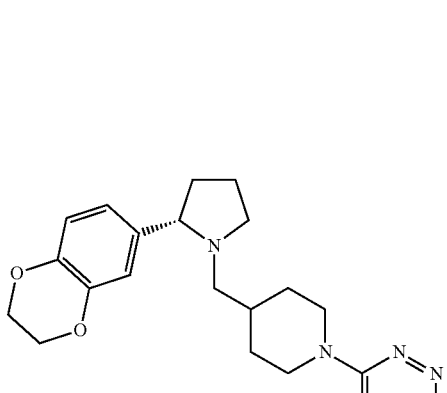 | 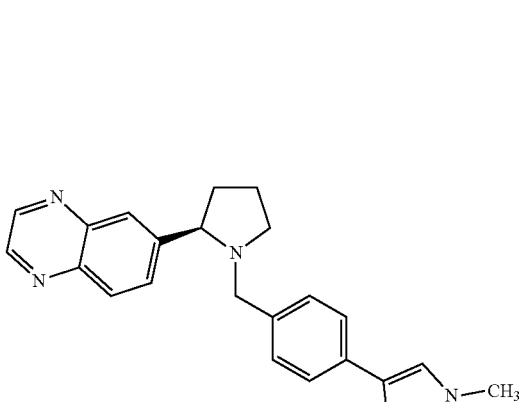 |

| 133 -continued | 134 -continued |
|---|---|
| Structure | Structure |
| 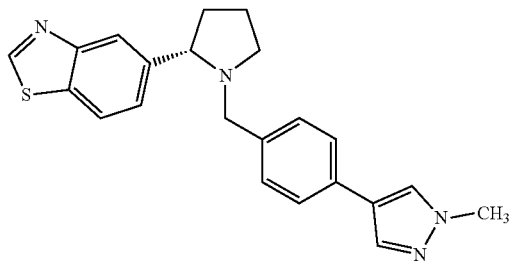 [SMILES: Cn1cc(-c2ccc(CN3CCC[C@H]3c3ccc4scnc4c3)cc2)cn1] | 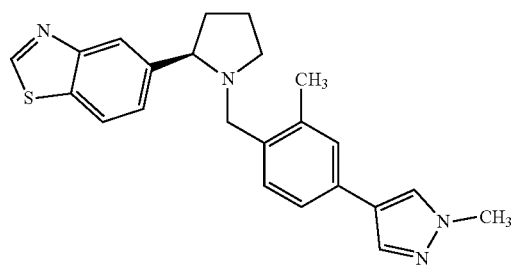 |
| 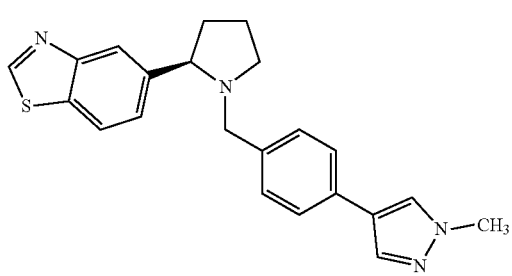 [SMILES: Cn1cc(-c2ccc(CN3CCC[C@@H]3c3ccc4scnc4c3)cc2)cn1] | 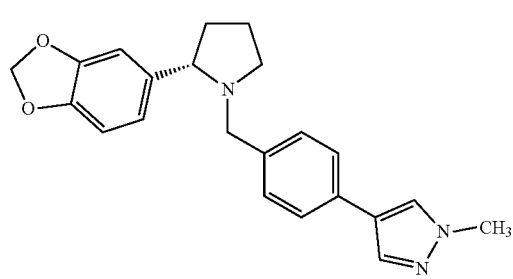 |
| 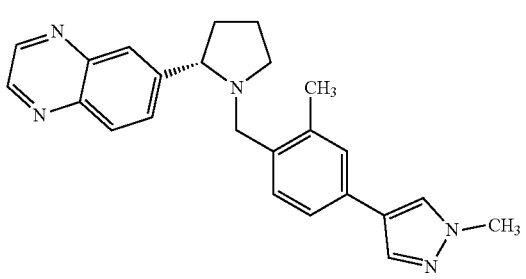 [SMILES: Cc1cc(-c2cnn(C)c2)ccc1CN1CCC[C@H]1c1ccc2nccnc2c1] | 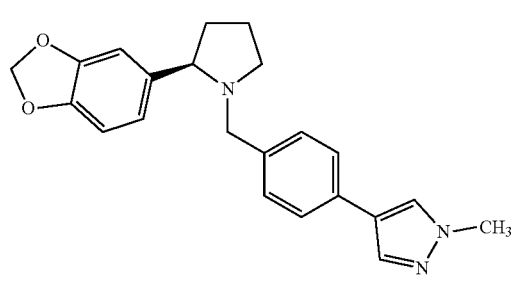 |
| 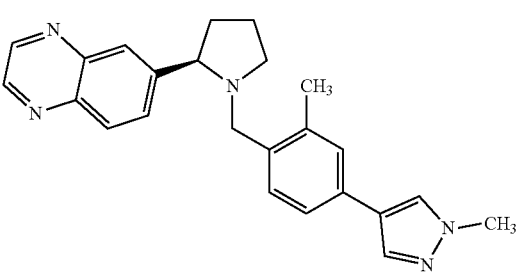 [SMILES: Cc1cc(-c2cnn(C)c2)ccc1CN1CCC[C@@H]1c1ccc2nccnc2c1] | 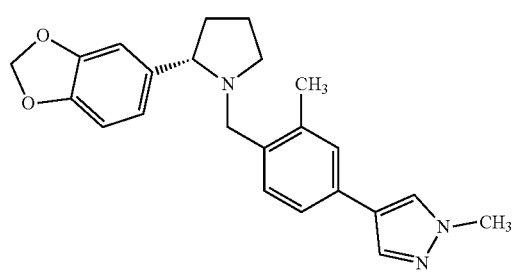 |
| 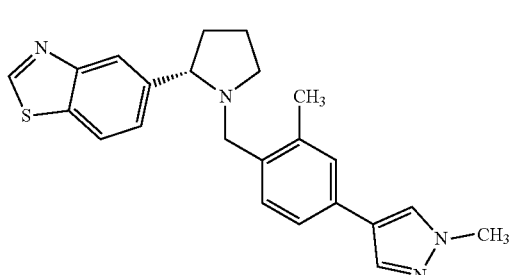 | 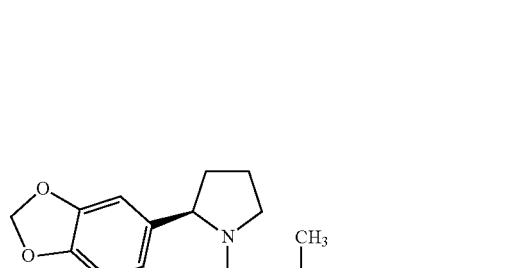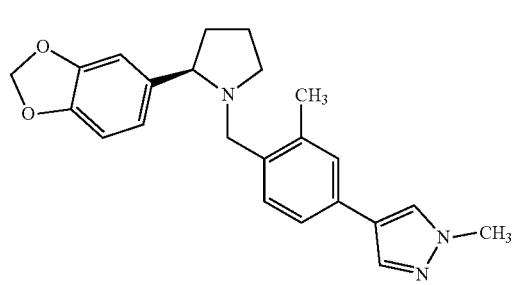 [SMILES: Cc1cc(-c2cnn(C)c2)ccc1CN1CCC[C@@H]1c1ccc2c(c1)OCO2] |

| 135 -continued | | 136 -continued |
|---|---|---|
| Structure | | Structure |
| 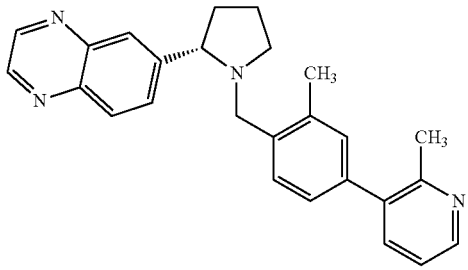 | | 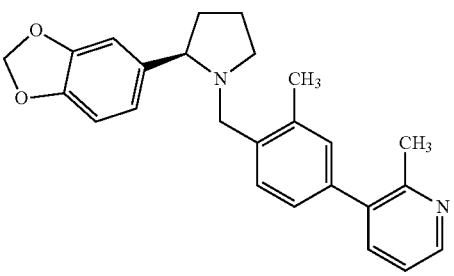 |
| 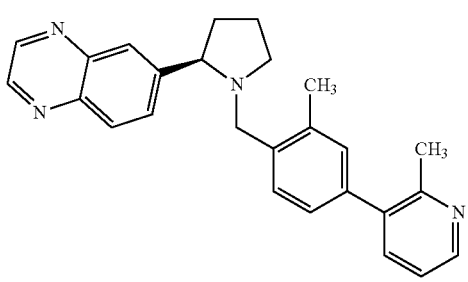 [SMILES: Cc1cc(-c2cccnc2C)ccc1CN1CCC[C@@H]1c1ccc2nccnc2c1] | | 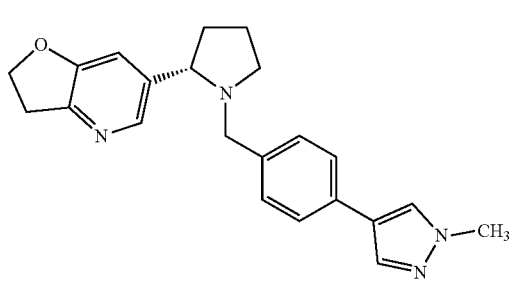 [SMILES: Cn1cc(-c2ccc(CN3CCC[C@H]3c3cnc4c(c3)OCC4)cc2)cn1] |
| 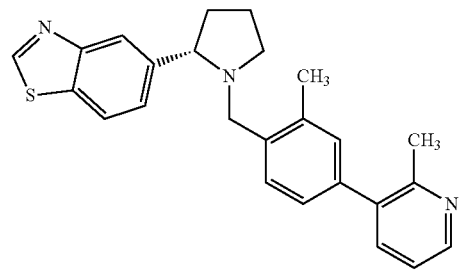 | | 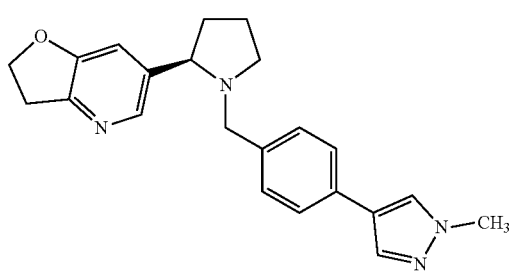 [SMILES: Cn1cc(-c2ccc(CN3CCC[C@@H]3c3cnc4c(c3)OCC4)cc2)cn1] |
| 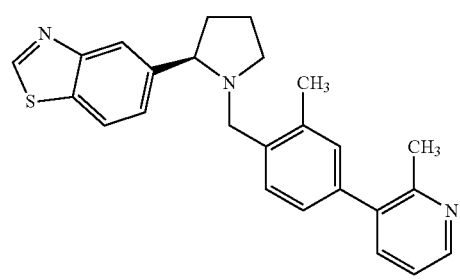 | | 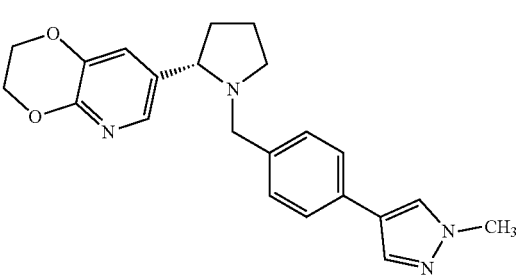 |
| 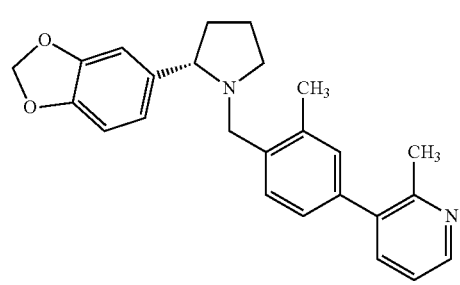 | | 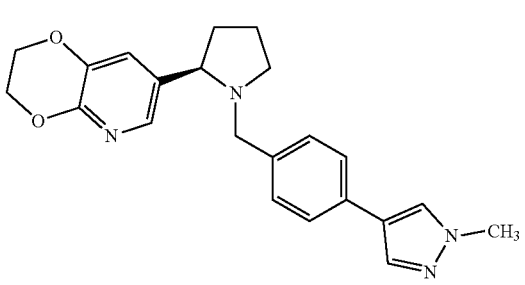 [SMILES: Cn1cc(-c2ccc(CN3CCC[C@@H]3c3cnc4c(c3)OCCO4)cc2)cn1] |

| 137 -continued | 138 -continued |
|---|---|
| Structure | Structure |
| 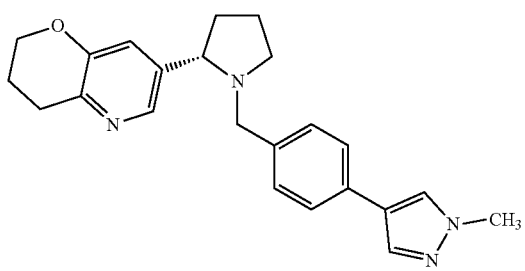 | 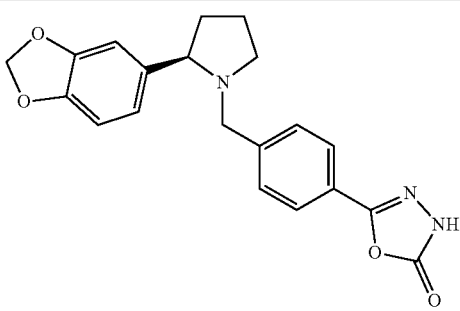 |
| 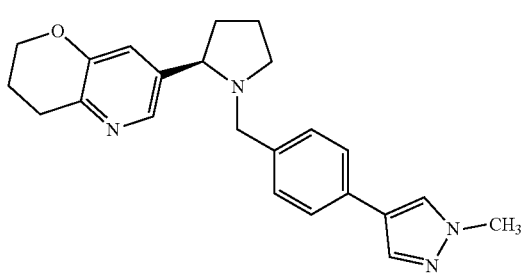 [SMILES: Cn1cc(-c2ccc(CN3CCC[C@@H]3c3cnc4c(c3)OCCC4)cc2)cn1] | 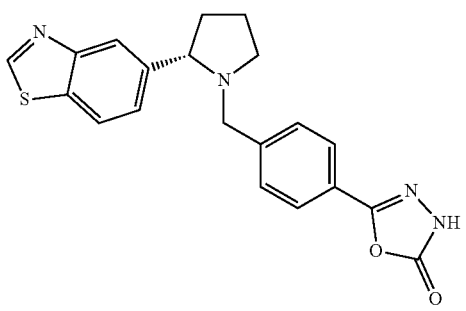 [SMILES: O=c1[nH]nc(-c2ccc(CN3CCC[C@H]3c3ccc4scnc4c3)cc2)o1] |
| 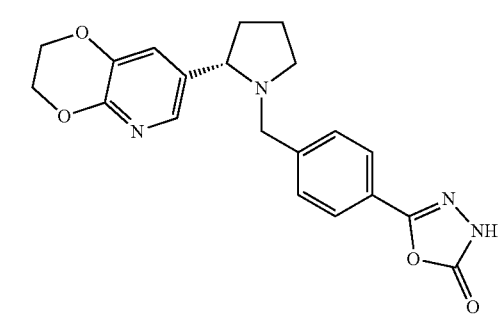 | 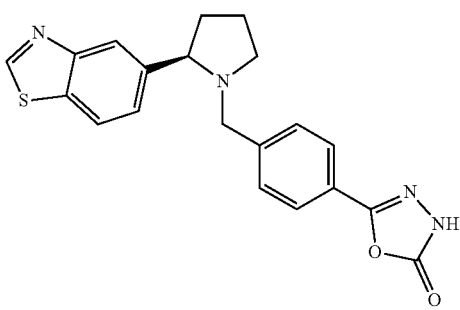 [SMILES: O=c1[nH]nc(-c2ccc(CN3CCC[C@@H]3c3ccc4scnc4c3)cc2)o1] |
| 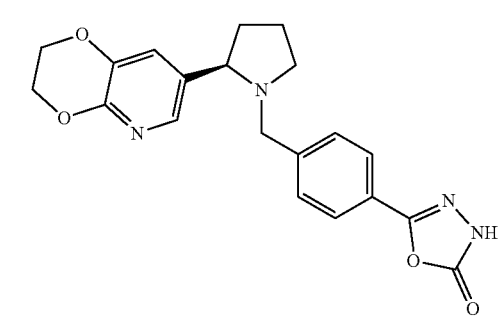 | 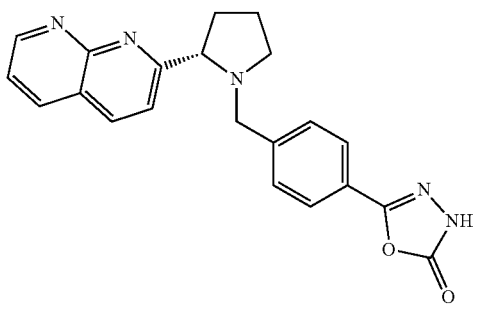 |
| 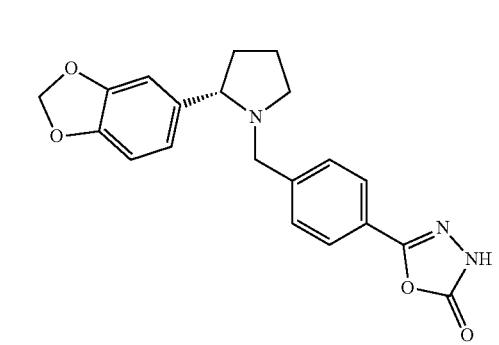 | 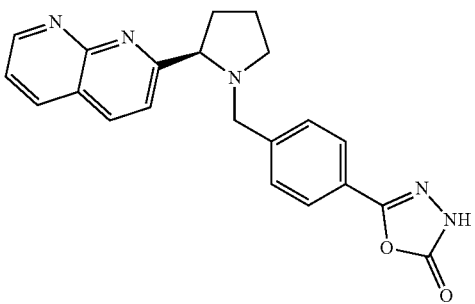 [SMILES: O=c1[nH]nc(-c2ccc(CN3CCC[C@@H]3c3ccc4cccnc4n3)cc2)o1] |

| 139 -continued | 140 -continued |
|---|---|
| Structure | Structure |
| 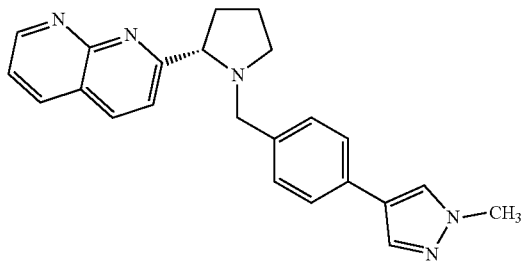 [SMILES: Cn1cc(-c2ccc(CN3CCC[C@H]3c3ccc4cccnc4n3)cc2)cn1] | 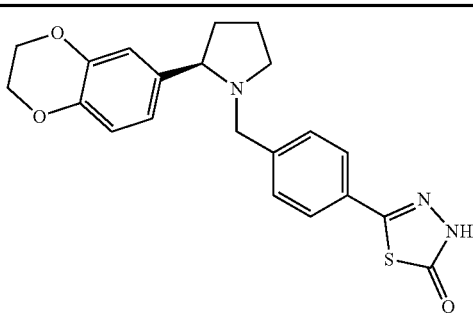 |
| 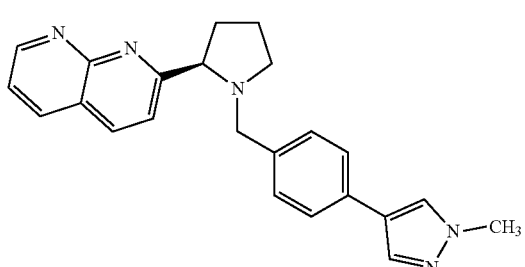 | 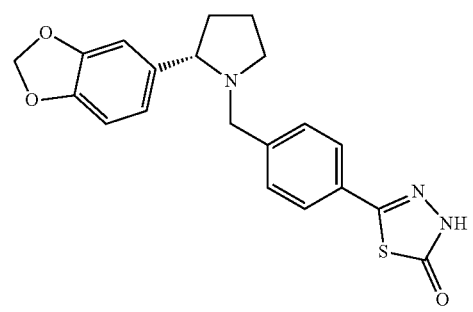 |
| 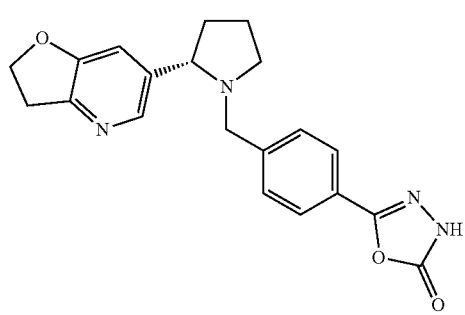 [SMILES: O=c1[nH]nc(-c2ccc(CN3CCC[C@H]3c3cnc4c(c3)OCC4)cc2)o1] | 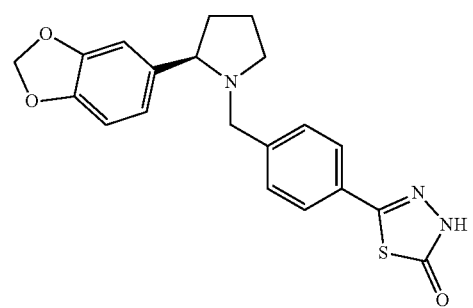 [SMILES: O=c1[nH]nc(-c2ccc(CN3CCC[C@@H]3c3ccc4c(c3)OCO4)cc2)s1] |
| 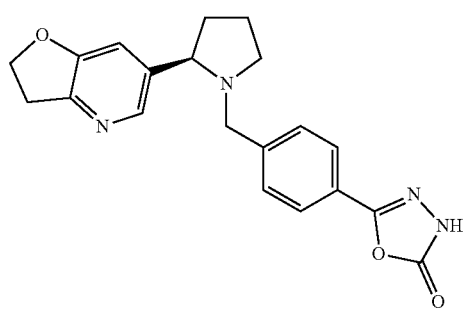 | 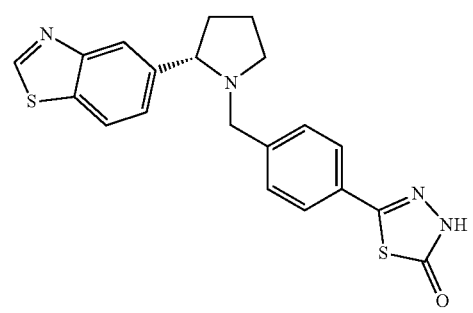 [SMILES: O=c1[nH]nc(-c2ccc(CN3CCC[C@H]3c3ccc4scnc4c3)cc2)s1] |
| 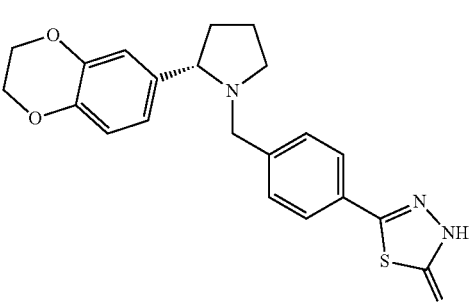 | 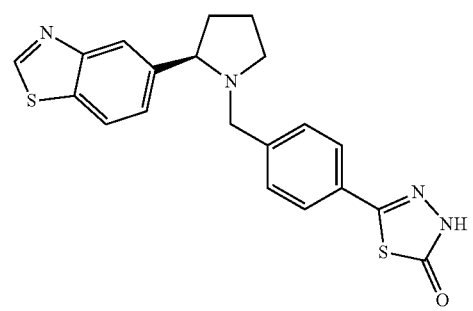 |

| 141 -continued | | 142 -continued |
|---|---|---|
| Structure | | Structure |
| 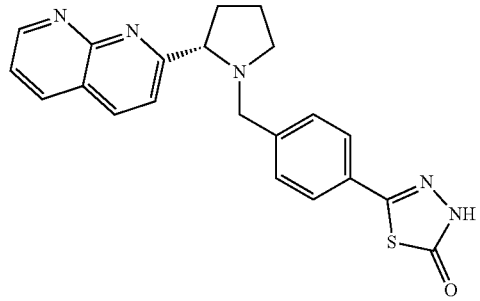 | | 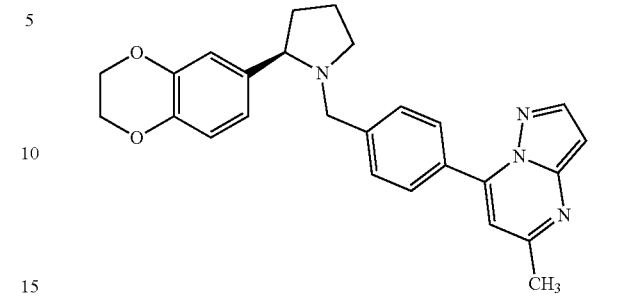 |
| 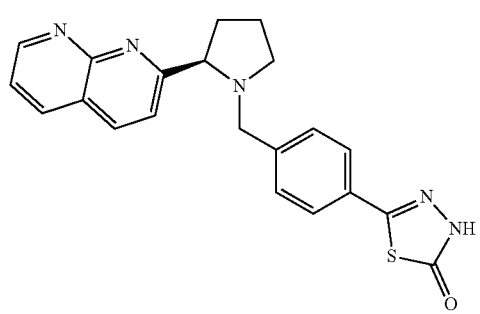 | | 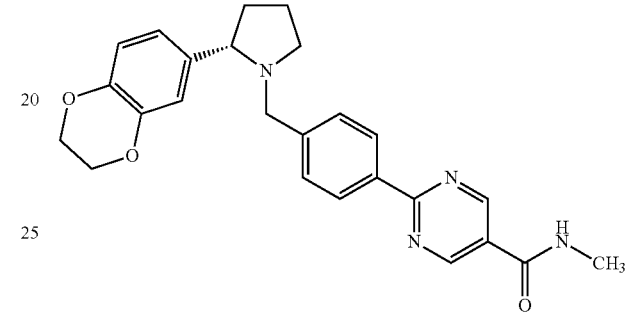 |
| 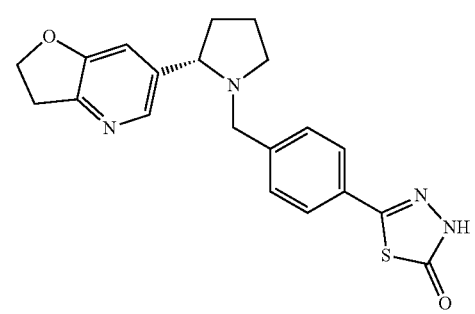 | | 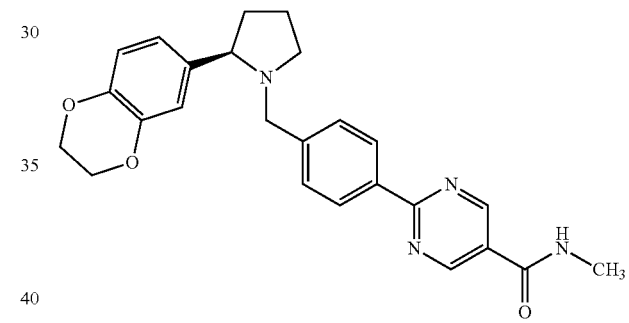 |
| 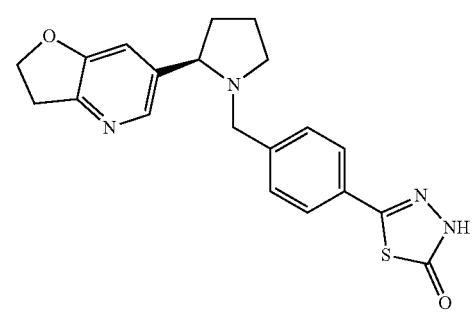 [SMILES: O=c1[nH]nc(-c2ccc(CN3CCC[C@@H]3c3cnc4c(c3)OCC4)cc2)s1] | | 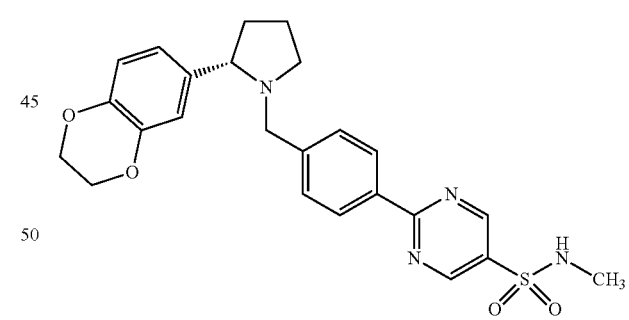 |
| 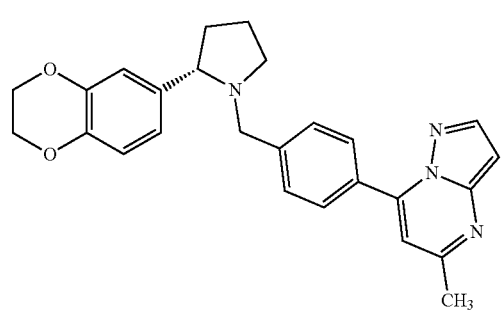 [SMILES: Cc1cc(-c2ccc(CN3CCC[C@H]3c3ccc4c(c3)OCCO4)cc2)n2nccc2n1] | | 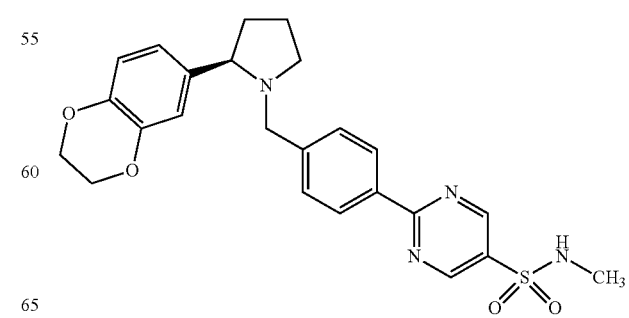 |

| 143 -continued | 144 -continued |
|---|---|
| Structure | Structure |
| 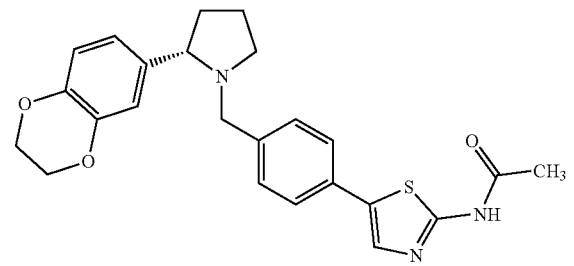 [SMILES: CC(=O)Nc1ncc(-c2ccc(CN3CCC[C@H]3c3ccc4c(c3)OCCO4)cc2)s1] | 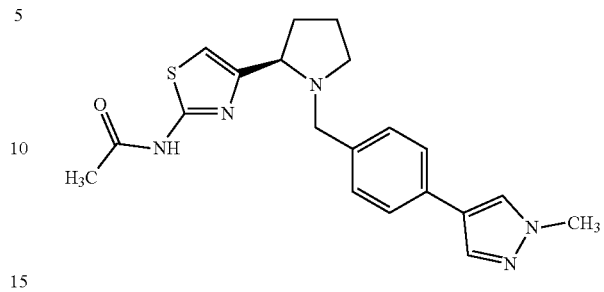 |
| 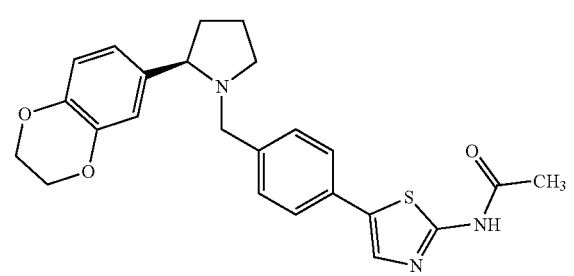 [SMILES: CC(=O)Nc1ncc(-c2ccc(CN3CCC[C@@H]3c3ccc4c(c3)OCCO4)cc2)s1] | 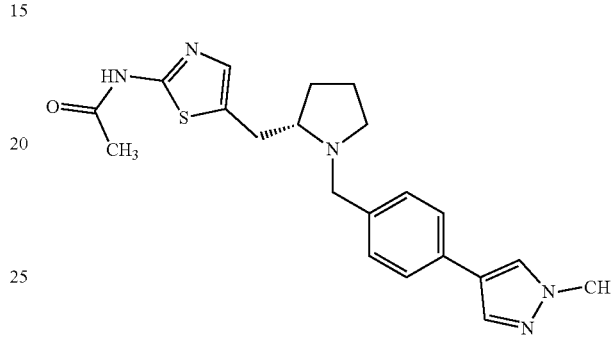 |
| 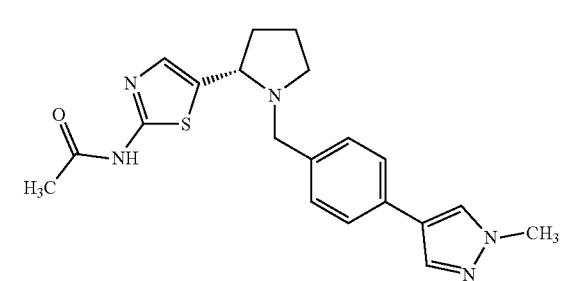 [SMILES: CC(=O)Nc1ncc([C@@H]2CCCN2Cc2ccc(-c3cnn(C)c3)cc2)s1] |  |
| 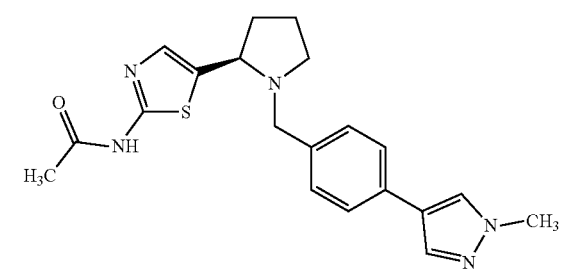 [SMILES: CC(=O)Nc1ncc([C@H]2CCCN2Cc2ccc(-c3cnn(C)c3)cc2)s1]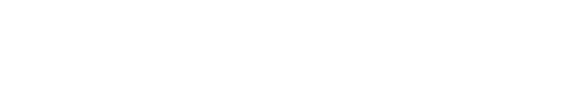 | 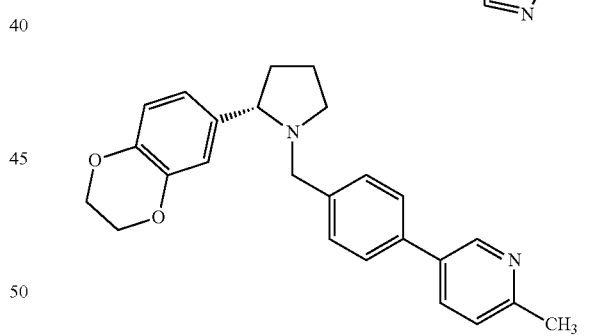 |
| 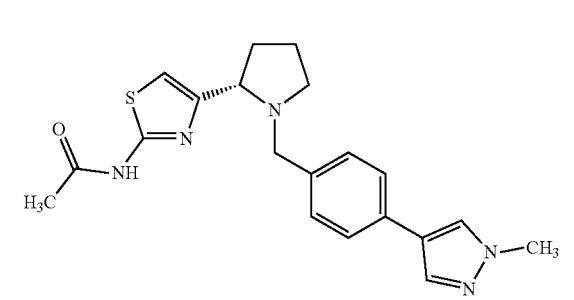 | 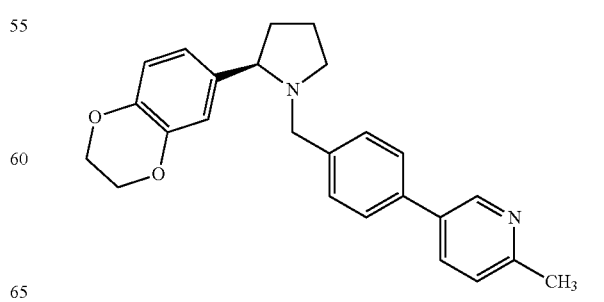 |

| 145 -continued | | 146 -continued | |
|---|---|---|---|
| Structure | | Structure | |
| 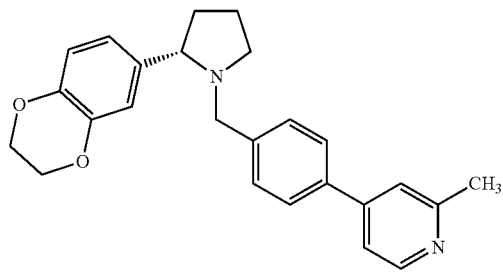 [SMILES: Cc1cc(-c2ccc(CN3CCC[C@H]3c3ccc4c(c3)OCCO4)cc2)ccn1] | | 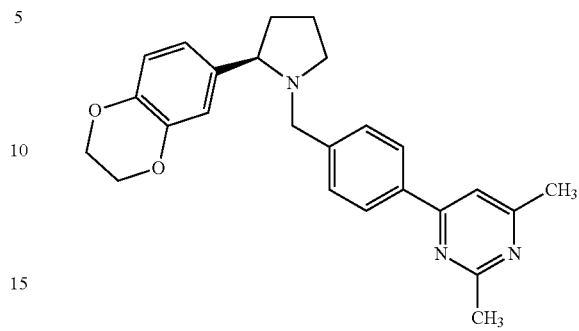 | |
| 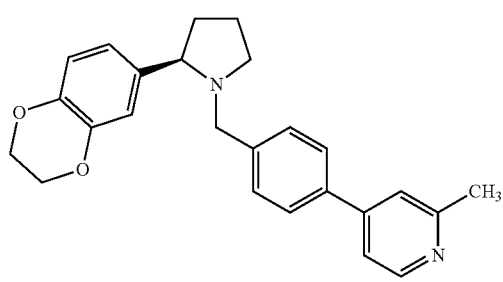 [SMILES: Cc1cc(-c2ccc(CN3CCC[C@@H]3c3ccc4c(c3)OCCO4)cc2)ccn1] | | 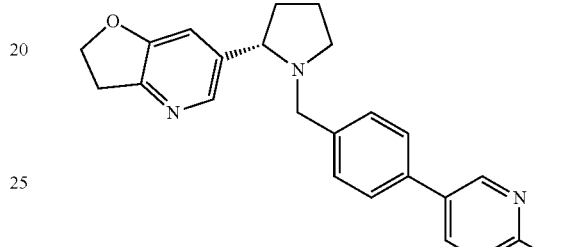 | |
| 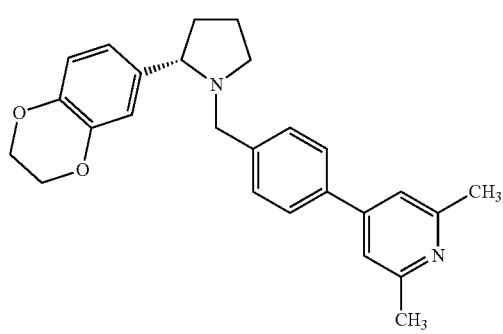 | | 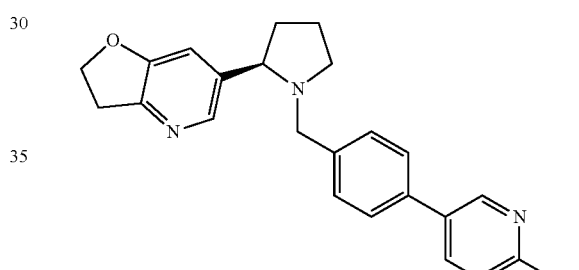 | |
| 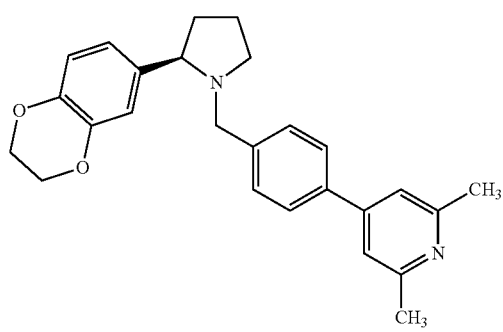 [SMILES: Cc1cc(-c2ccc(CN3CCC[C@@H]3c3ccc4c(c3)OCCO4)cc2)cc(C)n1] | | 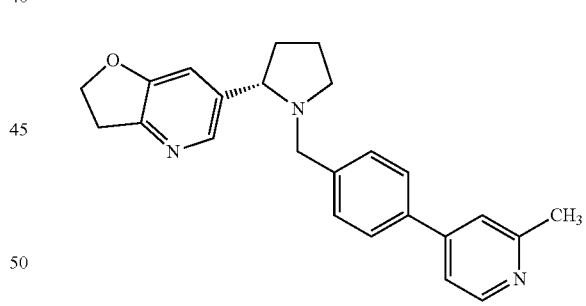 | |
| 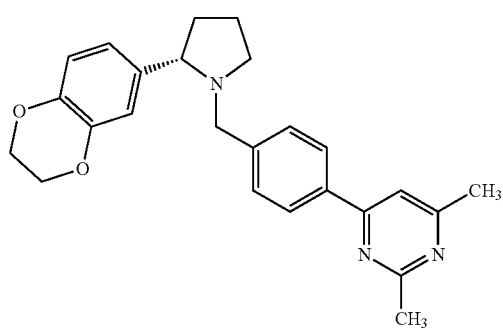 | | 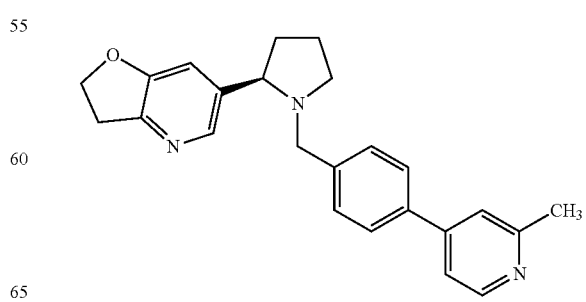 | |

| 147 -continued | | 148 -continued | |
|---|---|---|---|
| Structure | | Structure | |
| 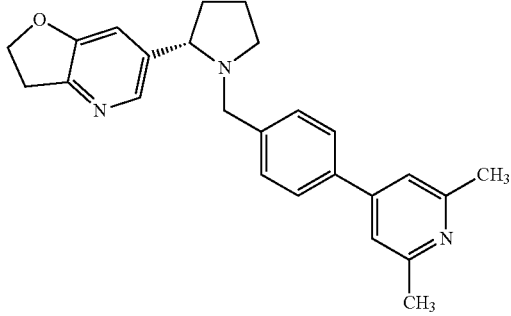 | | 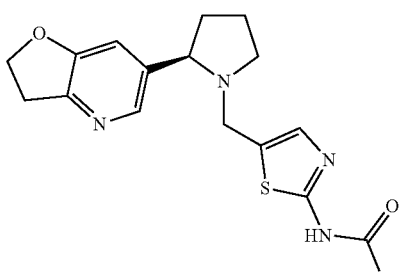 | |
| 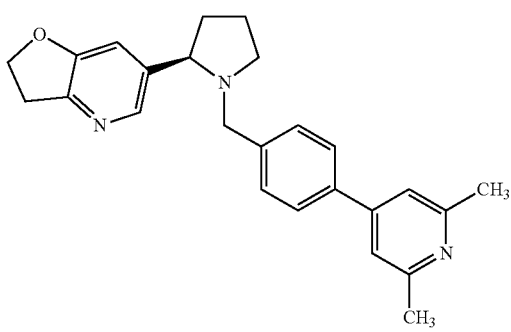 [SMILES: Cc1cc(-c2ccc(CN3CCC[C@@H]3c3cnc4c(c3)OCC4)cc2)cc(C)n1] | | 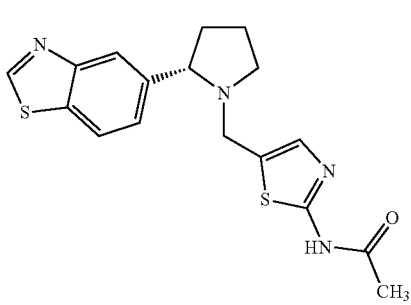 | |
| 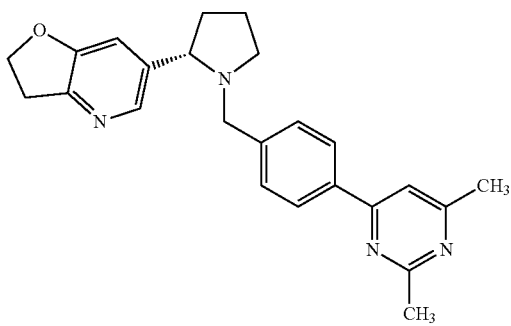 | | 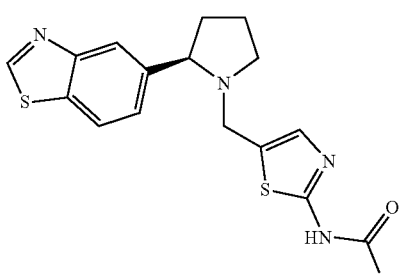 | |
| 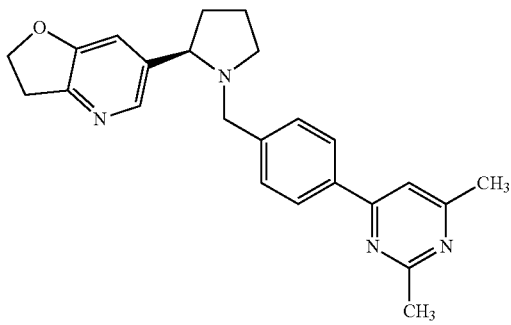 [SMILES: Cc1cc(-c2ccc(CN3CCC[C@@H]3c3cnc4c(c3)OCC4)cc2)nc(C)n1] | | 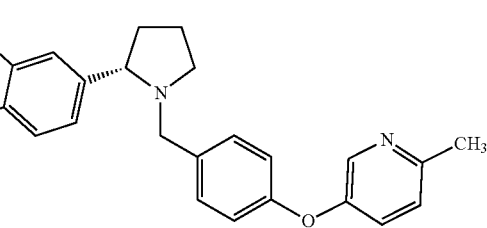 | |
| 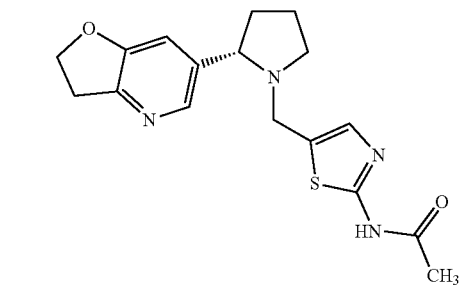 [SMILES: CC(=O)Nc1ncc(CN2CCC[C@H]2c2cnc3c(c2)OCC3)s1] | | 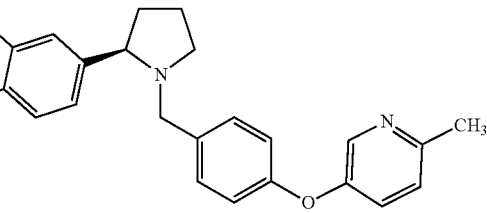 | |
| | | 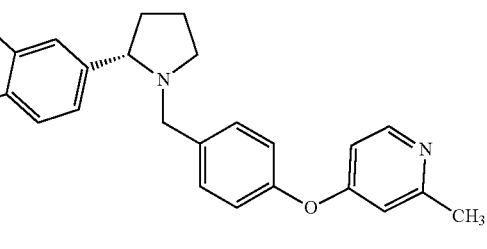 | |

| 149 -continued | 150 -continued |
|---|---|
| Structure | Structure |
| 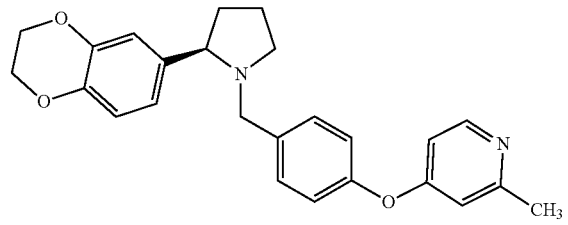 [SMILES: Cc1cc(Oc2ccc(CN3CCC[C@@H]3c3ccc4c(c3)OCCO4)cc2)ccn1] | 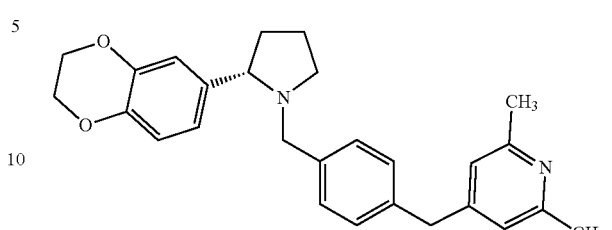 |
| 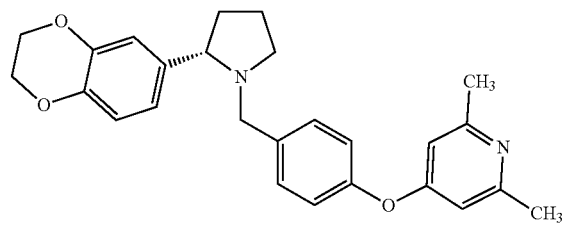 | 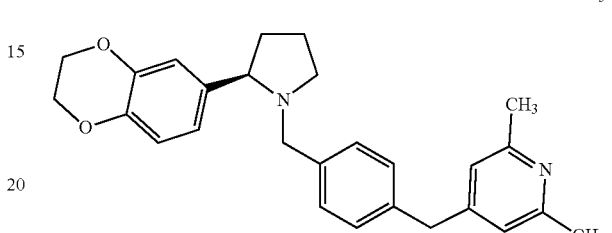 |
| 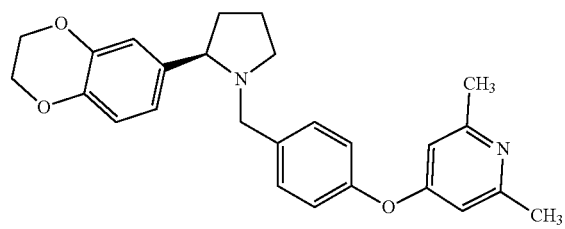 [SMILES: Cc1cc(Oc2ccc(CN3CCC[C@@H]3c3ccc4c(c3)OCCO4)cc2)cc(C)n1] | 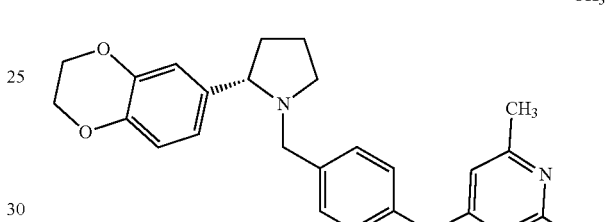 |
| 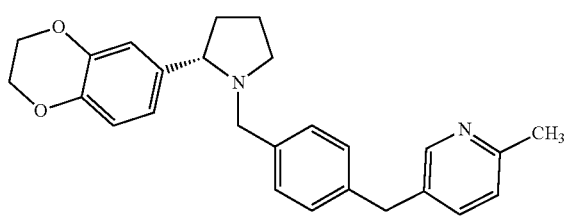 [SMILES: Cc1ccc(Cc2ccc(CN3CCC[C@H]3c3ccc4c(c3)OCCO4)cc2)cn1] | 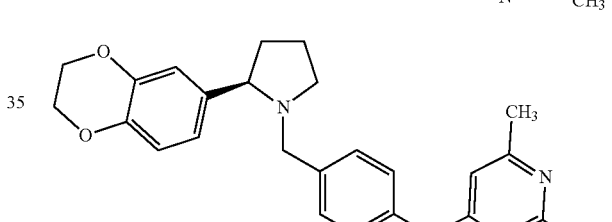 |
| 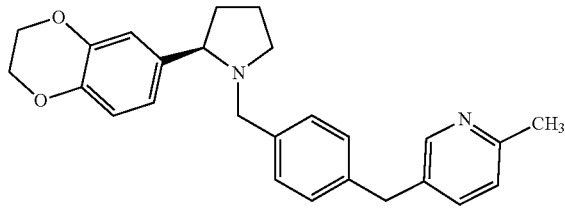 [SMILES: Cc1ccc(Cc2ccc(CN3CCC[C@@H]3c3ccc4c(c3)OCCO4)cc2)cn1] | 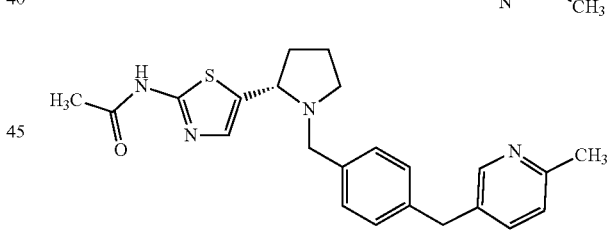 |
| 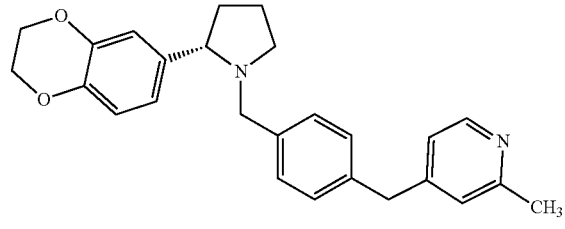 [SMILES: Cc1cc(Cc2ccc(CN3CCC[C@H]3c3ccc4c(c3)OCCO4)cc2)ccn1] | 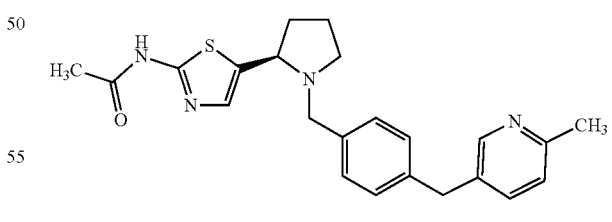 |
| 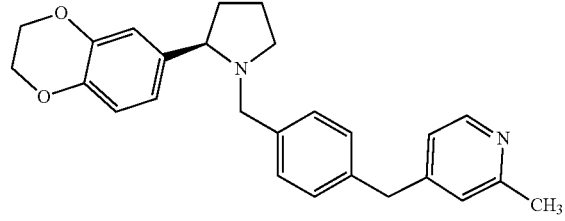 | 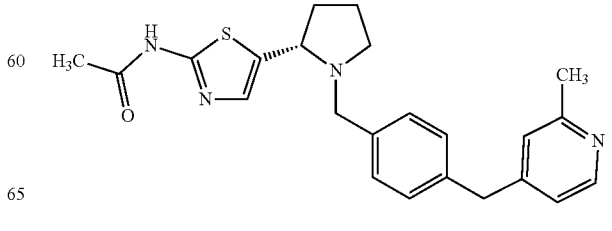 |

| 151 -continued | 152 -continued |
|---|---|
| Structure | Structure |
| 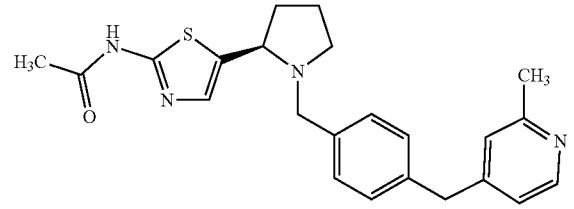 [SMILES: CC(=O)Nc1ncc([C@H]2CCCN2Cc2ccc(Cc3ccnc(C)c3)cc2)s1] | 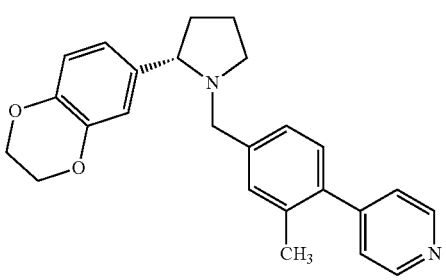 |
| 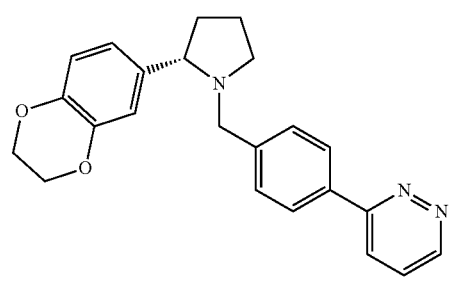 [SMILES: c1cnnc(-c2ccc(CN3CCC[C@H]3c3ccc4c(c3)OCCO4)cc2)c1] | 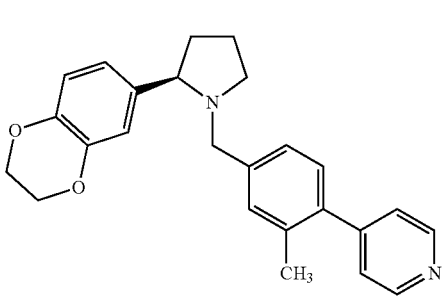 |
| 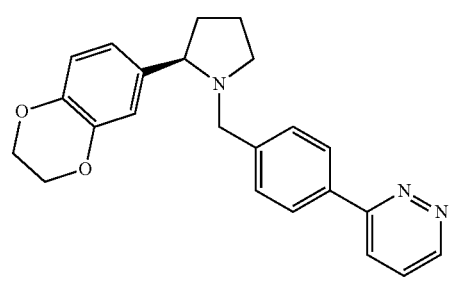 [SMILES: c1cnnc(-c2ccc(CN3CCC[C@@H]3c3ccc4c(c3)OCCO4)cc2)c1] | 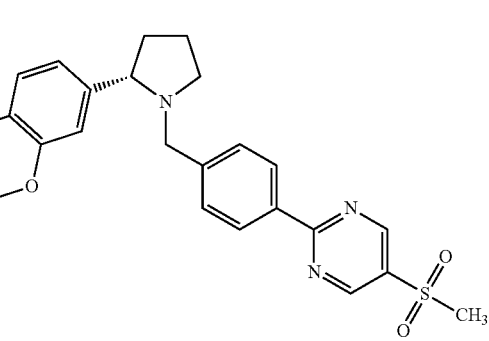 |
| 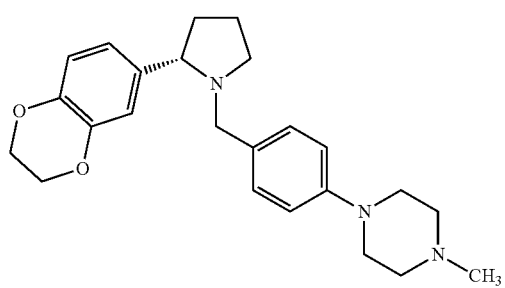 [SMILES: CN1CCN(c2ccc(CN3CCC[C@H]3c3ccc4c(c3)OCCO4)cc2)CC1] | 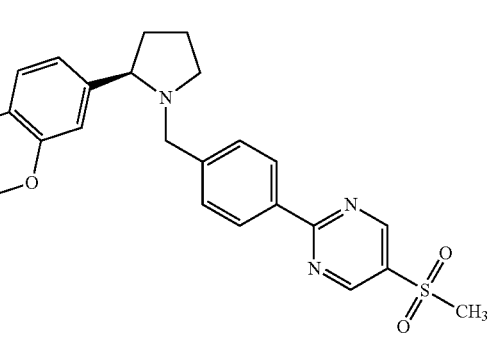 |
|  | |
| 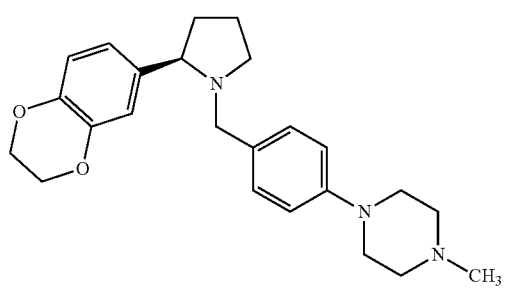 [SMILES: CN1CCN(c2ccc(CN3CCC[C@@H]3c3ccc4c(c3)OCCO4)cc2)CC1] | 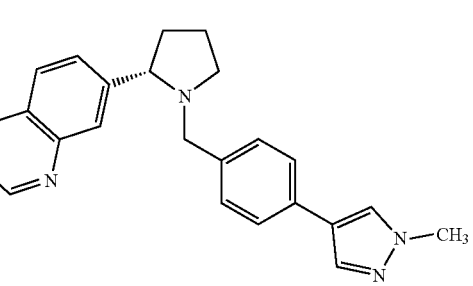 |

| 153 -continued | | 154 -continued | |
|---|---|---|---|
| Structure | | Structure | |
| 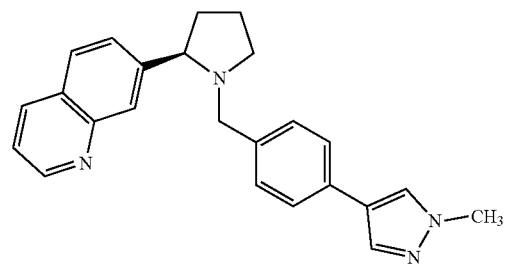 [SMILES: Cn1cc(-c2ccc(CN3CCC[C@@H]3c3ccc4cccnc4c3)cc2)cn1] | | 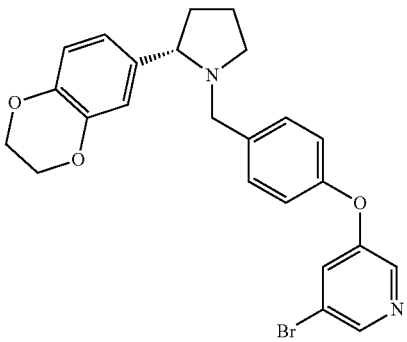 | |
| 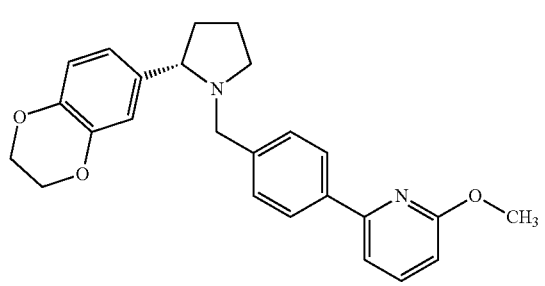 [SMILES: COc1cccc(-c2ccc(CN3CCC[C@H]3c3ccc4c(c3)OCCO4)cc2)n1] | | 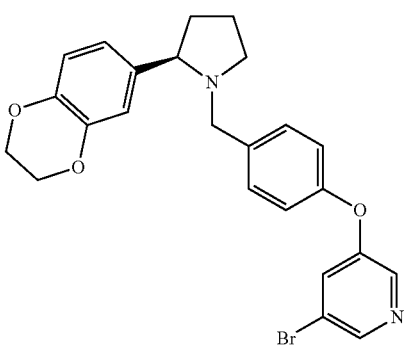 [SMILES: Brc1cncc(Oc2ccc(CN3CCC[C@@H]3c3ccc4c(c3)OCCO4)cc2)c1] | |
| 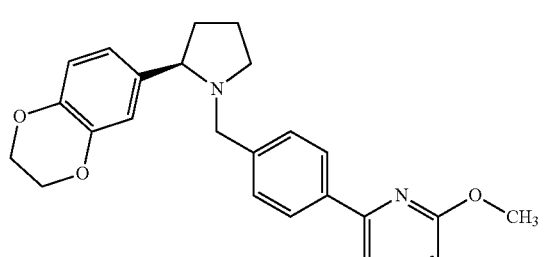 | | 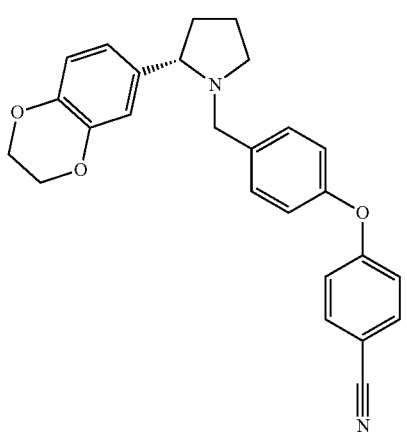 [SMILES: N#Cc1ccc(Oc2ccc(CN3CCC[C@H]3c3ccc4c(c3)OCCO4)cc2)cc1] | |
| 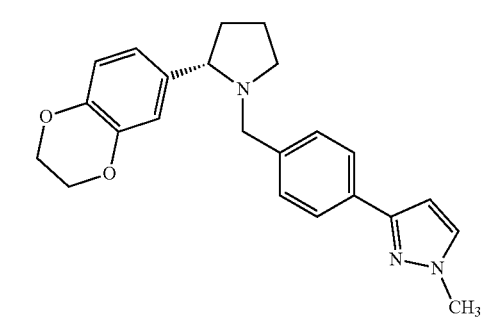 | | 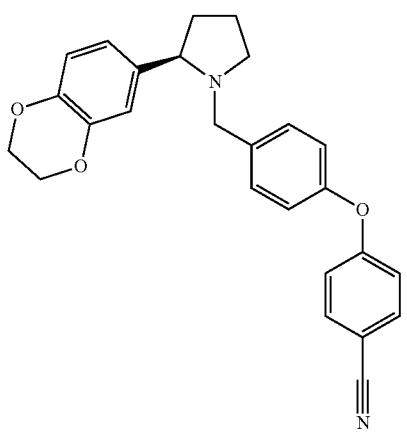 [SMILES: N#Cc1ccc(Oc2ccc(CN3CCC[C@@H]3c3ccc4c(c3)OCCO4)cc2)cc1] | |
| 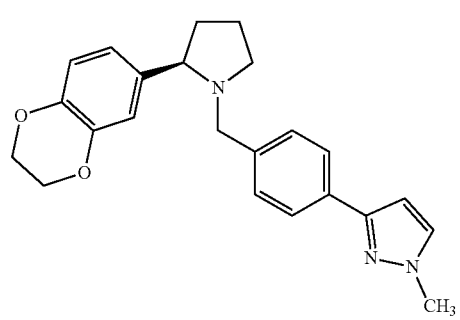 | | | |

| Structure | | Structure |
|---|---|---|
| 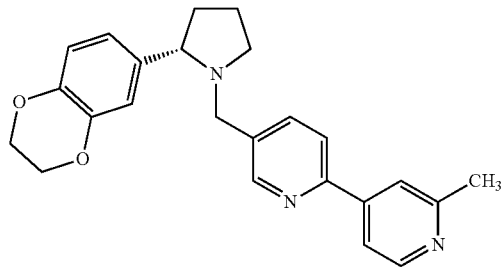 [SMILES: Cc1cc(-c2ccc(CN3CCC[C@H]3c3ccc4c(c3)OCCO4)cn2)ccn1] | | 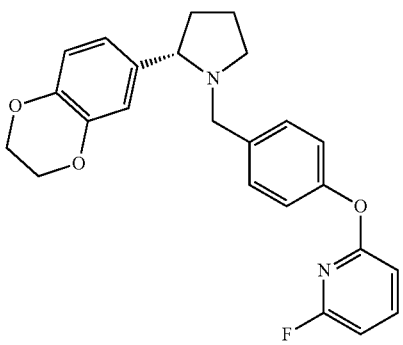 |
| 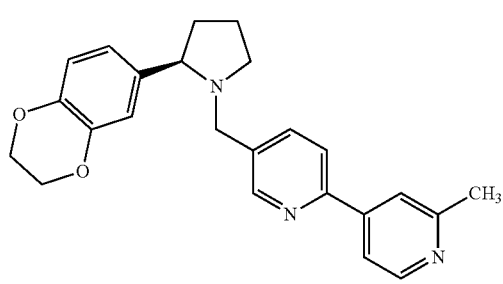 [SMILES: Cc1cc(-c2ccc(CN3CCC[C@@H]3c3ccc4c(c3)OCCO4)cn2)ccn1] | | 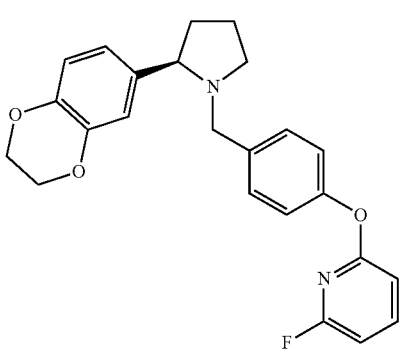 |
| 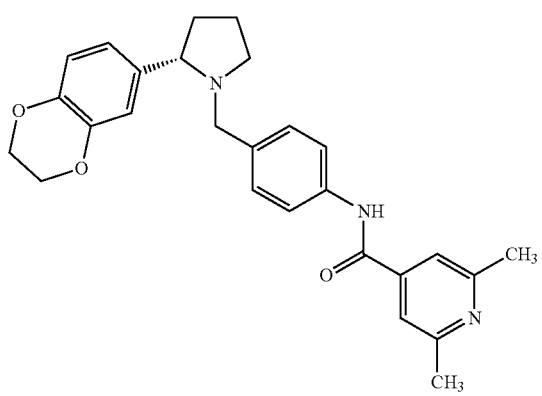 [SMILES: Cc1cc(C(=O)Nc2ccc(CN3CCC[C@H]3c3ccc4c(c3)OCCO4)cc2)cc(C)n1] | | 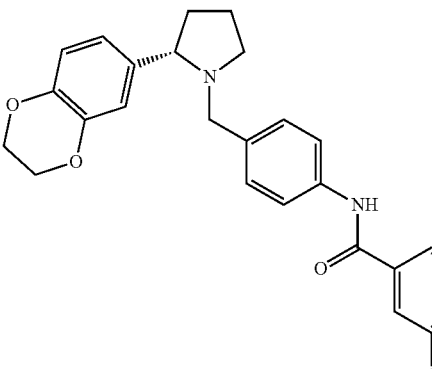 |
|  | |  |

| Structure |
|---|
| 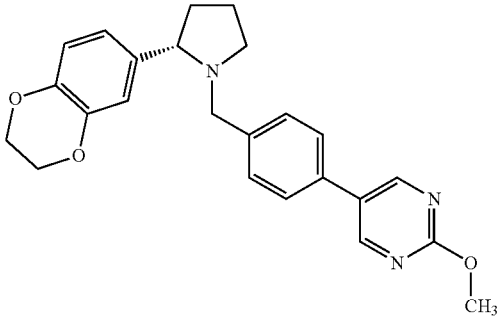 [SMILES: COc1ncc(-c2ccc(CN3CCC[C@H]3c3ccc4c(c3)OCCO4)cc2)cn1] |
| 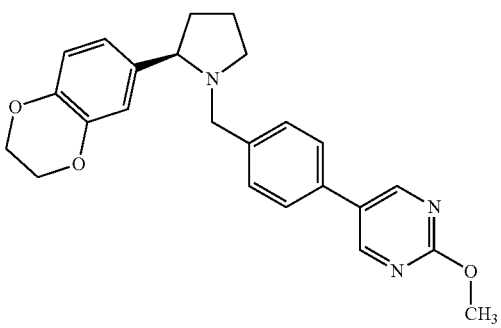 [SMILES: COc1ncc(-c2ccc(CN3CCC[C@@H]3c3ccc4c(c3)OCCO4)cc2)cn1] |
| 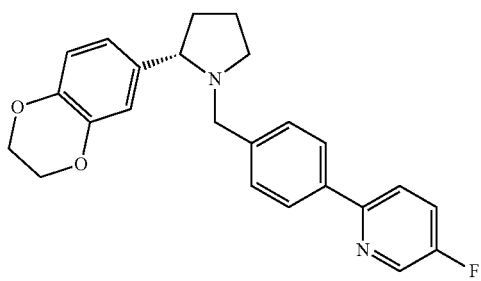 [SMILES: Fc1ccc(-c2ccc(CN3CCC[C@H]3c3ccc4c(c3)OCCO4)cc2)nc1] |
| 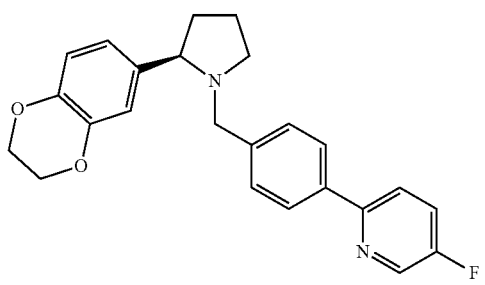 [SMILES: Fc1ccc(-c2ccc(CN3CCC[C@@H]3c3ccc4c(c3)OCCO4)cc2)nc1] |
| 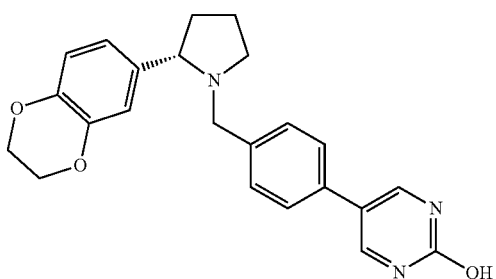 [SMILES: Oc1ncc(-c2ccc(CN3CCC[C@H]3c3ccc4c(c3)OCCO4)cc2)cn1] |

| Structure |
|---|
| 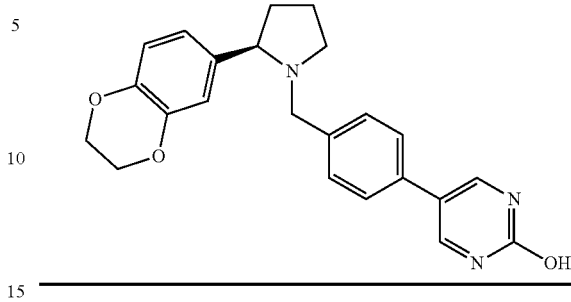 |

Preferred compounds of the present invention demonstrate adequate properties for use as a drug. In particular, such preferred compounds show a high solid state stability, high stability in the presence of liver microsome, high oxidation stability and suitable permeability. Further preferred compounds of the present invention demonstrate their suitability as drugs by potent biological activity, such as the level of O-GlcNAcylation of total proteins measured in brain extracts. Relevant tests for determining such parameters are known by the person skilled in the art, e.g. solid state stability (Waterman K. C. (2007) *Pharm Res* 24(4); 780-790), stability in the presence of liver microsome (Obach R. S. (1999) *Drug Metab Dispos* 27(11); 1350-135) and the permeability (e.g. Caco-2 permeability assay, Calcagno A. M. (2006) *Mol Pharm* 3(1); 87-93); alternatively, they are described in Examples below, such as Example B02 describing the determination of 0-GlcNAcylation level of total proteins measured in brain extracts. Compounds of the present invention that show a high potency in OGA inhibition assays and one or more of the above properties are especially suitable as a drug for the indications mentioned in the present specification.

The compounds according to formula (I) and the starting materials for its preparation, respectively, are produced by methods known per se, as described in the literature, i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The following abbreviations refer respectively to the definitions below: Ac (acetyl), aq (aqueous), h (hour), g (gram), L (liter), mg (milligram), MHz (Megahertz), μM (micromolar), min (minute), mm (millimeter), mmol (millimole), mM (millimolar), m.p. (melting point), equiv (equivalent), mL (milliliter), μL (microliter), ACN (acetonitrile), AcOH (acetic acid), BINAP (2,2'-bis(disphenylphosphino)-1,1'-binaphthalene, BOC (tert-butoxy-carbonyl), CBZ (carbobenzoxy), CDCl$_3$ (deuterated chloroform), CD$_3$OD (deuterated methanol), CH$_3$CN (acetonitrile), c-hex (cyclohexane), DCC (dicyclohexyl carbodiimide), DCM (dichloromethane), DHP (0-(2,4-dinitrophenyl)-hydroxylamine), dppf (1,1'-bis(diphenylphosphino)ferrocene), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-amino-propyl)-3-ethylcarbodiimide), ESI (Electrospray ionization), EtOAc (Ethyl acetate), Et₂O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K₂CO₃ (potassium carbonate), LC (Liquid Chromatography), m-CPBA (3-chloroperbenzoic acid), MD Autoprep (Mass directed Autoprep), MeOH (methanol), MgSO₄ (magnesium sulfate), MS (mass spectrometry), MSH (O-mesitylenesulfonylhydroxylamine), MTBE (Methyl tert-butyl ether), Mtr. (4-Methoxy-2,3,6-trimethylbenzensulfonyl), MW(microwave), NBS (N-bromo succinimide), NaHCO₃ (sodium bicarbonate), NaBH₄ (sodium borohydride), NMM (N-methyl morpholine), NMR (Nuclear Magnetic Resonance), POA (phenoxyacetate), Py (pyridine), PyBOP® (benzotriazole-1-yl-oxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluromium tetrafluoro borate), TEA (triethylamine), TFA (trifluoroacetic acid), THF (tetrahydrofurane), TLC (Thin Layer Chromatography), UV (Ultraviolet).

In general, the compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those having ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by a person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3ʳᵈ Edition 1999.

A "leaving group" LG denotes a chemical moiety which can be removed or replaced by another chemical group. Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p-tolylsulfonyloxy). When a leaving group LG is attached to an aromatic or heteroaromatic ring, LG can denote in addition SO₂-alkyl or F. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example through addition of HOBt, N-hydroxysuccinimide or HATU.

Depending on the nature of A, Z and W, different synthetic strategies may be selected for the synthesis of compounds of Formula (Ia) and (Ib). In the process illustrated in the following schemes, A, Z and W are as above-defined in the description unless otherwise mentioned.

Compounds of Formula (Ia) and (Ib), wherein A, Z and W are defined as above, can be prepared from alternative compounds of Formula (Ia) and (Ib), using suitable interconversion procedures such as those described hereinafter in the examples, or conventional interconversion procedures well known by one skilled in the art.

A racemic mixture of compounds of formula (Ia) and (Ib), compound of formula (I), can be separated into compounds of formula (Ia) and (Ib) by chiral chromatography or by chiral resolution, re-crystallization with use of an optically active acid, using methods known by one skilled in the art and as described below in the examples (Scheme 1).

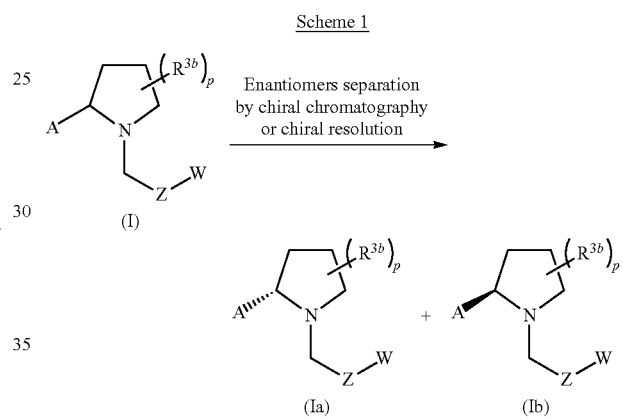

Compounds of formula (I), wherein A, R³ᵇ, Z, W and p are defined as above, can be prepared from alternative compounds of formula (I), using methods and reactions known by a person skilled in the art. Such reactions can be but are not limited to aromatic substitution, alkylation, metal catalzed cross-coupling reaction.

Compounds of formula (I), wherein A, R³ᵇ, Z, W and p are defined as above, can be prepared from the corresponding amine (III) by reductive alkylation with aldehyde (III), using conditions known to the one skilled in the art, such as but not limited to the use of NaBH(OAc)₃ as reducing agent, in the presence of one equivalent of AcOH in DCE (Scheme 2). Alternatively, reductive alkylation can be performed in two steps, with first imine formation, that can be catalysed by Ti(OiPr)₄, followed by reduction with suitable reducing agent, such as but not limited to NaBH₄ in MeOH (Abdel-Magid, A. F. at al. *J. Org. Chem.* 1996, 61, 3849-3862). Alternatively, aldehydes (III) can be reduced into the corresponding alcohol (IV) using usual reductive agents such as NaBH₄ in an alcoholic solvent, such as MeOH. Alcohol functionality can be then transformed into a suitable leaving group, such as but not limited to Cl or OMs, using conditions known to a person skilled in the art. The addition of amine (II) to intermediates (V) would yield the formation of compounds (I) (Scheme 2). The addition of amines (IIa) or (IIb) to the same intermediates would yield the formation of compounds (Ia) or (Ib) respectively.

Scheme 2

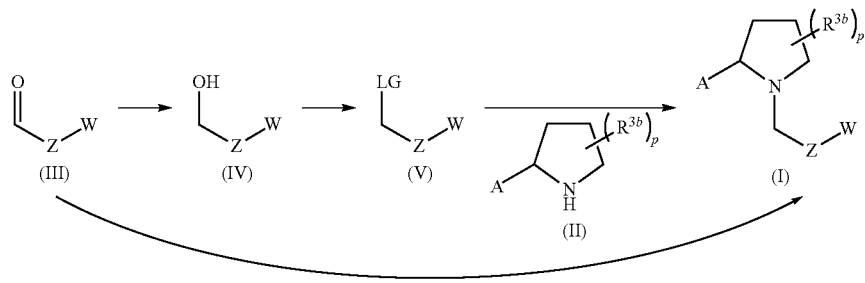

Compounds of formula (II) can be separated into compounds of formula (IIa) and (IIb) by chiral chromatography or chiral resolution by re-crystallization with an optically active acid, using methods known by one skilled in the art and as described below in the examples (Scheme 3). Compounds of formula (IIa) and (IIb) can be respectively transformed into compounds of formula (Ia) and (Ib).

Scheme 3

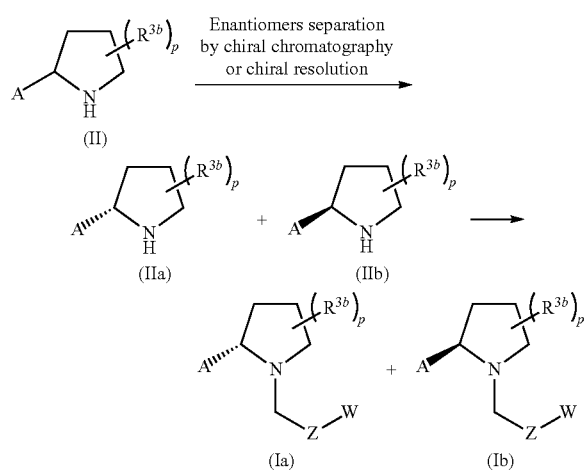

Alternatively, amines of formula (II), (IIa) and (IIb) can be synthesized from different precursors, depending on the nature of A, $R^{3b}$ and p, using methods known by a person skilled in the art. Compound of formula (VI), where Hal is an halogen as defined above, is first activated into a nucleophile (VII), such as but not limited to an alkyl lithium or a Grignard reagent (M=Li or MgBr). Amine of formula (II) is obtained by the addition of compound (VII) to a lactame (VIII), followed by amine (IX) deprotection and its cyclization by reductive animation (Scheme 4).

Scheme 4

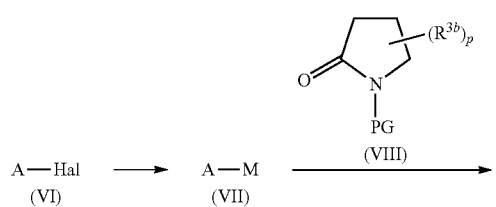

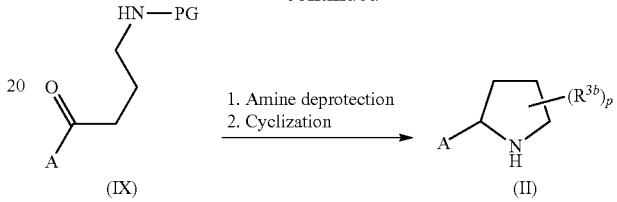

The sulfoximine group and related functionalities as indicated in the definitions can be introduced or generated at any stage of the synthesis of compounds of formulat (1), as described below in the examples using methods known by one skilled in the art (Frings, M. et al. *Eur. J. Med. Chem.* 2017, 126, 225-245 and cited references).

When a reaction is preferably performed under basic conditions, a suitable base might be selected from metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia), alkaline metal carbonates (e.g., sodium bicarbonate) and several organic bases (e.g., N,N-diisopropylethylamine, piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to TFA, DMF, dichloromethane, THF, $H_2O$, methanol, tert. butanol, tert. amylalcohol, triethylamine or dioxane.

Depending on the conditions used, the reaction time is between a few minutes and 14 days, the reaction temperature is between about −80° C. and 140° C., normally between −50° C. and 120° C., preferably between −20° C. and 100° C.

The compounds of formula (I) and sub-formulae thereof are accessible via the routes above. The starting materials, are usually known to the skilled artisan, or they can be easily prepared by known methods.

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization.

General chemical modifications are known to the one skilled in the art. Halogenation of aryls or hydroxy substitution by halogens of acids, alcohols, phenols, and their tautomeric structures can be preferably carried out by use of $POCl_3$, or $SOCl_2$, $PCl_5$, $SO_2Cl_2$. In some instances oxalyl chloride is also useful. Temperatures can vary from 0° C. to reflux depending on the task to halogenate a pyridone structure or a carboxylic acid or a sulfonic acid. Time will also be adjusted from minutes to several hours or even overnight. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like $Et_3N$, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd $(PPh_3)_4$, or $Pd(OAc)_2$, $PdCl_2$ type precursors of PdO catalysts have advanced to more complex ones with more efficient ligands. In C—C arylations, instead of boronic acids and esters, aryl-trifluoroborate potassium salts (Suzuki-Miyaura coupling), organo silanes (Hiyama coupling), Grignard reagents (Kumada), organozinc compounds (Negishi coupling) and stannanes (Stille coupling) may be useful. This experience can be transferred to N- and O-arylations. Numerous papers and methods are available and useful for the one skilled in the art in respect of N-arylation and even of electron deficient anilines, and with aryl chlorides and anilines as well as for O-arylation by using Cu catalysis and Pd catalysis.

In the final step of the processes above, a salt of the compounds, preferably those of formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by the reaction of the compound with a suitable base to give the corresponding base-addition salt. Such bases are, for example, alkali metal hydroxides, including potassium hydroxide, sodium hydroxide and lithium hydroxide; alkaline earth metal hydroxides, such as magnesium hydroxide, calcium hydroxide and barium hydroxide; alkali metal alkoxides, for example potassium ethoxide and sodium propoxide; and various organic bases, such as piperidine, diethanolamine and N-methyl-glucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. The aluminum salts of the compounds according to the invention are likewise included. In the case of certain compounds of the formula I, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as methanesulfonate, ethanesulfonate, toluenesulfonate and benzenesulfonate, and other organic acids and corresponding salts thereof, such as carbonate, acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprate, caprylate, chloride, chlorobenzoate, citrate, cyclamate, cinnamate, cyclopentanepropionate, digluconate, dihydrogenphosphate, dinitrobenzoate, dodecylsulfate, ethanesulfonate, formate, glycolate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Both types of salts may be formed or interconverted preferably using ion-exchange resin techniques.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine. This is not intended to represent a restriction.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound of the formula (I) contains more than one group which is capable of forming pharmaceutically acceptable salts of this type, the formula I also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, di-O-p-toluoyl-tartaric acid, mandelic acid, malic acid, lactic acid, suitable N-protected amino acids (for example N-benzoylproline or N-benzenesulfonylproline), or the various optically active camphorsulfonic acids. The suitably formed salt with optically active acid is crystallized using various combinations of solvents, such as but not limited to methanol, ethanol, isopropanol, THF, water, diethyl ether, acetone, methyl tert-butyl ethers and other solvents known to the person skilled in the art. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

When discovering and developing therapeutic agents, the person skilled in the art attempts to optimize pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula (I) with improved stability through resistance to such oxidative metabolism. Significant improvements in the pharmacokinetic profiles of compounds of the formula (I) are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

A further aspect of the invention relates to the use of compounds according to formula (I) and/or physiologically acceptable salts thereof for inhibiting a glycosidase. Such use may be therapeutic or non-therapeuic in character. The term "inhibition" denotes any reduction in glycosidase activity, which is based on the action of the specific inventive compounds capable to interact with the target glycosidase in such a manner that makes recognition, binding and blocking possible. It shall be understood that the compounds of the invention finally interact with the target to unfold the effect. The compounds are characterized by such an appreciable affinity to at least one glycoside hydrolase which ensures a reliable binding and preferably a complete blocking of glycosidase activity. More preferably, the substances are mono-specific in order to guarantee an exclusive and directed recognition with the chosen single glycosidase target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is preferably characterized by high affinity, high selectivity and minimal or even lacking cross-reactivity to other target molecules to exclude unhealthy and harmful impacts to the treated subject.

In a preferred embodiment of the present invention, the glycosidase comprises glycoside hydrolases, more preferably family 84 glycoside hydrolases, most preferably O-glycoprotein-2-acetamido-2deoxy-β-D-glucopyranosidase (OGA), highly preferably a mammalian O-GlcNAcase. It is particularly preferred that the compounds of formula (I) according to the invention selectively bind an O-GlcNAcase, e.g. thereby selectively inhibiting the cleavage of 2-acetamido-2-deoxy-β-D-glucopyranoside (O-GlcNAc) while they do not substantially inhibit a lysosomal β-hexosaminidase.

The compounds according to the invention preferably exhibit an advantageous biological activity, which is easily demonstrated in enzyme activity assays as described herein or known from prior art. In such in-vitro assays, the compounds preferably exhibit and cause an inhibitory effect. $IC_{50}$ is the concentration of a compound that produces 50% of the maximal inhibition for that compound. The glycosidase target is especially half inhibited by the compounds described herein if the concentration of the compounds amounts to less than 100 µM, preferably less than 10 µM, more preferably less than 1 µM, most preferably less than 0.2 µM. Most preferably, compounds of Formula (I) exhibit an $IC_{50}$ less than 0.02 µM.

A further aspect of the present invention relates to a method for inhibiting a glycosidase, wherein a system capable of expressing the glycosidase, particularly expressing said glycosidase, is contacted with at least one compound of formula (I) according to the invention and/or physiologically acceptable salts thereof, under conditions such that said glycosidase is inhibited. In a preferred embodiment of the method, the glycosidase is contacted with a compound selectively inhibiting O-GlcNAcase and more preferably having an $IC_{50}$ of less than 0.2 µM. It is also preferred that the method is performed in-vitro and/or that the method is not practiced on the human body. A cellular system is preferred in the scope of the method. The cellular system is defined to be any subject provided that the subject comprises cells. The cell refers to any type of primary cells or genetically engineered cells, whether in the isolated status, in culture, as cell line, assembled in tissue, organs or intact laboratory mammals, provided that they are capable of expressing the glycosidase. It shall also be understood that the cell expresses the glycosidase as inherent pre-condition to put the methods of inhibition into practice. Although it is particularly preferred that the cells are capable of expressing or do express the glycosidase, it shall not be excluded that glycosidase-deficient cells can be used and the glycosidase is artificially added to the cellular system. The assay of the invention can be even completely performed in-vitro such that the cell is waived but a glycosidase is contacted with at least one compound of formula (I) according to the invention and/or physiologically acceptable salts thereof. Hence, an amount of isolated glycosidase is provided in crude or purified form for this purpose.

As discussed herein, the glycosidase-signaling pathways are relevant for various diseases, preferably neurodegenerative diseases, diabetes, cancer, cardiovascular diseases and stroke. Accordingly, the compounds according to the invention are useful in the prophylaxis and/or treatment of diseases that are dependent on the said signaling pathways by interaction with one or more of them. The present invention therefore relates to the therapeutic and non-therapeutic use of compounds according to the invention as inhibitors of the signaling pathways described herein, preferably of the OGA-mediated signaling.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate glycosidase activity, usually between about one hour and one week. In-vitro treatment can be carried out using cultivated cells from any sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing OGA-dependent signal transduction pathways in animals and/or cell culture models or in the clinical diseases mentioned in this application.

The use according to the previous paragraphs of the specification may be either performed in-vitro or in-vivo models. The inhibition can be monitored by the techniques described in the course of the present specification. The in-vitro use is preferably applied to samples of humans suffering from neurodegenerative diseases, diabetes, cancer, cardiovascular diseases and stroke. Testing of several specific compounds and/or derivatives thereof makes the selection of that active ingredient possible that is best suited for the treatment of the human subject. The in-vivo dose rate of the chosen derivative is advantageously pre-adjusted to the glycosidase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of glycosidase activity, preferably OGA activity, if expedient.

A further aspect of the invention relates to a medicament comprising at least one compound according to the invention and/or pharmaceutically usable derivatives, salts, solvates and stereoisomers thereof, including mixtures thereof in all ratios. A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with OGA activity, in such a way that a pathogenic modification of their overall condition or of the condition of particular regions of the organism could establish at least temporarily.

Consequently, the invention also relates to a pharmaceutical composition comprising as active ingredient an effective amount of at least one compound of formula (I) according to the invention and/or physiologically acceptable salts thereof together with pharmaceutically tolerable adjuvants and/or excipients.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The present compounds are suitable for combination with agents known to those of skill in the art (e.g., WO 2008/025170) and are useful with the compounds of the invention.

In some embodiments, a compound according to the invention, or for use according to the invention, may be provided in combination with any other active agents or pharmaceutical compositions where such combined therapy may be useful to modulate O-GlcNAcase activity, for example to treat neurodegenerative, inflammatory, cardiovascular, or immunoregulatory diseases or any condition described herein. In some embodiments, a compound according to the invention, or for use according to the invention, may be provided in combination with one or more agents useful in the prevention or treatment of tauopathies and Alzheimer's disease. Examples of such agents may include, without limitation, Acetylcholine esterase inhibitors (AChEIs) such as Aricept® (Donepezil), Exelon®(Rivastigmine), Razadyne® (Razadyne ER®, Reminyl®, Nivalin®, Galantamine), Cognex®(Tacrine), NMDA antagonists such as memantine (Axura®, Ebixa®), Huperzine A, Phenserine, Debio-9902 SR (ZT-1 SR), Zanapezil (TAK0147), ganstigmine, NP7557, α7 nicotinic acetylcholine receptor agonists, 5-HT6 receptor antagonists, M1 muscarinic acetylcholine receptor agonists and positive allosteric modulators, etc Tau aggregation inhibitors such as methylene blue, etc Agents blocking tau aggregation seeding and propagation such as tau antibodies and tau vaccines, etc Microtubule stabilizers such as AL-108, AL-208, paclitaxel, etc Amyloid-β(A β) peptide lowering agents such as β-secretase (BACE-1) inhibitors, senile plaque-clearing biologics such as Aβ antibodies and Aβ vaccines The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intra-dermal) methods. Such formulations can be prepared using processes known in the pharmaceutical art by, e.g., combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Accordingly, the invention also relates to a pharmaceutical composition comprising as active ingredient an effective amount of at least one compound of formula (I) according to the invention and/or physiologically acceptable salts thereof together with pharmaceutically tolerable adjuvants for oral administration, optionally in combination with at least another active pharmaceutical ingredient. The prior teaching of the present specification concerning administration route and combination product, respectively, is valid and applicable without restrictions to the combination of both features if expedient.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neurodegenerative diseases, for example tauopathies and Alzheimer's disease, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by OGA activity. It is particularly preferred that the diseases are neurodegenerative diseases, diabetes, cancer, cardiovascular diseases and stroke, more preferably neurodegenerative diseases, most preferably one or more tauopathies, highly preferably Alzheimer's disease and dementia. It shall be understood that the host of the compound is included in the present scope of protection according to the present invention.

Another aspect of the present invention relates to compounds of formula (I) according to the invention and/or physiologically acceptable salts thereof for use in the prophylactic or therapeutic treatment and/or monitoring of diseases that are caused, mediated and/or propagated by OGA activity. Another aspect of the invention concerns compounds of formula (I) according to the invention and/or physiologically acceptable salts thereof for use in the prophylactic or therapeutic treatment and/or monitoring of neurodegenerative diseases, diabetes, cancer, cardiovascular diseases and stroke. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of neurodegenerative diseases, diabetes, cancer, cardiovascular diseases and stroke.

Another aspect of the invention relates to a method for treating a disease that is caused, mediated and/or propagated by OGA activity, wherein an effective amount of at least one compound of formula (I) according to the invention and/or physiologically acceptable salts thereof is administered to a mammal in need of such treatment. Another aspect of the invention relates to a method for treating neurodegenerative diseases, diabetes, cancer, cardiovascular diseases and stroke, preferably a tauopathy, wherein an effective amount of at least one compound of formula (I) according to the invention and/or physiologically acceptable salts thereof is administered to a mammal in need of such treatment. The preferred treatment is an oral administration. The prior teaching of the invention and its embodiments is valid and applicable without restrictions to the methods of treatment if expedient.

The neurodegenerative disease or condition is more preferably selected from the group of one or more tauopathies and Alzheimer's disease, Amyotrophic lateral sclerosis (ALS), Amyotrophic lateral sclerosis with cognitive impairment (ALSci), Argyrophilic grain disease, Behavior variant frontotemporal dementia (bvFTD), Bluit disease, Corticobasal degeneration (CBP), Dementia pugilistica, Dementia with Lewy Bodies, Diffuse neurofibrillary tangles with calcification, Down's syndrome, Familial British dementia, Familial Danish dementia, Frontotemporal dementia with parkinsonism linked to chromosome 17 (FTDP-17), Frontotemporal Lobar Degeneration (FTLD), Ganglioglioma, Gangliocytoma, Gerstmann-Straussler-Scheinker disease, Globular glial tauopathy, Guadeloupean parkinsonism, Hallevorden-Spatz disease (neurodegeneration with brain iron accumulation type 1), Lead encephalopathy, Lipofuscinosis, Meningioangiomatosis, Multiple system atrophy, Myotonic dystrophy, Niemann-Pick disease (type C), Pallido-ponto-nigral degeneration, Parkinson's disease, Parkinson's disease dementia (PDD), Parkinsonism-dementia complex of Guam, Pick's disease (PiD), Postencephalitic parkinsonism (PEP), Primary progressive aphasia, Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Pure Autonomic Failure, Richardson's syndrome, Subacute sclerosing panencephalitis, Tangle-only dementia, Tuberous Sclerosis, Huntington's disease. Most preferred are one ore more tauopathies and Alzheimer's disease.

The invention also relates to the use of compounds according to formula (I) and/or physiologically acceptable salts thereof for the prophylactic or therapeutic treatment and/or monitoring of diseases that are caused, mediated and/or propagated by OGA activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by OGA activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with OGA activity in advance or to treat the arising and continuing symptoms. The disorders as concerned by the invention are preferably neurodegenerative diseases, diabetes, cancer, cardiovascular diseases and stroke.

In the meaning of the invention, prophylactic treatment is advisable if the subject possesses any preconditions for the aforementioned physiological or pathological conditions, such as a familial disposition, a genetic defect, or a previously passed disease.

In the scope of the present invention, compounds of formula (I) are provided for the first time. The low molecular weight compounds of the invention are strong and selective glycosidase inhibitors with improved passive permeability. The compounds of formula (I) have been shown to be competitive with PUGNAc, a known OGA inhibitor that binds in the substrate pocket. The endogenous substrate is an O-GlcNAcylated protein. O-GlcNAcylation of nuclear and cytoplasmic proteins is one of the most common post-translational modifications in animals and plants. O-GlcNAc cycling modulates a number of cellular processes, and evidence is mounting that dysregulation of O-GlcNAcylation plays a role in the etiology of several diseases, including tauopathies and Alzheimer's disease. O-GlcNAc transferase (OGT) and O-GlcNAcase (OGA) are the two enzymes that regulate O-GlcNAc cycling. Emerging data suggest that inhibitors that block OGA may help maintain healthy O-GlcNAc levels in tauopathies and Alzheimer's disease patients and thereby inhibit the formation of neurofibrillary tangles. Hence, the current invention comprises the use of compounds of formula (I) in the regulation, modulation and/or inhibition of the glycosidase signal cascade, which can be advantageously applied as research tool, for diagnosis and/or in treatment of any disorders that are responsive to OGA signaling and inhibition.

The low molecular weight inhibitors can be applied either themselves and/or in combination with physical measurements for diagnostics of treatment effectiveness. Medicaments and pharmaceutical compositions containing said compounds and the use of said compounds to treat glycosidase-mediated conditions is a promising, novel approach for a broad spectrum of therapies causing a direct and immediate improvement in the state of health, whether in man and animal. The impact is of special benefit to efficiently combat tauopathies and Alzheimer's disease, either alone or in combination with other neurodegenerative treatments.

Due to the surprisingly appreciable inhibitory activity on OGA, along with passive permeability, the compounds of the invention can be advantageously administered at lower doses compared to other less potent or selective inhibitors of prior art while still achieving equivalent or even superior desired biological effects. In addition, such a dose reduction advantageously leads to less or even no medicinal adverse effects.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All the references cited herein are incorporated by reference in the disclosure of the invention hereby.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again provided that the technical problem of the invention is solved. Similarly, the features of any claim can be combined with the features of one or more other claims.

EXPERIMENTAL PART

The compounds according to Formula (I) can be prepared from readily available starting materials by several synthetic approaches, using both solution-phase and solid-phase chemistry protocols or mixed solution and solid phase protocols. Examples of synthetic pathways are described below in the examples. All reported yields are non optimized yields. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich, Sigma, ACROS, ABCR, Combi-Blocks, Matrix, Apollo scientific, Alfa Aesar, Ark Pharma, unless otherwise reported.

The HPLC, MS and NMR data provided in the examples described below are obtained as followed:

$^1$H NMR analyses were carried out using BRUKER NMR, model AV-II and AV-Ill 400 MHz FT-NMR. Residual signal of deuterated solvent was used as internal reference. Chemical shifts (δ) are reported in ppm in relative to the residual solvent signal (δ=2.50 for $^1$H NMR in DMSO-$d_6$, and 7.26 in CDCl$_3$). s (singlet), d (doublet), t (triplet), q (quadruplet), br (broad), quint (quintuplet).

LCMS Analysis Condition:
Instrument name: Agilent Technologies 1290 infinity 11.
Method A: A-0.1% TFA in H$_2$O:MeCN (95:5); B-0.1% TFA in MeCN; flow Rate:1.5 ml/min; Eclipse XDB-C18 (50×4.6 mm, 3.5 μm), +ve mode
Method B: Method: A-0.1% NH$_4$HCO$_3$ in H$_2$O, B-MeCN; flow rate: 1.5 ml/min; column: ZORBAX
Method C: A-0.1% HCOOH in H$_2$O, B-MeCN; flow rate: 1.5 ml/min; column: ZORBAX Eclipse XDB-C18 (50×4.6 mm, 3.5 μm), +ve mode HPLC Analysis Condition:
Instrument name: Agilent 1200 Series instruments as followed using % with UV detection (maxplot).
Method A: Method: A-0.1% TFA in H$_2$O, B-0.1% TFA in MeCN; flow rate: 2.0 mL/min; column: XBridge C8 (50×4.6 mm, 3.5 μm).
Method B: Method: A-10 mM NH$_4$HCO$_3$ in H$_2$O, B-MeCN; flow rate: 1.0 mL/min; column: XBridge C8 (50×4.6 mm, 3.5 μm).

Chiral SFC Analysis Condition:
Instrument name: THAR-SFC 80 and THAR-SFC 200 (analytical) Ratio between CO$_2$ and co-solvent is ranging between 50:50 and 90:10

Method A: Mobile Phase: 0.5% Isopropyl Amine in IPA, 3 mL/min COLUMN: Chiracel OJ-H (250×4.6 mm, 5 μm).
Method B: Mobile Phase: 40% IPA, 3 mL/min COLUMN: Chiracel OD-H (250×4.6 mm, 5 μm).
Method C: Mobile Phase: 0.5% Isopropyl Amine in IPA, 3 mL/min COLUMN: Chiralpak OX-H (250×4.6 mm, 5 μm).
Method D: Mobile Phase: 20% Methanol, 3 mL/min COLUMN: Chiracel OJ-H (250×4.6 mm, 5 μm).
Method E: Mobile Phase: 0.5% Isopropyl Amine in IPA, 3 mL/min COLUMN: YMC Cellulose-SB (250×4.6 mm, 5 μm).
Method F: Mobile Phase: 0.5% Isopropyl Amine in MeOH, 3 mL/min COLUMN: YMC Amylose-SA (250×4.6 mm, 5 μm).
Method G: Mobile Phase: 0.5% Isopropyl Amine in MeOH, 3 mL/min COLUMN: Chiracel OD-H (250×4.6 mm, 5 μm).
Method H: Mobile Phase: 40% IPA, 3 mL/min COLUMN: Chiracel OJ-H (250×4.6 mm, 5 μm).
Method I: Mobile Phase: 0.5% Isopropyl Amine in IPA, 3 mL/min COLUMN: Lux A1 (250×4.6 mm, 5 μm).
Method J: Mobile Phase: 40% IPA, 3 mL/min COLUMN: Lux A1 (250×4.6 mm, 5 μm).
Method K: Mobile Phase: 0.5% Isopropyl Amine in MeOH, 3 mL/min COLUMN: Chiracel OJ-H (250×4.6 mm, 5 μm).

Prep-HPLC Analysis Condition:
Method A: A-0.1% TFA in H$_2$O, B-MeOH or CAN; column: Sunfire C8 (19×250 mm, 5 μm) or Sunfire C18 (30×250 mm, 10 μm).
Method B: A-10 mM NH$_4$HCO$_3$ in H$_2$O, B-MeOH or MeCN, Column: Sunfire C8 (19×250 mm, 5 μm) or Sunfire C18 (30×250 mm, 10 μm).

Chiral Preparative SFC Analysis Condition:
Instrument name: THAR-SFC 80, THAR-SFC 200 and PIC SFC 10-150
Ratio between CO$_2$ and co-solvent is ranging between 50:50 and 90:10
Method A: Mobile Phase: 0.5% Isopropyl Amine in IPA, 5 mL/min COLUMN: Chiracel OJ-H (250×30 mm, 5 μm).
Method B: Mobile Phase: 40% IPA, 5 mL/min COLUMN: Chiracel OD-H (250×30 mm, 5 μm).
Method C: Mobile Phase: 0.5% Isopropyl Amine in IPA, 5 mL/min COLUMN: Chiralpak OX-H (250×30 mm, 5 μm).
Method D: Mobile Phase: 20% Methanol, 5 mL/min COLUMN: Chiracel OJ-H (250×30 mm, 5 μm).
Method E: Mobile Phase: 0.5% Isopropyl Amine in IPA, 5 mL/min COLUMN: YMC Cellulose-SB (250×30 mm, 5 μm).
Method F: Mobile Phase: 0.5% Isopropyl Amine in MeOH, 5 mL/min COLUMN: YMC Amylose-SA (250×30 mm, 5 μm).
Method G: Mobile Phase: 0.5% Isopropyl Amine in MeOH, 5 mL/min COLUMN: Chiracel OD-H (250×30 mm, 5 μm).
Method H: Mobile Phase: 40% IPA, 5 mL/min COLUMN: Chiracel OJ-H (250×30 mm, 5 μm).
Method I: Mobile Phase: 0.5% Isopropyl Amine in IPA, 5 mL/min COLUMN: Lux A1 (250×30 mm, 5 μm).
Method J: Mobile Phase: 40% IPA, 5 mL/min COLUMN: Lux A1 (250×30 mm, 5 μm).
Method K: Mobile Phase: 0.5% Isopropyl Amine in MeOH, 5 mL/min COLUMN: Chiracel OJ-H (250×30 mm, 5 μm).

General flash chromatography conditions used for the purification of intermediates or compounds of Formula I:

Intermediate 1: 2-(2,3-dihydrobenzo[b][1,4]dioxin-6-yl)pyrrolidine

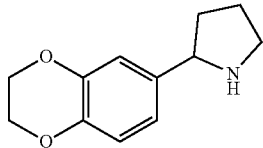 [SMILES: c1cc2c(cc1C1CCCN1)OCCO2]

Step 1: tert-butyl (4-(2,3-dihydrobenzo[b][1,4]dioxin-6-yl)-4-oxobutyl)carbamate

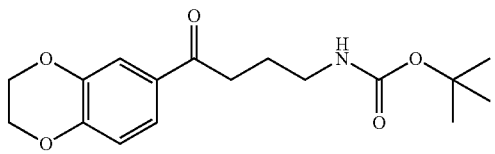 [SMILES: CC(C)(C)OC(=O)NCCCC(=O)c1ccc2c(c1)OCCO2]

To an oven-dried round bottom flask containing Mg turnings (2.56 g, 0.10 mol) and LiCl (3.70, 0.087 mol) was added dry THF (100 mL) at RT and the mixture was stirred for 5 min. DIBAL-H (0.7 mL, 0.69 mmol, 1 mol %, 1 M in THF) was added dropwise at RT and the mixture was further stirred for 5 minutes. It was then cooled to 0° C. and 6-bromo-2,3-dihydrobenzo[b][1,4]dioxine (15 g, 0.07 mol, 1.0 equiv.) in dry THF (15 mL) was added dropwise. After the initial heat evolution the reaction mixture was removed from the ice bath and allowed to stir for 1 h at RT.

To the stirred solution of tert-butyl 2-oxopyrrolidine-1-carboxylate (11.66 g, 0.06 mol) in dry THF (100 mL), above Grignard reagent was added at −78° C. dropwise and stirred at same temperature for 2 h. After completion of reaction the reaction mixture was warmed to RT and quenched with 1.5M HCl (50 mL). The aqueous phase was extracted with EtOAc (2×250 mL). The combined organic phase was washed with brine, dried over anhydrous Na$_2$SO$_4$, and concentrated under vacuum. The resulting crude product was purified by flash chromatography (Eluent: 25% EtOAc in pet ether) to give the title compound. Yield: 86% (19 g, Pale yellow solid). $^1$H NMR (400 MHz, DMSO-d$_6$): δ 7.46 (d, J=8.4 Hz, 2H), 6.97 (d, J=8.8 Hz, 1H), 6.85 (s, 1H), 4.29 (s, 4H), 2.99-2.90 (m, 4H), 1.71-1.66 (m, 2H), 1.37 (s, 9H). LCMS: (Method A) 222.1(M-Boc), Rt. 2.72 min, 75.31% (Max).

Step 2: 2-(2,3-dihydrobenzo[b][1,4]dioxin-6-yl)pyrrolidine

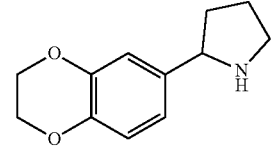 [SMILES: c1cc2c(cc1C1CCCN1)OCCO2]

The compound tert-butyl (4-(2,3-dihydrobenzo[b][1,4]dioxin-6-yl)-4-oxobutyl)carbamate (19 g, 0.06 mol), was dissolved in TFA (19 mL, 1.0 V) and was stirred at RT for 2 h. Then the reaction mixture was evaporated under vacuum. The resulting crude residue was co-distilled with toluene and dried completely by applying vacuum. Then to this crude cyclized intermediate dry MeOH was added. To this reaction mixture sodium borohydride (2.24 g, 0.06 mol) was added slowly at 0° C., and stirred for about 3 h at RT. Upon completion, the reaction mixture was quenched by the addition of a saturated NH$_4$Cl solution (50 mL) and extracted with EtOAc (2×150 mL). The combined organic layer was washed with water, brine solution, dried over Na$_2$SO$_4$ and evaporated under vacuum.

The resulting crude product was purified by flash chromatography (Eluent: 9.0% Methanol in DCM) to give the title compound. Yield: 33% (4.0 g, Pale yellow solid). $^1$H NMR (400 MHz, DMSO-d$_6$): δ 6.95 (d, J=2.0 Hz, 1H), 6.91 (dd, J=8.4, 2.4 Hz, 1H), 6.85 (s, 1H), 4.50-4.35 (m, 1H), 4.28-4.24 (m, 4H), 3.34-3.25 (m, 2H), 2.37-2.06 (m, 4H). LCMS: (Method A) 206.2 (M+H), Rt. 1.67 min, 96.86% (Max).

Intermediate 2: 5-(chloromethyl)-2-(p-tolyl)oxazole

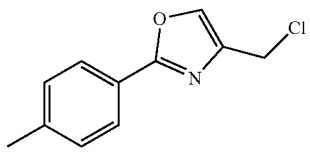

To a stirred solution of 4-methylbenzamide (2.0 g, 0.014 mol) in dry toluene (10 mL), 1,3-dichloropropan-2-one (2.25 mL, 0.017 mol) was added at RT and the reaction mixture was stirred for overnight at 140° C. Upon completion, the reaction mixture was diluted with water and extracted with EtOAc (2×50 mL). The combined organic layer was washed with water, brine solution, dried over Na$_2$SO$_4$ and evaporated under vacuum. The resulting crude product was taken for the next step without further purification. Yield: 52% (1.6 g, Pale brown solid). $^1$H NMR (400 MHz, CDCl$_3$): δ 8.22 (s, 1H), 7.82 (d, J=8.4 Hz, 2H), 7.36-7.23 (d, J=8.3 Hz, 2H), 4.73 (d, J=2.4 Hz, 2H), 2.37 (s, 3H). LCMS: (Method A) 208.0 (M+H), Rt. 2.85 min, 83.3% (Max).

Intermediate 3: 4-4-(chloromethyl)phenyl)-1-methyl-1H-pyrazole

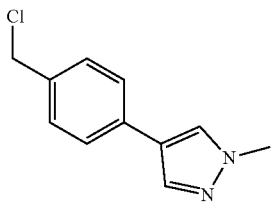

Step 1: (4-(1-methyl-1H-pyrazol-4-yl)phenyl)methanol

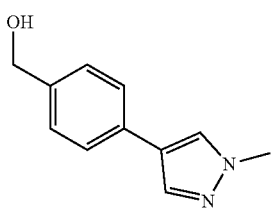

To a stirred solution of (4-bromophenyl)methanol (2.96 g, 15.86 mmol) and 2-methyl-4-(4,4,5,5-tetramethyl-1,3,2-dioxaborolan-2-yl)-2H-pyrrole (3.0 g, 14.42 mmol) in dioxane:water (10 mL, 9:1), $Cs_2CO_3$ (14.0 g, 43.248 mmol) was added at RT. The resulting reaction mixture was flushed with nitrogen for 15 min. Tetrakis(triphenylphosphine)palladium(0) (0.83 g, 0.72 mmol) was added and the mixture was stirred overnight at 90° C. The completion of the reaction was monitored by TLC. The reaction mixture was filtered through celite and the filtrate was concentrated under vacuum. The resulting residue was purified by flash chromatography (Eluent: 5% MeOH in DCM) to afford the title compound. Yield: 78% (2.1 g, off white solid). $^1$H NMR (400 MHz, DMSO-$d_6$): δ 8.10 (s, 1H), 7.84 (s, 1H), 7.51 (d, J=7.6 Hz, 2H), 7.29 (d, J=7.6 Hz, 2H), 5.14 (t, J=5.6 Hz, 1H), 4.47 (d, J=5.6 Hz, 2H), 3.86 (s, 3H). LCMS: (Method A) 189.1 (M+H), Rt. 1.07 min, 91.53% (Max).

Step 2: 4-(4-(chloromethyl)phenyl)-1-methyl-1H-pyrazole

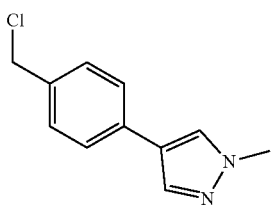

To a stirred solution of (4-(1-methyl-1H-pyrazol-4-yl)phenyl)methanol (210 mg, 1.0 mmol)) in dry DCM (3 mL), $SOCl_2$ (1.2 mL, 3.3 mmol) was added at 0° C. and the reaction mixture was stirred for 3 h at RT. After completion of the reaction, the reaction mixture was concentrated under vacuum. The resulting residue was co-distilled with DCM (2×10 m) to get the titled product. This compound was used in the next step without further purification. Yield: 92% (200 mg, light brown solid). LCMS: (Method A) 207.1 (M+H), Rt. 1.98 min, 79.9% (Max).

Intermediate 4: 5-(chloromethyl)-2-(1-methyl-1H-pyrazol-4-pyridine

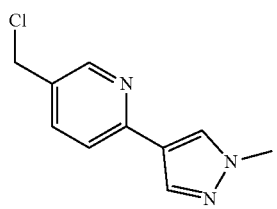

Step 1: (6-(1-methyl-1H-pyrazol-4-yl)pyridin-3-yl)methanol

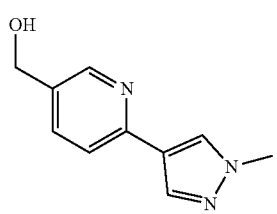

To a stirred solution of (6-chloropyridin-3-yl)methanol (1.02 g, 6.9 mmol) and 2-methyl-4-(4,4,5,5-tetramethyl-1,3,2-dioxaborolan-2-yl)-2H-pyrrole (1.65 g, 7.6 mmol) in dry dioxane (9 mL), a solution of cesium carbonate (4.52 g, 13.9 mmol) in water (1.0 mL) was added at RT and the resulting mixture was flushed with nitrogen. Tetrakis(triphenylphosphine)palladium(0) (161 mg, 0.1 mmol) was then added and and the mixture was stirred at 100° C. overnight. After completion of the reaction, the reaction mixture was filtered through celite pad and the filtrate was concentrated under vacuum. The resulting residue was purified by flash chromatography (Eluent: 5% MeOH in DCM) to afford the title compound. Yield: 64% (850 mg, light brown solid). $^1$H NMR (400 MHz, DMSO-$d_6$): δ 8.44 (s, 1H), 8.25 (s, 1H), 7.97 (s, 1H), 7.68 (q, J=1.2 Hz, 1H), 7.60 (d, J=8.0 Hz, 1H), 5.26 (t, J=5.6 Hz, 1H), 4.50 (d, J=5.6 Hz, 2H), 3.88 (s, 3H). LCMS: (Method A) 190.0 (M+H), Rt. 0.51 min, 97% (Max).

Step 2: 5-(chloromethyl)-2-(1-methyl-1H-pyrazol-4-yl)pyridine

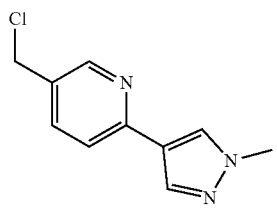

To a stirred solution of 5-(chloromethyl)-2-(1-methyl-1H-pyrazol-4-yl)pyridine (210 mg, 0.7 mmol)) in dry DCM (2 mL), SOCl₂ ((1.2 mL, 3.3 mmol)) was added at 0° C. and stirred for 3 h at RT. After completion of the reaction, the reaction mixture was concentrated under vacuum. The resulting crude product was co-distilled with DCM (2×10 mL), affording the title product that was used in next step without further purification. Yield: 93% (180 mg, off white solid). LCMS: (Method A) 208.1 (M+H), Rt. 0.99 min, 96.7% (Max).

Intermediate 5: 2-(2,3-dihydrobenzofuran-6-yl)pyrrolidine

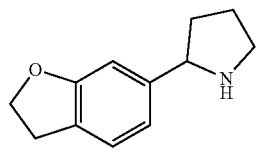 [SMILES: c1cc2c(cc1C1CCCN1)OCC2]

Step 1: tert-butyl (4-(2,3-dihydrobenzofuran-6-yl)-4-oxobutyl)carbamate

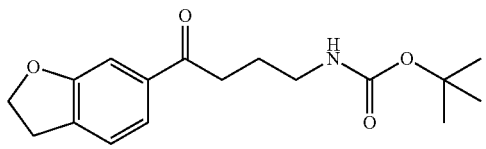 [SMILES: CC(C)(C)OC(=O)NCCCC(=O)c1ccc2c(c1)OCC2]

To an oven-dried round bottom flask containing Mg turnings (1.16 g, 48.3 mmmol) and LiCl (3.70, 87.0 mmol) was added dry THE (50 mL) at RT and the mixture was stirred for 5 minutes. 1,2 Dibromo ethane (0.1 mL) and 6-bromo-2,3-dihydrobenzofuran (6.4 g, 32.0 mmol) dissolved in dry THE (150 mL) were added slowly dropwise at RT. The reaction mixture was then heated at 65° C. for 2 h to ensure the starting material consumption.

To a stirred solution of tert-butyl 2-oxopyrrolidine-1-carboxylate (5.40 g, 2.1 mmol) in dry THE (50 mL), the Grignard reagent generated above was added slowly at −78° C. and the resulting mixture was stirred at the same temperature for 2 h. The reaction was quenched by sat. NH₄Cl at −40 ° C. and was extracted with EtOAc (2×50 mL). The combine organic layer was washed with water (10 mL), brine (10 mL), dried over Na₂SO₄ and concentrated under vacuum. The resulting crude product was purified by flash chromatography (Eluent: 15% EtOAc in hexane) to afford the title compound. Yield: 37% (2.78 g, white solid). ¹H NMR (400 MHz, DMSO-d₆): δ 7.47 (d, J=7.6 Hz, 1H), 7.36 (d, J=7.6 Hz, 1H), 7.26 (s, 1H), 6.86 (s, 1H), 4.58 (t, J=8.8 Hz, 2H), 3.24 (t, J=8.8 Hz, 2H), 3.00-2.94 (m, 4H), 1.72-1.66 (m, 2H), 1.37 (s, 9H). LCMS: (Method A) 206.1 (M+H), Rt. 2.86 min, 95.32% (Max).

Step 2: 2-(2,3-dihydrobenzo[b][1,4]dioxin-6-yl)pyrrolidine

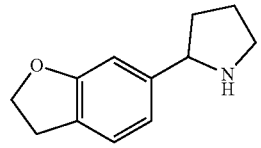 [SMILES: c1cc2c(cc1C1CCCN1)OCC2]

TFA (30 mL, 10V) was added to tert-butyl (4-(2,3-dihydrobenzofuran-6-yl)-4-oxobutyl)carbamate (2.75 g, 9.0 mmol) at 0° C. and the reaction mixture was stirred at RT for 2 h. It was concentrated under vacuum and resulting crude product was co-distilled with toluene (2×20 mL). This intermediate was dissolved in MeOH and NaBH₄ (610 mg, 1.6 mmol) was added portion wise at 0° C. The reaction was stirred at RT for 2 h, was then quenched with the addition of ice water (10 mL) and extracted with DCM (2×150 mL). The combined organic layer was washed with water (20 mL), brine (20 mL), dried over Na₂SO₄ and concentrated under vacuum. The resulting crude product was purified by flash chromatography (Eluent: 10% DCM in MeOH) to afford the title compound. Yield: 23% (0.61 g, white solid). ¹H NMR (400 MHz, DMSO-d₆): δ 7.12 (d, J=7.6 Hz, 1H), 6.81-6.77 (m, 2H), 4.49 (t, J=8.8 Hz, 2H), 3.97 (t, J=7.6 Hz, 2H), 3.14-3.02 (m, 2H), 3.02-2.98 (m, 1H), 2.87-2.85 (m, 1H), 2.09-2.04 (m, 1H), 1.76-1.71 (m, 2H), 1.47-1.42 (m, 1H). LCMS: (Method A) 190.1 (M+H), Rt. 1.76 min, 96.14% (Max).

Intermediate 6: 1-(4-bromobenzyl)-2-(2,3-dihydrobenzo[b] [1,4]dioxin-6-yl)pyrrolidine

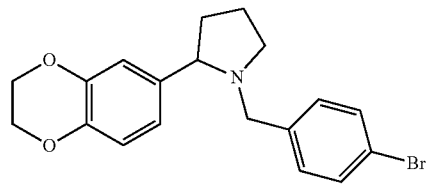 [SMILES: Brc1ccc(CN2CCCC2c2ccc3c(c2)OCCO3)cc1]

Step 1: 1-bromo-4-(chloromethyl)benzene

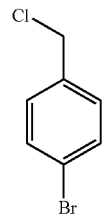

To a stirred solution of (4-bromophenyl)methanol (1.0 g, 5.4 mmol) in dry DCM (4 mL), SOCl₂ (1.2 mL, 16.2 mmol) was added at 0° C. and the resulting mixture was stirred for 3 h at RT. The completion of the reaction was monitored by TLC. After completion of the reaction, the reaction mixture was concentrated under reduced vacum. The resulting chloro compound was co-distilled with DCM (2×10 mL) to get the title compound that was used in the next step without further purification. Yield: 88.0% (960 mg, colorless liquid). $^1$H NMR (400 MHz, DMSO-$d_6$): δ 7.59 (d, J=10.8 Hz, 2H), 7.41 (d, J=11.2 Hz, 2H), 4.76 (s, 2H).

Step 2:1-(4-bromobenzyl)-2-(2,3-dihydrobenzo[b][1,4]dioxin-6-yl)pyrrolidine

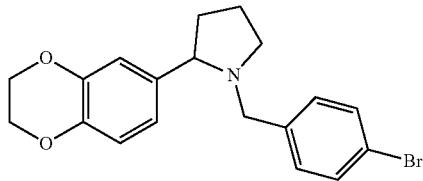 [SMILES: Brc1ccc(CN2CCCC2c2ccc3c(c2)OCCO3)cc1]

To a stirred solution of intermediate 1 (860 mg, 4.2 mmol) in dry MeCN (10 mL), 1-bromo-4-(chloromethyl)benzene (960 mg, 4.7 mmol) and TEA (1.3 mL, 9.4 mmol) were added at RT. Then the reaction mixture was stirred overnight at same temperature. After completion of the reaction, the reaction mixture was concentrated under vacuum. To the resulting crude product water was added and aqueous suspension was extracted with EtOAc (2×100). The combined organic layer was washed with water (50 mL), brine (10 mL), dried over Na$_2$SO$_4$ and concentrated under vacuum. The resulting crude product was purified by flash chromatography (eluent: 20% EtOAc in pet ether) to afford the title compound. Yield: 72% (1300 mg, colorless gummy solid). $^1$H NMR (400 MHz, DMSO-$d_6$): δ 7.41 (d, J=8.4 Hz, 2H), 7.18 (d, J=8.4 Hz, 2H), 6.98-6.84 (m, 3H), 4.28 (s, 4H), 3.80 (d, J=13.6 Hz, 1H), 3.26 (t, J=8.0 Hz, 1H), 3.04-2.98 (m, 2H), 2.18-2.14 (m, 2H), 1.74-1.72 (m, 1H), 1.60-1.54 (m, 2H). LCMS: (Method A) 374.2 (M+H), Rt. 2.33 min, 95.2% (Max).

Intermediate 7: 2-(benzo[d][1,3]dioxol-5-yl)pyrrolidine

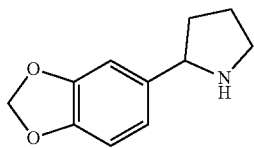 [SMILES: c1cc2c(cc1C1CCCN1)OCO2]

Step 1: tert-butyl (4-(benzo[d][1,3]dioxol-5-yl)-4-oxobutyl)carbamate

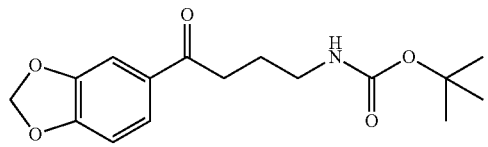 [SMILES: CC(C)(C)OC(=O)NCCCC(=O)c1ccc2c(c1)OCO2]

In an oven-dried round bottom flask Mg turnings (0.41 g, 0.015 mol) and LiCl (0.52 g, 0.012 mol) were weighed. The flask was then sealed, evacuated and back-filled with nitrogen. To this flask dry THF (10 mL) was added at RT and stirred for 5 minutes. Then DIBAL-H (0.1 mL, 0.09 mmol, 1 mol %, 1 M in THF) was added dropwise at RT and further stirred for 5 minutes. The resulting reaction mixture was then cooled to 0° C. and 5-bromobenzo[d][1,3]dioxole (2.0 g, 9.9 mmol, 1.0 equi) in dry THF (5 mL) was added dropwise. After the initial heat evolution the mixture was removed from the ice bath and allowed to stir for 1 h at RT.

To the stirred solution of tert-butyl 2-oxopyrrolidine-1-carboxylate (2.0 g, 0.011 mol) in dry THF (10 mL), cooled at −78° C., above Grignard reagent was added dropwise and stirred at same temperature for 2 h. After completion of reaction the reaction mixture was warmed to RT and quenched with 1.5 M HCl (5 mL). The aqueous phase was extracted with EtOAc (2×25 mL). The combined organic phase was washed with brine, dried over anhydrous Na$_2$SO$_4$, and concentrated under vacuum. The resulting crude product was purified by flash chromatography (Eluent: 25% EtOAc in pet ether) to give the title compound. Yield: 50% (1.5 g, Pale yellow solid). $^1$H NMR (400 MHz, DMSO-$d_6$): δ 7.58 (dd, J=8.0, 1.2, Hz, 1H), 7.45 (dd, J=1.6, Hz, 1H), 6.86 (t, J=4.4 Hz, 1H), 6.06 (s, 2H), 4.68 (s,1 H), 3.22 (q, J=6.4 Hz, 2H), 2.96 (t, J=6.8 Hz, 2H), 2.06-1.90 (m, 2H), 1.45 (s, 9H). LCMS: (Method A) 208.1(M-Boc), Rt. 2.74 min, 67.64% (Max).

Step 2: 2-(benzo[d][1,3]dioxol-5-yl)pyrrolidine

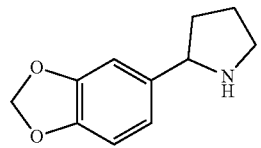

TFA (3.0 mL, 2.0 V) was added to tert-butyl (4-(benzo[d][1,3]dioxol-5-yl)-4-oxobutyl)carbamate (1.5 g, 4.8 mmol) at 0° C. and the resulting mixture was stirred at RT for 2 h. It was evaporated under vacuum and the resulting crude product was co-distilled with toluene. It was dissolved in dry MeOH (15 mL) and sodium borohydride (185 mg, 4.8 mmol) was added slowly at 0° C. and the reaction mixture was stirred at RT for 3 h. It was quenched with sat. NH$_4$Cl (20 mL) at 0° C. and extracted with EtOAc (2×20 mL). The combined organic layer was washed with water, brine solution, dried over Na$_2$SO$_4$ and evaporated under vacuum. The resulting crude product was purified by flash chromatography (Eluent: 9.0% Methanol in DCM) to give the title compound. Yield: 32% (0.3 g, Pale yellow solid). $^1$H NMR (400 MHz, DMSO-$d_6$): δ 6.91 (d, J=1.2 Hz, 1H), 6.84 (dd, J=8.0, 1.2 Hz, 1H), 6.77 (d, J=8.0 Hz, 1H), 5.95 (s, 2H), 4.07 (t, J=7.6 Hz, 1H), 3.22-3.18 (m, 1H), 3.05-3.00 (m, 1H), 2.18-2.12 (m, 1H), 1.94-1.86 (m, 2H), 1.68-1.63 (m, 1H). LCMS: (Method A) 192.1 (M+H), Rt. 1.55 min, 86.00% (Max).

Intermediate 8: 1-(chloromethyl)-4-(methylsulfonyl)benzene

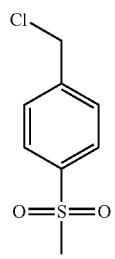

To a stirred solution of (4-(methylsulfonyl)phenyl)methanol (0.15 g, 50.0 mmol) in dry DCM (10 mL), SOCl$_2$ (1.2 mL, 10.0 mmol) was added at 0° C. and stirred for 2 h at RT. After completion of the reaction, the reaction mixture was concentrated under vacuum and co-distilled with DCM (2×10 mL) to get the title compound as an off brown solid. It was used in the next step without further purification. Yield: 90% (0.11 g, brown solid). $^1$H NMR (400 MHz, DMSO-d$_6$): δ 7.96 (t, J=6.4 Hz, 2H), 7.61 (t, J=8.0 Hz, 2H), 4.65 (s, 2H), 3.08 (s, 3H). LCMS: (Method A) 258 (M+H), Rt. 2.35 min, 98% (Max).

Intermediate 9: 2-(chloromethyl)-5-(4-(methyl sulfonyl)phenyl)pyridine

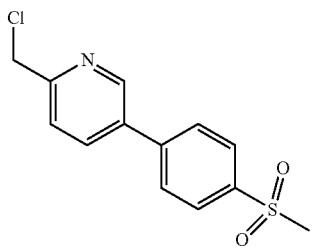 [SMILES: CS(=O)(=O)c1ccc(-c2ccc(CCl)nc2)cc1]

Step 1: (5-(4-(methylsulfonyl)phenyl)pyridin-2-yl)methanol

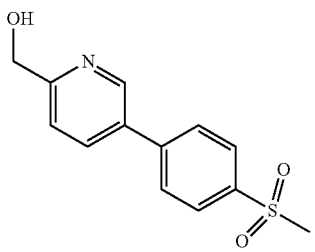 [SMILES: CS(=O)(=O)c1ccc(-c2ccc(CO)nc2)cc1]

To a stirred solution of (5-bromopyridin-2-yl)methanol (420 mg, 2.6 mmol) and 4,4,5,5-tetramethyl-2-(4-(methylsulfonyl)phenyl)-1,3,2-dioxaborolane (0.66 g, 2.7 mmol) in dry dioxane (4 mL), a solution of cesium carbonate (1.39 g, 4.3 mmol) in water (1 mL) was added at RT. The resulting mixture was flushed with nitrogen for 10 min. Then Tetrakis(triphenyl phosphine)palladium(0) (49 mg, 0.04 mmol) was added and the mixture was flushed again with nitrogen. The reaction mixture was stirred overnight at 100° C. After completion of the reaction, the reaction mixture was filtered through celite pad and the filtrate was concentrated under vacuum. The resulting crude product was purified by flash chromatography (Eluent: 7% MeOH in DCM) to afford the title compound. Yield: 36.0% (250 mg, white solid). $^1$H NMR (400 MHz, DMSO-d$_6$): δ 8.89 (s, 1H), 8.19 (t, J=10.4 Hz, 1H), 8.01 (d, J=9.6 Hz, 4H), 7.61 (d, J=10.4 Hz, 1H), 5.51 (t, J=7.6 Hz, 1H), 4.66 (d, J=9.6 Hz, 2H), 3.27 (s, 3H). LCMS: (Method A) 264.2 (M+H), Rt. 0.91 min, 90.2% (Max).

Step 2: 2-(chloromethyl)-5-(4-(methyl sulfonyl)phenyl)pyridine

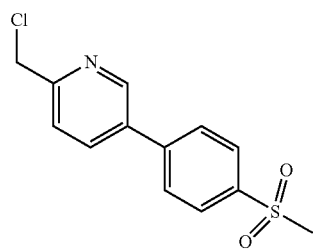 [SMILES: CS(=O)(=O)c1ccc(-c2ccc(CCl)nc2)cc1]

To a stirred solution of (5-(4-(methyl sulfonyl) phenyl) pyridin-2-yl) methanol (210 mg, 0.7 mmol)) in dry DCM (2 mL). SOCl$_2$ (0.2 mL. 2.3 mmol) was added at 0° C. and the mixture was stirred for 3 h at RT. After completion of the reaction, the reaction mixture was concentrated under vacuum. The resulting mixture was co-distilled with DCM (2×10 mL) to afford the title product. It was used in the next step without further purification. Yield: 93% (180 mg, yellow solid). LCMS: (Method A) 281.9 (M+H), 1.67 min, 97.9% (Max).

Intermediate 10: 2-(chloromethyl)-5-(1H-pyrazol-1-yl) pyridine

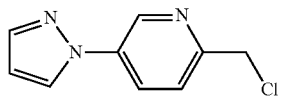 [SMILES: ClCc1ccc(-n2cccn2)cn1]

Step 1: Methyl 5-(1H-pyrazol-1-yl) picolinate

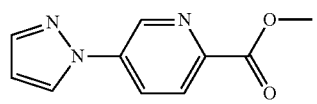

To a stirred solution of methyl 5-bromopicolinate (1.2 g, 8.7 mmol) in DMF (10 ml) were added 1H-pyrazole (1.4 g, 21.05 mmol), K$_3$PO$_4$ (3.7 g, 17.5 mmol), L-proline (0.8 g, 4.35 mmol) at RT and the reaction mixture was flushed with nitrogen for 10 min. Cupper iodide (0.5 g, 4.37 mmol) was then added and the mixture was stirred overnight at 80° C. After completion of reaction, the reaction mixture was quenched with ice-cold water and extracted with EtOAc (3×50 mL). The combined organic layer was dried over anhydrous Na$_2$SO$_4$, filtered and concentrated under vacuum. The resulting crude material was purified by flash chromatography (Eluent: 25% EtOAc in pet-ether) to afford the title compound. Yield: 9% (0.18 g, off white solid). $^1$H NMR (400 MHz, DMSO-d$_6$): δ 9.26 (d, J=2.8 Hz, 1H), 8.75 (d, J=3.6 Hz, 1H), 8.44-8.41 (m, 1H), 8.20 (d, J=11.2 Hz, 1H), 7.91 (s, 1H), 6.68 (d, J=2.4 Hz, 1H), 3.91 (s, 3H). LCMS: (Method A) 204.2 (M+H), Rt. 1.82 min, 96.5% (Max).

Step 2: (5-(1H-pyrazol-1-yl) pyridin-2-yl) methanol

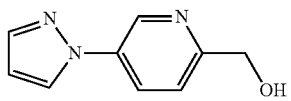 [SMILES: OCc1ccc(-n2cccn2)cn1]

To a stirred solution of methyl 5-(1 H-pyrazol-1-yl) picolinate (0.18 g, 0.88 mmol) in THF (5 mL), was added LAH (0.6 mL, 1.33 mmol, 2M in THF) at 0° C. and the reaction mixture was stirred for 2 h at the same temperature. After completion of reaction, the reaction mixture was quenched with 2M NaOH solution (2 mL) and extracted with EtOAc (2×20 mL). The combined organic layer was dried over Na$_2$SO$_4$, filtered and concentrated under vacuum. The resulting crude material was purified by flash chromatography (Eluent: 20% EtOAc in pet-ether) to afford the title compound. Yield: 77% (0.12 g, pale yellow gummy solid). $^1$H NMR (400 MHz, DMSO-d$_6$): δ 9.00 (s, 1H), 8.57 (s, 1H), 8.23 (d, J=11.2 Hz, 1H), 7.80 (s, 1H), 7.59 (d, J=11.6 Hz, 1H), 6.59 (s, 1H), 5.51 (t, J=7.6 Hz, 1H), 4.60 (d, J=7.6 Hz, 2H). LCMS: (Method A) 174.1 (M+H), Rt. 2.29 min, 94.32% (Max).

Step 3: 2-(chloromethyl)-5-(1H-pyrazol-1-yl) pyridine

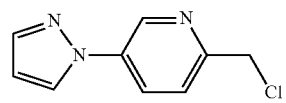 [SMILES: ClCc1ccc(-n2cccn2)cn1]

To a stirred solution of methyl (5-(1H-pyrazol-1-yl)pyridin-2-yl)methanol (0.12 g, 0.68 mmol) in DCM (10 mL) was added SOCl$_2$ (0.1 mL, 1.37 mmol) at 0° C. and the reaction mixture was stirred for 2 h at same temperature. After completion of reaction, the reaction mixture was concentrated under vacuum and co-distilled with DCM get the title compound. It was used in the next step without further purification. Yield: (0.170 g, brown gummy solid). $^1$H NMR (400 MHz, DMSO-d$_6$): δ 9.10 (s, 1H), 8.63 (d, J=3.2 Hz, 1H), 8.31-8.27 (m, 1H), 7.84 (s, 1H), 7.70 (d, J=11.6 Hz, 1H), 6.62 (s, 1H), 4.84 (s, 2H).

Intermediate 11: 1-(4-(chloromethyl) phenyl)-1 H-pyrazole

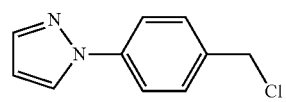

Step 1: Methyl 4-(1H-pyrazol-1-yl) benzoate

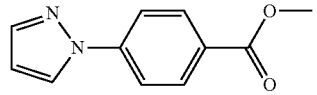

To a stirred solution of methyl 4-bromobenzoate (1 g, 7.35 mmol) in DMF (10 mL) 1H-pyrazole (1.2 g, 18.38 mmol), K$_3$PO$_4$ (2.3 g, 11.02 mmol) and L-proline (0.8 g, 4.41 mmol) were added at RT and the reaction mixture was flushed with nitrogen. Cupper iodide (0.4 g, 2.20 mmol) was added and the resulting mixture was stirred overnight at 80° C. After completion of reaction, the reaction mixture was quenched with ice-cold water and extracted with EtOAc (3×40 mL). The combined organic layer was dried over Na$_2$SO$_4$, filtered and concentrated under vacuum. The resulting crude material was purified by flash chromatography (Eluent: 25% EtOAc in pet ether) to afford the title compound. Yield: 27% (0.4 g, off white solid). $^1$H NMR (400 MHz, DMSO-d$_6$): δ 8.65 (d, J=3.2 Hz, 1H), 8.09-8.00 (m, 4H), 7.83 (s, 1H), 6.62 (t, J=5.6 Hz, 1H), 3.87 (s, 3H). LCMS: (Method A) 203.2 (M+H), Rt. 2.36 min, 99.13% (Max).

Step 2: (4-(1H-pyrazol-1-yl) phenyl) methanol

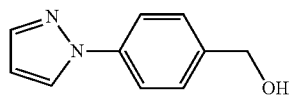

To a stirred solution of methyl 4-(1H-pyrazol-1-yl) benzoate (0.45 g, 0.2.25 mmol) in THF (5 ml), LAH (2.2 mL, 0.39 mmol, 2M in THF) was added at 0° C. The resulting mixture was stirred at 0° C. for 2 h. After completion of reaction, the reaction mixture was quenched with 2M NaOH solution (2 mL), extracted with EtOAc (2×20 mL). Combined organic layer was dried over Na$_2$SO$_4$, filtered and concentrated under vacuum. The resulting crude material was purified by flash chromatography (Eluent: 20% EtOAc in pet-ether), to afford the title compound. Yield: 91% (0.35 g, pale yellow gummy solid). $^1$H NMR (400 MHz, DMSO-d$_6$): δ 8.48 (s, 1H), 7.79 (d, J=7.6 Hz, 2H), 7.73 (s, 1H), 7.43 (d, J=7.6 Hz, 2H), 6.54 (s, 1H), 5.26 (t, J=5.6 Hz, 1H), 4.53 (d, J=5.2 Hz, 2H). LCMS: (Method A) 175.1 (M+H), Rt. 2.20 min, 94.32% (Max).

Step 3: 1-(4-(chloromethyl) phenyl)-1H-pyrazole

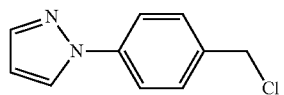 [SMILES: ClCc1ccc(-n2cccn2)cc1]

To a stirred solution of 4-(1H-pyrazol-1-yl)phenyl)methanol (0.2 g, 1.14 mmol) in DCM (10 mL), SOCl$_2$ (0.2 mL, 2.29 mmol) was added at 0° C. and the reaction mixture was stirred for 2 h. After completion of reaction, the reaction mixture was concentrated under vacuum and co-distilled with DCM to get the title compound. It was used in the next step without further purification. Yield: (0.170 g, brown gummy solid). LCMS: (Method A) 193.1 (M+H), Rt. 3.46 min, 94.32% (Max).

Intermediate 12: 2-(chloromethyl)-5-(4-(methylsulfonyl)phenyl)pyridine

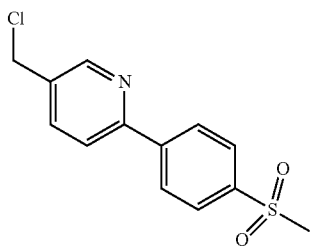 [SMILES: CS(=O)(=O)c1ccc(-c2ccc(CCl)cn2)cc1]

Step 1: (6-(4-(methylsulfonyl)phenyl)pyridin-3-yl)methanol

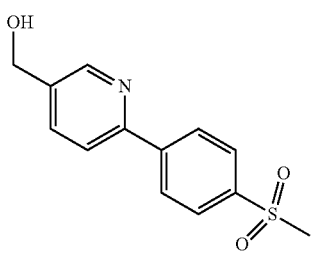 [SMILES: CS(=O)(=O)c1ccc(-c2ccc(CCl)cn2)cc1]

To a stirred solution of (6-chloropyridin-3-yl)methanol (0.32 g, 2.6 mmol) and 4,4,5,5-tetramethyl-2-(4-(methylsulfonyl)phenyl)-1,3,2-dioxaborolane (0.66 g, 2.7 mmol) in dry dioxane (2 mL), a solution of cesium carbonate (1.3 g, 4.3 mmol) in water (1 mL) was added at RT. The reaction mixture was purged with nitrogen for 10 min. Tetrakis(triphenylphosphine)palladium(0) (0.04 g, 0.4 mmol) was then added at RT and the reaction mixture was heated overnight at 100° C. The reaction mixture was filtered through celite pad and the filtrate was concentrated under vacuum. The resulting crude product was purified by flash chromatography (Eluent: 70% EtOAc in pet ether) to afford the title compound. Yield: 69.0% (200 mg, off white solid). $^1$H NMR (400 MHz, DMSO-$d_6$): δ 8.68 (s, 1H), 8.37-8.34 (m, 2H), 8.10-8.02 (m, 3H), 7.90-7.88 (m, 1H), 4.61 (d, J=5.6 Hz, 2H), 3.27 (s, 3H). LCMS: (Method A) 264.2 (M+H), 1.17 min, 93.8% (Max).

Step 2: 2-(chloromethyl)-5-(4-(methylsulfonyl)phenyl)pyridine

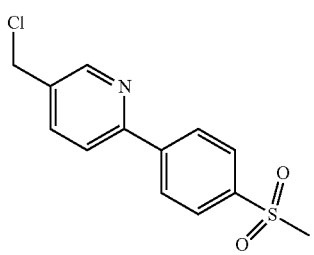

To a stirred solution of (5-(4-(methylsulfonyl)phenyl)pyridin-2-yl)methanol (0.11 g, 0.4 mmol) in dry DCM (2 mL), SOCl$_2$ (0.6 mL, 0.8 mmol) was added at 0° C. and the resulting mixture was stirred for 3 h at RT. After completion of the reaction, the reaction mixture was concentrated under vacuum.

The resulting crude product was co-distilled with DCM (2×10 mL) to afford the title product. It was used in the next step without further purification. Yield: 80% (100 mg, pale yellow solid). $^1$H NMR (400 MHz, DMSO-$d_6$): δ 8.81 (s, 1H), 8.36 (d, J=10.8 Hz, 2H), 8.15 (d, J=11.2 Hz, 1H), 8.05 (d, J=11.2 Hz, 3H), 4.91 (s, 2H). LCMS: (Method A) 282.0 (M+H), 2.40 min, 93.5% (Max).

Intermediate 13: 2-(chloromethyl)-5-(1-methyl-1H-pyrazol-4-yl)pyridine

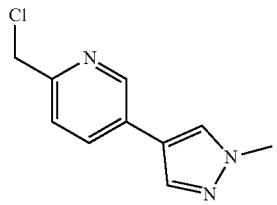

Step 1: (5-(1-methyl-1H-pyrazol-4-yl)pyridin-2-yl)methanol

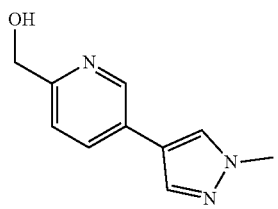

To a solution of (5-bromopyridin-2-yl)methanol (2.5 g, 13.3 mmol) and 2-methyl-4-(4,4,5,5-tetramethyl-1,3,2-dioxaborolan-2-yl)-2H-pyrrole (3.0 g, 14.6 mmol) in dioxane:water (10 mL, 9:1), potassium carbonate (4.6 g, 33.2 mmol) was added at RT and the resulting mixture was flushed with nitrogen for 15 min. Tetrakis(triphenylphosphine)palladium(0) (0.77 g, 0.7 mmol) was added and the mixture heated overnight at 90° C. After completion of the reaction, the reaction mixture was filtered through celite pad and the filtrate was concentrated under vacuum. The resulting crude product was purified by flash chromatography (Eluent: 5% MeOH in DCM) to afford the title compound. Yield: 88% (2.2 g, off white solid). $^1$H NMR (400 MHz, DMSO-$d_6$): δ 8.72-8.72 (m, 1H), 8.23 (s, 1H), 7.96-7.94 (m, 2H), 7.44 (d, J=8.4 Hz, 1H), 5.39 (t, J=6.0 Hz, 1H), 4.55 (d, J=5.6 Hz, 2H), 3.88 (s, 3H). LCMS: (Method A) 190.1 (M+H), Rt. 0.61 min, 94.48% (Max).

Step 2: 2-(chloromethyl)-5-(1-methyl-1H-pyrazol-4-yl)pyridine

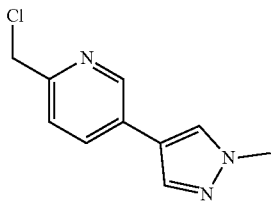

To a stirred solution of (5-(1-methyl-1H-pyrazol-4-yl)pyridin-2-yl)methanol (0.2 g, 1.1 mmol) in dry DCM (2 mL), SOCl$_2$ (0.3 mL, 3.2 mmol) was added slowly at 0° C. and the reaction mixture was stirred at RT for 1 h. The reaction mixture was concentrated under vacuum and the resulting solid was co-distilled with DCM (2×10 mL). It was used in the next step without any purification. Yield: 96% (0.21 g, off white solid). LCMS: (Method A) 208.2 (M+H), Rt. 1.73 min, 99.82% (Max).

Intermediate 14: 6-(chloromethyl)quinoline

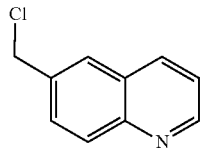 [SMILES: ClCc1ccc2ncccc2c1]

To a stirred solution of quinolin-6-ylmethanol (0.21 g, 1.3 mol)) in dry DCM (3 mL), SOCl$_2$ (0.3 mL, 3.9 mmol) was added at 0° C. and the mixture was stirred for 3 h at RT. After completion of the reaction, the reaction mixture was evaporated under vacuum. The resulting crude product was co-distilled with DCM (2×10 mL) to afford the title compound. It was used in the next step without any further purification. Yield: 80% (200 mg, pale yellow solid). LCMS: (Method A) 178.1(M+H), Rt. 1.68 min, 98.2% (Max).

Intermediate 15: 5-(chloromethyl)-1-methyl-1H-indazole

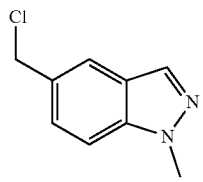

To a stirred solution of (1-methyl-1 H-indazol-5-yl)methanol (0.15 g, 9.0 mmol)) in dry DCM (3 mL), SOCl$_2$ (0.2 mL, 2.8 mmol) was added at 0° C. and the mixture was stirred for 3 h at RT. The completion of the reaction was monitored by TLC. After completion of the reaction, the reaction mixture was concentrated under vacuum. The resulting crude product was co-distilled with DCM (2×10 mL) to afford the title compound. It was used in the next step without any further purification. Yield: 71% (120 mg, pale yellow solid). $^1$H NMR: (400 MHz, CDCl$_3$-d$_6$): δ 8.01 (s, 1H), 7.76 (s, 1H), 7.49 (d, J=1.6 Hz, 2H), 4.76 (s, 2H), 4.11 (s, 3H).

Intermediate 16: 4-(3-(chloromethyl)phenyl)-1-methyl-1H-pyrazole

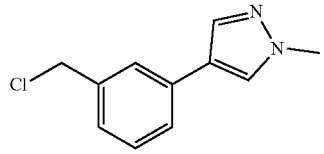

Step 1: (3-(1-methyl-1H-pyrazol-4-yl)phenyl methanol

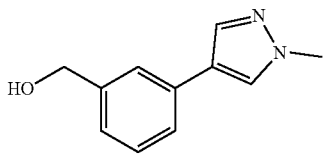

To a stirred solution of 1-methyl-4-(4,4,5,5-tetramethyl-1,3,2-dioxaborolan-2-yl)-1H-pyrazole (0.35 g, 1.68 mmol) and 3-bromophenyl)methanol (0.34 g, 1.85 mmol) in dry dioxane (4 mL), a solution of potassium carbonate (0.7 g, 5.04 mmol) in water (1 mL) was added at RT and the resulting mixture was purged 10 min with nitrogen. Tetrakis(triphenylphosphine)palladium(0) (0.19 g, 0.68 mmol) was then added and the reaction mixture was heated overnight at 100° C. The reaction mixture was filtered through celite pad and the filtrate was concentrated under vacuum. The resulting crude product was purified by flash chromatography (Eluent: 70% EtOAc in pet ether) to afford the title compound. Yield: 78.0% (250 mg, Off white solid). $^1$H NMR (400 MHz, DMSO-d$_6$): δ 8.11 (s, 1H), 7.83 (s, 1H), 7.49-7.56 (m, 1H), 7.31 (d, J=3.6 Hz, 2H), 7.13-7.14 (m, 1H), 5.18 (t, J=2.4 Hz, 1H), 4.50 (s, 2H), 3.86 (s, 3H). LCMS: (Method A) 189.0. (M+H), Rt. 1.37 min, 83.62% (max).

Step 2: 4-(3-(chloromethyl)phenyl)-1-methyl-1H-pyrazole

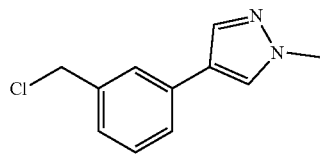

To a stirred solution of 3-(1-methyl-1H-pyrazol-4-yl)phenyl)methanol) (0.25 g, 1.3 mmol) in dry DCM (5 mL) cooled at 0° C., SOCl$_2$ was added (1.57 g, 13.2 mmol) and the resulting mixture was stirred at 0° C. for 1 h. The reaction mixture was concentrated under vacuum and the resulting crude product was co-distilled with toluene (20 mL), to afford the title compound. It was used in the next step without any further purification. Yield: 88% (0.24 g, pale yellow solid). ¹H NMR (400 MHz, CDCl₃): δ 8.13 (s, 1H), 7.98 (s, 1H), 7.68 (t, J=4.8 Hz, 1H), 7.41-7.47 (m, 3H), 4.63 (s, 2H), 4.35 (s, 3H). LCMS: (Method A) 207.1 (M+H), Rt. 2.76 min, 98.21% (Max).

Intermediate 17:
4-(4-(chloromethyl)phenyl)thiomorpholine

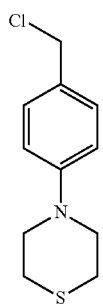 [SMILES: ClCc1ccc(N2CCSCC2)cc1]

Step 1: Methyl 4-thiomorpholinobenzoate

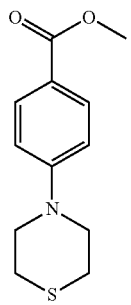 [SMILES: COC(=O)c1ccc(N2CCSCC2)cc1]

To a stirred solution of methyl 4-fluorobenzoate (120 mg, 0.7 mmol) and thiomorpholine (90 mg, 0.9 mmol) in dry DMSO (2 mL), K₂CO₃ (190 mg, 1.4 mmol) was added at RT and the resulting mixture was heated overnight at 140° C. After completion of reaction, the reaction mixture was filtered through celite pad and the filtrate was concentrated under vacuum. The resulting crude product was purified by flash chromatography (Eluent: 40% EtOAc in pet ether) to afford the title compound. Yield: 21% (34 mg, white solid). ¹H NMR (400 MHz, DMSO-d₆): δ 7.79 (dd, J=8.8, 2.0 Hz, 2H), 6.96 (dd, J=9.2, 2.0 Hz, 2H), 3.78 (s, 3H), 3.78-3.67 (m, 4H), 2.64-2.62 (m, 4H). LCMS: (Method A) 238.2 (M+H), Rt. 2.71 min, 99.7% (Max).

Step 2: (4-thiomorpholinophenyl)methanol

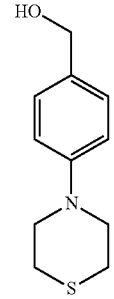

To a stirred solution of methyl 4-thiomorpholinobenzoate (210 mg, 8.4 mmol) in dry THF (3 mL), LAH (0.8 mL, 8.4 mmol, 1M in THF) was added at −78° C. and the resulting mixture was stirred for 2 h at RT. After completion of the reaction, the reaction mixture was quenched with the addition of EtOAc and Na₂SO₄ solution. The reaction mixture was extracted with EtOAc (2×20 mL). The combined organic layer was washed with water (10 mL), brine (5 mL), dried over Na₂SO₄ and concentrated under vacuum. The resulting residue was purified by flash chromatography (Eluent: 36% EtOAc in pet ether) to afford the title compound. Yield: 56% (103 mg, off white solid). ¹H NMR (400 MHz, DMSO-d₆): δ 7.15 (d, J=8.4 Hz, 2H), 6.87 (d, J=8.4 Hz, 2H), 4.95 (t, J=5.6 Hz, 1H), 4.36 (d, J=5.6 Hz, 2H), 3.48-3.46 (m, 4H), 2.66-2.64 (m, 4H). LCMS: (Method A) 210.2 (M+H), Rt. 0.893 min, 92.48% (Max).

Step 3: 4-(4-(chloromethyl)phenyl)thiomorpholine

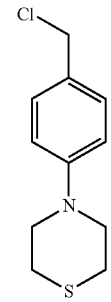

To a stirred solution of (4-thiomorpholinophenyl)methanol (130 mg, 0.6 mmol)) in dry DCM (2 mL), SOCl₂ ((0.1 mL, 2.0 mmol) was added at 0° C. and the resulting mixture was stirred for 3 h at RT. The completion of the reaction was monitored by TLC. After completion of the reaction, the reaction mixture was concentrated under vacuum. The resulting crude product was co-distilled with DCM (2×10 mL), affording the title compound that was used in the next step without further purification. Yield: 83% (120 mg, plae yellow solid). LCMS: (Method A) 224.2 (M+H), Rt. 1.80 min, 78.62% (Max).

Intermediate 18: 2-(4-(chloromethyl)phenyl)pyridine

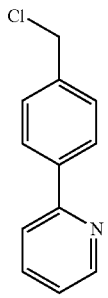 [SMILES: ClCc1ccc(-c2ccccn2)cc1]

Step 1: 4-(pyridin-2-yl)benzaldehyde

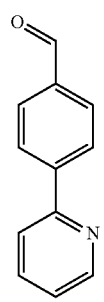 [SMILES: O=Cc1ccc(-c2ccccn2)cc1]

To a stirred solution of (4-formylphenyl) boronic acid (610 g, 4.0 mmol) and methyl 2-chloropyridine (0.43 mL, 4.4 mmol) in dry dioxane (9 mL), a solution of cesium carbonate (2.62 g, 8.0 mmol) in water (1 mL) was added at RT. Nitrogen was flushed through this mixture, before the addition of Tetrakis (triphenylphosphine)palladium(0) (0.92 g, 0.8 mmol). The mixture was then stirred at 100° C. overnight. After completion of the reaction, the reaction mixture was filtered through celite pad and the filtrate was concentrated under vacuum. To the resulting crude product water was added and the aqueous suspension was extracted with EtOAc (2×40 mL). The combined organic layer was washed with water (10 mL) and brine (2 mL), dried over $Na_2SO_4$ and concentrated under vacuum. The resulting residue was purified by flash chromatography (Eluent: 24% EtOAc in pet ether) to afford the title compound. Yield: 35% (250 mg, off white liquid). $^1$H NMR (400 MHz, $CDCl_3$): δ 10.11 (s, 1H), 8.78-8.76 (m, 1H), 8.15 (t, J=8.0 Hz, 2H), 8.02 (d, J=8.8 Hz, 2H), 7.85-7.82 (m, 2H), 7.36-7.33 (m, 1H). LCMS: (Method A) 184.3 (M+H), Rt. 1.43 min, 75.9% (Max).

Step 2: (4-(pyridin-2-yl)phenyl)methanol

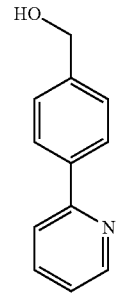 [SMILES: OCc1ccc(-c2ccccn2)cc1]

To a stirred solution of 4-(pyridin-2-yl)benzaldehyde (210 mg, 1.0 mmol) in dry DCM (4 mL), $NaBH_4$ (60 mg, 1.6 mmol) was added at 0° C. and the resulting mixture was stirred for 2 h at RT. After completion of the reaction, the reaction mixture was quenched with the addition of ice and was extracted with DCM (2×20 mL). The combined organic layer was washed with water (10 mL), brine (2 mL), dried over $Na_2SO_4$ and concentrated under vacuum. The resulting residue was purified by flash chromatography (Eluent: 30% EtOAc in pet ether) to afford the title compound. Yield: 88% (180 mg, off white solid). $^1$H NMR (400 MHz, DMSO-$d_6$): δ 8.66 (d, J=4.4 Hz, 1H), 8.06 (d, J=8.0 Hz, 2H), 7.95 (d, J=8.0 Hz, 1H), 7.89-7.86 (m, 1H), 7.45-7.41 (m, 1H), 7.34 (t, J=5.6 Hz, 1H), 5.26 (t, J=5.6 Hz, 1H), 4.56 (d, J=5.2 Hz, 2H). LCMS: (Method A) 186.2 (M+H), Rt. 0.62 min, 55.8% (Max).

Step 3: 2-(4-(chloromethyl)phenyl)pyridine

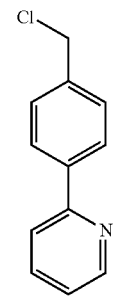

To a stirred solution of (4-(pyridin-2-yl) phenyl) methanol (210 mg, 0.7 mmol)) in dry DCM (4 mL), $SOCl_2$ (0.3 mL, 3.2 mmol) was added at 0° C. and the resulting mixture was stirred for 3 h at RT. The completion of the reaction was monitored by TLC. After completion of the reaction, the reaction mixture was concentrated under vacuum. The resulting product was co-distilled with DCM (2×10 mL) and used in the next step without further purification. Yield: 86% (190 mg, pale yellow solid). $^1$H NMR (400 MHz, DMSO-$d_6$): δ 8.98 (s, 1H), 8.39 (s, 1H), 8.22 (d, J=8.4 Hz, 2H), 8.09 (d, J=8.0 Hz, 1H), 7.80 (s, 1H), 7.69-7.67 (m, 2H), 4.67 (s, 2H). LCMS: (Method A) 204.2 (M+H), Rt. 1.89 min, 99.4% (Max).

Intermediate 19:
3-(4-(chloromethyl)phenyl)pyridine

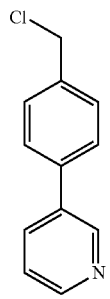 [SMILES: ClCc1ccc(-c2cccnc2)cc1]

Step 1: Methyl 4-(pyridin-3-yl)benzoate

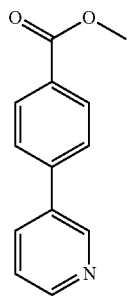 [SMILES: COC(=O)c1ccc(-c2cccnc2)cc1]

To a stirred solution of 3-(4,4,5,5-tetramethyl-1,3,2-dioxaborolan-2-yl)pyridine (521 mg, 2.5 mmol) and methyl 4-bromobenzoate (500 mg, 2.0 mmol) in dry dioxane (4 mL), a solution of cesium carbonate (1.3 g, 5.0 mmol) in water (1 mL) was added at RT and the resulting solution was flushed with nitrogen during 10 min. Tetrakis (triphenylphosphine)palladium(0) (0.04 g, 0.4 mmol) was added and the reaction mixture was heated to 100° C. overnight. The reaction mixture was filtered through celite pad and the filtrate was concentrated under vacuum. The resulting crude product was purified by flash chromatography (Eluent: 40% EtOAc in pet ether) to afford the title compound. Yield: 73% (405 mg, white solid). $^1$H NMR (400 MHz, DMSO-$d_6$): δ 8.97 (s, 1H), 8.64 (d, J=4.8 Hz, 1H), 8.17-8.06 (m, 3H), 7.90 (d, J=10.8 Hz, 2H), 7.55-7.51 (m, 1H), 3.89 (s, 3H). LCMS: (Method A) 214.2 (M+H), Rt. 1.763 min, 97.0% (Max).

Step 2: (4-(pyridin-3-yl)phenyl)methanol

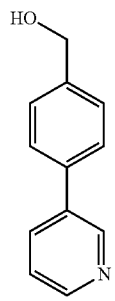

To a stirred solution of methyl 4-(pyridin-3-yl)benzoate (250 mg, 1.17 mmol) in dry THF (3 mL), LAH (1.1 mL, 1.1 mmol)) was added at −78° C. and the reaction mixture was stirred for 2 h at RT. After completion of the reaction, it was quenched by using EtOAc and $Na_2SO_4$ solution. The two phases were separated and the aqueous phase was extracted with EtOAc (2×20 mL). The combined organic layer was washed with water (10 mL), dried over $Na_2SO_4$, and concentrated under vacuum. The resulting residue was purified by flash chromatography (Eluent: 30% EtOAc in pet ether) to give the title compound. Yield: 61% (130 mg, off white solid). $^1$H NMR (400 MHz, DMSO-$d_6$): δ 8.89 (d, J=2.0 Hz, 1H), 8.57-8.55 (m, 1H), 8.09-8.05 (m, 1H), 7.69 (t, J=8.8 Hz, 2H), 7.50-7.44 (m, 3H), 5.25 (d, J=7.2 Hz, 1H), 4.56 (d, J=6.4 Hz, 2H). LCMS: (Method A) 186.2 (M+H), Rt. 0.69 min, 92.5% (Max).

Step 3: 3-(4-(chloromethyl)phenyl)pyridine

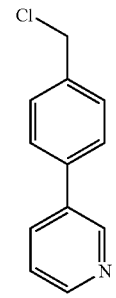

To a stirred solution of (4-(pyridin-3-yl) phenyl) methanol (0.13 g, 0.6 mmol)) in dry DCM (2 mL), $SOCl_2$ (0.1 mL, 2.0 mmol) was added at 0° C. and the resulting mixture was stirred for 3 h at RT. The completion of the reaction was monitored by TLC. The reaction mixture was concentrated under vacuum. The resulting product was co-distilled with DCM (2×10 mL) and was used in the next step without further purification. Yield: 80% (120 mg, pale yellow solid). $^1$H NMR (400 MHz, DMSO-$d_6$): δ 8.89 (d, J=2.0 Hz, 1H), 8.57-8.55 (m, 1H), 8.09-8.05 (m, 1H), 7.69 (t, J=8.8 Hz, 2H), 7.50-7.44 (m, 3H), 4.56 (d, J=6.4 Hz, 2H). LCMS: (Method A) 204.2 (M+H), Rt. 1.94 min, 98.1% (Max).

Intermediate 20:
3-(3-chloro-4-(chloromethyl)phenyl)pyridine

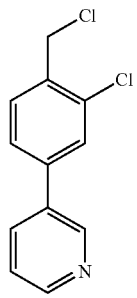 [SMILES: ClCc1ccc(-c2cccnc2)cc1Cl]

Step 1: (2-chloro-4-(pyridin-3-yl)phenyl)methanol

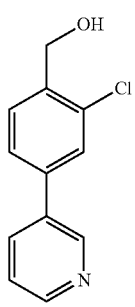

To a stirred solution of 3-(4,4,5,5-tetramethyl-1,3,2-dioxaborolan-2-yl)pyridine (350 mg, 1.68 mmol) and (4-bromo-2-chlorophenyl)methanol (340 mg, 1.85 mmol) in dry dioxane (4 mL), a solution of potassium carbonate (710 mg, 5.04 mmol) in water (1 mL) was added at RT and the resulting solution was flushed with nitrogen for 10 min. Tetrakis (triphenylphosphine)palladium(0) (190 mg, 0.68 mmol) was added and the reaction mixture was heated at 100° C. overnight. After completion of reaction, the reaction mixture was filtered through celite pad and the filtrate was concentrated under vacuum. The resulting crude product was purified by flash chromatography (Eluent: 55% EtOAc in pet ether) to afford the title compound. Yield: 62% (230 mg, off white solid). $^1$H NMR (400 MHz, DMSO-$d_6$): δ 8.93 (d, J=2.8 Hz, 1H), 8.58-8.60 (m, 1H), 8.12 (dd, J=6.6, 2.8 Hz, 1H), 7.73-7.80 (m, 3H), 7.73-7.75 (m, 1H), 5.48 (t, J=7.6 Hz, 1H), 4.62 (d, J=7.6 Hz, 2H). LCMS: (Method A) 220.2. (M+H), Rt. 1.12 min, 98.33% (max).

Step 2: 3-(3-chloro-4-(chloromethyl)phenyl)pyridine

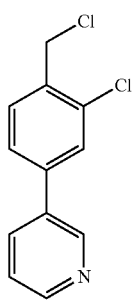 [SMILES: ClCc1ccc(-c2cccnc2)cc1Cl]

To a stirred solution of (2-chloro-4-(pyridin-3-yl)phenyl)methanol (230 mg, 0.96 mmol) in dry DCM (5 mL) cooled at 0° C., was added SOCl$_2$ (0.32 mL, 4.81 mmol) and the resulting mixture was stirred at 0° C. for 1 h. After completion of reaction, the reaction mixture was concentrated under vacuum and the resulting product was co-distilled with toluene (20 mL), affording the title compound that was used in the next step without further purification. Yield: 70% (0.17 g, Pale yellow solid). $^1$H NMR (400 MHz, DMSO-$d_6$): δ 8. 8.93 (d, J=2.8 Hz, 1H), 8.58-8.60 (m, 1H), 8.12 (dd, J=6.6, 2.8 Hz, 1H), 7.73-7.80 (m, 3H), 7.73-7.75 (m, 1H), 4.78 (s, 2H). LCMS: (Method A) 238.2 (M+H), Rt. 2.15 min, 98.77% (Max).

Intermediate 21: 3-(4-(chloromethyl)-3-fluorophenyl)pyridine

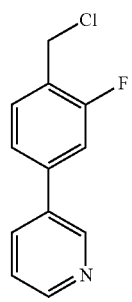

Step 1: (2-fluoro-4-(pyridin-3-yl)phenyl)methanol

To a stirred solution of 3-(4,4,5,5-tetramethyl-1,3,2-dioxaborolan-2-yl)pyridine (350 mg, 1.68 mmol) and 4-bromo-2-fluorophenyl)methanol (340 mg, 1.85 mmol) in dry dioxane (4 mL), a solution of potassium carbonate (700 mg, 5.04 mmol) in water (1 mL) was added at RT and the resulting solution was flushed with nitrogen for 10 min. Tetrakis (triphenylphosphine)palladium(0) (191 mg, 0.68 mmol) was added at RT. The reaction mixture was heated at 100° C. overnight. After completion of reaction, the reaction mixture was filtered through celite pad and the filtrate was concentrated under vacuum. The resulting crude product was purified by flash chromatography (Eluent: 50% EtOAc in pet ether) to afford the title compound. Yield: 69% (235 mg, pale yellow gummy solid). $^1$H NMR (400 MHz, DMSO-$d_6$): δ 8.93 (d, J=2.4 Hz, 1H), 8.59 (dd, J=6.2, 1.6 Hz, 1H), 8.58-8.09 (m, 1H), 7.47-7.60 (m, 4H), 5.35 (t, J=7.6 Hz, 1H), 4.60 (d, J=7.6 Hz, 2H). LCMS: (Method A) 204.2 (M+H), Rt. 0.74 min, 94.66% (max).

Step 2: 3-(4-(chloromethyl)-3-fluorophenyl)pyridine

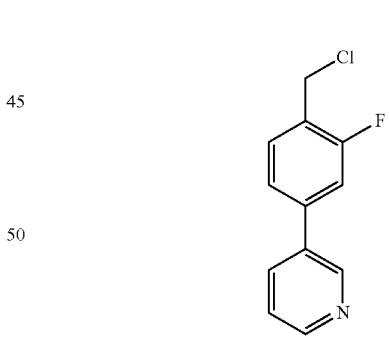

To a stirred solution of (2-fluoro-4-(pyridin-3-yl)phenyl)methanol (235 mg, 1.12 mmol) in dry DCM (5 mL) at 0° C., was added SOCl$_2$ (0.34 mL, 5.63 mmol) and the resulting mixture was stirred at 0° C. for 1 h. It was concentrated under vacuum and the resulting crude product was co-distilled with toluene (20 mL), affording the title compound that was used in the next step without further purification. Yield: 72% (180 mg, pale yellow gummy oil). $^1$H NMR (400 MHz, CDCl$_3$): δ 8.93 (d, J=2.4 Hz, 1H), 8.59 (dd, J=6.2, 1.6 Hz, 1H), 8.58-8.09 (m, 1H), 7.47-7.60 (m, 4H), 4.72 (s, 2H). LCMS: (Method A) 222.2 (M+H), Rt. 2.05 min, 98.19% (max).

Intermediate 22:
3-(4-(chloromethyl)-3-methylphenyl)pyridine

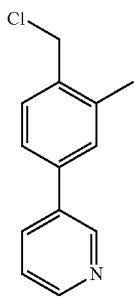

Step 1: (2-Methyl-4-(pyridin-3-yl)phenyl)methanol

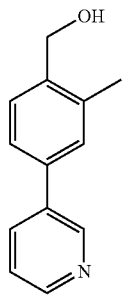

To a stirred solution of 3-(4,4,5,5-tetramethyl-1,3,2-dioxaborolan-2-yl)pyridine (450 mg, 2.2 mmol) and (4-bromo-2-methylphenyl)methanol (400 mg, 2.0 mol) in dry dioxane (4 mL), a solution of cesium carbonate (1.3 g, 4.0 mmol) in water (1 mL) was added at RT and the resulting solution was flushed with nitrogen for 10 min. Tetrakis(triphenylphosphine)palladium(0) (460 mg, 0.4 mmol) was added at RT and the mixture was heated at 100° C. overnight. The reaction was filtered through celite pad and the filtrate was concentrated under vacuum. The resulting crude product was purified by flash chromatography (Eluent: 28% EtOAc in pet ether) to afford the title compound. Yield: 89% (380 mg, white solid). $^1$H NMR (400 MHz, DMSO-$d_6$): δ 8.88 (s, 1H), 8.55 (s, 1H), 8.07-8.05 (m, 1H), 7.65-7.46 (m, 5H), 5.15 (t, J=5.2 Hz, 1H), 4.55 (d, J=5.2 Hz, 2H), 2.33 (s, 3H). LCMS: (Method A) 200.2 (M+H), Rt. 1.43 min, 88.27% (Max).

Step 2:
3-(4-(chloromethyl)-3-methylphenyl)pyridine

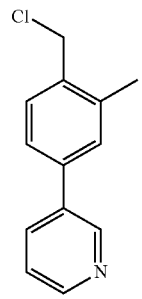

To a stirred solution of (2-methyl-4-(pyridin-3-yl)phenyl)methanol (380 mg, 2.0 mmol) in dry DCM (4 mL), SOCl$_2$ (0.29 mL, 4.0 mmol) was added at 0° C. and the resulting mixture was stirred for 3 h at RT. The completion of the reaction was monitored by TLC. After completion of the reaction, the reaction mixture was concentrated under vacuum. The resulting product was co-distilled with DCM (2×10 mL) affording the title compound that was used without further purification. Yield: 78% (338 mg, pale yellow solid). LCMS: (Method A) 218.2 (M+H), Rt. 2.06 min, 80.44% (Max).

Intermediate 23:
1-(4-(chloromethyl)phenyl)-1H-1,2,4-triazole

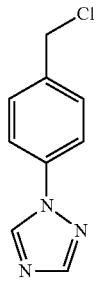 [SMILES: ClCc1ccc(-n2cncn2)cc1]

Step 1: 4-(1 H-1,2,4-triazol-1-yl)benzaldehyde

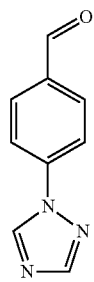 [SMILES: O=Cc1ccc(-n2cncn2)cc1]

To a stirred solution of 4-fluro benzaldehyde (1.0 g, 0.8 mmol) in dry DMF (5 mL), 1 H-1,2,4-triazole (660 mg, 0.9 mmol) and K$_2$CO$_3$ (2.2 g, 1.6 mmol) were added at RT and the resulting mixture was stirred overnight at 110° C. After completion of reaction, ice water (2 mL) was added and the mixture was extracted with EtOAc (2×20 mL). The combined organic layer was washed with brine (2 mL), dried over $Na_2SO_4$ and concentrated under vacuum. The resulting product was used in next step without further purification. Yield: 46% (610 mg, white solid). LCMS: (Method A) 174.1 (M+H), Rt. 1.27 min, 67.51% (Max).

Step 2: (4-(1H-1,2,4-triazol-1-yl)phenyl)methanol

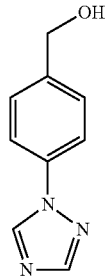 [SMILES: OCc1ccc(-n2cncn2)cc1]

To a stirred solution of 4-(1 H-1,2,4-triazol-1-yl)benzaldehyde (400 mg, 2.28 mmol) in dry MeOH (5 mL), $NaBH_4$ (93 mg, 2.74 mmol) was added at 0° C. and the resulting mixture was stirred at RT for 2 h. After completion of the reaction, ice water was added and the mixture was extracted with EtOAc (2×20 mL). The combined organic layer was washed with brine (2 mL), dried over $Na_2SO_4$ and concentrated under vacuum. The resulting crude product was purified by flash chromatography (Eluent: 34% EA in pet ether) to get the title product. Yield: 67% (271 mg, white solid). $^1$H NMR (400 MHz, DMSO-$d_6$): δ 9.27 (s, 1H), 9.25 (s, 1H), 7.78 (d, J=8.6 Hz, 2H), 7.13 (d, J=8.6 Hz, 2H), 4.85 (s, 1H), 3.96 (s, 2H). LCMS: (Method A) 176.1 (M+H), Rt. 1.04 min, 99.79% (Max).

Step 3: 1-(4-(chloromethyl)phenyl)-1H-1,2,4-triazole

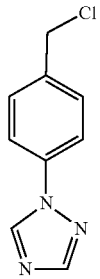 [SMILES: ClCc1ccc(-n2cncn2)cc1]

To a stirred solution of (4-(1 H-1,2,4-triazol-1-yl)phenyl) methanol (133 mg, 0.76 mmol) in dry DCM (2 mL), $SOCl_2$ (0.1 mL, 1.52 mol) was added at 0° C. and the resulting mixture was stirred for 3 h at RT. The completion of the reaction was monitored by TLC. The reaction mixture was concentrated under vacuum and the resulting product was co-distilled with DCM (2×10 mL) to get the title compound that was used without any further purification. Yield: 60% (110 mg, pale yellow solid). $^1$H NMR (400 MHz, DMSO-$d_6$): δ 9.33 (s, 1H), 8.26 (s, 1H), 7.89 (d, 8.8 Hz, 2H), 7.64 (d, J=8.8 Hz, 2H), 4.85 (s, 2H). LCMS: (Method A) 194.1 (M+H), Rt. 1.73 min, 79.10% (Max).

Intermediate 24: (1-(Pyrimidin-2-yl)piperidin-4-yl)methyl methanesulfonate

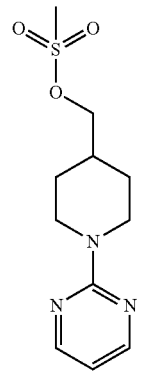 [SMILES: CS(=O)(=O)OCC1CCN(c2ncccn2)CC1]

Step 1: Methyl 1-(pyrimidin-2-yl)piperidine-4-carboxylate

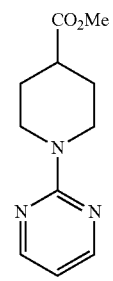

To a stirred solution of 2-chloropyrimidine (610 mg, 5.2 mmol) in dry DMF (5 mL), methyl piperidine-4-carboxylate (0.85 mL, 6.3 mmol) and TEA (0.2 mL, 1.3 mol) were added and the resulting mixture was stirred 3 h at RT. After completion of the reaction, the reaction mixture was concentrated under vacuum. To the resulting crude, water (25 mL) was added and the aqueous suspension was extracted with EtOAc (2×40 mL). The combined organic layer was washed with water (20 mL), brine (2 mL), dried over $Na_2SO_4$ and concentrated under vacuum. The crude product was purified by flash chromatography (Eluent: 19% EtOAc in pet ether) to afford the title compound. Yield: 73% (800 mg, off white liquid). $^1$H NMR (400 MHz, $CDCl_3$): δ 8.32 (d, J=4.4 Hz, 2H), 6.49 (t, J=4.8 Hz, 1H), 4.67 (d, J=13.2 Hz, 2H), 3.72 (s, 3H), 3.07 (t, J=11.6 Hz, 2H), 2.61 (t, J=10.8 Hz, 1H), 2.00 (d, J=13.2 Hz, 2H), 1.78-1.68 (m, 2H). LCMS: (Method A) 222.3 (M+H), Rt. 1.66 min, 99.8% (Max).

Step 2: (1-(Pyrimidin-2-yl)piperidin-4-yl)methanol

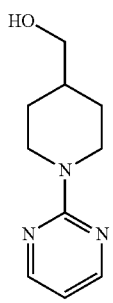

To a stirred solution of methyl 1-(pyrimidin-2-yl)piperidine-4-carboxylate (500 mg, 2.2 mmol) in dry THE (4 mL), LAH (2.7 mL, 2.7 mmol, 1M in THF) was added at −78° C. and the resulting mixture was stirred 2 h at RT. The completion of the reaction was monitored by TLC. The reaction was quenched by using EtOAc and $Na_2SO_4$ solution. The reaction mixture was partially evaporated under vacuum and the resulting mixture was extracted with EtOAc (2×20 mL). Combined organic layer was washed with water (10 mL), dried over $Na_2SO_4$ and concentrated under vacuum. The residue was purified by flash chromatography (Eluent: 40% EtOAc in pet ether) to afford the title compound. Yield: 91% (400 mg, off white liquid). $^1$H NMR (400 MHz, DMSO-$d_6$): δ 8.32 (d, J=6.4 Hz, 2H), 6.56 (t, J=6.4 Hz, 1H), 4.66 (d, J=18.0 Hz, 2H), 4.47 (t, J=7.2 Hz, 1H), 3.38-3.21 (m, 4H), 2.98-2.73 (m, 3H), 1.71 (d, J=14.4 Hz, 2H), 1.12-1.06 (m, 1H). LCMS: (Method A) 194.2 (M+H), Rt. 0.59 min, 69.6% (Max).

Step 3: (1-(Pyrimidin-2-yl)piperidin-4-yl)methyl methanesulfonate

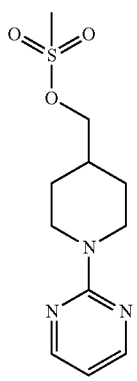

To a stirred solution of (1-(pyrimidin-2-yl)piperidin-4-yl)methanol (210 mg, 1.0 mmol) in dry DCM (4 mL), TEA (0.4 mL, 3.1 mmol) and mesyl chloride (0.1 mL, 1.2 mmol) were added at 0° C. and the resulting mixture was stirred 2 h at RT. The completion of the reaction was monitored by TLC. After completion of the reaction, it was concentrated under vacuum. Water was added (20 mL) and the aqueous suspension was extracted with DCM (2×20 mL). The combined organic layer was washed with water (10 mL), brine (2 mL), dried over $Na_2SO_4$ and concentrated under vacuum to get the title compound. It was used in the next step without any further purification. Yield: 88% (250 mg, pale yellow solid). LCMS: (Method A) 272.2 (M+H), Rt. 1.676 min, 97.7% (Max).

Intermediate 25: 3-(4-(chloromethyl)-3-methylphenyl)pyridine

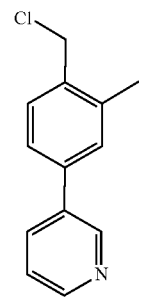

Step 1: (2-methyl-4-(pyridin-3-yl)phenyl)methanol

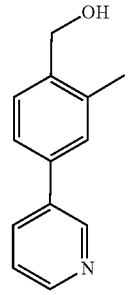

To a stirred solution of 3-(4,4,5,5-tetramethyl-1,3,2-dioxaborolan-2-yl)pyridine (450 g, 2.2 mmol) and (4-bromo-2-methylphenyl)methanol (400 mg, 2.0 mmol) in dry dioxane (4 mL), a solution of cesium carbonate (1.3 g, 4.0 mmol) in water (1 mL) was added at RT and the resulting solution was flushed with nitrogen for 10 min. Tetrakis(triphenylphosphine)palladium(0) (460 mg, 0.04 mmol) was added and the mixture was heated overnight at 100° C. It was filtered through celite pad and the filtrate was concentrated under vacuum. The resulting crude product was purified by flash chromatography (Eluent: 28% EtOAc in pet ether) to afford the title compound. Yield: 89% (380 mg, white solid). $^1$H NMR (400 MHz, DMSO-$d_6$): δ 8.88 (s, 1H), 8.55 (s, 1H), 8.07-8.05 (m, 1H), 7.65-7.46 (m, 5H), 5.15 (t, J=5.2 Hz, 1H), 4.55 (d, J=5.2 Hz, 2H), 2.33 (s, 3H). LCMS: (Method A) 200.2 (M+H), Rt. 1.43 min, 88.27% (Max).

Step 3:
3-(4-(chloromethyl)-3-methylphenyl)pyridine

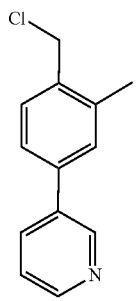

To a stirred solution of (2-methyl-4-(pyridin-3-yl)phenyl)methanol (440 mg, 2.0 mmol) in dry DCM (4 mL), SOCl$_2$ ((0.29 mL, 4.0 mmol) was added at 0° C. and the resulting mixture was stirred for 3 h at RT. The completion of the reaction was monitored by TLC. After completion of the reaction, the reaction mixture was concentrated under vacuum. The resulting product was co-distilled with DCM (2×10 mL), affording the title compound that was used without further purification. Yield: 78% (338 mg, pale yellow solid). LCMS: (Method A) 218.2 (M+H), Rt. 2.06 min, 80.44% (Max).

Intermediate 26:
5-(4-(chloromethyl)phenyl)pyrimidine

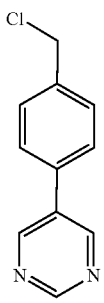

Step 1: Methyl 4-(pyrimidin-5-yl)benzoate

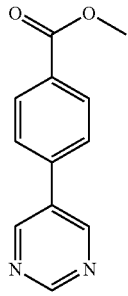

To a stirred solution of 5-(4,4,5,5-tetramethyl-1,3,2-dioxaborolan-2-yl)pyrimidine (520 mg, 2.5 mmol) and methyl 4-bromobenzoate (510 mg, 2.0 mmol) in dry dioxane (4 mL), a solution of cesium carbonate (1.3 g, 5.0 mmol) in water (1 mL) was added at RT and the resulting mixture was flushed with nitrogen for 10 min. Tetrakis (triphenylphosphine)palladium(0) (40 mg, 0.4 mmol) was added and the reaction mixture was heated overnight at 100° C. It was filtered through celite pad and the filtrate was concentrated under vacuum. The resulting crude product was purified by flash chromatography (Eluent: 36% EtOAc in pet ether) to afford the title compound. Yield: 35% (190 mg, yellow solid). $^1$H NMR (400 MHz, DMSO-d$_6$): δ 9.24 (d, J=8.8 Hz, 3H), 8.10 (d, J=11.2 Hz, 2H), 8.00 (d, J=11.2 Hz, 2H), 3.93 (s, 3H). LCMS: (Method A) 215.0 (M+H), Rt. 2.198 min, 99.0% (Max).

Step 2: (4-(pyrimidin-5-yl)phenyl)methanol

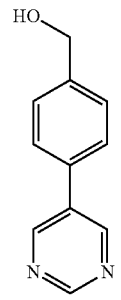 [SMILES: OCc1ccc(-c2cncnc2)cc1]

To a stirred solution of methyl 4-(pyrimidin-5-yl)benzoate (250 mg, 1.7 mmol) in dry THF (3 mL), LAH (1.17 mL, 1.7 mmol, 1M in THF) was added at −78° C. and the resulting mixture was stirred 2 h at RT. The reaction was quenched by using EtOAc and Na$_2$SO$_4$ solution. Then the reaction mixture was concentrated under vacuum to remove the THF. The resulting solution was extracted with EtOAc (2×20 mL). The combined organic layer was washed with water (10 mL), brine (5 mL), dried over Na$_2$SO$_4$ and concentrated under vacuum. The residue was purified by flash chromatography (Eluent: 43% EtOAc in pet ether) to afford the title compound. Yield: 46% (102 mg, yellow solid). LCMS: (Method A) 187.1 (M+H), Rt. 0.425 min, 74.2% (Max).

Step 3: 5-(4-(chloromethyl)phenyl)pyrimidine

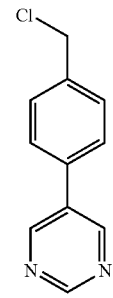 [SMILES: ClCc1ccc(-c2cncnc2)cc1]

To a stirred solution of (4-(pyrimidin-5-yl) phenyl)methanol (0.130 mg, 0.6 mmol) in dry DCM (2 mL), SOCl$_2$ (0.1 mL, 2.0 mmol) were added at 0° C. and the resulting mixture was stirred for 3 h at RT. The completion of the reaction was monitored by TLC. After completion of the reaction, the reaction mixture was concentrated under vacuum. The resulting product was co-distilled with DCM (2×10 mL), affording the title compound that was used without further purification. Yield: 67% (97 mg, yellow solid). LCMS: (Method A) 207.2 (M+H), Rt. 2.02 min, 63.1% (Max).

Intermediate 27: 2-(4-(chloromethyl)-3-fluorophenyl)pyridine

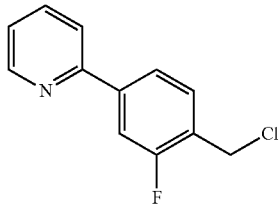

Step 1:(2-fluoro-4-(4,4,5,5-tetramethyl-1,3,2-dioxaborolan-2-yl)phenyl)methanol

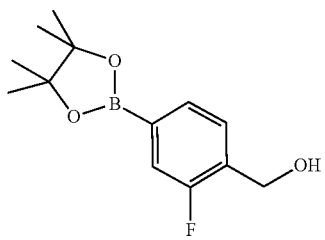 [SMILES: CC1(C)OB(c2ccc(CO)c(F)c2)OC1(C)C]

To a stirred solution of (4-bromo-2-fluorophenyl) methanol (500 mg, 2.451 mmol) in dry 1,4-dioxane (10 mL), potassium acetate (253.94 mg, 2.941 mmol) and bis(pinacolato)diboron (747 mg, 2.941 mmol) were added at RT and the solution was flushed with nitrogen for 20 min. Then Pd(dppf)Cl₂-DCM (200 mg, 0.245 mmol) was added and the mixture was heated overnight at 100° C. The reaction mixture was filtered through celite pad that was washed with EtOAc (50 mL). Combined filtrate was concentrated under reduced vacuum, affording the title compound that was used in the next step without any further purification. Yield: 100% (618 mg, light black colour liquid).

Step-2: (2-fluoro-4-(pyridin-2-yl)phenyl)methanol

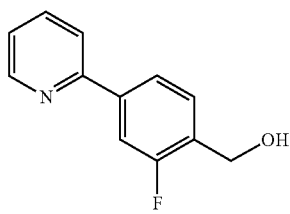

To a stirred solution of 2-chloropyridine (250 mg, 2.201 mmol) in 1,4-dioxane:water (9:1, 10 mL), (2-fluoro-4-(4,4,5,5-tetramethyl-1,3,2-dioxaborolan-2-1)phenyl) methanol (660 mg. 2.642 mmol) and cessium carbonate (2.15 g, 6.60 mmol) were added at RT and the resulting solution was flushed with nitrogen for 20 min. Then Tetrakis (triphenyl phosphine) palladium (0) (254 mg. 0.221 mmol) was added and the mixture was heated overnight at 100° C. The reaction mixture was filtered through celite pad that was washed with EtOAc (50 mL). Combine filtrate was washed with water (2×25 mL), dried over Na₂SO₄, and concentrated under reduced vacuum. The resulting crude compound was purified by flash chromatography (Eluent: 25% EtOAc: Hexane) to afford the title compound. Yield: 67.07% (300 mg, colourless liquid). LCMS: (Method C) 204.0 (M+H), Rt. 1.313 min, 99.25% (Max).

Step-3: 2-(4-(chloromethyl)-3-fluorophenyl)pyridine

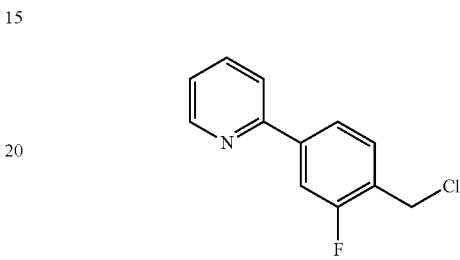

To a stirred solution of (2-fluoro-4-(pyridin-2-yl)phenyl) methanol (327 mg, 1.476 mmol) in DCM (5 mL), SOCl₂ (1 mL) was added at 0° C. and the resulting solution was stirred at RT for 3 h. The reaction was monitored by TLC. The reaction mixture was concentrated under reduced vacuum and resulting product was co-distilled with DCM (2×20 mL) to afford the title compound, which was used in the next step without any further purification. Yield: 100% (327 mg, off white solid).

Intermediate 28: 2-(4-(chloromethyl)-3-methylphenyl) pyridine from (2-methyl-4-(pyridin-2-yl)phenyl)methanol

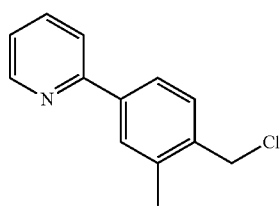

Step 1: (2-methyl-4-(4,4,5,5-tetramethyl-1,3,2-dioxaborolan-2-yl)phenyl)methanol from (4-bromo-2-methylphenyl)methanol

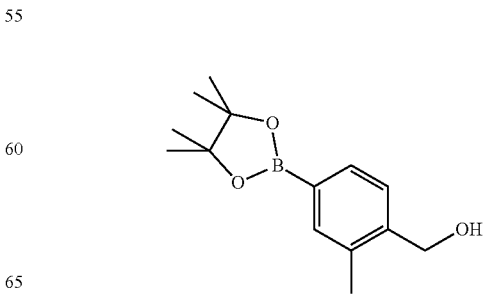

To a stirred solution of (4-bromo-2-methylphenyl) methanol (500 mg, 2.5 mmol) in dry 1,4-Dioxane (10 mL), potassium acetate (736 mg, 7.5 mmol) and bis(pinacolato) diboron (656 mg, 3.0 mmol) were added at RT and the reaction mixture was flushed with nitrogen for 10 min. Then Pd(dppf)Cl$_2$-DCM (204 mg, 0.25 mmol) was added and the mixture was heated overnight at 100° C. The reaction mixture was filtered through celite pad that was washed with EtOAc (50 mL). Combined filtrate was dried over Na$_2$SO$_4$ and concentrated under vacuum to afford the title compound that was used in the next step without further purification. Yield: 100% (620 mg, black colour liquid).

Step 2: Preparation of (2-methyl-4-(pyridin-2-yl)phenyl)methanol

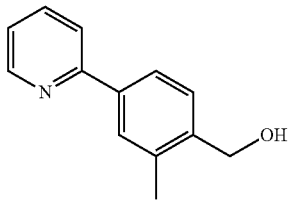

To a stirred solution of 2-chloropyridine (250 mg, 2.2 mmol) in 1,4-dioxane:water (9:1, 10 mL), (2-methyl-4-(4,4,5,5-tetramethyl-1,3,2-dioxaborolan-2-yl)phenyl) methanol (655 mg 2.642 mmol) and cessium carbonate (2.15 g, 6.60 mmol) were added at RT. The reaction mixture was flushed with nitrogen for 20 min. Tetrakis (triphenyl phosphine) palladium (0) (254 mg. 0.22 mmol) was added and the mixture was heated overnight at 100° C. It was filtered through celite pad that was washed with EtOAc (50 mL). Combined filtrate was washed with water (2×25 mL), dried over Na$_2$SO$_4$ and concentrated under vacuum. The resuting crude compound was purified by flash chromatography (Eluent: 25% EtOAc: Hexane) to afford the title compound. Yield: 44.32% (200 mg, colourless liquid). $^1$H NMR (400 MHz, DMSO-d$_6$): δ 8.64 (d, J=3.60 Hz, 1H), 7.94-7.83 (m, 4H), 7.46 (d, J=8.4 Hz, 1H), 7.32 (t, J=7.2 Hz, 1H), 5.14 (t, J=5.2 Hz, 1H), 4.54 (d, J=5.2 Hz, 2H), 2.32 (s, 3H). LCMS: (Method C) 200.1 (M+H), Rt. 0.79 min, 98.42% (Max).

Step 3: 2-(4-(chloromethyl)-3-methylphenyl) pyridine

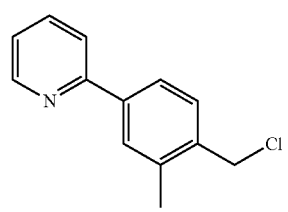

To a stirred solution of 2-(4-(chloromethyl)-3-methylphenyl)pyridine (200 mg, 1.0 mmol) in DCM (5 mL), SOCl$_2$ (1 mL) was added at 0° C. and the resulting mixture was stirred for 3 h. The reaction was monitored by TLC. The reaction mixture was concentrated under vacuum. The resulting product was co-distilled with DCM (2×20 mL) to afford the title compound that was used in the next step without further purification. Yield: 46% (200 mg, off white solid). $^1$H NMR (400 MHz, DMSO-d$_6$): δ 8.79 (d, J=6.8 Hz, 1H), 8.30-8.22 (m, 2H), 8.25 (t, J=10.0 Hz, 2H), 7.72 (t, J=8.0 Hz, 1H), 7.60 (d, J=10.8 Hz, 1H), 4.88 (s, 2H), 2.50 (s, 3H). LCMS: Method C, 218.0 (M+H), Rt. 1.817 min, 97.90% (Max).

Intermediate 29: 2-(3-chloro-4-(chloromethyl) Phenyl) pyridine

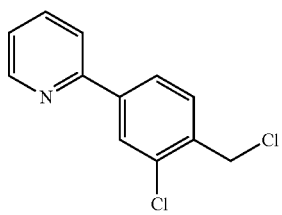 [SMILES: Fc1cc(-c2ccccn2)ccc1CCl]

Step 1: (2-chloro-4-(4,4,5,5-tetramethyl-1,3,2-dioxaborolan-2-yl)phenyl)methanol

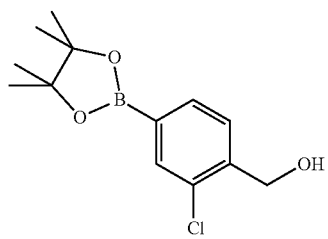 [SMILES: CC1(C)OB(c2ccc(CO)c(Cl)c2)OC1(C)C]

To a stirred solution of (4-bromo-2-chlorophenyl)methanol (500 mg, 2.273 mmol) in dry 1,4-Dioxane (10 mL), potassium acetate (669 mg, 6.820 mmol) and bis(pinacolato) diboron (692 mg, 2.728 mmol) were added at RT and the reaction mixture was flushed with nitrogen for 10 min. Then Pd(dppf)Cl$_2$-DCM (185 mg, 0.227 mmol) was added and the resulting mixture was heated overnight at 100° C. It was filtered through celite pad that was washed with EtOAc (50 mL). Combined filtrate was dried over Na$_2$SO$_4$ and concentrated under vacuum to afford the title compound that was used in the next step without further purification. Yield: 100% (610 mg, black colour liquid).

Step 2: (2-chloro-4-(pyridin-2-yl)phenyl) methanol

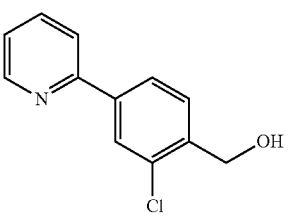 [SMILES: OCc1ccc(-c2ccccn2)cc1Cl]

To a stirred solution of 2-chloropyridine (250 mg, 2.201 mmol) in 1,4-Dioxane:water (9:1, 10 mL), (2-chloro-4-(4,4,5,5-tetra methyl-1,3,2-dioxaborolan-2-yl)phenyl)methanol (709 mg, 2.642 mmol) and cessium carbonate (2.15 gm, 6.603 mmol) were added at RT. The reaction mixture was flushed with nitrogen for 20 min. Tetrakis (triphenyl phosphine) palladium (0) (254 mg. 0.221 mmol) was added and the mixture was heated overnight at 100° C. The reaction mixture was filtered through celite pad that was then washed with EtOAc (50 mL). Combined filtrate was washed with water (2×25 mL), dried over Na$_2$SO$_4$ and concentrated under vacuum. The resulting crude compound was purified by flash chromatography (Eluent: 25% EtOAc: Hexane) to afford the title compound. Yield: 21% (200 mg, colourless liquid). $^1$H NMR (400 MHz, DMSO-d$_6$): δ 8.68 (d, J=4.80 Hz, 1H), 8.12-8.01 (m, 2H), 7.93-7.88 (m, 2H), 7.67 (d, J=10.8 Hz, 1H), 7.39 (t, J=8.8 Hz, 1H), 5.48 (t, J=7.2 Hz, 1H), 4.63 (d, J=7.2 Hz, 2H). LCMS: Method C, 220.0 (M+H), Rt. 1.34 Min, 98.70% (Max).

Step 3:2-(3-chloro-4-(chloromethyl) phenyl) pyridine

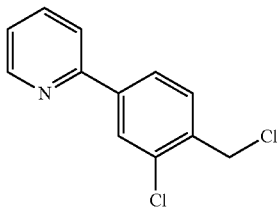 [SMILES: ClCc1ccc(-c2ccccn2)cc1Cl]

To a stirred solution of (2-fluoro-4-(pyridin-2-yl)phenyl) methanol (200 mg, 0.910 mmol) in DCM (5 mL), SOCl$_2$ (1 mL) was added at 0° C. and the resulting solution was stirred at RT for 3 h. The reaction was monitored by TLC. The reaction mixture was concentrated under vacuum and the resulting product was co-distilled with DCM (2×20 mL) to afford the title compound that was used in the next step without further purification. Yield: 100% (216 mg, off white solid). $^1$H NMR (400 MHz, DMSO-d$_6$): δ 9.49 (s, 1H), 8.79 (t, J=4.0 Hz, 3H), 8.10-8.10 (m, 1H), 7.80 (d, J=8.0 Hz, 1H), 7.67 (d, J=5.2 Hz, 1H), 4.91 (s, 2H). LCMS: (Method C) 238.0 (M+H), Rt. 2.32 min, 96.73% (Max).

Intermediate 30: 4'-(chloromethyl)-3-(methylsulfonyl)-1,1'-biphenyl

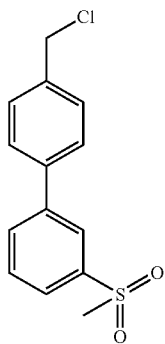 [SMILES: CS(=O)(=O)c1cccc(-c2ccc(CCl)cc2)c1]

Step 1: 3'-(methylsulfonyl)-[1,1'-biphenyl]-4-carbaldehyde

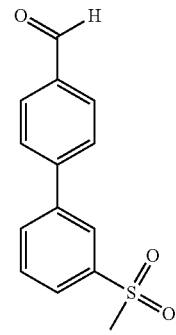

To a stirred solution of 1-bromo-3-(methylsulfonyl)benzene (400 mg, 2.66 mmol) and (4-formylphenyl) boronic acid in dioxane:water (10 mL, 9:1), Cesium Carbonate (2.6 g, 7.99 mmol) was added at RT and the resulting solution was flushed with nitrogen for 10 min. Tetrakis(triphenylphosphine)palladium(0) (153 mg, 0.13 mmol) was added and the resulting reaction mixture was stirred at 100° C. After completion of reaction, the reaction mixture was filtered off through celite pad, and the filtrate was concentrated under vacuum. Water was added and the aqueous suspension was extracted with EtOAc (2×20 mL). The combined organic layer was washed with brine (3.0 mL), dried over Na$_2$SO$_4$ and concentrated. The crude product was purified by flash chromatography (Eluent: 50-60% EtOAc in pet ether) to afford the title compound. Yield: 97% (660 mg, Pale yellow gummy solid). LCMS: (Method B), no ionization, Rt. 1.98 min, 85.07% (Max).

Step 2: (3'-(methylsulfonyl)-[1,1'-biphenyl]-4-yl) methanol

To a stirred solution of 3'-(methylsulfonyl)-[1,1'-biphenyl]-4-carbaldehyde (660 mg, 2.53 mmol) in dry MeOH (5 mL), NaBH$_4$ was added slowly at 0° C. and the resulting mixture was stirred at RT for 2 h. Completion of the reaction was confirmed by TLC. The reaction mixture was quenched with ice cold water (20 mL) and extracted with EtOAc (2×50 mL). The combined organic layer was dried over Na$_2$SO$_4$ and concentrated. The resulting crude product was purified by flash chromatography (Eluent: 50-60% EtOAc in pet ether) to give the title compound. Yield: 67% (450 mg, pale brown solid). $^1$H NMR (400 MHz, DMSO-d$_6$): δ 8.15 (s, 1H), 8.03 (d, J=8.0 Hz, 1H), 7.90 (d, J=7.6 Hz, 1H), 7.75-7.73 (m, 3H), 7.46 (d, J=8.0 Hz, 2H), 5.27 (m, J=5.6 Hz, 1H), 4.56 (d, J=5.6 Hz, 2H), 3.32 (s, 3H).

Step 3: 4'-(chloromethyl)-3-(methylsulfonyl)-1,1'-biphenyl

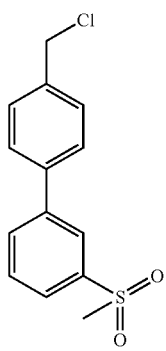 [SMILES: CS(=O)(=O)c1cccc(-c2ccc(CCl)cc2)c1]

To a stirred solution of (3'-(methylsulfonyl)-[1,1'-biphenyl]-4-yl)methanol (0.2 g, 0.76 mmol) in dry DCM (10 mL), SOCl$_2$ (0.2 mL, 2.2 mmol) was added dropwise at 0° C. and the resulting solution was stirred at RT for 1 h. The reaction mixture was concentrated under vacuum and the crude product was co-distilled with DCM (20 mL), affording the title compound that was used in next step without further purification. Yield: 98% (200 mg, pale brown solid). $^1$H NMR (400 MHz, DMSO-d$_6$): δ 8.17 (s, 1H), 8.05 (d, J=7.2 Hz, 1H), 7.92 (d, J=7.6 Hz, 1H), 7.81-7.73 (m, 3H), 7.58 (d, J=7.6 Hz 2H), 4.84 (s, 2H), 3.32 (s, 3H).

Intermediate 31: 4-(4-(Chloromethyle)-3-Methylphenyl-1-Methyl-1 H-Pyrazole

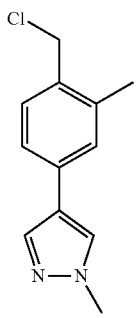

Step 1: (2-methyl-4-(1-methyl-1H-pyrazol-4-yl)phenyl)methanol

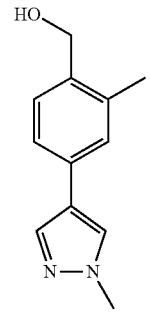

To a stirred solution of (4-bromo-2-methylephenyl)methanol (400 mg, 1.989 mmol) and 1-methyle-4-(4,4,5,5-tetramethyle-1,3,2 dioxaborolan-2-yl)-1 H-pyrazole in dioxane:water (10 mL, 9:1), cesium carbonate (1.9 g, 5.96 mmol) was added at RT and the resulting solution was flushed with nitrogen for 10 min. Pd(dppf)Cl$_2$ (81.2 mg, 0.09 mmol) was added and the reaction mixture was stirred overnight at 100° C. The reaction mixture was filtered off through celite pad and the filtrate was concentrated under vacuum. To the resulting crude product water was added and the resulting aqueous suspension was extracted with EtOAc (2×20.0 mL). The combined organic layer was washed with brine (3.0 mL), dried over Na$_2$SO$_4$ and concentrated to get a crude product. It was purified by flash chromatography (Eluent: 50-60% EtOAc in pet ether) to afford the title compound. Yield: 67% (270 mg, pale yellow gummy solid). $^1$H NMR (400 MHz, DMSO-d$_6$): δ 8.07 (s, 1H), 7.81 (s, 1H), 7.33-7.28 (m, 3H), 5.0 (t, J=6.4 Hz, 1H), 4.47 (d, J=7.2 Hz, 2H), 3.85 (s, 3H), 2.61 (s, 3H). LCMS: (Method B) 203.1 (M+H), Rt. 1.39 min, 99.90% (Max), 99.06% (220 nm).

Step 2: 4-(4-(Chloromethyle)-3-Methylphenyl-1-Methyl-1H-Pyrazole

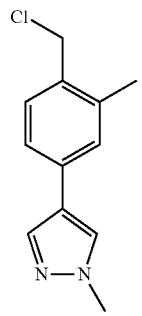

To a stirred solution of (2-methyl-4-(1-methyl-1 H-pyrazol-4-yl)phenyl)methanol (270 mg, 0.98 mmol) in dry DCM (10 mL), thionyl chloride (0.6 mL, 3.26 mmol) was added dropwise at 0° C. and the resulting mixture was stirred at RT for 1 h. It was concentrated under vacuum and the resuting product was co-distilled with DCM (20 mL) to get the title compound that was used without further purification. Yield: 98% (200 mg, pale brown solid). LCMS: (Method B) 221.1 (M+H), Rt. 2.17 min, 69.96% (Max).

Intermediate 32: 4-(4-(chloromethyl)phenyl)pyridine

Step 1: ((4-(pyridin-4-yl)phenyl)methanol

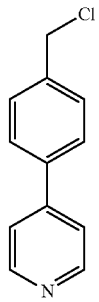 [SMILES: ClCc1ccc(-c2ccncc2)cc1]

To a stirred solution of 4-(4,4,5,5-tetramethyl-1,3,2-dioxaborolan-2-yl)pyridine (350 mg, 1.68 mmol) and (4-bromophenyl)methanol (355 mg, 1.85 mmol) in dry 1,4-dioxane (4 mL), a solution of potassium carbonate (0.7 g, 5.04 mmol) in water (2 mL) was added at RT. The reaction mixture was flushed with nitrogen for 10 min, before the addition of Tetrakis (triphenylphosphine)palladium(0) (190 mg, 0.68 mmol) at RT. The mixture was heated overnight at 100° C. It was filtered through celite pad and the filtrate was concentrated under vacuum. The resulting crude product was purified by flash chromatography (Eluent: 45% EtOAc in pet ether) to afford the title compound. Yield: 61.2% (190 mg, pale yellow gum). $^1$H NMR (400 MHz, DMSO-$d_6$): δ 8.62 (d, J=6.0 Hz, 2H), 7.77 (d, J=8.0 Hz, 2H), 7.70 (d, J=6.0 Hz, 2H), 7.46 (d, J=8.0 Hz, 2H), 5.31 (t, J=5.6 Hz, 1H), 4.56 (d, J=5.6 Hz, 2H). LCMS: (Method A) 186.1 (M+H), Rt. 0.47 min, 85% (max).

Step 2: 4-(4-(chloromethyl)phenyl)pyridine

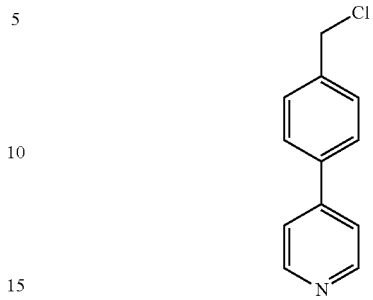

To a stirred solution of (4-(pyridin-4-yl)phenyl)methanol (180 g, 1.12 mmol) in dry DCM (5 mL) at 0° C., was added SOCl$_2$ (0.32 mL, 5.63 mmol) and the resuling mixture was stirred at 0° C. for 1 h. After completion of reaction, it was concentrated and the crude product was co-distilled with toluene (20 mL), affording the title compound that was used without further purification. Yield: 60.9% (120 mg, pale yellow solid). $^1$H NMR (400 MHz, DMSO-$d_6$): δ 8.95 (d, J=6.4 Hz, 2H), 8.36 (d, J=6.0 Hz, 2H), 8.04 (d, J=8.0 Hz, 2H), 7.68 (d, J=8.4 Hz, 2H), 4.88 (s, 2H). LCMS: (Method A) 204.0 (M+H), Rt. 1.39 min, 71.1% (max).

Intermediate 33: 2-(4-(chloro methyl)-2-methyl phenyl) pyridine

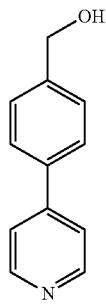 [SMILES: OCc1ccc(-c2ccncc2)cc1]

Step 1: 3-methyl-4-(pyridin-3-yl) benzaldehyde

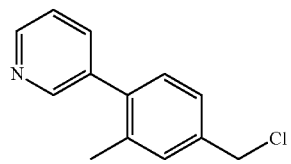

To a stirred solution of 4-bromo-3-methylbenzaldehyde (500 mg, 2.51 mmol) in 1,4-dioxane:water (9:1, 10 mL), 3-(4,4,5,5-tetramethyl-1,3,2-dioxaborolan-2-yl)pyridine (515 mg, 2.51 mmol) and cesium carbonate (2.45 mg, 7.53 mmol) were added at RT and the reaction mixture was flushed with nitrogen for 20 min. Tetrakis (triphenyl phosphine) palladium (0) (290 mg, 0.251 mmol) was added at RT and the resulting mixture was heated ovenight at 100° C. The reaction mass was filtered through celite pad that was washed with EtOAc (50 mL). Combined filtrate was washed with water (2×25 mL), dried over Na$_2$SO$_4$ and concentrated under vacuum. The resulting crude compound was purified by flash chromatography (Eluent: 27% EtOAc: hexane) affording the title compound. Yield: 80% (400 mg, colourless liquid). $^1$H NMR (400 MHz, DMSO-d$_6$): δ 10.05 (s, 1H), 8.64 (d, J=8.4 Hz, 2H), 7.85 (t, J=10.8 Hz, 3H), 7.52 (d, J=10.4, Hz, 2H), 2.33 (s, 3H). LCMS (Method A) 198.1 (M+H), Rt. 1.18 min, 99.48% (Max).

Step 2: (3-methyl-4-(pyridin-3-yl)phenyl) methanol

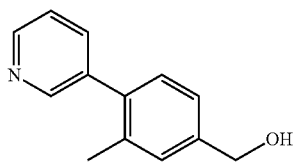

To a stirred solution of 3-methyl-4-(pyridin-3-yl)benzaldehyde (400 mg, 2.02 mmol) in methanol (10 mL), sodium borohydride (115 mg, 3.042 mmol) was added at 0° C. and the resulting mixture was stirred at RT for 30 min. It was quenched with ice water (30 mL) and extracted with EtOAc (2×25 mL). The combined organic layer was dried over Na$_2$SO$_4$ and concentrated under vacuum. The resulting crude compound was purified by flash chromatography (Eluent: 45% EtOAc: Hexane) to afford the title compound. Yield: 87% (350 mg, colourless liquid). $^1$H NMR (400 MHz, DMSO-d$_6$): δ 8.56-8.54 (m, 2H), 7.78-7.76 (m, 1H), 7.47-7.44 (m, 1H), 7.27-7.18 (m, 3H), 5.21 (t, J=5.6 Hz, 1H), 4.52 (d, J=5.6 Hz, 2H), 2.23 (s, 3H). LCMS: (Method C) 200.1 (M+H), Rt. 0.606 min, 72.31% (Max).

Step 3: 2-(4-(chloro methyl)-2-methyl phenyl) pyridine

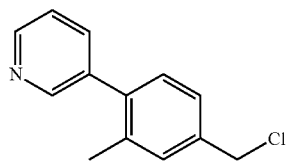

To a stirred solution of (3-methyl-4-(pyridin-3-yl) phenyl) methanol (350 mg, 1.75 mmol) in DCM (5 mL), SOCl$_2$ (2 mL) was added at 0° C. and the resulting mixture was stirred at RT for 3 h. After completion of the reaction, monitored by TLC, it was concentrated under vacuum and the resulting crude product was co-distilled with DCM (2×20 mL), affording the title compound that was used without further purification. Yield: 65% (250 mg, off white solid). $^1$H NMR (400 MHz, DMSO-d$_6$): δ 8.94 (s, 1H), 8.88 (d, J=5.2 Hz, 1H), 8.50 (d, J=8.0 Hz, 1H), 8.02 (t, J=7.6 Hz, 1H), 7.45 (t, J=7.6 Hz, 2H), 7.38 (d, J=8.0 Hz, 1H), 4.82 (s, 2H), 2.28 (s, 3H). LCMS (Method A) 218.1 (M+H), Rt. 1.28 min, 99.53% (Max).

Intermediate 34: 2-(2,3-dihydrobenzo[b] [1,4]dioxin-6-yl)-1-(4-(4,4,5,5-tetramethyl-1,3,2-dioxaborolan-2-yl)benzyl)pyrrolidine

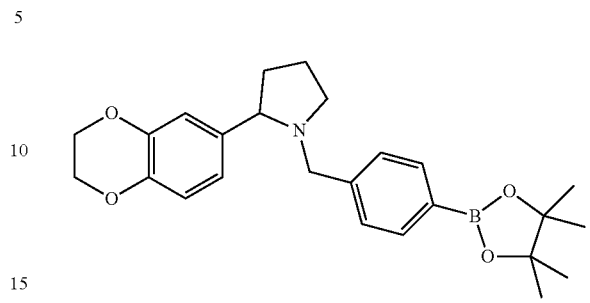

To a stirred solution of intermediate 6 and bis(pinacolato) diboron (382 mg, 1.50 mmol) in dry 1,4 dioxane (5 mL), potassium acetate (367 mg, 3.75 mmol) was added at RT. The resulting reaction mixture was flushed with nitrogen for 10 min. Pd(dppf)Cl$_2$—CH$_2$Cl$_2$ (102 mg, 0.125 mmol) was added and the reaction mixture was heated overnight at 100° C. The reaction mixture was filtered through celite pad and the filtrate was concentrated under vacuum. The resulting boranic ester was taken as such in the next step. Yield: 85% (1.4 g, dark brown solid). LCMS: (Method A) 217.3 (M+H), Rt. 1.96 min, 75.06% (Max).

Intermediate 35: 4-(4-(chloromethyl)-3-methylphenyl)pyridine

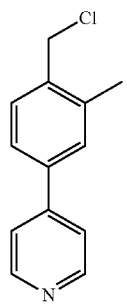

Step 1: (2-methyl-4-(pyridin-4-yl)phenyl)methanol

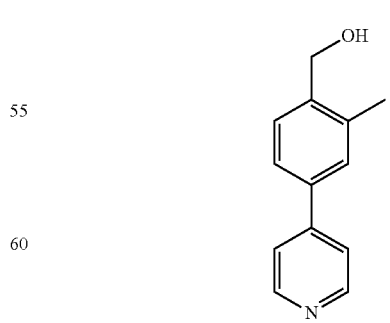

To a stirred solution of 4-(4,4,5,5-tetramethyl-1,3,2-dioxaborolan-2-yl)pyridine (0.5 g, 2.42 mmol) and (4-bromo-2-methylphenyl)methanol (0.58 g, 2.91 mmol) in dioxane (4 mL), Cs₂CO₃ (2.3 g, 7.28 mmol) and water (0.4 mL) were added at RT. The reaction mixture was flushed with nitrogen for 10 min. Tetrakis (triphenyl phosphine) palladium (0) (0.28 g, 0.24 mmol) was added and the resulting reaction mixture was heated overnight at 100° C. The reaction mixture was filtered through celite pad and the filtrate was concentrated under vacuum. The resulting crude product was purified by flash chromatography (Eluent: 45% EtOAc in PE) to afford the title compound. Yield: 62% (300 mg, pale yellow gum). ¹H NMR (400 MHz, DMSO-d₆): δ 8.6 (d, J=6.0 Hz, 2H), 7.69 (d, J=6.0 Hz, 2H), 7.62 (s, 1H), 7.56-7.60 (m, 1H), 7.50 (d, J=7.6 Hz, 1H), 5.19 (t, J=5.2 Hz, 1H), 4.54 (d, J=5.2 Hz, 2H), 2.31 (s, 3H). LCMS: (Method A) 200.1 (M+H), Rt. 0.83 min, 81% (max).

Step 2:
4-(4-(chloromethyl)-3-methylphenyl)pyridine

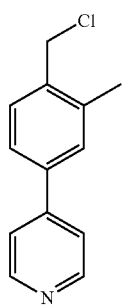

To a stirred solution of (2-methyl-4-(pyridin-4-yl)phenyl) methanol (0.3 g, 1.5 mmol) in dry DCM (5 mL) at 0° C. was added SOCl₂ (0.4 mL) and the resulting mixture was stirred at 0° C. for 1 h. After completion, the reaction mixture was concentrated under vacuum and co-distilled with toluene to give title compound. It was used in the next step without further purification. Yield: 64% (210 mg, pale yellow gummy liquid). ¹H NMR (400 MHz, DMSO-d₆): δ 8.93 (d, J=6.0 Hz, 2H), 8.33 (d, J=5.6 Hz, 2H), 7.91 (s, 1H), 7.85 (d, J=7.6 Hz, 1H), 7.61-7.64 (m, 1H), 4.88 (s, 2H), 2.50 (s, 3H). LCMS: (Method A) 218.1 (M+H), Rt. 1.52 min, 71.1% (max).

Intermediate 36:
N-(5-(chloromethyl)thiazol-2-yl)acetamide

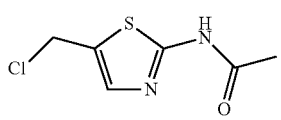

Step 1: ethyl 2-acetamidothiazole-5-carboxylate

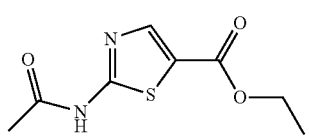

To a stirred solution of ethyl-2-amino thiazole-5-carboxylate (10.0 g, 58.1 mmol), pyridine (9.47 mL, 116.27 mmol) and DMAP (200 mg, 1.6 mmol) in DCM (100 mL), acetic anhydride (8.89 g, 87.20 mmol) was added at 0° C. and the resulting mixture was refluxed for 2 h. It was concentrated under vacuum and HCl (1.5 N in water, 50 mL) was added. The mixture was stired for 10 min. The resulting precipitate was filtered and washed with water (250 mL) and hexane (50 mL) to give title compound. Yield: 98% (12.1 g, off white solid). ¹H NMR (300 MHz, DMSO-d₆): δ 8.10 (s, 1H), 4.24 (q, J=6.2, 2H), 2.17 (s, 3H), 1.26 (t, J=6.2 Hz, 3H). LCMS: (Method A) 215.0 (M+H), Rt. 2.77 min, 97.11% (Max).

Step 2: N-(5-(hydroxymethyl)thiazol-2-yl)acetamide

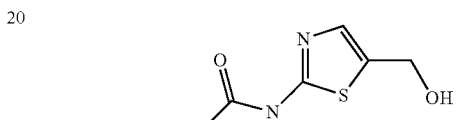

To a stirred solution of ethyl 2-acetamidothiazole-5-carboxylate (4.0 g 18.6 mmol) in dry toluene (110 mL), lithium triethylborohydride (36.0 mL, 37.3 mmol, 1 M solution in THF) was added slowly at 0° C. The reaction mixture was stirred at RT for 2 h. The completion of the reaction was monitored by TLC. Reaction mixture was quenched with MeOH (2.0 mL). Water (20 mL) was added and the solution was stirred for 10 min. Two layers were separated and aqueous layer was washed with hexane (3×25 mL). The aqueous layer was acidified to pH 4 with AcOH (4 mL). The resulting precipitate was recovered by filtration, washed with water (10 mL) and hexane (20 mL) and dried under vacuum to give the title compound. Yield: 84% (2.7 g, white solid). ¹H NMR (400 MHz, DMSO-d₆): δ 11.86 (s, 1H), 7.23 (br.s, 1H), 5.32 (s, 1H), 4.54 (s, 2H), 2.09 (s, 3H). LCMS: (Method A) 173.0 (M+H), Rt. 2.02 min, 99.89% (Max).

Step 3: N-(5-(chloromethyl)thiazol-2-yl)acetamide

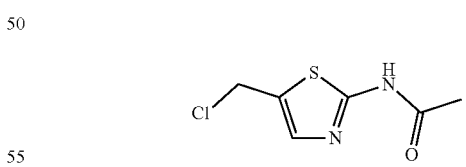

To a stirred solution of N-(5-(hydroxymethyl)thiazol-2-yl)acetamide (10.0 g, 58.1 mmol) in dry DCM (27 mL), thionyl chloride (12.9 mL, 174.4 mmol) was added slowly at 0° C. and refluxed for 3 h. The reaction mixture was concentrated under vacuum. The resulting residue was co-distilled with DCM (2×50 mL) and Et₂O (50 mL) to give title compound. Yield: 92% (10.2 g, pale yellow solid). ¹HNMR (400 MHz, DMSO-d₆): δ 12.18 (s, 1H), 7.50 (s, 1H), 5.02 (s, 2H), 2.14 (s, 3H). LCMS: (Method A) 187.0 (M+H), Rt. 1.77 min, 90.36% (Max).

Intermediate 37:
4-bromo-1-(4-(chloromethyl)phenyl)-1 H-pyrazole

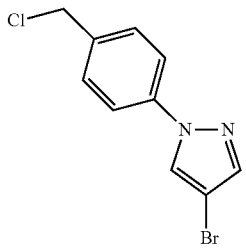 [SMILES: ClCc1ccc(-n2cc(Br)cn2)cc1]

Step 1: 4-(4-bromo-1H-pyrazol-1-yl)benzaldehyde

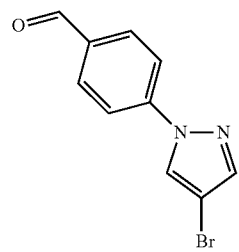 [SMILES: O=Cc1ccc(-n2cc(Br)cn2)cc1]

To a stirred solution of 4-fluorobenzaldehyde (500 mg, 4.02 mmol) in dry DMF (10 mL), $K_2CO_3$ (1.67 g, 12.08 mmol) and 4-bromo-1H-pyrazole (651 mg, 4.43 mmol) were added at RT and the reaction mixture was heated overnight at 100° C. It was quenched with ice water (20 mL) and extracted with EtOAc (2×20 mL). The combined organic layer was dried over $Na_2SO_4$ and concentrated under vacuum. The resulting crude compound was purified by flash chromatography (Eluent: 8% EtOAc:Hexane) to afford the title compound. Yield: 79% (800 mg, white solid). $^1$H NMR (400 MHz, DMSO-$d_6$): δ 10.02 (s, 1H), 8.98 (s, 1H), 8.06 (br s, 4H), 7.99 (s, 1H).

Step 2:
(4-(4-bromo-1H-pyrazol-1-yl)phenyl)methanol

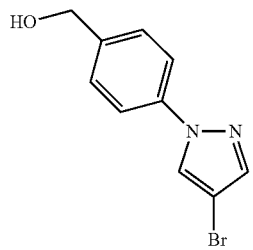 [SMILES: OCc1ccc(-n2cc(Br)cn2)cc1]

To a stirred solution of 4-(4-bromo-1H-pyrazol-1-yl) benzaldehyde (800 mg, 3.18 mmol) in MeOH (10 mL), $NaBH_4$ (180 mg, 4.77 mmol) was added slowly portion wise at 0° C. Then the reaction mixture was stirred for 30 min at RT. The reaction mixture was quenched with ice water (20 mL) and extracted with EtOAc (2×20 mL). The combined organic layer was dried over $Na_2SO_4$ and concentrated under vacuum to afford the title compound. It was used in the next step without further purification. Yield: 93% (750 mg, white solid). $^1$H NMR (400 MHz, DMSO-$d_6$): δ 8.77 (s, 1H), 7.87 (s, 1H), 7.78 (d, J=8. Hz, 2H), 7.44 (d, J=8.4 Hz, 2H), 5.28 (t, J=5.6 Hz, 1H), 4.54 (d, J=5.6 Hz, 2H). LCMS: (Method A), 253.0 (M+H), Rt. 1.82 min, 98.83% (Max).

Step 3:
4-bromo-1-(4-(chloromethyl)phenyl)-1H-pyrazole

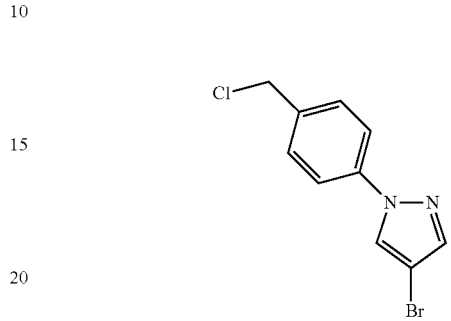

To a stirred solution of (4-(4-bromo-1H-pyrazol-1-yl) phenyl)methanol (805 mg, 2.96 mmol) in DCM (10 mL), $SOCl_2$ (5 mL) was added at 0° C. and the resulting mixture was stirred for 3 h at RT. It was concentrated under vacuum and co-distilled with DCM (2×20 mL) to afford the title compound. It was used in the next step without further purification. Yield: 100% (805 mg, white solid). $^1$H NMR (400 MHz, DMSO-$d_6$): δ 8.82 (s, 1H), 7.86 (d, J=8.8 Hz, 3H), 7.59 (d, J=2.4 Hz, 1H), 7.57 (s, 1H), 4.82 (s, 2H). LCMS: (Method A), 273.0 (M+H), Rt. 2.40 min, 98.14% (Max).

Intermediate 38: 1-(4-(chloromethyl)phenyl)-1H-pyrazole-4-carbonitrile

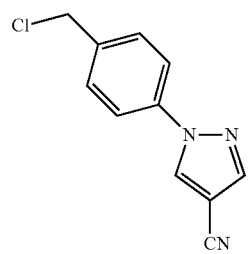 [SMILES: N#Cc1cnn(-c2ccc(CCl)cc2)c1]

Step 1:
1-(4-formylphenyl)-1H-pyrazole-4-carbonitrile

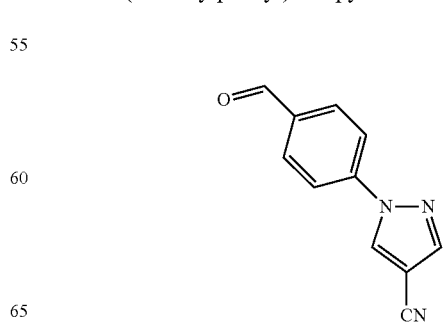

To a stirred solution of 4-fluorobenzaldehyde (500 mg, 4.02 mmol) in dry DMF (10 mL), K₂CO₃ (1.67 g, 12.08 mmol) and 1H-pyrazole-4-carbonitrile (412 mg, 4.43 mmol) were added at RT. The reaction mixture was heated overnight at 100° C. The reaction was monitored by TLC. It was quenched with ice water (20 mL) and extracted with EtOAc (2×20 mL). The combined organic layer was dried over Na₂SO₄ and concentrated under vacuum. The resulting crude compound was purified by flash chromatography (Eluent: 10% EtOAc:Hexane) to afford the title compound. Yield: 25% (200 mg, white solid). ¹H NMR: (400 MHz, DMSO-d₆): δ 10.05 (s, 1H), 9.51 (s, 1H), 8.45 (s, 1H), 8.10 (d, 4H).

Step 2: 1-(4-(hydroxymethyl)phenyl)-1H-pyrazole-4-carbonitrile

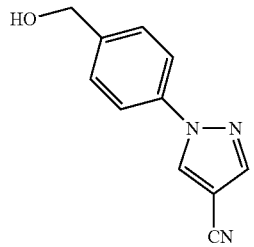 [SMILES: N#Cc1cnn(-c2ccc(CO)cc2)c1]

To a stirred solution 1-(4-formylphenyl)-1H-pyrazole-4-carbonitrile (200 mg, 1.01 mmol) in MeOH (10 mL), NaBH₄ (58 mg, 1.52 mmol) was added slowly portion wise at 0° C. and the resulting mixture was stirred at RT for 30 min. It was quenched with ice water (20 mL) and extracted with EtOAc (2×20 mL). The combined organic layer was dried over Na₂SO₄, concentrated under vacuum to afford the title compound. It was used in the next step without further purification. Yield: 49% (100 mg, white solid). ¹H NMR (400 MHz, DMSO-d₆): δ 9.31 (s, 1H), 8.35 (s, 1H), 7.81 (d, J=11.2 Hz, 2H), 7.49 (d, J=10.8 Hz, 2H), 5.32 (t, J=7.6 Hz, 1H), 4.56 (d, J=7.6 Hz, 2H). LCMS: (Method A) 200.1 (M+H), Rt. 1.47 min, 95.88% (Max).

Step 3: 1-(4-(chloromethyl)phenyl)-1H-pyrazole-4-carbonitrile

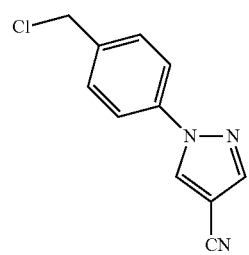 [SMILES: N#Cc1cnn(-c2ccc(CCl)cc2)c1]

To a stirred solution of 1-(4-(hydroxymethyl)phenyl)-1H-pyrazole-4-carbonitrile (100 mg, 0.50 mmol) in DCM (5 mL), SOCl₂ (2 mL) was added at 0° C. and the resulting mixture was stirred at RT for 3 h. Reaction was monitored by TLC, concentrated under vacuum, co-distilled with DCM (2×20 mL) and dried under vacuum to give the title compound. It was used in the next step without further purification. Yield: 100% (109 mg, white solid). ¹H NMR (400 MHz, DMSO-d₆): δ 9.36 (s, 1H), 8.38 (s, 1H), 7.88 (d, J=11.6 Hz, 2H), 7.63 (d, J=11.6 Hz, 2H), 4.84 (s, 2H).

Intermediate 39: 3-(4-(chloromethyl)-3-methylphenyl)-2-methylpyridine

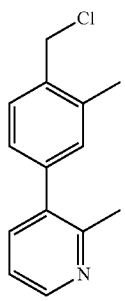 [SMILES: Cc1cc(-c2cccnc2C)ccc1CCl]

Step 1: 2-methyl-4-(4,4,5,5-tetramethyl-1,3,2-dioxaborolan-2-yl)benzaldehyde

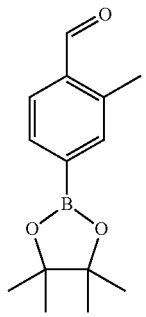

To a stirred solution of 4-bromo-2-methylbenzaldehyde (0.5 g, 2.47 mmol) in dioxane (5 mL), potassium acetate (0.7 g, 7.42 mmol) and bis(pinacolato)diboron (1.2 g, 495 mmol) were added at RT. The reaction mixture was flushed with nitrogen for 10 minutes before the addition of Pd(dppf)Cl₂-DCM (0.2 g, 0.24 mmol). The reaction mixture was stirred overnight at 100° C. After completion of reaction, the reaction mixture was filtered through celite and the filtrate was concentrated under vacuum affording the title compound. It was used in the next step without further purification. Yield: 85% (530 mg, pale brown gum). ¹H NMR (400 MHz, DMSO-d₆): δ 10.28 (s, 1H), 7.82 (d, J=7.52 Hz, 1H), 7.69 (d, J=7.60 Hz, 1H), 7.57 (s, 1H), 3.33 (s, 3H), 1.32 (s, 12H).

Step 2: 2-methyl-4-(2-methylpyridin-3-yl)benzaldehyde

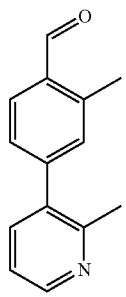 [SMILES: Cc1cc(-c2cccnc2C)ccc1C=O]

To a stirred solution of 2-methyl-4-(4,4,5,5-tetramethyl-1,3,2-dioxaborolan-2-yl)benzaldehyde (250 mg, 1.0 mmol) and 3-bromo-2-methylpyridine (206 mg, 1.2 mmol) in dioxane (4 mL), cesium carbonate (975 mg, 3.01 mmol) and water (0.4 mL) were added at RT. The reaction mixture was flushed with nitrogen for 10 minutes before addition of tetrakis(triphenylphosphine)palladium(0) (115 mg, 0.1 mmol). Then the resulting reaction mixture was heated at 100° C. overnight. It was filtered through celite and the filtrate was concentrated under vacuum. The resulting crude product was purified by flash chromatography (Eluent: 15-20% EtOAc in PE) to afford the title compound. Yield: 75.5% (160 mg, pale yellow gummy solid). $^1$H NMR (400 MHz, DMSO-$d_6$): δ 10.28 (s, 1H), 8.51 (s, 1H), 7.91 (d, J=8.0 Hz, 1H), 7.65-7.56 (m, 2H), 7.55-7.44 (m, 1H), 7.56-7.58 (m, 1H), 2.67 (s, 3H), 2.21 (s, 3H). LCMS: (Method A) 212.1 (M+H), Rt. 1.17 min, 77.1% (Max).

Step 3: (2-methyl-4-(2-methylpyridin-3-yl)phenyl)methanol

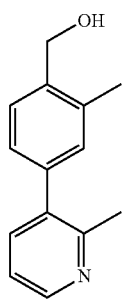 [SMILES: Cc1cc(-c2cccnc2C)ccc1CO]

To a stirred solution of 2-methyl-4-(2-methylpyridin-3-yl)benzaldehyde (0.16 g, 0.75 mmol) in MeOH (5 mL), NaBH$_4$ (85 mg, 2.26 mmol) was added at 0° C. and the reaction mixture was stirred at RT for 2 h. After completion, the reaction mixture was quenched with saturated NH$_4$Cl solution (10 mL) and extracted with EtOAc (2×10 mL). The combined organic layers were dried over Na$_2$SO$_4$ and concentrated under vacuum. The resulting crude material was purified by flash chromatography (Eluent: 25% EtOAc in PE) to give the title compound. Yield: 92% (150 mg, pale yellow gummy solid). $^1$H NMR (400 MHz, DMSO-$d_6$): δ 8.52 (s, 1H), 8.45 (d, J=1.6 Hz, 1H), 7.94 (s, 1H), 7.94-7.48 (m, 2H), 7.34-7.29 (m, 1H), 5.14 (t, J=5.2 Hz, 1H), 4.55 (d, J=4.8 Hz, 2H), 2.43 (s, 3H), 2.29 (s, 3H). LCMS: (Method A) 214.2 (M+H), Rt. 0.98 min, 75.4% (Max).

Step 4: 3-(4-(chloromethyl)-3-methylphenyl)-2-methylpyridine

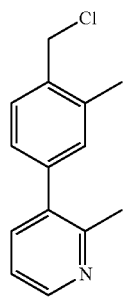 [SMILES: Cc1cc(-c2cccnc2C)ccc1CCl]

To a stirred solution of (2-methyl-4-(2-methylpyridin-3-yl)phenyl)methanol (150 mg, 0.74 mmol) in dry DCM (5 mL), SOCl$_2$ (0.3 mL) was added at 0° C. and the mixture was stirred at RT for 1 h. The reaction mixture was concentrated under vacuum and resulting crude product was co-distilled with DCM (2×10 mL), affording the title compound. It was used in the next step without further purification. Yield: 62% (172 mg, light yellow gummy solid). LCMS: (Method A) 232.1 (M+H), Rt. 1.65 min, 66.94% (Max).

Intermediate 40: 4-(4-(chloromethyl)-3-methylphenyl)-3-methylpyridine

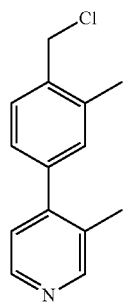

Step 1: 2-methyl-4-(3-methylpyridin-4-yl)benzaldehyde

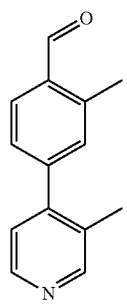

To a stirred solution of step 1 of Intermediate 39 (250 mg, 1.0 mmol) and 4-bromo-3-methylpyridine (206 mg, 1.2 mmol) in dioxane (4 mL), cesium carbonate (975 mg, 3.01 mmol) and water (0.4 mL) were added at RT. The reaction mixture was flushed with nitrogen for 10 min. Tetrakis(triphenylphosphine)palladium(0) (115 mg, 0.1 mmol) was added and the reaction mixture was heated at 100° C. overnight. Completion of the reaction was monitored by TLC. The reaction mixture was filtered through celite pad and the filtrate was concentrated under vacuum. The resulting crude product was purified by flash chromatography (Eluent: 15-20% EtOAc in PE) to afford the title compound. Yield: 80% (172 mg, pale yellow gummy solid). $^1$H NMR (400 MHz, DMSO-d$_6$): δ 10.29 (s, 1H), 8.52 (s, 1H), 8.46 (d, J=6.4 Hz, 1H), 7.97-7.86 (m, 1H), 7.47-7.34 (m, 3H), 2.67 (s, 3H), 2.24 (s, 3H). LCMS: (Method A) 212.2 (M+H), Rt. 1.23 min, 80.1% (Max).

Step 2: (2-methyl-4-(3-methylpyridin-4-yl)phenyl)methanol

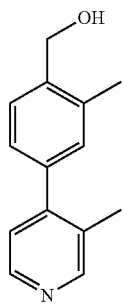 [SMILES: Cc1cc(-c2ccncc2C)ccc1CCl]

To a stirred solution of 2-methyl-4-(2-methylpyridin-3-yl)benzaldehyde (170 mg, 0.80 mmol) in MeOH (5 mL), NaBH$_4$ (0.091 g, 2.40 mmol) was added at 0° C. and the reaction mixture was stirred at RT for 2 h. After completion of reaction, the reaction mixture was quenched with saturated NH$_4$Cl solution (10 mL) and extracted with EtOAc (2×10 mL). The combined organic layers were dried over Na$_2$SO$_4$ and concentrated under vacuum. The resulting crude material was purified by flash chromatography (Eluent: 25-30% EtOAc in PE) to give the title compound. Yield: 91% (155 mg, pale yellow gummy oil). $^1$H NMR (400 MHz, DMSO-d$_6$): δ 8.49-8.40 (m, 1H), 7.95 (s, 1H), 7.46 (d, J=10.8 Hz, 1H), 7.33-7.09 (m, 3H), 5.19 (t, J=5.2 Hz, 1H), 4.54 (d, J=6.8 Hz, 2H), 2.57 (s, 3H), 2.29 (s, 3H). LCMS: (Method A) 214.1 (M+H), Rt. 1.04 min, 95.79% (Max).

Step 3: 4-(4-(chloromethyl)-3-methylphenyl)-3-methylpyridine

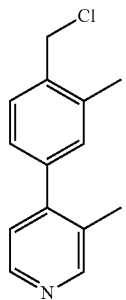 [SMILES: Cc1cc(-c2ccncc2C)ccc1CCl]

To a stirred solution of (2-methyl-4-(2-methylpyridin-3-yl)phenyl)methanol (150 mg, 0.74 mmol) in dry DCM (5 mL), SOCl$_2$ (0.3 mL) was added at 0° C. and the resulting mixture was stirred at RT for 1 h. It was concentrated under vacuum and the resulting product was co-distilled with DCM (2×10 mL) to get the title compound. It was used in the next step without further purification. Yield: 66% (180 mg, light brown gummy oil). $^1$H NMR (400 MHz, DMSO-d$_6$): δ 8.79 (d, J=5.6 Hz, 1H), 8.37 (s, 1H), 7.93-7.64 (m, 1H), 7.65-7.53 (m, 2H), 7.39-7.34 (m, 1H), 4.88 (s, 2H), 2.66 (s, 3H), 2.46 (s, 3H). LCMS: (Method A) 232.0 (M+H), Rt. 1.62 min, 74.24% (Max).

Intermediate 41:
4-(4-(chloromethyl)phenyl)morpholin-3-one

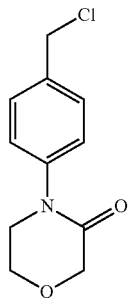 [SMILES: O=C1COCCN1c1ccc(CCl)cc1]

Step 1: 4-(4-(((tert-butyldimethylsilyl)oxy)methyl)phenyl) morpholin-3-one

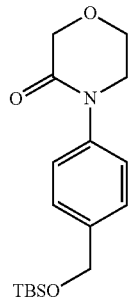 [SMILES: CC(C)(C)[Si](C)(C)OCc1ccc(N2CCOCC2=O)cc1]

To a stirred solution of (4-bromobenzyl)oxy)(tert-butyl)dimethylsilane (300 mg, 0.996 mmol) and morpholin-3-one (151.16 mg, 1.49 mmol) in Toluene (10 mL), K$_2$CO$_3$ (275.3 mg, 1.99 mmol) was added at RT. The reaction mixture was flushed with nitrogen about 10 min before addition of CuI (18.96 mg, 0.09 mmol) and DMEDA (17.55 mg, 0.19 mmol). The resulting reaction mixture was heated at 105° C. overnight. It was filtered through celite pad that was washed with EtOAc (20 mL). Combined filtrate was washed with water (10 mL), brine solution (10 mL), dried over Na$_2$SO$_4$, and concentrated under vacuum. The crude product was purified by flash chromatography (Eluent: 50% EtOAc:hexane) to afford the title compound. Yield: 64% (300 mg, pale yellow gummy solid). LCMS: (Method A) 322.2 (M+H), Rt. 2.493 min, 92.45% (Max).

Step 2: 4-(4-(hydroxymethyl)phenyl)morpholin-3-one

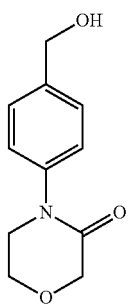 [SMILES: O=C1COCCN1c1ccc(CO)cc1]

To a stirred solution of 4-(4-(hydroxymethyl)phenyl)morpholin-3-one (300 mg, 0.93 mmol) in dry THF (5 mL), TBAF (1.12 mL, 1.11 mmol, 1M in THF solution) was added slowly dropwise at 0° C. The reaction mixture was stirred for 2 h at RT. It was quenched with sat NaHCO$_3$ solution (10 mL) and extracted with DCM (2×20 mL). The combined organic layer was dried over Na$_2$SO$_4$ and concentrated under vacuum to afford the title compound. It was used in the next step without further purification. Yield: 100% (193 mg, colourless liquid). LCMS: (Method A) 208.1 (M+H), Rt. 0.757 min, 69.03% (Max), 74.66% (220 nm).

Step 3: 4-(4-(chloromethyl)phenyl)morpholin-3-one

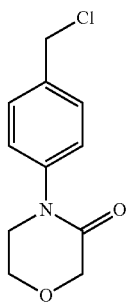

To a stirred solution of 4-(4-(hydroxymethyl)phenyl)morpholin-3-one (200 mg, 0.965 mmol) in DCM (5 mL), SOCl$_2$ (2 mL) was added at 0° C. and the resulting mixture was stirred at RT for 3 h. The reaction mixture was concentrated under vacuum and the crude material was co-distilled with DCM (2×10 mL) to afford the title compound. It was used in the next step without further purification. Yield: 100% (217 mg, colourless liquid).

Intermediate 42: 1-(4-(chloromethyl)phenyl)piperidin-2-one

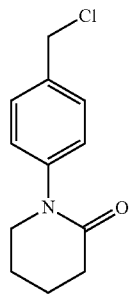 [SMILES: O=C1CCCCN1c1ccc(CCl)cc1]

Step 1: 1-(4-(((tert-butyldimethylsilyl)oxy)methyl)phenyl)piperidin-2-one

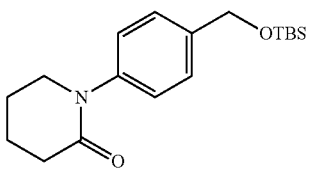 [SMILES: CC(C)(C)[Si](C)(C)OCc1ccc(N2CCCCC2=O)cc1]

To the reaction mixture of (4-bromobenzyl)oxy)(tert-butyl)dimethylsilane (300 mg, 0.996 mmol) and piperidin-2-one (148 mg, 1.49 mmol) in toluene (10 mL), K$_2$CO$_3$ (275.3 mg, 1.992 mmol) was added at RT and the resulting mixture was flushed with nitrogen for 10 min. DMEDA (17.55 mg, 0.19 mmol) and CuI (18.96 mg, 0.099 mmol) were added at RT and the reaction mixture was stirred at 105° C. overnight. The catalyst was filtered off through celite pad and the filtrate was concentrated under vacuum. The resulting crude product was suspended in water (30.0 mL) and extracted with EtOAc (2×20.0 mL). The combined organic layer was washed with brine (3.0 mL), dried over Na$_2$SO$_4$ and concentrated. The resulting crude product was purified by flash chromatography (Eluent: 10 to 30% EtOAc in PE) to afford the title compound. Yield: 48% (150 mg, pale yellow gummy solid). LCMS: (Method A) 320.3 (M+H), Rt. 2.619 min, 85.62% (Max).

Step 2: 1-(4-(hydroxymethyl)phenyl)piperidin-2-one

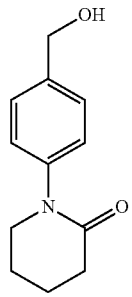 [SMILES: O=C1CCCCN1c1ccc(CO)cc1]

To a stirred solution of 1-(4-(tert-butyldimethylsilyl)oxy)methyl)phenyl)piperidin-2-one (150 mg, 0.46 mmol, in dry THF (5 mL), TBAF (0.7 ml, 0.74 mmol, 1M in THF solution) was added at 0° C. and the resulting mixture was stirred at RT for 2 h. It was quenched with NaHCO₃ (3 mL) and extracted with DCM (2×50 mL). The combined organic layer was dried over Na₂SO₄ and concentrated under vacuum to give the title compound. It was used in the next step without further purification. Yield: 93.75% (90 mg, brown solid). LCMS: (Method D) 206.1 (M+H), Rt. 0.93 min, 62.40% (Max).

Step 3: 1-(4-(chloromethyl)phenyl)piperidin-2-one

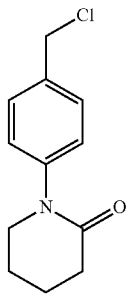

To a stirred solution of 1-(4-(hydroxymethyl)phenyl)piperidin-2-one (90 mg, 0.43 mmol) in dry DCM (10 mL), SOCl₂ (0.9 mL, 1.31 mmol) was added dropwise at 0° C. and the mixture was stirred at RT for 1 h. It was concentrated under vacuum and the resulting crude product was co-distilled with DCM (20 mL) to get the title compound. It was used in the next step without further purification.

Yield: 98% (90 mg, brown solid). LCMS: (Method A) 224.1 (M+H), Rt. 1.78 min, 92.53% (Max).

Intermediate 43: 3-(4-(chloromethyl)phenyl)-5-(methylsulfonyl)pyridine

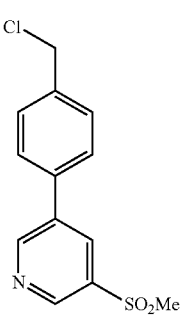 [SMILES: CS(=O)(=O)c1cncc(-c2ccc(CCl)cc2)c1]

Step 1: (4-(5-(methylsulfonyl)pyridin-3-yl)phenyl)methanol

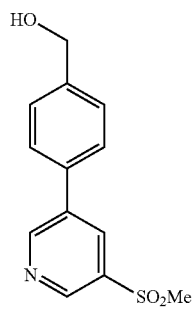

To a stirred solution of 4-(5-(methylsulfonyl)pyridin-3-yl)benzaldehyde (200 mg, 0.5 mmol) in dry methanol (5 mL), NaBH₄ (87 mg, 2.2 mmol) was added at 0° C. and the resulting solution was stirred at RT for 3 h. After completion of the reaction, the reaction mixture was quenched with ice and extracted with DCM (2×20 mL). The combined organic layer was washed with water (10 mL), dried over Na₂SO₄ and concentrated under vacuum. The resulting crude product was purified by flash chromatography (Eluent: 80% EtOAc in PE) to afford the title compound. Yield: 83% (250 mg, white solid). LCMS: (Method A) 264.1 (M+H), Rt. 1.27 min, 78.9% (Max).

Step 2: 3-(4-(chloromethyl)phenyl)-5-(methylsulfonyl)pyridine

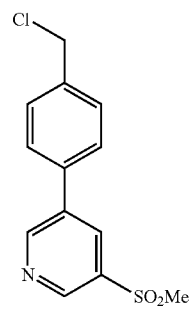

To a stirred solution of (4-(5-(methylsulfonyl)pyridin-3-yl)phenyl)methanol (200 mg, 0.7 mmol) in dry DCM (4 mL), SOCl₂ (0.1 mL, 2.2 mmol) was added at 0° C. and the resulting solution was stirred for 3 h at RT. After completion of the reaction, the reaction mixture was concentrated under vacuum. The resulting product was co-distilled with DCM (2×20 mL) to afford the title compound. It was used in the next step without further purification. Yield: 85% (180 mg, pale yellow solid). LCMS: (Method A) 279.1 (M+H), Rt. 1.955 min, 37.6% (Max).

Intermediate 44: 2-(4-(chloromethyl)phenyl)pyrazine

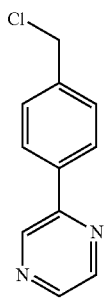 [SMILES: ClCc1ccc(-c2cnccn2)cc1]

Step 1: (4-(4,4,5,5-tetramethyl-1,3,2-dioxaborolan-2-yl)phenyl)methanol

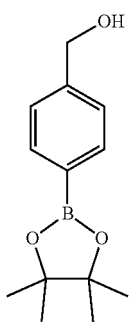

To a stirred solution of (4-bromophenyl)methanol (3.0 g, 16 mmol) and bis(pinacolato)diboron (4.94 g, 19 mmol) in dioxane (30 mL), potassium acetate (4.71 g, 48 mmol) was added at RT. The mixture was flushed with nitrogen for 10 minutes before addition of Pd(dppf)Cl$_2$-DMC (1.3 g, 1.6 mmol) at RT. The resulting reaction mixture was heated at 100° C. overnight. It was filtered through celite pad and the filtrate was concentrated undere vacuum, affording the title compound. Yield: 91% (3.5 g, pale brown solid). LCMS: (Method A) 217.2 (M+H), Rt. 1.98 min, 85.50% (Max).

Step 2: (4-(pyrazin-2-yl)phenyl)methanol

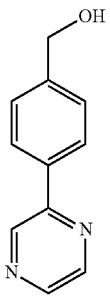

To a stirred solution of 2-chloropyrazine (500 mg, 4.38 mmol) and (4-(4,4,5,5-tetramethyl-1,3,2-dioxaborolan-2-yl)phenyl)methanol (1.5 g, 6.57 mmol) in dry dioxane (4 mL), potassium carbonate (1.18 g, 8.76 mmol) and water (1 mL) were added at RT. The reaction mixture was flushed with nitrogen for 10 minutes before addition of tetrakis (triphenyl phosphine) palladium (0) (101 mg, 0.08 mmol) at RT. The resulting reaction mixture was heated at 100° C. overnight. It was filtered through celite pad and the filtrate was concentrated under vacuum. The resulting crude product was purified by flash chromatography (Eluent: 32% EtOAc in hexane) to afford the title compound. It was used in the next step without further purification. Yield: 61% (410 mg, pale yellow solid). $^1$H NMR (400 MHz, DMSO-d$_6$): δ 9.25 (d, J=2.0 Hz, 1H), 8.72-8.70 (m, 1H), 8.60 (d, J=3.2 Hz, 1H), 8.11 (d, J=10.8 Hz, 2H), 7.57 (d, J=3.6 Hz, 2H), 5.31 (t, J=7.6 Hz, 1H), 4.58 (d, J=7.6 Hz, 2H). LCMS: (Method A) 187.1 (M+H), Rt. 1.19 min, 77.23% (Max).

Step 3: 2-(4-(chloromethyl)phenyl)pyrazine

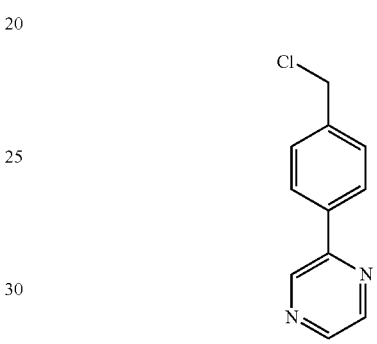

To a stirred solution of (4-(pyrazin-2-yl) phenyl)methanol (400 mg, 2.16 mmol) in dry DCM (4 mL), SOCl$_2$ (0.30 mL, 4.30 mmol)) was added at 0° C. and the reaction mixture was stirred for 3 h at RT. The completion of the reaction was monitored by TLC. The reaction mixture was concentrated under vacuum. The resulting crude product was co-distilled with DCM (2×10 mL) to get the title compound. It was used in the next step without further purification. Yield: 72% (315 mg, yellow solid). $^1$H NMR (400 MHz, DMSO-d$_6$): δ 9.28 (d, J=1.4 Hz, 1H), 8.74-8.74 (m, 1H), 8.64 (d, J=2.5 Hz, 1H), 8.17 (d, J=8.3 Hz, 2H), 7.61 (d, J=8.4 Hz, 2H), 4.85 (s, 2H). LCMS: (Method A) 205.1 (M+H), Rt. 1.96 min, 97.73% (Max).

Intermediate 45: (2-(4-(chloromethyl)phenoxy)ethyl)(methyl)sulfane

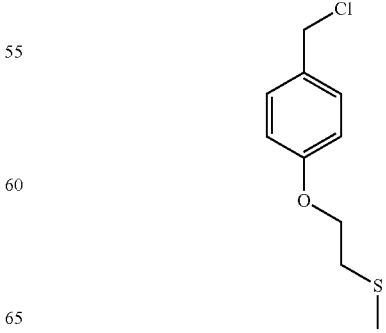

Step 1: Methyl 4-(2-(methylthio)ethoxy)benzoate

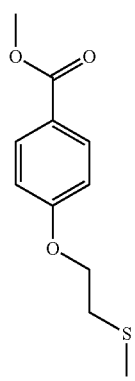

To a stirred solution of methyl 4-hydroxybenzoate (500 mg, 3.2 mmol) in dry DMF (5 mL), NaH (57 mg, 3.9 mmol) was added at 0° C. and after 10 minutes stirring (2-chloroethyl)(methyl)sulfane (0.4 mL, 3.9 mmol) was added at the same temperature. The resulting reaction mixture was stirred 5 h at RT. The reaction was quenched with ice water (10 mL) and extracted with EtOAc (2×50 mL). The combined organic layer was washed with water (20 mL), brine (5 mL), dried over $Na_2SO_4$ and concentrated under vacuum. The resulting residue was purified by flash chromatography (Elutent: 10% EtOAc in PE) to afford the title compound. Yield: 34% (250 mg, colorless liquid). $^1$H NMR (400 MHz, $CDCl_3$): δ 8.01 (dd, J=6.8, 2.0 Hz, 2H), 6.94 (dd, J=6.8, 2.0 Hz, 2H), 4.22 (d, J=6.8 Hz, 2H), 3.91 (s, 3H), 2.93 (t, J=6.8 Hz, 2H), 2.25 (s, 3H).

Step 2: (4-(2-(methylthio)ethoxy)phenyl)methanol

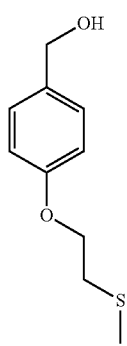

To a stirred solution of methyl 4-(2-(methylthio)ethoxy) benzoate (250 mg, 1.1 mmol) in dry THF (3 mL), LAH (1.3 mL, 1.3 mmol)) was added at −78° C. and the resulting mixture was stirred for 2 h at RT. The completion of the reaction was monitored by TLC. The reaction mixture was quenched by using EtOAc and $Na_2SO_4$ solution. Phases were separated and the aqueous phase was further extracted with EtOAc (2×20 mL). The combined organic layer was washed with water (10 mL), dried over $Na_2SO_4$ and concentrated under vacuum. The resulting crude product was purified by flash chromatography (Elutent: 13% EtOAc in PE) to afford the title compound. Yield: 90% (200 mg, off white solid). $^1$H NMR (400 MHz, $CDCl_3$): δ 7.32 (t, J=6.4 Hz, 2H), 6.93 (t, J=2.4 Hz, 2H), 4.66 (d, J=7.6 Hz, 2H), 4.20 (t, J=8.8 Hz, 2H), 2.92 (t, J=9.2 Hz, 2H), 2.25 (s, 3H).

Step 3: (2-(4-(chloromethyl)phenoxy)ethyl)(methyl)sulfane

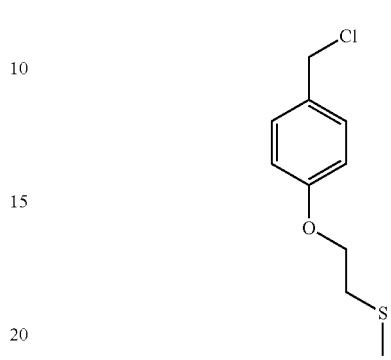

To a stirred solution of (4-(2-(methylthio)ethoxy)phenyl) methanol (200 mg, 1.0 mmol) in dry DCM (3 mL), $SOCl_2$ (0.13 mL, 2.0 mmol) was added at 0° C. and the resulting mixture was stirred 3 h at RT. The completion of the reaction was monitored by TLC. The reaction mixture was concentrated under vacuum and the resulting crude product was co-distilled with DCM (2×20 mL) to afford the title compound. It was used in the next step without further purification. Yield: 91% (200 mg, off white gummy solid). $^1$H NMR (400 MHz, DMSO-$d_6$): δ 7.35 (t, J=2.8 Hz, 2H), 6.94 (t, J=2.8 Hz, 2H), 4.72 (s, 2H), 4.15 (t, J=8.8 Hz, 2H), 2.84 (t, J=8.8 Hz, 2H), 2.15 (s, 3H).

Intermediate 46: thiomorpholine 1,1-dioxide hydrochloride

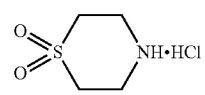

Step 1: Tert-butyl thiomorpholine-4-carboxylate

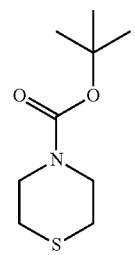

To a stirred solution of thiomorpholine (700 mg, 6.78 mmol) in dry DCM (7 mL), TEA (1.1 mL, 8.13 mmol) was added at R, followed by boc anhydride (1.7 mL, 7.46 mmol) at 0° C. The resulting mixture was stirred 3 h at RT. It was diluted with DCM (10 mL) and washed with water (20 mL), brine (5 mL), dried over $Na_2SO_4$ and concentrated under vacuum to get the title compound. It was used in the next step without further purification. Yield: 91% (1.25 g, white solid). LCMS: (Method A) 104.2 (M+H), Rt. 2.15 min, 97.12% (Max).

Step 2: Tert-butyl thiomorpholine-4-carboxylate 1,1-dioxide

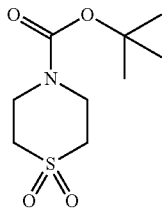

To a stirred solution of tert-butyl thiomorpholine-4-carboxylate (1.2 g, 5.91 mmol) in dry DCM (3 mL), m-CPBA (3.05 g, 17.73 mmol) was added at 0° C. and the resulting mixture was stirred 3 h at RT. After completion of the reaction, the reaction mixture was quenched with the addition of sat. NaHCO3 solution at 0° C. It was extracted with DCM (2×50 mL). The combined organic layer was washed with water (20 mL), brine (5 mL), dried over $Na_2SO_4$ and concentrated under vacuum to get the title compound. It was used in the next step without further purification. Yield: 87% (1.05 g, white solid). $^1$H NMR (400 MHz, $CDCl_3$): δ 3.95 (t, J=5.2 Hz, 4H), 3.03 (t, J=4.8 Hz, 4H), 1.50 (s, 9H). LCMS: (Method A) 136.1 (M+H), Rt. 1.65 min, 99.97% (Max).

Step 3: thiomorpholine 1,1-dioxide hydrochloride

To a stirred solution of tert-butyl thiomorpholine-4-carboxylate 1,1-dioxide (1.05 g, 4.46 mmol) in dry MeOH (10 mL), 4M HCl in dioxane (2.45 mL, 9.87 mmol) was added at 0° C. and the resulting mixture was stirred 3 h at RT. It was concentrated under vacuum and the resulting residue was trituated with DCM (5 mL), EtOAc (5 mL) to get the title compound. Yield: 46% (277 mg, white solid). LCMS: (Method A) 136.1 (M+H), Rt. 0.47 min, 99.95% (Max).

Intermediate 47: 4-(4-(chloromethyl)phenyl)thiomorpholin-3-one

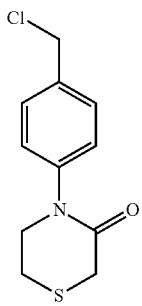 [SMILES: O=C1CSCCN1c1ccc(CCl)cc1]

Step 1:4-(4-(tert-butyldimethylsilyl)oxy)methyl) phenyl)thiomorpholin-3-one

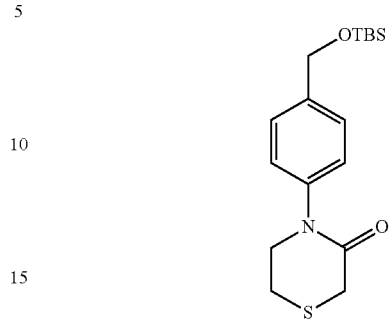

To a stirred solution of ((4-bromobenzyl)oxy)(tert-butyl) dimethylsilane (600 mg, 1.99 mmol) and thiomorpholin-3-one (350 mg, 2.99 mmol) in toluene (10 mL), potassium carbonate (550.07 mg, 3.98 mmol) was added at RT. The resulting reaction mixture was flushed with nitrogen for 10 min before additon of CuI (37.89 mg, 0.199 mmol) and DMEDA (35.08 mg, 0.39 mmol) at RT. The resulting reaction mixture was stirred at 105° C. overnight. It was filtered off through celite pad and the filtrate was concentrated. The resulting crude product was suspended in water (3.0 mL) and extracted with EtOAc (2×20.0 mL). The combined organic layer was washed with brine (3.0 mL), dried over $Na_2SO_4$ and concentrated. The resulting crude product was purified by flash chromatography (Eluent: 20-40% EtOAc in PE) to afford the title compound. Yield: 81% (550 mg, white solid). $^1$H NMR (400 MHz, DMSO-$d_6$): δ 7.36 (d, J=8.4 Hz, 2H), 7.25 (d, J=8.4 Hz, 2H), 4.74 (s, 2H), 3.40-3.96 (m, 2H), 3.48 (s, 2H), 3.05-3.03 (m, 2H), 0.95 (s, 9H), 0.11 (s, 6H). LCMS: (Method A) 338.1 (M+H), Rt. 2.65 min, 80.25% (Max).

Step 2: 4-(4-(hydroxymethyl)phenyl)thiomorpholin-3-one

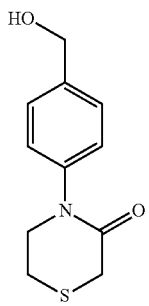

To a stirred solution of 4-(4-(((tert-butyldimethylsilyl) oxy)methyl)phenyl)thiomorpholin-3-one (550 mg, 1.62 mmol) in dry THF (5 mL), TBAF (1.9 mL, 1.95 mmol, 1M in THF solution) was added at 0° C. and the resulting mixture was stirred at RT for 2 h. The reaction mixture was quenched with $NaHCO_3$ (3 mL) and extracted with DCM (2×50 mL). The combined organic layer was dried over $Na_2SO_4$ and concentrated under vacuum. The crude product was purified by flash chromatography (Eluent: 60% EtOAc in PE) to afford the title compound. It was used in the next step without further purification. Yield: 61% (220 mg, brown solid). ¹H NMR (400 MHz, DMSO-$d_6$): δ 7.32 (d, J=8.2 Hz, 2H), 7.23 (d, J=8.2 Hz, 2H), 5.21 (s, 1H), 4.50 (d, J=5.6 Hz, 2H), 3.94 (t, J=6.0 Hz, 2H), 3.39 (s, 2H), 3.04 (t, J=6.0 Hz, 2H). LCMS: (Method A) 224.1 (M+H), Rt. 1.12 min, 97.39% (Max).

Step 3:
4-(4-(chloromethyl)phenyl)thiomorpholin-3-one

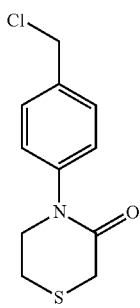 [SMILES: O=C1CSCCN1c1ccc(CCl)cc1]

To a stirred solution 4-(4-(hydroxymethyl)phenyl)thiomorpholin-3-one (220 mg, 0.98 mmol) in dry DCM (10 mL), SOCl$_2$ (0.2 mL, 2.9 mmol) was added dropwise at 0° C. and the resulting mixture was stirred at RT for 1 h. It was concentrated under vacuum and the resulting product was co-distilled with DCM (20 mL) to get the title product. It was used in the next step without any further purification. Yield: 98% (220 mg, brown solid). LCMS: (Method D) 242.1 (M+H), Rt. 1.85 min, 94.55% (Max).

Intermediate 48:
2-(4-(chloromethyl)phenyl)pyrimidine

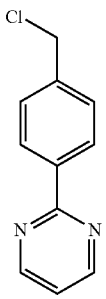 [SMILES: ClCc1ccc(-c2ncccn2)cc1]

Step 1:(4-(pyrimidin-2-yl)phenyl)methanol

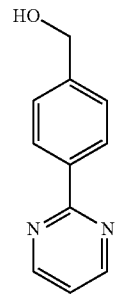 [SMILES: OCc1ccc(-c2ncccn2)cc1]

To a stirred solution of 2-chloropyrimidine (400 mg, 3.5 mmol) and (4-(4,4,5,5-tetramethyl-1,3,2-dioxaborolan-2-yl)phenyl)methanol (1231 mg, 5.2 mmol) in dioxane (5 mL), cesium carbonate (280 mg, 7.0 mmol) and water (1 mL) were added at RT. The reaction mixture was flushed with nitrogen before addition of Tetrakis(triphenylphosphine)palladium(0) (81 mg, 0.07 mmol). The resulting reaction mixture was stirred at 100° C. overnight. The reaction mixture was filtered through celite and filtrate was concentrated under vacuum. The resulting crude product was suspended in water and extracted with EtOAc (2×100 mL). The combined organic layer was washed with water (50 mL), brine (5 mL), dried over Na$_2$SO$_4$ and concentrated. The resulting residue was purified by flash chromatography (Eluent: 39% EtOAc in PE) to afford the title compound. Yield: 79% (510 mg, white solid). LCMS: (Method A) 187.1 (M+H), Rt. 1.233 min, 86.1% (Max).

Step 2: 2-(4-(chloromethyl)phenyl)pyrimidine

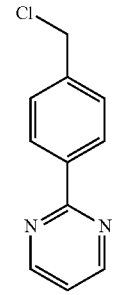

To a stirred solution of (4-(pyrimidin-2-yl)phenyl)methanol (510 mg, 2.7 mmol)) in dry DCM (5 mL), SOCl$_2$ (0.4 mL, 5.4 mmol) was added at 0° C. and the resulting mixture was stirred for 3 h at RT. The completion of the reaction was monitored by TLC. After completion of the reaction, the reaction mixture was concentrated under vacuum. The resulting residue was co-distilled with DCM (2×20 mL) to afford the title compound. It was used in the next step without any further purification. Yield: 87% (490 mg, pale yellow solid). LCMS: (Method A) 205.1 (M+H), Rt. 2.046 min, 95.3% (Max).

Intermediate 49: 4-(4-(chloromethyl)-2-methylphenyl)-3-methylpyridine

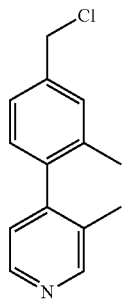 [SMILES: Cc1cnccc1-c1ccc(CCl)cc1C]

Step 1: 3-methyl-4-(3-methylpyridin-4-yl)benzaldehyde

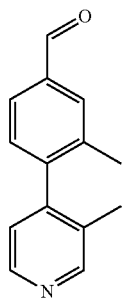 [SMILES: Cc1cnccc1-c1ccc(C=O)cc1C]

To a stirred solution of 3-methyl-4-(4,4,5,5-tetramethyl-1,3,2-dioxaborolan-2-yl)benzaldehyde (250 mg, 1.0 mmol, example 53 first step) and 4-bromo-3-methylpyridine (206 mg, 1.2 mmol) in dioxane (4 mL), cesium carbonate (975 mg, 3.01 mmol) and water (0.4 mL) were added at RT. The reaction mixture was flushed with nitrogen for 10 minutes before addition of tetrakis(triphenylphosphine)palladium(0) (115 mg, 0.1 mmol). The reaction mixture was stirred overnight at 100° C. It was filtered through celite and the filtrate was concentrated to get the title compound. It was used in the next step without any further purification. Yield: 79.8% (300 mg, Pale yellow liquid). $^1$H NMR (400 MHz, DMSO-d$_6$): δ 10.03 (s, 1H), 8.52 (s, 1H), 8.46 (d, J=6.4 Hz, 1H), 7.97-7.86 (m, 1H), 7.47-7.34 (m, 3H), 2.58 (s, 3H), 2.01 (s, 3H). LCMS: (Method A) 212.2 (M+H), Rt. 1.21 min, 51.4% (Max).

Step 2: (3-methyl-4-(3-methylpyridin-4-yl)phenyl)methanol

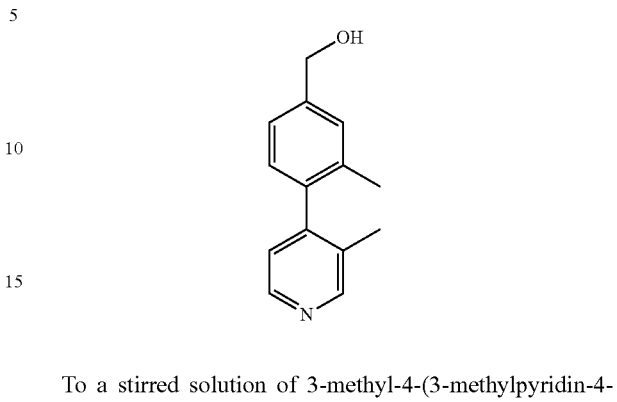

To a stirred solution of 3-methyl-4-(3-methylpyridin-4-yl)benzaldehyde (300 mg, 1.41 mmol) in MeOH (10 mL), NaBH$_4$ (170 mg, 4.22 mmol) was added at 0° C. and the reaction mixture was stirred at RT for 2 h. The reaction mixture was quenched with saturated NH$_4$Cl solution (10 mL) and was extracted with EtOAc (2×10 mL). The combined organic layer was dried over Na$_2$SO$_4$ and concentrated under vacuum. The resulting crude material was purified by flash chromatography (Eluent: 25% EtOAc in PE) to afford the title compound. Yield: 69% (210 mg, pale yellow liquid). $^1$H NMR (400 MHz, DMSO-d$_6$): δ 8.49-8.40 (m, 1H), 7.95 (s, 1H), 7.59-7.51 (m, 1H), 7.33-7.09 (m, 3H), 5.20 (t, J=5.6 Hz, 1H), 4.49 (d, J=5.6 Hz, 2H), 2.01 (s, 3H), 1.31 (s, 3H). LCMS: (Method A) 214.1 (M+H), Rt. 1.04 min, 75.5% (Max).

Step 4: 4-(4-(chloromethyl)-2-methylphenyl)-3-methylpyridine

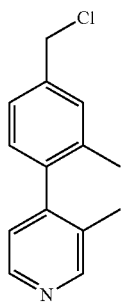

To a stirred solution of (3-methyl-4-(3-methylpyridin-4-yl)phenyl)methanol (200 mg, 0.93 mmol) in dry DCM (4 mL), SOCl$_2$ (0.4 mL) was added at 0° C. and the resulting solution was stirred at RT for 1 h. After completion of reaction, the reaction mixture was concentrated under vacuum. The resulting crude product was co-distilled with DCM (2×10 mL) to give the title compound. It was used in the next step without any further purification. Yield: 69.1% (180 mg, light brown gummy solid). LCMS: (Method A) 232.1 (M+H), Rt. 1.45 min, 65.4% (Max).

Intermediate 50: 3-(4-(chloromethyl)-2-methylphenyl)-2-methylpyridine

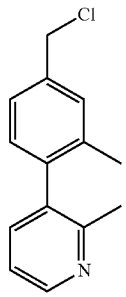 [SMILES: Cc1cc(CCl)ccc1-c1cccnc1C]

Step 1: 3-methyl-4-(4,4,5,5-tetramethyl-1,3,2-dioxaborolan-2-yl)benzaldehyde

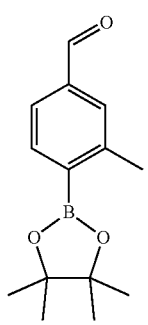

To a stirred solution of 4-bromo-3-methylbenzaldehyde (0.5 g, 2.47 mmol) in dioxane (15 mL), potassium acetate (0.7 g, 7.42 mmol) and bis(pinacolato)diboron (1.2 g, 495 mmol) were added at RT. The reaction mixture was flushed with nitrogen for 10 minutes. Pd(dppf)Cl$_2$-DCM (0.17 g, 0.27 mmol) was added and the mixture was heated at 100° C. overnight. It was filtered through celite and the filtrate was concentrated under vacuum to get the title compound. It was used in the next step without any further purification. Yield: 83% (510 mg, light brown liquid). $^1$H NMR (400 MHz, DMSO-d$_6$): δ 10.33 (s, 1H), 7.81 (d, J=10.4 Hz, 1H), 7.69-7.61 (m, 2H), 2.52 (s, 3H), 1.37 (s, 12H).

Step 2: 3-methyl-4-(2-methylpyridin-3-yl)benzaldehyde

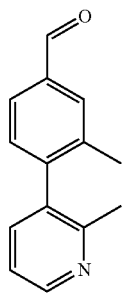 [SMILES: Cc1cc(C=O)ccc1-c1cccnc1C]

To a stirred solution of 3-methyl-4-(4,4,5,5-tetramethyl-1,3,2-dioxaborolan-2-yl)benzaldehyde (250 mg, 1.0 mmol) and 3-bromo-2-methylpyridine (206 mg, 1.2 mmol) in dioxane (4 mL), cesium carbonate (975 mg, 3.01 mmol) and water (0.4 mL) were added at RT. The reaction mixture was flushed with nitrogen for 10 minutes before addition of tetrakis(triphenylphosphine)palladium(0) (115 mg, 0.1 mmol). The resulting reaction mixture was heated to 100° C. overnight. It was filtered through celite and the filtrate was concentrated under vacuum to get the title compound. It was used in the next step without any further purification. Yield: 70% (310 mg, pale yellow gummy solid). $^1$H NMR (400 MHz, DMSO-d$_6$): δ 10.05 (s, 1H), 8.57 (s, 1H), 8.52-8.44 (m, 2H), 7.23-7.16 (m, 3H), 2.01 (s, 3H), 1.29 (s, 3H). LCMS: (Method A) 212.2 (M+H), Rt. 1.25 min, 55.3% (Max).

Step 3: (3-methyl-4-(2-methylpyridin-3-yl)phenyl)methanol

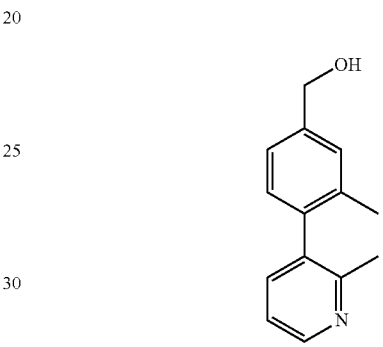

To a stirred solution of 3-methyl-4-(2-methylpyridin-3-yl)benzaldehyde (250 mg, 1.17 mmol) in MeOH (5 mL), NaBH$_4$ (140 mg, 3.52 mmol) was added at 0° C. and the reaction mixture was stirred at RT for 2 h. It was quenched with saturated NH$_4$Cl solution (10 mL) and extracted with EtOAc (2×10 mL). The combined organic layer was dried over Na$_2$SO$_4$ and concentrated under vacuum. The resulting crude material was purified by flash chromatography (Eluent: 25% EtOAc in PE) to give the title compound. Yield: 87% (220 mg, pale yellow gummy solid). $^1$H NMR (400 MHz, DMSO-d$_6$): δ 8.46 (d, J=4.8 Hz, 1H), 7.62-7.52 (m, 3H), 7.46 (d, J=7.6 Hz, 1H 7.28-7.19 (m, 1H), 5.20 (t, J=5.6 Hz, 1H), 4.52 (d, J=6.0 Hz, 2H), 2.19 (s, 3H), 1.97 (s, 3H). LCMS: (Method A) 214.1 (M+H), Rt. 0.66 min, 75.6% (Max).

Step 4: 3-(4-(chloromethyl)-2-methylphenyl)-2-methylpyridine

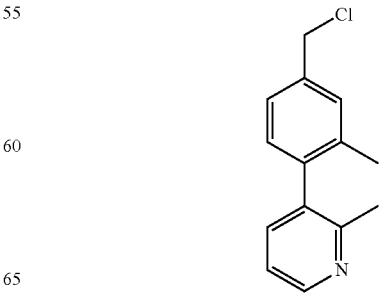

To a stirred solution of (3-methyl-4-(2-methylpyridin-3-yl)phenyl)methanol (200 mg, 0.93 mmol) in dry DCM (5 mL), SOCl$_2$ (0.4 mL) was added at 0° C. and the resulting mixture was stirred at RT for 1 h. The reaction completion was monitored by TLC. After concentration of the solvents, the resulting residue was co-distilled with DCM (2×10 mL) to give the title compound. It was used in the next step without any further purification. Yield: 66% (160 mg, light brown liquid). $^1$H NMR (400 MHz, DMSO-d$_6$): δ 8.83 (d, J=4.8 Hz, 1H), 8.35 (d, J=7.60 Hz, 1H), 7.84 (t, J=8.0 Hz, 1H), 7.63-7.53 (m, 2H), 7.30-7.23 (m, 1H), 4.81 (s, 2H), 2.67 (s, 3H), 1.15 (s, 3H). LCMS: (Method A) 232.0 (M+H), Rt. 1.62 min, 81.24% (Max).

Intermediate 51: 2-(3-methoxyphenyl)pyrrolidine

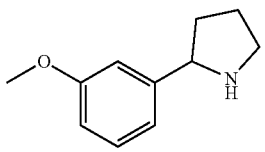

Step 1: tert-butyl (4-(3-methoxyphenyl)-4-oxobutyl)carbamate

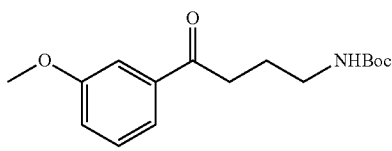 [SMILES: COc1cccc(C(=O)CCCNC(=O)OC(C)(C)C)c1]

In an oven-dried round bottom flask, Mg turnings (0.385 g, 16.0 mmol) and LiCl (0.566 mg, 13.36 mmol) were weighed. The flask was put under vacuum and back-filled with nitrogen. To this flask dry THF (10 mL) was added at RT and the suspension was stirred for 5 minutes. Then Iodine (1 pinch) was added at RT and the mixture was further stirred for 5 minutes. It was then cooled to 0° C. and 1-bromo-3-methoxybenzene (2 g, 10.69 mmol) in dry THF (5 mL) was added dropwise. After the initial heat evolution the mixture was heated to reflux for 1 h.

To the stirred solution of tert-butyl 2-oxopyrrolidine-1-carboxylate (1.98 g, 10.69 mmol) in dry THF (10 mL), above Grignard reagent was added at −78° C. dropwise and the mixture was stirred at the same temperature for 2 h. After completion of reaction, the reaction mixture was warmed to RT and quenched with 1.5M HCl (25 mL). The aqueous phase was extracted with EtOAc (2×50 mL). The combined organic phase was washed with brine, dried over anhydrous Na$_2$SO$_4$, and concentrated under vacuum to give the title compound. It was used for next step without further purification. Yield: (2.0 g, pale yellow gummy liquid). LCMS: (Method A)238.1(M-$^t$Bu, Rt. 2.18 min, 50.30% (Max).

Step 2: 2-(3-methoxyphenyl)pyrrolidine

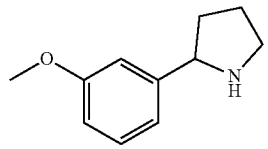

Tert-butyl (4-(3-methoxyphenyl)-4-oxobutyl)carbamate (2.0 g, 6.8 mmol) was dissolved in TFA (2.0 mL) and the mixture was stirred 2 h at RT. Then the reaction mixture was evaporated under vacuum. The resulting crude residue was co-distilled with toluene (10 mL) and dried under vacuum. It was dissolved in dry MeOH (20 mL) and NaBH$_4$ (518 mg, 13.65 mmol) was added slowly at 0° C. The resulting reaction mixture was stirred for 3 h at RT. Upon completion of reaction, the reaction mixture was quenched with the addition of saturated NH$_4$Cl solution (25 mL) and extracted with 10% MeOH/DCM (2×25 mL). The combined organic layer was washed with water (10 mL), brine solution (10 mL), dried over Na$_2$SO$_4$ and evaporated under vacuum. The resulting crude product was purified by flash chromatography (Eluent: 11% Methanol in DCM) to give the title compound.

Yield: 37.5% (450 mg, off white solid). $^1$H NMR (400 MHz, DMSO-d$_6$): δ 7.23 (t, J=7.6 Hz, 1H), 6.96 (d, J=5.6 Hz, 1H), 6.94 (s, 1H), 6.81 (d, J=8.0 Hz, 1H), 4.10 (t, J=8.0 Hz, 1H), 3.7 (s, 3H), 2.98-2.97 (m, 1H), 2.95-2.94 (m, 2H), 2.17-2.16 (m, 2H), 1.59-1.57 (m, 1H). LCMS: (Method A) 178.11 (M+H), Rt. 1.144 min, 79.38% (Max).

Intermediate 52: 5-(4-(chloromethyl)phenyl)-1,3,4-oxadiazol-2(3H)-one

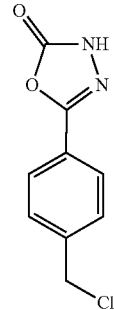

Step 1: 4-(hydroxymethyl)benzohydrazide

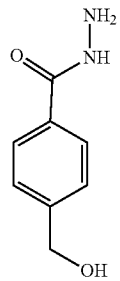

To a stirred solution of methyl 4-(hydroxymethyl)benzoate (4.0 g, 24.07 mmol) in EtOH (40 mL) NH$_2$NH$_2$—H$_2$O (12 mL, 240.70 mmol) was added and the resulting mixture was stirred overnight at 80° C. Completion of the reaction was monitored by TLC and the reaction mixture was' concentrated under vacuum. The resulting crude product was purified by flash chromatography (Eluent: 5-7% MeOH in DCM) to afford the title compound. Yield: 77% (3.1 g, off white solid). $^1$H NMR (400 MHz, DMSO-d$_6$): δ 9.72 (s, 1H), 7.79 (d, J=8.0 Hz, 2H), 7.38 (d, J=8.0 Hz, 2H), 5.30 (s, 1H), 4.54 (s, 2H), 4.47 (s, 2H). LCMS: (Method A) 167.1 (M+H), Rt. 0.52 min, 99.77% (Max).

Step 2: 5-(4-(hydroxymethyl)phenyl)-1,3,4-oxadiazol-2(3H)-one

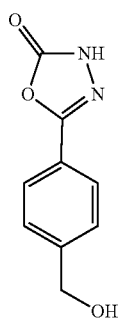 [SMILES: O=c1[nH]nc(-c2ccc(CO)cc2)o1]

To a stirred solution of 4-(hydroxymethyl)benzohydrazide (2.0 g, 12.05 mmol) in THF (40 mL) CDI (4.88 g, 30.12 mmol) and TEA (5 mL, 36.14 mmol) were added at RT. The resulting reaction mixture was stirred overnight at the same temperature. The reaction mixture was diluted with aq. 1.5 N HCl (25 mL) and extracted with EtOAc (2×50 mL). The combined organic layer was dried over Na$_2$SO$_4$ and concentrated under vacuum. The resulting anhydride was hydrolysed using 1N NaOH (5 mL) in Methanol (10 mL) at RT for 1 h. After completion of hydrolysis, the mixture was acidified by 1N HCl and extracted with EtOAc (2×50 mL). The combined organic layer was dried over Na$_2$SO$_4$ and concentrated. The resulting crude product was purified by flash chromatography (Eluent: 1-2% MeOH in DCM) to afford the title compound. Yield: 35% (0.8 g, off white solid). $^1$H NMR (400 MHz, DMSO-d$_6$): δ 12.55 (s, 1H), 7.76 (d, J=8.4 Hz, 2H), 7.48 (d, J=8.4 Hz, 2H), 5.37 (t, J=5.6 Hz, 1H), 4.57 (d, J=5.2 Hz, 2H). LCMS: (Method A) No isonisaton (M+H), Rt. 1.11 min, 91.26% (Max).

Step 3: 5-(4-(chloromethyl)phenyl)-1,3,4-oxadiazol-2(3H)-one

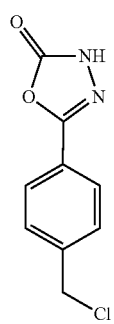 [SMILES: O=c1[nH]nc(-c2ccc(CCl)cc2)o1]

To a stirred solution of 5-(4-(hydroxymethyl)phenyl)-1,3,4-oxadiazol-2(3H)-one (0.25 g, 1.30 mmol) in dry DCM (2.5 mL), SOCl$_2$ (0.3 mL, 3.90 mmol) was added slowly at 0° C. and the resulting mixture was stirred at RT for 1 h. The reaction mixture was concentrated under vacuum and the resulting residue was co-distilled with DCM (3×10 mL) to give the title compound. It was used in the next step without further purification. Yield: 95% (0.26 g, off white solid). LCMS: (Method A) No ionisation (M+H), Rt. 1.83 min, 82.31% (Max).

Example 1: 5-((2-(2,3-dihydrobenzo[b] [1,4]dioxin-6-yl)pyrrolidin-1-yl)methyl)-2-(p-tolyl)oxazole

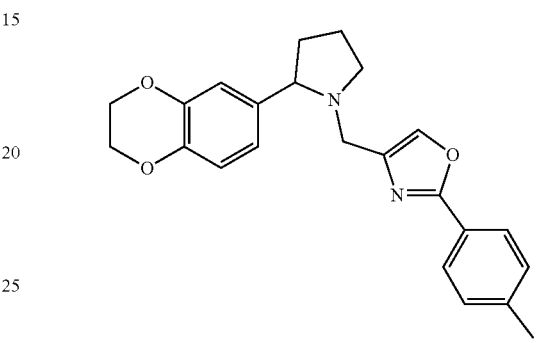

To a stirred solution of intermediate 1 (0.2 g, 0.97 mmol) in dry MeCN (3.0 mL), TEA (0.5 mL 2.92 mmol) and intermediate 2 (230 mg, 1.07 mmol) were added sequentially at RT and the resulting mixture was stirred overnight at 70° C. The reaction mixture was evaporated under vacuum. To the resulting crude product, water was added and was extracted with EtOAc (2×20 mL). The combined organic layer was dried over anhydrous Na$_2$SO$_4$, filtered and concentrated. The resulting crude product was purified by flash chromatography (eluent: 12% EtOAc in pet ether) to give the title compound. Yield: 33% (120 mg, Pale yellow gum solid). $^1$H NMR (400 MHz, DMSO-d$_6$): δ 7.96 (s, 1H), 7.83 (d, J=8.0 Hz, 2H), 7.33 (d, J=8.0 Hz, 2H), 6.90 (d, J=1.6 Hz, 1H), 6.86 (dd, J=8.4, 1.6 Hz, 1H), 6.80 (d, J=8.4 Hz, 1H), 4.21 (s, 4H), 3.61 (d, J=14.4 Hz, 1H), 3.40-3.36 (m, 1H), 3.20-3.15 (m, 2H), 2.37 (s, 3H), 2.35-2.33 (m, 1H), 2.13-2.04 (m, 1H), 1.83-1.77 (m, 2H), 1.60-1.50 (m, 1H). LCMS: (Method A) 377.1 (M+H), Rt. 2.48 min, 99.12% (Max). HPLC: (Method A) Rt. 3.72 min, 98.79% (Max).

Example 2: (S)-4-((2-(benzo[d] [1,3]dioxol-5-yl)pyrrolidin-1-yl)methyl)-2-(D-tolyl)oxazole or (R)-4-((2-(benzo[d] [1,3]dioxol-5-yl)pyrrolidin-1-yl)methyl)-2-(D-tolyl)oxazole

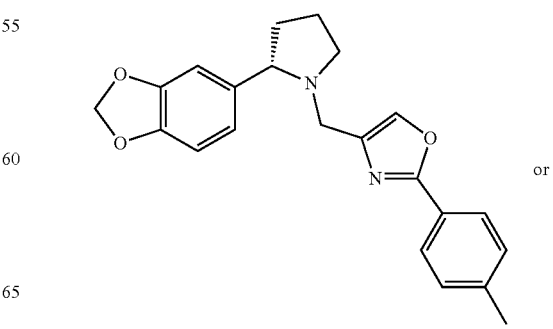

or

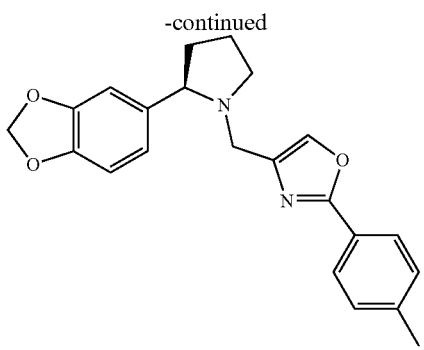

To a stirred solution of Intermediate 7 (0.2 g, 1.0 mmol) in dry MeCN (3.0 mL), TEA (0.3 mL 2.09 mmol), and intermediate 2 (233 mg, 1.0 mmol) were added at RT and the reaction mixture was stirred overnight at 65° C. The completion of the reaction was monitored by TLC and the reaction mixture was evaporated under vacuum. To the resulting crude product, water was added and the aqueous suspension was extracted with EtOAc (2×10 mL). The combined organic layer was dried over anhydrous $Na_2SO_4$, filtered and concentrated. The resulting crude product was purified by flash chromatography (Eluent: 75% EtOAc in pet ether) to give the racemic compound. The two enantiomers of this racemic compound were separated by chiral preparative SFC (mobile phase: 0.5% Isopropyl Amine in IPA; column: Chiracel OJ-H (Method A)). The second eluting compound was concentrated to give example 2. Yield: 33% (20 mg, Pale brown gummy solid). $^1$H NMR (400 MHz, DMSO-$d_6$): δ 7.97 (s, 1H), 7.84 (d, J=8.0 Hz, 2H), 7.33 (d, J=8.0 Hz, 2H), 6.99 (s, 1H), 6.86-6.84 (m, 2H), 5.98 (s, 2H), 3.60 (d, J=13.8 Hz, 1H), 3.38 (t, J=8.4 Hz, 1H), 3.20-3.17 (m, 2H), 2.40-2.33 (m, 4H), 2.11-2.08 (m, 1H), 1.81-1.75 (m, 2H), 1.75-1.74 (m, 1H). LCMS: (Method A) 363.1 (M+H), Rt. 2.49 min, 99.75% (Max). HPLC: (Method A) Rt. 3.82 min, 99.51% (Max). Chiral SFC: (Method A) Rt. 5.35 min, 100% (Max).

Example 3: 5-((2-(2,3-dihydrobenzo[b] [1,4]dioxin-6-yl)pyrrolidin-1-yl)methyl)-2-(p-tolyl)thiazole

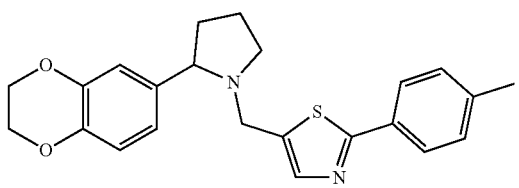 [SMILES: Cc1ccc(-c2ncc(CN3CCCC3c3ccc4c(c3)OCCO4)s2)cc1]

Step 1: 5-(chloromethyl)-2-(p-tolyl)thiazole

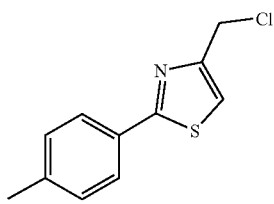

To a stirred solution of 4-methylbenzothioamide (1.0 g, 6.6 mmol) in dry IPA (10 mL), 1,3-dichloropropan-2-one (0.9 mL, 0.017 mol) was added at RT. Then the reaction mixture was heated with microwave irradiation for about 1 h at 120° C. Upon completion, the reaction mixture was diluted with water and extracted with EtOAc. The combined organic layer was washed with water, brine solution, dried over $Na_2SO_4$ and evaporated under vacuum. The resulting crude product was taken for the next step without purification. Yield: 51% (0.75 g, Pale yellow solid). $^1$H NMR (400 MHz, CDCl$_3$): δ 7.9-7.7 (m, 3H), 7.4-7.2 (m, 2H), 4.86 (s, 2H), 2.35 (s, 3H). LCMS: (Method A) 224.1 (M+H), Rt. 2.9 min, 86.88% (Max).

Step 2: 5-((2-(2,3-dihydrobenzo[b][1,4]dioxin-6-yl)pyrrolidin-1-yl)methyl)-2-(p-tolyl)thiazole

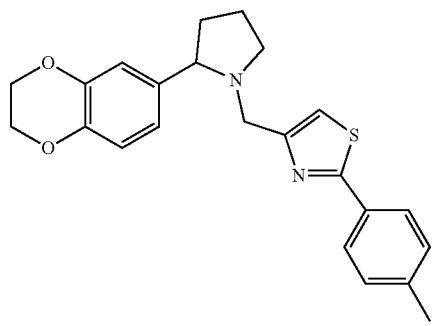 [SMILES: Cc1ccc(-c2nc(CN3CCCC3c3ccc4c(c3)OCCO4)cs2)cc1]

To a stirred solution of intermediate 1 (0.2 g, 0.97 mmol) in dry MeCN (3.0 mL), under nitrogen atmosphere, TEA (0.5 mL 2.92 mmol), and 5-(chloromethyl)-2-(p-tolyl)thiazole (240 mg, 1.07 mmol) were added sequentially at RT and the resulting mixture was stirred overnight at 70° C. It was evaporated under vacuum. To the resulting crude product, water (20 mL) was added and was extracted with EtOAc (2×20 mL). The combined organic layer was dried over anhydrous $Na_2SO_4$, filtered and concentrated. The resulting crude product was purified by flash chromatography (Eluent: 12% EtOAc in pet ether) to give the title compound. Yield: 34% (130 mg, Pale yellow gum solid). $^1$H NMR (400 MHz, DMSO-$d_6$): δ 7.79 (d, J=8.4 Hz, 2H), 7.38 (s, 1H), 7.30 (d, J=8.4 Hz, 2H), 6.93 (s, 1H), 6.87 (dd, J=8.0, 1.6 Hz, 1H), 6.80 (d, J=8.4 Hz, 1H), 4.21 (s, 4H), 3.77 (d, J=14.0 Hz, 1H), 3.42-3.38 (m, 1H), 3.20 (q, J=8.0 Hz, 1H), 2.40-2.30 (m, 4H), 2.17-2.09 (m, 1H), 1.85-1.70 (m, 2H), 1.59-1.52 (m, 1H). LCMS: (Method A) 393.2 (M+H), Rt. 2.54 min, 99.48% (Max). HPLC: (Method A) Rt. 3.87 min, 99.76% (Max).

Example 4: 4-(4-((2-(2,3-dihydrobenzo[b] [1,4]dioxin-6-yl)pyrrolidin-1-yl)methyl)phenyl)-1-methyl-1H-pyrazole

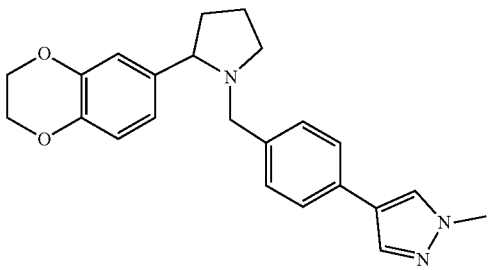 [SMILES: Cn1cc(-c2ccc(CN3CCCC3c3ccc4c(c3)OCCO4)cc2)cn1]

To a stirred solution of intermediate 1 in dry MeCN (2 mL), intermediate 3 (0.23 g, 0.9 mmol) and TEA (0.4 mL, 2.4 mmol) were added RT and the solution was stirred overnight at same temperature. After completion of the reaction, the reaction mixture was concentrated under vacuum. Water (10 mL) was added and extracted with DCM (2×10 mL). The combined organic layer was washed with water (5 mL), brine (5 mL) dried over $Na_2SO_4$ and concentrated under vacuum. The resulting crude product was purified by flash chromatography (Eluent: 39% EtOAc in pet ether) to afford the title compound. Yield: 50% (180 mg, Brown gummy solid). $^1$H NMR (400 MHz, DMSO-$d_6$): δ 8.08 (s, 1H), 7.81 (s, 1H), 7.48 (d, J=8.0 Hz, 2H), 7.21 (d, J=8.0 Hz, 2H), 6.93-6.88 (m, 2H), 6.83 (d, J=8.4 Hz, 1H), 4.23 (s, 4H), 3.86 (s, 3H), 3.68 (d, J=13.2 Hz, 1H), 3.28 (d, J=13.0 Hz, 1H), 2.98 (t, J=16.0 Hz, 2H), 2.18-2.09 (m, 2H), 1.75-1.71 (m, 2H), 1.56-1.52 (m, 1H). LCMS: (Method A) 376.0(M+H), Rt. 2.06 min, 96.4% (Max). HPLC: (Method A) Rt. 2.88 min, 96.45% (Max), 96.91% (220 nm)

Example 5: 5-((2-(2,3-dihydrobenzo[b] [1,4]dioxin-6-yl)pyrrolidin-1-yl)methyl)-2-(1-methyl-1H-pyrazol-4-yl)pyridine

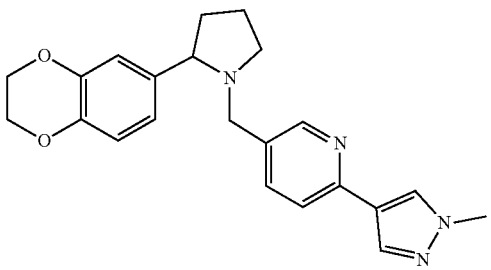 [SMILES: Cn1cc(-c2ccc(CN3CCCC3c3ccc4c(c3)OCCO4)cn2)cn1]

To a stirred solution of intermediate 1 (0.26 g, 1.3 mmol) in dry MeCN (3 mL), intermediate 4 (0.21 g, 1.0 mmol)) and TEA (0.4 mL, 2.6 mmol) were added at RT and the resulting mixture was stirred overnight at the same temperature. After completion of the reaction, the reaction mixture was concentrated under vacuum. To the resulting crude mixture, DCM (20 mL) was added and was washed with water (5 mL), dried over $Na_2SO_4$ and concentrated under vacuum. The resulting crude product was purified by flash chromatography (Elutent: 8% MeOH in DCM) to afford the title compound. Yield: 40% (160 mg, Brown gummy solid). $^1$H NMR (400 MHz, DMSO-$d_6$): δ 8.33 (s, 1H), 8.23 (s, 1H), 7.95 (s, 1H), 7.57 (s, 2H), 6.92-6.88 (m, 2H), 6.83 (d, J=8.0 Hz, 1H), 4.22 (s, 4H), 3.88 (s, 3H), 3.66 (d, J=13.6 Hz, 1H), 3.29-3.17 (m, 2H), 3.08 (d, J=13.6 Hz, 1H), 2.95 (t, J=8.0 Hz, 1H), 2.22-2.08 (m, 2H), 1.80-1.59 (m, 2H), 1.57-1.53 (m, 1H). LCMS: (Method A) 377.1 (M+H), Rt. 1.627 min, 94.8% (Max). HPLC: (Method B) Rt. 5.60 min, 99.31% (Max), 94.43% (220 nm)

Example 6: (S)-4-(4-((2-(2,3-dihydrobenzo[b] [1,4]dioxin-6-yl)pyrrolidin-1-yl)methyl)phenyl)-1-methyl-1H-pyrazole or (R)-4-(4-((2-(2,3-dihydrobenzo[b] [1,4]dioxin-6-yl)pyrrolidin-1-yl)methyl)phenyl)-1-methyl-1 H-pyrazole

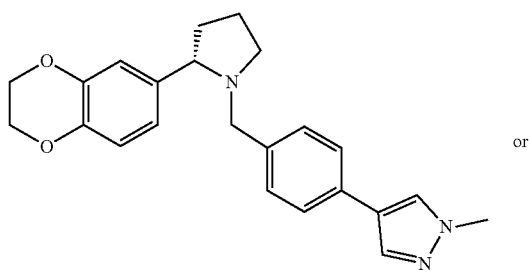

or

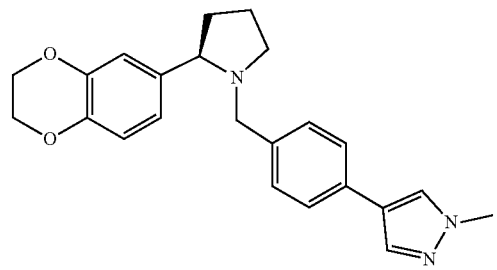

The enantiomers of Example 4 were separated by chiral preparative SFC (mobile phase: 40% IPA, column: Chiralcel OD-H (Method B). The second eluting peak was concentrated to afford Example 6.

Analysis of second eluting fraction (Example 6): Yield: 51% (57 mg, brown gummy solid). $^1$H NMR (400 MHz, DMSO-$d_6$): δ 8.08 (s, 1H), 7.81 (s, 1H), 7.48 (d, J=8.0 Hz, 2H), 7.21 (d, J=8.0 Hz, 2H), 6.93-6.88 (m, 2H), 6.83 (d, J=8.4 Hz, 1H), 4.23 (s, 4H), 3.86 (s, 3H), 3.68 (d, J=13.2 Hz, 1H), 3.28-3.26 (m, 1H), 2.98 (t, J=16.0 Hz, 1H), 2.98-2.93 (m, 1H), 2.18-2.09 (m, 2H), 1.75-1.71 (m, 2H), 1.56-1.54 (m, 1H). LCMS: (Method A) 376.1(M+H), Rt. 2.081 min, 97.8% (Max). HPLC: (Method A) Rt. 2.90 min, 98.25% (Max), 95.11% (220 nm). Chiral SFC: (Method B) Rt. 4.11 min, 99.35% (Max)

Example 7: (S)-5-((2-(2,3-dihydrobenzo[b] [1,4]dioxin-6-yl)pyrrolidin-1-yl)methyl)-2-(1-methyl-1H-pyrazol-4-yl)pyridine or (R)-5-((2-(2,3-dihydrobenzo[b] [1,4]dioxin-6-yl)pyrrolidin-1-yl)methyl)-2-(1-methyl-1H-pyrazol-4-yl)pyridine

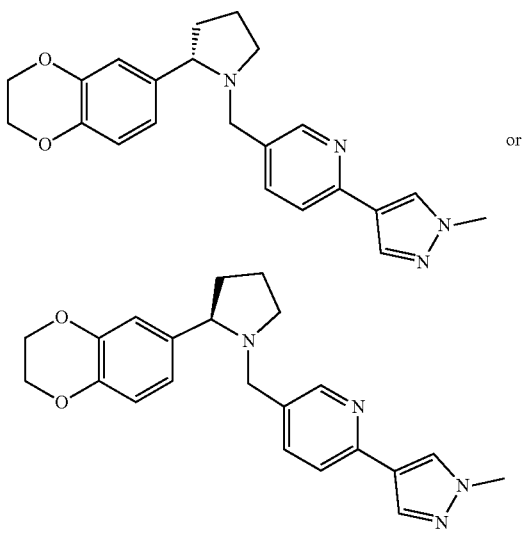

The enantiomers of Example 5 were separated by chiral preparative SFC (mobile phase: 0.5% Isopropyl Amine in Methanol, column: Chiralpak OX-H (method C)). The second eluting peak was concentrated to afford Example 7.

Analysis of second eluting fraction (Example 7): Yield: 11.5% (25 mg, brown gummy solid). $^1$H NMR (400 MHz, DMSO-d$_6$): δ 8.32 (s, 1H), 8.23 (s, 1H), 7.95 (s, 1H), 7.56 (s, 2H), 6.90-6.87 (m, 2H), 6.81 (d, J=6.4 Hz, 1H), 4.21 (s, 4H), 3.86 (s, 3H), 3.64 (d, J=13.6 Hz, 1H), 3.29-3.17 (m, 1H), 3.08 (d, J=13.6 Hz, 1H), 2.95 (t, J=8.0 Hz, 1H), 2.22-2.08 (m, 2H), 1.80-1.59 (m, 2H), 1.57-1.53 (m, 1H). HPLC: (Method A) Rt. 2.02 min, 95.20% (Max), 98.16% (220 nm). LCMS: (Method A) 377.1 (M+H), Rt. 1.654 min, 96.6% (Max). Chiral SFC: (Method C) Rt. 3.84 min, 99.47% (Max).

Example 8: 2-(2,3-dihydrobenzo[b] [1,4]dioxin-6-yl)-1-(4-(methylsulfonyl) benzyl) pyrrolidine

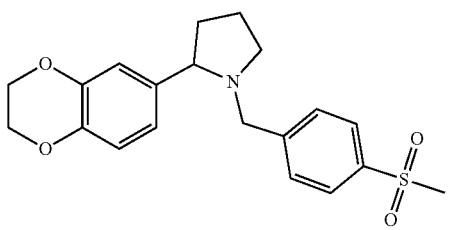 [SMILES: CS(=O)(=O)c1ccc(CN2CCCC2c2ccc3c(c2)OCCO3)cc1]

To a stirred solution Intermediate 1 (120 mg, 48.0 mmol) in dry MeCN (1 mL), TEA (0.1 mL, 73.0 mmmol) and Intermediate 8 (0.11 g, 58.0 mmol) was added at RT and the reaction mixture was stirred overnight at RT. After completion of the reaction, the reaction mixture was concentrated under vacuum. To the resulting crude product, water (10 mL) was added and was extracted with EtOAc (2×10 mL). The combined organic layer was washed with water (5 mL), brine (5 mL), dried over Na$_2$SO$_4$ and concentrated under vacuum. The resulting crude product was purified by flash chromatography (Eluent: 35% EtOAc in pet ether) to afford the title compound.

Yield: 42% (42 mg, brown gummy solid). $^1$H NMR (400 MHz, DMSO-d$_6$): δ 7.86 (d, J=8.4 Hz, 2H), 7.52 (d, J=8.4 Hz, 2H), 6.92-6.88 (m, 2H), 6.81 (d, J=8.4 Hz, 1H), 4.21 (s, 4H), 3.76 (d, J=14.0 Hz, 1H), 3.21-3.19 (m, 4H), 2.98-2.94 (m, 1H), 2.18-2.10 (m, 2H), 1.80-1.76 (m, 2H), 1.74-1.57 (m, 1H). LCMS: (Method A) 374.0 (M+H), Rt. 1.95 min, 99.28% (Max). HPLC: (Method A) Rt. 2.40 min, 99.91% (Max), 99.26% (220 nm).

Example 9: 1-([1,1'-biphenyl]-4-ylmethyl)-2-(2,3-dihydrobenzo[b] [1,4]dioxin-6-yl)pyrrolidine

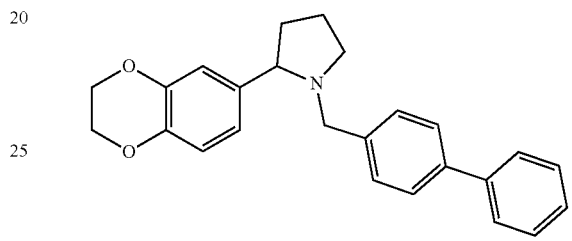

To a stirred solution intermediate 1 (0.21 g, 0.97 mmol) in dry MeCN (2 mL), TEA (0.2 mL,1.46 mmol) and 4-(bromomethyl)-1,1'-biphenyl (0.26 g,1.07 mmol) were added at RT and the resulting solution was stirred overnight at the same temperature. After completion of the reaction, the reaction mixture was concentrated under vacuum. To the resulting crude product, water was added and extracted with EtOAc (2×20 mL). The combine organic layer was washed with water (5 mL), brine (5 mL), dried over Na$_2$SO$_4$ and concentrated under vacuum. The crude product was purified by flash chromatography (Eluent: 23% EtOAc in pet ether) to afford the title compound. Yield: 56% (104 mg, brown gummy solid). $^1$H NMR (400 MHz, DMSO-d$_6$): δ 7.66-7.59 (m, 4H), 7.48-7.44 (m, 2H), 7.35-7.33 (m, 3H), 6.95-6.90 (m, 2H), 6.83 (d, J=8.4 Hz, 1H), 4.23 (s, 4H), 3.74 (d, J=13.2 Hz, 1H), 3.34-3.28 (m, 2H), 3.07 (d, J=13.6 Hz, 1H), 3.01-2.97 (m, 1H), 2.20-2.12 (m, 2H), 2.10-1.77 (m, 2H), 1.57-1.53 (m, 1H). LCMS: (Method A) 377.0 (M+H), Rt. 2.57 min, 98.72% (Max). HPLC: (Method A) Rt. 3.95 min, 99.33% (Max), 98.53% (220 nm).

Example 10: 2-(2,3-dihydrobenzofuran-6-yl)-1-(4-(methylsulfonyl)benzyl)pyrrolidine

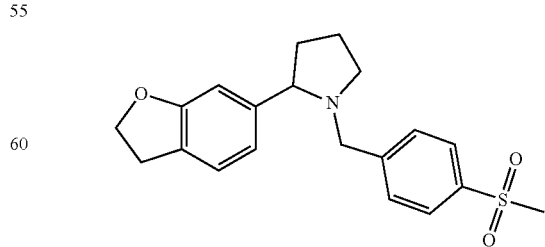

To a stirred solution intermediate 5 (60 mg, 0.31 mmol) in dry MeCN (1 mL), TEA (0.1 mL, 0.77 mmol) and intermediate 8 (0.11 g, 0.38 mmol) were added at RT and the resulting solution was stirred overnight at same temperature. After completion of the reaction, the reaction mixture was concentrated under vacuum. To the resulting crude product, water (10 mL) was added and was extracted with EtOAc (2×10 mL). The combine organic layer was washed with water (5 mL), brine (5 mL), dried over Na$_2$SO$_4$ and concentrated under vacuum. The crude product was purified by flash chromatography (Eluent: 35% EtOAc in pet ether) to afford the title compound.

Yield: 67% (42 mg, brown gummy solid). $^1$H NMR (400 MHz, DMSO-d$_6$): δ 7.87-7.83 (m, 2H), 7.52 (d, J=7.6 Hz, 2H), 7.16 (d, J=7.6 Hz, 1H), 6.88 (d, J=7.6 Hz, 1H), 6.84 (s, 1H), 3.76 (t, J=14.4 Hz, 2H), 3.78-3.74 (m, 1H), 3.22-3.10 (m, 5H), 2.96 (t, J=8.0 Hz, 1H), 2.19-2.12 (m, 2H), 1.80-1.74 (m, 2H), 1.57-1.53 (m, 1H). LCMS: (Method A) 358.0 (M+H), Rt. 1.99 min, 97.07% (Max). HPLC: (Method A) Rt. 2.49 min, 98.63% (Max), 97.74% (220 nm).

Example 11: 4-(4-((2-(2,3-dihydrobenzofuran-6-yl)pyrrolidin-1-yl)methyl)phenyl)-1-methyl-1H-pyrazole

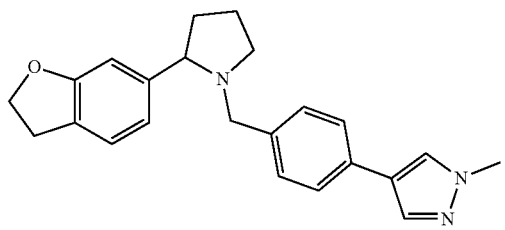 [SMILES: Cn1cc(-c2ccc(CN3CCCC3c3ccc4c(c3)OCC4)cc2)cn1]

To a stirred solution of intermediate 5 (0.06 g, 0.31 mmol) in dry MeCN (1 mL) intermediate 3 (0.07 g, 0.38 mmol) and TEA (0.11 mL, 0.79 mmol) were added at RT and the resulting mixture was stirred overnight. After completion of the reaction, the reaction mixture was concentrated under vacuum. To the resulting crude product water added (10 mL). The aqueous suspension was extracted with EtOAc (2×5 mL). The combined organic layer was washed with water (5 mL), dried over Na$_2$SO$_4$ and concentrated under vacuum. The resulting crude product was purified by flash chromatography (Eluent: 13% EtOAc in pet ether) to afford the title compound. Yield: 55% (69 mg, brown gummy solid). $^1$H NMR (400 MHz, DMSO-d$_6$): δ 8.08 (s, 1H), 7.81 (s, 1H), 7.48 (d, J=8.0 Hz, 2H), 7.23-7.17 (m, 3H), 6.90 (t, J=7.2 Hz, 2H), 6.86 (s, 1H), 4.51 (t, J=8.8 Hz, 2H), 3.85 (s, 3H), 3.68 (d, J=13.2 Hz, 1H), 3.15 (t, J=8.4 Hz, 2H), 3.03-2.96 (m, 2H), 2.16-2.11 (m, 2H), 1.76-1.67 (m, 2H), 1.55-1.52 (m, 1H). LCMS: (Method A) 360.0 (M+H), Rt. 2.14 min, 95.61% (Max). HPLC: (Method A) Rt. 2.94 min, 97.75% (Max), 95.62% (220 nm).

Example 12: 5-((2-(2,3-dihydrobenzofuran-6-yl)pyrrolidin-1-yl)methyl)-2-(1-methyl-1H-pyrazol-4-yl)pyridine

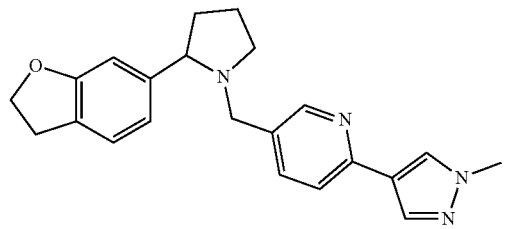 [SMILES: Cn1cc(-c2ccc(CN3CCCC3c3ccc4c(c3)OCC4)cn2)cn1]

To a stirred solution of intermediate 5 (0.06 g, 0.31 mmol) in dry MeCN (1 mL), intermediate 4 (0.07 g, 0.38 mmol)) and TEA (0.11 mL, 0.79 mmol) were added at RT and the resulting mixture was stirred overnight at same temperature. After completion of the reaction, the reaction mixture was concentrated under vacuum. To the resulting crude product, water (10 mL) was added. The aqueous suspension was extracted with EtOAc (2×5 mL). The combined organic layer was washed with water (5 mL), dried over Na$_2$SO$_4$ and concentrated. The resulting crude product was purified by flash chromatography (Eluent: 60% EtOAc in pet ether) to afford the title compound.

Yield: 56% (67 mg, brown gummy solid). $^1$H NMR (400 MHz, DMSO-d$_6$): δ 8.33 (s, 1H), 8.22 (s, 1H), 7.94 (s, 1H), 7.56 (d, J=8.0 Hz, 2H), 7.17 (d, J=7.6 Hz, 1H), 6.89 (d, J=7.2 Hz, 1H), 6.84 (s, 1H), 4.50 (t, J=8.8 Hz, 2H), 3.87 (s, 3H), 3.66 (d, J=13.2 Hz, 1H), 3.16-3.10 (m, 3H), 2.94 (t, J=6.0 Hz, 2H), 2.19-2.10 (m, 2H), 1.75-1.68 (m, 2H), 1.57-1.53 (m, 1H). LCMS: (Method A) 361.1 (M+H), Rt. 1.74 min, 95.61% (Max). HPLC: (Method A) Rt. 1.99 min, 95.33% (Max), 94.64% (220 nm).

Example 13: (S)-2-(2,3-dihydrobenzo[b] [1,4]dioxin-6-yl)-1-(4-(methylsulfonyl) benzyl) pyrrolidine or (R)-2-(2,3-dihydrobenzo[b] [1,4]dioxin-6-yl)-1-(4-(methylsulfonyl) benzyl) pyrrolidine

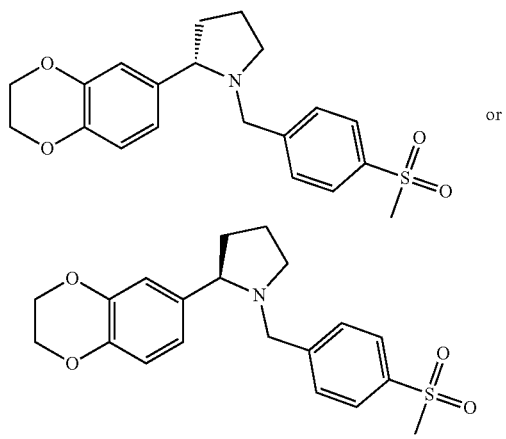

The enantiomers of Example 8 were separated by chiral preparative SFC (mobile phase: 20% methanol, column: Chiracel OJ-H (Method D)). The first eluting peak was concentrated to afford Example 13.

Analysis of the first eluting fraction (Example 13): Yield: 12% (22 mg, yellow gummy solid). $^1$H NMR (400 MHz, DMSO-d$_6$): δ 7.86 (d, J=8.0 Hz, 2H), 7.53 (d, J=8.0 Hz, 2H), 6.91 (s, 1H), 6.88 (d, J=8.4 Hz, 1H), 6.81 (d, J=8.4 Hz, 1H), 4.21 (s, 4H), 3.76 (d, J=14.0 Hz, 1H), 3.33-3.30 (m, 1H), 3.21-3.18 (m, 4H), 2.97 (t, J=4.0 Hz, 1H), 2.17-2.11 (m, 2H), 1.78-1.73 (m, 2H), 1.65-1.57 (m, 1H). LCMS: (Method A) 374.1 (M+H), Rt. 1.97 min, 94.70% (Max). HPLC: (Method A) Rt. 2.40 min, 99.42% (Max), 99.4% (220 nm). Chiral SFC: (Method D) Rt. 6.84 min, 91.14% (Max).

Example 14: 2-((2-(2,3-dihydrobenzo[b] [1,4]dioxin-6-yl)pyrrolidin-1-yl)methyl)-5-(4-(methylsulfonyl)phenyl)pyridine

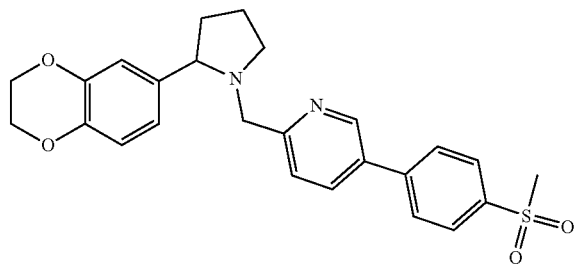 [SMILES: CS(=O)(=O)c1ccc(-c2ccc(CN3CCCC3c3ccc4c(c3)OCCO4)nc2)cc1]

To a stirred solution of intermediate 1 (260 mg, 1.3 mmol) in dry DMF (3 mL), Intermediate 9 (210 mg, 1.0 mmol) and TEA (0.4 mL, 2.6 mmol) were added at RT and the resulting solution was stirred overnight. After completion of the reaction, the reaction mixture was concentrated under vacuum. To the resulting crude product, water (10 mL) was added and the aqueous suspension was extracted with EtOAc (2×20 mL). The combined organic layer was washed with water (10 mL), dried over Na$_2$SO$_4$ and concentrated under vacuum. The crude product was purified by flash chromatography (Eluent: 35% EtOAc in pet ether) to afford the title compound. Yield: 37.5% (120 mg, brown gummy solid). $^1$H NMR (400 MHz, DMSO-d$_6$): δ 8.85 (d, J=2.0 Hz, 1H), 8.14 (dd, J=8.0, 2.4 Hz, 1H), 8.04-7.98 (m, 4H), 7.53 (d, J=8.0 Hz, 1H), 6.94-6.89 (m, 2H), 6.81 (d, J=8.4 Hz, 1H), 4.21 (s, 4H), 3.83 (d, J=14.4 Hz, 1H), 3.40 (t, J=8.4 Hz, 1H), 3.32 (d, J=12.8 Hz, 1H), 3.28 (s, 3H), 3.08 (t, J=8.4 Hz, 1H), 2.27 (q, J=8.8 Hz, 1H), 2.14-2.11 (m, 1H), 1.83-1.74 (m, 2H), 1.60-1.56 (m, 1H). LCMS: (Method B) 455.1, (M+H), Rt. 3.165 min, 93.5% (Max). HPLC: (Method B) Rt. 3.165 min, 96.1% (Max), 91.8% (220 nm).

Example 15: 5-((2-(2, 3-dihydrobenzo[b] [1, 4]dioxin-6-yl)pyrrolidin-1-yl)methyl)-2-(1H-pyrazol-1-yl)pyridine

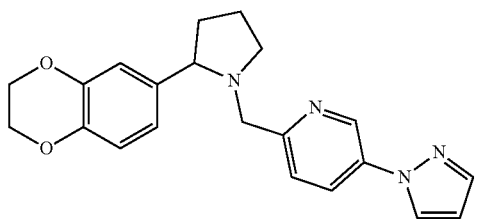 [SMILES: c1cnn(-c2ccc(CN3CCCC3c3ccc4c(c3)OCCO4)nc2)c1]

To a stirred solution of intermediate 1 (0.15 g, 0.73 mmol) in MeCN (10 mL), Intermediate 10 (0.16 g, 0.87 mmol) and trimethylamine (0.3 mL, 2.19 mmol) were added at RT and the reaction mixture was stirred overnight. After completion of reaction, the reaction mixture was quenched with water (10 mL) and extracted with EtOAc (3×30 mL). The organic layer was washed with brine (30 mL), dried over Na$_2$SO$_4$) filtered and concentrated under vacuum. The resulting crude material was purified by prep-HPLC (Method B) to get the title product. Yield: 3% (7 mg, white solid). $^1$H NMR (400 MHz, DMSO-d$_6$): δ 8.96 (d, J=2.4 Hz, 1H), 8.56 (d, J=2.4 Hz, 1H), 8.19 (dd, J=8.8, 1.6 Hz 1H), 7.80 (d, J=1.6 Hz, 1H), 7.49 (d, J=8.8 Hz, 1H), 6.93-6.88 (m, 2H), 6.81 (d, J=8.0 Hz, 1H), 6.60-6.58 (m, 1H), 4.20 (s, 4H), 3.79 (d, J=13.7 Hz, 1H), 3.06-3.03 (m, 2H), 2.27-2.25 (m, 1H), 2.13-2.12 (m, 2H), 1.80-1.77 (m, 2H), 1.60-1.57 (m, 1H). LCMS: (Method A) 363.1 (M+H), Rt. 2.46 min, 88.96% (Max). HPLC: (Method A) Rt. 2.66 min, 94.20% (Max).

Example 16: 1-(4-((2-(2,3-dihydrobenzo[b] [1,4] dioxin-6-yl) pyrrolidin-1-yl) methyl)phenyl)-1H-pyrazole

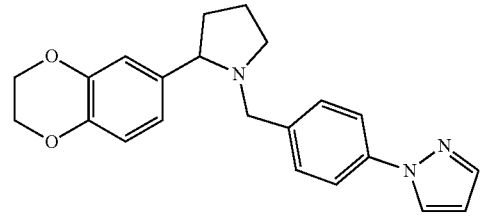 [SMILES: c1cnn(-c2ccc(CN3CCCC3c3ccc4c(c3)OCCO4)cc2)c1]

To a stirred solution of intermediate 1 (0.15 g, 0.73 mmol) in MeCN (10 mL), were added Intermediate 11 (0.14 g, 0.75 mmol) and trimethylamine (0.27 mL, 1.86 mmol) at RT and the resulting mixture was stirred overnight at RT. After completion of reaction, the reaction mixture was quenched with water (10 mL) and extracted with EtOAc (3×30 mL). The combined organic layer was washed with brine (30 mL), dried over Na$_2$SO$_4$, filtered and concentrated under vacuum. The resulting crude material was purified by prep-HPLC (Method B) to get desired compound. Yield: 39% (90 mg, White solid). $^1$H NMR (400 MHz, DMSO-d$_6$): δ 8.45 (d, J=2.0 Hz, 1H), 7.77-7.73 (m, 3H), 7.35 (d, J=8.4 Hz, 2H), 6.93-6.82 (m, 3H), 6.53 (s, 1H), 4.22 (s, 4H), 3.72 (d, J=13.2 Hz, 1H), 3.33-3.27 (m, 1H), 3.09-3.06 (m, 1H), 2.97 (t, J=7.6 Hz, 1H), 2.19-2.06 (m, 2H), 1.81-1.71 (m, 2H), 1.70-1.56 (m, 1H). LCMS: (Method A) 362.1 (M+H), Rt. 97.70 min, 88.96% (Max). HPLC: (Method A) Rt. 2.88 min, 97.88% (Max).

Example 17: 2-((2-(2,3-dihydrobenzo[b] [1,4]dioxin-6-yl)pyrrolidin-1-yl)methyl)-5-(4-(methylsulfonyl)phenyl)pyridine

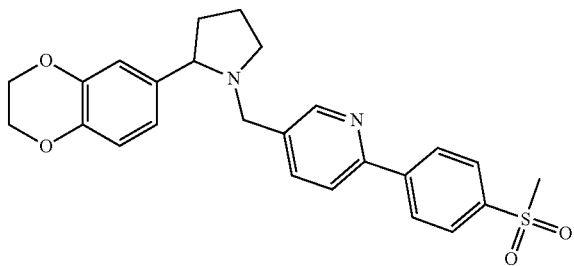 [SMILES: CS(=O)(=O)c1ccc(-c2ccc(CN3CCCC3c3ccc4c(c3)OCCO4)cn2)cc1]

To a stirred solution of intermediate 1 (0.11 g, 0.5 mol) in dry MeCN (2 mL), Intermediate 12 (0.16 g, 0.6 mmol) and TEA (0.2 mL, 0.8 mmol) were added at RT and the reaction mixture was stirred overnight at the same temperature. After completion of the reaction, the reaction mixture was evaporated under vacuum. To the resulting crude mixture, water was added and the aqueous suspension was extracted with EtOAc (2×5 mL). The combined organic layer was washed with water (5 mL), dried over $Na_2SO_4$ and concentrated under vacuum. The crude product was purified by flash chromatography (Eluent: 60% EtOAc in pet ether) to afford the title compound. Yield: 67% (80 mg, brown gummy solid). $^1$H NMR (400 MHz, DMSO-$d_6$): δ 8.57 (d, J=1.2 Hz, 1H), 8.33 (d, J=8.4 Hz, 2H), 8.05-8.02 (m, 3H), 7.79 (dd, J=8.0, 1.6 Hz, 1H), 6.93-6.88 (m, 2H), 6.82 (d, J=8.0, 1H), 4.22 (s, 4H), 3.74 (d, J=13.6 Hz, 1H), 3.27-3.19 (m, 4H), 2.99 (t, J=8.0 Hz, 1H), 2.26-2.11 (m, 2H), 1.83-1.76 (m, 2H), 1.57-1.55 (m, 1H). LCMS: (Method A) 451.0(M+H), Rt. 2.876 min, 96.5% (Max).

Example 18: (S)-2-((2-(2,3-dihydrobenzo[b] [1,4]dioxin-6-yl)pyrrolidin-1-yl)methyl)-5-(1-methyl-1H-pyrazol-4-yl)pyridine or (R)-2-((2-(2,3-dihydrobenzo[b] [1,4]dioxin-6-yl)pyrrolidin-1-yl)methyl)-5-(1-methyl-1H-pyrazol-4-yl)pyridine

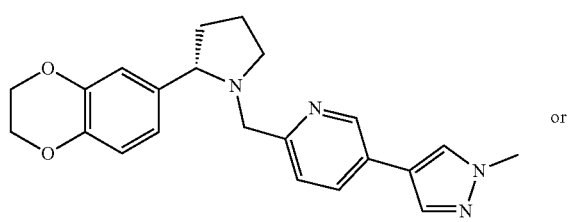

or

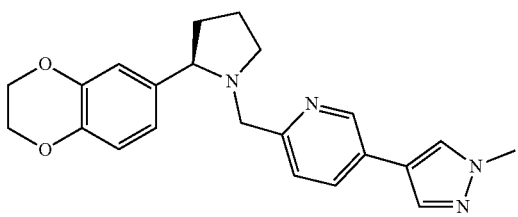

To a stirred solution of intermediate 1 (0.2 g, 1.0 mmol) and TEA (0.4 mL, 2.5 mmol) in MeCN (2 mL), Intermediate 13 (0.2 g, 1.0 mmol) was added at RT and the resulting mixture was stirred overnight at RT. The reaction mixture was evaporated under vacuum. The resulting crude product was suspended with water (10 mL) and extracted with EtOAc (2×25 mL). The combined organic layer was dried over $Na_2SO_4$ and concentrated. The crude product was purified by Prep-HPLC (Method B) to get the racemic mixture of the title compound. The enantiomers were separated by chiral preparative SFC (mobile phase: 0.5% Isopropyl Amine in IPA, column: YMC Cellulose-SB (Method E)). The first eluting compound was concentrated to afford Example 18. Yield: 27% (0.04 g, pale brown gummy solid). $^1$H NMR (400 MHz, DMSO-$d_6$): δ 8.68 (s, 1H), 8.20 (s, 1H), 7.92-7.88 (m, 2H), 7.34 (d, J=8.0 Hz, 1H), 6.92 (s, 1H), 6.88 (d, J=8.0 Hz, 1H), 6.81 (d, J=8.0 Hz, 1H), 4.21 (s, 4H), 3.88 (s, 3H), 3.75 (d, J=14.0 Hz, 1H), 3.39-3.31 (m, 1H), 3.22 (d, J=13.6 Hz, 1H), 3.05-3.01 (m, 1H), 2.33-2.23 (m, 1H), 2.21-2.10 (m, 1H), 1.80-1.72 (m, 2H), 1.58-1.54 (m, 1H).

LCMS: (Method A) 377.1 (M+H), Rt. 2.52 min, 96.01% (Max). HPLC: (Method A) Rt, 2.32 min, 97.14% (Max). Chiral SFC: (Method E) Rt. 2.57 min, 100% (Max).

Example 19: 6-((2-(2,3-dihydrobenzo[b] [1,4]dioxin-6-yl)pyrrolidin-1-yl)methyl)quinoline

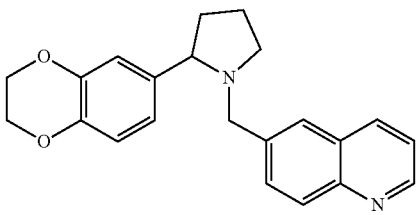 [SMILES: c1cnc2ccc(CN3CCCC3c3ccc4c(c3)OCCO4)cc2c1]

To a stirred solution of intermediate 1 (0.29 g, 1.4 mmol) in dry DMF (3 mL), Intermediate 14 (0.21 g, 1.1 mmol) and TEA (0.4 mL, 2.4 mmol) were added at RT and the reaction mixture was stirred at RT overnight. After completion of the reaction, the reaction mixture was concentrated under vacuum. Water (10 mL) was added and the aqueous suspension was extracted with EtOAc (2×20 mL). The combined organic layer was washed with water (10 mL), dried over $Na_2SO_4$ and concentrated under vacuum. The crude product was purified by flash chromatography (Eluent: 38% EtOAc in pet ether) to afford the title compound. Yield: 19.4% (76 mg, brown gummy solid). $^1$H NMR (400 MHz, DMSO-$d_6$): δ 8.85 (dd, J=4.4, 1.6 Hz, 1H), 8.33 (d, J=8.0 Hz, 1H), 7.95 (d, J=8.8 Hz, 1H), 7.81 (s, 1H), 7.64 (dd, J=8.6, 1.6 Hz, 1H), 7.51 (dd, J=8.4, 4.4 Hz, 1H), 6.83-6.92 (m, 2H), 6.82 (d, J=8.4 Hz, 1H), 4.21 (s, 4H), 3.87 (d, J=13.2 Hz, 1H), 3.25-3.17 (m, 1H), 2.97 (d, J=13.2 Hz, 1H), 2.95 (t, J=5.6 Hz, 1H), 2.22-2.11 (m, 2H), 1.82-1.73 (m, 2H), 1.62-1.56 (m, 1H).

LCMS: (Method A) 347.1 (M+H), Rt. 2.063 min, 93.5% (Max). HPLC: (Method B) Rt. 1.897 min, 95.0% (Max), 96.2% (220 nm).

Example 20: 5-((2-(2,3-dihydrobenzo[b] [1,4]dioxin-6-yl)pyrrolidin-1-yl)methyl)-1-methyl-1H-indazole

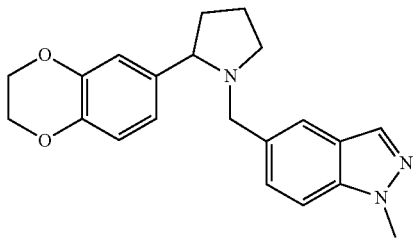 [SMILES: Cn1ncc2cc(CN3CCCC3c3ccc4c(c3)OCCO4)ccc21]

To a stirred solution of intermediate 1 (0.13 g, 0.6 mmol) in dry MeCN (3 mL), Intermediate 15 (0.11 g, 0.5 mmol) and TEA (0.2 mL, 1.3 mmol) were added at RT and the resulting mixture was stirred overnight at RT. After completion of the reaction, the reaction mixture was concentrated under vacuum. To the resulting crude product, water was added and the aqueous suspension was extracted with DCM (2×20 mL). The combined organic layer was washed with water (10 mL), dried over $Na_2SO_4$ and concentrated under vacuum. The crude product was purified by flash chromatography (Eluent: 30% EtOAc in pet ether) to afford the title compound. Yield: 5% (14 mg, brown gummy solid). LCMS: (Method A) 350.1 (M+H), Rt. 2.577 min, 99.1% (Max). HPLC: (Method B) Rt. 2.698 min, 98.1% (Max), 99.5% (220 nm). $^1$H NMR (400 MHz, DMSO-$d_6$): δ 7.99 (s, 1H), 7.59-7.54 (m, 2H), 7.27 (d, J=8.4 Hz, 1H), 6.96-6.91 (m, 2H), 6.84 (d, J=8.0 Hz, 1H), 4.23 (s, 4H), 3.80 (d, J=12.8 Hz, 1H), 3.27 (d, J=8.0 Hz, 1H), 3.10 (d, J=12.8 Hz, 1H), 2.90 (t, J=8.0 Hz, 1H), 2.14-2.09 (m, 2H), 1.73-1.69 (m, 2H), 1.57-1.55 (m, J=8.00 Hz, 1H).

Example 21: 4-(3-((2-(2,3-dihydrobenzo[b] [1,4]dioxin-6-yl)pyrrolidin-1-yl)methyl)phenyl)-1-methyl-1H-Pyrazole

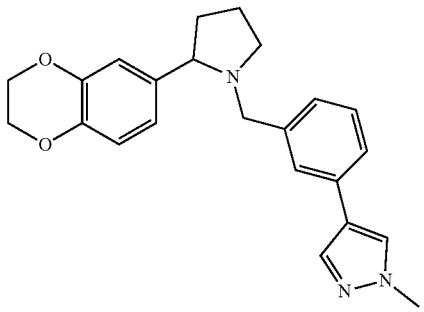 [SMILES: Cn1cc(-c2cccc(CN3CCCC3c3ccc4c(c3)OCCO4)c2)cn1]

To a stirred solution of intermediate 1 (0.1 g, 0.48 mmol) in DMF (5 mL), Intermediate 16 (0.11 g, 0.53 mmol) and trimethylamine (0.3 mL, 2.19 mmol) were added at RT and the resulting mixture was stirred overnight at 50° C. It was diluted with 10% aq. $NaHCO_3$ (10 mL), and extracted with EtOAc (2×10 mL). The combined organic layer was dried over $Na_2SO_4$ and concentrated. The resulting crude product was purified by prep-HPLC (Method A) to afford the title compound. Yield: 21.3% (38.6 mg, pale yellow gummy solid). $^1$H NMR (400 MHz, DMSO-$d_6$): δ: 8.09 (s, 1H), 7.80 (s, 1H), 7.38-7.41 (m, 2H), 7.26-7.30 (m, 1H), 7.08 (d, J=7.6 Hz, 1H), 6.90-6.94 (m, 2H), 6.83 (d, J=8.0 Hz, 1H), 4.23 (s, 4H), 3.87 (s, 3H), 3.71 (d, J=13.6 Hz, 1H), 3.27-3.28 (m, 1H), 2.97-3.06 (m, 2H), 2.10-2.18 (m, 2H), 2.10-2.15 (m, 2H), 1.75-1.73 (m, 1H). LCMS: (Method A) 376.1 (M+H), Rt. 2.89 min, 97.15% (Max). HPLC: (Method A) Rt. 2.82 min, 95.65% (Max).

Example 22: 1-([1,1'-biphenyl]-4-ylmethyl)-2-(2,3-dihydrobenzofuran-6-yl)pyrrolidine

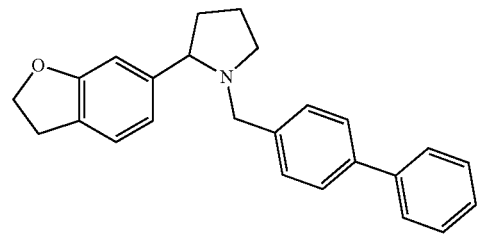 [SMILES: c1ccc(-c2ccc(CN3CCCC3c3ccc4c(c3)OCC4)cc2)cc1]

To a stirred solution of intermediate 5 (0.05 g, 0.26 mmol) in dry MeCN (1 mL), 4-(bromomethyl)-1,1'-biphenyl (0.07 g, 0.29 mmol)) and TEA (0.4 mL,1.39 mmol) were added and the resulting mixture was stirred overnight at RT. After completion of the reaction, the reaction mixture was concentrated under vacuum. The resulting residue was suspended in water (10 mL) and extracted with EtOAc (2×5 mL). The combined organic layer was washed with water (5 mL), dried over $Na_2SO_4$ and concentrated under vacuum. The resulting crude product was purified by flash chromatography (Eluent: 13% EtOAc in pet ether) to afford the title compound. Yield: 71% (61 mg, brown gummy solid). $^1$H NMR (400 MHz, DMSO-$d_6$): δ 7.65-7.59 (m, 4H), 7.45 (t, J=7.6 Hz, 2H), 7.36-7.32 (m, 3H), 7.18 (d, J=7.6 Hz, 1H), 6.92-6.88 (m, 2H), 4.50 (t, J=8.8 Hz, 2H), 3.74 (d, J=13.6 Hz, 1H), 3.16-3.05 (m, 3H), 2.98 (t, J=6.4 Hz, 1H), 2.20-2.11 (m, 2H), 1.78-1.72 (m, 2H), 1.58-1.56 (m, 1H). HPLC: (Method A) Rt. 4.04 min, 99.37% (Max), 97.91% (220 nm). LCMS: (Method A) 356.2 (M+H), Rt. 3.58 min, 96.70% (Max).

Example 23: 4-(4-((2-(2,3-dihydrobenzo[b] [1,4]dioxin-6-yl)pyrrolidin-1-yl)methyl)phenyl)morpholine

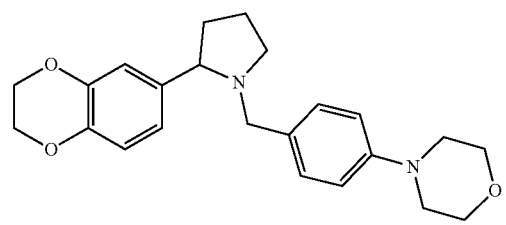 [SMILES: c1cc(N2CCOCC2)ccc1CN1CCCC1c1ccc2c(c1)OCCO2]

265

Step 1: 4-(4-(chloromethyl)phenyl)morpholine

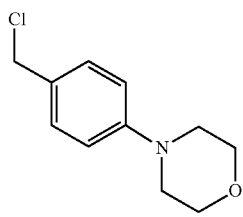 [SMILES: ClCc1ccc(N2CCOCC2)cc1]

To a stirred solution of 4-morpholinophenyl)methanol (0.4 g, 2.0 mmol) in dry DCM (2 mL), SOCl$_2$ (0.6 mL, 3.0 mmol) was added slowly at 0° C. and the reaction mixture was stirred at RT for 1 h. The reaction mixture was concentrated under vacuum and the resulting solid was co-distilled with DCM (10 mL), affording the title that was used in the next step without any further purification.

Yield: 96% (0.42 g, Pale Brown gum). LCMS: (Method A) 212.1 (M+H), Rt. 1.73 min, 99.82% (Max).

Step 2: 4-(4-((2-(2,3-dihydrobenzo[b][1,4]dioxin-6-yl)pyrrolidin-1-yl)methyl)phenyl) morpholine

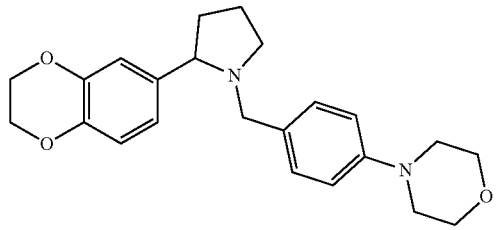 [SMILES: c1cc(N2CCOCC2)ccc1CN1CCCC1c1ccc2c(c1)OCCO2]

To a stirred solution of intermediate 1 (0.15 g, 0.7 mmol), TEA (0.3 mL, 1.9 mmol) in MeCN (3 mL), 4-(4-(chloromethyl)phenyl)morpholine (0.19 g, 0.9 mmol) was added at RT and the resulting mixture was stirred overnight at RT. Completion of the reaction was monitored by TLC and the reaction mixture was evaporated at under vacuum. The resulting residue was suspended with water (10 mL) and extracted with EtOAc (2×25 mL). The combined organic layer was dried over Na$_2$SO$_4$ and concentrated. The crude product was purified by Prep-HPLC (Method B) to get the title compound. Yield: 5% (0.01 g, pale brown gum). $^1$H NMR (400 MHz, DMSO-d$_6$): δ 7.09 (d, J=8.8 Hz, 2H), 6.91-6.81 (m, 5H), 4.23 (s, 4H), 3.74-3.73 (m, 4H), 3.62 (d, J=12.8 Hz, 1H), 3.24-3.20 (m, 1H), 3.07-3.06 (m, 4H), 2.93-2.89 (m, 2H), 2.12-2.07 (m, 2H), 1.72-1.69 (m, 2H), 1.52-1.51 (m, 1H). LCMS: (Method B) 381.2 (M+H), Rt. 3.50 min, 97.59% (Max). HPLC: (Method B) Rt, 6.32 min, 97.75% (Max).

266

Example 24: 4-(4-((2-(2,3-dihydrobenzofuran-6-yl)pyrrolidin-1-yl)methyl)phenyl)morpholine

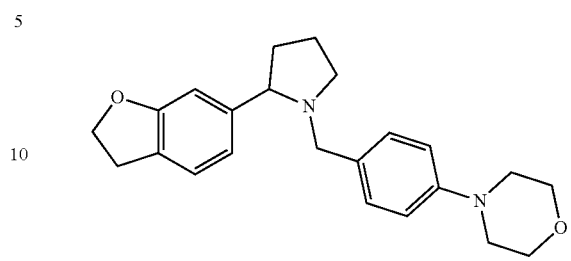

To a stirred solution of intermediate 5 (0.15 g, 0.8 mmol), TEA (0.3 mL, 2.0 mmol) in MeCN (3 mL), 4-(4-(chloromethyl)phenyl)morpholine (step 2 of example 23, 0.2 g, 1.0 mmol) was added at RT and the resulting mixture was stirred overnight. It was evaporated under vacuum and the resulting crude product was suspended in water (10 mL) extracted with EtOAc (2×25 mL). The combined organic layer was dried over Na$_2$SO$_4$ and concentrated. The crude product was purified by flash chromatography (Eluent: 1-2% MeOH in DCM) to get the title compound. Yield: 19% (0.05 g, pale brown gummy solid). $^1$H NMR (400 MHz, DMSO-d$_6$): δ 7.17 (d, J=7.6 Hz, 1H), 7.09 (d, J=8.0 Hz, 2H), 6.89-3.84 (m, 4H), 4.51 (t, J=8.8 Hz, 2H), 3.74-3.72 (m, 4H), 3.62 (d, J=12.8 Hz, 1H), 3.27 (t, J=8.4 Hz, 1H), 3.14 (t, J=8.8 Hz, 2H), 3.07-3.05 (m, 4H), 2.94-2.90 (m, 2H), 2.15-2.08 (m, 2H), 1.73-1.69 (m, 2H), 1.57-1.51 (m, 1H). LCMS: (Method A) 365.2 (M+H), Rt. 2.74 min, 96.71% (Max). HPLC: (Method B) Rt, 6.71 min, 98.21% (Max).

Example 25: (S)-6-((2-(2,3-dihydrobenzo[b] [1,4]dioxin-6-yl)pyrrolidin-1-yl)methyl)quinolone or (R)-6-((2-(2,3-dihydrobenzo[b] [1,4]dioxin-6-yl)pyrrolidin-1-yl)methyl)quinolone

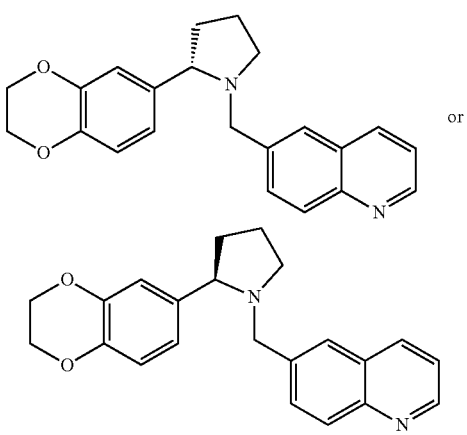

The enantiomers of Example 19 were separated by chiral preparative SFC (mobile phase: 0.5% Isopropyl amine in MeOH, column: YMC Amylose-SA (Method F)). The first eluting peak was concentrated to afford the example 25. Yield: 6% (14.7 mg, brown gummy solid). $^1$H NMR (400 MHz, DMSO-d$_6$): δ 8.86 (dd, J=8.8, 1.6 Hz, 1H), 8.34 (d, J=8.4 Hz, 1H), 7.96 (d, J=8.8 Hz, 1H), 7.82 (s, 1H), 7.65 (dd, J=8.4, 1.6 Hz, 1H), 7.53-7.49 (m, 1H), 6.97-6.93 (m, 2H), 6.84 (d, J=8.0 Hz, 1H), 4.22 (s, 4H), 3.88 (d, J=13.6 Hz, 1H), 3.36-3.35 (m, 1H), 3.24 (d, J=13.6 Hz, 1H), 2.96 (q, J=8.4 Hz, 1H), 2.21-2.12 (m, 2H), 1.80-1.74 (m, 2H), 1.74-1.59 (m, 1H). HPLC: (Method A) Rt. 1.899 min, 99.6% (Max), 99.4% (220 nm). CHIRAL SFC: (Method F) Rt. 2.96 min, 100.0% (Max).

Example 26: 3-((2-(2,3-dihydrobenzo[b] [1,4]dioxin-6-yl)pyrrolidin-1-yl)methyl)quinoline

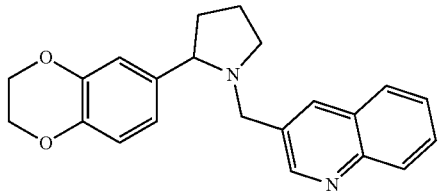 [SMILES: c1ccc2ncc(CN3CCCC3c3ccc4c(c3)OCCO4)cc2c1]

Step 1: 3-(chloromethyl)quinoline

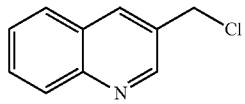

To a stirred solution of quinolin-3-ylmethanol (0.21 g, 1.32 mmol)) in dry DCM (2 mL), $SOCl_2$ (0.14 mL, 1.98 mmol) was added at 0° C. and the reaction mixture was stirred for 3 h at RT. The completion of the reaction was monitored by TLC. After completion of the reaction, the reaction mixture was concentrated under vacuum. The resulting crude product was co-distilled with DCM (2×10 mL) to afford the title product that was used without further purification. Yield: 72% (180 mg, pale yellow solid). $^1$H NMR (400 MHz, DMSO-$d_6$): δ 9.14 (d, J=8.6 Hz, 1H), 8.76 (s, 1H), 8.18-8.15 (m, 2H), 7.94 (t, J=8.0 Hz, 1H), 7.78 (t, J=8.0 Hz, 1H), 5.08 (s, 2H). LCMS: (Method A) 178.1 (M+H), 1.81 min, 96.1% (Max).

Step 2: 3-((2-(2,3-dihydrobenzo[b][1,4]dioxin-6-yl)pyrrolidin-1-yl)methyl)quinoline

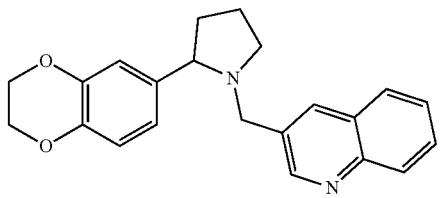 [SMILES: c1ccc2ncc(CN3CCCC3c3ccc4c(c3)OCCO4)cc2c1]

To a stirred solution of intermediate 1 (0.11 g, 0.49 mmol) in dry MeCN (2 mL) 3-(chloromethyl)quinoline (0.10 g, 0.58 mmol)) and TEA (0.2 mL, 1.22 mmol) were added and the reaction mixture was stirred overnight at RT. After completion of the reaction, the reaction mixture was concentrated under vacuum. The resulting crude product was suspended in water (10 mL) and extracted with EtOAc (2×5 mL). The combined organic layer was washed with water (5 mL), dried over $Na_2SO_4$ and concentrated under vacuum. The resulting crude product was purified by flash chromatography (Eluent: 35% EtOAc in pet ether) to afford the title compound. Yield: 54% (76 mg, brown gummy solid). $^1$H NMR (400 MHz, DMSO-$d_6$): δ 8.75 (s, 1H), 8.16 (s, 1H), 7.98 (t, J=8.8 Hz, 2H), 7.72 (t, J=6.8 Hz, 1H), 7.59 (t, J=8.0 Hz, 1H), 6.95-6.94 (m, 2H), 6.83 (d, J=8.0 Hz, 1H), 4.21 (s, 4H), 3.88 (d, J=13.6 Hz, 1H), 3.33-3.29 (m, 1H), 2.98 (t, J=6.0 Hz, 1H), 2.25-2.25 (m, 1H), 2.14-12.12 (m, 1H), 1.78-1.74 (m, 2H), 1.61-1.59 (m, 1H). HPLC: (Method A) Rt. 2.14 min, 96.32% (Max), 97.02% (220 nm). LCMS: (Method A) 347.1 (M+H), Rt. 2.036 min, 98.84% (Max).

Example 27: (S)-1-(4-((2-(2,3-dihydrobenzo[b] [1,4]dioxin-6-yl)pyrrolidin-1-yl)methyl)phenyl)-1 H-pyrazole or (R)-1-(4-((2-(2,3-dihydrobenzo[b] [1,4]dioxin-6-yl)pyrrolidin-1-yl)methyl)phenyl)-1H-pyrazole

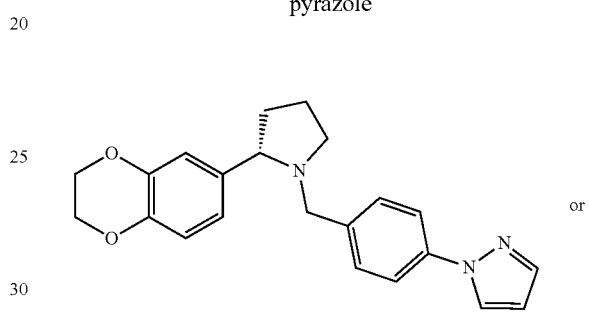

or

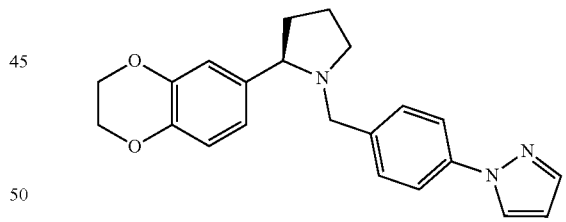

The enantiomers of Example 16 were separated by chiral preparative SFC (mobile phase: 0.5% Isopropyl amine in MeOH, column: YMC Amylose-SA (Method F)). The first eluting peak was concentrated to afford the example 27. Yield: 56% (26 mg, off white gummy solid). $^1$H NMR (400 MHz, DMSO-$d_6$): δ 8.45 (d, J=2.0 Hz, 1H), 7.77-7.73 (m, 3H), 7.35 (d, J=8.4 Hz, 2H), 6.93-6.88 (m, 2H), 6.81 (d, J=8.2 Hz, 1H), 6.53 (s, 1H), 4.22 (s, 4H), 3.72 (d, J=13.2 Hz, 1H), 3.33-3.27 (m, 1H), 3.08 (d, J=13.4 Hz, 1H), 2.97 (t, J=7.6 Hz, 1H), 2.19-2.06 (m, 2H), 1.81-1.71 (m, 2H), 1.70-1.56 (m, 1H). LCMS: (Method A) 362.2 (M+H), Rt. 2.09 min, 99.81% (Max). HPLC: (Method A) Rt. 2.97 min, 99.84% (Max). CHIRAL SFC: (Method F) Rt. 2.14 min, 100.0% (Max).

Example 28: 4-(4-((2-(2,3-dihydrobenzo[b] [1,4]dioxin-6-yl)pyrrolidin-1-yl)methyl) Phenyl) thiomorpholine

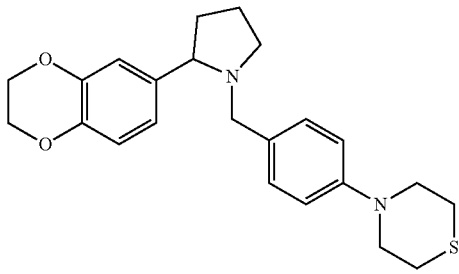 [SMILES: c1cc(N2CCSCC2)ccc1CN1CCCC1c1ccc2c(c1)OCCO2]

To a stirred solution of intermediate 1 (160 mg, 0.7 mmol) in dry MeCN (2 mL), Intermediate 17 (0.2 g, 0.8 mmol)) and TEA (0.22 mL, 1.5 mmol) were added at RT and the resulting mixture was stirred overnight at RT. After completion of the reaction, the reaction mixture was under vacuum. The resulting crude product was suspended in water (10 mL) and was extracted with EtOAc (2×20 mL). The combined organic layer was washed with water (10 mL), brine (5 mL), dried over $Na_2SO_4$ and concentrated under vacuum. The resulting crude product was purified by prep HPLC (method A) to afford the title compound. Yield: 17% (53 mg, brown gummy solid). $^1$H NMR (400 MHz, DMSO-$d_6$): δ 7.07 (d, J=11.2 Hz, 2H), 6.91-6.80 (m, 5H), 4.22 (s, 4H), 3.60 (d, J=17.6 Hz, 1H), 3.51-3.44 (m, 4H), 3.24 (t, J=6.4 Hz, 2H), 2.93-2.88 (m, 2H), 2.67-2.64 (m, 3H), 2.15-2.06 (m, 2H), 1.68-1.71 (m, 2H), 1.52-1.51 (m, 1H). LCMS: (Method A) 397.2 (M+H), Rt. 2.218 min, 97.65% (Max). HPLC: (Method A) Rt. 3.06 min, 96.83% (Max), 95.36% (220 nm).

Example 29: 2-(4-((2-(2,3-dihydrobenzo[b] [1,4]dioxin-6-yl)pyrrolidin-1-yl)methyl)phenyl)pyridine

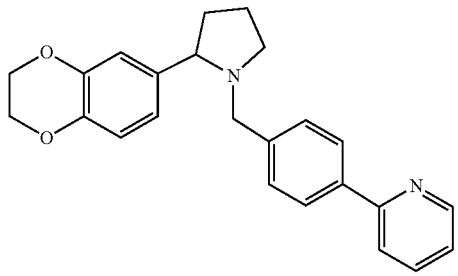 [SMILES: c1ccc(-c2ccc(CN3CCCC3c3ccc4c(c3)OCCO4)cc2)nc1]

To a stirred solution of intermediate 1 (180 mg, 0.82 mmol) in dry MeCN (4 mL), Intermediate 18 (150 g, 0.75 mmol) and TEA (0.3 mL, 1.8 mmol) were added and the resulting mixture was stirred overnight at RT. After completion of the reaction, the reaction mixture was concentrated under vacuum. The resulting crude product was suspended in water (10 mL) and was extracted with EtOAc (2×20 mL). Combined organic layer was washed with water (10 mL), brine (2 mL), dried over $Na_2SO_4$ and concentrated under vacuum. The resulting crude product was purified by flash chromatography (Eluent: 24% EtOAc in pet ether) to afford the title compound. Yield: 17% (46 mg, yellow gummy solid). $^1$H NMR (400 MHz, DMSO-$d_6$): δ 8.66 (t, J=0.8 Hz, 1H), 8.02 (d, J=8.4 Hz, 2H), 7.93 (d, J=8.0 Hz, 1H), 7.89-7.85 (m, 1H), 7.38-7.32 (m, 3H), 6.95 (d, J=1.6 Hz, 1H), 6.92 (d, J=8.4 Hz 1H), 6.83 (d, J=8.4 Hz, 1H), 4.23 (s, 4H), 3.76 (d, J=13.6 Hz, 1H), 3.33-3.34 (m, 1H), 3.04 (d, J=13.8 Hz, 1H), 2.98 (t, J=6.8 Hz, 1H), 2.20-2.10 (m, 2H), 1.82-1.70 (m, 2H), 1.58-1.54 (m, 1H). LCMS: (Method A) 373.2 (M+H), Rt. 1.736 min, 99.3% (Max). HPLC: (Method A) Rt. 7.385 min, 99.6% (Max), 93.4% (220 nm).

Example 30: 3-(4-((2-(2,3-dihydrobenzo[b] [1,4]dioxin-6-yl)pyrrolidin-1-yl)methyl)phenyl) pyridine

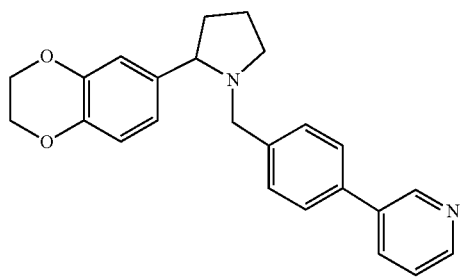 [SMILES: c1cncc(-c2ccc(CN3CCCC3c3ccc4c(c3)OCCO4)cc2)c1]

To a stirred solution of intermediate 1 (110 mg, 0.4 mmol) in dry MeCN (2 mL), Intermediate 19 (120 mg, 0.5 mmol) and TEA (0.3 mL, 0.9 mmol) were added at RT and the resulting mixture was stirred overnight at RT. After completion of the reaction, the reaction mixture was concentrated under vacuum. To the resulting crude mixture, water (10 mL) was added and the aqueous suspension was extracted with EtOAc (2×20 mL). The combined organic layer was washed with water (10 mL), dried over $Na_2SO_4$ and concentrated under vacuum. The resulting crude product was purified by flash chromatography (Eluent: 24% EtOAc in pet ether) to afford the title compound.

Yield: 66% (120 mg, yellow gummy solid). $^1$H NMR (400 MHz, DMSO-$d_6$): δ 8.88 (s, 1H), 8.57-8.55 (dd, J=8.8, 1.6 Hz, 1H), 8.08-8.04 (m, 1H), 7.67 (d, J=10.8 Hz, 2H), 7.49 (dd, J=10.4, 6.4 Hz, 1H), 7.38 (d, J=10.8 Hz, 2H), 6.95-6.89 (m, 3H), 4.22 (s, 4H), 3.75 (d, J=17.6 Hz, 1H), 3.18-3.16 (m, 1H), 3.01 (d, J=13.6 Hz, 1H), 2.99 (t, J=10.8 Hz, 1H), 2.27-2.06 (m, 3H), 1.79-1.73 (m, 2H), 1.70-1.53 (m, 1H). LCMS: (Method A) 373.2 (M+H), Rt. 1.715 min, 92.8% (Max). HPLC: (Method b) Rt. 2.025 min, 96.2% (Max), 95.6% (220 nm).

Example 31: 3-(3-chloro-4-((2-(2,3-dihydrobenzo[b] [1,4]dioxin-6-yl)pyrrolidin-1-yl)methyl)phenyl)pyridine

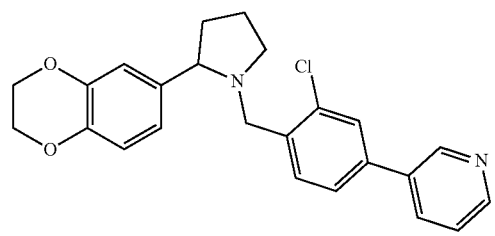 [SMILES: Clc1cc(-c2cccnc2)ccc1CN1CCCC1c1ccc2c(c1)OCCO2]

To a stirred solution of intermediate 1 (0.1 g, 0.42 mmol) in DMF (5 mL) were added Intermediate 20 (0.095 g, 0.46 mmol) and trimethylamine (0.18 mL, 1.26 mmol) at RT and the resulting mixture was stirred at 50° C. for 12 h. After completion reaction, the reaction mixture was diluted with 10% aq. NaHCO$_3$ (10 mL), and was extracted with EtOAc (2×10 mL). The combined organic layer was dried over Na$_2$SO$_4$ and concentrated. The crude product was purified by flash chromatography (Eluent: 60-65% EtOAc in pet ether), to afford the title compound. Yield: 35% (59.82 mg, Pale yellow gum). $^1$H NMR (400 MHz, DMSO-d$_6$): δ: 8.91 (s, 1H), 8.60-8.59 (m, 1H), 8.11 (d, J=8.0 Hz, 1H), 7.77 (s, 1H), 7.71 (d, J=1.6 Hz, 1H), 7.62 (d, J=8.0 Hz, 1H), 7.50 (dd, J=8.0, 1.6 Hz, 1H 1 H), 6.93 (s, 1H), 6.89 (d, d, J=8.4 Hz, 1 H 1 H), 6.80 (d, J=8.4 Hz, 1H), 4.20 (s, 4H), 3.69 (d, J=14.4 Hz, 1H), 3.42-3.36 (m, 2H), 3.09 (t, J=6.0 Hz, 1H), 2.20-2.13 (m, 2H), 1.86-1.75 (m, 2H), 1.61-1.57 (m, 1H). LCMS: (Method A) 407.2 (M+H), Rt. 1.89 min, 97.15% (Max). HPLC: (Method A) Rt. 2.28 min, 99.28% (Max).

Example 32: 3-(4-((2-(2,3-dihydrobenzo[b] [1,4] dioxin-6-yl)pyrrolidin-1-yl)methyl)-3-fluorophenyl) pyridine

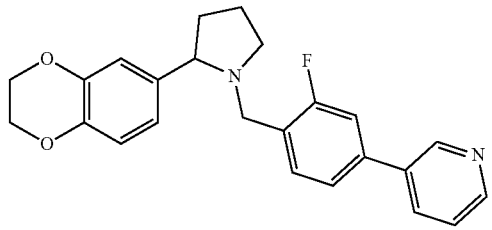 [SMILES: Fc1cc(-c2cccnc2)ccc1CN1CCCC1c1ccc2c(c1)OCCO2]

To a stirred solution of intermediate 1 (100 mg, 0.48 mmol) in DMF (4 mL) were added Intermediate 21 (130 mg, 0.58 mmol) and TEA (0.2 mL, 1.45 mmol) at RT and the resulting mixture was stirred at 50° C. overnight. The reaction mixture was diluted with 10% aq. NaHCO$_3$ (10 mL), and extracted with EtOAc (2×10 mL). The combined organic layer was dried over Na$_2$SO$_4$ and concentrated. The resulting crude product was purified by flash chromatography (Eluent: 63% EtOAc in pet ether) to afford the title compound. Yield: 37% (65.2 mg, pale yellow gummy solid). $^1$H NMR (400 MHz, DMSO-d$_6$): δ: 8.91 (s, 1H), 8.58 (t, J=3.2 Hz, 1H), 8.09 (dd, J=8.0, 1.2 Hz, 1H), 7.50-7.54 (m, 2H), 7.44-7.49 (m, 2H), 6.87-6.92 (m, 2H), 6.80 (d, J=8.4, 1H), 4.21 (s, 4H), 3.69 (d, J=13.2 Hz, 1H), 3.22-3.29 (m, 2H), 3.00 (t, J=8.0 Hz, 1H), 2.23-2.22 (m, 1H), 2.09-2.11 (m, 1H), 1.72-1.76 (m, 2H), 1.551.52 (m, 1H). LCMS: (Method A) 391.2 (M+H), Rt. 1.74 min, 99.38% (Max). HPLC: (Method A) Rt. 2.14 min, 99.15% (Max).

Example 33: (S)-3-(4-((2-(2,3-dihydrobenzo[b] [1,4]dioxin-6-yl)pyrrolidin-1-ylmethyl)-3-methylphenyl)pyridine or (R)-3-(4-((2-(2,3-dihydrobenzo [b] [1,4]dioxin-6-yl)pyrrolidin-1-yl)methyl)-3-methylphenyl)pyridine

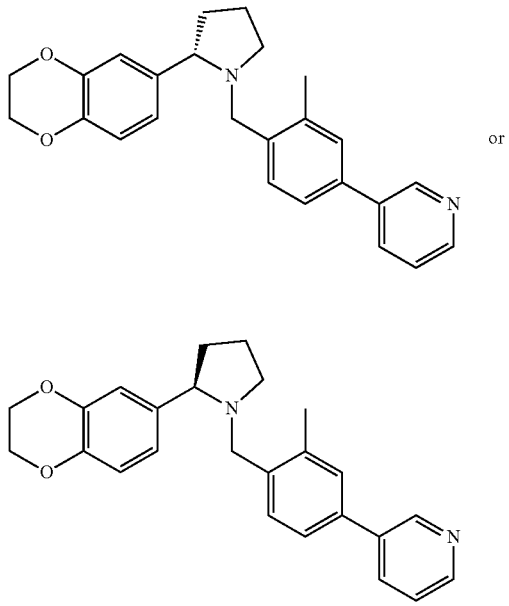

To a stirred solution of intermediate 1 (330 g, 1.6 mmol) in dry MeCN (2 mL), Intermediate 22 (338 mg, 1.8 mmol) and TEA (0.5 mL, 3.6 mmol) were added and the resulting mixture was stirred 16 h at RT. After completion of the reaction, the reaction mixture was concentrated under vacuum. Water (10 mL) was added and the aqueous suspension was extracted with EtOAc (2×20 mL). The combined organic layer was washed with water (10 mL), brine (5 mL), dried over Na$_2$SO$_4$ and concentrated under vacuum. The resulting crude product was purified by flash chromatography (Eluent: 24% EtOAc in pet ether) to get racemic compound (120 mg).

The two enantiomers of the racemic compound were separated by chiral preparative SFC (mobile phase: 0.5% Isopropyl amine in IPA, column: Chiralcel OJ-H (Method A)). The second eluting peak was concentrated to afford the example 33. Yield: 14% (30 mg, brown gummy solid). $^1$H NMR (400 MHz, DMSO-d$_6$): δ 8.86 (s, 1H), 8.53 (d, J=4.6 Hz, 1H), 8.04 (d, J=8.0 Hz, 1H), 7.49-7.41 (m, 4H), 6.90-6.87 (m, 2H), 6.81 (d, J=8.4 Hz, 1H), 4.21 (s, 4H), 3.67 (d, J=13.2 Hz, 1H), 3.43-3.32 (m, 1H), 3.10 (d, J=4.0 Hz, 1H), 2.94 (t, J=12.0 Hz, 1H), 2.24 (s, 3H), 2.18-2.13 (m, 2H), 1.78-1.74 (m, 2H), 1.67-1.60 (m, 1H). LCMS: (Method A) 387.2 (M+H), Rt. 1.80 min, 99.78% (Max). HPLC: (Method B) Rt. 2.18 min, 99.57% (Max), 99.26% (220 nm). Chiral SFC: (Method A) Rt. 3.06 min, 99.08% (Max).

Example 34: 1-(4-((2-(2,3-dihydrobenzo[b][1,4]dioxin-6-yl)pyrrolidin-1-yl)methyl)phenyl)-1H-1,2,4-triazole

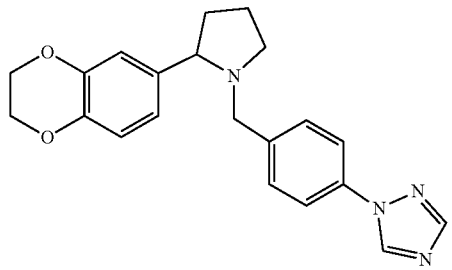 [SMILES: c1ncn(-c2ccc(CN3CCCC3c3ccc4c(c3)OCCO4)cc2)n1]

To a stirred solution of intermediate 1 (244 mg, 1.19 mmol) in dry MeCN (2 mL), Intermediate 23 (230 mg, 1.19 mmol)) and TEA (0.5 mL, 3.57 mmol) were added and the resulting mixture was stirred overnight at RT. After completion of the reaction, the reaction mixture was concentrated under vacuum and water (10 mL) was added. The aqueous suspension was extracted with EtOAc (2×10 mL). The combined organic layer was washed with water (4 mL), brine (5 mL), dried over $Na_2SO_4$ and concentrated under vacuum. The crude product was purified by flash chromatography (Eluent: 35% EtOAc in pet ether) to get the title product. Yield: 35% (151 mg, pale brown solid). $^1$H NMR (400 MHz, DMSO-$d_6$): δ 9.25 (s, 1H), 8.23 (s, 1H), 7.79 (d, J=8.8 Hz, 2H), 7.42 (d, J=8.4 Hz, 2H), 6.94-6.89 (m, 2H), 6.83 (d, J=8.4 Hz, 1H), 4.22 (s, 4H), 3.74 (d, J=13.2 Hz, 1H), 3.36-3.32 (m, 1H), 3.17 (d, J=5.2 Hz, 1H), 3.18-3.16 (m, 2H), 2.20-2.09 (m, 2H), 1.79-1.71 (m, 2H), 1.59-1.54 (m, 1H). LCMS: (Method A) 363.2 (M+H), Rt. 1.36 min, 96.81% (Max). HPLC: (Method A) Rt. 2.47 min, 95.68% (Max), 94.60% (220 nm).

Example 35: 2-(4-((2-(2,3-dihydrobenzo[b][1,4]dioxin-6-yl)pyrrolidin-1-yl)methyl)piperidin-1-yl)pyrimidine

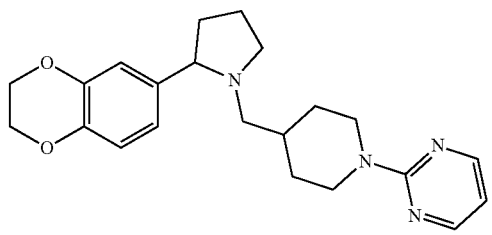 [SMILES: c1cnc(N2CCC(CN3CCCC3c3ccc4c(c3)OCCO4)CC2)nc1]

To a stirred solution of intermediate 1 (130 mg, 0.6 mmol) in dry DMF (4 mL), Intermediate 24 (250 mg, 0.7 mmol) and TEA (0.3 mL, 2.2 mmol) were added at RT and the resulting mixture was heated at 70° C. overnight. After completion of the reaction, the reaction mixture was concentrated under vacuum. Water (10 mL) was added and the aquous suspension was extracted with EtOAc (2×20 mL). The combined organic layer was washed with water (10 mL), brine (2 mL), dried over $Na_2SO_4$ and concentrated under vacuum. The crude product was purified by Prep. HPLC (Method A) to afford the title compound. Yield: 18% (50 mg, yellow gummy solid). $^1$H NMR (400 MHz, DMSO-$d_6$): δ 8.29 (t, J=4.4 Hz, 2H), 6.78-6.75 (m, 3H), 6.54 (t, J=4.8 Hz, 1H), 4.62-4.55 (m, 2H), 4.19 (s, 4H), 3.33-3.28 (m, 2H), 3.08 (t, J=8.4 Hz, 1H), 2.82 (t, J=12.8 Hz, 2H), 2.17-1.93 (m, 4H), 1.81-1.74 (m, 3H), 1.57-1.41 (m, 2H), 0.89-0.79 (m, 3H). LCMS: (Method A) 381.2 (M+H), Rt. 1.308 min, 95.3% (Max). HPLC: (Method A) Rt. 2.287 min, 95.6% (Max), 94.7% (220 nm).

Example 36: 1-(4-((2-(2,3-dihydrobenzo[b][1,4]dioxin-6-yl)pyrrolidin-1-yl)methyl)phenyl)-4-(methylsulfonyl)piperazine

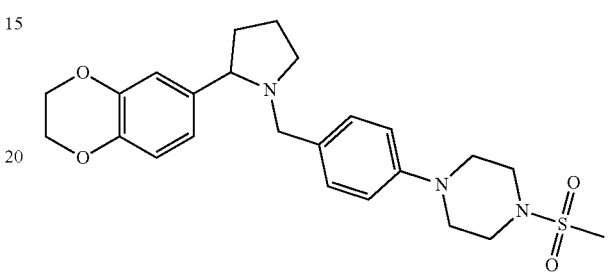

To a stirred solution of intermediate 6 (200 mg, 0.53 mmol) and 1-(methylsulfonyl)piperazine hydrochloride (87 mg, 0.53 mmol) in dry toluene (5 mL), sodium tert butoxide (150 mg, 1.6 mmol) was added at RT and the resulting solution was flushed with nitrogen for 10 min. BINAP (66 mg, 0.1 mmol), $Pd_2(dba)_3$ (98 mg, 0.1 mmol) were added and the reaction mixture was flushed again with nitrogen for 10 min. It was then stirred at 100° C. overnight. After completion of the reaction, the reaction mixture was diluted with EtOAc (20 mL) and filtered through celite pad. The filtrate was concentrated under vacuum and resulting crude product was purified by flash chromatography (Eluent: 47% EtOAC in pet ether) to afford the title compound. Yield: 5% (11.3 mg, off-white solid). $^1$H NMR (400 MHz, DMSO-$d_6$): δ 7.09 (d, J=8.4 Hz, 2H), 6.92-6.90 (m, 3H), 6.85 (d, J=2.0 Hz, 1H), 6.82-6.80 (m, 1H), 4.22 (s, 4H), 3.61 (d, J=12.8 Hz, 1H), 3.23-3.20 (m, 10H), 2.92 (s, 3H), 2.11-2.06 (m, 2H), 1.72-1.68 (m, 2H), 1.56-1.48 (m, 1H). LCMS: (Method A) 458.1(M+H), Rt. 1.570 min, 99.4% (Max). HPLC: (Method A) Rt. 3.038 min, 99.5% (Max), 99.4% (220 nm).

Example 37: 1-(4-(4-((2-(2,3-dihydrobenzo[b][1,4]dioxin-6-yl)pyrrolidin-1-yl)methyl)phenyl)piperazin-1-yl)ethan-1-one

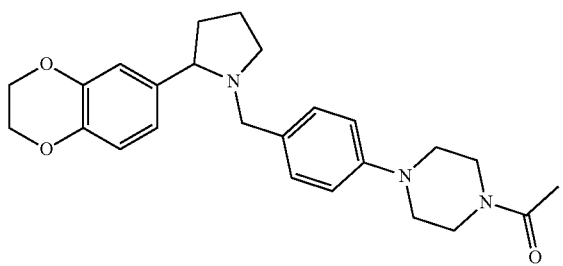 [SMILES: CC(=O)N1CCN(c2ccc(CN3CCCC3c3ccc4c(c3)OCCO4)cc2)CC1]

To a stirred solution of intermediate 6 (200 mg, 0.53 mmol) and 1-acetylpiperazine hydrochloride (68 mg, 0.53 mmol) in dry toluene (5 mL), sodium tert butoxide (147 mg, 1.6 mmol) was added at RT and the resulting mixture was flushed with nitrogen for 10 min. BINAP (66 mg, 0.1 mmol) and Pd$_2$(dba)$_3$ (98 mg, 0.1 mmol) were added and the reaction mixture was flushed again with nitrogen for 10 min. It was stirred at 100° C. overnight. After completion of the reaction, the reaction mixture was diluted with EtOAc (20 mL) and filtered through celite pad. The filtrate was washed with water (10 mL), brine (2 mL), dried over Na$_2$SO$_4$ and concentrated under vacuum. The crude product was purified by flash chromatography (Eluent: 36% EtOAc in pet ether) to afford the title compound. Yield: 16.0% (36 mg, brown gummy solid). $^1$H NMR (400 MHz, DMSO-d$_6$): δ 7.08 (d, J=8.8 Hz, 2H), 6.90-6.80 (m, 5H), 4.21 (s, 4H), 3.62-3.55 (m, 5H), 3.22 (d, J=8.4 Hz, 2H), 3.17 (t, J=7.2 Hz, 2H), 3.10 (t, J=5.2 Hz, 2H), 2.92-2.89 (m, 2H), 2.10-2.06 (m, 2H), 2.03 (s, 3H), 1.71-1.67 (m, 2H), 1.56-1.43 (m, 1H). LCMS: (Method A) 422.2 (M+H), Rt. 1.374 min, 97.6% (Max). HPLC: (Method A) Rt. 2.608 min, 98.5% (Max), 98.1% (220 nm).

Example 38: 3-(4-((2-(2,3-dihydrobenzo[b] [1,4] dioxin-6-yl)pyrrolidin-1-yl)methyl)-3-methylphenyl) pyridine

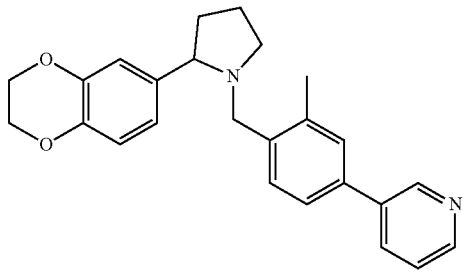 [SMILES: Cc1cc(-c2cccnc2)ccc1CN1CCCC1c1ccc2c(c1)OCCO2]

To a stirred solution of intermediate 1 (330 mg, 1.6 mmol) in dry MeCN (2 mL), intermediate 25 (338 mg, 1.8 mmol) and TEA (0.5 mL, 3.6 mmol) were added and the resulting mixture was stirred overnight at RT. After completion of the reaction, the reaction mixture was concentrated under vacuum. Water was added (10 mL) and the resulting suspension was extracted with EtOAc (2×20 mL). The combined organic layer was washed with water (10 mL), brine (5 mL), dried over Na$_2$SO$_4$ and concentrated under vacuum. The crude product was purified by flash chromatography (Eluent: 24% EtOAc in pet ether) to afford the title compound. Yield: 66% (120 mg, yellow gummy solid). $^1$H NMR (400 MHz, DMSO-d$_6$): δ 8.85 (d, J=2.0 Hz, 1H), 8.54 (dd, J=4.4, 1.6 Hz, 1H), 8.04 (dd, J=4.4, 1.6 Hz, 1H), 7.50-7.41 (m, 4H), 6.91-6.87 (m, 2H), 6.80 (d, J=8.0 Hz, 1H), 4.20 (s, 4H), 3.66 (d, J=13.6 Hz, 1H), 3.27 (t, J=7.6 Hz, 1H), 3.10 (d, J=13.2 Hz, 1H), 2.94 (t, J=8.4 Hz, 1H), 2.23 (s, 3H), 2.19-2.11 (m, 2H), 1.99-1.77 (m, 2H), 1.75-1.17 (m, 1H). HPLC: (Method B) Rt. 2.242 min, 95.89% (Max), 91.51% (220 nm). LCMS: (Method A) 387.2 (M+H), Rt. 1.81 min, 98.68% (Max).

Example 39: 5-(4-((2-(2,3-dihydrobenzo[b] [1,4] dioxin-6-yl)pyrrolidin-1-yl)methyl)phenyl)pyrimidine

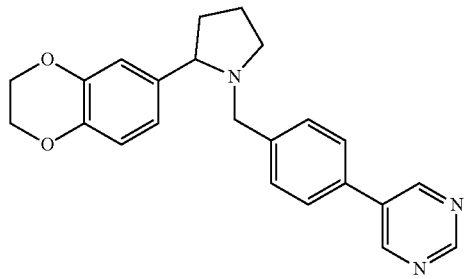 [SMILES: c1ncc(-c2ccc(CN3CCCC3c3ccc4c(c3)OCCO4)cc2)cn1]

To a stirred solution of intermediate 1 (110 mg, 0.4 mmol) in dry MeCN (2 mL), Intermediate 26 (120 mg, 0.5 mmol) and TEA (0.13 mL, 0.9 mmol) was added and stirred for overnight at RT. After completion of the reaction, the reaction mixture was concentrated under vacuum. To the resulting crude product water was added and aqueous suspension was extracted with EtOAc (2×20 mL). The combined organic layer was washed with water (10 mL), brine (2 mL), dried over Na$_2$SO$_4$ and concentrated under vacuum. The crude product was purified by prep. HPLC (method A) to afford the title compound. Yield: 66% (120 mg, yellow gummy solid). LCMS: (Method A) 374.2 (M+H), Rt. 1.52 min, 99.7% (Max). $^1$H NMR (400 MHz, DMSO-d$_6$): δ 9.17 (s, 1H), 9.12 (s, 2H), 7.75 (d, J=8.0 Hz, 2H), 7.41 (d, J=8.0 Hz, 2H), 6.94-6.89 (m, 2H), 6.82 (d, J=8.0 Hz, 1H), 4.22 (s, 4H), 3.75 (d, J=13.6 Hz, 1H), 3.32-3.29 (m, 1H), 3.16 (d, J=5.6 Hz, 1H), 2.97 (t, J=8.0 Hz, 1H), 2.20-2.10 (m, 2H), 1.81-1.70 (m, 2H), 1.57-1.53 (m, 1H). HPLC: (Method B) Rt. 2.57 min, 98.36% (Max), 96.21% (220 nm).

Example 40: (S)-2-(4-((2-(2,3-dihydrobenzo[b] [1,4]dioxin-6-yl)pyrrolidin-1-yl)methyl)phenyl)pyridine or (R)-2-(4-((2-(2,3-dihydrobenzo[b] [1,4]dioxin-6-yl)pyrrolidin-1-yl)methyl)phenyl)pyridine

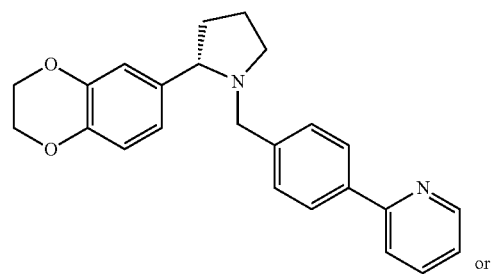

or

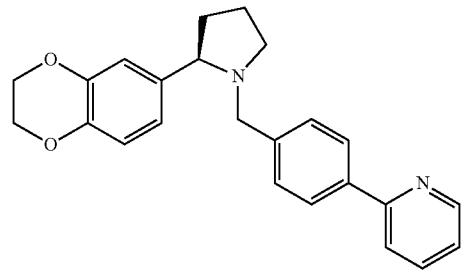

The enantiomers of Example 29 were separated by chiral preparative SFC (mobile phase: 0.5% Isopropyl amine in MeOH, column: Chiralcel OD-H (Method G)). The second eluting peak was concentrated to afford Example 40. Yield: 26% (22 mg, yellow gummy solid). LCMS: (Method A) 373.1(M+H), Rt. 1.208 min, 98.5% (Max). $^1$H NMR (400 MHz, DMSO-$d_6$): δ 8.66 (t, J=1.4 Hz, 1H), 8.02 (d, J=8.4 Hz, 2H), 7.93 (d, J=8.0 Hz, 1H), 7.89-7.87 (m, 1H), 7.38-7.32 (m, 3H), 6.95 (d, J=1.6 Hz, 1H), 6.92 (d, J=8.0 Hz, 1H), 6.84 (d, J=8.0 Hz, 1H), 4.23 (s, 4H), 3.76 (d, J=13.6 Hz, 1H), 3.29 (d, J=8.0 Hz, 1H), 3.09 (d, J=13.6 Hz, 1H), 2.98 (t, J=7.6 Hz, 1H), 2.20-2.10 (m, 2H), 1.82-1.70 (m, 2H), 1.61-1.55 (m, 1H). HPLC: (Method A) Rt. 2.134 min, 99.9% (Max), 99.9% (220 nm). Chiral SFC: (Method G) Rt. 5.64 min, 99.01% (Max).

Example 41: 2-(4-((2-(2,3-dihydrobenzo[b] [1,4] dioxin-6-yl)pyrrolidin-1-yl)methyl)-3-fluorophenyl) pyridine

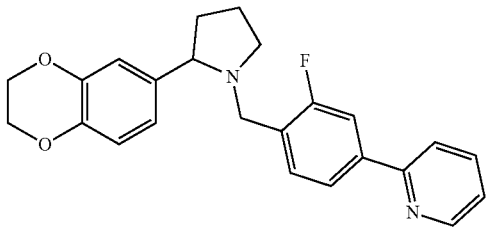 [SMILES: Fc1cc(-c2ccccn2)ccc1CN1CCCC1c1ccc2c(c1)OCCO2]

To a stirred solution of intermediate 1 (200 mg, 0.974 mmol) in MeCN (5 mL), TEA (0.41 mL, 2.923 mmol) and Intermediate 27 (238 mg, 1.072 mmol) were added at 0° C. and the resulting mixture was stirred overnight at RT. The reaction was diluted with water (50 mL) and extracted with EtOAc (2×25 mL). The combined organic layer was dried over Na$_2$SO$_4$ and concentrated under vacuum. The resulting crude product was purified by flash chromatography (Eluent: 8% EtOAc in hexane) affording the title compound. Yield: 31.41% (120 mg, gummy liquid). $^1$H NMR (400 MHz, DMSO-$d_6$): δ 8.67 (d, J=4.0 Hz, 1H), 8.00 (d, J=4.0 Hz, 1H), 7.91-7.82 (m, 3H), 7.46 (t, J=8.0 Hz, 1H), 7.39 (t, J=8.0 Hz, 1H), 6.93 (s, 1H), 6.89 (d, J=8.4 Hz, 1H), 6.82 (d, J=8.0 Hz, 1H), 4.22 (s, 4H), 3.71 (d, J=13.2 Hz, 1H), 3.31-3.22 (m, 2H), 3.01 (t, J=7.2 Hz, 1H), 2.15-2.06 (m, 2H), 1.72-1.78 (m, 2H), 1.56-1.54 (m, 1H). LCMS: (Method C) 391.2 (M+H), Rt. 1.262 min, 99.23% (Max). HPLC: (Method A) Rt. 2.447 min, 97.21% (Max).

Example 42: 3-(4-((2-(2,3-dihydrobenzo[b] [1,4] dioxin-6-yl)pyrrolidin-1-yl)methyl)-3-methylphenyl) pyridine from 2-(4-(chloromethyl)-3-methylphenyl) pyridine

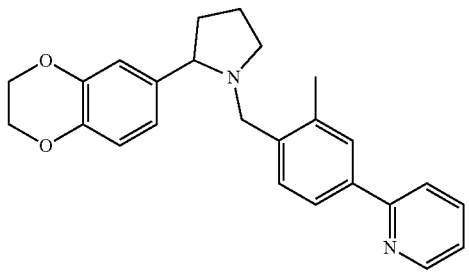 [SMILES: Cc1cc(-c2ccccn2)ccc1CN1CCCC1c1ccc2c(c1)OCCO2]

To a stirred solution of intermediate 1 (200 mg, 0.972 mmol) in MeCN (5 mL), TEA (0.41 mL, 2.919 mmol), and Intermediate 28 (211 mg, 0.972 mmol) were added at 0° C. The reaction mixture was srtirred at RT overnight. It was diluted with water (50 mL) and extracted with EtOAc (2×25 mL). The combined organic layer was dried over Na$_2$SO$_4$ and concentrated under vacuum. The resulting crude compound was purified by flash chromatography (Eluent: 8% EtOAc in hexane) to afford the title compound. Yield: 33.24% (125 mg, colourless gummy liquid). $^1$H NMR: (400 MHz, DMSO-$d_6$): δ 8.64 (t, J=4.0 Hz, 1H), 7.93-7.83 (m, 4H), 7.42 (d, J=8.4 Hz, 1H), 7.34-7.32 (m, 1H), 6.93-6.88 (m, 2H), 6.81 (d, J=8.4 Hz, 1H), 4.21 (s, 4H), 3.67 (d, J=13.2 Hz, 1H), 3.43-3.36 (m, 1H), 3.09 (d, J=13.2 Hz, 1H), 2.97-2.92 (m, 1H), 2.24 (s, 3H), 2.17-2.08 (m, 2H), 1.78-1.73 (m, 2H), 1.62-1.60 (m, 1H). LCMS: Method C, 387.1 (M+H), Rt. 1.053 min, 99.57% (Max). HPLC: Method A, Rt. 2.321 min, 96.82% (Max).

Example 43: (3-chloro-4-((2-(2,3-dihydrobenzo[b] [1,4]dioxin-6-yl) pyrrolidin-1-yl)methyl)phenyl) pyridine from 2-(3-chloro-4-(chloromethyl)phenyl) pyridine

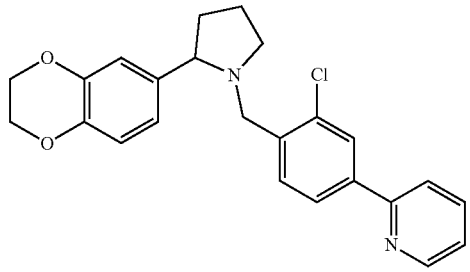 [SMILES: Clc1cc(-c2ccccn2)ccc1CN1CCCC1c1ccc2c(c1)OCCO2]

To a stirred solution of intermediate 1 (200 mg, 0.972 mmol) in MeCN (5 mL) and TEA (0.4 mL, 2.918 mmol) and Intermediate 29 (232 mg, 0.972 mmol) were added at 0° C. The reaction mixture was stirred at RT overnight. It was diluted with water (50 mL) and extracted with EtOAc (2×25 mL). The combined organic layer was dried over Na$_2$SO$_4$ and concentrated under vacuum. The resulting crude compound was purified by flash chromatography (Eluent: 8% EtOAc: Hexane) to afford the title compound. Yield: 20.21% (80 mg, colourless gummy liquid). $^1$H NMR (400 MHz, DMSO-$d_6$): δ 8.67 (d, J=4.4 Hz, 1H), 8.05-8.01 (m, 3H), 7.97-7.92 (m, 1H), 7.91-7.89 (m, 1H), 7.40-7.37 (m, 1H), 6.93-6.88 (m, 2H), 6.80 (d, J=8.0 Hz, 1H), 4.20 (s, 4H), 3.69 (d, J=14.4 Hz, 1H), 3.41-3.34 (m, 2H), 3.10-3.06 (m, 1H), 2.21-2.08 (m, 2H), 1.84-1.80 (m, 2H). 1.58-1.56 (m, 1H). LCMS: Method C, 407.1 (M+H), Rt. 1.40 min, 99.38% (Max). HPLC: Method A, Rt. 2.653 min, 96.55% (Max).

Example 44: 2-(2,3-dihydrobenzo[b] [1,4]dioxin-6-yl)-1-((3'-(methylsulfonyl)-[1,1'-biphenyl]-4-yl)methyl)pyrrolidine

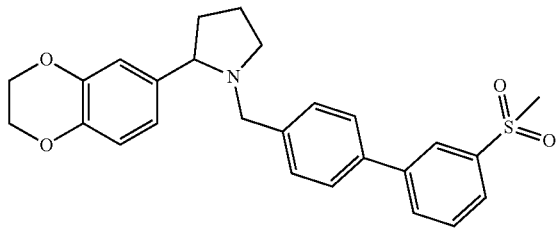 [SMILES: CS(=O)(=O)c1cccc(-c2ccc(CN3CCCC3c3ccc4c(c3)OCCO4)cc2)c1]

To a stirred solution of intermediate 1 (140 mg, 0.70 mmol), Intermediate 30 (180 mg, 0.64 mmol) in a MeCN (5 mL), TEA (0.25 mL, 1.92 mmol) was added at RT and the resulting mixture was stirred overnight at same temperature. It was concentrated and water (30 mL) was added. The aqueous suspension was extracted with EtOAc (2×50 mL). The combined organic layer was dried over $Na_2SO_4$ and concentrated. The crude product was purified by flash chromatography (Eluent: 50-60% EtOAc in pet ether) to get the title compound. Yield: 28% (80 mg, white solid). $^1$H NMR (400 MHz, DMSO-$d_6$): δ 8.13 (s, 1H), 8.02 (d, J=7.2 Hz, 1H), 7.90 (d, J=7.6 Hz, 1H), 7.79-7.69 (m, 3H), 7.40 (d, J=8.0 2H), 6.94-6.90 (m, 2H), 6.83 (d, J=8.4 Hz, 1H), 4.22 (s, 4H), 3.75 (d, J=13.2 Hz, 1H), 3.29 (s, 3H), 3.11 (d, J=13.6 Hz, 1H), 2.99-2.95 (m, 1H), 2.19-2.16 (m, 3H), 1.77-1.75 (m, 2H), 1.61-1.54 (m, 1H). LCMS: (Method A) 450.2 (M+H), Rt. 1.46 min, 98.49% (Max) 96.96% (220 nm). HPLC: (Method A) Rt, 3.33 min, 96.36% (Max).

Example 45: 4-(4-((2-(2,3-dihydrobenzo[b] [1,4]dioxin-6-yl)pyrrolidin-1-yl)methyl)-3-methylphenyl)-1-methyl-1H-pyrazole

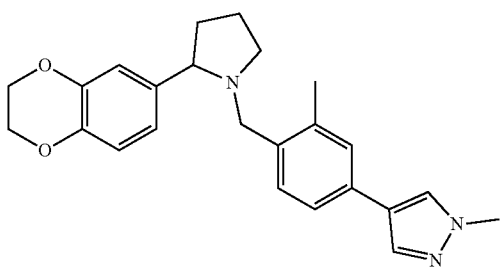 [SMILES: Cc1cc(-c2cnn(C)c2)ccc1CN1CCCC1c1ccc2c(c1)OCCO2]

To a stirred solution of intermediate 1 (100 mg, 0.49 mmol) and Intermediate 31 (100 mg, 0.45 mmol) in MeCN (4 mL), TEA (0.18 mL, 1.35 mmol) was added at RT and the resulting mixture was stirred overnight at the same temperature. It was diluted with water (3 mL) and extracted with EtOAc (2×20 mL). The combined organic layer was dried over $Na_2SO_4$ and concentrated. The crude product was purified by flash chromatography (Eluent: 50-60% EtOAc in pet ether) to get the title compound. Yield: 22% (40 mg, pale yellow gummy solid). $^1$H NMR (400 MHz, DMSO-$d_6$): δ 8.05 (s, 1H), 7.78 (s, 1H), 7.30-7.22 (m, 2H), 7.24-7.22 (m, 1H), 6.90-6.85 (m, 2H), 6.79 (d, J=8.0 Hz, 1H), 4.20 (s, 4H), 3.83 (s, 3H), 3.60 (d, J=13.2 Hz, 1H), 3.22 (t, J=8.0 Hz, 1H), 2.98 (d, J=13.2 Hz, 1H), 2.90 (t, J=7.2 Hz, 1H), 2.15-2.09 (m, 5H), 1.75-1.67 (m, 2H), 1.60-1.55 (m, 1H). LCMS: (Method A) 390.2 (M+H), Rt. 1.59 min, 97.04% (Max), 96.88% (220 nm). HPLC: (Method A) Rt, 3.082 min, 97.79% (Max).

Example 46: 4-(4-((2-(2,3-dihydrobenzo[b] [1,4]dioxin-6-yl)pyrrolidin-1-yl)methyl)phenyl)pyridine

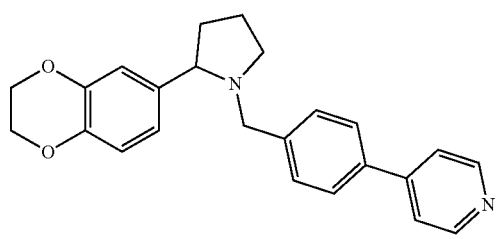 [SMILES: c1cc(-c2ccc(CN3CCCC3c3ccc4c(c3)OCCO4)cc2)ccn1]

To a stirred solution of intermediate 1 (0.11 g, 0.53 mmol) in DMF (4 mL), Intermediate 32 (88 mg, 0.43 mmol) and TEA (0.22 mL, 1.62 mmol) were added at RT. The resulting reaction mixture was stirred at 50° C. for 12 h. After completion of reaction, the reaction mixture was diluted with 10% aq. $NaHCO_3$ (10 mL), and extracted with EtOAc (2×10 mL). The combined organic layer was dried over $Na_2SO_4$ and concentrated. The resulting crude product was purified by flash chromatography (Eluent: 65% EtOAc in pet ether) to afford the title compound. Yield: 30% (60.3 mg, pale brown gummy solid). $^1$H NMR (400 MHz, DMSO-$d_6$): δ 8.62 (d, J=5.6 Hz, 2H), 7.74 (d, J=8.0 Hz, 2H), 7.69 (d, J=6.0 Hz, 2H), 7.39 (d, J=8.0 Hz, 2H), 6.89-6.93 (m, 2H), 6.82 (J=8.4 Hz, 1H), 4.21 (s, 4H), 3.74 (d, J=13.6 Hz, 1H), 3.32-3.30 (m, 1H), 3.10 (d, J=13.6 Hz, 1H), 2.97 (t, J=7.2 Hz, 1H), 2.09-2.19 (m, 2H), 1.74-1.78 (m, 2H), 1.70-1.72 (m, 1H). LCMS: (Method A) 373.2 (M+H), Rt. 1.16 min, 96.15% (Max). HPLC: (Method A) Rt. 2.11 min, 92.69% (Max).

Example 47: 2-(4-((2-(2,3-dihydrobenzo[b] [1,4]dioxin-6-yl)pyrrolidin-1-yl)methyl)-3-methylphenyl)pyridine from 2-(4-(chloro methyl)-2-methylphenyl)pyridine

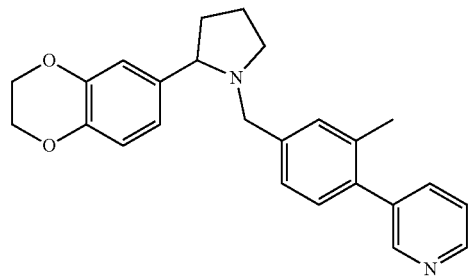 [SMILES: Cc1cc(CN2CCCC2c2ccc3c(c2)OCCO3)ccc1-c1cccnc1]

To a stirred solution of Intermediate 33 (232 mg,1.07 mmol) in MeCN (5 mL), TEA (0.41 mL, 2.91 mmol) and Intermediate 1 (200 mg, 0.97 mmol) were added at 0° C. The resulting mixture was stirred overnight at RT. It was quenched with water (20 mL) and extracted with EtOAc (2×25 mL). The combined organic layer was dried over $Na_2SO_4$ and concentrated under vacuum. The resulting crude compound was purified by flash chromatography (Eluent: 30% EtOAc: Hexane) to afford the title compound. Yield: 32% (120 mg, colourless gummy liquid). ¹H NMR: (400 MHz, DMSO-d₆): δ 8.56-8.54 (m, 2H), 7.77 (d, J=7.6 Hz, 1H), 7.46 (dd, d, J=8.4, 1.6 Hz, 1H), 7.18 (s, 3H), 6.93-6.88 (m, 2H), 6.82 (d, J=8.0 Hz, 1H), 4.22 (s, 4H), 3.72 (d, J=13.2 Hz, 1H), 3.32 (s, 1H), 3.06-2.99 (m, 2H), 2.22 (s, 3H), 2.21-2.10 (m, 2H), 1.81-1.79 (m, 2H), 1.74-1.70 (m, 1H). LCMS: Method A, 387.2 (M+H), Rt1.21 min, 95.33% (Max). HPLC: Method A, Rt. 2.23 min, 95.42% (Max).

Example 48: (S)-1-(4-((2-(2,3-dihydrobenzo[b][1,4]dioxin-6-yl)pyrrolidin-1-yl)methyl) Phenyl)-1H-1,2,4-triazole or (R)-1-(4-((2-(2,3-dihydrobenzo[b][1,4]dioxin-6-yl)pyrrolidin-1-yl)methyl) phenyl)-1 H-1,2,4-triazole

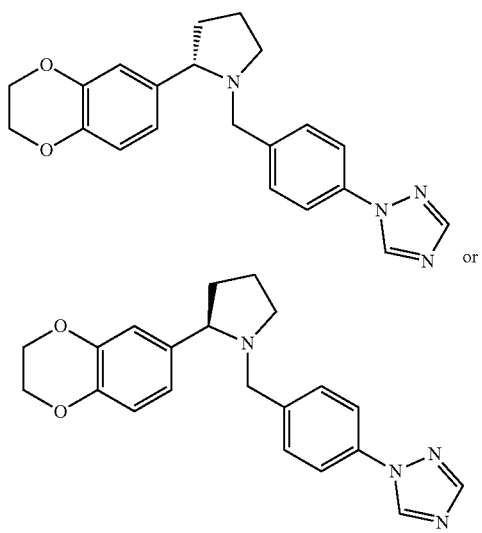

The enantiomers of Example 34 were separated by chiral preparative SFC (mobile phase: 40% IPA, column: Chiracel OJ-H (Method H)). The second eluting peak was concentrated to afford the example 48. Yield: 20% (30 mg, brown gummy solid). ¹H NMR (400 MHz, DMSO-d₆): δ 9.25 (s, 1H), 8.23 (s, 1H), 7.79 (d, J=8.4 Hz, 2H), 7.42 (d, J=8.0 Hz, 2H), 6.93-6.90 (m, 2H), 6.83 (d, J=8.4 Hz, 1H), 4.22 (s, 4H), 3.74 (d, J=13.6 Hz, 1H), 3.40-3.38 (m, 1H), 3.09 (d, J=4.4 Hz, 1H), 2.97 (t, J=8.0 Hz, 1H), 2.18-2.11 (m, 2H), 1.79-1.73 (m, 2H), 1.65-1.54 (m, 1H). LCMS: (Method A) 363.2 (M+H), Rt. 1.95 min, 97.73% (Max). HPLC: (Method B) Rt. 2.42 min, 98.46% (Max), 96.29% (220 nm). Chiral SFC: (Method H) Rt. 3.79 min, 100% (Max).

Example 49: 4-(4-((2-(2,3-dihydrobenzo[b][1,4]dioxin-6-yl)pyrrolidin-1-yl)methyl)-3-methylphenyl)pyridine

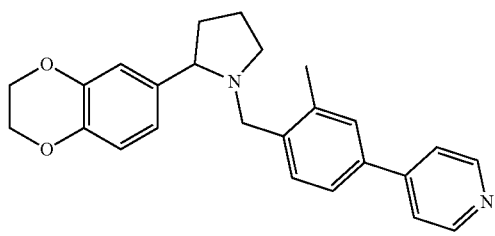 [SMILES: Cc1cc(-c2ccncc2)ccc1CN1CCCC1c1ccc2c(c1)OCCO2]

To a stirred solution of intermediate 1 (141 mg, 0.68 mmol) in ACN (4 mL) were added intermediate 35 (150 mg, 0.68 mmol) and TEA (0.29 mL, 2.06 mmol) at RT and the resulting mixture was stirred at 50° C. for 12 h. After completion of the reaction, the mixture was diluted with 10% aq. NaHCO₃ (10 mL) and extracted with EtOAc (2×10 mL). The combined organic layer was dried over Na₂SO₄ and concentrated under vacuum. The resulting crude product was purified by prep HPLC (Method A) to afford the title compound. Yield: 22% (58 mg, pale brown gummy solid). ¹H NMR (400 MHz, DMSO-d₆): δ 8.61 (d, J=5.6 Hz, 2H), 7.68 (d, J=5.6 Hz, 2H), 7.58-7.56 (m, 2H), 7.46 (d, J=8.0 Hz, 1H), 6.91 (s, 1H), 6.88 (d, J=8.0 Hz, 1H), 6.81 (d, J=8.0 Hz, 1H), 4.21 (s, 4H), 3.66 (d, J=12.8 Hz, 1H), 3.34-3.35 (m, 1H), 3.12 (d, J=13.2 Hz, 1H), 2.95 (t, J=8.0 Hz, 1H), 2.24 (s, 3H), 2.12-2.18 (m, 2H).1.17-1.79 (m, 2H), 1.59-1.61 (m, 1H). LCMS: (Method A) 387.3 (M+H), Rt. 1.23 min, 97.8% (Max). HPLC: (Method A) Rt. 2.27 min, 96.9% (Max).

Example 50: N-(5-((2-(2,3-dihydrobenzo[b][1,4]dioxin-6-yl)pyrrolidin-1-yl)methyl)thiazol-2-yl)acetamide

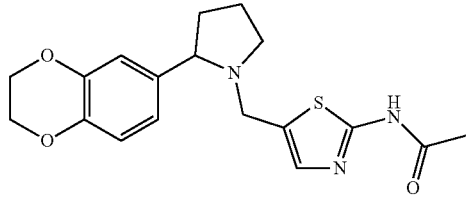 [SMILES: CC(=O)Nc1ncc(CN2CCCC2c2ccc3c(c2)OCCO3)s1]

To a stirred solution of intermediate 1 (0.2 g, 0.975 mmol), TEA (0.2 mL, 2.92 mmol) in ACN (3 mL), intermediate 36 (0.185 g, 0.975 mmol) was added at RT and the resulting mixture was stirred at the same temperature for 1 h. Completion of the reaction was monitored by TLC and the reaction mixture was evaporated under vacuum. The resulting crude product was suspended in water and extracted with EtOAc (2×15 mL). The combined organic layer was washed with water (5 mL), brine solution (5 mL), dried over anhydrous Na₂SO₄ and evaporated under vacuum. The crude product was purified by flash chromatography (Eluent: 2% methanol in DCM) to afford the title compound Yield: 41% (160 mg, off white solid). ¹H NMR (400 MHz, DMSO-d₆): δ 11.94 (s, 1H), 7.18 (s, 1H), 6.88 (s, 1H), 6.83 (d, J=1.6 Hz, 2H), 4.22 (s, 4H), 3.72 (d, J=14.0 Hz, 1H), 3.34-3.25 (m, 2H), 3.03-3.01 (m, 1H), 2.26-2.19 (m, 1H), 2.11-2.08 (m, 4H), 1.77-1.71 (m, 2H), 1.54-1.50 (m, 1H). LCMS: (Method A) 360.1 (M+H), Rt. 1.76 min, 99.91% (Max). HPLC: (Method A) Rt. 2.24 min, 99.72% (Max).

Example 51: 4-bromo-1-(4-((2-(2,3-dihydrobenzo[b][1,4]dioxin-6-yl)pyrrolidin-1-yl)methyl)phenyl)-1H-pyrazole

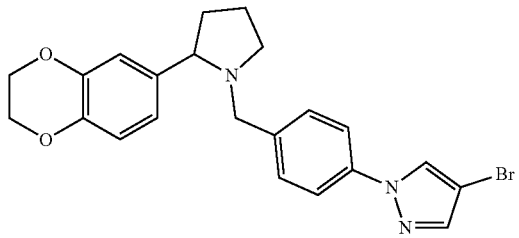 [SMILES: Brc1cnn(-c2ccc(CN3CCCC3c3ccc4c(c3)OCCO4)cc2)c1]

To a stirred solution of intermediate 1 (550 mg, 2.67 mmol) in ACN (10 mL), TEA (1.12 mL, 8.02 mmol) and intermediate 37 (799 mg, 2.94 mmol) were added at 0° C. The reaction mixture was stirred overnight at RT. It was quenched with water (50 mL) and extracted with EtOAc (2×25 mL). The combined organic layer was dried over $Na_2SO_4$ and concentrated under vacuum. The resulting crude compound was purified by flash chromatography (Eluent: 8% EtOAc:Hexane) to afford the title compound. Yield: 42% (500 mg, white solid). $^1$H NMR (400 MHz, MeOD): δ 8.35 (s, 1H), 7.70 (s, 1H), 7.65 (d, J=8.4 Hz, 2H), 7.38 (d, J=8.4 Hz, 2H), 6.95 (d, J=1.6 Hz, 1H), 6.89 (d, J=2.0 Hz, 1H), 6.81 (s, 1H), 4.23 (d, J=4.8 Hz, 4H), 3.80 (d, J=12.8 Hz, 1H), 3.38-3.32 (m, 1H), 3.03-3.13 (m, 2H), 2.24 (d, J=9.2 Hz, 1H), 2.16 (t, J=4.8 Hz, 1H), 1.81-1.85 (m, 2H). LCMS: (Method A), 442.1 (M+H), Rt. 1.82 min, 99.24% (Max). HPLC: (Method A), Rt. 3.702 min, 99.17% (Max).

Example 52: 1-(4-((2-(2,3-dihydrobenzo[b][1,4]dioxin-6-yl)pyrrolidin-1-yl)methyl)phenyl)-1H-pyrazole-4-carbonitrile

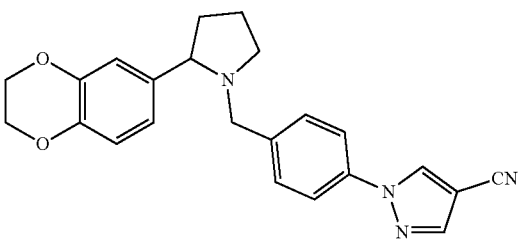 [SMILES: N#Cc1cnn(-c2ccc(CN3CCCC3c3ccc4c(c3)OCCO4)cc2)c1]

To a stirred solution of intermediate 1 (100 mg, 0.48 mmol) in ACN (5 mL), TEA (0.21 mL, 1.45 mmol) and intermediate 38 (106 mg, 0.48 mmol) were added at 0° C. The reaction mixture was stirred overnight at RT. It was quenched with water (50 mL) and extracted with EtOAc (2×25 mL). The combined organic layer was dried over $Na_2SO_4$ and concentrated under vacuum. The resulting crude product was purified by flash chromatography (Eluent: 8% EtOAc:Hexane) to afford the title compound. Yield: 10% (20 mg, white solid). $^1$H NMR (400 MHz, DMSO-$d_6$): δ 9.27 (s, 1H), 8.32 (s, 1H), 7.76 (d, J=8.8 Hz, 2H), 7.39 (d, J=8.4 Hz, 2H), 6.89 (dd, J=12.0, 1.6 Hz, 1H), 6.81-6.79 (m, 2H), 4.20 (s, 4H), 3.71 (d, J=13.2 Hz, 1H), 3.28 (t, J=8.0 Hz, 1H), 3.09 (d, J=13.6 Hz, 1H), 2.91-2.95 (m, 1H), 2.07-2.17 (m, 2H), 1.69-1.79 (m, 2H), 1.52-1.57 (m, 1H). LCMS: (Method A) 387.2 (M+H), Rt. 1.66 min, 97.37% (Max). HPLC: (Method A), Rt. 3.151 min, 98.73% (Max).

Example 53: (S)-1-(4-((2-(2,3-dihydrobenzo[b][1,4]dioxin-6-yl)pyrrolidin-1-yl)methyl) phenyl)-4-(methylsulfonyl)piperazine or (R)-1-(4-((2-(2,3-dihydrobenzo[b][1,4]dioxin-6-yl)pyrrolidin-1-yl)methyl) phenyl)-4-(methylsulfonyl)piperazine

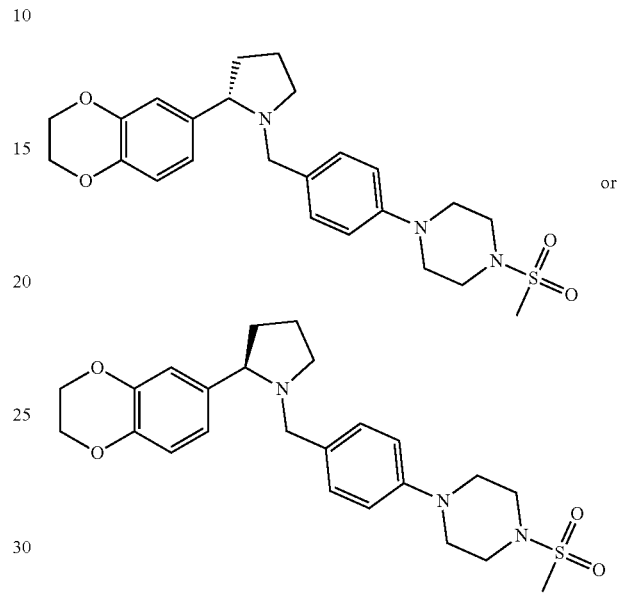

The enantiomers of Example 36 were separated by chiral preparative SFC (mobile phase: 0.5% Isopropyl Amine in IPA, column: Lux A1 (Method I)). The first eluting peak was concentrated to afford the example 53. Yield: 7% (15 mg, off-white solid). $^1$H NMR: (400 MHz, DMSO-$d_6$): δ 7.09 (d, J=8.4 Hz, 2H), 6.85-6.92 (m, 4H), 6.81 (d, J=8.4 Hz, 1H), 4.22 (s, 4H), 3.61 (d, J=13.6 Hz, 1H), 3.22 (s, 3H), 3.32-3.20 (m, 9H), 2.91 (t, J=8.0 Hz, 5H), 2.11-2.06 (m, 2H), 1.73-1.68 (m, 2H), 1.53-1.48 (m, 1H). LCMS: (Method A) 458.1 (M+H), Rt. 1.60 min, 98.7% (Max). HPLC: (Method A) Rt. 3.04 min, 99.0% (Max), 98.8% (220 nm). Chiral SFC: (Method I) Rt. 3.06 min, 100.0% (Max).

Example 54: 4-(4-((2-(2,3-dihydrobenzo[b][1,4]dioxin-6-yl)pyrrolidin-1-yl)methyl)phenyl)-3,5-dimethylisoxazole

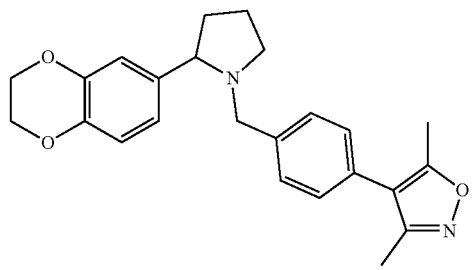 [SMILES: Cc1noc(C)c1-c1ccc(CN2CCCC2c2ccc3c(c2)OCCO3)cc1]

To a stirred solution of intermediate 6 (100 mg, 0.2 mmol) and 3,5-dimethyl-4-(4,4,5,5-tetramethyl-1,3,2-dioxaborolan-2-yl)isoxazole (60 mg, 0.2 mmol) in 1,4-dioxane (2 mL), a solution of potassium phosphate (170 mg, 0.8 mmol) in water (0.5 mL) was added at RT. The resulting reaction mixture was flushed with nitrogen for 10 minutes before addition of Pd₂(dppf)Cl₂-DCM (43 mg, 0.05 mmol) at RT. The reaction mixture was stirred at 100° C. overnight. It was filtered through celite pad and the filtrate was concentrated under vacuum. The resulting crude product was suspended in water and extracted with EtOAc (2×20 mL). The organic layer was washed with water (10 mL), brine (2 mL), dried over Na₂SO₄ and concentrated under vacuum. The residue was purified by flash chromatography (Eluent: 48% EtOAc in PE) to afford the title compound. Yield: 29% (32 mg, pale yellow solid). ¹H NMR (400 MHz, DMSO-d₆): δ 7.36-7.27 (m, 4H), 6.95-6.86 (m, 2H), 6.81 (d, J=8.0 Hz, 1H), 4.21 (s, 4H), 3.72 (d, J=13.6 Hz, 1H), 3.35-3.27 (m, 1H), 3.08 (d, J=13.6 Hz, 1H), 3.03-2.96 (m, 1H), 2.38 (s, 3H), 2.21 (s, 3H), 2.19-2.06 (m, 2H), 1.84-1.66 (m, 2H), 1.62-1.51 (m, 1H). LCMS: (Method A) 391.2 (M+H), Rt. 1.7 min, 99.9% (Max). HPLC: (Method A) Rt. 3.3 min, 99.6% (Max), 99.0% (220 nm).

Example 55: 4-(4-((2-(2,3-dihydrobenzo[b] [1,4]dioxin-6-yl)pyrrolidin-1-yl)methyl)phenyl)-1,3,5-trimethyl-1H-pyrazole

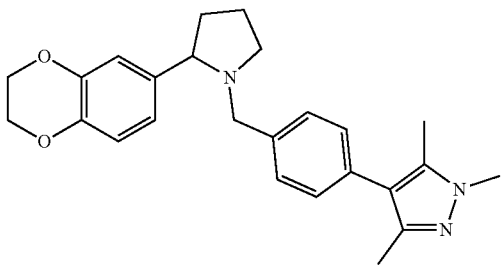 [SMILES: Cc1nn(C)c(C)c1-c1ccc(CN2CCCC2c2ccc3c(c2)OCCO3)cc1]

To a stirred solution of intermediate 6 (100 mg, 0.26 mmol) and 1,3,5-trimethyl-4-(4,4,5,5-tetramethyl-1,3,2-dioxaborolan-2-yl)-1 H-pyrazole (63 mg, 0.26 mmol) in dioxane (2 mL), potassium phosphate (170 mg, 0.8 mmol) and water (0.5 mL) were added at RT. Then the reaction mixture was flushed with nitrogen for 10 minutes before addtion of Pd₂(dppf)Cl₂-DCM (43 mg, 0.05 mmol) at RT. The reaction mixture was stirred at 100° C. overnight. After completion of the reaction, the reaction mixture was filtered through celite pad and the filtrate was concentrated under vacuum. The resulting residue was suspended in water (10 mL) and extracted with EtOAc (2×20 mL). The combined organic layer was washed with water (10 mL), brine (2 mL), dried over Na₂SO₄ and concentrated. The resulting residue was purified by preparative HPLC (Method A) to get the title compound. Yield: 17% (20 mg, pale yellow solid). ¹H NMR (400 MHz, DMSO-d₆): δ 7.27 (d, J=8.0 Hz, 2H), 7.17 (d, J=8.0 Hz, 2H), 6.96-6.85 (m, 2H), 6.81 (d, J=8.0 Hz, 1H), 4.21 (s, 4H), 3.72-3.68 (m, 4H), 3.32-3.24 (m, 1H), 3.06-2.95 (m, 2H), 2.19-2.08 (m, 8H), 1.82-1.67 (m, 2H), 1.60-1.48 (m, 1H). LCMS: (Method A) 404.3 (M+H), Rt. 1.4 min, 98.3% (Max). HPLC: (Method A) Rt. 2.7 min, 99.1% (Max), 98.1% (220 nm).

Example 56: 3-(4-((2-(2,3-dihydrobenzo[b] [1,4]dioxin-6-yl)pyrrolidin-1-yl)methyl)-3-methylphenyl)-2-methylpyridine

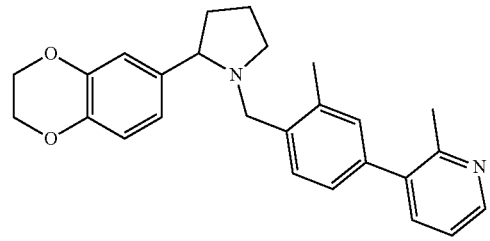 [SMILES: Cc1cc(-c2cccnc2C)ccc1CN1CCCC1c1ccc2c(c1)OCCO2]

To a stirred solution of intermediate 1 (124 mg, 0.61 mmol) and TEA (0.25 mL, 1.81 mmol) in ACN (3 mL), intermediate 39 (140 mg, 0.61 mmol) was added at RT and the resulting mixture was stirred at 50° C. for 12 h. After completion of reaction, the reaction mixture was diluted with water (10 mL) and extracted with EtOAc (2×10 mL). The combined organic layer was dried over Na₂SO₄ and concentrated under vacuum. The resulting crude material was purified by flash chromatography (Eluent: 27-30% EtOAc in PE) to get the title compound. Yield: 17% (43 mg, pale yellow gummy solid). ¹H NMR (400 MHz, DMSO-d₆): δ 8.42 (dd, J=4.4, 3.2 Hz, 1H), 7.55 (d, J=7.6, 1.6 Hz, 1H), 7.39 (d, J=7.6 Hz, 1H), 7.31-7.23 (m, 1H), 7.16 (d, J=8.0 Hz, 1H), 7.11 (s, 1H), 6.91-6.87 (m, 2H), 6.80 (d, J=8.4 Hz, 1H), 4.20 (s, 4H), 3.65 (d, J=13.2 Hz, 1H), 3.31-3.23 (m, 1H), 3.11 (d, J=13.2 Hz, 1H), 2.98 (t, J=7.2 Hz, 1H), 2.41 (s, 3H), 2.19 (s, 3H), 2.16-2.09 (m, 2H), 1.82-1.71 (m, 2H), 1.63-1.54 (m, 1H). LCMS: (Method A) 401.2 (M+H), Rt. 1.29 min, 96.99% (Max). HPLC: (Method A) Rt. 2.34 min, 97.28% (Max), 93.79% (220 nm).

Example 57: 4-(4-((2-(2,3-dihydrobenzo[b] [1,4]dioxin-6-yl)pyrrolidin-1-yl)methyl)-3-methylphenyl)-3-methylpyridine

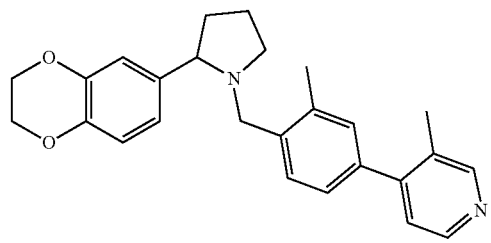 [SMILES: Cc1cc(-c2ccncc2C)ccc1CN1CCCC1c1ccc2c(c1)OCCO2]

To a stirred solution of intermediate 1 (0.124 g, 0.61 mmol) and TEA (0.25 mL, 1.81 mmol) in ACN (3 mL), intermediate 40 (142 g, 0.61 mmol) was added at RT and the resulting mixture was stirred at 50° C. for 12 h. After completion of reaction, the reaction mixture was diluted with water (10 mL) and extracted with EtOAc (2×10 mL). The combined organic layer was dried over Na₂SO₄ and concentrated under vacuum. The resulting crude material was purified by flash chromatography (Eluent: 27-30% EtOAc in PE) to afford the title compound. Yield: 16% (38 mg, pale yellow gummy solid). ¹H NMR (400 MHz, DMSO-d₆): δ 8.47 (s, 1H), 8.41 (d, J=4.8 Hz, 1H), 7.41 (d, J=8.0 Hz, 1H), 7.29-7.13 (m, 3H), 6.91-6.85 (m, 2H), 6.79

(d, J=8.0 Hz, 1H), 4.26 (s, 4H), 3.65 (d, J=13.6 Hz, 1H), 3.37-3.32 (m, 1H), 3.13 (d, J=13.6 Hz, 1H), 2.97 (t, J=7.6 Hz, 1H), 2.23 (s, 3H), 2.20 (s, 3H), 2.18-2.09 (m, 2H), 1.78-1.71 (m, 2H), 1.59-1.51 (m, 1H). LCMS: (Method A) 401.2 (M+H), Rt. 1.31 min, 94.86% (Max). HPLC: (Method A) Rt. 2.39 min, 95.38% (Max), 90.49% (220 nm).

Example 58: 2-(4-((2-(2,3-dihydrobenzo[b] [1,4] dioxin-6-yl)pyrrolidin-1-yl)methyl)phenyl)thiazole

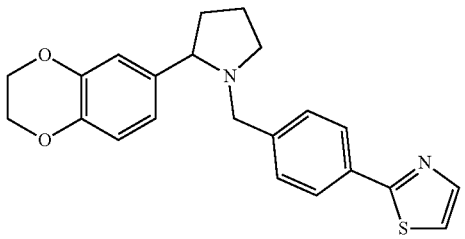 [SMILES: c1csc(-c2ccc(CN3CCCC3c3ccc4c(c3)OCCO4)cc2)n1]

To a stirred solution of Intermediate 34 (100 mg, 0.2 mmol), 2-bromothiazole (0.02 mL, 0.2 mmol) and water (0.5 mL) in dioxane (3 mL), cesium carbonate (231 mg, 0.7 mmol) was added at RT. The reaction mixture was flushed with nitrogen before addition of tetrakis(triphenylphosphine)palladium(0) (54 mg, 0.04 mmol) at RT. The reaction mixture was flushed with nitrogen again and was stirred at 100° C. overnight. After completion of the reaction, the reaction mixture was filtered through celite pad and the filtrate was concentrated under vacuum. The resulting crude product was suspended in water and extracted with EtOAc (2×20 mL). The combined organic layer was washed with water (10 mL), brine (2 mL), dried over $Na_2SO_4$ and concentrated. The resulting crude product was purified by flash chromatography (Eluent: 30% EtOAc in PE) to afford the title compound. Yield: 15% (15 mg, brown gummy solid). $^1$H NMR (400 MHz, DMSO-$d_6$): δ 7.92-7.86 (m, 3H), 7.76 (d, J=3.2 Hz, 1H), 7.37 (d, J=8.0 Hz, 1H), 7.93-7.87 (m, 2H), 6.82 (d, J=8.0 Hz, 1H), 4.21 (s, 4H), 3.72 (d, J=14.0 Hz, 1H), 3.35-3.26 (m, 1H), 3.09 (d, J=13.6 Hz, 1H), 3.00-2.92 (m, 1H), 2.19-2.05 (m, 2H), 1.83-1.65 (m, 2H), 1.62-1.51 (m, 1H). HPLC: (Method A) Rt. 3.1 min, 96.1% (Max), 94.8% (220 nm). LCMS: (Method A) 379.1 (M+H), Rt. 1.6 min, 96.1% (Max).

Example 59: 2-(4-((2-(2,3-dihydrobenzo[b] [1,4] dioxin-6-yl)pyrrolidin-1-yl)methyl)phenyl)-5-methylthiazole

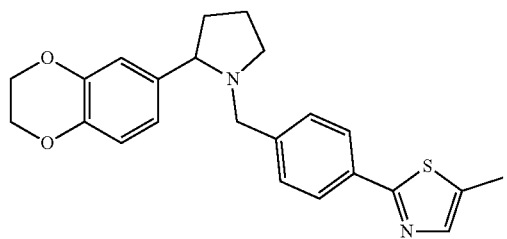 [SMILES: Cc1cnc(-c2ccc(CN3CCCC3c3ccc4c(c3)OCCO4)cc2)s1]

To a stirred solution of 2-bromo-5-methylthiazole (200 mg, 1.12 mmol) and intermediate 34 (709 mg, 1.68 mmol) in dry dioxane (2 mL), water (0.3 mL) and cesium carbonate (728 mg, 2.24 mmol) were added at RT. The resulting reaction mixture was flushed with nitrogen for 10 minutes before the addition of tetrakis(triphenylphosphine)palladium(0) (25 mg, 0.02 mmol). The reaction mixture was heated at 100° C. overnight. It was filtered through celite pad and the filtrate was concentrated under vacuum. The resuting crude product was purified by prep HPLC (method A) to afford the title compound. Yield: 26% (115 mg, brown gummy solid). $^1$H NMR (400 MHz, DMSO-$d_6$): δ 7.80 (d, J=8.0 Hz, 2H), 7.57 (d, J=0.8 Hz, 1H), 7.34 (d, J=8.0 Hz, 2H), 6.92-6.88 (m, 2H), 6.81 (d, J=8.0 Hz, 2H), 4.21 (s, 4H), 3.71 (d, J=13.6 Hz, 1H), 3.32-3.09 (m, 1H), 2.98 (d, J=13.6 Hz, 1H), 2.94 (t, J=2.4 Hz, 1H), 2.48 (s, 3H), 2.15-2.08 (m, 2H), 1.78-1.71 (m, 2H), 1.58-1.54 (m, 1H). LCMS: (Method A) 393.1 (M+H), Rt. 1.73 min, 98.44% (Max). HPLC: (Method A) Rt. 3.34 min, 97.87% (Max), 96.31% (220 nm).

Example 60: 2-(4-((2-(2,3-dihydrobenzo[b] [1,4] dioxin-6-yl)pyrrolidin-1-yl)methyl)phenyl)thiazole-5-carbonitrile

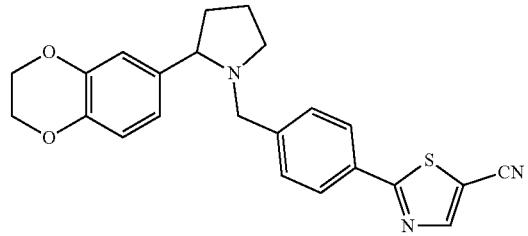 [SMILES: N#Cc1cnc(-c2ccc(CN3CCCC3c3ccc4c(c3)OCCO4)cc2)s1]

To a stirred solution of 2-bromothiazole-5-carbonitrile (50 mg, 0.26 mmol), intermediate 34 (123 mg, 0.29 mmol) and water (0.3 mL) in dioxane (1 mL), cesium carbonate (258 mg, 0.79 mmol) was added at RT. The resulting reaction mixture was flushed with nitrogen for 10 minutes before addition of tetrakis(triphenylphosphine)palladium(0) (30 mg, 0.02 mmol) at RT. Then the reaction mixture was heated to 100° C. overnight. After completion of reaction, the reaction mixture was filtered through celite pad and the filtrate was concentrated under vacuum. The resulting crude product was purified by Prep HPLC (method A) to afford the title compound. Yield: 8% (10 mg, brown gummy solid). $^1$H NMR (400 MHz, DMSO-$d_6$): δ 8.74 (s, 1H), 7.96 (d, J=8.0 Hz, 2H), 7.44 (d, J=8.0 Hz, 2H), 6.92-6.88 (m, 2H), 6.81 (d, J=8.4 Hz, 1H), 4.21 (s, 4H), 3.73 (d, J=14.0 Hz, 1H), 3.32-3.31 (m, 1H), 3.14 (d, J=14.0 Hz, 1H), 2.95 (t, J=5.6 Hz, 1H), 2.19-2.09 (m, 2H), 1.82-1.70 (m, 2H), 1.61-1.54 (m, 1H). LCMS: (Method A) 404.2 (M+H), Rt. 1.71 min, 95.08% (Max). HPLC: (Method A) Rt. 3.34 min, 97.63% (Max), 97.02% (220 nm).

Example 61: 4-(4-((2-(2,3-dihydrobenzo[b] [1,4]dioxin-6-yl)pyrrolidin-1-yl)methyl)phenyl) morpholin-3-one

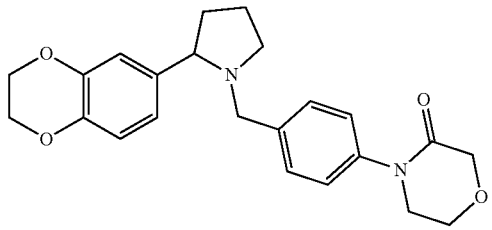 [SMILES: O=C1COCCN1c1ccc(CN2CCCC2c2ccc3c(c2)OCCO3)cc1]

To a stirred solution of intermediate 1 (219 mg, 0.97 mmol) and intermediate 41 (200 mg, 0.97 mmol) in MeCN (5 mL), TEA (0.41 mL, 2.918 mmol) was added at 0° C. Then the reaction mixture was stirred overnight at RT. The reaction mixture was diluted with water (10 mL) and extracted with EtOAc (2×20 mL). The combined organic layer was dried over $Na_2SO_4$ and concentrated under vacuum. The resulting crude compound was purified by flash chromatography (Eluent: 65% EtOAc:Hexane) to afford the title compound. Yield: 8% (33 mg, pale brown solid). $^1$H NMR (400 MHz, DMSO-$d_6$): δ 7.33 (d, J=2.0 Hz, 2H), 7.28 (d, J=8.4 Hz, 2H), 6.93 (d, J=1.6 Hz, 1H), 6.88 (d, J=1.6 Hz, 1H), 6.83 (s, 1H), 4.21 (d, J=5.2 Hz, 4H), 4.20 (s, 2H), 3.97 (t, J=5.2 Hz, 2H), 3.70 (t, J=7.2 Hz, 3H), 3.27-3.34 (m, 1H), 3.06 (s, 1H), 2.97 (s, 1H), 2.09-2.15 (m, 2H), 1.72-1.78 (m, 2H), 1.545 (s, 1H). LCMS: (Method A) 395.2 (M+H), Rt. 1.332 min, 95.68% (Max). HPLC: (Method A), $R_t$. 2.441 min, 95.65% (Max), 94.285% (220).

Example 62: 1-(4-((2-(2,3-dihydrobenzo[b] [1,4]dioxin-6-yl)pyrrolidin-1-yl)methyl)phenyl)piperidin-2-one

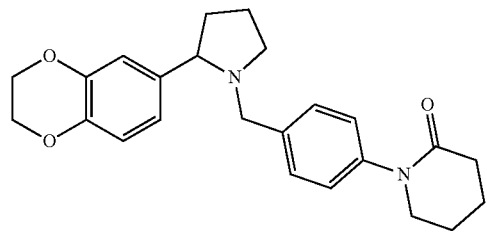 [SMILES: O=C1CCCCN1c1ccc(CN2CCCC2c2ccc3c(c2)OCCO3)cc1]

To a stirred solution of intermediate 1 (90 mg, 0.44 mmol), intermediate 42 (90 mg, 0.40 mmol) in a MeCN, TEA (0.18 mL, 1.20 mmol) was added at RT and the reaction mixture was stirred overnight at the same temperature. It was diluted with water (3 mL) and extracted with EtOAc (2×50 mL). The combined organic layer was dried over $Na_2SO_4$ and concentrated under vacuum. The crude product was purified by flash chromatography (Eluent: 80% EtOAc in PE) to give the title compund. Yield: 7% (12 mg, brown gummy solid). $^1$H NMR 400 MHz, DMSO-$d_6$: δ 7.24 (d, J=8.4 Hz, 1H), 7.18 (d, J=8.4 Hz, 1H), 6.92 (7.24 (d, J=1.6 Hz, 1H), 6.89 (dd, J=8.4, 1.6 Hz, 1H), 6.81 (d, J=8.4 Hz, 1H), 4.22 (s, 4H), 3.68 (d, J=13.2 Hz, 1H), 3.57 (t, J=6.0 Hz, 2H), 3.33-3.26 (m, 2H), 3.04-2.95 (m, 2H), 2.37 (t, J=6.0 Hz, 2H), 2.15-2.09 (m, 2H), 1.84-1.78 (m, 4H), 1.75-1.69 (m, 2H), 1.54-1.52 (m, 1H). LCMS: (Method A) 393.2 (M+H), Rt. 1.46 min, 96.39% (Max) 94.71% (220 nm). HPLC: (Method A) Rt. 2.76 min, 94.42% (Max).

Example 63: 3-(4-((2-(2,3-dihydrobenzo[b] [1,4]dioxin-6-yl)pyrrolidin-1-yl)methyl)phenyl)-5-(methylsulfonyl)pyridine

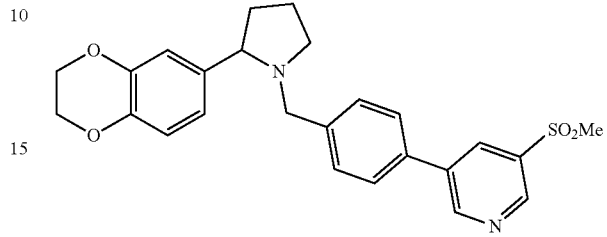

To a stirred solution of intermediate 1 (100 mg, 0.4 mmol), TEA (0.2 mL, 1.4 mmol) in dry MeCN (3 mL), intermediate 43 (160 mg, 0.5 mmol) was added and the resulting mixture was stirred overnight at RT. After completion of the reaction, the reaction mixture was concentrated under vacuum. The resulting crude product was suspended in water (2 mL) and extracted with EtOAc (2×20 mL). The combined organicl layer was washed with water (10 mL), brine (2 mL), dried over $Na_2SO_4$ and concentrated under vacuum. The crude product was purified by flash chromatography (Eluent: 32% EtOAc in PE) to afford the title compound. Yield: 18% (38 mg, brown gummy solid). $^1$H NMR (400 MHz, DMSO-$d_6$): δ 9.22 (s, 1H), 9.21 (s, 1H), 8.50 (d, J=1.6 Hz, 1H), 7.79 (d, J=8.0 Hz, 2H), 7.42 (d, J=7.6 Hz, 2H), 6.94-6.88 (m, 2H), 6.82 (d, J=8.0 Hz, 1H), 4.21 (s, 4H), 3.76 (d, J=13.6 Hz, 1H), 3.40 (s, 3H), 3.35-3.27 (m, 1H), 3.12 (d, J=13.6 Hz, 1H), 3.01-2.96 (m, 1H), 2.21-2.06 (m, 2H), 1.83-1.68 (m, 2H), 1.62-1.51 (m, 1H). LCMS: (Method A) 451.1 (M+H), Rt. 1.5 min, 93.2% (Max). HPLC: (Method A) Rt. 2.9 min, 94.9% (Max), 90.3% (220 nm).

Example 64: 2-(4-((2-(2,3-dihydrobenzo[b] [1,4]dioxin-6-yl)pyrrolidin-1-yl)methyl)phenyl)pyrazine

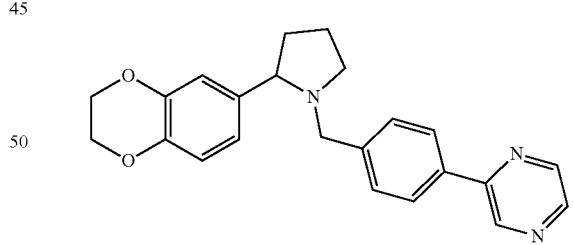

To a stirred solution of intermediate 1 (150 mg, 0.73 mmol) in dry MeCN (2 mL), intermediate 44 (179 mg, 0.87 mmol) and TEA (0.1 mL, 1.46 mmol) were added at RT and the resulting mixture was stirred overnight at the same temperature. It was concentrated under vacuum. To the resulting crude product water was added (20 mL) and was extracted with EtOAc (2×20 mL). The combined organic layer was washed with water (10 mL), brine (10 mL), dried over $Na_2SO_4$ and concentrated under vacuum. The resulting crude product was purified by flash chromatography (Eluent: 45% EtOAc in PE) to afford the title compound. Yield: 23% (43 mg, brown gummy solid). $^1$H NMR (400 MHz, DMSO-d$_6$): δ 9.23 (s, 1H), 8.70 (s, 1H), 8.59 (s, 1H), 8.08 (d, J=8.0 Hz, 2H), 7.41 (d, J=8.0 Hz, 2H), 6.94-6.90 (m, 2H), 6.83 (d, J=8.4 Hz, 1H), 4.22 (s, 4H), 3.76 (d, J=13.6 Hz, 1H), 3.11 (d, J=13.2 Hz, 1H), 2.98 (t, J=6.4 Hz, 1H), 2.18-2.10 (m, 2H), 1.78-1.71 (m, 2H), 1.59-1.54 (m, 1H). LCMS: (Method A) 374.2.2 (M+H), Rt. 1.47 min, 98.52% (Max). HPLC: (Method A) Rt. 2.75 min, 97.68% (Max), 96.09% (220 nm).

Example 65: 2-(2,3-dihydrobenzo[b] [1,4]dioxin-6-yl)-1-(4-(2-(methylsulfonyl) ethoxy)benzyl)pyrrolidine

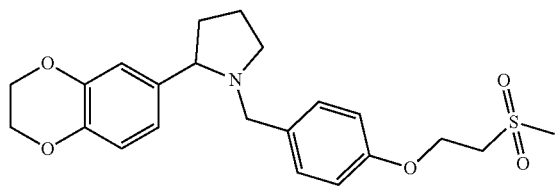 [SMILES: CS(=O)(=O)CCOc1ccc(CN2CCCC2c2ccc3c(c2)OCCO3)cc1]

Step 1: 2-(2,3-dihydrobenzo[b][1,4]dioxin-6-yl)-1-(4-(2-(methylthio)ethoxy)benzyl)pyrrolidine

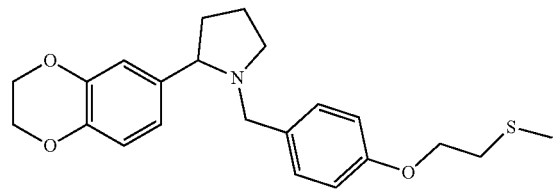 [SMILES: CSCCOc1ccc(CN2CCCC2c2ccc3c(c2)OCCO3)cc1]

To a stirred solution of intermediate 1 (200 mg, 0.5 mmol) in dry ACN (3 mL), intermediate 45 (115 mg, 0.5 mmol)) and TEA (0.2 mL, 1.6 mmol) were added at RT and the resulting mixture was stirred overnight at the same temperature. The completion of the reaction was monitored by TLC. The reaction mixture was concentrated under vacuum. The resulting crude product was suspended in water and extracted with EtOAc (2×20). The combined organic layer was washed with water (10 mL), brine (10 mL), dried over Na$_2$SO$_4$ and concentrated under vacuum. The resulting crude product was purified by flash chromatography (Elutent: 26% EtOAc in PE) to afford the title compound. Yield: 63% (120 mg, pale brown gummy solid). LCMS: (Method A) 386.2 (M+H), Rt. 1.849 min, 96.5% (Max).

Step 2: 2-(2,3-dihydrobenzo[b][1,4]dioxin-6-yl)-1-(4-(2-(methylsulfonyl) ethoxy) benzyl) pyrrolidine

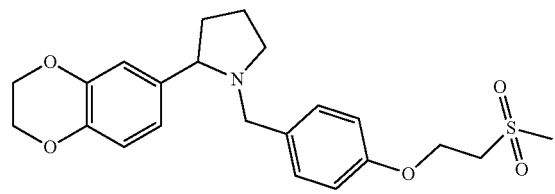 [SMILES: CS(=O)(=O)CCOc1ccc(CN2CCCC2c2ccc3c(c2)OCCO3)cc1]

To a stirred solution of 2-(2,3-dihydrobenzo[b][1,4]dioxin-6-yl)-1-(4-(2-(methylthio)ethoxy) benzyl)pyrrolidine (120 mg, 0.3 mmol)) in dry DCM (5 mL), m-CPBA (107 mg, 0.6 mmol) was added at 0° C. and the resulting mixture was stirred for 1.5 h at RT. The completion of the reaction was monitored by TLC. The reaction mixture was quenched with saturated NaHCO$_3$ solution and extracted with DCM (2×15 mL). The combined organic layer was dried over Na$_2$SO$_4$ and concentrated under vacuum. The resulting crude product was purified by Prep. HPLC (Method B) to afford the title compound. Yield: 7.0% (8.5 mg, pale yellow gummy solid). $^1$H NMR (400 MHz, DMSO-d$_6$): δ 7.41 (d, J=8.4 Hz, 2H), 7.27 (s, 1H), 7.07 (d, J=8.0 Hz, 1H), 6.91 (d, J=8.0 Hz, 2H), 6.83 (d, J=8.0 Hz, 1H), 4.49-4.38 (m, 2H), 4.25 (s, 4H), 4.18 (d, J=8.0 Hz, 1H), 3.52-3.45 (m, 3H), 3.25-3.23 (m, 1H), 3.07 (d, J=4.0 Hz, 1H), 2.63 (s, 3H), 2.67-2.61 (m, 2H), 2.04-1.98 (m, 2H), 1.88-1.78 (m, 1H). LCMS: (Method A) 418.1 (M+H), Rt. 1.376 min, 99.3% (Max). HPLC: (Method B) Rt. 3.34 min, 99.60% (Max), 95.69% (220 nm).

Example 66: 4-(4-((2-(2,3-dihydrobenzo[b] [1,4]dioxin-6-yl)pyrrolidin-1-yl)methyl)phenyl)thiomorpholine 1,1-dioxide

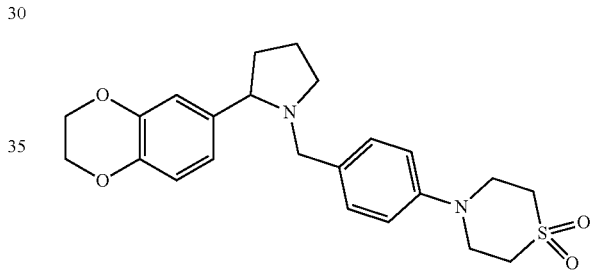

To a stirred solution of intermediate 6 (100 mg, 0.26 mmol), intermediate 46 (137 mg, 0.80 mmol) in dry THF (5 mL), K$_3$PO$_4$—H$_2$O (184 mg, 0.80 mmol) was added and the resulting mixture was flushed with nitrogen for 10 min before addition of X-Phos aminobiphenyl palladium chloride precatalyst (8.4 mg, 0.01 mmol) at RT. The resulting reaction mixture was heated at 100° C. overnight. The reaction mixture was filtered through celite pad and the filtrate was concentrated. The resulting crude product was suspended in water and extracted with EtOAc (2×20 mL). The combined organic layer was washed with water (10 mL), brine (10 mL), dried over Na$_2$SO$_4$ and concentrated under vacuum. The residue was purified by flash chromatography (Eluent: 45% EtOAC in PE) to afford the title compound. Yield: 62% (41 mg, white solid). $^1$H NMR (400 MHz, DMSO-d$_6$): δ 7.10 (d, J=8.0 Hz, 2H), 6.95 (d, J=8.4 Hz, 2H), 6.90-6.85 (m, 2H), 6.80 (d, J=8.4 Hz, 1H), 4.21 (s, 4H), 3.72 (br s, 4H), 3.60 (d, J=13.2 Hz, 1H), 3.22 (t, J=8.0 Hz, 1H), 3.10 (br s, 4H), 2.94-2.90 (m, 2H), 2.14-2.07 (m, 2H), 1.71-1.68 (m, 2H), 1.53-1.49 (m, 1H). LCMS: (Method A) 429.2 (M+H), Rt. 1.46 min, 96.95% (Max). HPLC: (Method B) Rt. 2.72 min, 95.03% (Max), 94.78% (220 nm).

Example 67: 4-(4-((2-(2,3-dihydrobenzo[b] [1,4]dioxin-6-yl)pyrrolidin-1-yl)methyl)phenyl)thiomorpholin-3-one

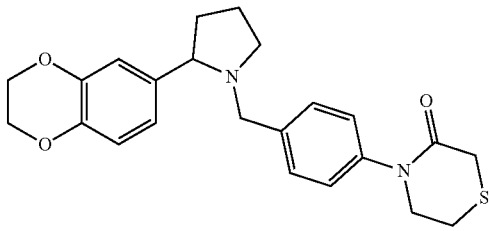 [SMILES: O=C1CSCCN1c1ccc(CN2CCCC2c2ccc3c(c2)OCCO3)cc1]

To a stirred solution of intermediate 1 (205 mg, 1.0 mmol), TEA (0.36 mL, 2.73 mmol) in a MeCN (5.0 mL), intermediate 47 (220 mg, 0.91 mmol) was added at RT and the resulting mixture was stirred overnight at the same temperature. It was diluted with water and extracted with EtOAc (2×50 mL). The combined organic layer was dried over Na$_2$SO$_4$ and concentrated under vacuum. The crude product was purified by flash chromatography (Eluent: 80% EtOAc in PE) to give the title compound. Yield: 32% (120 mg, off white solid). $^1$H NMR (400 MHz, DMSO-d$_6$): δ 7.26 (d, J=8.4 Hz, 2H), 7.21 (d, J=8.4 Hz, 2H), 6.92 (d, J=1.6 Hz, 1H), 6.90-6.87 (m, 1H), 6.81 (d, J=8.0 Hz, 1H), 4.22 (s, 4H), 3.94 (t, J=6.0 Hz, 2H), 3.68 (d, J=13.2 Hz, 1H), 3.41 (s, 2H), 3.31-3.28 (m, 1H), 3.06-3.02 (m, 3H), 2.30 (t, J=7.6 Hz, 1H), 2.15-2.08 (m, 2H), 1.76-1.69 (m, 2H), 1.56-1.52 (m, 1H). LCMS: (Method A) 411.1 (M+H), Rt. 1.55 min, 96.27% (Max). HPLC: (Method A) Rt. 2.77 min, 98.34% (Max).

Example 68: 2-(4-((2-(2,3-dihydrobenzo[b] [1,4]dioxin-6-yl)pyrrolidin-1-yl)methyl)phenyl)-4-methylthiazole

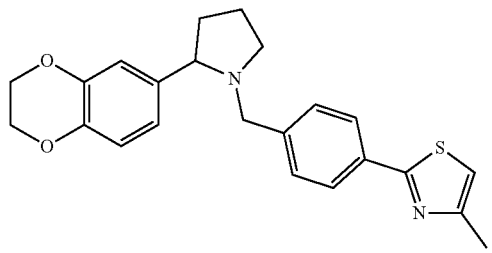 [SMILES: Cc1csc(-c2ccc(CN3CCCC3c3ccc4c(c3)OCCO4)cc2)n1]

To a stirred solution of 2-bromo-4-methylthiazole (200 mg, 1.12 mmol) and intermediate 34 (709 mg, 1.68 mmol) in dioxane (2 mL), cesium carbonate (728 mg, 2.24 mmol) and water (0.3 mL) were added at RT. Then the reaction mixture was flushed with nitrogen for 10 minutes before the addition of tetrakis(triphenylphosphine)palladium(0) (25 mg, 0.02 mmol). The resulting reaction mixture was stirred overnight at 100° C. The reaction mixture was filtered through celite and the fitrate was concentrated under vacuum. The resulting crude product was purified by Prep HPLC (method A) to afford the title compound. Yield: 28% (125 mg, yellow gummy solid). $^1$H NMR (400 MHz, DMSO-d$_6$): δ 7.83 (d, J=8.0 Hz, 2H), 7.35 (d, J=8.0 Hz, 2H), 7.29 (s, 1H), 6.92-6.88 (m, 2H), 6.81 (d, J=8.4 Hz, 1H), 4.21 (s, 4H), 3.72 (d, J=13.6 Hz, 1H), 3.32-3.27 (m, 1H), 3.08 (d, J=13.6 Hz, 1H), 2.96 (t, J=7.6 Hz, 1H), 2.41 (s, 3H), 2.16-2.09 (m, 2H), 1.79-1.72 (m, 2H), 1.70-1.56 (m, 1H). LCMS: (Method A) 393.1(M+H), Rt. 1.69 min, 99.24% (Max). HPLC: (Method A) Rt. 3.24 min, 99.94% (Max), 99.95% (220 nm).

Example 69: 2-(4-((2-(2,3-dihydrobenzo[b] [1,4]dioxin-6-yl)pyrrolidin-1-yl)methyl) phenyl) pyrimidine

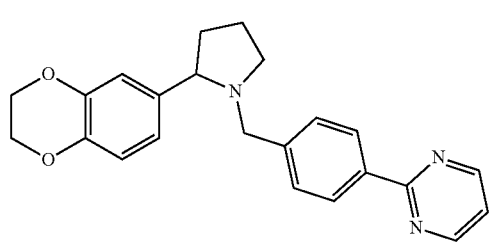 [SMILES: c1cnc(-c2ccc(CN3CCCC3c3ccc4c(c3)OCCO4)cc2)nc1]

To a stirred solution of intermediate 1 (480 mg, 2.3 mmol) in dry MeCN (5 mL), intermediate 48 (482 mg, 2.35 mmol) and TEA (0.7 mL, 4.7 mmol) were added at RT and the resulting mixture was stirred overnight at the same temperature. It was concentrated under vacuum. To the resulting crude product water (10 mL) was added and was extracted with EtOAc (2×50 mL). The combined organic layer was washed with water (5 mL), brine (5 mL), dried over Na$_2$SO$_4$ and concentrated. The resulting crude product was purified by flash chromatography (Eluent: 26% EtOAc in PE) to afford the title compound. Yield: 81% (15 mg, yellow gummy solid). $^1$H NMR (400 MHz, DMSO-d$_6$): δ 8.89 (d, J=4.8 Hz, 2H), 8.33 (d, J=8.4 Hz, 2H), 7.44-7.38 (m, 3H), 6.95-6.88 (m, 2H), 6.82 (d, J=8.0 Hz, 1H), 4.21 (s, 4H), 3.76 (d, J=13.6 Hz, 1H), 3.35-3.27 (m, 1H), 3.10 (d, J=13.6 Hz, 1H), 3.01-2.94 (m, 1H), 2.19-2.04 (m, 2H), 1.83-1.67 (m, 2H), 1.62-1.51 (m, 1H). LCMS: (Method A) 374.2 (M+H), Rt. 1.5 min, 97.3% (Max). HPLC: (Method A) Rt. 2.8 min, 97.7% (Max), 97.7% (220 nm).

Example 70: 4-(4-((2-(2,3-dihydrobenzo[b] [1,4]dioxin-6-yl)pyrrolidin-1-yl)methyl)-2-methylphenyl)-3-methylpyridine

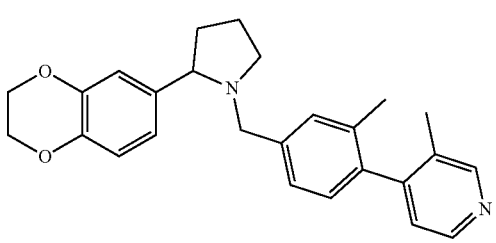 [SMILES: Cc1cnccc1-c1ccc(CN2CCCC2c2ccc3c(c2)OCCO3)cc1C]

To a stirred solution of intermediate 1 (0.127 g, 0.62 mmol) in MeCN (3 mL), TEA (0.29 mL, 2.08 mmol) and intermediate 49 (0.15 g, 0.69 mmol) were added at RT. The resulting reaction mixture was stirred at 50° C. for 12 h. It was diluted with water (10 mL) and was extracted with EtOAc (2×10 mL). The combined organic layer was dried over Na$_2$SO$_4$ and concentrated under vacuum. The resulting crude material was purified by prep HPLC (method A) to afford the title compound. Yield: 6.8% (19 mg, light brown gummy solid). ¹H NMR (400 MHz, DMSO-d₆): δ 8.51 (s, 1H), 8.43 (d, J=4.8 Hz, 1H), 7.21-7.11 (m, 3H), 7.02 (d, J=7.6 Hz, 1H), 6.94-6.88 (m, 2H), 6.82 (d, J=8.4 Hz, 1H), 4.22 (s, 4H), 3.73 (d, J=13.6 Hz, 1H), 3.38-3.28 (m, 1H), 3.06 (d, J=13.6 Hz, 1H), 3.05-2.95 (m, 1H), 2.21-2.11 (m, 2H), 1.99 (s, 6H), 1.83-1.73 (m, 2H), 1.58-1.49 (m, 1H). LCMS: (Method A) 401.2 (M+H), Rt. 1.27 min, 98.56% (Max). HPLC: (Method A) Rt. 2.33 min, 98.44% (Max), 98.17% (220 nm).

Example 71: 3-(4-((2-(2,3-dihydrobenzo[b] [1,4]dioxin-6-yl)pyrrolidin-1-yl)methyl)-2-methylphenyl)-2-methylpyridine

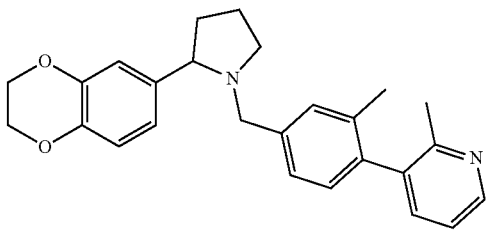 [SMILES: Cc1cc(CN2CCCC2c2ccc3c(c2)OCCO3)ccc1-c1cccnc1C]

To a stirred solution of intermediate 1 (127 mg, 0.62 mmol) in MeCN (3 mL), TEA (0.29 mL, 2.08 mmol) and intermediate 50 (150 mg, 0.69 mmol) were added at RT and the resulting mixture was stirred at 50° C. for 12 h. It was diluted with water (10 mL) and extracted with EtOAc (2×10 mL). The combined organic layer was dried over Na₂SO₄ and concentrated under vacuum. The resulting crude material was purified by flash chromatography (Eluent: 30% EtOAc in PE) to afford the title compound. Yield: 19% (52 mg, pale yellow gummy solid). ¹H NMR (400 MHz, DMSO-d₆): δ 8.45 (dd, J=5.0, 1.6 Hz, 1H), 7.47 (dd, J=6.4, 2.2 Hz, 1H), 7.29-7.25 (m, 1H), 7.18-7.13 (m, 2H), 7.47 (d, J=6.4 Hz, 1H), 6.93 (s, 1H), 6.91 (d, J=9.2 Hz, 1H), 6.89 (d, J=2.0 Hz, 1H), 4.22 (s, 4H), 3.72 (d, J=13.2 Hz, 1H), 3.26-3.29 (m, 1H), 3.01-3.07 (m, 2H), 2.17 (s, 3H), 2.13-2.16 (m, 2H), 1.97 (s, 3H), 1.77-1.71 (m, 2H), 1.55-1.52 (m, 1H). LCMS: (Method A) 401.2 (M+H), Rt. 1.28 min, 93.98% (Max). HPLC: (Method A) Rt. 2.29 min, 93.29% (Max).

Example 72: 4-(4-((2-(benzo[d] [1,3]dioxol-5-yl)pyrrolidin-1-yl)methyl)phenyl)-1-methyl-1H-pyrazole

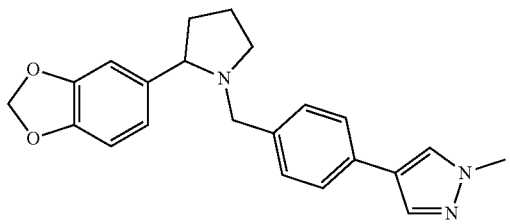 [SMILES: Cn1cc(-c2ccc(CN3CCCC3c3ccc4c(c3)OCO4)cc2)cn1]

To a stirred solution of intermediate 7 (60 mg, 0.73 mmol) in dry MeCN (6 mL), intermediate 3 (97 mg, 0.476 mmol) and TEA (0.12 mL, 1.46 mmol) were added at RT and the resulting mixture was stirred overnight at the same temperature. Then reaction mixture was concentrated under vacuum. To the resulting crude product, water was added and extracted with EtOAc (2×10 mL). The combined organic layer was washed with water (5 mL), brine (5 mL), dried over Na₂SO₄ and concentrated under vacuum. The resulting crude product was purified by Prep HPLC (Method B) to afford the title compound. Yield: 16% (18.23 mg, pale brown gummy solid). ¹H NMR (400 MHz, DMSO-d₆): δ 8.08 (s, 1H), 7.81 (s, 1H), 7.48 (d, J=8.0 Hz, 2H), 7.22 (d, J=8.0 Hz, 2H), 7.02 (s, 1H), 6.90 (d, J=1.2 Hz, 1H), 6.88 (d, J=2.4 Hz, 1H), 6.0 (s, 2H), 3.9 (s, 3H), 3.7 (d, J=13.2 Hz, 1H), 3.34-3.34 (m, 1H), 3.0 (d, J=13.2 Hz, 1H), 2.98-2.96 (m, 1H), 2.14-2.12 (m, 2H), 1.78-1.76 (m, 2H), 1.73-1.72 (m, 1H). LCMS: (Method A) 362.1 (M+H), Rt. 1.528 min, 97.90% (Max). HPLC: (Method A) Rt. 2.872 min, 99.19% (Max), 97.17% (220 nm).

Example 73 and Example 74: (S)-4-(4-((2-(2,3-dihydrobenzo[b] [1,4]dioxin-6-yl)pyrrolidin-1-yl)methyl)phenyl)thiomorpholin-3-one and (R)-4-(4-((2-(2,3-dihydrobenzo[b] [1,4]dioxin-6-yl)pyrrolidin-1-yl)methyl)phenyl)thiomorpholin-3-one

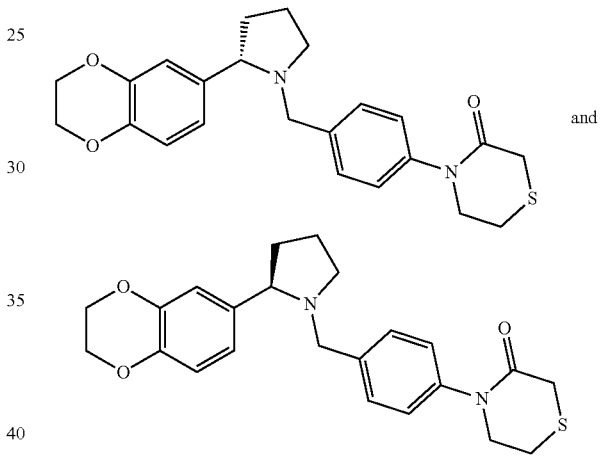

The enantiomers of Example 67 were separated by chiral preparative SFC (mobile phase: 0.5% Isopropylamine in Methanol; column: Chiralcel OJ-H (Method K)). The first fraction was collected to get Example 73 and the second fraction was collected to get Example 74.

Example 73: Yield: 30% (24 mg, pale brown solid). ¹H NMR (400 MHz, DMSO-d₆): δ 7.26 (d, J=8.0 Hz, 2H), 7.22 (d, J=8.4 Hz, 2H), 6.92-6.87 (m, 2H), 6.81 (d, J=8.4 Hz, 1H), 4.22 (s, 4H), 3.94 (t, J=5.6 Hz, 2H), 3.68 (d, J=13.2 Hz, 1H), 3.41 (s, 2H), 3.31-3.25 (m, 2H), 3.06-3.02 (m, 3H), 2.97 (t, J=7.6 Hz, 1H), 2.15-2.06 (m, 2H), 1.76-1.69 (m, 2H), 1.56-1.52 (m, 1H). LCMS: (Method A) 411.1 (M+H), Rt. 2.98 min, 99.54% (Max). HPLC: (Method A) Rt. 2.76 min, 99.02% (Max), 98.40% (200 nM). Chiral SFC: (Method K) Rt. 3.2 min, 100.00% (Max).

Example 74: Yield: 39% (33 mg, pale brown solid). ¹H NMR (400 MHz, DMSO-d₆): δ 7.26 (d, J=8.4 Hz, 2H), 7.22 (d, J=8.4 Hz, 2H), 6.92-6.80 (m, 3H), 4.22 (s, 4H), 3.95 (t, J=5.6 Hz, 2H), 3.68 (d, J=13.2 Hz, 1H), 3.41 (s, 2H), 3.31-3.25 (m, 2H), 3.06-3.02 (m, 3H), 2.97 (t, J=7.6 Hz, 1H), 2.15-2.06 (m, 2H), 1.76-1.69 (m, 2H), 1.56-1.52 (m, 1H). LCMS: (Method A) 411.1 (M+H), Rt. 2.08 min, 98.24% (Max). HPLC: (Method A) Rt. 2.77 min, 97.56% (Max), 96.89 (220 nM). Chiral SFC: (Method K) Rt. 3.53 min, 96.01% (Max).

Example 75: (S)-2-(4-((2-(2,3-dihydrobenzo[b][1,4]dioxin-6-yl)pyrrolidin-1-yl)methyl)phenyl)pyrimidine or (R)-2-(4-((2-(2,3-dihydrobenzo[b][1,4]dioxin-6-yl)pyrrolidin-1-yl)methyl)phenyl)pyrimidine

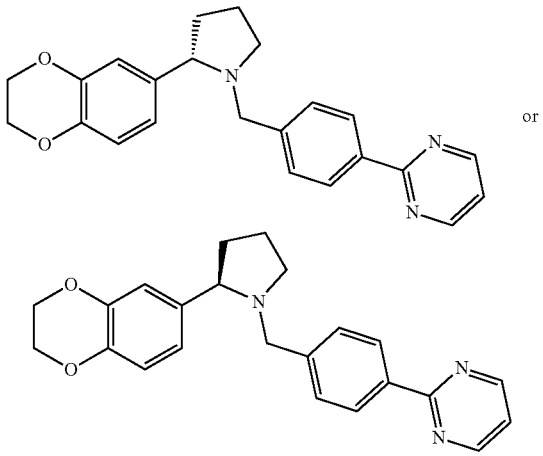

The enantiomers of Example 69 were separated by chiral preparative SFC (mobile phase: 40% IPA, column: Lux A1 (Method J)). The first fraction was collected to get Example 75 and the second fraction was collected to get the 2$^{nd}$ eluting compound.

Example 75: Yield: 15% (72.5 mg, pale yellow gummy solid). $^1$H NMR (400 MHz, DMSO-d$_6$): δ 8.90 (t, J=3.6 Hz, 2H), 8.34 (d, J=7.6 Hz, 2H), 7.45-7.40 (m, 3H), 6.94-6.82 (m, 2H), 6.83 (d, J=8.0 Hz, 1H), 4.22 (s, 4H), 3.77 (d, J=13.6 Hz, 1H), 3.33-3.30 (m, 1H), 3.11 (d, J=13.6 Hz, 1H), 2.99 (t, J=7.6 Hz, 1H), 2.20-2.10 (m, 2H), 1.85-1.71 (m, 2H), 1.64-1.58 (m, 1H). LCMS: (Method A) 374.2 (M+H), Rt. 1.501 min, 99.5% (Max). HPLC: (Method A) Rt. 2.850 min, 98.08% (Max), 97.04% (220 nm). Chiral SFC: (Method J) Rt. 3.96 min, 100.0% (Max).

2$^{nd}$ Eluting Compound: Yield: 14% (72.0 mg, pale yellow gummy solid). $^1$H NMR (400 MHz, DMSO-d$_6$): δ 8.90 (d, J=5.2 Hz, 2H), 8.34 (d, J=8.0 Hz, 2H), 7.45-7.40 (m, 3H), 6.95-6.91 (m, 2H), 6.84 (d, J=8.0 Hz, 1H), 4.22 (s, 4H), 3.78 (d, J=13.6 Hz, 1H), 3.30 (d, J=8.4 Hz, 1H), 3.11 (d, J=13.6 Hz, 1H), 3.00-2.96 (m, 1H), 2.18-2.08 (m, 2H), 1.79-1.71 (m, 2H), 1.69-1.54 (m, 1H). LCMS: (Method A) 374.1 (M+H), Rt. 1.501 min, 99.5% (Max). HPLC: (Method A) Rt. 2.849 min, 97.60% (Max), 97.56% (220 nm). Chiral SFC: (Method J) Rt. 5.31 min, 100.0% (Max).

Example 76: 5-(4-((2-(2,3-dihydrobenzo[b][1,4]dioxin-6-yl)pyrrolidin-1-yl)methyl)phenyl)-1,3,4-oxadiazol-2(3H)-one

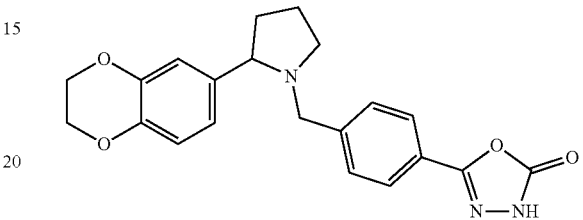

To a stirred solution of intermediate 1 (0.15 g, 0.73 mmol), TEA (0.26 mL, 1.83 mmol) in MeCN (2 mL), intermediate 52 (0.17 g, 0.81 mmol) was added at RT and the resulting mixture was stirred at the same temperature for 4 h. It was evaporated under vacuum. The residue was suspended in water (10 mL) and extracted with EtOAc (2×25 mL). The combined organic layer was dried over Na$_2$SO$_4$ and concentrated. The crude product was purified by flash chromatography (Eluent: 1-2% MeOH in DCM), followed by Prep HPLC (Method B) to get the title compound. Yield: 15% (41 mg, off white solid). $^1$H NMR (400 MHz, DMSO-d$_6$): δ 12.53 (s, 1H), 7.72 (d, J=8.0 Hz, 2H), 7.41 (d, J=8.4 Hz, 2H), 6.91-6.90 (m, 2H), 6.81 (d, J=8.4 Hz, 1H), 4.21 (s, 4H), 3.73 (d, J=13.6 Hz, 1H), 3.32-3.29 (m, 1H), 3.10 (d, J=13.6 Hz, 1H), 2.95-2.92 (m, 1H), 2.17-2.07 (m, 2H), 1.78-1.70 (m, 2H), 1.57-1.53 (m, 1H). LCMS: (Method A) 380.2 (M+H), Rt. 1.43 min, 99.29% (Max). HPLC: (Method A) Rt, 2.60 min, 99.63% (Max) 99.02% (220 nm).

The examples below were synthesized according to procedures described in the previous examples. These compounds and their tautomers, enantiomers, and salts are further preferred embodiments of the present invention.

| No | Structure | Optical rotation | Configuration specification | 1H NMR |
| --- | --- | --- | --- | --- |
| 125 | 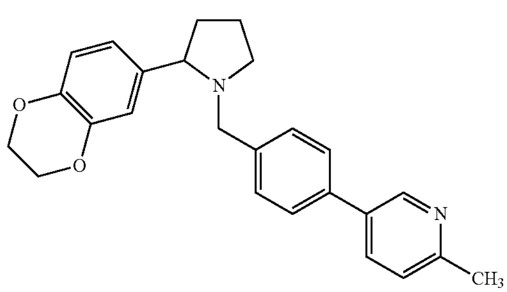 [SMILES: Cc1ccc(-c2ccc(CN3CCCC3c3ccc4c(c3)OCCO4)cc2)cn1] | | Racemic | 1H NMR (400 MHz, DMSO-d6): δ 8.74 (d, J = 2.0 Hz, 1H), 7.96-7.93 (m, 1H), 7.64 (d, J = 8.4 Hz, 2H), 7.37-7.32 (m, 3H), 6.95-6.82 (m, 3H), 4.23 (s, 4H), 3.74 (d, J = 13.6 Hz, 1H), 3.33-3.27 (m, 1H), 3.08 (d, J = 13.6 Hz, 1H), 3.01-2.94 (m, 1H), 2.55-2.47 (m, 3H), 2.20-2.07 (m, 2H), 1.81-1.71 (m, 2H), 1.61-1.50 (m, 1H). |

| No | Structure | Optical rotation | Configuration specification | 1H NMR |
|---|---|---|---|---|
| 126 | 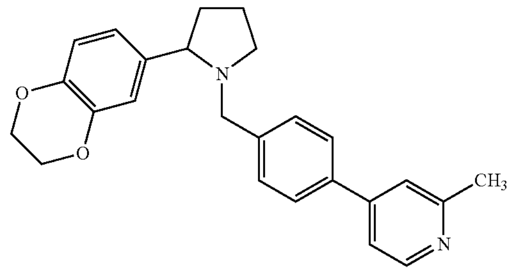 [SMILES: Cc1cc(-c2ccc(CN3CCCC3c3ccc4c(c3)OCCO4)cc2)ccn1] | | Racemic | 1H NMR (400 MHz, DMSO-d6): δ 8.40 (d, J = 5.2 Hz, 1H), 7.65 (d, J = 8.0 Hz, 2H), 7.56 (s, 1H), 7.48 (d, J = 5.6 Hz, 1H), 7.38 (d, J = 8.4 Hz, 2H), 6.93-6.86 (m, 2H), 6.78 (d, J = 8.4 Hz, 1H), 4.21 (s, 4H), 3.81 (d, J = 13.2 Hz, 1H), 3.32-3.24 (m, 1H), 3.11 (d, J = 12.8 Hz, 1H), 3.05 (t, J = 7.2 Hz, 1H), 2.57 (s, 3H), 2.27-2.11 (m, 2H), 1.89-1.62 (m, 3H). |
| 127 | 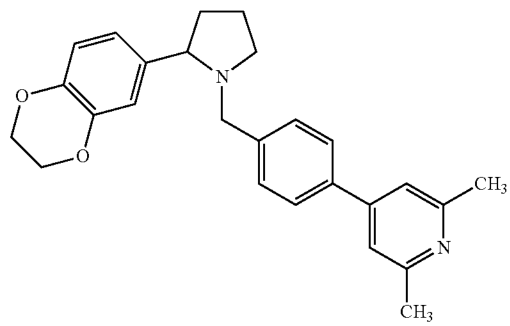 [SMILES: Cc1cc(-c2ccc(CN3CCCC3c3ccc4c(c3)OCCO4)cc2)cc(C)n1] | | Racemic | 1H NMR (400 MHz, DMSO-d6): δ 7.70 (d, J = 8.4 Hz, 2H), 7.38-7.34 (m, 4H), 6.94-6.89 (m, 2H), 6.83 (d, J = 8.0 Hz, 1H), 4.23 (s, 4H), 3.75 (d, J = 13.2 Hz, 1H), 3.33-3.28 (m, 1H), 3.10 (d, J = 13.6 Hz, 1H), 2.97 (t, J = 5.6 Hz, 1H), (s, 6H), 2.119-2.10 (m, 2H), 1.82-1.68 (m, 2H), 1.62-1.51 (m, 1H). |
| 128 | 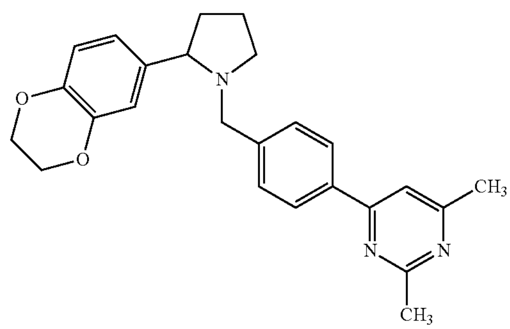 [SMILES: Cc1cc(-c2ccc(CN3CCCC3c3ccc4c(c3)OCCO4)cc2)nc(C)n1] | | Racemic | 1H NMR (400 MHz, DMSO-d6): δ 8.10 (d, J = 8.0 Hz, 2H), 7.74 (s, 1H), 7.40 (d, J = 8.0 Hz, 2H), 6.95-6.89 (m, 2H), 6.84 (d, J = 8.4 Hz, 1H), 4.22 (bs, 4H), 3.78-3.75 (m, 1H), 3.32-3.28 (m, 1H), 3.14-3.10 (m, 1H), 2.99-2.95 (m, 1H), 2.62 (s, 3H), 2.54 (s, 3H), 2.18-2.11 (m, 2H), 1.84-1.75 (m, 2H), 1.73-1.54 (m, 1H). |
| 135 | 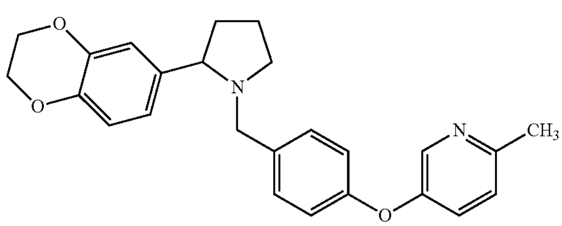 [SMILES: Cc1ccc(Oc2ccc(CN3CCCC3c3ccc4c(c3)OCCO4)cc2)cn1] | | Racemic | 1H NMR (400 MHz, DMSO-d6): δ 8.21 (d, J = 2.4 Hz, 1H), 7.33-7.23 (s, 4H), 6.96-6.78 (m, 5H), 4.21 (s, 4H), 3.65 (d, J = 13.2 Hz, 1H), 3.30-3.22 (m, 1H), 3.03-2.90 (m, 2H), 2.44 (s, 3H), 2.16-2.06 (m, 2H), 1.79-1.64 (m, 2H), 1.58-1.49 (m, 1H). |
| 136 | 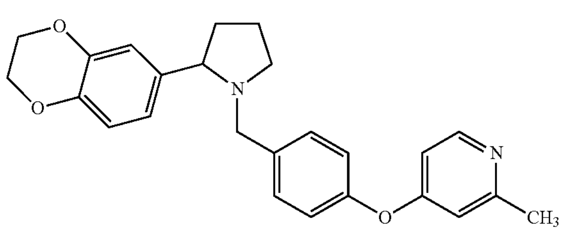 [SMILES: Cc1cc(Oc2ccc(CN3CCCC3c3ccc4c(c3)OCCO4)cc2)ccn1] | | Racemic | 1H NMR (400 MHz, DMSO-d6): δ 8.30 (d, J = 6.0 Hz, 1H), 7.34 (d, J = 8.4 Hz, 2H), 7.09 (d, J = 8.4 Hz, 2H), 6.93-6.88 (m, 2H), 6.82 (d, J = 8.4 Hz, 1H), 6.76 (s, 1H), 6.70-6.68 (m, 1H), 4.22 (s, 4H), 3.70 (d, J = 13.2 Hz, 1H), 3.31-3.23 (m, 1H), 3.08 (d, J = 13.2 Hz, 1H), 2.99 (t, J = 7.6 Hz, 1H), 2.40 (s, 3H), 2.19-2.08 (m, 2H), 1.81-1.70 (m, 2H), 1.61-1.50 (m, 1H). |

| No | Structure | Optical rotation | Configuration specification | 1H NMR |
|---|---|---|---|---|
| 137 | 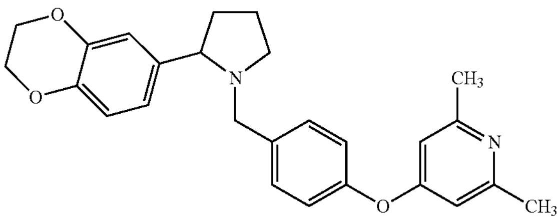 [SMILES: Cc1cc(Oc2ccc(CN3CCCC3c3ccc4c(c3)OCCO4)cc2)cc(C)n1] | | Racemic | 1H NMR (400 MHz, DMSO-d6): δ 7.32 (d, J = 8.4 Hz, 2H), 7.05 (d, J = 8.0 Hz, 2H), 6.92-6.87 (m, 2H), 6.81 (d, 8.4 Hz, 1H), 6.55 (s, 2H), 4.21 (s, 4H), 3.69 (d, J = 13.2 Hz, 1H), 3.34-3.27 (m, 1H), 3.05 (d, J = 13.6 Hz, 1H), 2.97 (t, J = 7.6 Hz, 1H), 2.34 (s, 6H), 2.18-2.08 (m, 2H), 1.82-1.65 (m, 2H), 1.61-1.50 (d, J = 8.0 Hz, 1H). |
| 138 | 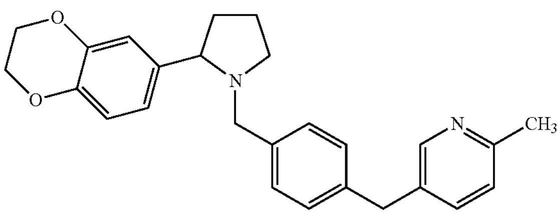 [SMILES: Cc1ccc(Cc2ccc(CN3CCCC3c3ccc4c(c3)OCCO4)cc2)cn1] | | Racemic | 1H NMR (400 MHz, DMSO-d6): δ 8.27 (s, 1H), 7.56-7.53 (m, 1H), 7.23-7.13 (m, 5H), 6.94 (d, J = 1.6 Hz, 1H), 6.89-6.86 (m, 1H), 6.80 (d, J = 8.4 Hz, 1H), 4.24 (s, 4H), 3.96 s, 2H), 3.76 (d, J = 12.8 Hz, 1H), 3.24 (t, J = 8.0 Hz, 1H), 3.05-3.00 (m, 2H), 2.50 (s, 3H), 2.25-2.12 (m, 2H), 1.90-1.65 (m, 3H). |
| 139 | 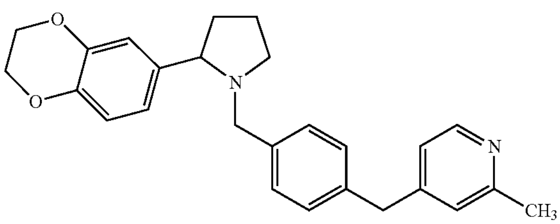 [SMILES: Cc1cc(Cc2ccc(CN3CCCC3c3ccc4c(c3)OCCO4)cc2)ccn1] | | Racemic | 1H NMR (400 MHz, DMSO-d6): δ 8.31 (d, J = 5.2 Hz, 1H), 7.16 (br s, 4H), 7.09 (s, 1H), 7.01 (d, J = 5.2 Hz, 1H), 6.90 (d, J = 1.6 Hz, 1H), 6.87-6.84 (m, 1H), 6.81-6.78 (m, 1H), 4.20 (s, 4H), 3.87 (s, 2H), 3.65 (d, J = 13.6 Hz, 1H), 3.27-3.22 (m, 1H), 2.99-2.89 (m, 2H), 2.39 (s, 3H), 2.14-2.03 (m, 2H), 1.78-1.61 (m, 2H), 1.57-1.48 (m, 1H). |
| 140 | 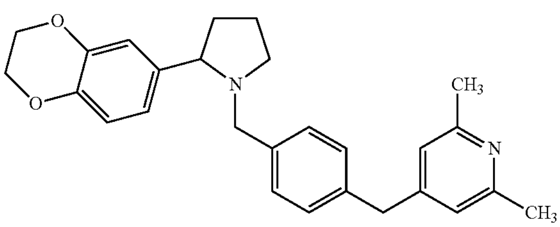 [SMILES: Cc1cc(Cc2ccc(CN3CCCC3c3ccc4c(c3)OCCO4)cc2)cc(C)n1] | | Racemic | 1H NMR (400 MHz, DMSO-d6): δ 7.16 (s, 4H), 6.92-6.78 (m, 5H), 4.21 (s, 4H), 3.81 (s, 2H), 3.64 (d, J = 13.2 Hz, 1H), 3.30-3.22 (m, 1H), 2.98-2.88 (m, 2H), 2.35 (s, 6H), 2.11-2.02 (m, 2H), 1.77-1.61 (m, 2H), 1.55-1.46 (m, 1H). |
| 141 | 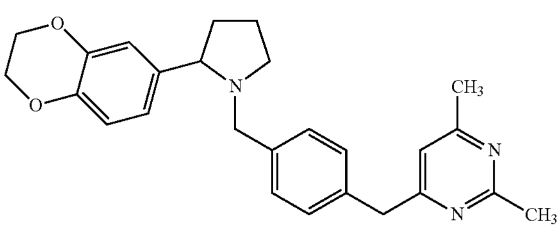 [SMILES: Cc1cc(Cc2ccc(CN3CCCC3c3ccc4c(c3)OCCO4)cc2)nc(C)n1] | | Racemic | 1H NMR (400 MHz, DMSO-d6): δ 7.32 (d, J = 8.4 Hz, 2H), 7.11 (d, J = 8.4 Hz, 2H), 6.94-6.88 (m, 2H), 6.83 (d, J = 8.4 Hz, 1H), 6.67 (s, 1H), 4.22 (br s, 4H), 3.71 (d, J = 13.2 Hz, 1H), 3.32-3.28 (m, 1H), 3.05-2.96 (m, 2H), 2.40 (s, 3H), 2.37 (s, 3H), 2.17-2.08 (m, 2H), 1.78-1.71 (m, 2H), 1.61-1.51 (m, 1H). |
| 144 | 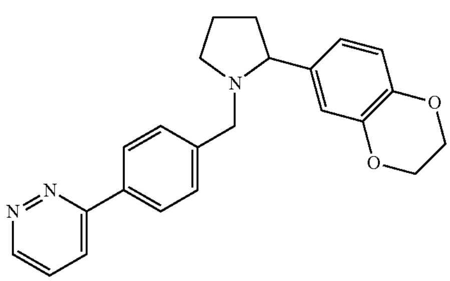 [SMILES: c1cnnc(-c2ccc(CN3CCCC3c3ccc4c(c3)OCCO4)cc2)c1] | | Racemic | 1H NMR (400 MHz, DMSO-d6): δ 9.20 (dd, J = 1.2, 5.6 Hz, 1H), 8.20 (dd, J = 1.6, 8.8 Hz, 1H), 8.10 (d, J = 8.0 Hz, 2H), 7.78 (dd, J = 4.8, 8.8 Hz, 1H), 7.44 (d, J = 8.4 Hz, 2H), 6.96-6.91 (m, 2H), 6.84 (d, J = 8.0 Hz, 1H), 4.23 (s, 4H), 3.8 (d, J = 13.6 Hz, 1H), 3.34-3.29 (m, 1H), 3.13 (d, J = 13.6 Hz, 1H), 3.03-2.97 (m, 1H), 2.20-2.07 (m, 2H), 1.84-1.71 (m, 2H), 1.64-1.52 (m, 1H). |

| No | Structure | Optical rotation | Configuration specification | 1H NMR |
|---|---|---|---|---|
| 145 | 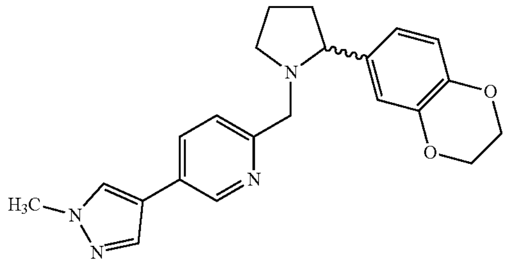 [SMILES: Cn1cc(-c2ccc(CN3CCCC3c3ccc4c(c3)OCCO4)nc2)cn1] | | Second elution on YMC Cellulose-SB (250 X 4.6) mm, 5 um, 20 mM, 0.5% isopropylamine in isopropylalcohol, Rt 3.75, The enantiomeric purity is 99.73%. | 1H NMR (400 MHz, DMSO-d6): δ 8.68 (s, 1H), 8.20 (s, 1H), 7.92-7.88 (m, 2H), 7.34 (d, J = 8.0 Hz, 1H), 6.92 (s, 1H), 6.88 (d, J = 8.0 Hz, 1H), 6.81 (d, J = 8.0 Hz, 1H), 4.21 (s, 4H), 3.88 (s, 3H), 3.75 (d, J = 14.0 Hz, 1H), 3.39-3.31 (m, 1H), 3.22 (d, J = 13.60 Hz, 1H), 3.05-3.01 (m, 1H), 2.33-2.23 (m, 1H), 2.21-2.10 (m, 1H), 1.80-1.72 (m, 2H), 1.58-1.54 (m, 1H). |
| 146 | 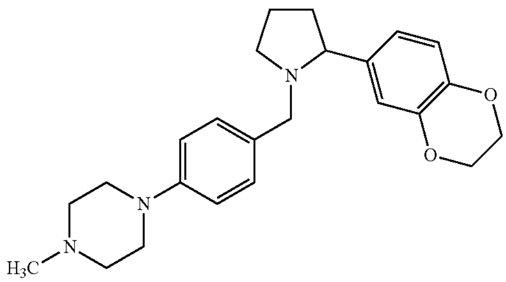 [SMILES: CN1CCN(c2ccc(CN3CCCC3c3ccc4c(c3)OCCO4)cc2)CC1] | | Racemic | 1H NMR (400 MHz, DMSO-d6): δ 7.05 (d, J = 8.4 Hz, 2H), 6.90-6.79 (m, 5H), 4.21 (s, 4H), 3.59 (d, J = 12.8 Hz, 1H), 3.24-3.18 (m, 1H), 3.08-3.06 (m, 4H), 2.90-2.87 (m, 2H), 2.46-2.38 (m, 4H), 2.20 (s, 3H), 2.10-2.05 (m, 2H), 1.69-1.67 (m, 2H), 1.52-1.48 (m, 1H). |
| 147 | 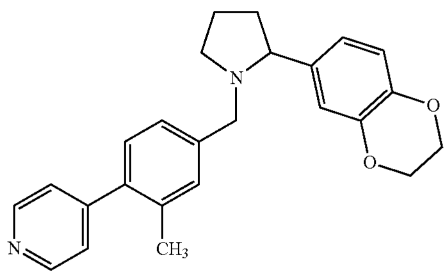 [SMILES: Cc1cc(CN2CCCC2c2ccc3c(c2)OCCO3)ccc1-c1ccncc1] | | Racemic | 1H NMR (400 MHz, DMSO-d6): δ 8.58 (d, J = 6.0 Hz, 2H), 7.42 (d, J = 6.0 Hz, 2H), 7.22-7.16 (m, 3H), 6.96 (d, J = 1.6 Hz, 1H), 6.91-6.88 (m, 1H), 6.81 (d, J = 8.4 Hz, 1H), 4.24 (s, 4H), 3.80 (d, J = 13.2 Hz, 1H), 3.27 (t, J = 8.0 Hz, 1H), 3.13-3.07 (m, 2H), 2.28-2.13 (m, 5H), 1.92-1.67 (m, 3H). |
| 148 | 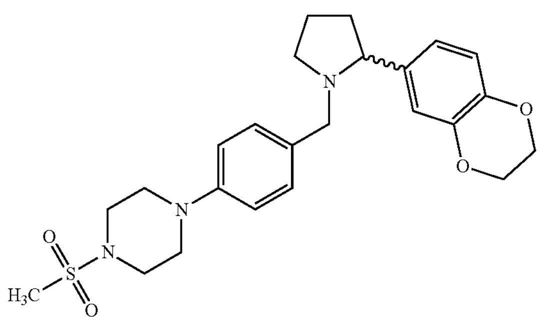 [SMILES: CS(=O)(=O)N1CCN(c2ccc(CN3CCCC3c3ccc4c(c3)OCCO4)cc2)CC1] | | Second elution on Lux A1 (250 X 4.6) mm, 5 um, 0.5% isopropylamine in isopropylalcohol, Rt 3.61. Enantiomeric purity is 99.19% | 1H NMR (400 MHz, DMSO-d6): δ 7.09 (d, J = 8.4 Hz, 2H), 6.92-6.85 (m, 4H), 6.81 (d, J = 8.4 Hz, 1H), 4.22 (s, 4H), 3.61 (d, J = 13.6 Hz, 1H), 3.26-3.17 (m, 9H), 2.92-2.87 (m, 5H), 2.11-2.04 (m, 2H), 1.73-1.62 (m, 2H), 1.53-1.48 (m, 1H). |
| 149 | 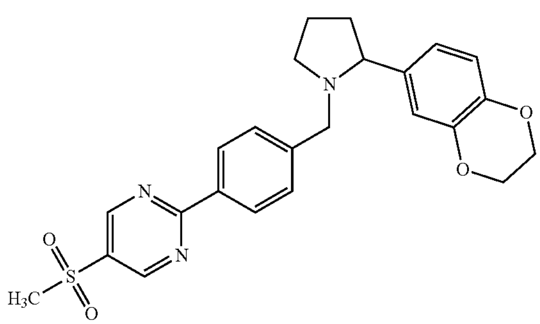 [SMILES: CS(=O)(=O)c1cnc(-c2ccc(CN3CCCC3c3ccc4c(c3)OCCO4)cc2)nc1] | | Racemic | 1H NMR (400 MHz, DMSO-d6): δ 9.33 (s, 2H), 8.42 (d, J = 8.0 Hz, 2H), 7.48 (d, J = 7.6 Hz, 2H), 6.95-6.90 (m, 2H), 6.83 (d, J = 8.0 Hz, 1H), 4.22 (s, 4H), 3.79 (d, J = 13.6 Hz, 1H), 3.44 (s, 3H), 3.35-3.30 (m, 1H), 3.16 (d, J = 14.0 Hz, 1H), 3.00 (t, J = 8.0 Hz, 1H), 2.11-2.21 (m, 2H), 1.84-1.71 (m, 2H), 1.63-1.55 (m, 1H). |

| No | Structure | Optical rotation | Configuration specification | 1H NMR |
|---|---|---|---|---|
| 150 | 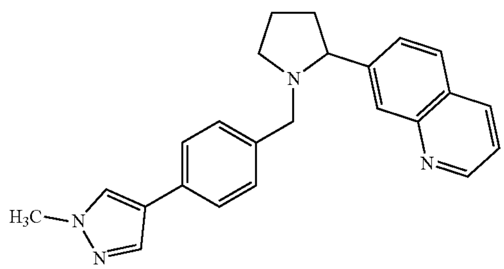 [SMILES: Cn1cc(-c2ccc(CN3CCCC3c3ccc4cccnc4c3)cc2)cn1] | | Racemic | 1H NMR (400 MHz, DMSO-d6): δ 8.89 (dd, J = 1.6, 4.4 Hz, 1H), 8.35 (d, J = 7.6 Hz, 1H), 8.08-7.99 (m, 3H), 7.76 (s, 1H), 7.78-7.75 (m, 1H), 7.53-7.47 (m, 3H), 7.25 (d, J = 8.0 Hz, 2H), 3.86 (s, 3H), 3.75-3.64 (m, 2H), 3.14 (d, J = 13.2 Hz, 1H), 3.06-3.03 (m, 1H), 2.32-2.25 (m, 2H), 1.90-1.81 (m, 2H), 1.79-1.68 (m, 1H). |
| 151 | 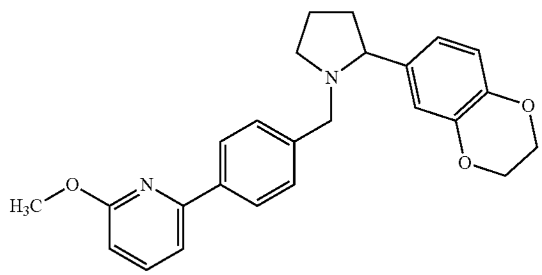 [SMILES: COc1cccc(-c2ccc(CN3CCCC3c3ccc4c(c3)OCCO4)cc2)n1] | | Racemic | 1H NMR (400 MHz, DMSO-d6): δ 8.04 (d, J = 8.0 Hz, 2H), 7.77 (t, J = 8.0 Hz, 1H), 7.53 (d, J = 7.2 Hz, 1H), 7.36 (d, J = 8.0 Hz, 2H), 6.95-6.90 (m, 2H), 6.83 (d, J = 8.0 Hz, 1H), 6.76 (d, J = 8.4 Hz, 1H), 4.23 (s, 4H), 3.95 (s, 3H), 3.75 (d, J = 13.6 Hz, 1H), 3.31-3.25 (m, 1H), 3.09 (d, J = 13.6 Hz, 1H), 2.98 (t, J = 7.6 Hz, 1H), 2.19-2.09 (m, 2H), 1.82-1.68 (m, 2H), 1.59-1.51 (m, 1H). |
| 152 | 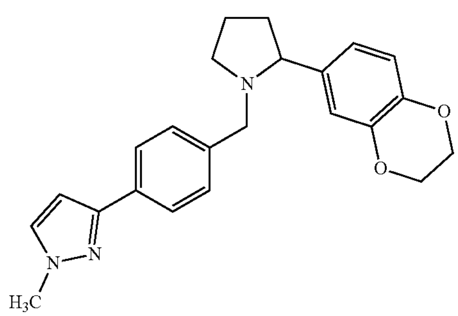 [SMILES: Cn1ccc(-c2ccc(CN3CCCC3c3ccc4c(c3)OCCO4)cc2)n1] | | Racemic | 1H NMR (400 MHz, DMSO-d6): δ 7.72-7.69 (m, 3H), 7.25 (d, J = 8.0 Hz, 2H), 6.94-6.89 (m, 2H), 6.83 (d, J = 8.4 Hz, 1H), 6.64 (d, J = 2.4 Hz, 1H), 4.23 (br s, 4H), 3.87 (s, 3H), 3.71 (d, J = 13.2 Hz, 1H), 3.28 (t, J = 8.0 Hz, 1H), 3.04-2.94 (m, 2H), 2.16-2.08 (m, 2H), 1.80-1.64 (m, 2H), 1.61-1.51 (m, 1H). |
| 153 | 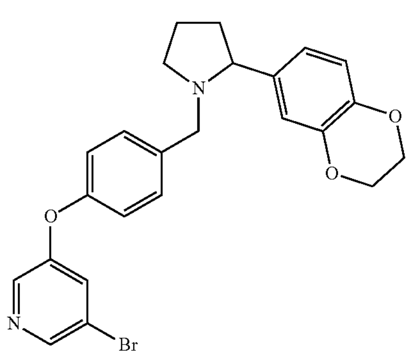 [SMILES: Brc1cncc(Oc2ccc(CN3CCCC3c3ccc4c(c3)OCCO4)cc2)c1] | | Racemic | 1H NMR (400 MHz, DMSO-d6): δ 8.49 (s, 1H), 8.36 (d, J = 1.6 Hz, 1H), 7.68 (d, J = 2.0 Hz, 1H), 7.31 (d, J = 8.0 Hz, 2H), 7.08 (d, J = 8.4 Hz, 2H), 6.92-6.87 (m, 2H), 6.82 (d, J = 8.4 Hz, 1H), 4.22 (s, 4H), 3.69 (d, J = 13.2 Hz, 1H), 3.34-3.26 (m, 1H), 3.05 (d, J = 13.2 Hz, 1H), 2.97 (t, J = 8.4 Hz, 1H), 2.17-2.06 (m, 2H), 1.82-1.67 (m, 2H), 1.61-1.52 (m, 1H). |

| No | Structure | Optical rotation | Configuration specification | 1H NMR |
|---|---|---|---|---|
| 154 | 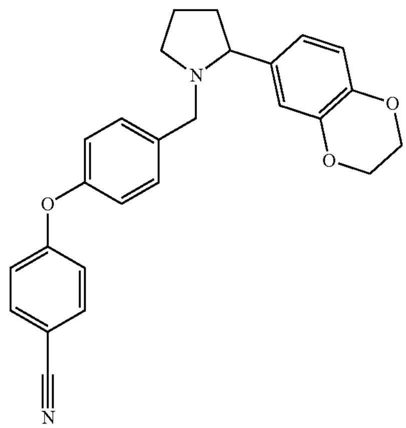 [SMILES: N#Cc1ccc(Oc2ccc(CN3CCCC3c3ccc4c(c3)OCCO4)cc2)cc1] | | Racemic | 1H NMR (400 MHz, DMSO-d6): δ 7.83 (d, J = 8.4 Hz, 2H), 7.34 (d, J = 8.0 Hz, 2H), 7.10-7.05 (m, 4H), 6.92-6.980 (m, 3H), 4.22 (s, 4H), 3.70 (d, J = 13.2 Hz, 1H), 3.32-3.27 (m, 1H), 3.08 (d, J = 13.2 Hz, 1H), 2.98 (t, J = 7.2 Hz, 1H), 2.18-2.07 (m, 2H), 1.83-1.67 (m, 2H), 1.61-1.51 (m, 1H). |
| 155 | 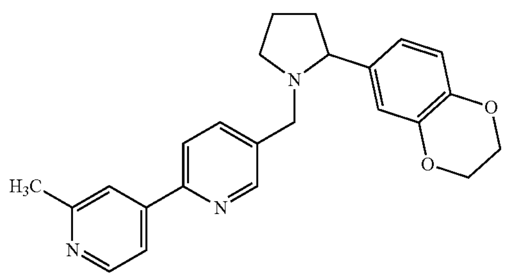 [SMILES: Cc1cc(-c2ccc(CN3CCCC3c3ccc4c(c3)OCCO4)cn2)ccn1] | | Racemic | 1H NMR (400 MHz, DMSO-d6): δ 8.57-8.54 (m, 2H), 8.03 (d, J = 8.0 Hz, 1H), 7.91 (s, 1H), 7.83-7.77 (m, 2H), 6.93-6.89 (m, 2H), 6.83 (d, J = 8.0 Hz, 1H), 4.22 (br s, 4H), 3.76-3.72 (m, 1H), 3.32-3.28 (m, 1H), 3.23-3.20 (m, 1H), 2.99-2.95 (m, 1H), 2.56 (s, 3H), 2.25-2.11 (m, 2H), 1.84-1.71 (m, 2H), 1.63-1.54 (m, 1H). |
| 156 | 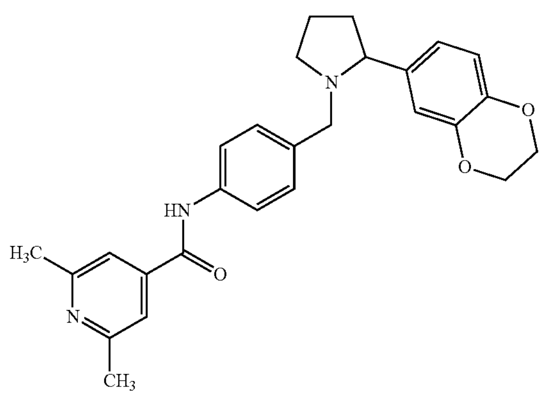 [SMILES: Cc1cc(C(=O)Nc2ccc(CN3CCCC3c3ccc4c(c3)OCCO4)cc2)cc(C)n1] | | Racemic | 1H NMR (400 MHz, DMSO-d6): δ 10.36 (s, 1H), 7.69 (d, J = 8.0 Hz, 2H), 7.51 (s, 2H), 7.24 (d, J = 8.4 Hz, 2H), 6.93-6.82 (m, 3H), 4.23 (br s, 4H), 3.69 (d, J = 13.2 Hz, 1H), 3.29-3.24 (s, 1H), 3.01-2.91 (m, 2H), 2.53 (s, 6H), 2.16-2.07 (m, 2H), 1.81-1.65 (m, 2H), 1.57-1.50 (m, 1H). |
| 157 | 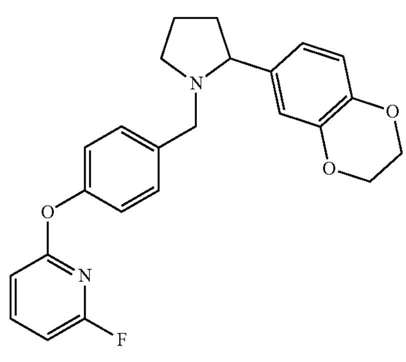 [SMILES: Fc1cccc(Oc2ccc(CN3CCCC3c3ccc4c(c3)OCCO4)cc2)n1] | | Racemic | 1H NMR (400 MHz, DMSO-d6): δ 8.04-7.98 (m, 1H), 7.31 (d, J = 8.4 Hz, 2H), 7.11 (d, J = 8.4 Hz, 2H), 6.94-6.81 (m, 5H), 4.23 (s, 4H), 3.71 (d, J = 13.6 Hz, 1H), 3.31-3.25 (m, 1H), 3.07 (d, J = 13.2 Hz, 1H), 3.03-2.97 (m, 1H), 2.18-2.08 (m, 2H), 1.84-1.67 (m, 2H), 1.61 (m, 1H). |

| No | Structure | Optical rotation | Configuration specification | 1H NMR |
|----|-----------|------------------|------------------------------|--------|
| 158 | 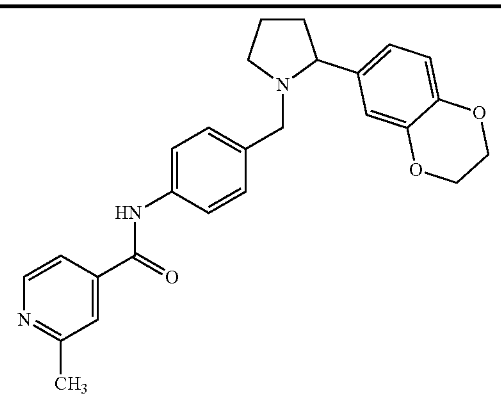 | | Racemic | 1H NMR (400 MHz, DMSO-d6): δ 10.41 (s, 1H), 8.62 (d, J = 5.2 Hz, 1H), 7.71-7.63 (m, 4H), 7.23 (d, J = 8.0 Hz, 2H), 6.92-6.81 (m, 3H), 4.22 (s, 4H), 3.68 (d, J = 13.2 Hz, 1H), 3.33-3.23 (m, 1H), 3.00-2.91 (m, 2H), 2.57 (s, 3H), 2.18-2.05 (m, 2H), 1.80-1.65 (m, 2H), 1.59-1.51 (m, 1H). |
| 159 | 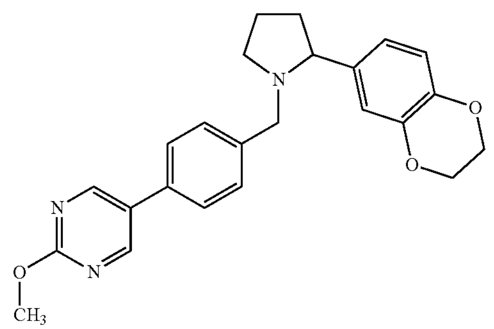 [SMILES: COc1ncc(-c2ccc(CN3CCCC3c3ccc4c(c3)OCCO4)cc2)cn1] | | Racemic | 1H NMR (400 MHz, DMSO-d6): δ 8.91 (s, 2H), 7.66 (d, J = 8.0 Hz, 2H), 7.36 (d, J = 8.0 Hz, 2H), 6.94-6.88 (m, 2H), 6.82 (d, J = 8.4 Hz, 1H), 4.22 (s, 4H), 3.96 (s, 3H), 3.73 (d, J = 13.2 Hz, 1H), 3.33-3.28 (m, 1H), 3.08 (d, J = 13.2 Hz, 1H), 2.96 (t, J = 6.0 Hz, 1H), 2.19-2.06 (m, 2H), 1.80-1.65 (m, 2H), 1.61-1.50 (m, 1H). |
| 160 | 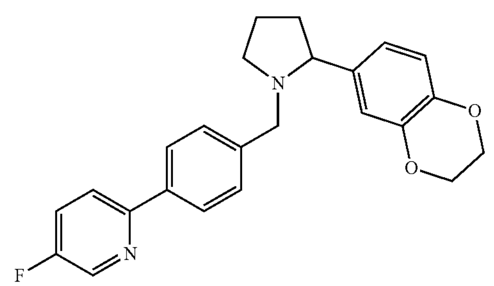 [SMILES: Fc1ccc(-c2ccc(CN3CCCC3c3ccc4c(c3)OCCO4)cc2)nc1] | | Racemic | 1H NMR (400 MHz, DMSO-d6): δ 8.64 (d, J = 2.8 Hz, 1H), 8.05-7.97 (m, 3H), 7.84-7.79 (m, 1H), 7.37 (d, J = 8.4 Hz, 2H), 6.95-6.90 (m, 2H), 6.83 (d, J = 8.0 Hz, 1H), 4.23 (s, 4H), 3.75 (d, J = 13.2 Hz, 1H), 3.32-3.27 (m, 1H), 3.09 (d, J = 13.6 Hz, 1H), 3.01-2.94 (m, 1H), 2.20-2.10 (m, 2H), 1.82-1.67 (m, 2H), 1.62-1.51 (m, 1H). |
| 161 | 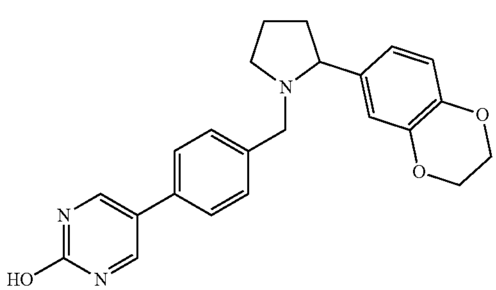 [SMILES: Oc1ncc(-c2ccc(CN3CCCC3c3ccc4c(c3)OCCO4)cc2)cn1] | | Racemic | 1H NMR (400 MHz, DMSO-d6): δ 12.19 (s, 1H), 8.59 (s, 2H), 7.55 (d, J = 8.0 Hz, 2H), 7.30 (d, J = 7.6 Hz, 2H), 6.93-6.81 (m, 3H), 4.22 (s, 4H), 3.71 (d, J = 13.2 Hz, 1H), 3.32-3.27 (m, 1H), 3.05 (d, J = 13.6 Hz, 1H), 2.98-2.92 (m, 1H), 2.17-2.08 (m, 2H), 1.82-1.68 (m, 2H), 1.59-1.51 (m, 1H). |

Example B01: Human O-GlcNAcase Enzyme Inhibition Assay

5 μl of the appropriate concentration of a solution of inhibitor in McIlvaine's Buffer (pH 6.5) in 2% DMSO (for a dose response curve calculation) is added into each well of a 384-well plate (Greiner, 781900). Then, 20 nM of His-Tagged hOGA and 10 μM of FL-GlcNAc (Fluorescein mono-beta-D-(2-deoxy-2-N-acetyl) glucopyranoside; Marker Gene Technologies Inc, M1485) were added to the 384-well plate for a final volume of 20 μl. After incubation for 60 min at room temperature, the reaction was terminated by the addition of 10 μL of stop buffer (200 mM glycine, pH 10.75). The level of fluorescence ($\lambda_{exc}$ 485 nm; ($\lambda_{emm}$ 520 nm) was read on a PHERAstar machine. The amount of fluorescence measured was plotted against the concentration of inhibitor to produce a sigmoidal dose response curve to calculate an $IC_{50}$. All individual data was corrected by subtraction of the background (Thiamet 3 uM=100% inhibition) whilst 0.5% DMSO was considered as the control value (no inhibition).

Example B02: Pharmacodynamic Model: Total Protein O-GlcNAcylation Immunoassay (RL2 mAb, Meso Scale Electrochemiluminescence (ECL) Assay)

The test compound was administered orally to C57BL/6J mice. At defined time intervals after compound administration, typically a time ranging between 2 and 48 hours, preferably between 4 and 24 hours, mice were sacrificed by decapitation for blood collection and forebrain dissection. Right brain hemispheres were placed in 2 ml Precellys tubes, snap frozen in dry ice and stored at -80° C. Left hemispheres were placed in 2 ml Eppendorf tubes, snap frozen in dry ice and stored at -80° C. until further processing. Blood samples were collected in Sarstedt tubes containing 35 IU of Heparin and kept at 4° C. After centrifugation for 10 min at 3800×g, 4° C., 50 μL of plasma from each sample was transferred to a 1.5 ml Eppendorf tube and stored at −80° C.

For the preparation of soluble brain protein for the immunoassay the hemispheres were homogenized in ice-cold Cytobuster reagent (71009—Merck Millipore) buffer with protease inhibitor cocktail. After centrifugation for 15 min at 17000×g at 4° C. the supernatants were transferred into polycarbonate tubes (1 ml). The supernatants were cleared by centrifugation for 1 h. at 100000×g, 4° C., and the protein concentrations were determined by using the BCA kit (23227—Pierce, Rockford, IL) according to the manufacturer's instructions.

Total Protein O-GlcNAcylation Immunoassay:

Samples were randomised and 120 μg/ml (25 μl/well) of soluble brain protein was directly coated on a Multi-array 96-well high bind plate (L15XB-3 High bind—Meso Scale Discovery) overnight at 4° C. After washing (3× with PBS-T buffer), the plate was blocked with MSD blocker A solution for 1 h. at room temperature (RT) under agitation. After washing (3× with PBS-T buffer), the plate was incubated with 0.1 μg/ml of a mouse monoclonal antibody directed against O-GlcNAc moieties (RL2; MA1-072—Thermo Scientific) for 1 h. at RT under agitation. For the ECL assay, after washing (3× with PBS-T buffer), 1 μg/ml of a SULFO-TAG™ labeled anti-mouse secondary antibody (Meso Scale Discovery) was added and the plate was incubated for 1 h. at RT under agitation and protected from light. After washing (3× with PBS-T buffer), 150 μl/well of 1× Read Buffer T was added to the plates before reading on a Sector Imager 6000 (Meso Scale Discovery).

Example B03: Pharmaceutical Preparations (A) Injection vials: A solution of 100 g of an active ingredient according to the invention and 5 g of disodium hydrogen phosphate in 3 l of bi-distilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of $NaH_2PO_4 \cdot 2 H_2O$, 28.48 g of $Na_2HPO_4 \cdot 2 H_2O$ and 0.1 g of benzalkonium chloride in 940 ml of bi-distilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated tablets: Tablets were pressed analogously to EXAMPLE E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bi-distilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

Example B04: Protein Binding in Mice Plasma Using Rapid Equilibrium Dialysis Materials
CD1 Mice Plasma: pooled male, K2-EDTA (MSEPLEDTA2, Bioreclammation, USA
Phosphate Buffered Saline (1×PBS), pH 7.4, 100 mM (Sigma, Cat No. P4417)
RED inserts (Pierce, Cat No. 9006, 8 kDa MWCO)
Sample Analysis: LC-MS/MS
Methods
Preparation of DMSO Stock Solution
From 20 mM DMSO stock solutions of reference and test compounds, 1 mM DMSO intermediate working solutions are prepared. From 1 mM intermediate working solutions, 100 μM DMSO working solutions are prepared.
Sample Preparation Procedure:
Selected plasma is brought from −20° C. to 37° C. using water bath before its use. Test solution is prepared by adding the DMSO working solution of the reference or test compound (2 μL; 100 μM) to the selected plasma (198 μL). Spiked plasma (200 μl) is transferred to sample compartment of RED insert placed in the teflon plate. 350 μl of 1×PBS is added in the buffer compartment of RED insert. The teflon plate is covered with sealing mat and agitated at 37° C. for 5 hours at 500 RPM in a Thermomixer. After incubation time, an aliquot of plasma (50 μl) from sample compartment is mixed with blank 1×PBS (50 μl). Similarly, an aliquot of buffer (50 μl) from buffer compartment is mixed with blank plasma (50 μl). Quenching solution (200 μL, acetonitrile containing internal standard tolbutamide (0.5 μg/mL)) is added and the resulting solutions are mixed using a vortex mixer and centrifuged (Eppendorf 5415, 13792 g).

Supernatants are analyzed using a Mass Spectrometer. The sample (supernatant fraction, 5 µL) is injected into the LC-MS/MS instrument.

Chromatographic Conditions:
LC-MS/MS: API 4000 LC-MS/MS
Software: Analyst Version 1.6.1
Column Phenomenex Synergy 30*4.6*5p
Column Oven: 40° C.
Mode: ESI Positive
Injection volume: 5 µl
Flow Rate: 1000 µL/mL
Buffer: 0.1% Formic acid in Water
Method: Isocratic Method/Gradient
Composition: A) 0.1% Formic acid in Water
B) 0.1% Formic acid in Methanol

| Time (Sec) | Flow (µL) | Mobile Phase A | Mobile Phase B |
|---|---|---|---|
| 0.01 | 1000 | 10 | 90 |
| 0.4 | 1000 | 10 | 90 |
| 0.8 | 1000 | 90 | 10 |
| 1.5 | 1000 | 90 | 10 |
| 1.8 | 1000 | 10 | 90 |
| 2.5 | 1000 | 10 | 90 |

Results Calculation

After the concentration of free drug and total drug has been determined by LCMS/MS, percent plasma protein binding can be calculated as follows:

$$\% \text{ fraction unbound} = \frac{\text{Drug concentration in buffer after 5 hours}}{\text{Drug concentration in plasma after 5 hours}} \times 100$$

Following this protocol, % fraction unbound in plasma from different species can be also measured.

Example B05: Determination of In Vitro Intrinsic Clearance ($CI_{int}$-In Vitro) with Mouse, Rat and Human Liver Microsomes In this assay, test compounds are incubated with liver microsomes from mouse, rat and human, and rate of disappearance of drug is determined using LC-MS/MS. Conditions used in the assay are summarized below:

Materials
CD-1 Mice liver microsomes, pooled male (Life Technologies, Cat No. MSMC-PL) (20 mg/ml)
SD Rat liver microsomes, pooled male (Life Technologies, Cat No. RTMCL-PL) (20 mg/ml)
Human liver microsomes, pooled mixed gender (Life Technologies, Cat No. HMMC-PL) (20 mg/ml)
NADPH (SRL Mumbai, Cat No. 99197)
Verapamil (Sigma, Cat No. V4629)
Atenolol (Sigma, Cat No. A7655)
Tolbutamide (Sigma Cat. No. T0891)
Assay buffer: 50 mM potassium phosphate buffer, pH 7.4
Test & reference compounds: DMSO stock solutions (10 mM concentration) are prepared and stored at room temperature. An intermediate 1 mM solution of test or reference compounds is prepared by mixing 10 µL of 10 mM DMSO stock with 90 µL of DMSO. The contents are mixed vigorously in a vortex mixer.

Methods
Preparation of Working Solutions of Test and Reference Compounds:

Working solution (100 µM concentration) is prepared by mixing 10 µL of 1 mM DMSO solution of test or reference compounds with 90 µL of assay buffer. The mixture is mixed vigorously in a vortex mixer. This resulting solution is containing 10% of DMSO. For the metabolic stability assay, 10 µL of this 100 µM working solution is added to a final assay volume of 1 mL, yielding final test concentration of 1 µM and DMSO concentration of 0.1%.

Metabolic Stability Assay

Metabolic stability assay is done in a final volume of 1 ml in 50 mM assay buffer, potassium phosphate buffer, pH 7.4. Assay is carried out in duplicates (n=2). A mixture containing 955 µL of assay buffer, 25 µL of liver microsomes and 10 µL of 100 µM test compound solution is pre-incubated for 10 minutes in a water-bath maintained at 37° C. After pre-incubation, reaction is started by adding 10 µL of 100 mM NADPH solution. The solution is mixed and incubated at 37° C. in a water-bath. The final concentration of the different components in the assay is: DMSO 0.1%, test compound 1 µM, liver microsome protein 0.5 mg/ml and NADPH 1 mM.

Aliquots (100 µL) are taken at various time-points (0, 5, 15, 30 and 45 minutes) and quenched with 100 µL of acetonitrile containing tolbutamide (500 ng/mL) as internal standard. Samples are mixed using a vortex mixer and centrifuged at 4000 rpm for 10 minutes (Eppendorf 5810R, 3000 g). The supernatants (5 µL) are transferred to 96 well plates and submitted for LC-MS/MS analysis.

Separate incubations in the same assay mixture, but in the absence of NADPH, are run in parallel as control for compound stability. This control assay is carried out in duplicates (n=2). After pre-incubation, addition of NADPH is omitted and replaced with 10 µL of assay buffer. The final assay volume is 1 mL and aliquots (100 µL) are withdrawn and processed for analysis as described for metabolic stability assay.

LC-MS/MS Conditions (Generic Method)
LC-MS/MS: API Sciex 4000 with Nexera™ UHPLC
Software: Analyst Version 1.6.1
Column: Phenomenex kinetex C18 50×3.0 mm, 2.6 µ
Column Oven: 40° C.
Mode: ESI Positive
Injection volume: 5 µl
Flow Rate: 1000 µL/mL
Buffer: 0.1% Formic acid in Water
Method: Isocratic Method/Gradient
Composition: A) 0.1% Formic acid in Water
B) 0.1% Formic acid in Methanol

| Time (Sec) | Flow (µL) | Mobile Phase A | Mobile Phase B |
|---|---|---|---|
| 0.01 | 1000 | 10 | 90 |
| 0.4 | 1000 | 10 | 90 |
| 1 | 1000 | 90 | 10 |
| 1.5 | 1000 | 90 | 10 |
| 1.8 | 1000 | 10 | 90 |
| 3 | 1000 | 10 | 90 |

Results Calculation

From LC-MS/MS data, amount of drug remaining at different time points was determined (% PCR). The logarithm of % PCR was plotted against time to get the slope value. From the slope value, in vitro $T_{1/2}$ was determined. In vitro intrinsic clearance ($CI_{int}$) was calculated using the following formulae:

$$CL_{int} = \frac{0.693}{\text{In vitro } t_{1/2}} \times \frac{\text{Volume of incubation}}{\text{mg of microsomal protein}}$$

$$\text{In vitro } t_{1/2} = \frac{0.693}{K_{el}}$$

Where $K_{ei}$ is Elimination Constant (slope)

Methods for treating the diseases mentioned in this specification, such as tauopathy, by administering one or more of the compounds of the present invention to a patient in need thereof are also object of this invention.

In further preferred embodiments, compounds of formula I bear an N-oxide group in the pyrrolidine moiety at the position of the tertiary N-atom of the pyrrolidine ring.

If chemical bonds in the structures above are drawn as follows:

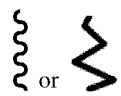

they indicate a defined preferred, i.e. R or S, stereochemistry at at least one of the atoms to which they are attached to.

This is exemplified below, wherein the structure

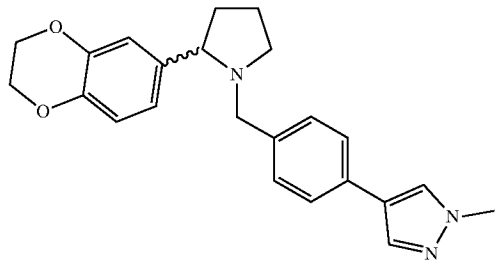 [SMILES: Cn1cc(-c2ccc(CN3CCCC3c3ccc4c(c3)OCCO4)cc2)cn1]

is representing preferably one of the two possible enantiomers,

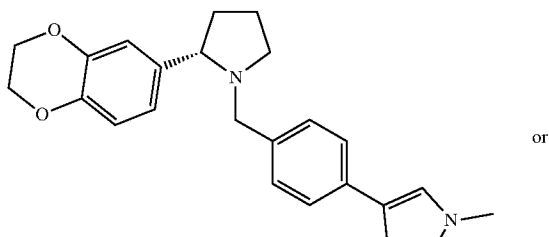

or

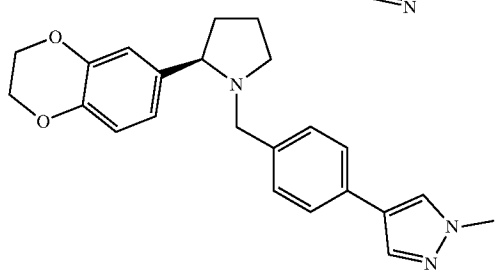

The invention claimed is:

1. A compound of formula (I)

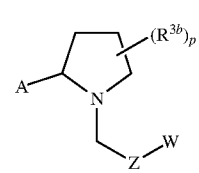

wherein

A is:

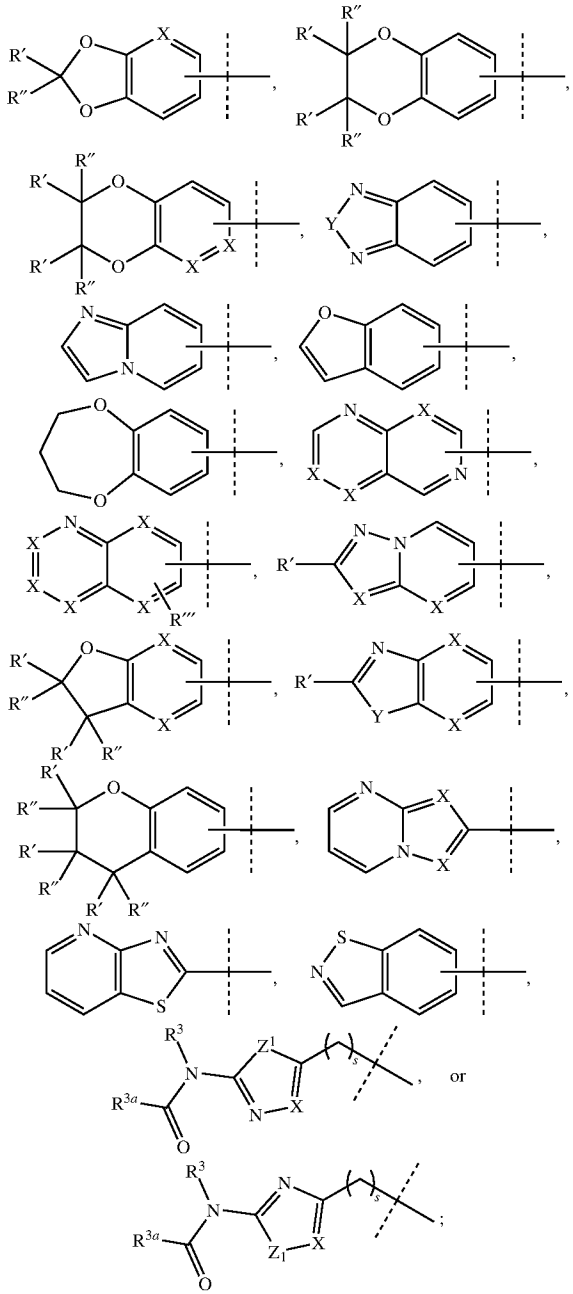

or A is selected from the following groups, wherein at least one X is not CH:

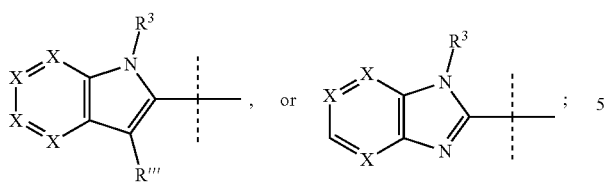

X is N or CR''';
$X^a$ is N, $NR^3$, C, or CR''';
$X^b$ is N or C;
Y is O, S, SO, or $SO_2$;
R', R'' are, independently H, Hal or straight chain or branched alkyl having 1 to 12 carbon atoms;
R''', R'''' are, independently, H, Hal, $NR^3R^4$, $CHR^3R^4$, $OR^3$, CN or a straight chain or branched alkyl having 1 to 12 carbon atoms, wherein 1 to 3 $CH_2$-groups may be replaced by a group selected from O, $NR^3$, S, SO, $SO_2$, $S(O)(NR^{3'})$, $N(SO)R^{3'}$ CO, COO, OCO, $CONR^3$, $NR^3CO$,

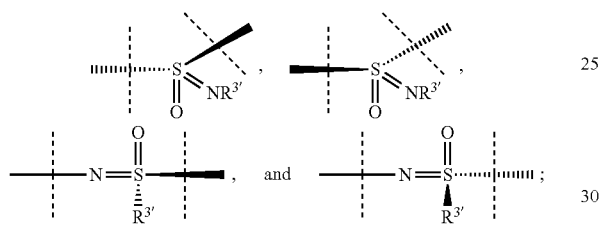

and wherein 1 to 5 hydrogen atoms may be replaced by Hal, $NR^3R^4$, $NO_2$,

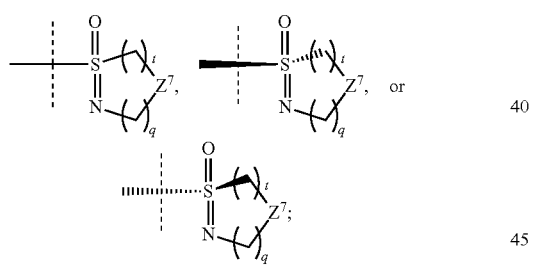

or R', R'''' are, independently:

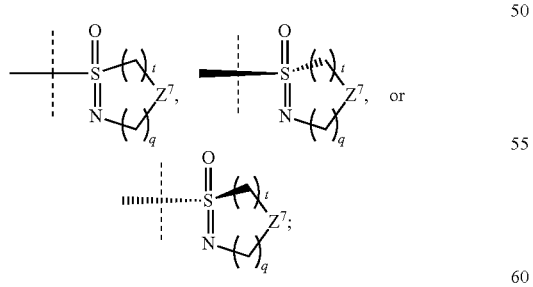

$R^3$, $R^4$ are, independently, H, or a straight chain or branched alkyl group having 1 to 12 carbon atoms;
$R^{3a}$ is a straight chain or branched alkyl group having 1 to 12 carbon atoms;
$R^{3b}$ is independently selected from the group consisting of H, Hal, and a straight chain or branched alkyl having 1 to 12 carbon atoms, wherein 1 to 3 $CH_2$-groups may be replaced by a group selected from O and $NR^3$, and wherein 1 to 5 hydrogen atoms may be replaced by CN or Hal; or two $R^{3b}$ substituents are bound to the same carbon atom and form together a cyclopropylidene radical;

W is R or Q;

Z is a six-membered aromatic or saturated ring, optionally containing one or two heteroatoms selected from N, O and S, which ring may be substituted by one or two substituents selected from $R^7$, or Z may also be a single bond if W is Q;

Q is:

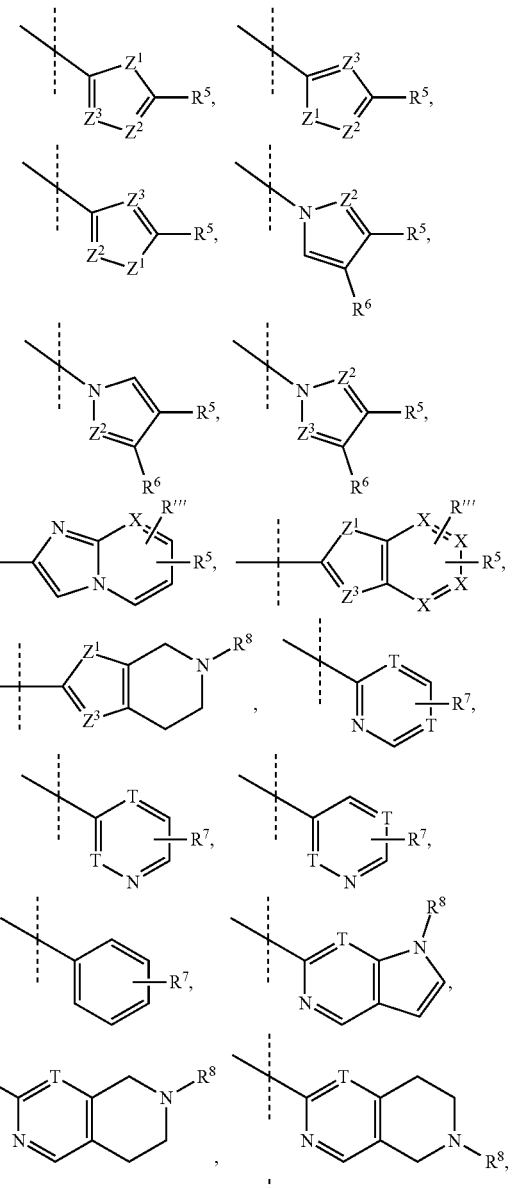

-continued
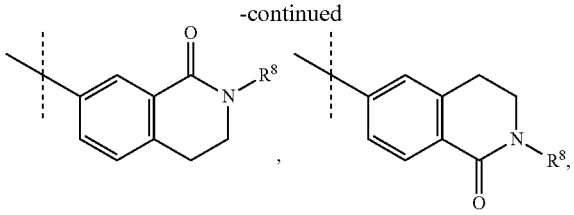
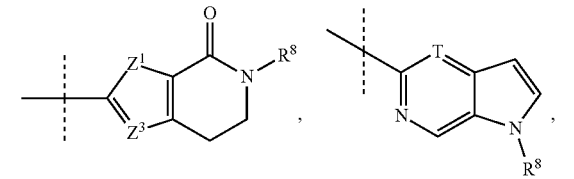
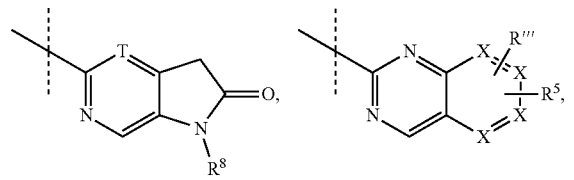
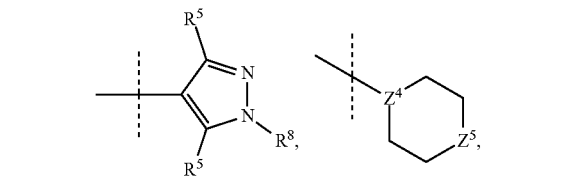
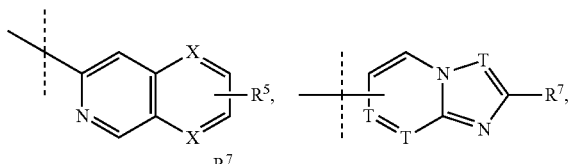
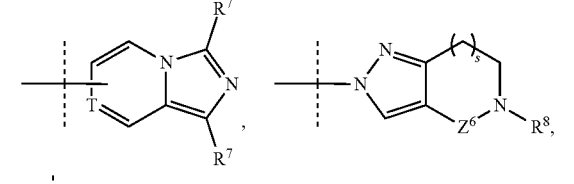
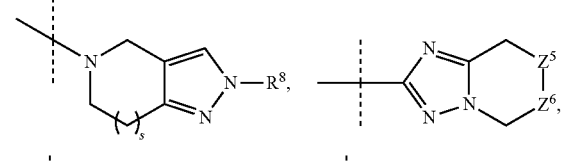
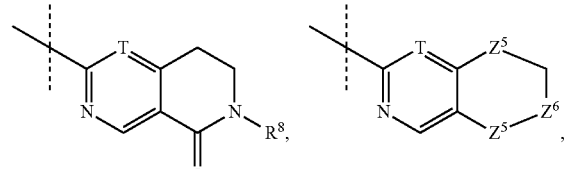
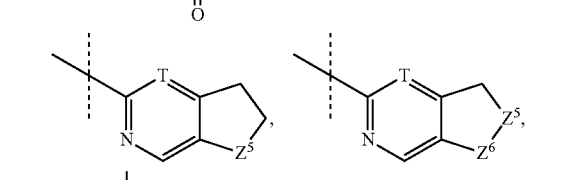
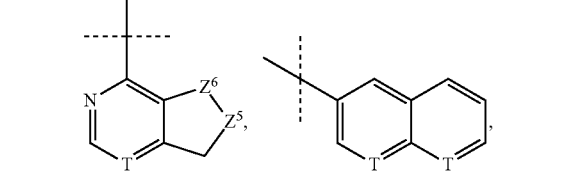
-continued
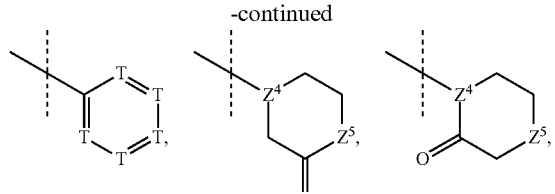
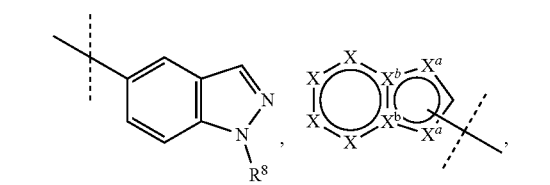
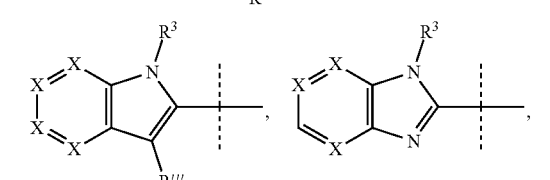
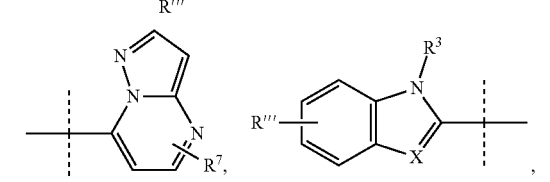
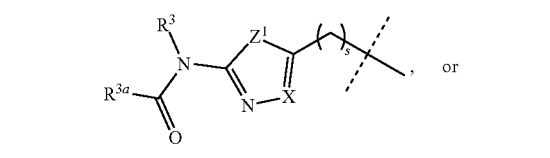
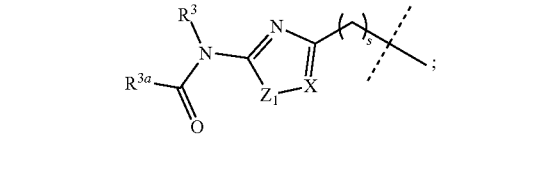
$Z^1$ is C, O, or $NR^3$;
$Z^2$, $Z^3$ are, independently, $CR^5$, $CR^6$, or N;
$Z^4$ is N, CH, CON, or COCH;
$Z^5$ is O, NR', $CHR^5$, $SO_2$, $S(O)(NR^{3'})$, $N(SO)R^{3'}$,
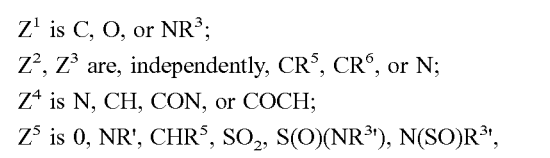
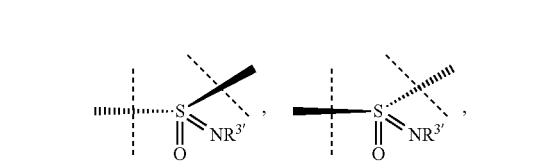
$Z^6$ is $CH_2$, CO, $S(O)(NR^{3'})$, $N(SO)R^{3'}$,
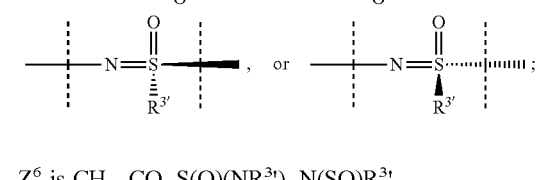
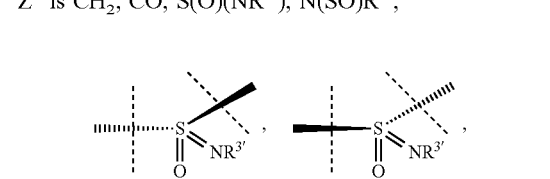

-continued

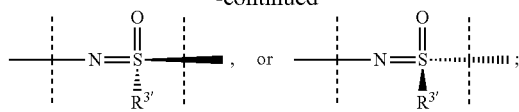

$Z^7$ is $C(R^{3'})_2$, S, O, or $NR^{3'}$;

p is 1, 2, or 3;

s is 0 or 1;

T is N, CH, or $CR^7$;

$R^{3'}$ is H or a straight chain or branched alkyl group having 1 to 12 carbon atoms, wherein 1 to 3 $CH_2$-groups may be replaced by a group selected from $SO_2$, CO, and O; and wherein 1 to 5 hydrogen atoms may be replaced by Hal;

R, $R^5$, $R^6$, and $R^7$ are, independently, H, Hal, CN, OH, $NR^3R^4$, $NO_2$, or a straight chain or branched alkyl having 1 to 12 carbon atoms, wherein 1 to 3 $CH_2$-groups may be replaced by a group selected from O, $NR^3$, S, SO, $SO_2$, $S(O)(NR^{3'})$, $N(SO)R^{3'}$, CO, COO, OCO, $CONR^3$, $NR^3CO$,

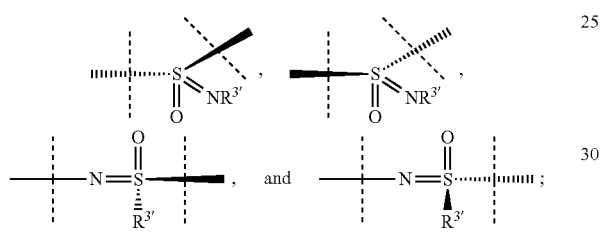

and wherein 1 to 5 hydrogen atoms may be replaced by Hal, $NR^3R^4$, $NO_2$, $OR^3$, Het, Ar, Cyc,

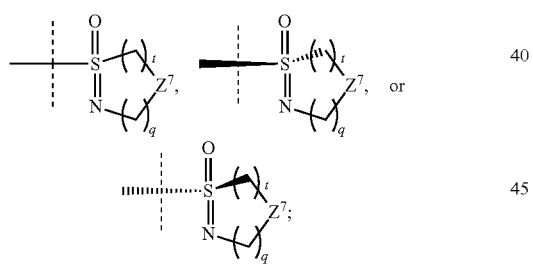

or R, $R^5$, $R^6$, and $R^7$ are Ar, Het, Cyc,

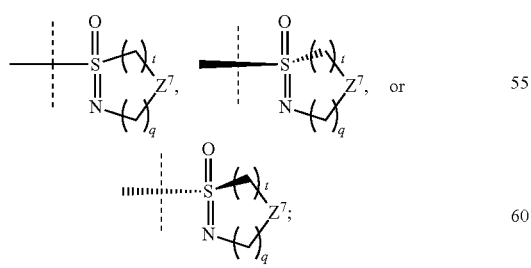

$R^8$ is H or straight chain or branched alkyl having 1 to 12 carbon atoms, wherein 1 to 3 $CH_2$-groups may be replaced by a group selected from SO, $SO_2$, $S(O)(NR^{3'})$ $N(SO)R^{3'}$, CO, COO, OCO, $CONR^3$, $NR^3CO$,

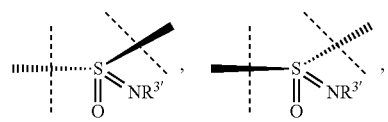

and further wherein 1 to 5 hydrogen atoms may be replaced by CN, $OR^3$, $SR^3$, Hal, $NR^3R^4$, $NO_2$,

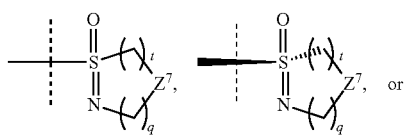

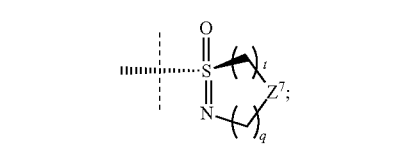

or $R^8$ is Ar, Het, Cyc,

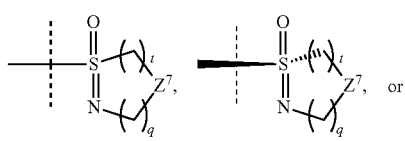

Hal is F, Cl, Br, or I;

Het is a saturated, unsaturated or aromatic ring, being monocyclic or bicyclic or fused bicyclic and having 3 to 8 members and containing 1 to 4 heteroatoms selected from N, O, and S, which may be substituted by 1 to 3 substituents selected from $R^5$, Hal, and $OR^3$;

Ar is a 6-membered carbocyclic aromatic ring or a fused or non-fused bicyclic aromatic ring system, which is optionally substituted by 1 to 3 substituents independently selected from $R^5$, $OR^3$, and Hal;

Cyc is a saturated or an unsaturated carbocyclic ring having from 3 to 8 carbon atoms which is optionally substituted by 1 to 3 substituents independently selected from $R^5$, Hal, and OH;

t and q are, independently, 0, 1, 2 or 3, with t+q≥1;

in its non-racemic form, or a solvate, salt, stereoisomer, tautomer, or compound of formula (I) wherein one or more H atoms are replaced by D (deuterium).

2. A compound according to claim 1, having formula (Ia) or (Ib)

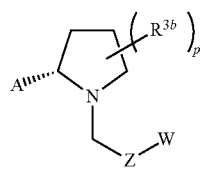

Ia

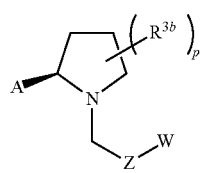

Ib wherein A, W, $R^{3b}$, Z and p have the meaning according to claim 1, or a solvate, salt, stereoisomer, tautomer, or compound of formula (Ia) or (Ib) wherein one or more H atoms are replaced by D (deuterium).

3. A compound according to claim 1, wherein Z is a single bond,

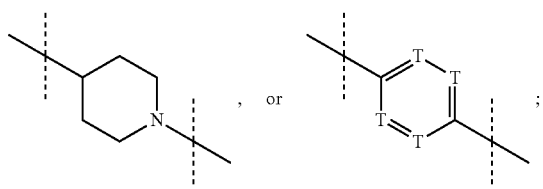

wherein T has the meaning given in claim 1.

4. A compound according to claim 1, wherein A is:

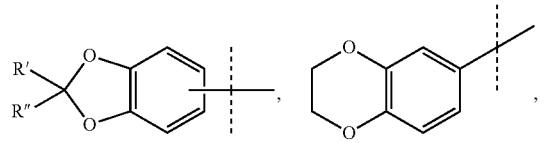

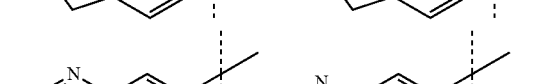

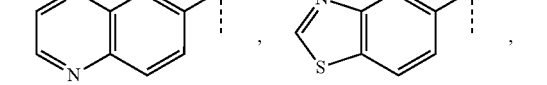

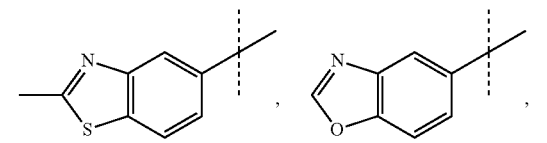

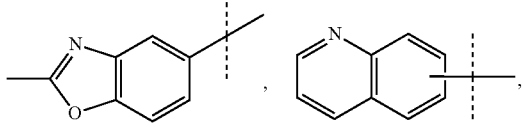

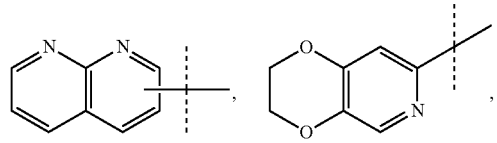

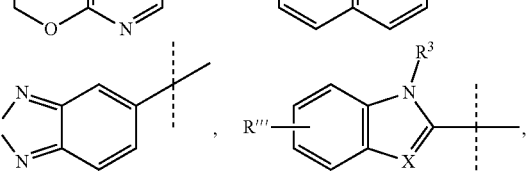

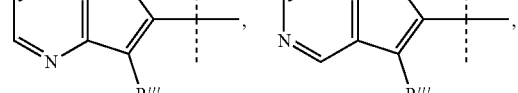

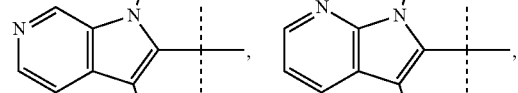

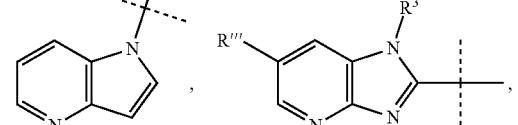

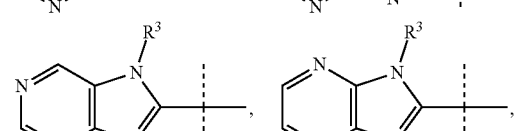

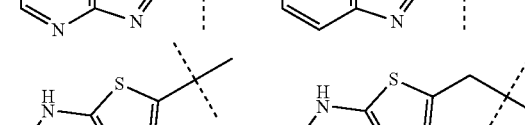

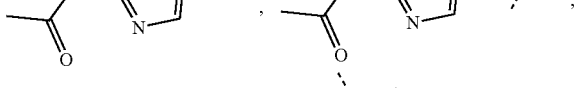

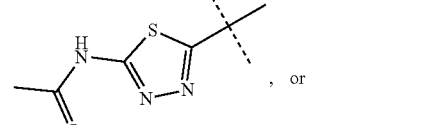

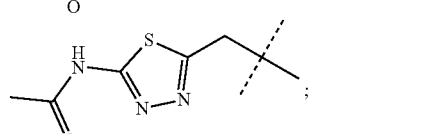

wherein $R^3$, X, R', R" and R'" have the meaning given in claim 1.

5. A compound according to claim 1, wherein Q is:
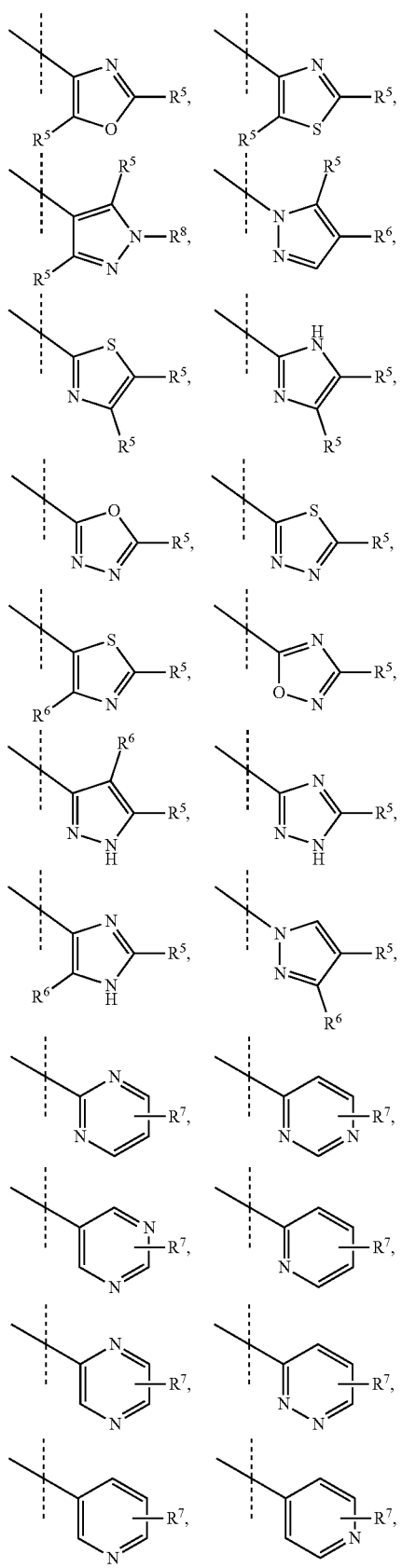
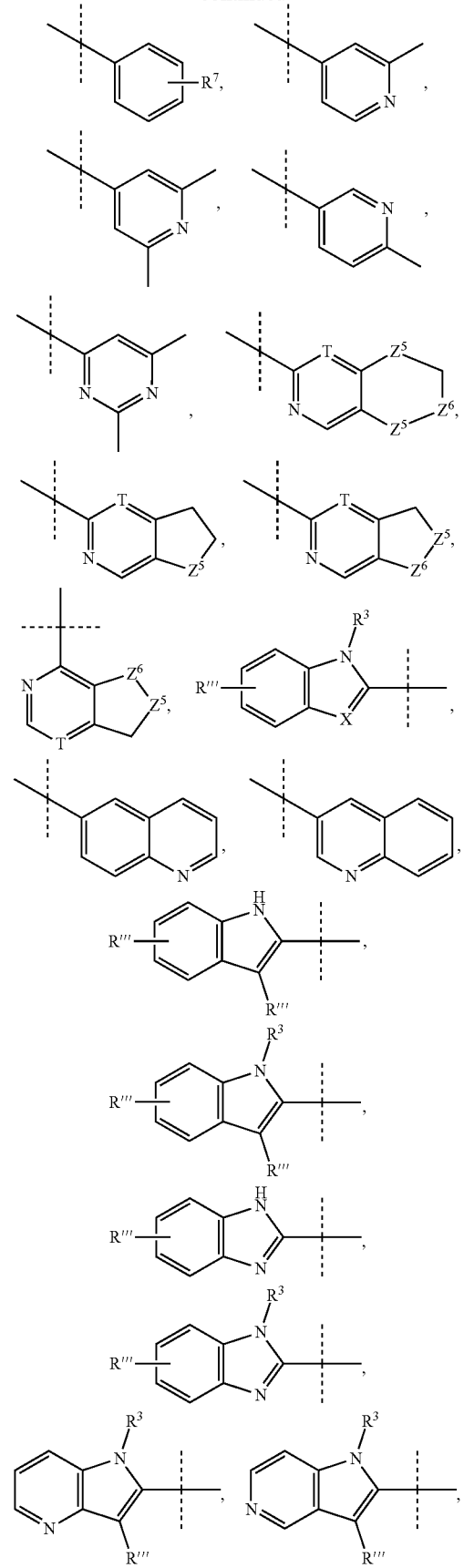

-continued

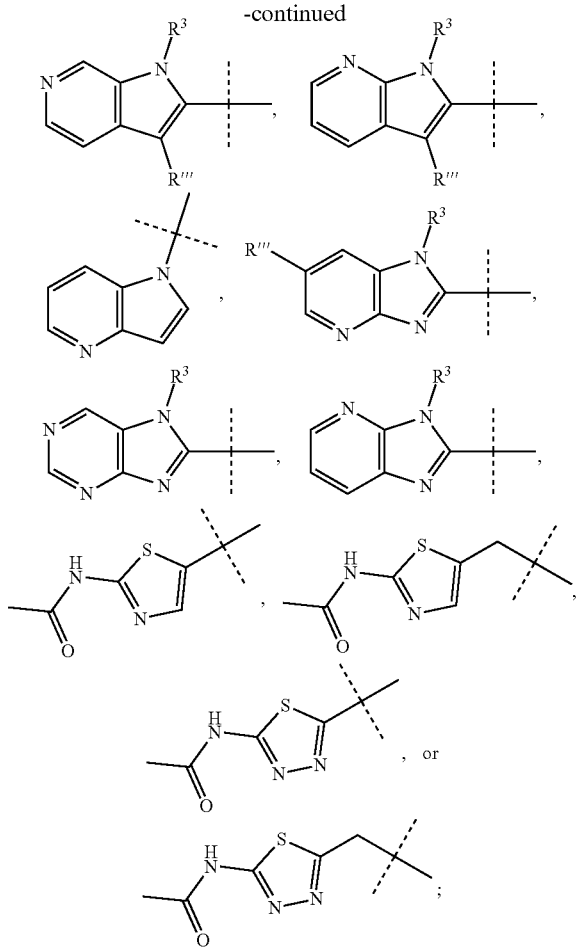

wherein X, R''', R³, T, Z⁵, Z⁶, R⁶ and R⁷ have the meaning given in claim 1.

6. A compound according to claim 1, wherein R, R⁵, R⁶, R⁷, and R⁸, if present, are independently selected from H, CN, $SO_2CH_3$, $SO_2CH_2CH_3$, $SO_2CH_2CH_2OH$, $SO_2CH_2CH_2OCH_3$, $S(O)(NR^{3'})CH_3$, $S(O)(NR^{3'})CH_2CH_3$, $S(O)(NR^{3'})CH_2CH_2OH$, $S(O)(NR^{3'})CH_2CH_2OCH_3$, $N(SO)R^{3'}CH_3$, $N(SO)R^{3'}CH_2CH_3$, $N(SO)R^{3'}CH_2CH_2OH$, $N(SO)R^{3'}CH_2CH_2OCH_3$, Hal, $NR^3R^4$, $NO_2$, $R^{3'}$-phenyl, $R^{3'}$-benzyl, $CH_2$—($R^{3'}$-pyridyl), O—($R^{3'}$-phenyl), O—($R^{3'}$-pyridyl), O-pyrimidinyl, O—($R^{3'}$-benzyl), 2-, 3- or 4-hydroxy or methoxyphenyl, alkyl, alkoxy, hydroxyalkylene, alkoxyalkylene, COOH, COOalkyl, CONHalkyl, $CONH_2$, $CON(CH_3)_2$, NHCOalkyl, $NHCOCH_3$, NHCO-phenyl, NHCOpyridyl, $NHCH_2CH_3$, $NHCH_2CH_2CH_3$, $NHCOCH_2CH_2OH$, CO—N-morpholinyl, $CON(CH_3)CH_2CH_2N(CH_3)_2$, CO-1-piperidinyl, CO-4-hydroxy-1-piperidinyl, CO-1-piperazinyl, CO-4-methyl-1-piperazinyl, $CH_2$—N-morpholinyl, $CH_2N(H)COCH_3$, $CH_2N(CH_3)COCH_3$, $CH_2NH_2$, $NH_2$, $CH(OH)CH_3$, $CH(OR^3)CH_3$,

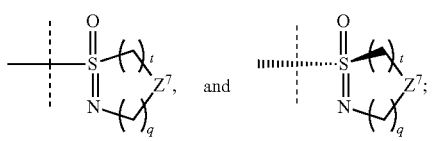

wherein t+q is 2 or 3; and $Z^7$, $R^{3'}$, $R^3$, and $R^4$ have the meaning given in claim 1.

7. A compound according to claim 1, wherein Z is not a single bond and T, if present, is CH or $CR^7$, wherein $R^7$ is Hal, CN, or alkyl having 1 to 6 carbon atoms, wherein 1 to 3 H-atoms may be replaced by Hal.

8. A compound according to claim 1, wherein $R^{3b}$ is H.

9. A compound selected from the group consisting of:

| No. | Structure |
|---|---|
| 1 | ![structure 1] |
| 3 | ![structure 3] |
| 4 | ![structure 4] |
| 5 | ![structure 5] |
| 8 | ![structure 8] |

| No. | Structure |
|---|---|
| 9 | 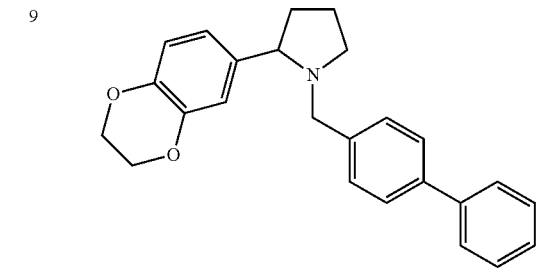 |
| 10 | 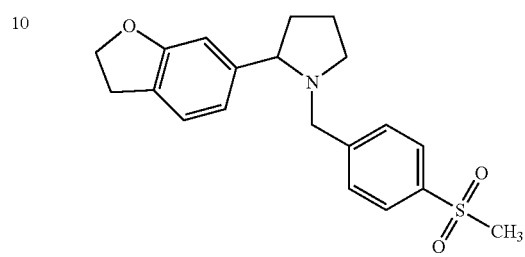 |
| 11 | 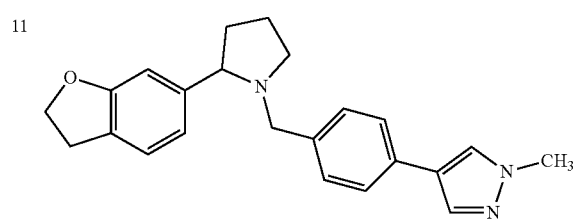 |
| 12 | 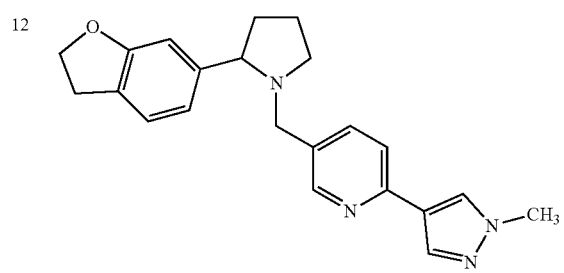 |
| 14 | 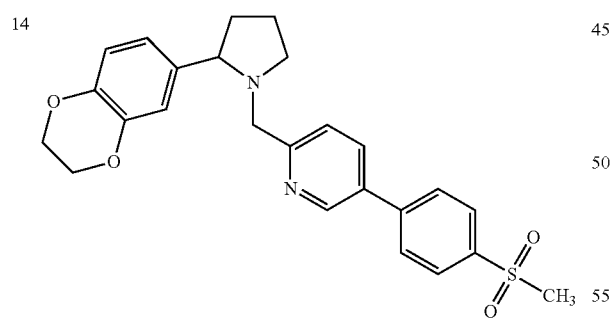 |
| 15 | 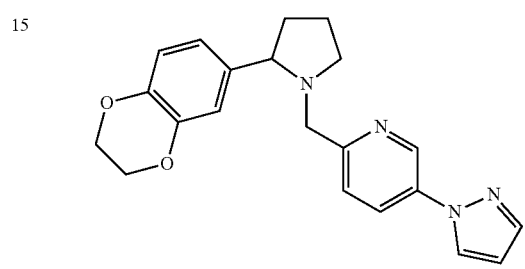 |
| No. | Structure |
|---|---|
| 16 | 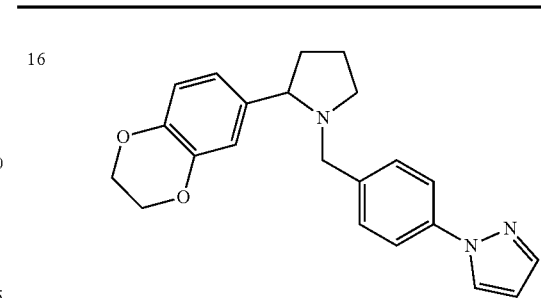 |
| 17 | 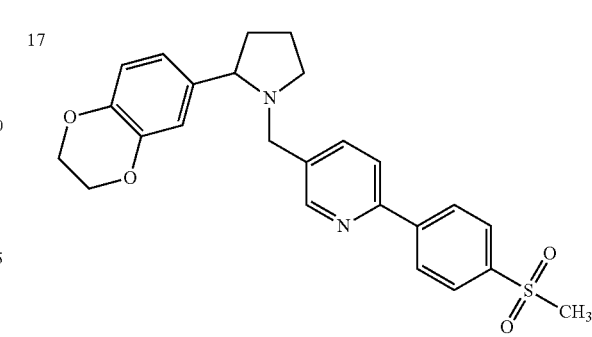 |
| | 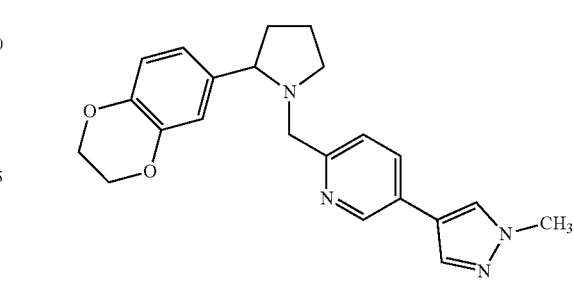 |
| 19 | 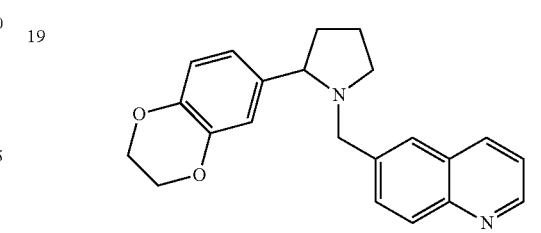 |
| |  |
| 20 | 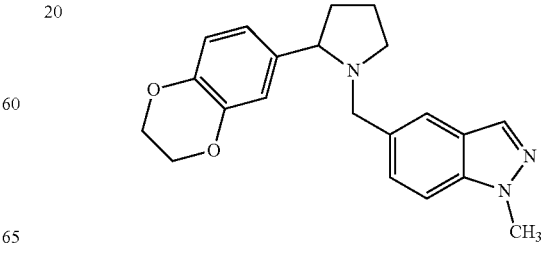 |

| No. | Structure |
|---|---|
| 21 | 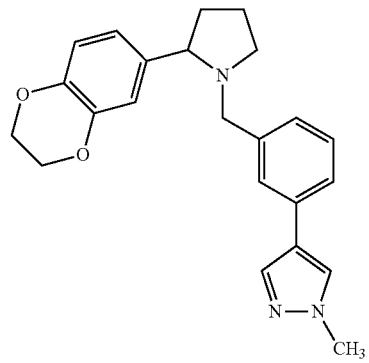 [SMILES: Cn1cc(-c2cccc(CN3CCCC3c3ccc4c(c3)OCCO4)c2)cn1] |
| 22 | 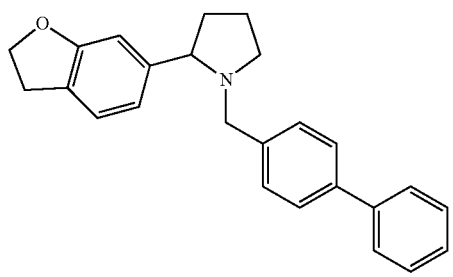 [SMILES: c1ccc(-c2ccc(CN3CCCC3c3ccc4c(c3)OCC4)cc2)cc1] |
| 23 | 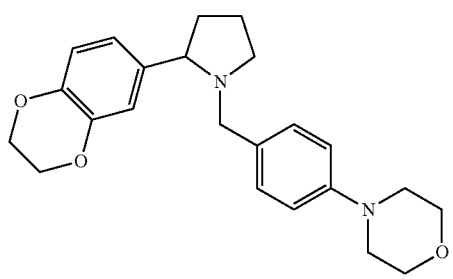 [SMILES: c1cc(N2CCOCC2)ccc1CN1CCCC1c1ccc2c(c1)OCCO2] |
| 24 | 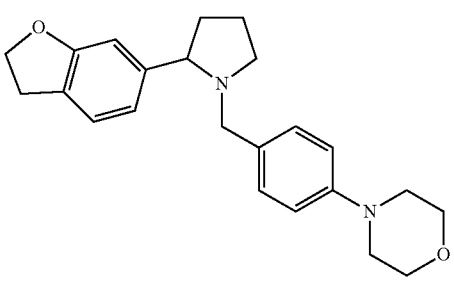 [SMILES: c1cc(N2CCOCC2)ccc1CN1CCCC1c1ccc2c(c1)OCC2] |
| 26 | 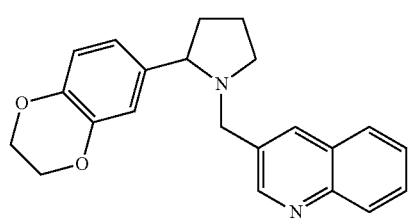 [SMILES: c1ccc2ncc(CN3CCCC3c3ccc4c(c3)OCCO4)cc2c1] |
| No. | Structure |
|---|---|
| 28 | 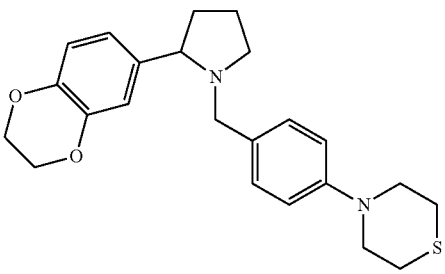 [SMILES: c1cc(N2CCSCC2)ccc1CN1CCCC1c1ccc2c(c1)OCCO2] |
| 29 | 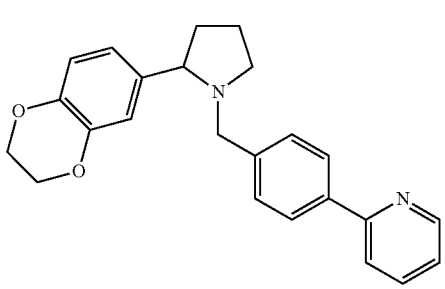 |
| 30 | 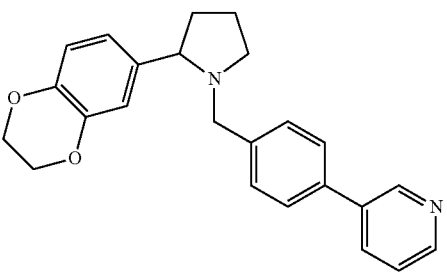 [SMILES: c1cncc(-c2ccc(CN3CCCC3c3ccc4c(c3)OCCO4)cc2)c1] |
| 31 | 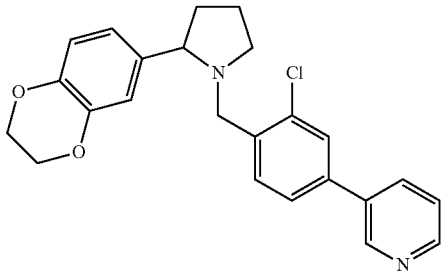 [SMILES: Clc1cc(-c2cccnc2)ccc1CN1CCCC1c1ccc2c(c1)OCCO2] |
| 32 | 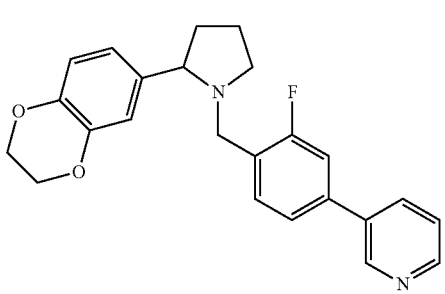 [SMILES: Fc1cc(-c2cccnc2)ccc1CN1CCCC1c1ccc2c(c1)OCCO2] |

| No. | Structure |
|---|---|
| | 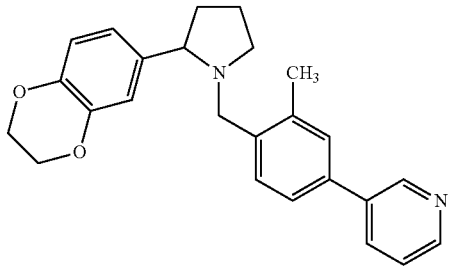 [SMILES: Cc1cc(-c2cccnc2)ccc1CN1CCCC1c1ccc2c(c1)OCCO2] |
| 34 | 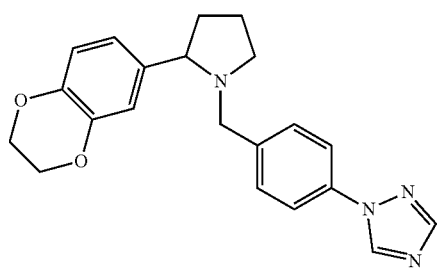 [SMILES: c1ncn(-c2ccc(CN3CCCC3c3ccc4c(c3)OCCO4)cc2)n1] |
| 35 | 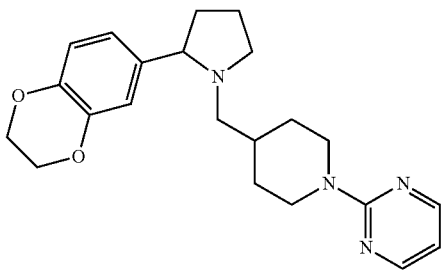 |
| 36 | 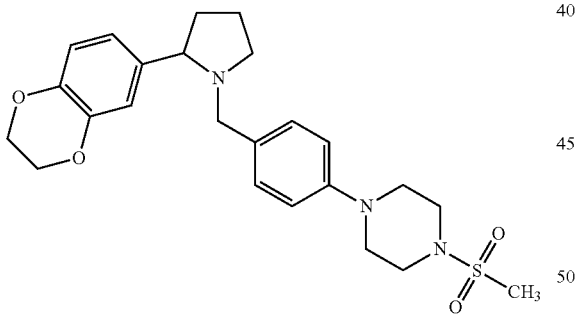 |
| 37 | 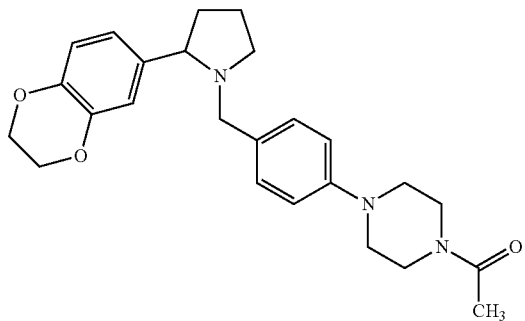 [SMILES: CC(=O)N1CCN(c2ccc(CN3CCCC3c3ccc4c(c3)OCCO4)cc2)CC1] |
| No. | Structure |
|---|---|
| 38 | 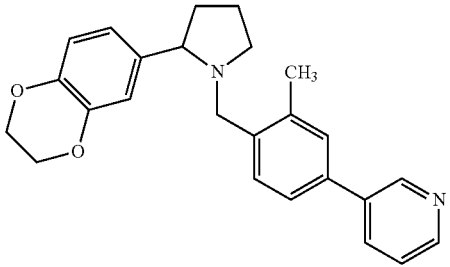 [SMILES: Cc1cc(-c2cccnc2)ccc1CN1CCCC1c1ccc2c(c1)OCCO2] |
| 39 | 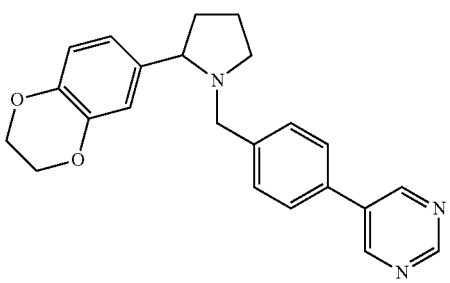 [SMILES: c1ncc(-c2ccc(CN3CCCC3c3ccc4c(c3)OCCO4)cc2)cn1] |
| 41 | 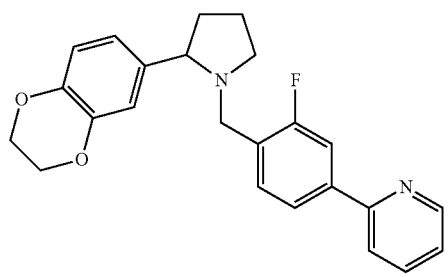 [SMILES: Fc1cc(-c2ccccn2)ccc1CN1CCCC1c1ccc2c(c1)OCCO2] |
| 42 | 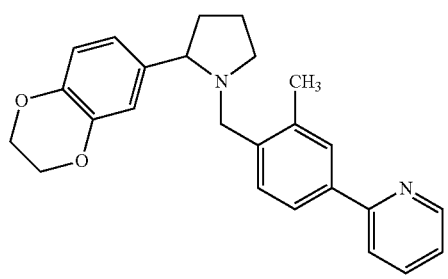 [SMILES: Cc1cc(-c2ccccn2)ccc1CN1CCCC1c1ccc2c(c1)OCCO2] |
| 43 | 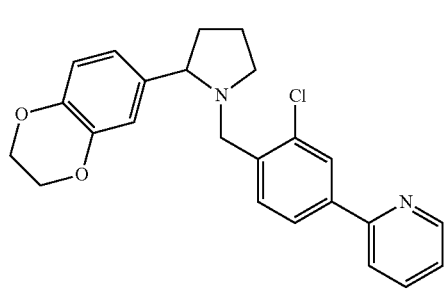 [SMILES: Clc1cc(-c2ccccn2)ccc1CN1CCCC1c1ccc2c(c1)OCCO2] |

| No. | Structure |
|-----|-----------|
| 44 | 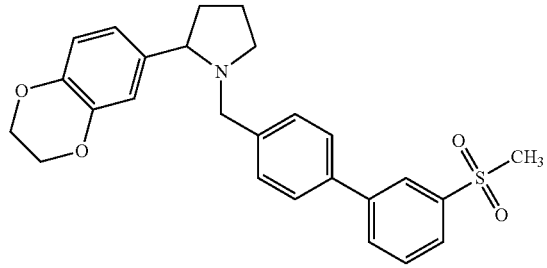 [SMILES: CS(=O)(=O)c1cccc(-c2ccc(CN3CCCC3c3ccc4c(c3)OCCO4)cc2)c1] |
| 45 | 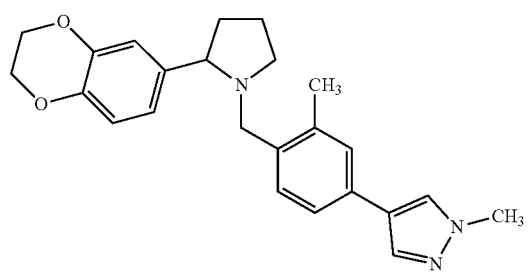 [SMILES: Cc1cc(-c2cnn(C)c2)ccc1CN1CCCC1c1ccc2c(c1)OCCO2] |
| 46 | 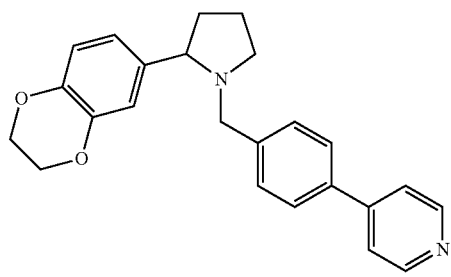 [SMILES: c1cc(-c2ccc(CN3CCCC3c3ccc4c(c3)OCCO4)cc2)ccn1] |
| 47 | 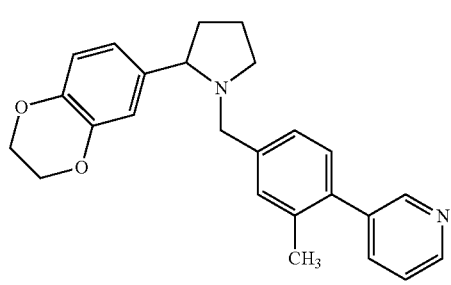 [SMILES: Cc1cc(CN2CCCC2c2ccc3c(c2)OCCO3)ccc1-c1cccnc1] |
| 48 | 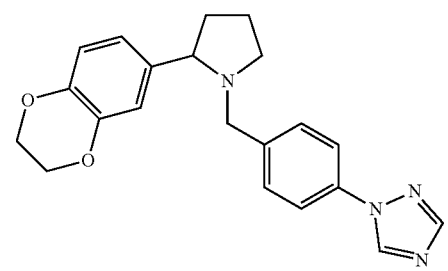 [SMILES: c1ncn(-c2ccc(CN3CCCC3c3ccc4c(c3)OCCO4)cc2)n1] |
| No. | Structure |
|-----|-----------|
| 49 | 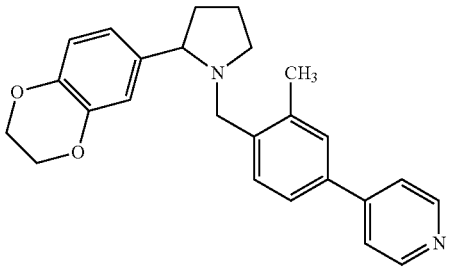 [SMILES: Cc1cc(-c2ccncc2)ccc1CN1CCCC1c1ccc2c(c1)OCCO2] |
| 50 | 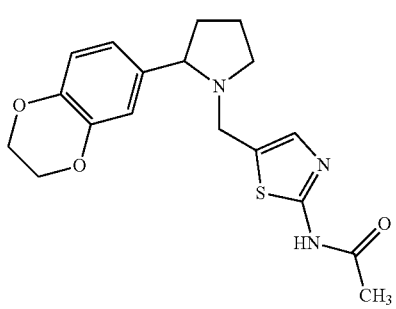 [SMILES: CC(=O)Nc1ncc(CN2CCCC2c2ccc3c(c2)OCCO3)s1] |
| 51 | 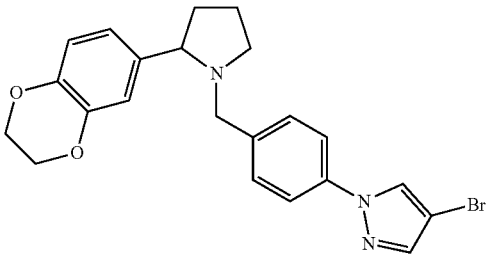 [SMILES: Brc1cnn(-c2ccc(CN3CCCC3c3ccc4c(c3)OCCO4)cc2)c1] |
| 52 | 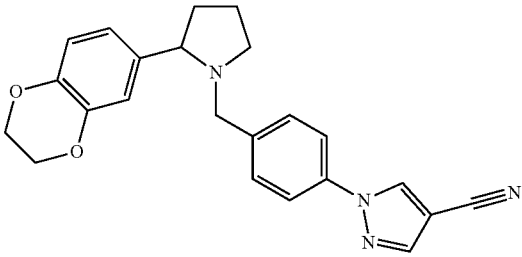 [SMILES: N#Cc1cnn(-c2ccc(CN3CCCC3c3ccc4c(c3)OCCO4)cc2)c1] |
| 53 | 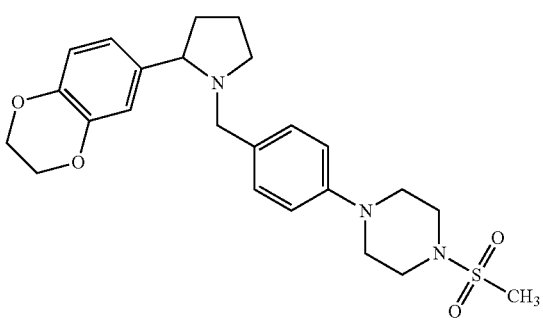 [SMILES: CS(=O)(=O)N1CCN(c2ccc(CN3CCCC3c3ccc4c(c3)OCCO4)cc2)CC1] |

| No. | Structure |
|---|---|
| 54 | 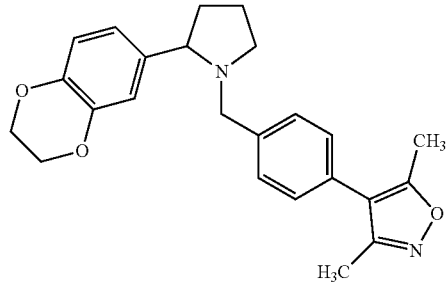 [SMILES: Cc1noc(C)c1-c1ccc(CN2CCCC2c2ccc3c(c2)OCCO3)cc1] |
| 55 | 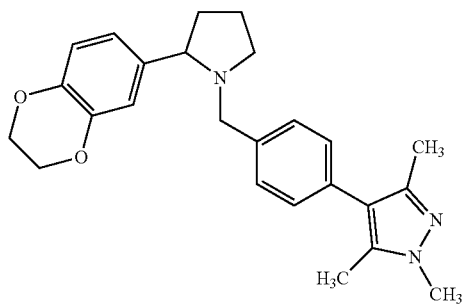 [SMILES: Cc1nn(C)c(C)c1-c1ccc(CN2CCCC2c2ccc3c(c2)OCCO3)cc1] |
| 56 | 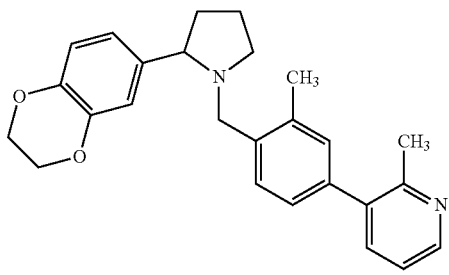 [SMILES: Cc1cc(-c2cccnc2C)ccc1CN1CCCC1c1ccc2c(c1)OCCO2] |
| 57 | 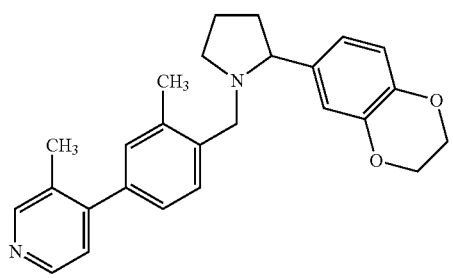 [SMILES: Cc1cc(-c2ccncc2C)ccc1CN1CCCC1c1ccc2c(c1)OCCO2] |
| 58 | 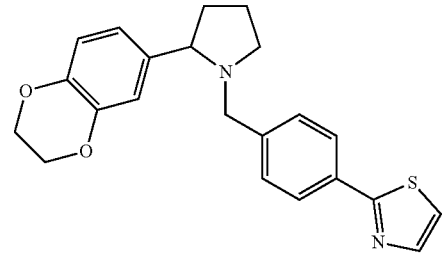 [SMILES: c1csc(-c2ccc(CN3CCCC3c3ccc4c(c3)OCCO4)cc2)n1] |
| No. | Structure |
|---|---|
| 59 | 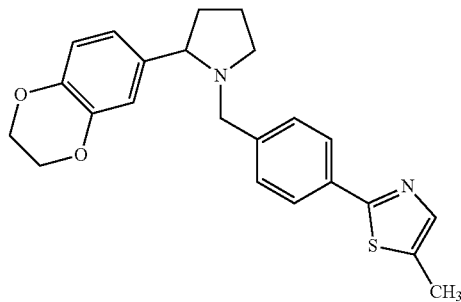 [SMILES: Cc1cnc(-c2ccc(CN3CCCC3c3ccc4c(c3)OCCO4)cc2)s1] |
| 60 | 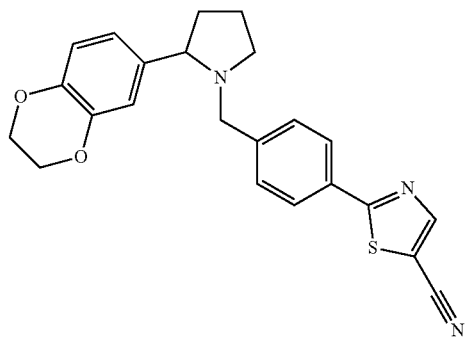 [SMILES: N#Cc1cnc(-c2ccc(CN3CCCC3c3ccc4c(c3)OCCO4)cc2)s1] |
| 61 | 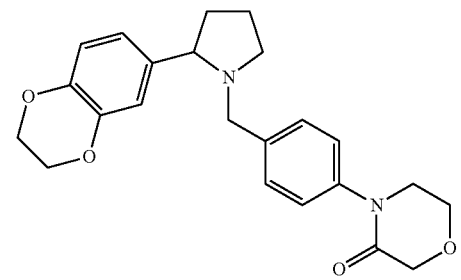 [SMILES: O=C1COCCN1c1ccc(CN2CCCC2c2ccc3c(c2)OCCO3)cc1] |
| 62 | 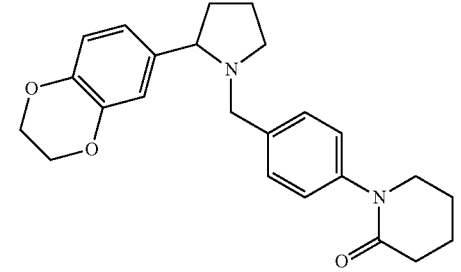 [SMILES: O=C1CCCCN1c1ccc(CN2CCCC2c2ccc3c(c2)OCCO3)cc1] |
| 63 | 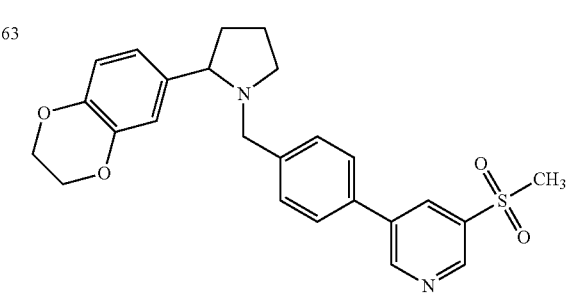 |

| No. | Structure |
|---|---|
| 64 | 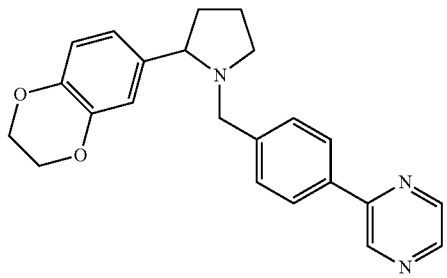 [SMILES: c1cnc(-c2ccc(CN3CCCC3c3ccc4c(c3)OCCO4)cc2)cn1] |
| 65 | 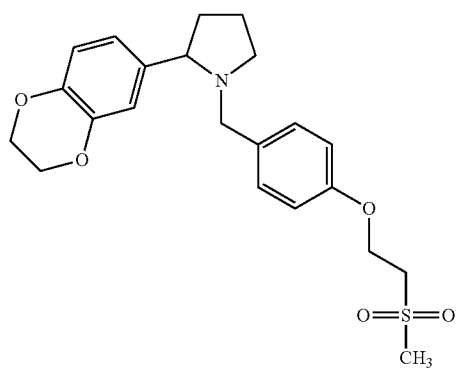 [SMILES: CS(=O)(=O)CCOc1ccc(CN2CCCC2c2ccc3c(c2)OCCO3)cc1] |
| 66 | 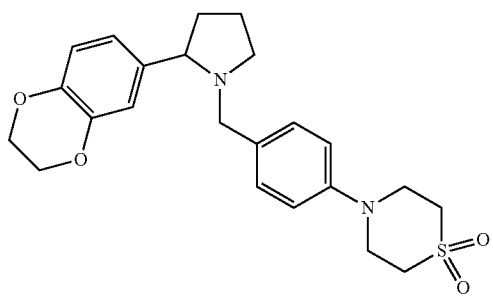 [SMILES: O=S1(=O)CCN(c2ccc(CN3CCCC3c3ccc4c(c3)OCCO4)cc2)CC1] |
| 67 | 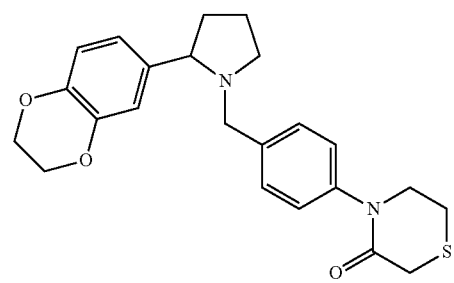 [SMILES: O=C1CSCCN1c1ccc(CN2CCCC2c2ccc3c(c2)OCCO3)cc1] |
| 68 | 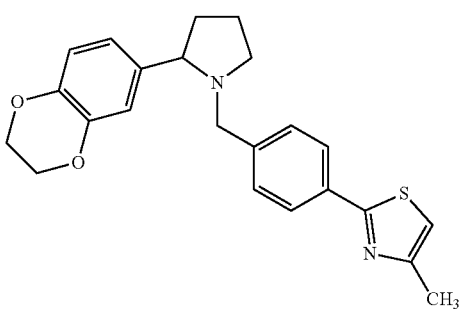 [SMILES: Cc1csc(-c2ccc(CN3CCCC3c3ccc4c(c3)OCCO4)cc2)n1] |
| No. | Structure |
|---|---|
| 69 | 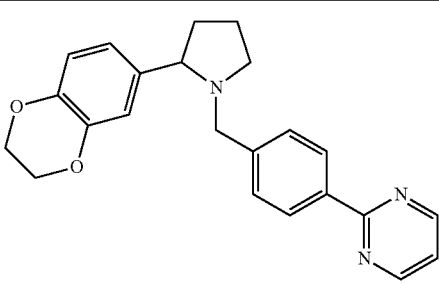 |
| 70 | 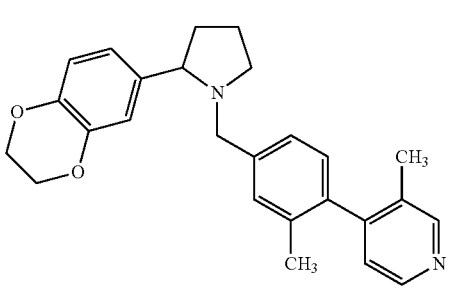 [SMILES: Cc1cnccc1-c1ccc(CN2CCCC2c2ccc3c(c2)OCCO3)cc1C] |
| 71 | 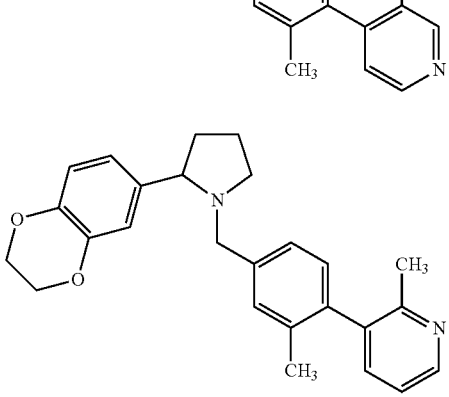 |
| 72 | 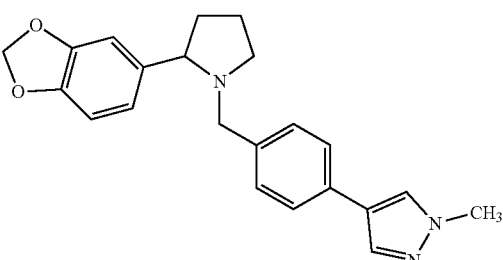 |
| | 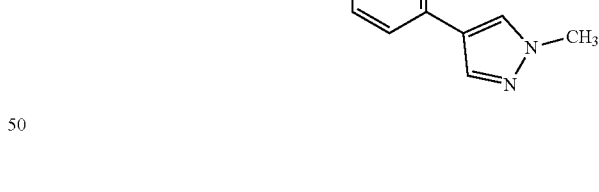 |
| | 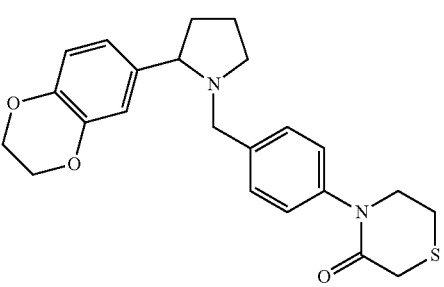 [SMILES: O=C1CSCCN1c1ccc(CN2CCCC2c2ccc3c(c2)OCCO3)cc1] |

| No. | Structure |
|---|---|
| 75 | 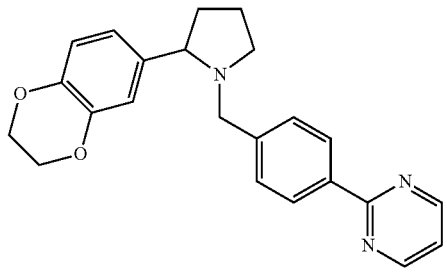 [SMILES: c1cnc(-c2ccc(CN3CCCC3c3ccc4c(c3)OCCO4)cc2)nc1] |
| 76 | 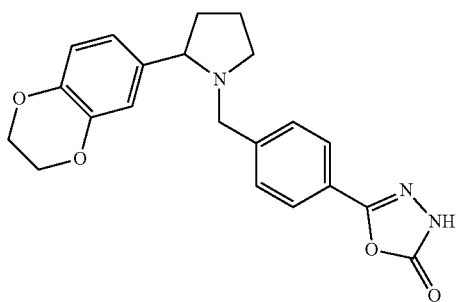 [SMILES: O=c1[nH]nc(-c2ccc(CN3CCCC3c3ccc4c(c3)OCCO4)cc2)o1] |
| 77 | 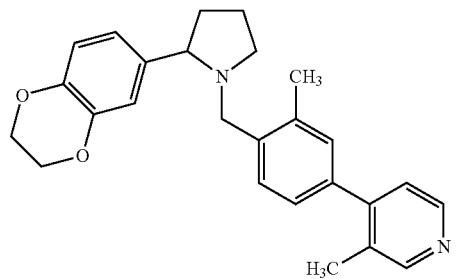 [SMILES: Cc1cc(-c2ccncc2C)ccc1CN1CCCC1c1ccc2c(c1)OCCO2] |
| 78 | 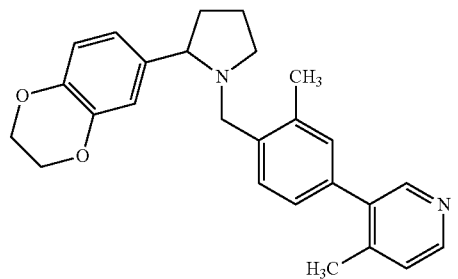 [SMILES: Cc1cc(-c2cnccc2C)ccc1CN1CCCC1c1ccc2c(c1)OCCO2] |
| 79 | 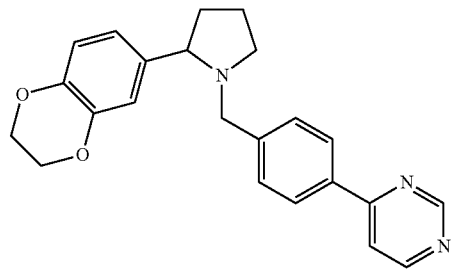 [SMILES: c1cc(-c2ccc(CN3CCCC3c3ccc4c(c3)OCCO4)cc2)ncn1] |
| No. | Structure |
|---|---|
| 80 | 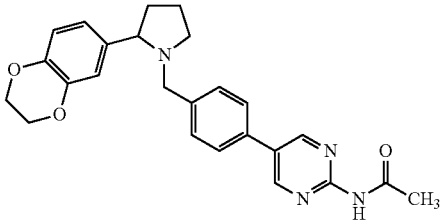 [SMILES: CC(=O)Nc1ncc(-c2ccc(CN3CCCC3c3ccc4c(c3)OCCO4)cc2)cn1] |
| 81 | 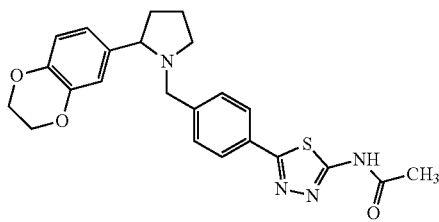 [SMILES: CC(=O)Nc1nnc(-c2ccc(CN3CCCC3c3ccc4c(c3)OCCO4)cc2)s1] |
| 82 | 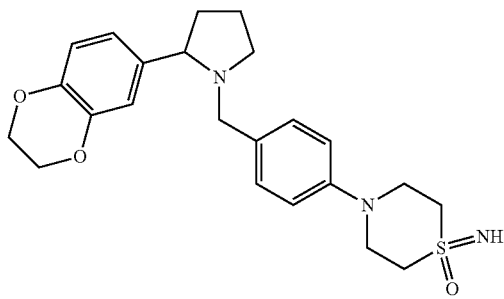 [SMILES: N=S1(=O)CCN(c2ccc(CN3CCCC3c3ccc4c(c3)OCCO4)cc2)CC1] |
| 83 | 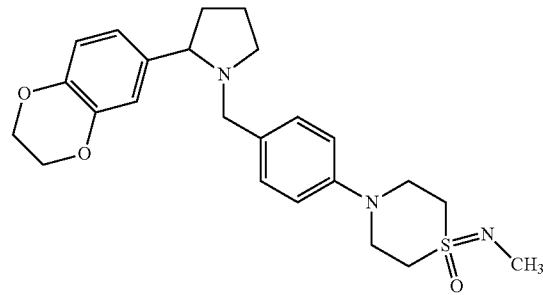 [SMILES: CN=S1(=O)CCN(c2ccc(CN3CCCC3c3ccc4c(c3)OCCO4)cc2)CC1] |
| 84 | 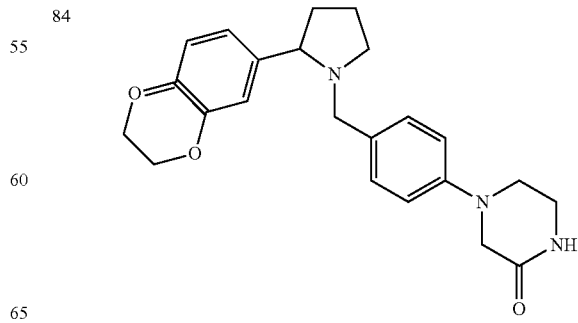 |

343
-continued
| No. | Structure |
|---|---|
| 85 | 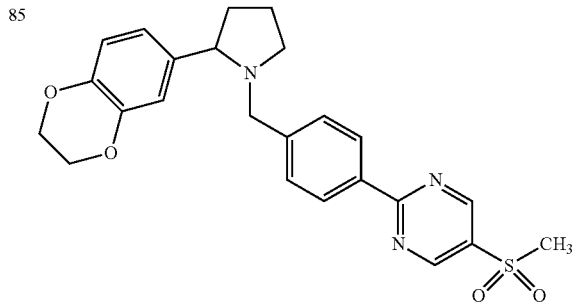 |
| 86 | 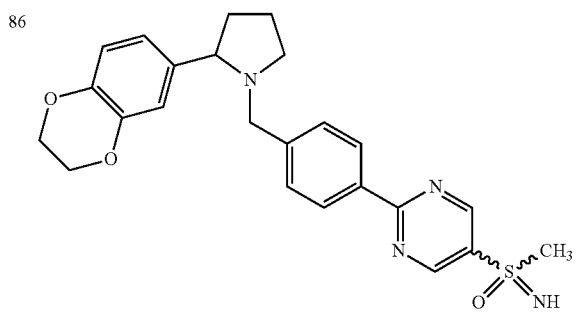 |
| 87 | 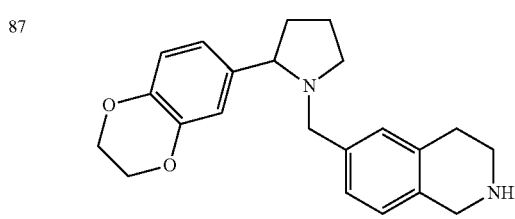 |
| 88 | 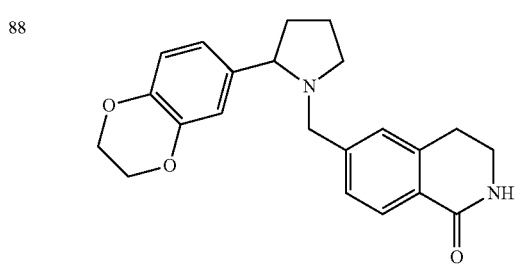 |
| 89 | 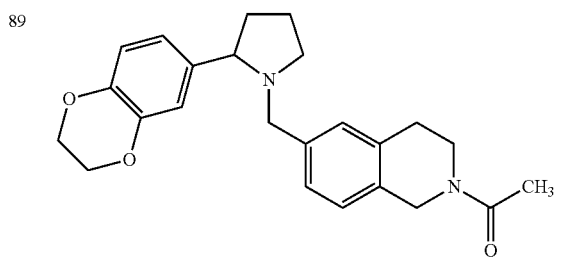 |
344
-continued
| No. | Structure |
|---|---|
| 90 | 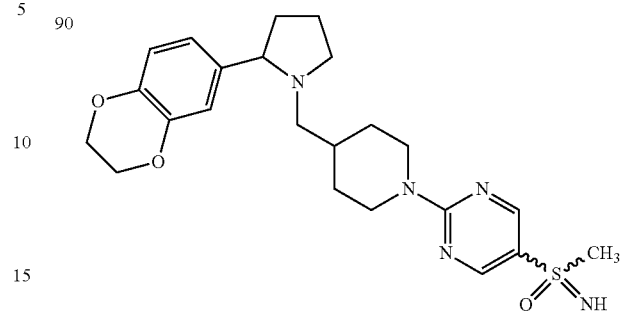 |
| 91 | 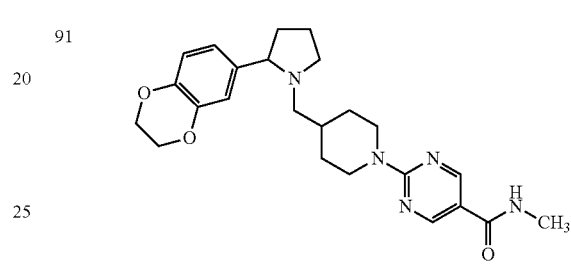 |
| 92 | 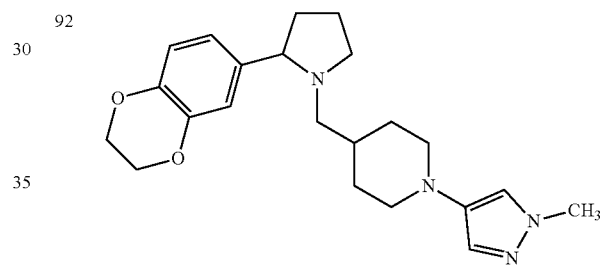 |
| 93 | 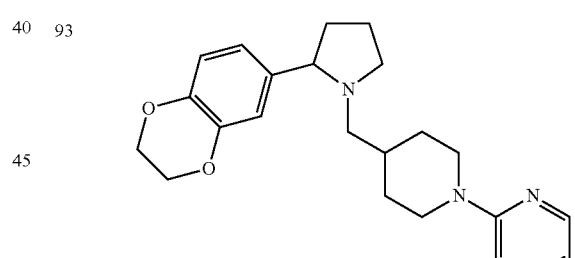 |
| 94 | 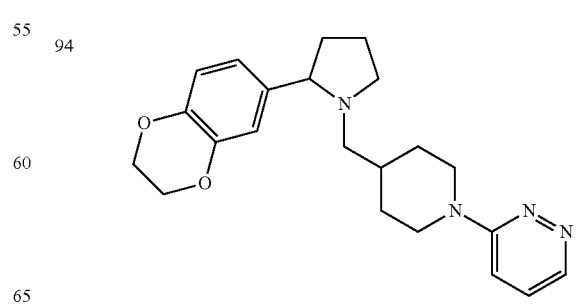 |

| No. | Structure |
|---|---|
| 95 | 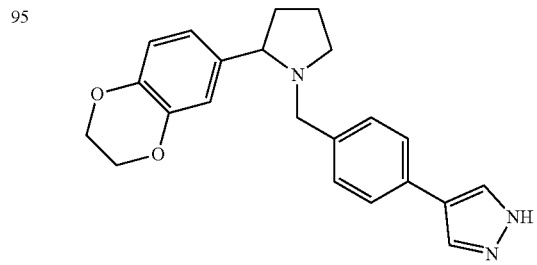 |
| 96 | 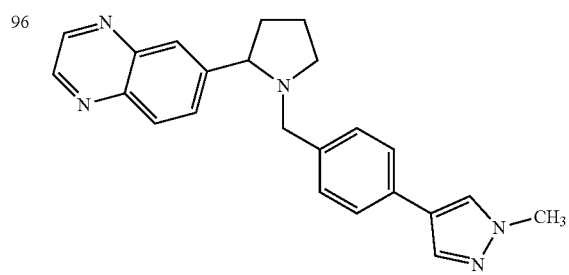 |
| 97 | 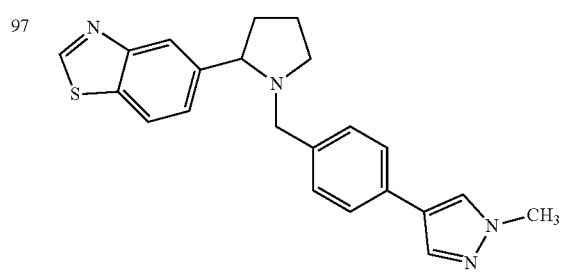 |
| 98 | 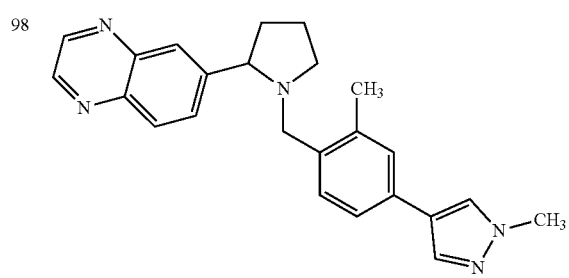 |
| 99 | 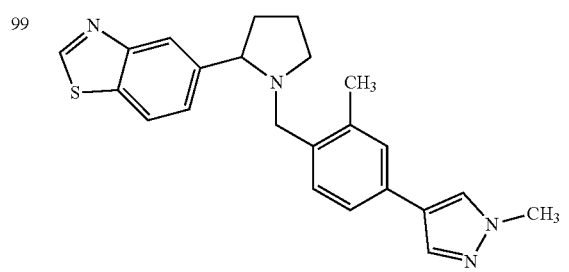 |
| No. | Structure |
|---|---|
| 100 | 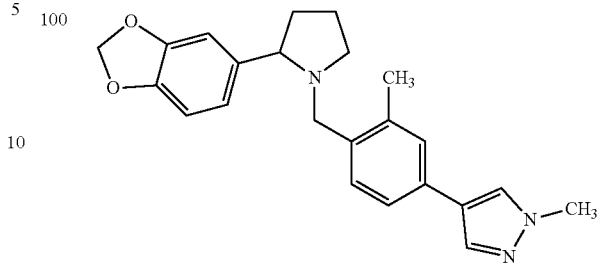 |
| 101 | 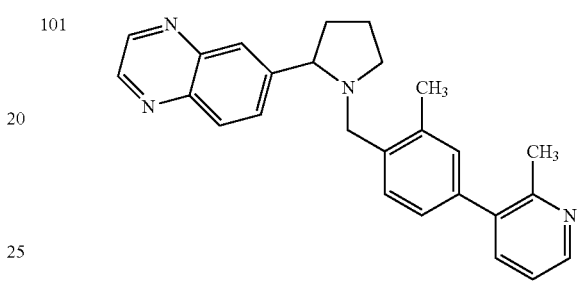 |
| 102 | 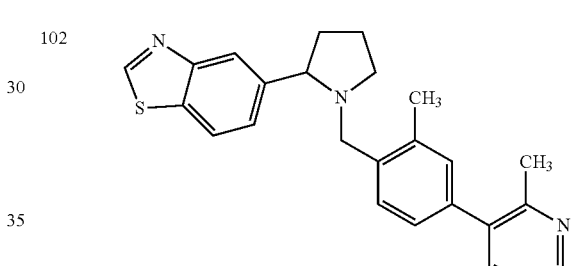 |
| 103 | 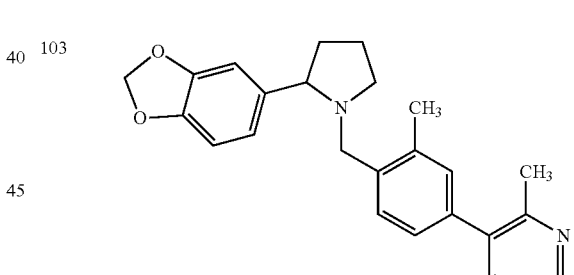 |
| 104 | 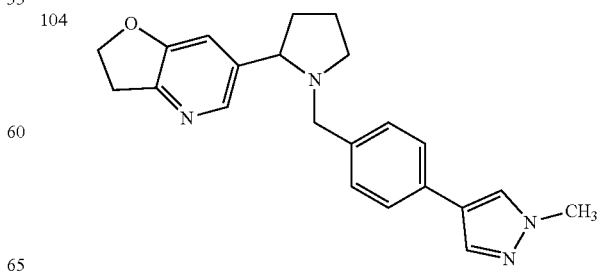 |

| No. | Structure |
|---|---|
| 105 | 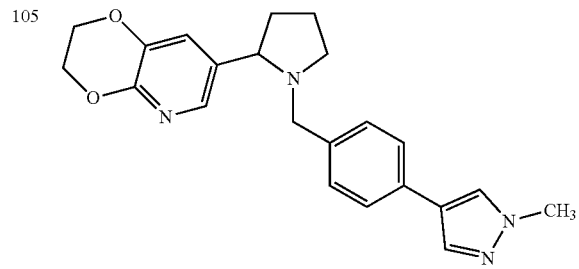 |
| 106 | 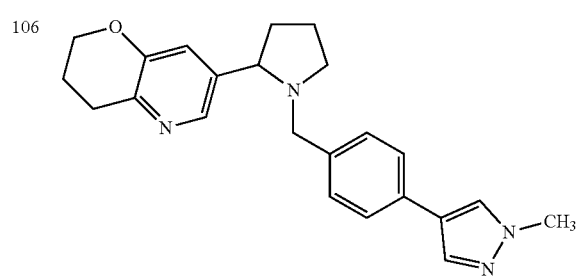 |
| 107 | 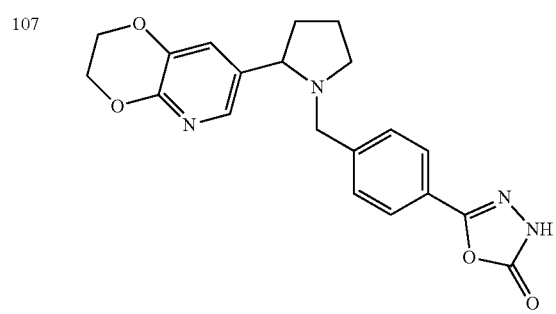 |
| 108 | 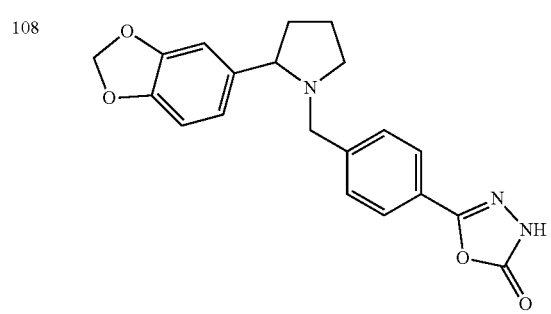 |
| 109 | 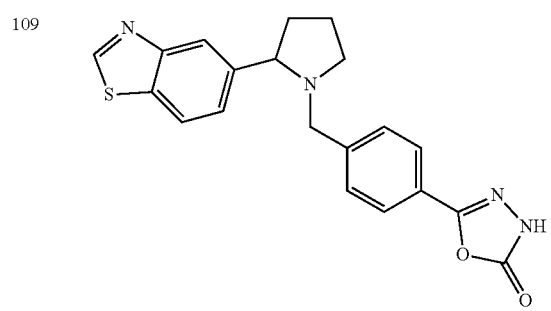 |
| No. | Structure |
|---|---|
| 110 | 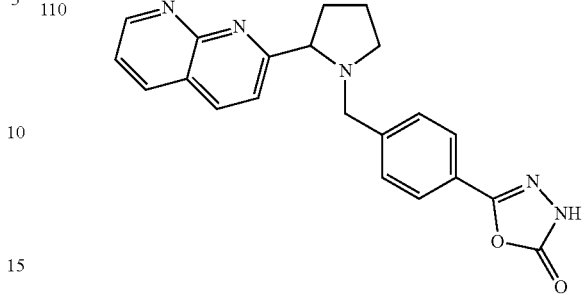 |
| 111 | 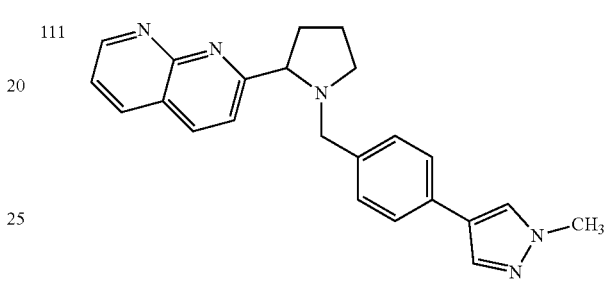 |
| 112 | 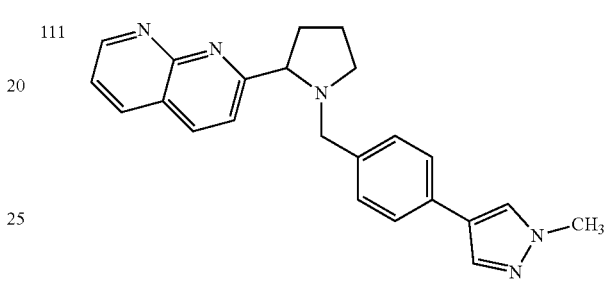 |
| 113 | 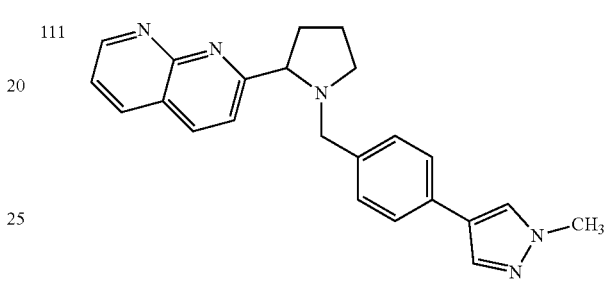 |
| 114 | 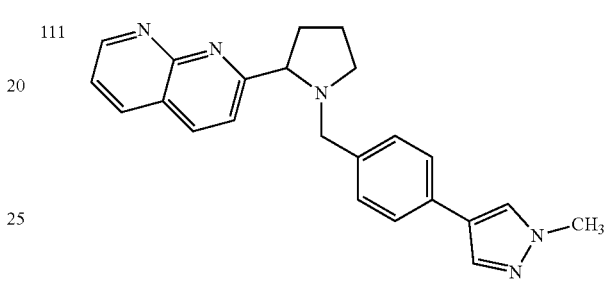 |

| No. | Structure |
|-----|-----------|
| 115 | 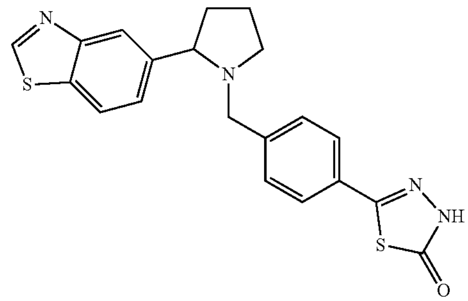 [SMILES: O=c1[nH]nc(-c2ccc(CN3CCCC3c3ccc4scnc4c3)cc2)s1] |
| 116 | 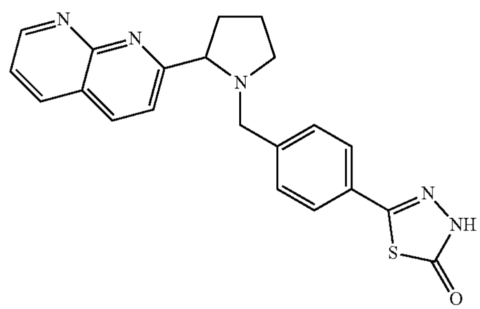 [SMILES: O=c1[nH]nc(-c2ccc(CN3CCCC3c3ccc4cccnc4n3)cc2)s1] |
| 117 | 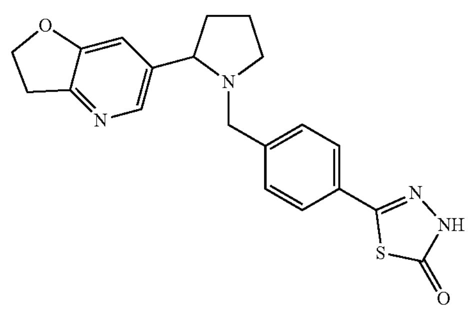 |
| 118 | 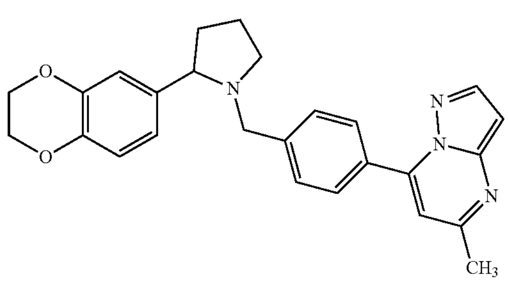 [SMILES: Cc1cc(-c2ccc(CN3CCCC3c3ccc4c(c3)OCCO4)cc2)n2nccc2n1] |
| 119 | 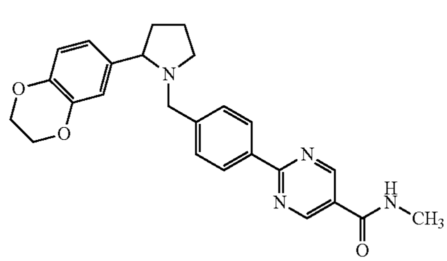 [SMILES: CNC(=O)c1cnc(-c2ccc(CN3CCCC3c3ccc4c(c3)OCCO4)cc2)nc1] |
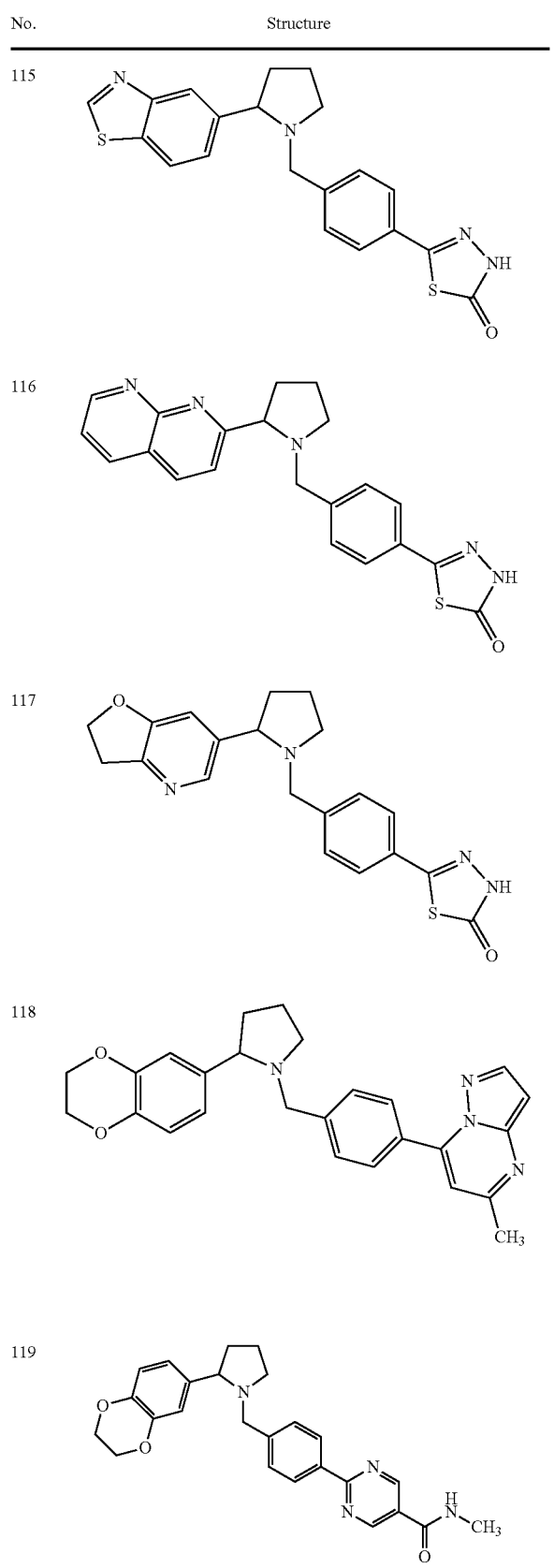
| No. | Structure |
|-----|-----------|
| 120 | 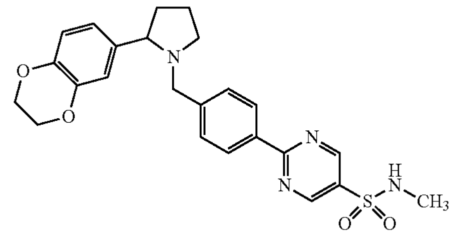 [SMILES: CNS(=O)(=O)c1cnc(-c2ccc(CN3CCCC3c3ccc4c(c3)OCCO4)cc2)nc1] |
| 121 | 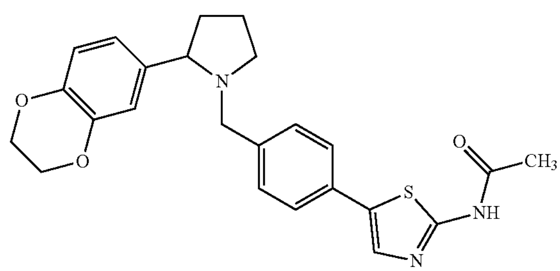 [SMILES: CC(=O)Nc1ncc(-c2ccc(CN3CCCC3c3ccc4c(c3)OCCO4)cc2)s1] |
| 122 | 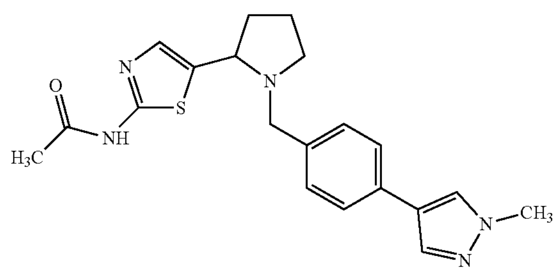 [SMILES: CC(=O)Nc1ncc(C2CCCN2Cc2ccc(-c3cnn(C)c3)cc2)s1] |
| 123 | 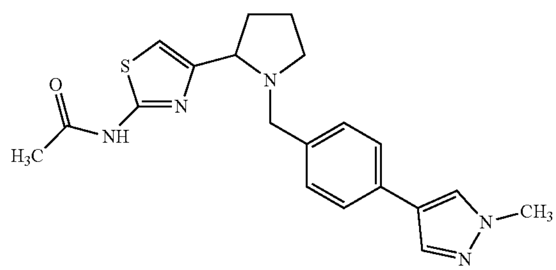 [SMILES: CC(=O)Nc1nc(C2CCCN2Cc2ccc(-c3cnn(C)c3)cc2)cs1] |
| 124 | 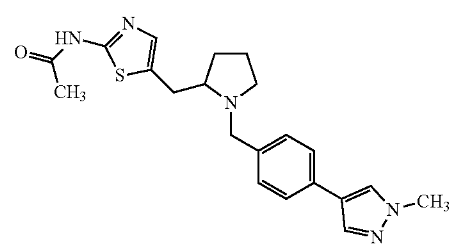 [SMILES: CC(=O)Nc1ncc(CC2CCCN2Cc2ccc(-c3cnn(C)c3)cc2)s1] |
| 125 | 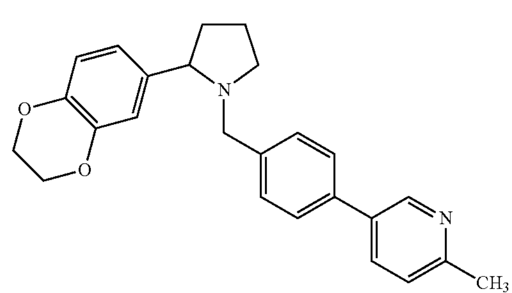 [SMILES: Cc1ccc(-c2ccc(CN3CCCC3c3ccc4c(c3)OCCO4)cc2)cn1] |
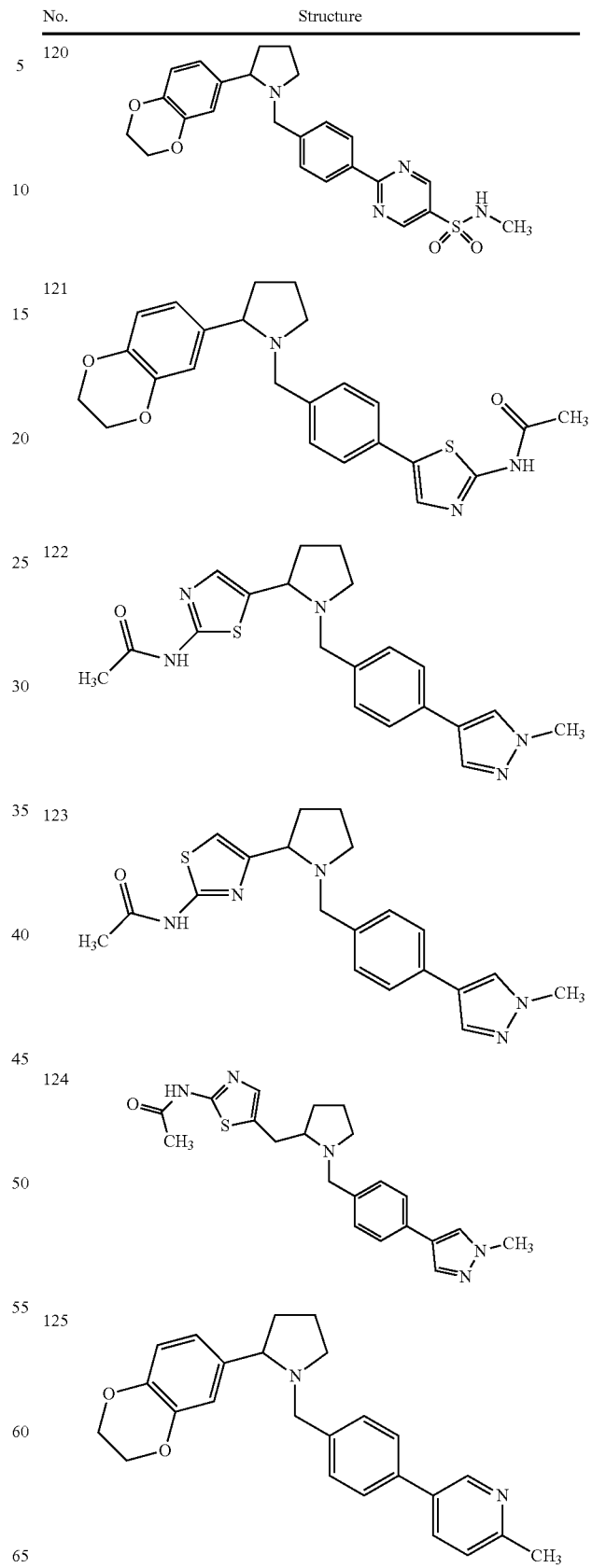

| No. | Structure |
|---|---|
| 126 | 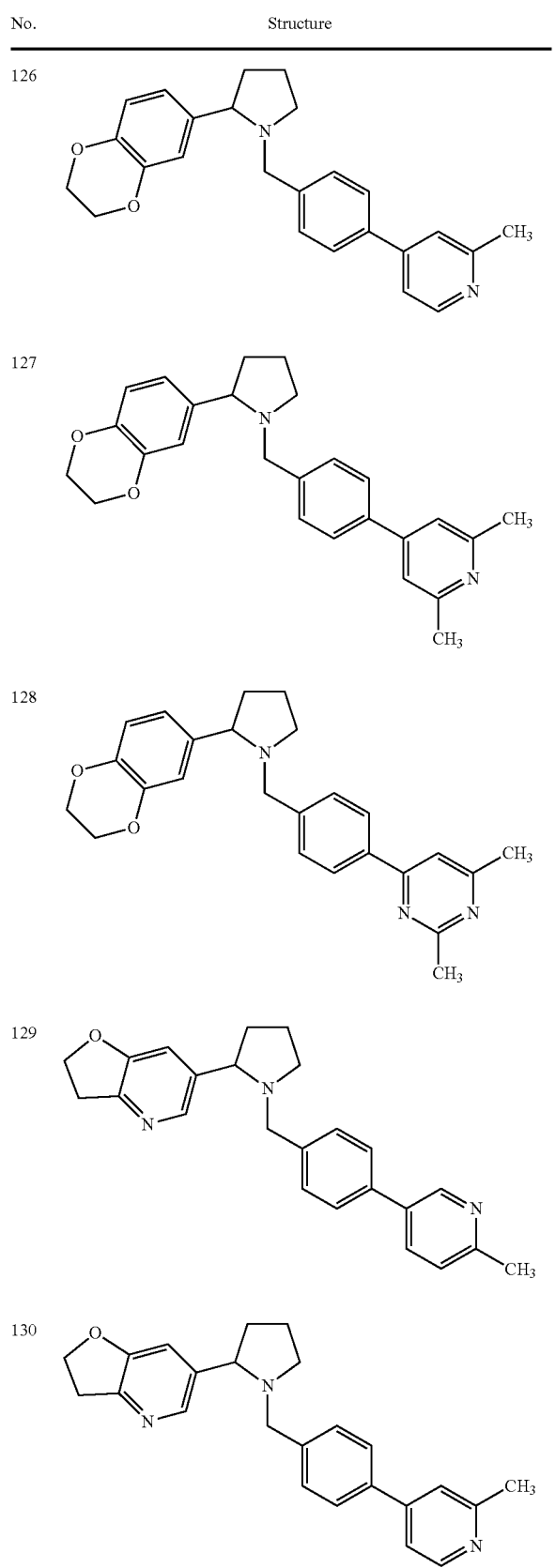 |
| 127 | |
| 128 | |
| 129 | |
| 130 | |
| No. | Structure |
|---|---|
| 131 | 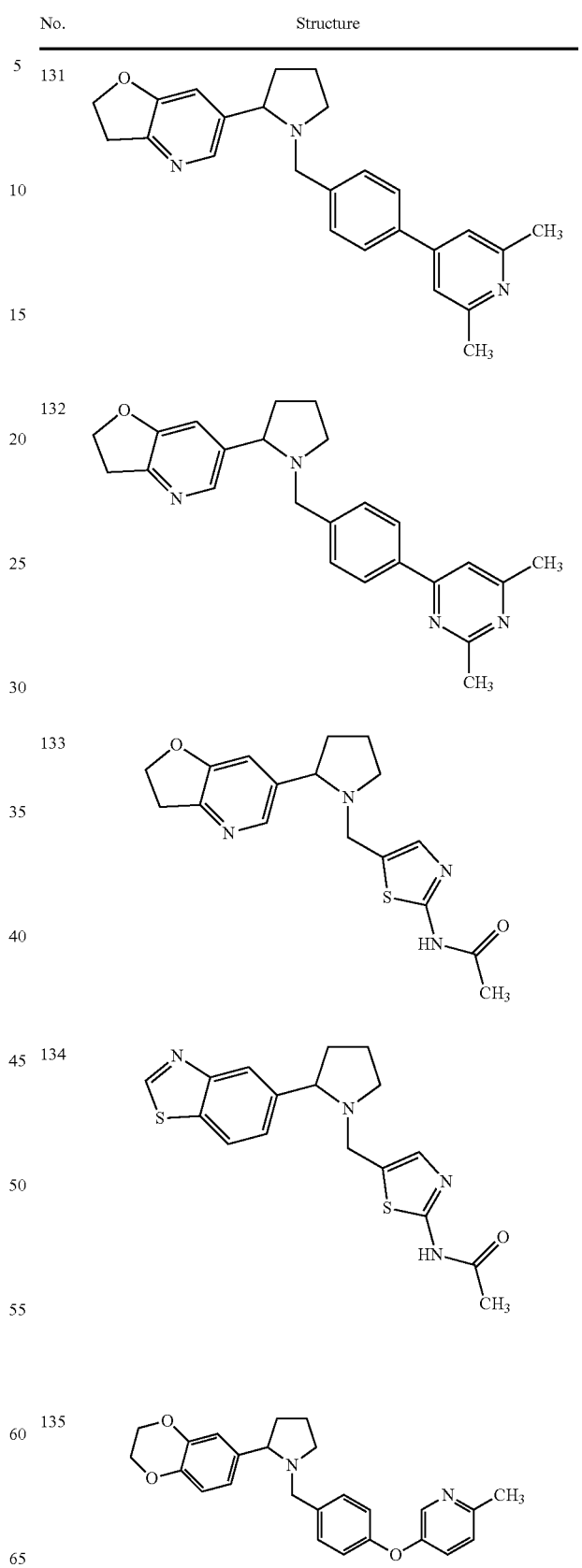 |
| 132 | |
| 133 | |
| 134 | |
| 135 | |

| No. | Structure |
|---|---|
| 136 | 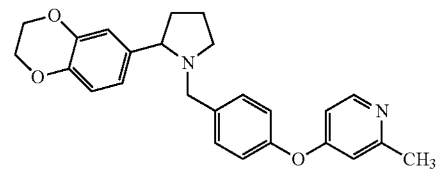 [SMILES: Cc1cc(Oc2ccc(CN3CCCC3c3ccc4c(c3)OCCO4)cc2)ccn1] |
| 137 | 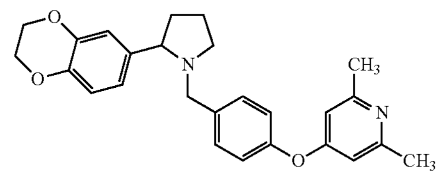 [SMILES: Cc1cc(Oc2ccc(CN3CCCC3c3ccc4c(c3)OCCO4)cc2)cc(C)n1] |
| 138 | 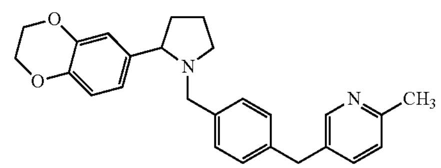 [SMILES: Cc1ccc(Cc2ccc(CN3CCCC3c3ccc4c(c3)OCCO4)cc2)cn1] |
| 139 | 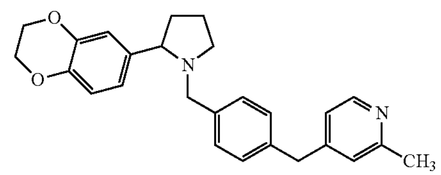 [SMILES: Cc1cc(Cc2ccc(CN3CCCC3c3ccc4c(c3)OCCO4)cc2)ccn1] |
| 140 | 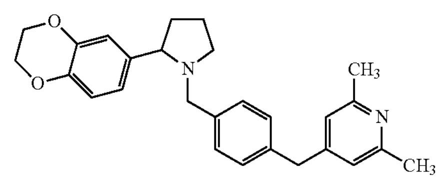 [SMILES: Cc1cc(Cc2ccc(CN3CCCC3c3ccc4c(c3)OCCO4)cc2)cc(C)n1] |
| 141 | 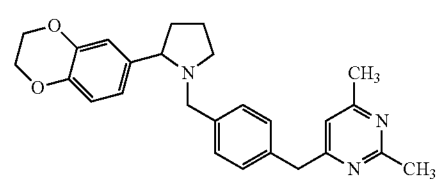 [SMILES: Cc1cc(Cc2ccc(CN3CCCC3c3ccc4c(c3)OCCO4)cc2)nc(C)n1] |
| 142 | 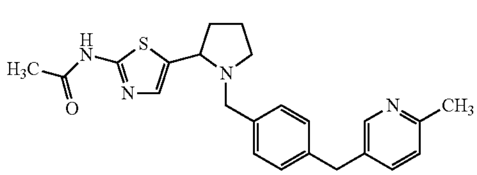 [SMILES: CC(=O)Nc1ncc(C2CCCN2Cc2ccc(Cc3ccc(C)nc3)cc2)s1] |
| 143 | 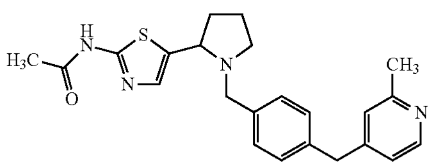 [SMILES: CC(=O)Nc1ncc(C2CCCN2Cc2ccc(Cc3ccnc(C)c3)cc2)s1] |

| No. | Structure |
|---|---|
| 144 | 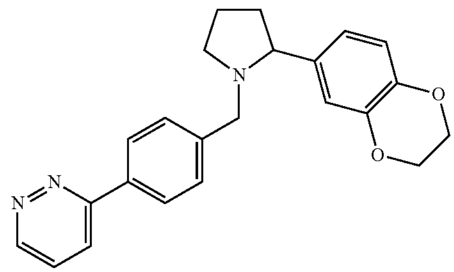 [SMILES: c1cnnc(-c2ccc(CN3CCCC3c3ccc4c(c3)OCCO4)cc2)c1] |
| 146 | 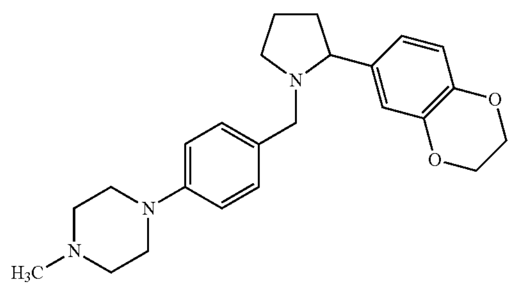 [SMILES: CN1CCN(c2ccc(CN3CCCC3c3ccc4c(c3)OCCO4)cc2)CC1] |
| 147 | 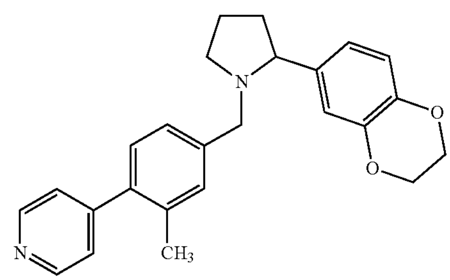 [SMILES: Cc1cc(CN2CCCC2c2ccc3c(c2)OCCO3)ccc1-c1ccncc1] |

355
-continued
| No. | Structure |
|---|---|
| 149 | 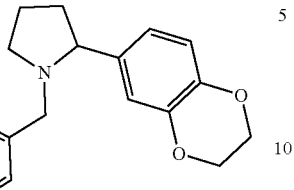 |
| 150 | 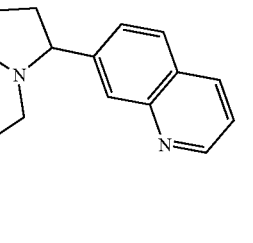 |
| 151 | 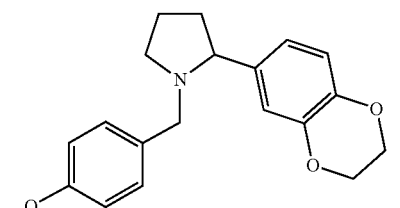 |
| 152 | 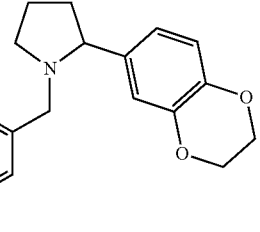 |
| 153 | 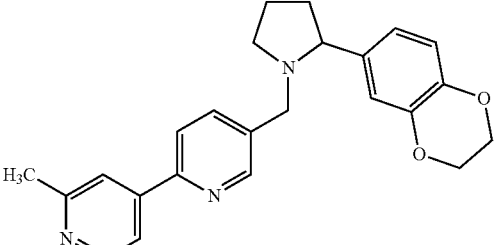 |
356
-continued
| No. | Structure |
|---|---|
| 154 | 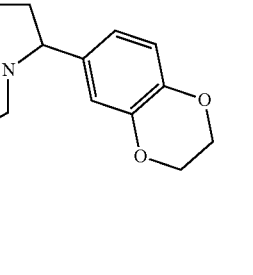 |
| 155 | 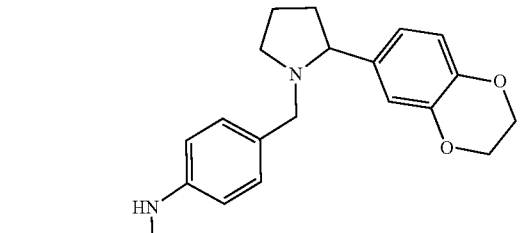 |
| 156 | 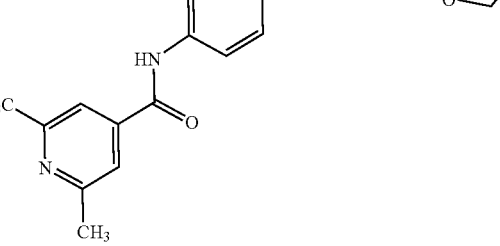 |
| 157 | 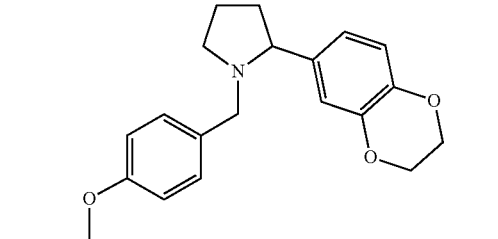 |

| No. | Structure |
|---|---|
| 158 | 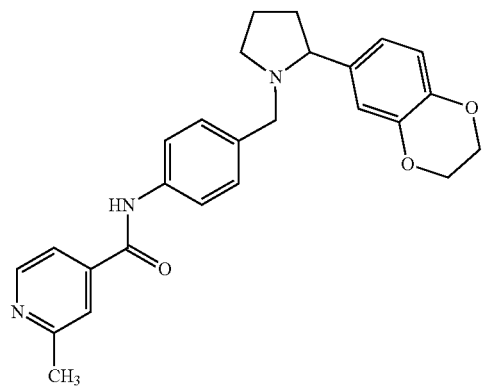 [SMILES: Cc1cc(C(=O)Nc2ccc(CN3CCCC3c3ccc4c(c3)OCCO4)cc2)ccn1] |
| 159 | 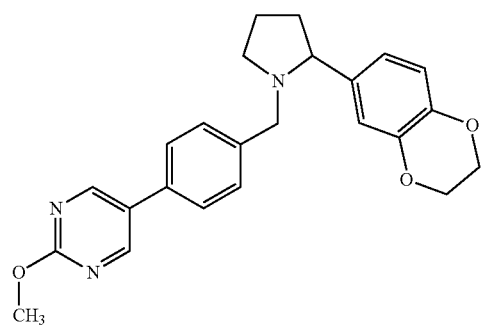 [SMILES: COc1ncc(-c2ccc(CN3CCCC3c3ccc4c(c3)OCCO4)cc2)cn1] |
| 160 | 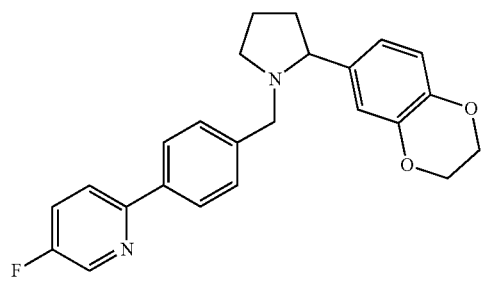 [SMILES: Fc1ccc(-c2ccc(CN3CCCC3c3ccc4c(c3)OCCO4)cc2)nc1] |
| 161 | 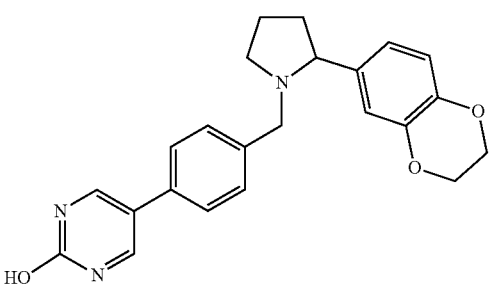 [SMILES: Oc1ncc(-c2ccc(CN3CCCC3c3ccc4c(c3)OCCO4)cc2)cn1] |
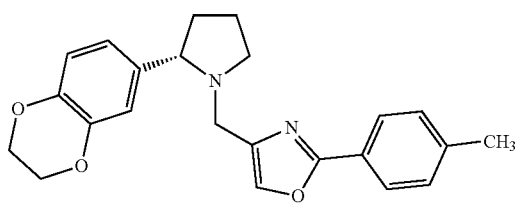
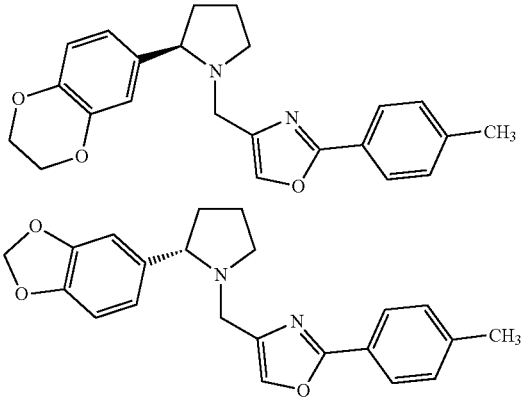
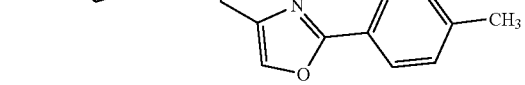
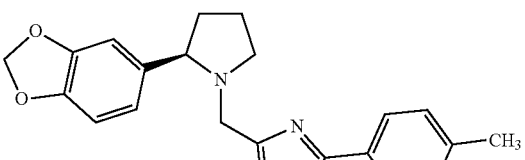
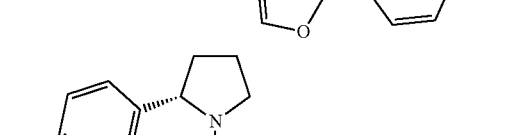
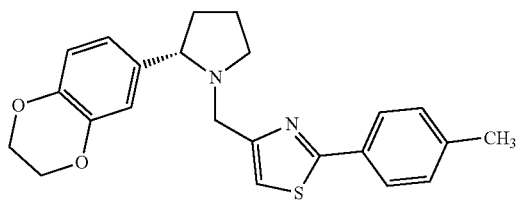
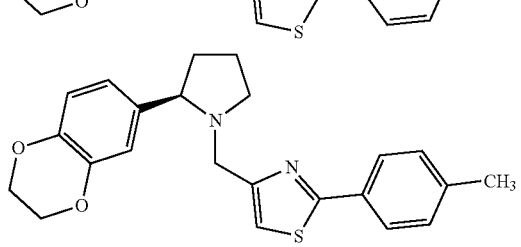
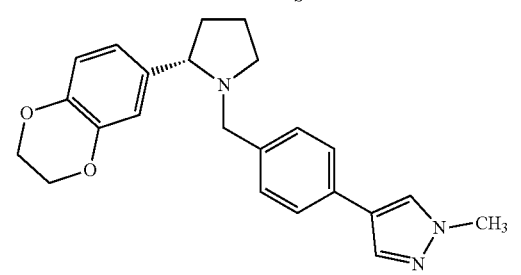
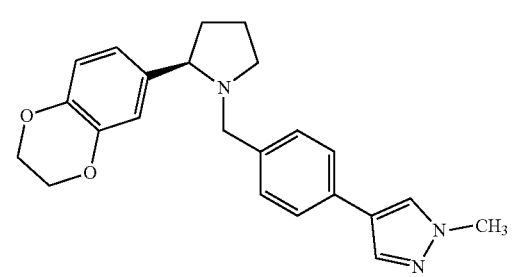

359
-continued
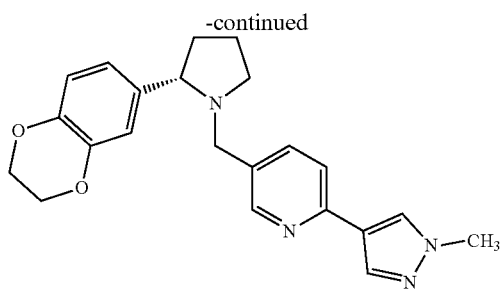
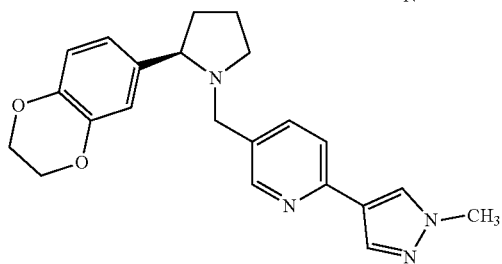
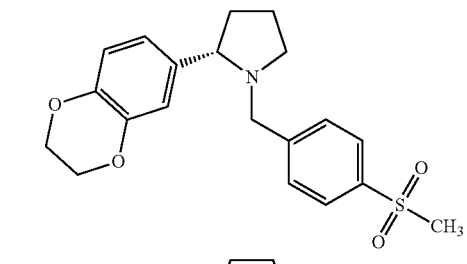
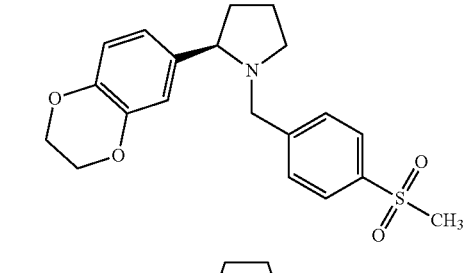
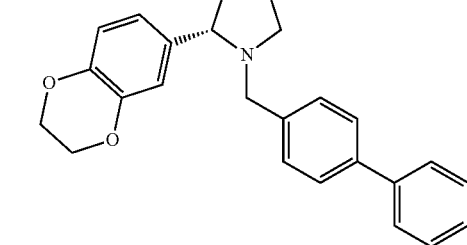
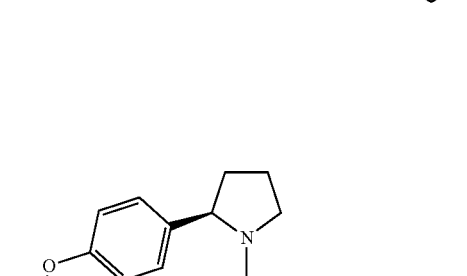
360
-continued
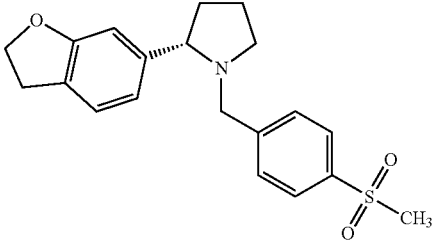
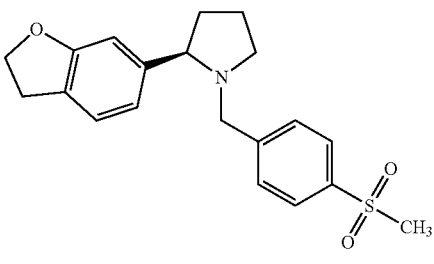
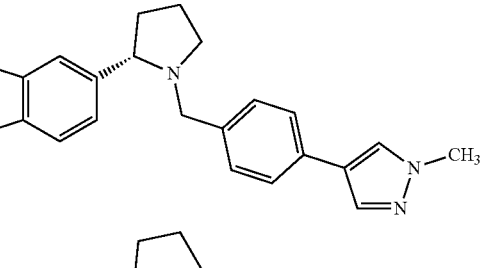
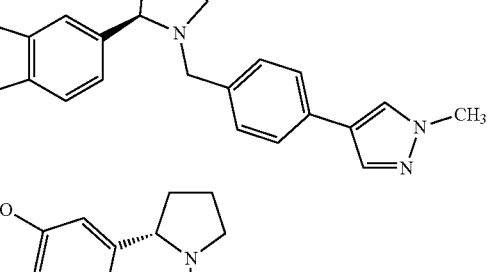
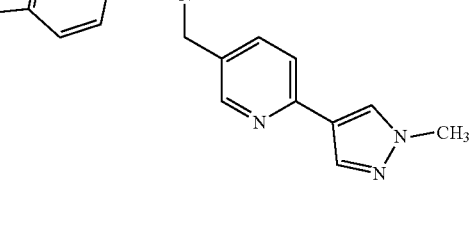
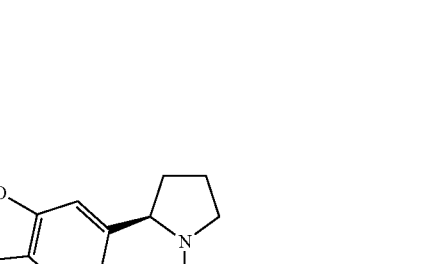

361
-continued
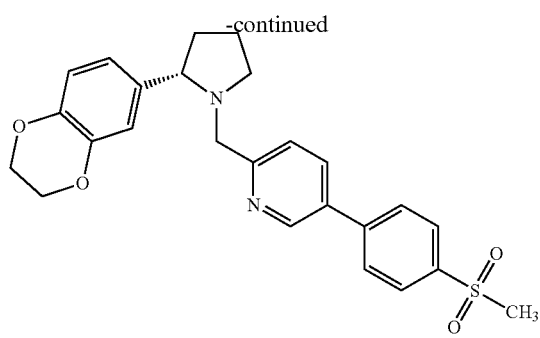
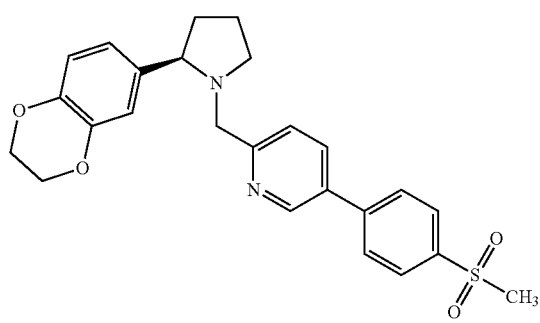
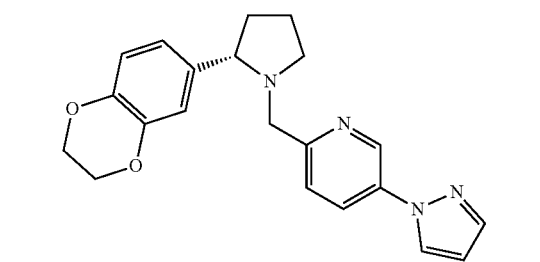
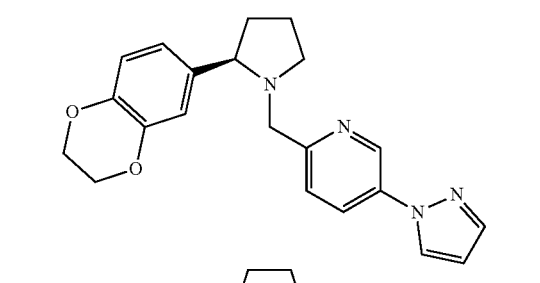
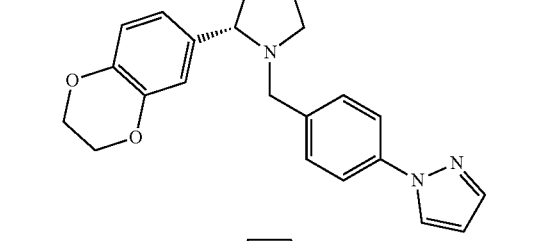
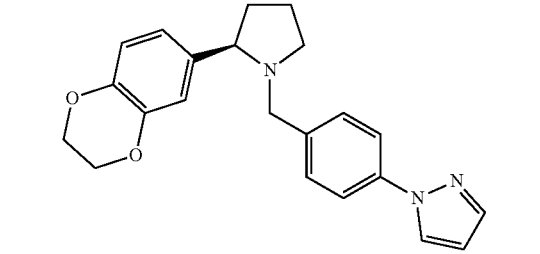
362
-continued
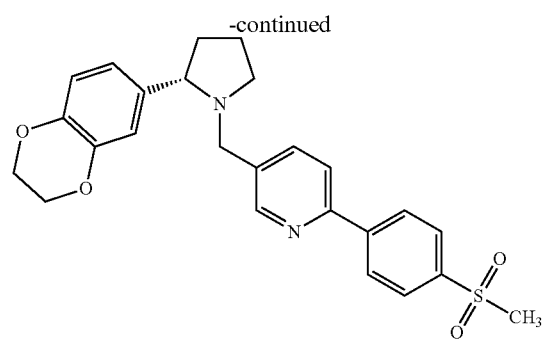
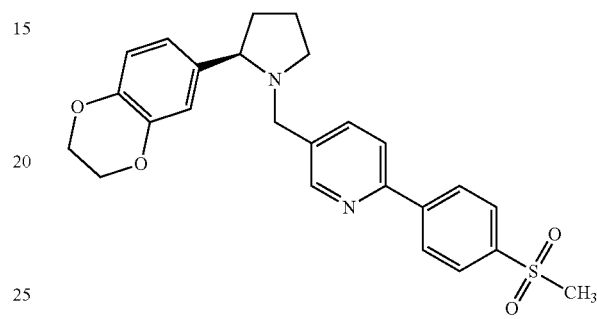
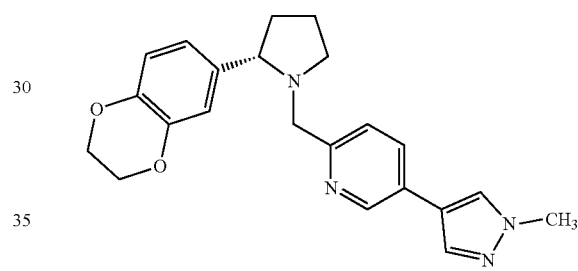
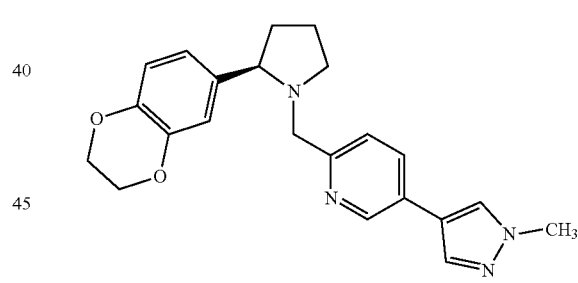
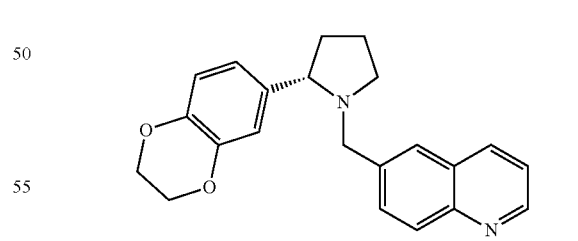
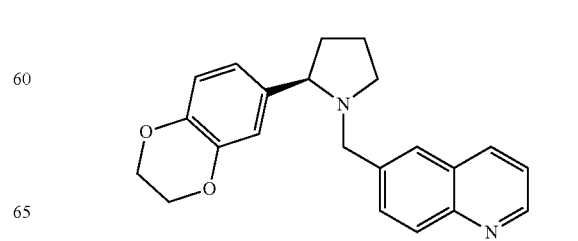

363
-continued
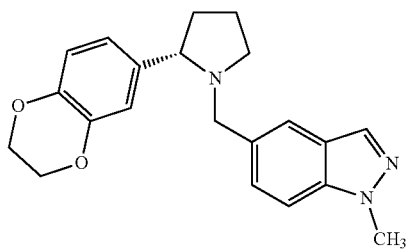
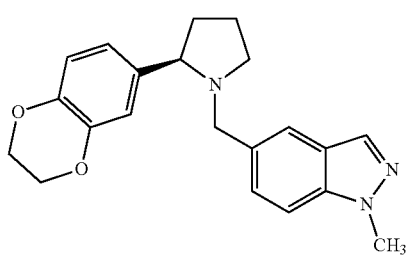
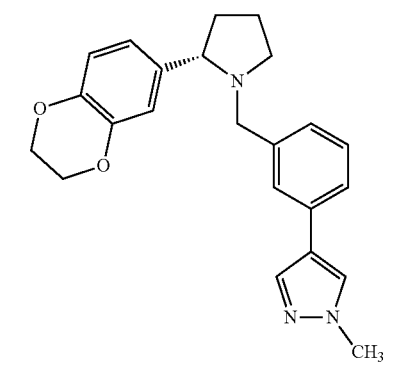
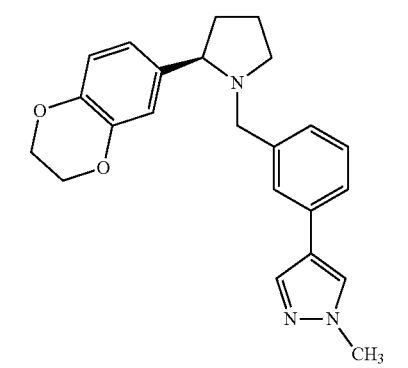
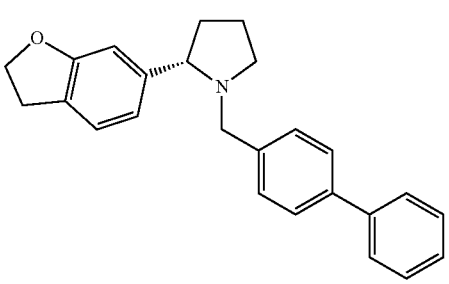
364
-continued
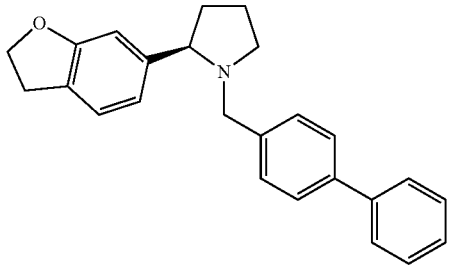
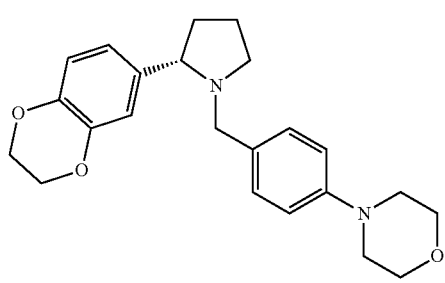
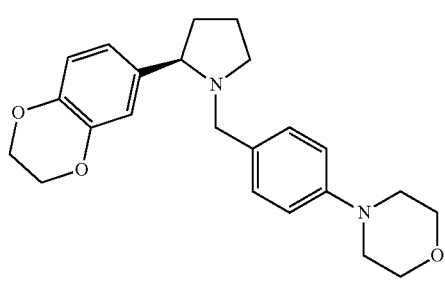
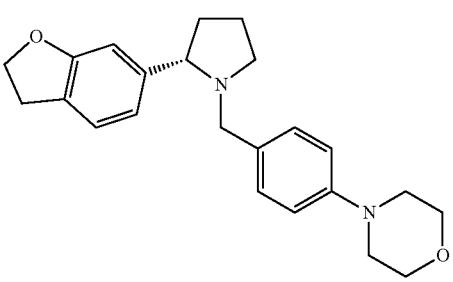
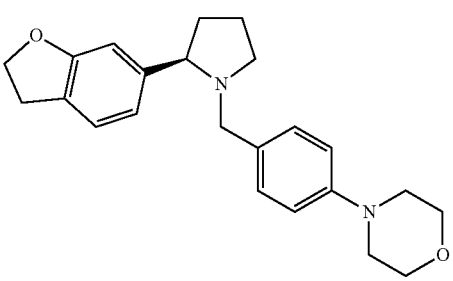
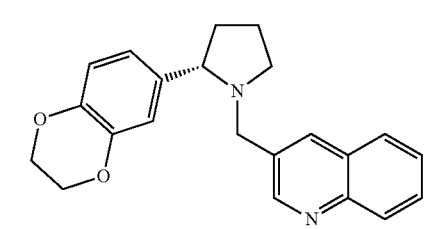

365
-continued
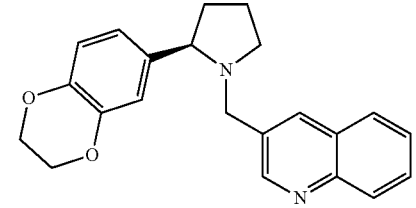
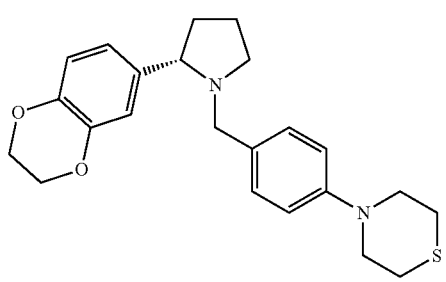
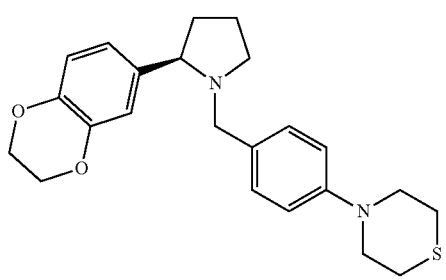
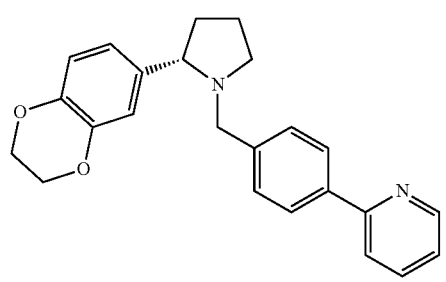
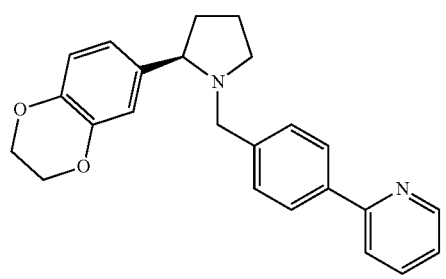
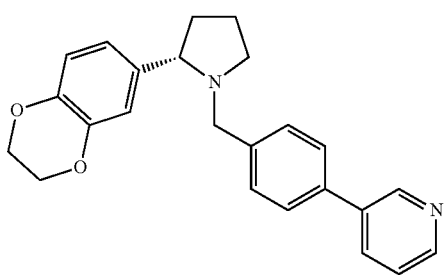
366
-continued
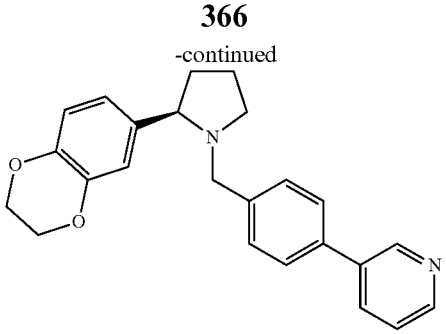
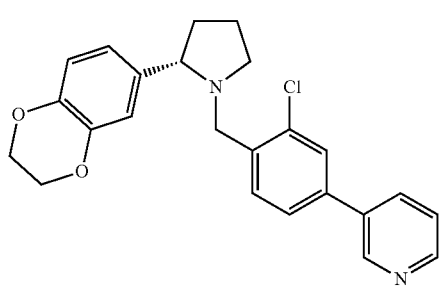
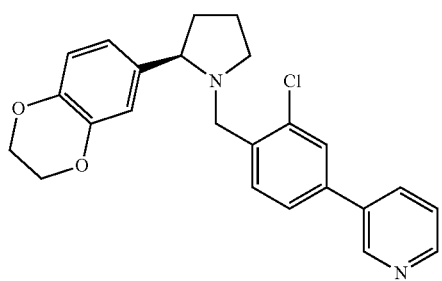
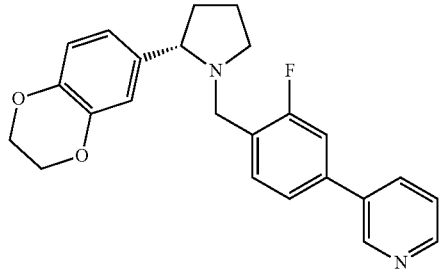
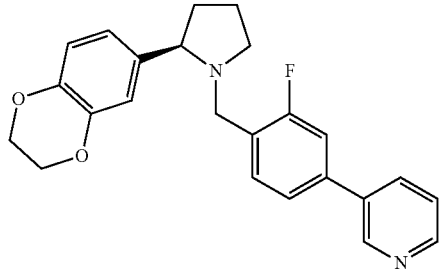
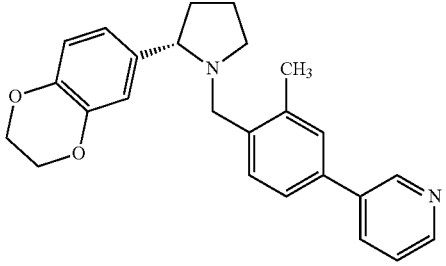

-continued
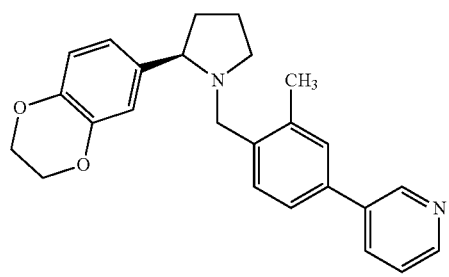
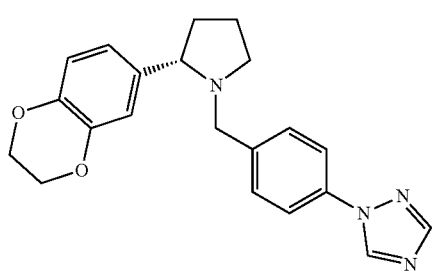
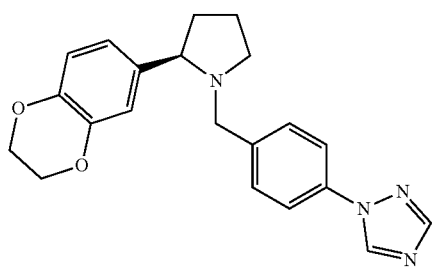
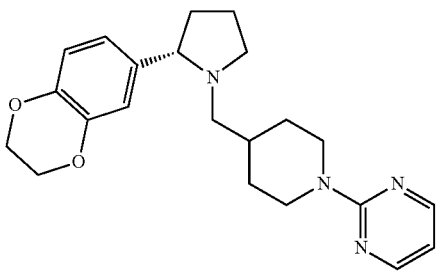
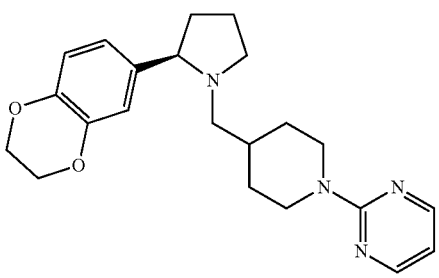
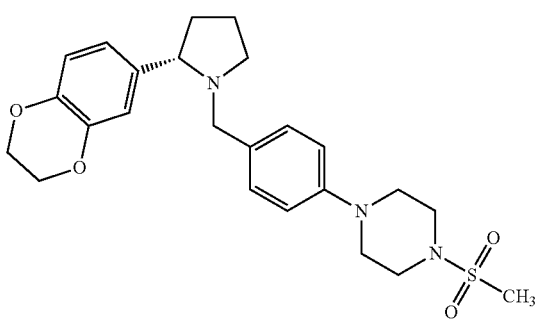
-continued
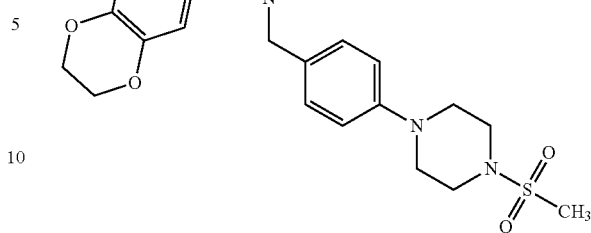
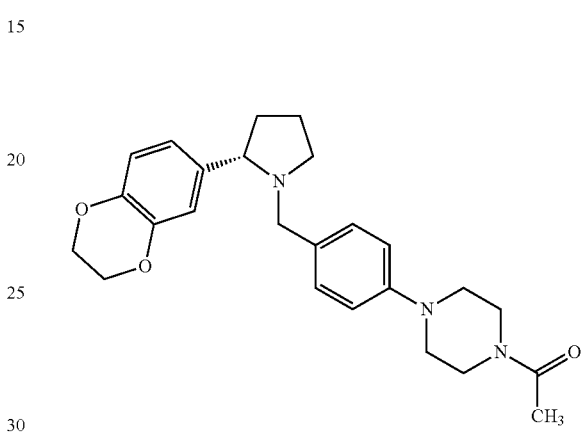
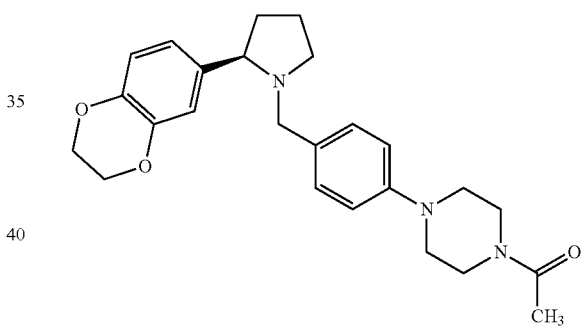
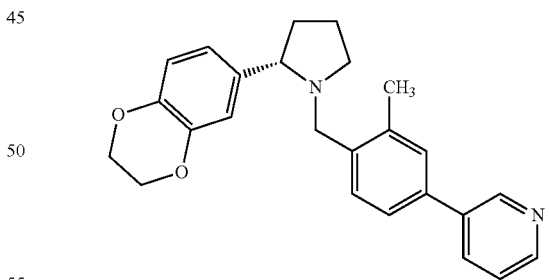
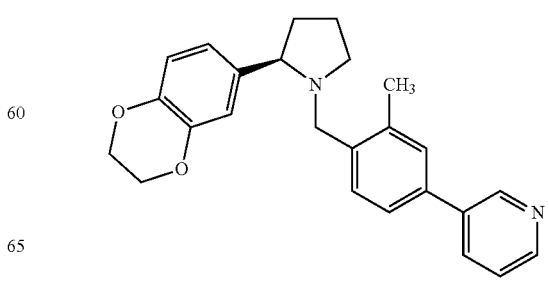

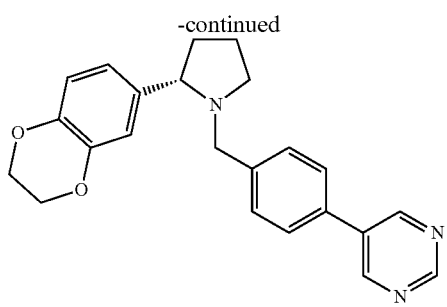
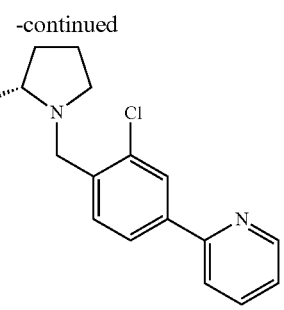
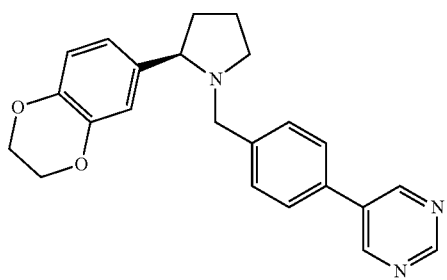
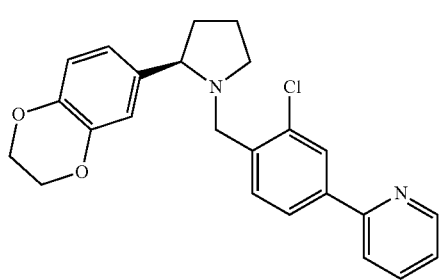
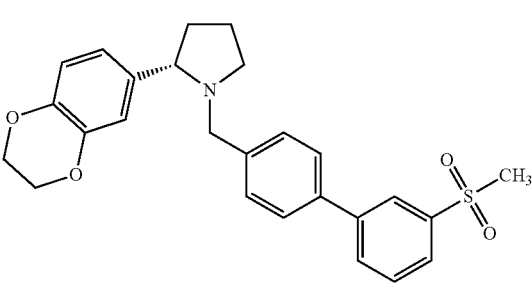
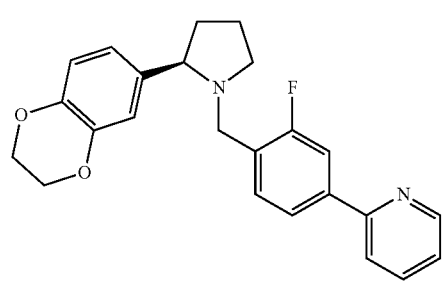
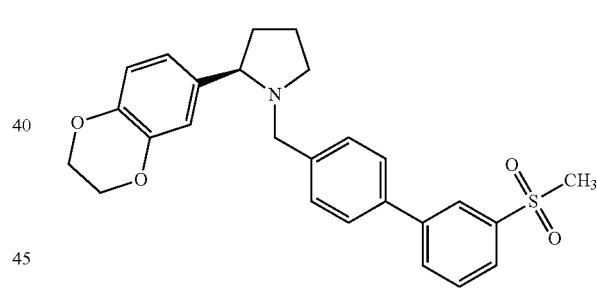
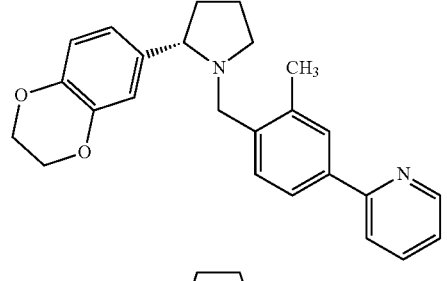
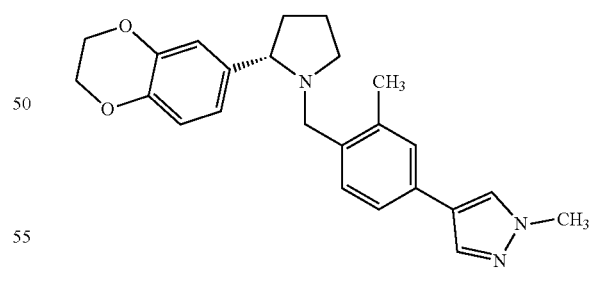
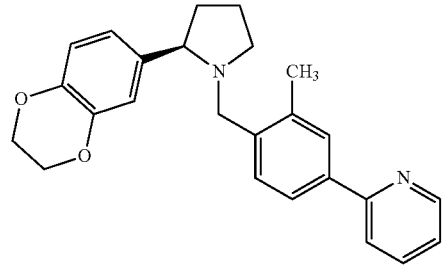
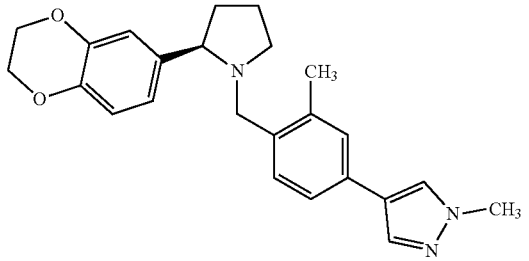

371
-continued
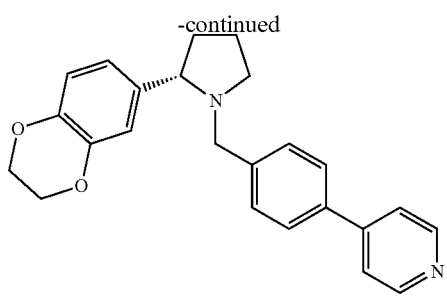
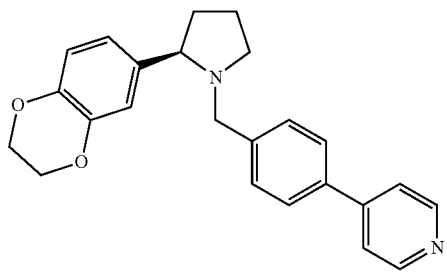
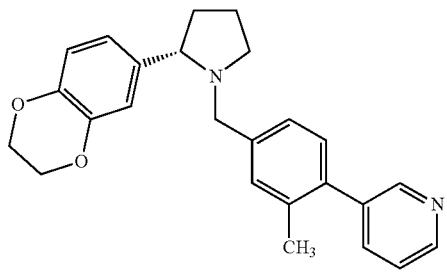
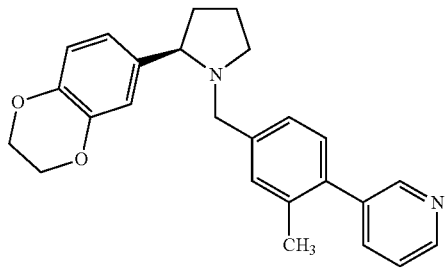
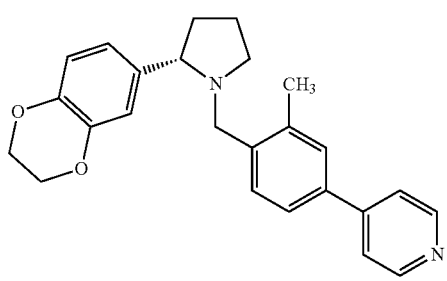
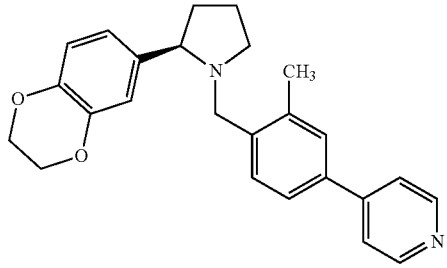
372
-continued
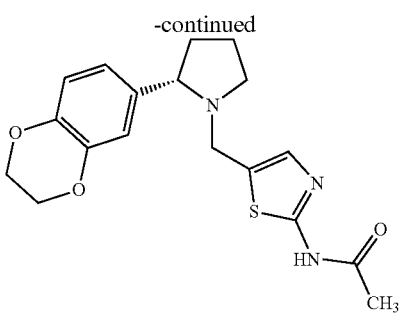
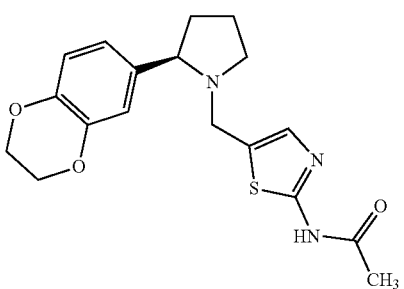
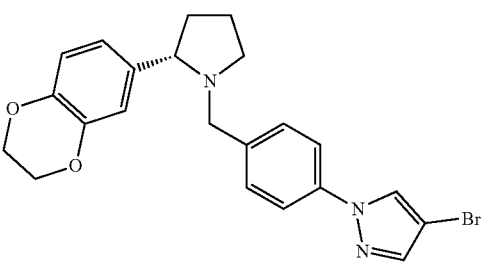
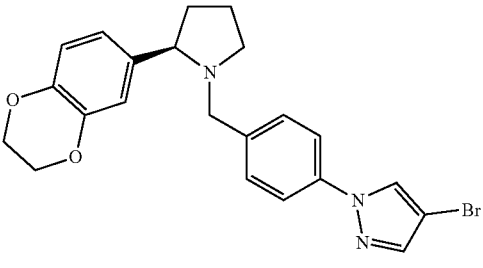
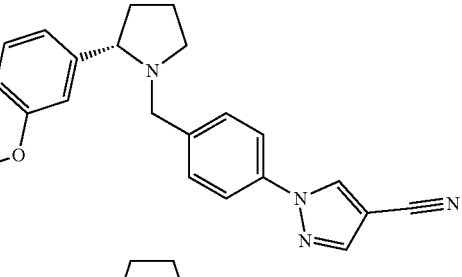
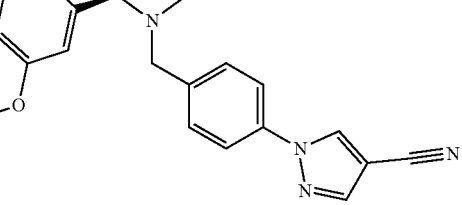

373
-continued
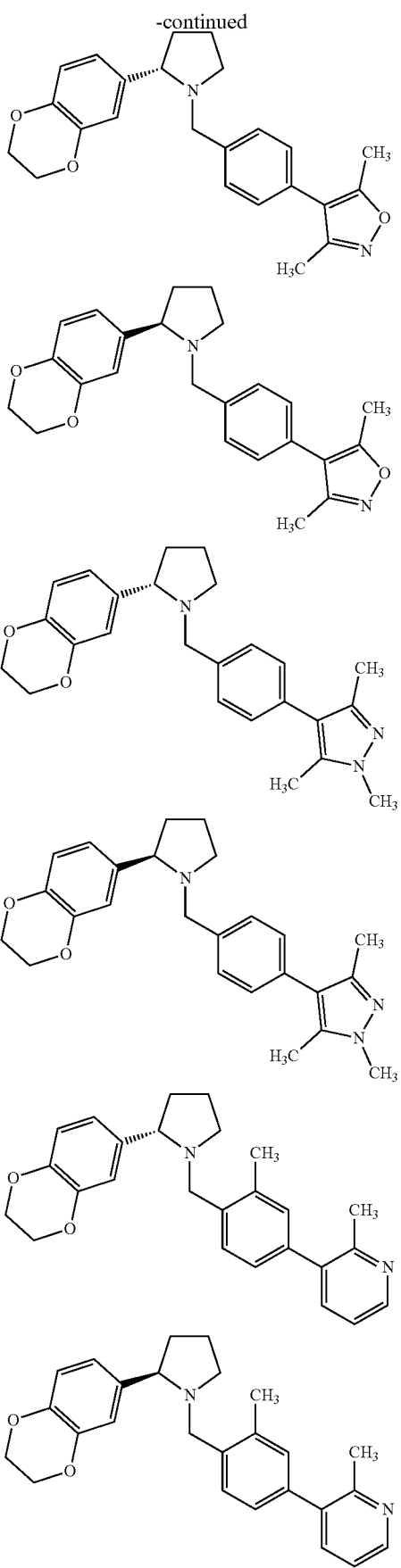
374
-continued
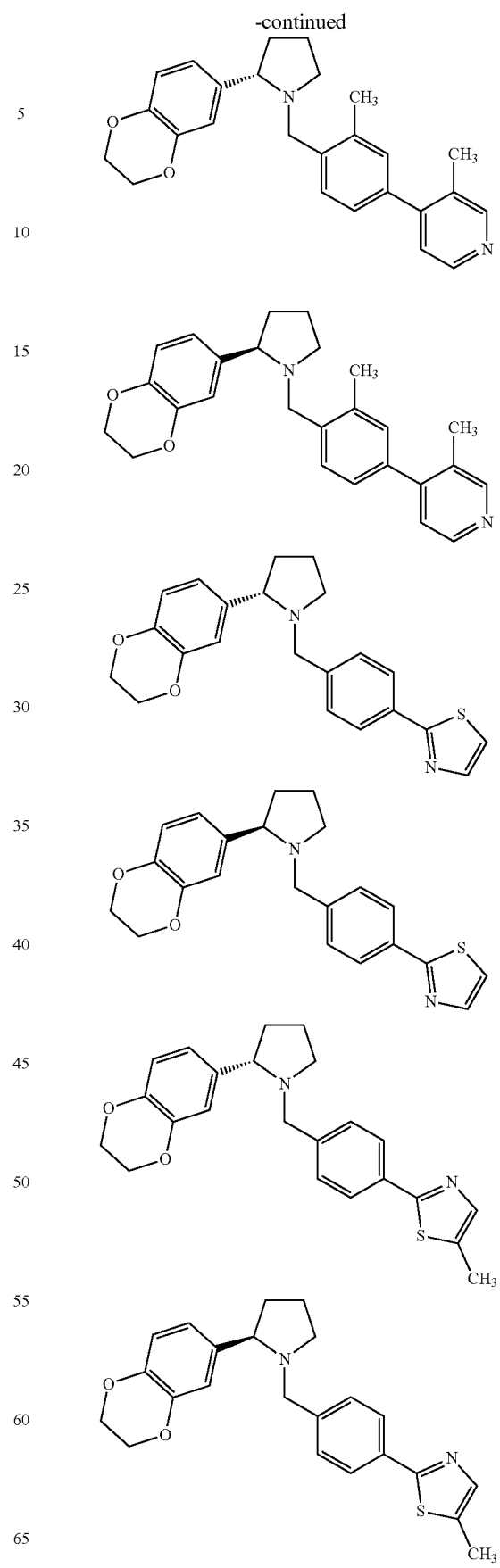

375
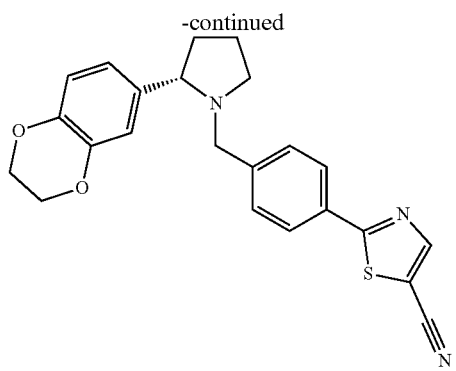
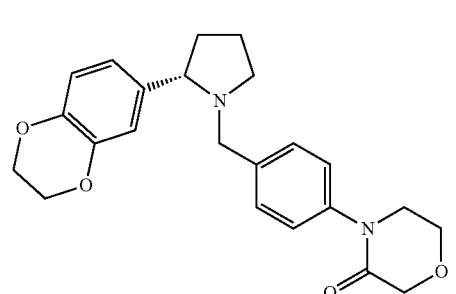
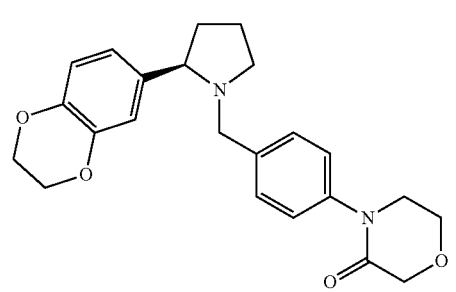
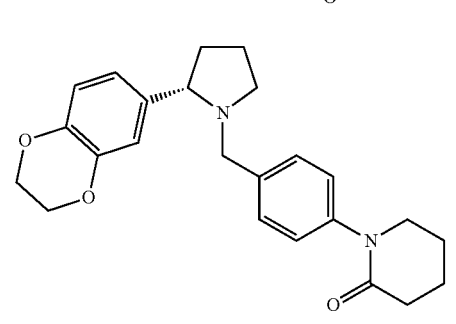
376
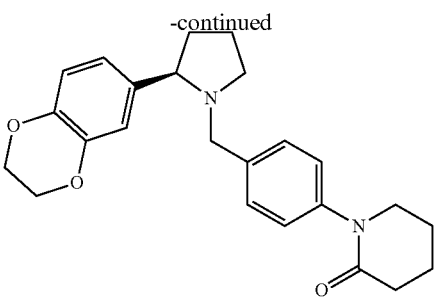
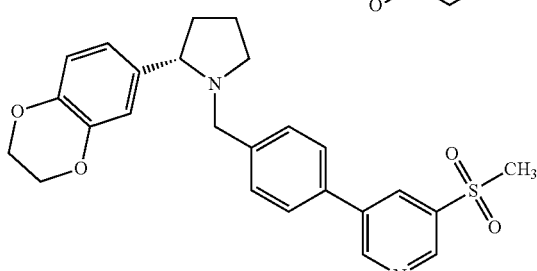
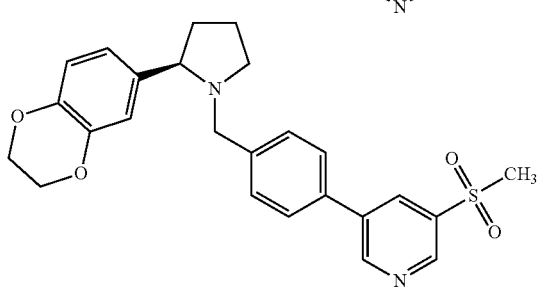
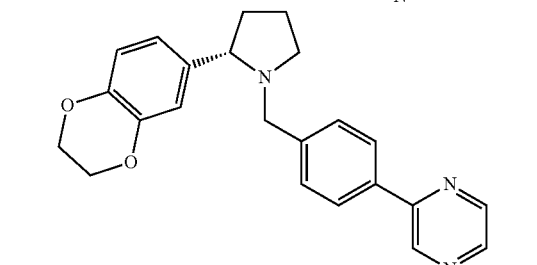
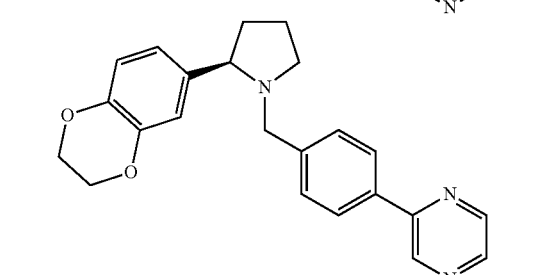
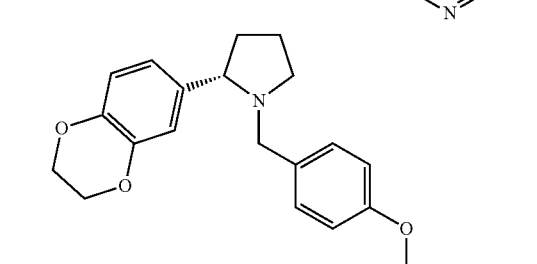

377
-continued
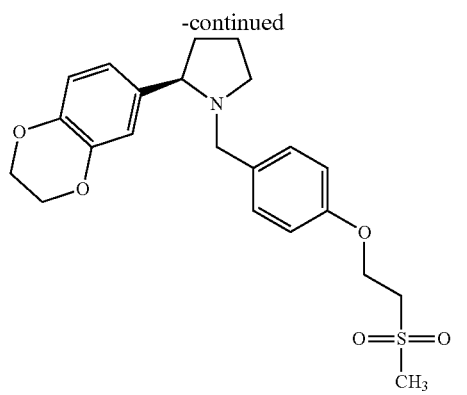
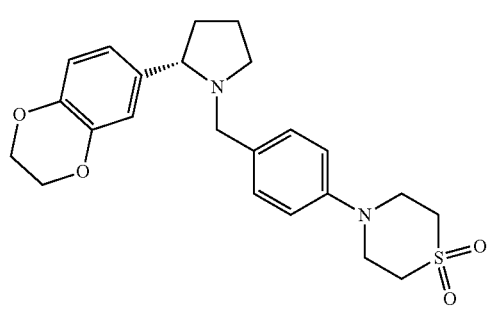
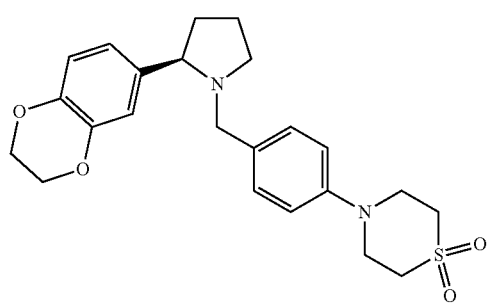
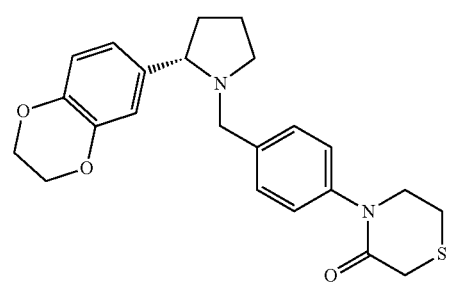
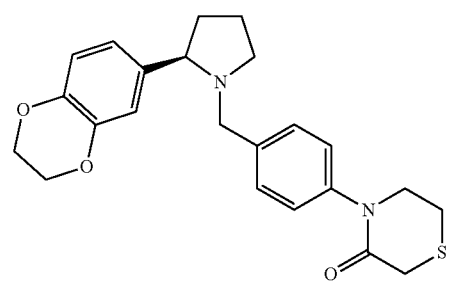
378
-continued
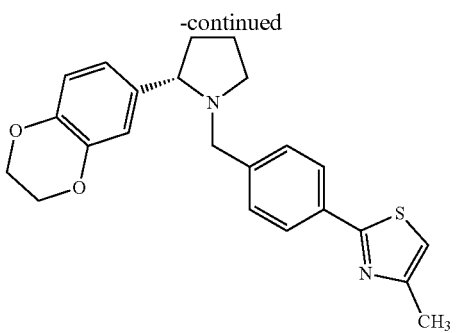
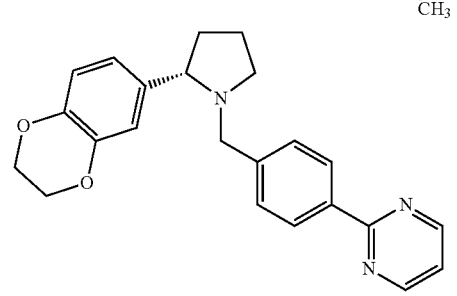
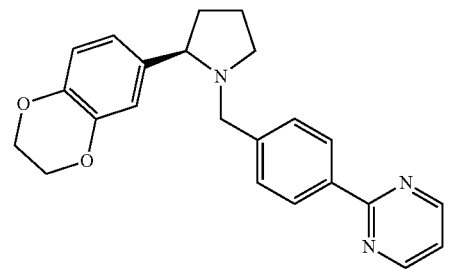
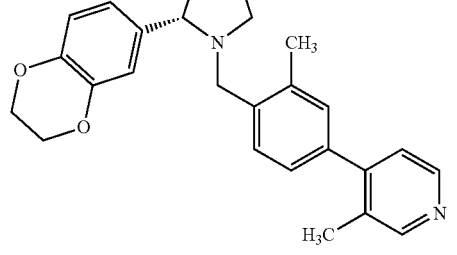
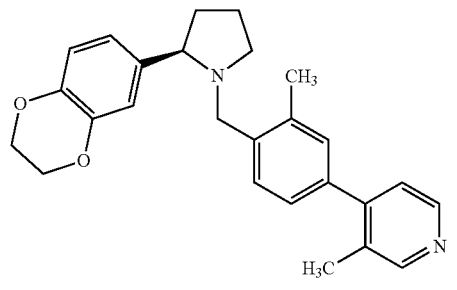

379
-continued
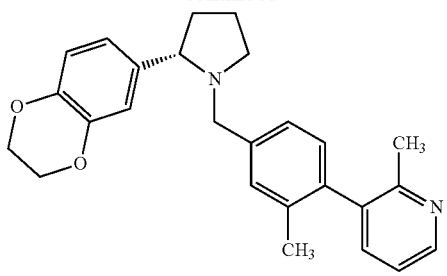
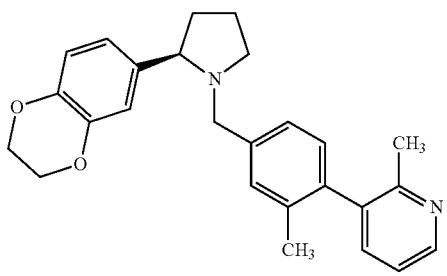
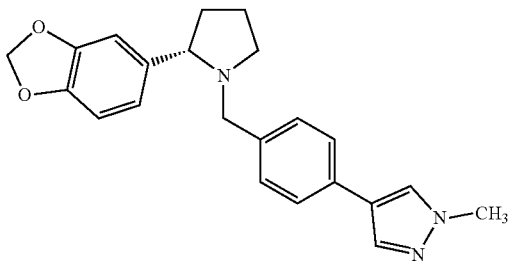
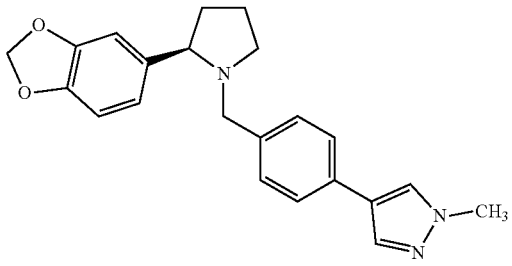
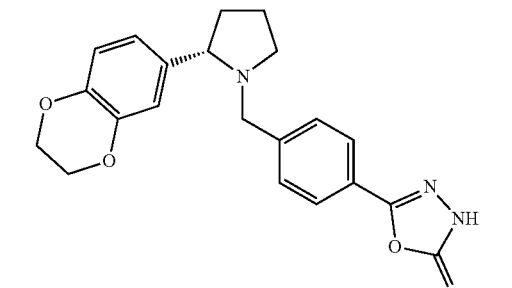
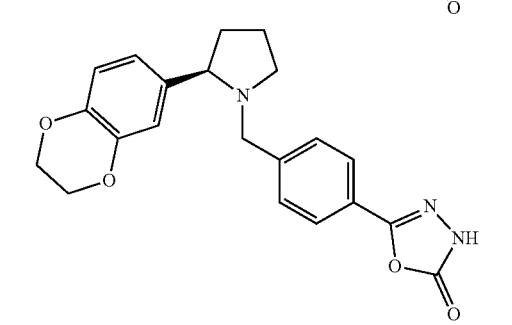
380
-continued
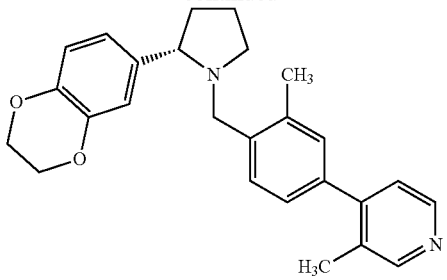
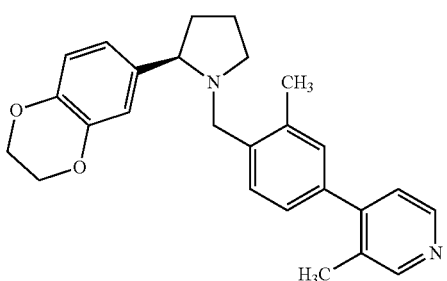
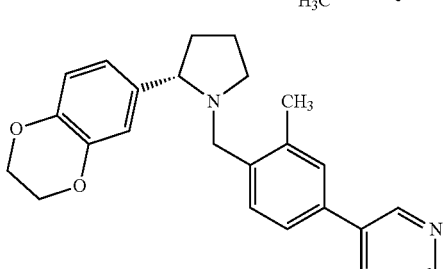
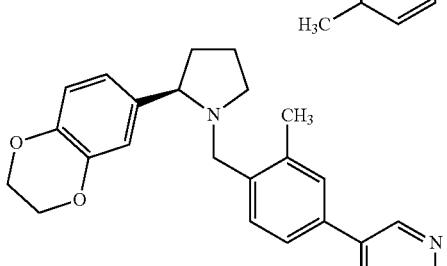
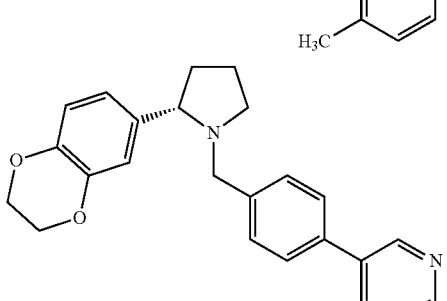
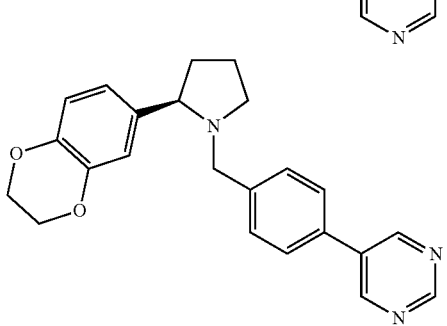

381
-continued
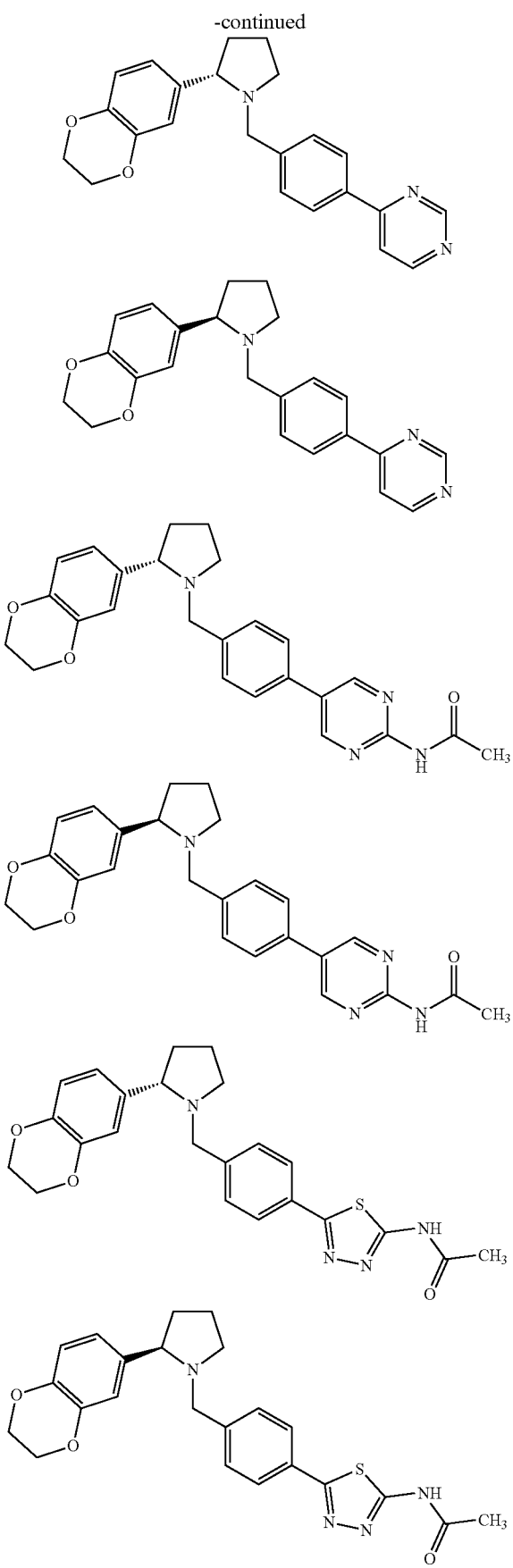
382
-continued
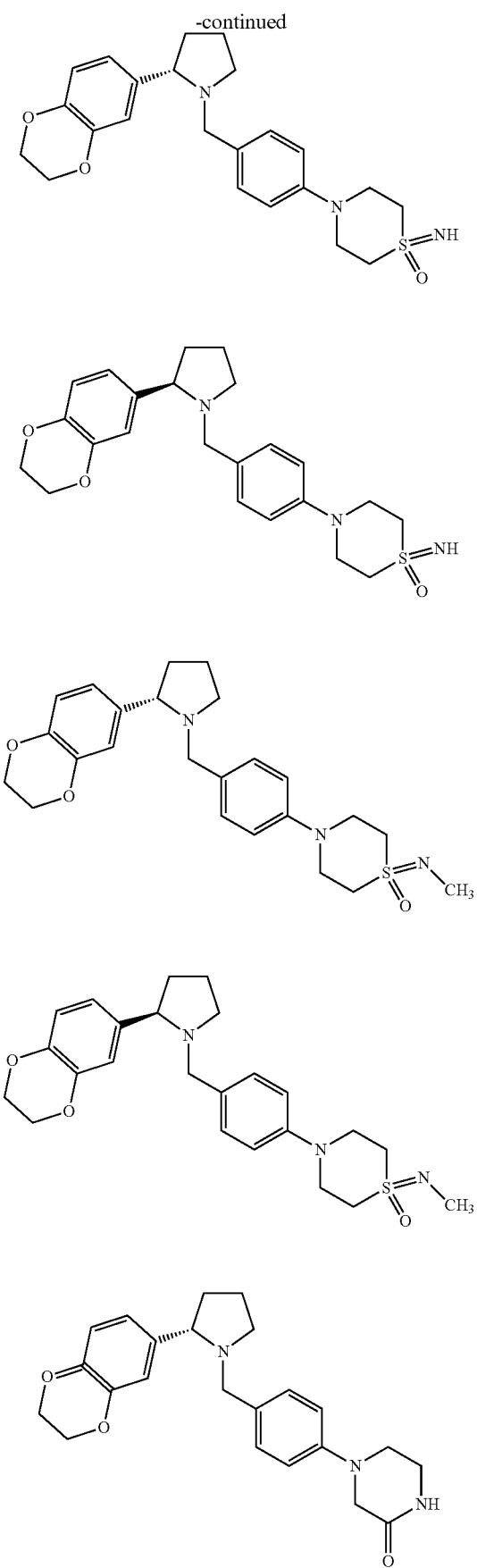

383
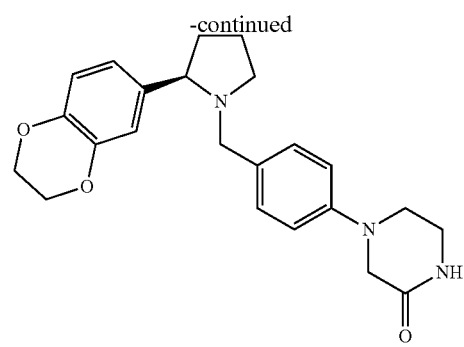
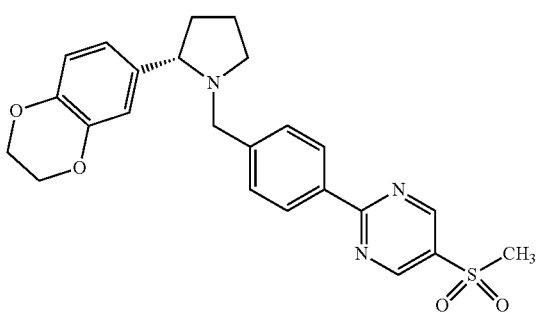
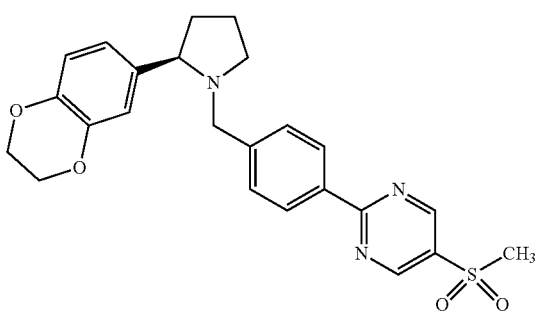
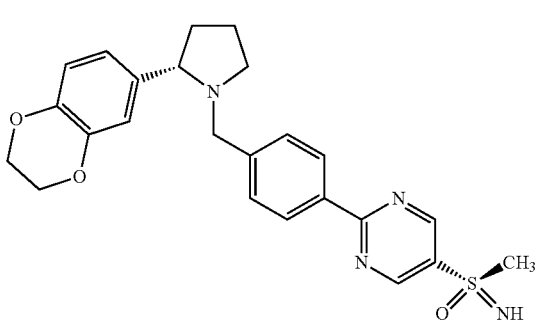
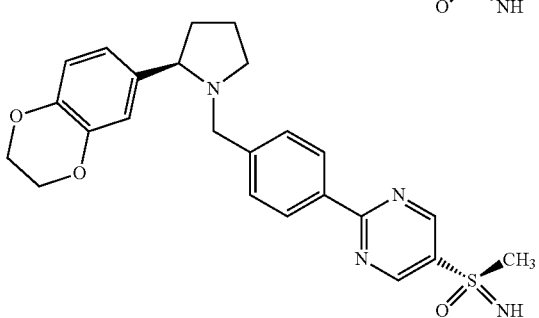
384
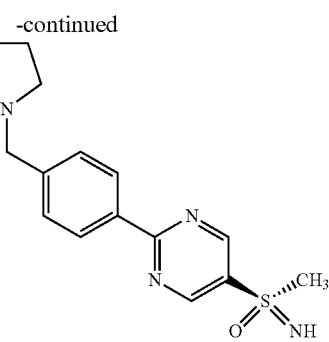
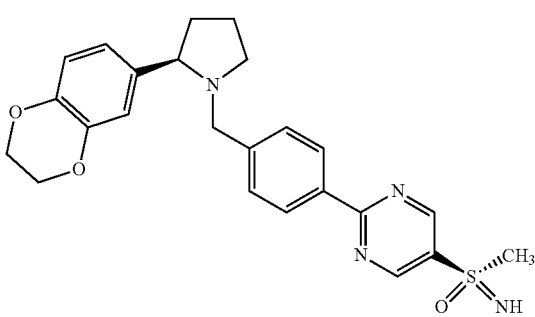
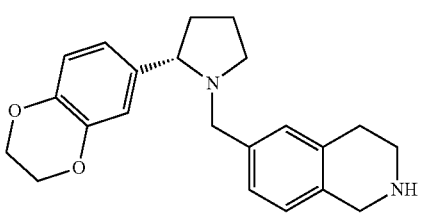
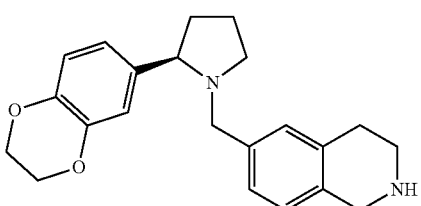
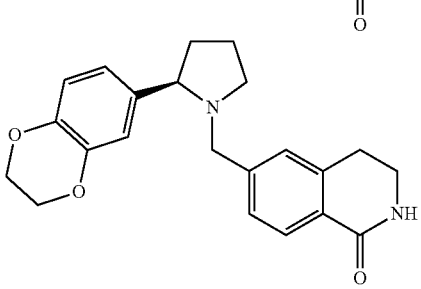

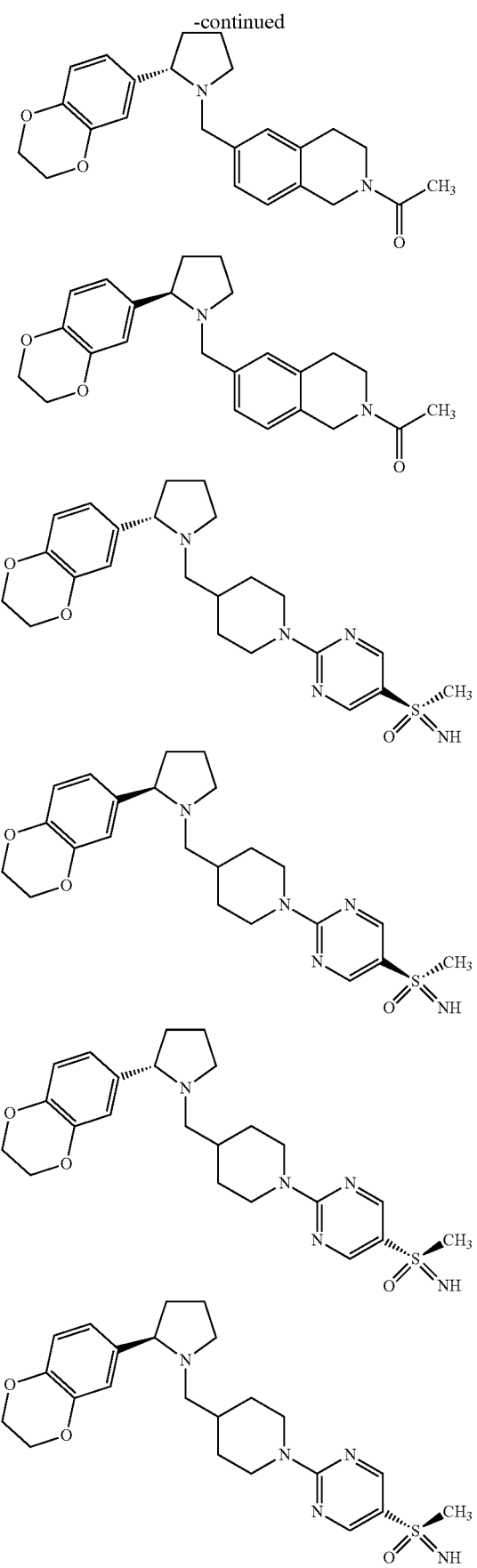
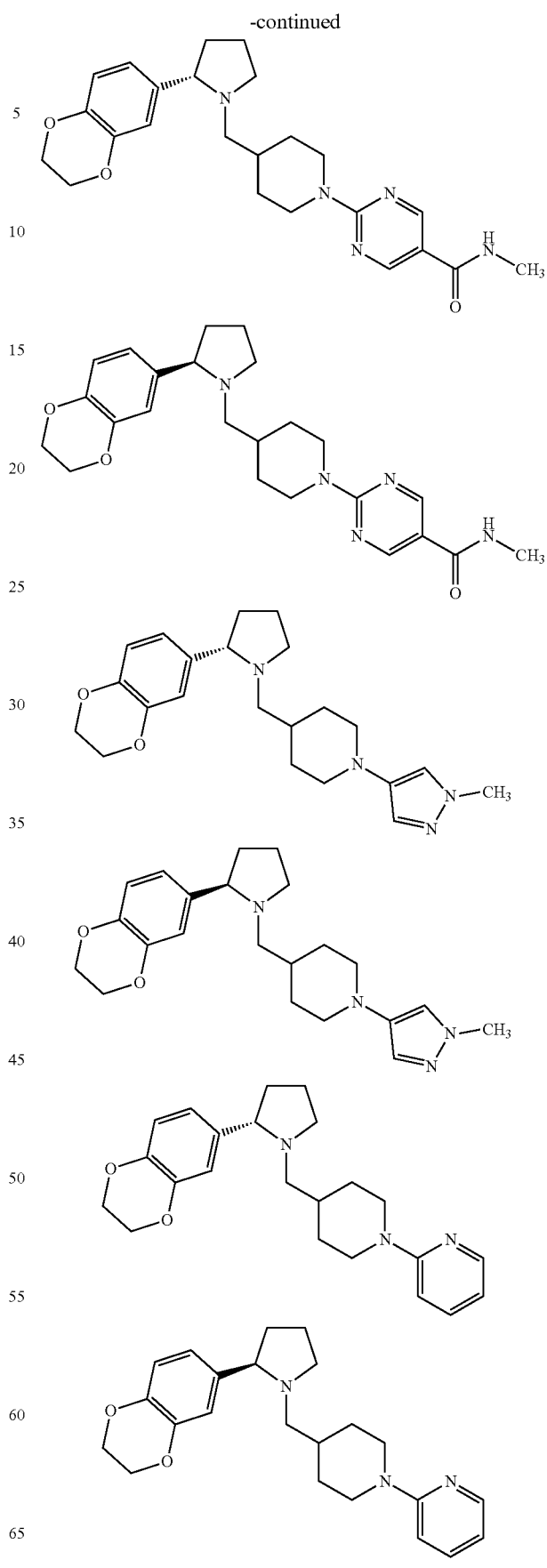

387
-continued
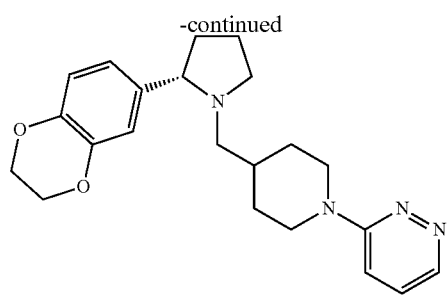
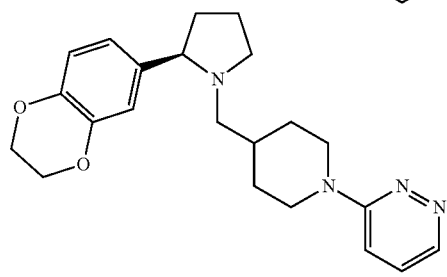
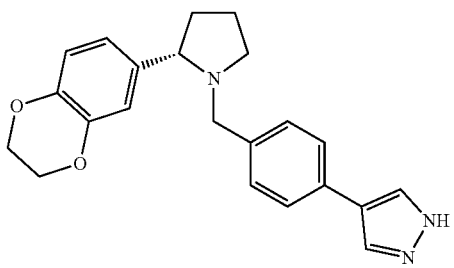
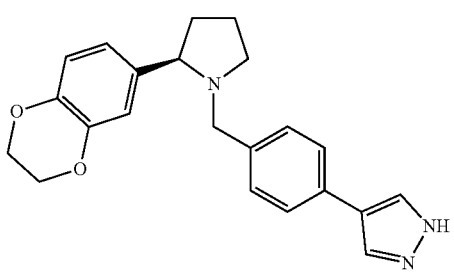
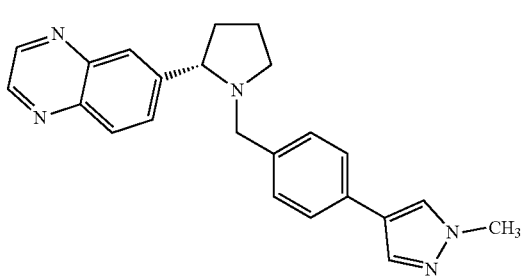
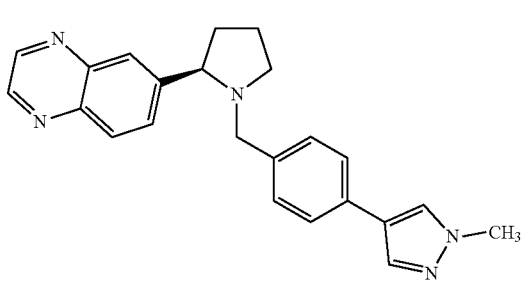
388
-continued
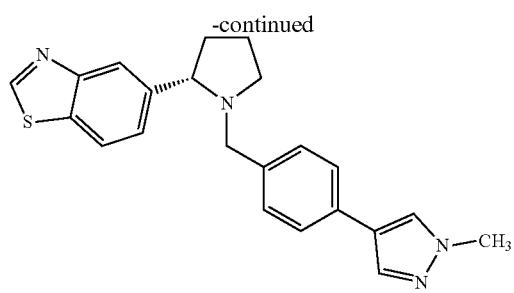
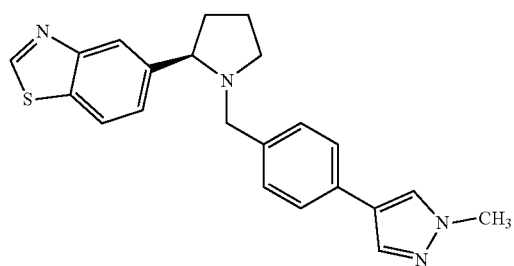
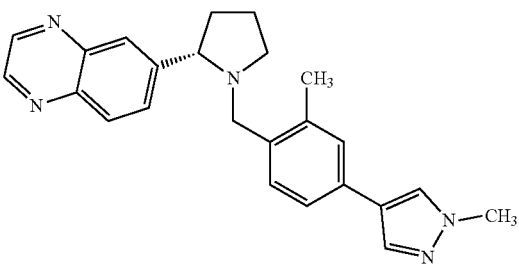
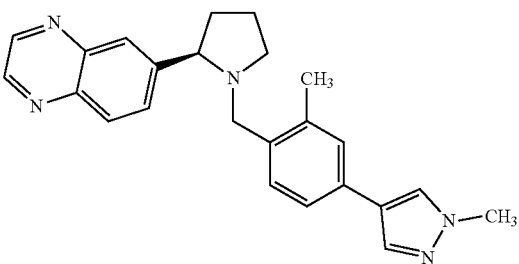
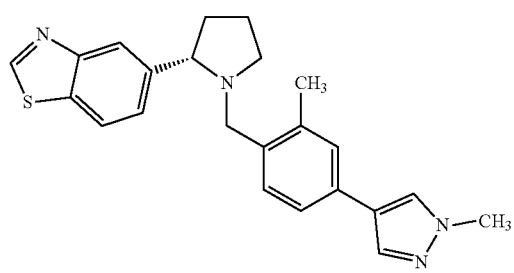
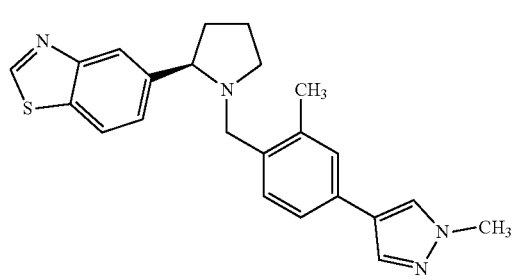

-continued
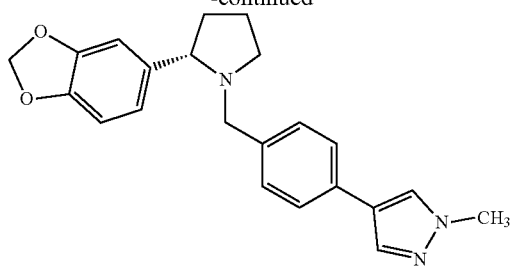
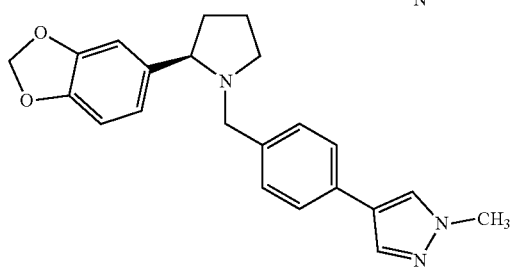
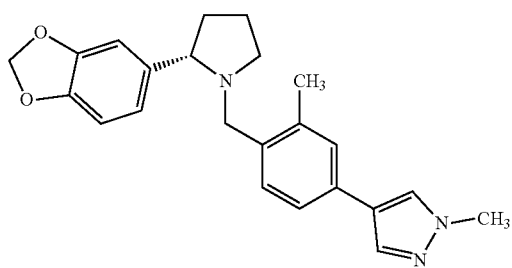
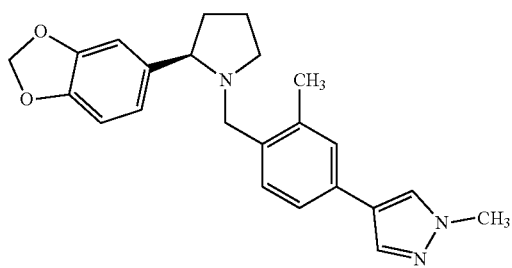
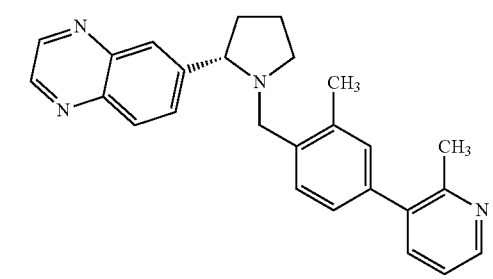
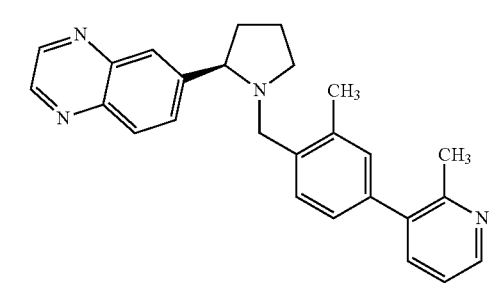
-continued
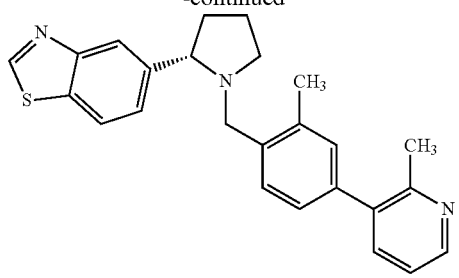
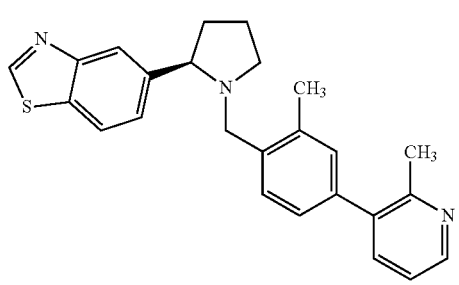
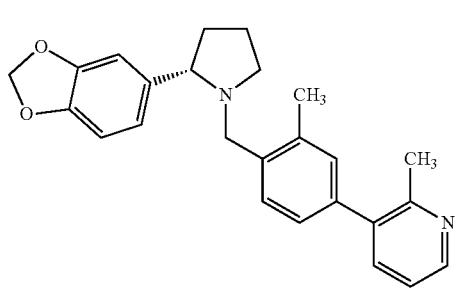
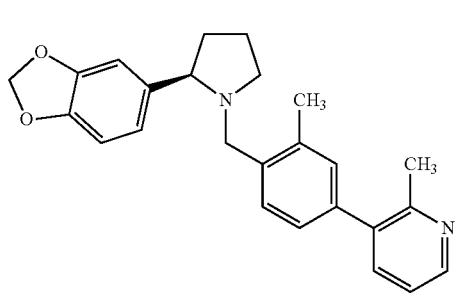
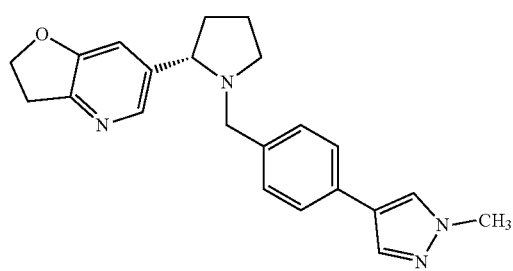
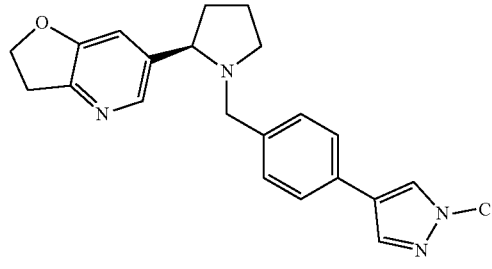

391
-continued
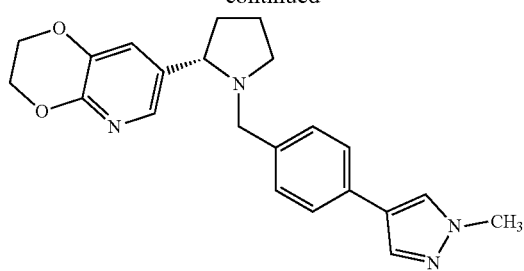
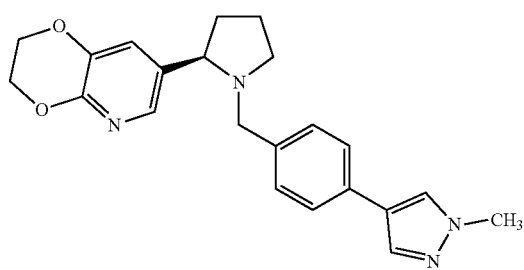
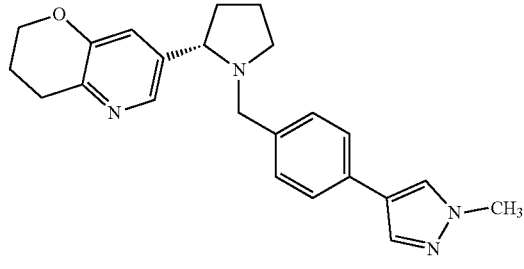
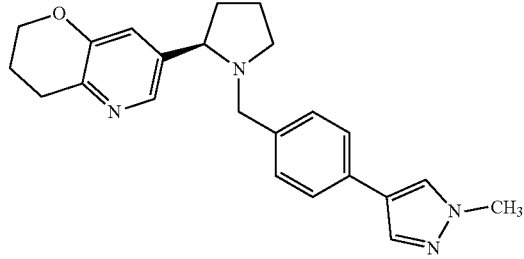
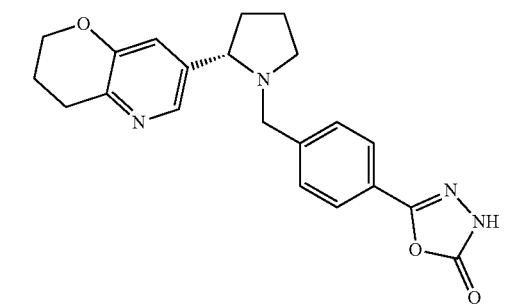
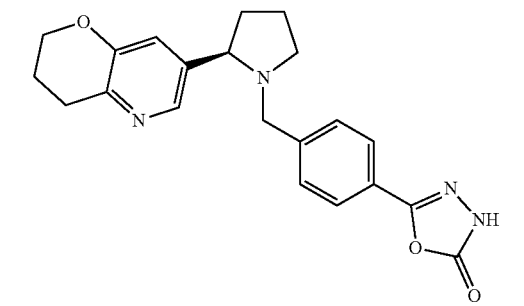
392
-continued
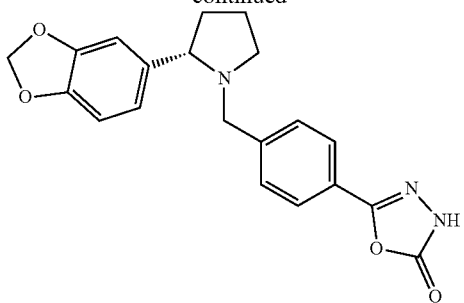
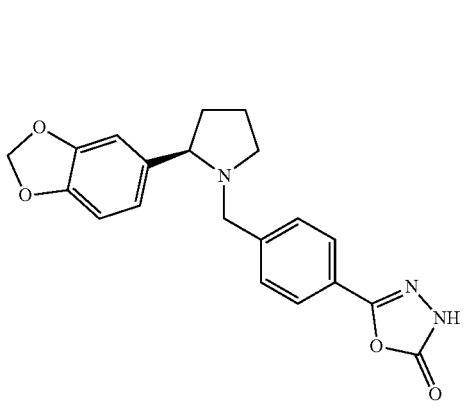
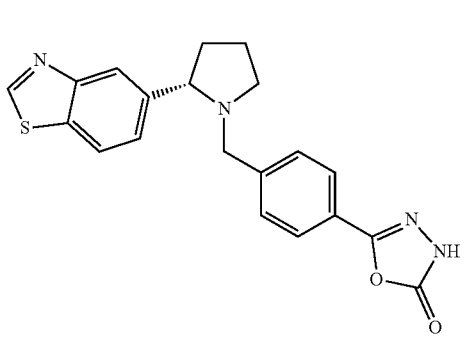
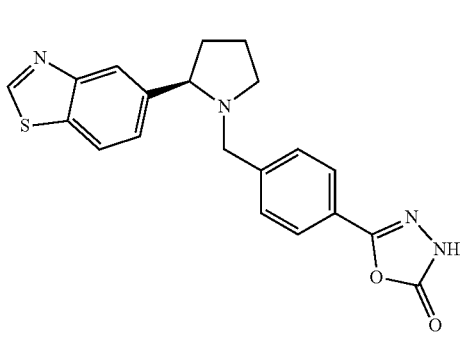
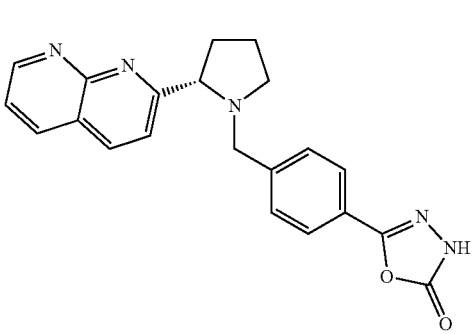

-continued
393
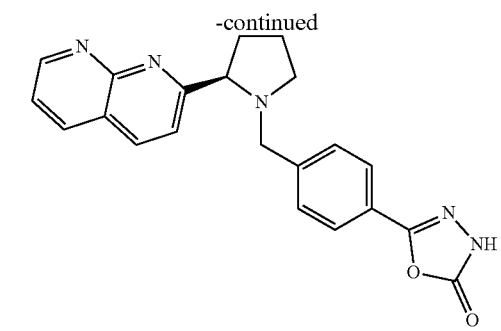
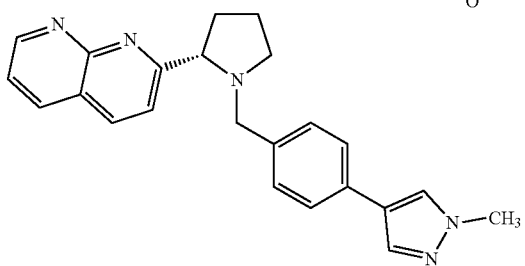
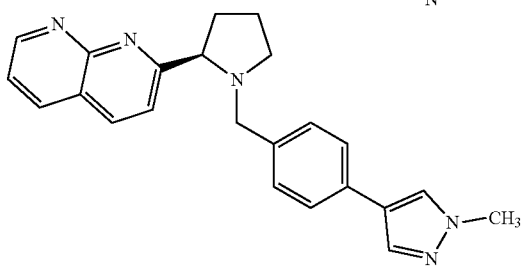
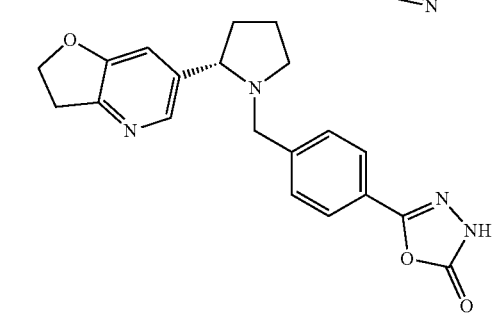
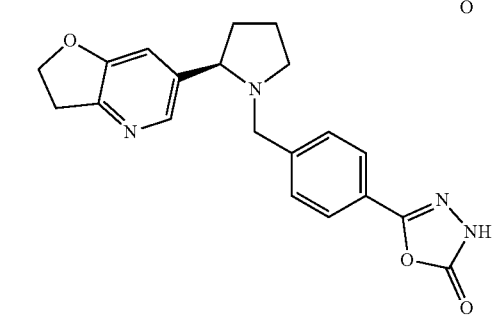
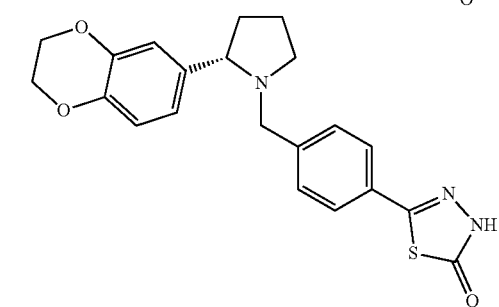
394
-continued
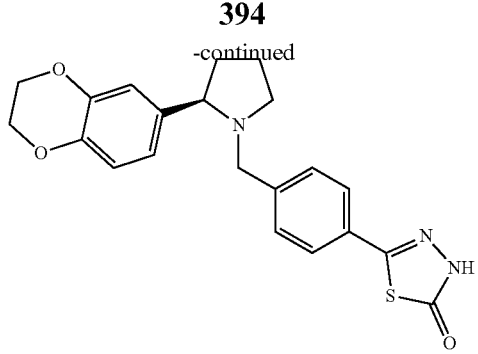
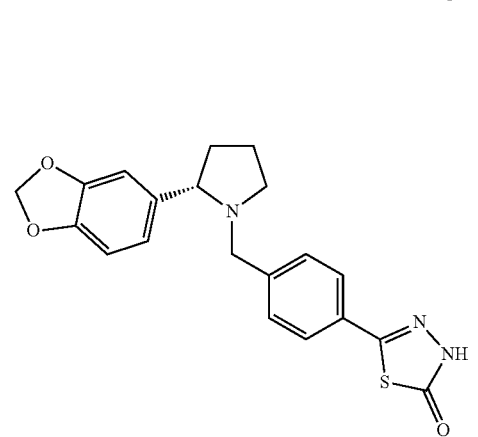
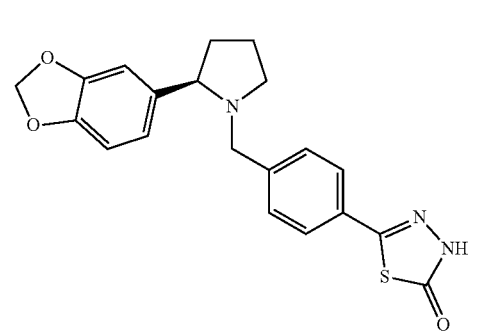
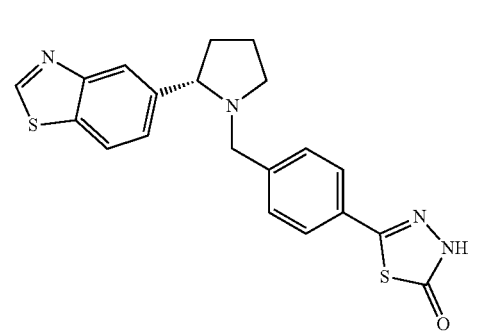
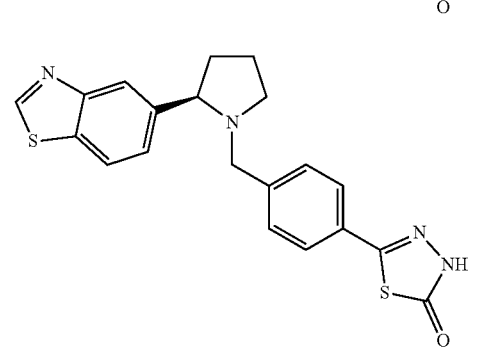

395
-continued
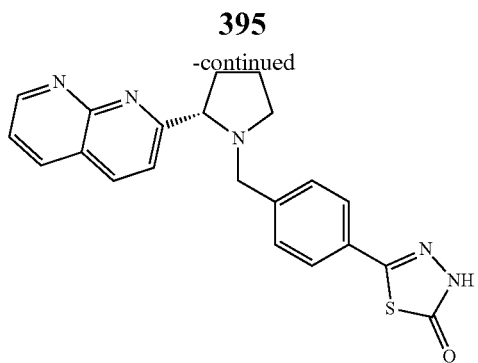
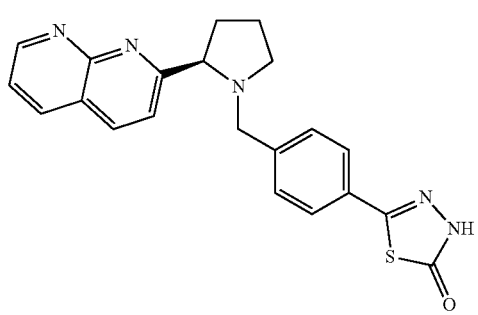
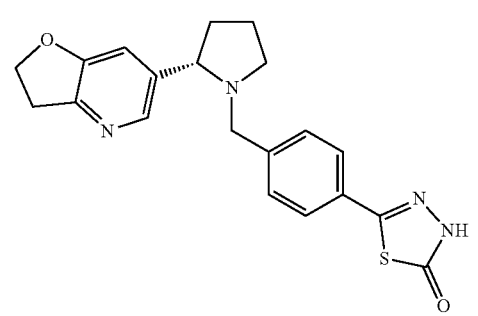
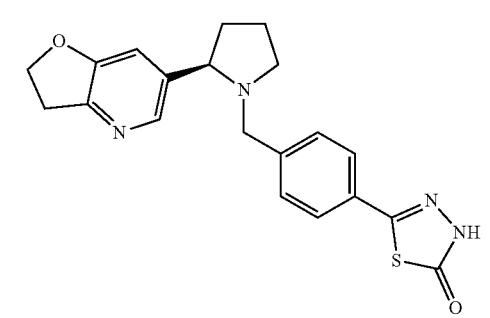
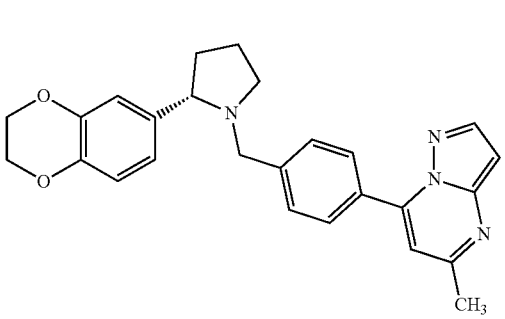
396
-continued
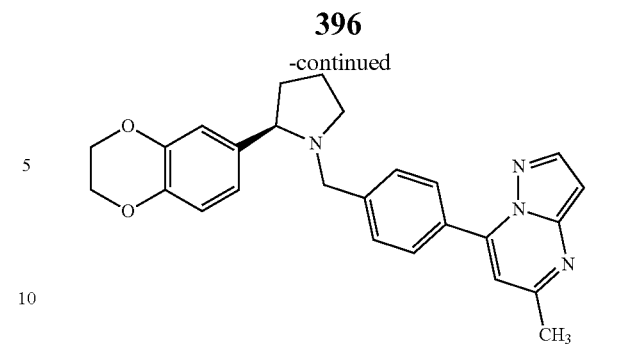
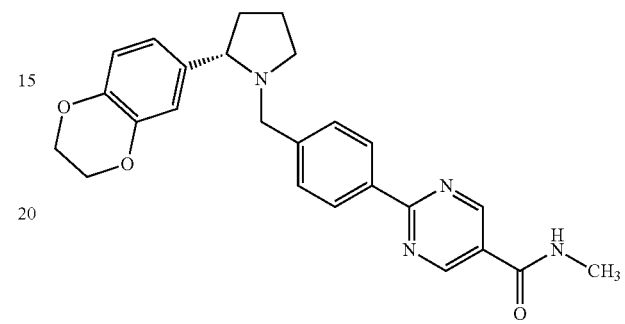
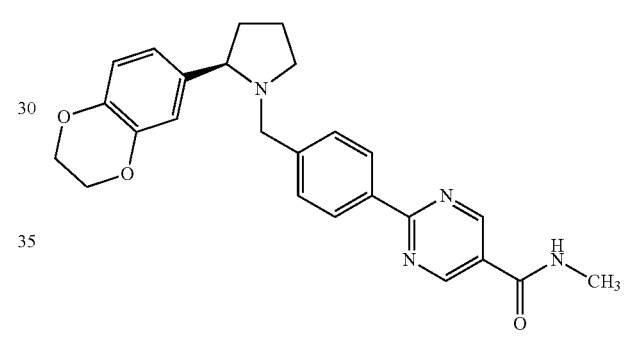
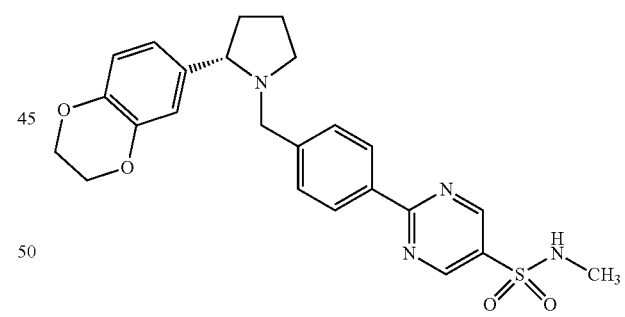
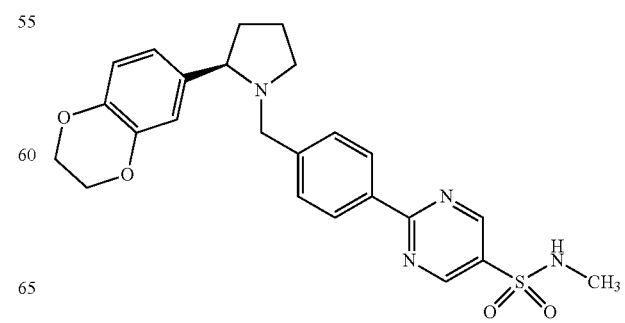

-continued
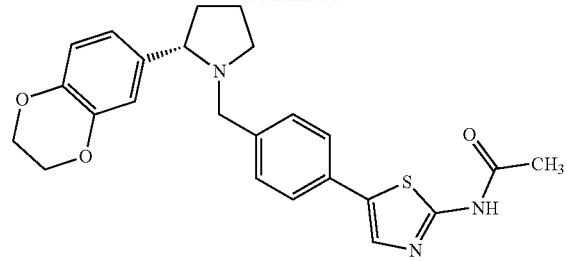
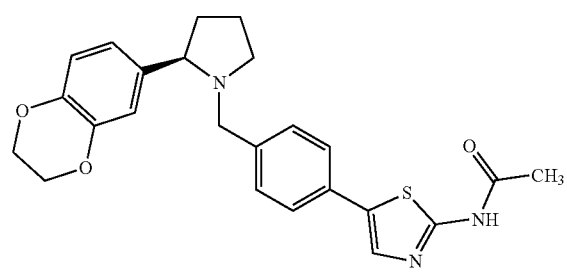
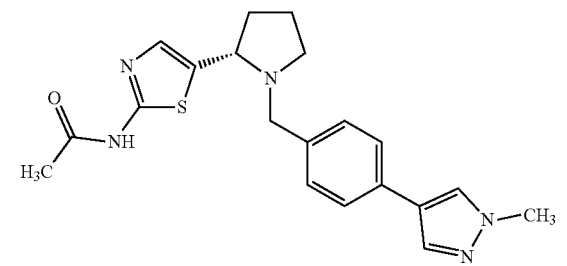
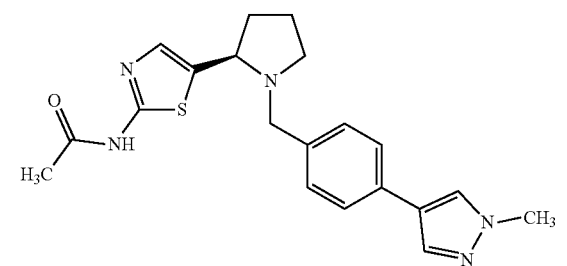
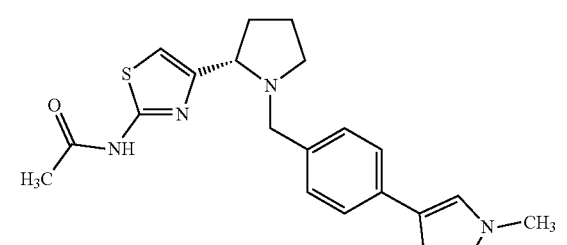
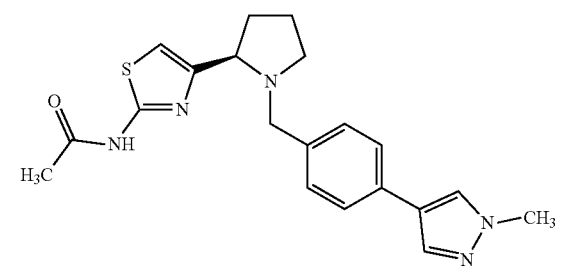
-continued
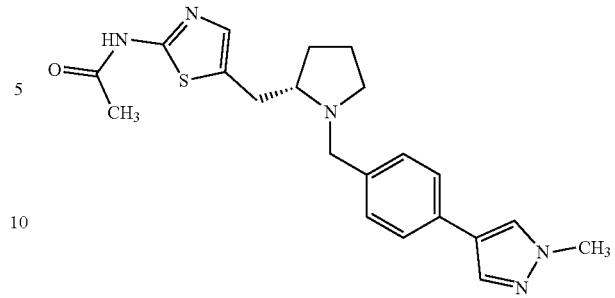
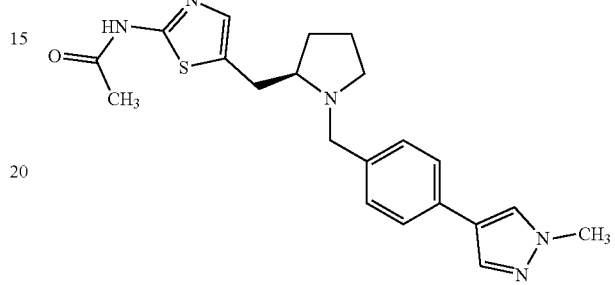
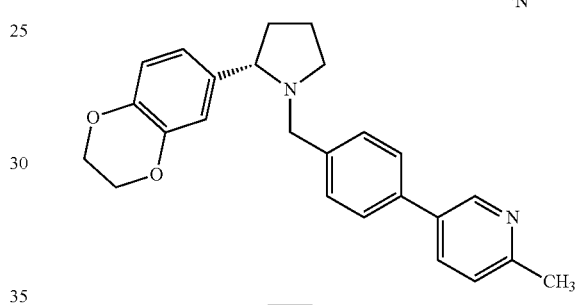
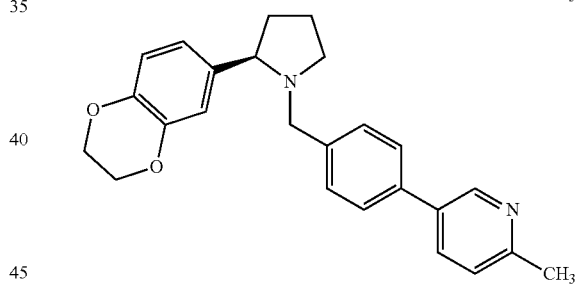
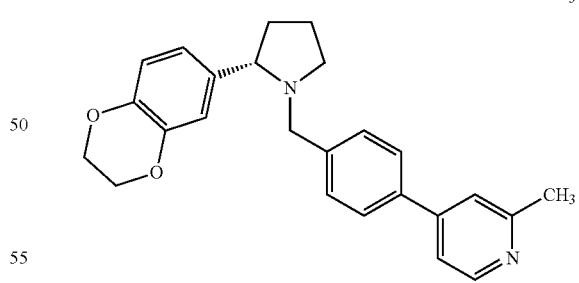
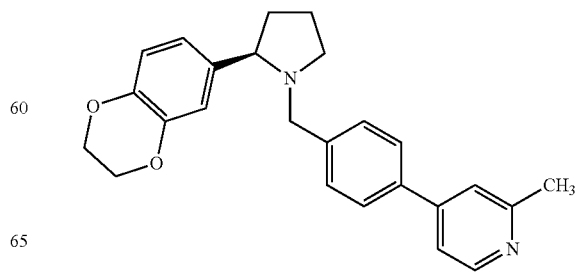

399
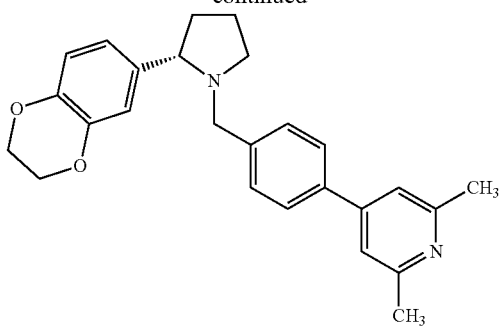
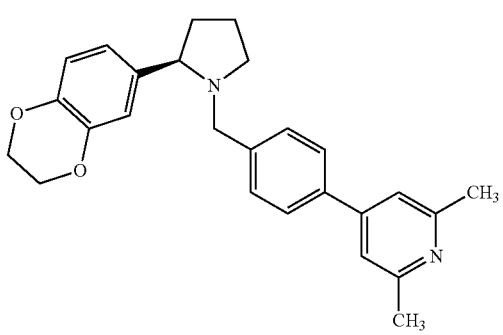
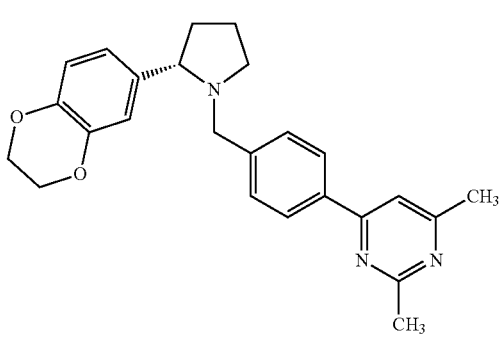
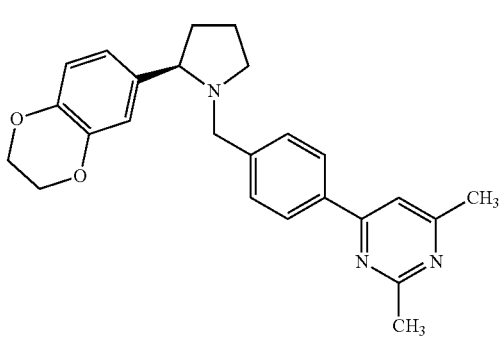
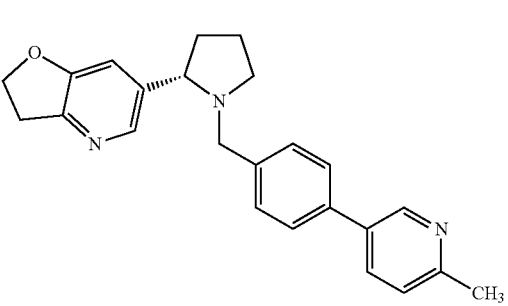
400
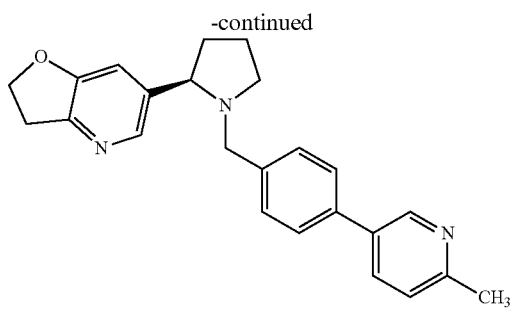
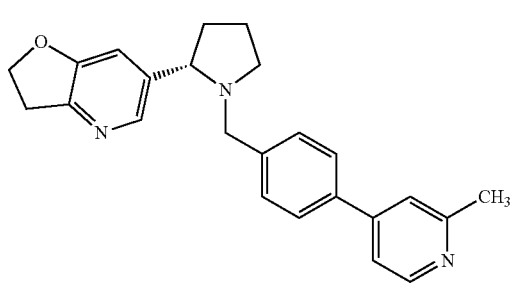
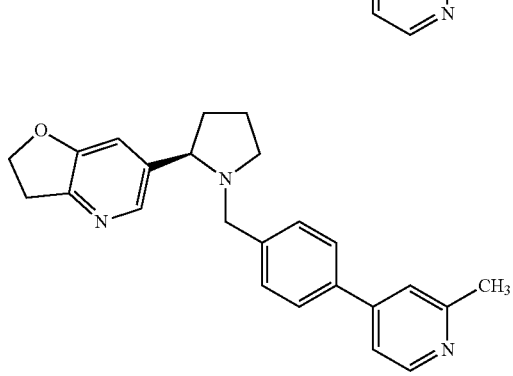
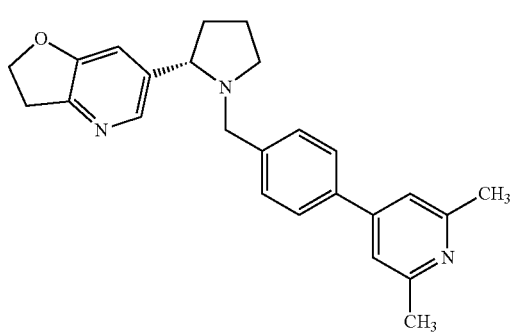
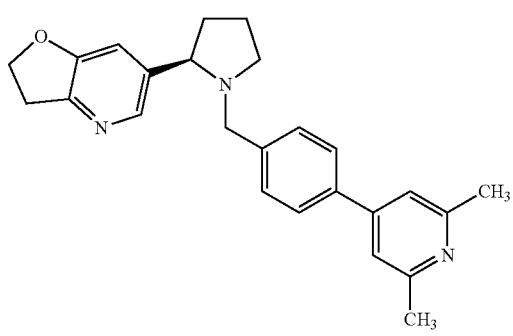

401
-continued
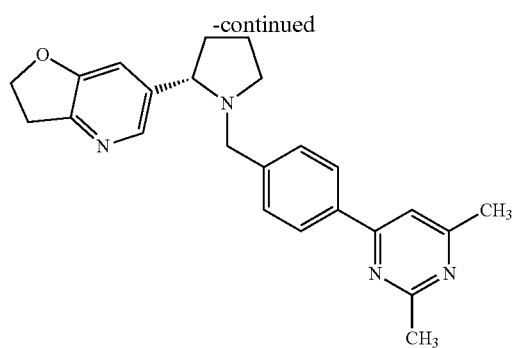
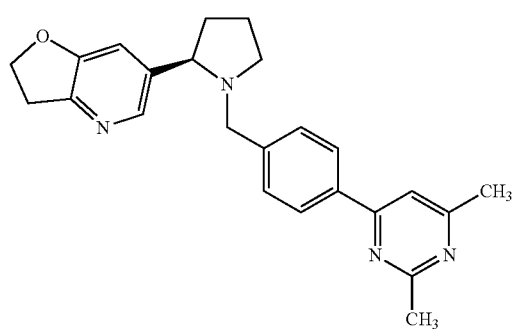
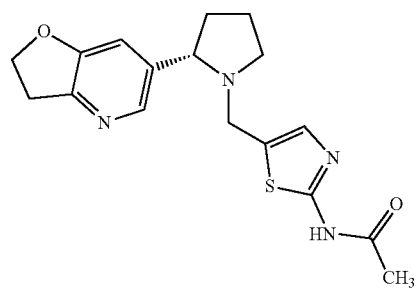
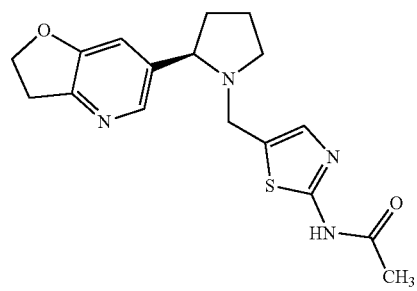
402
-continued
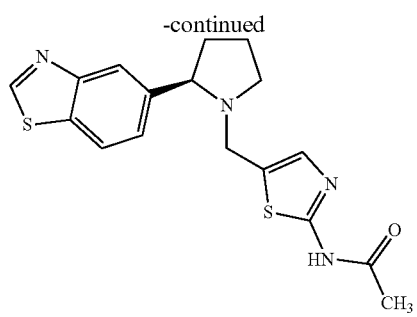
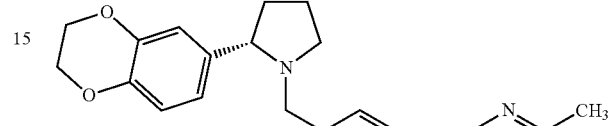
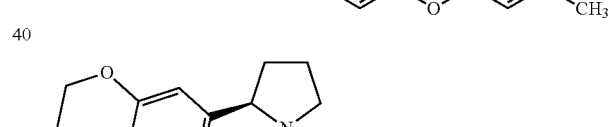
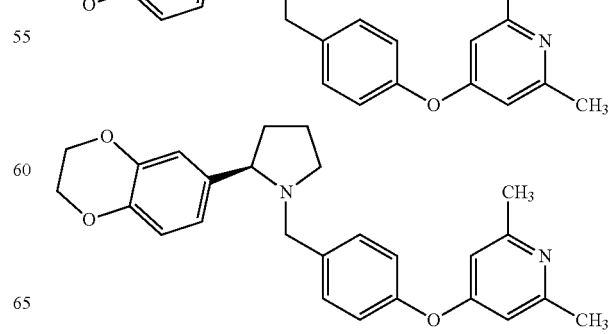

403
-continued
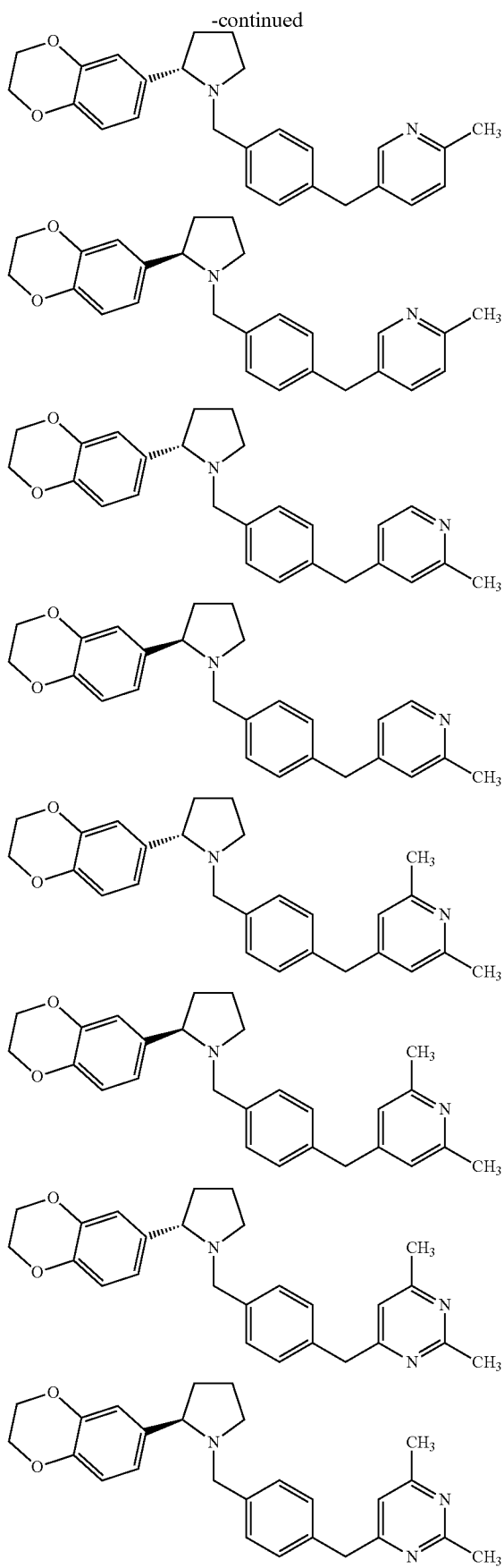
404
-continued
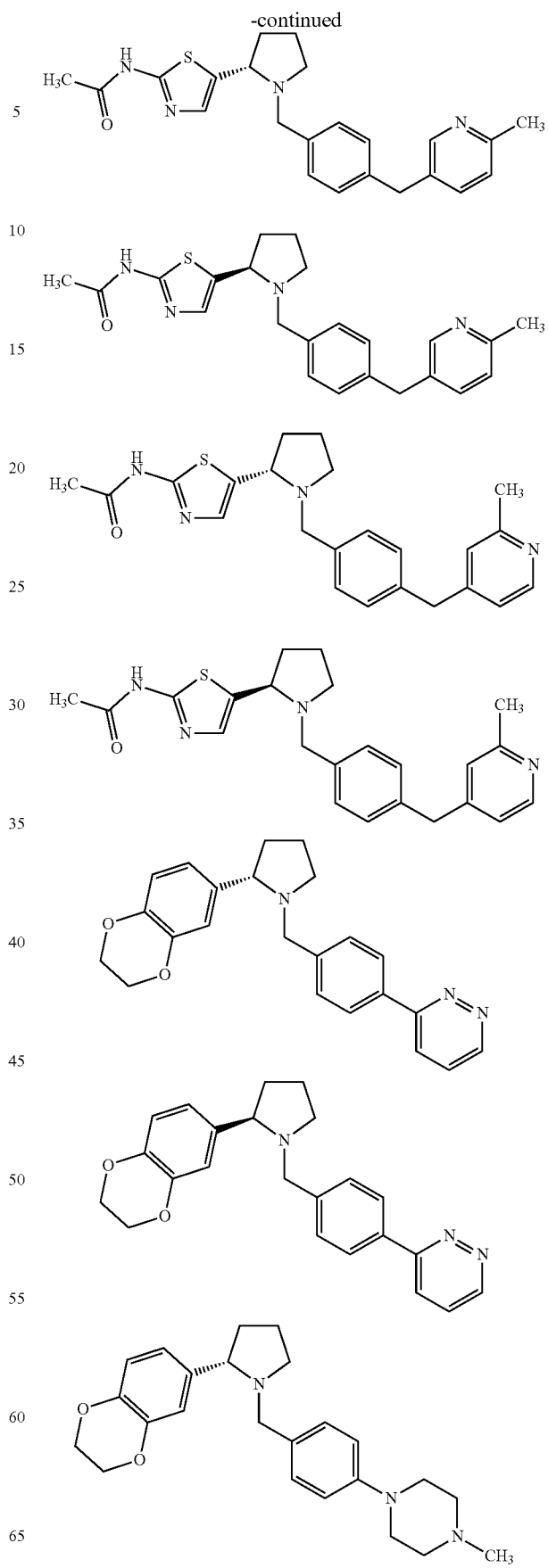

405
-continued
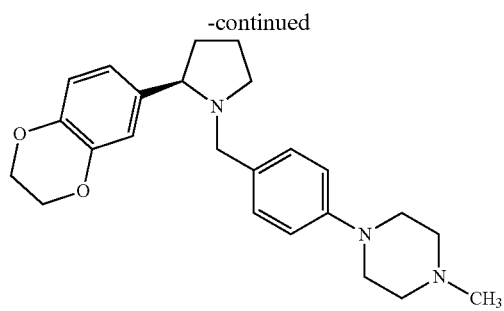
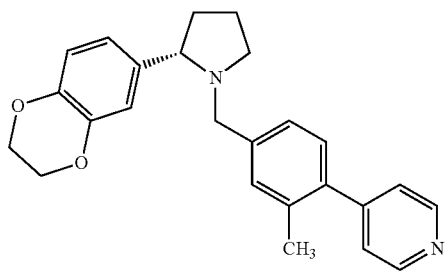
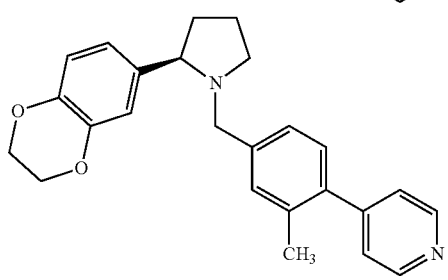
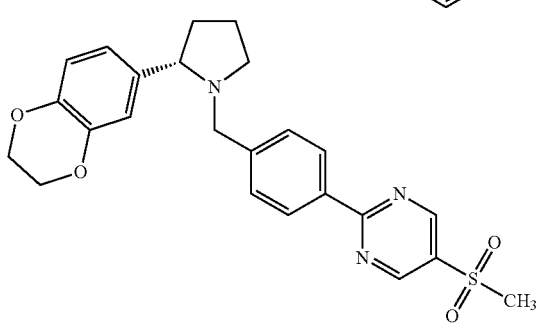
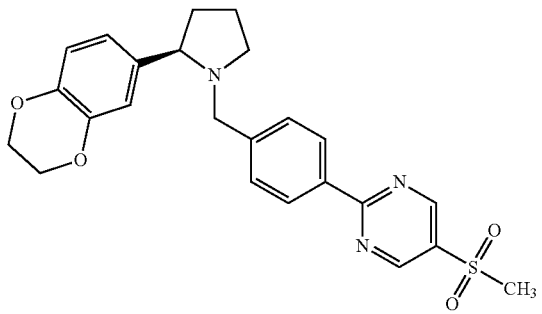
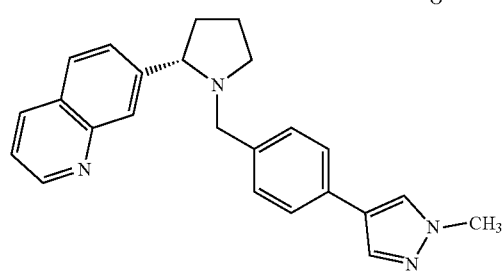
406
-continued
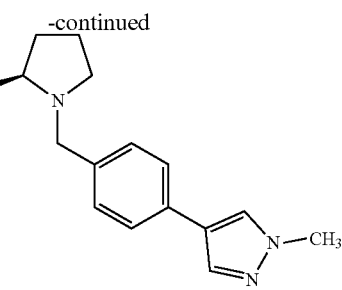
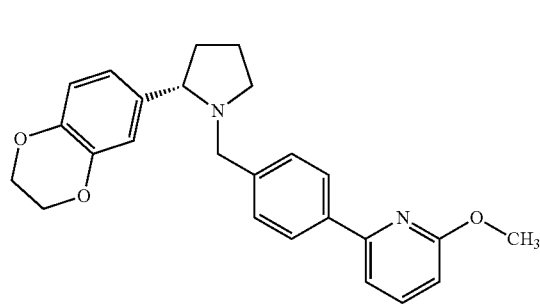
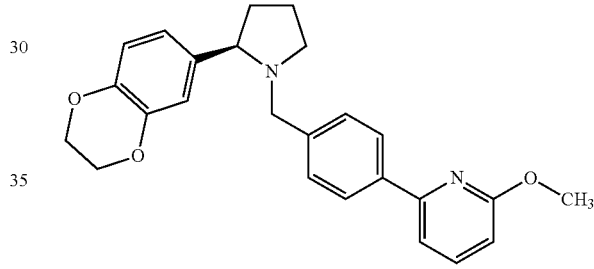
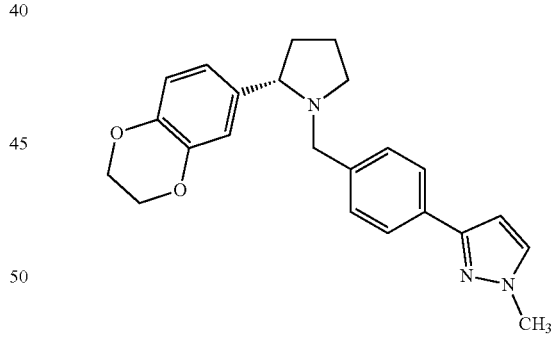
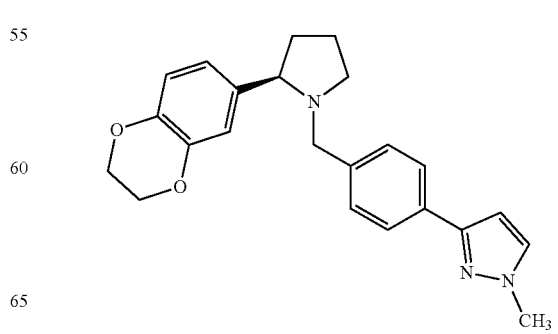

407
-continued
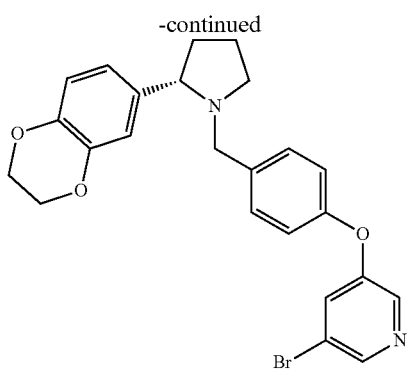
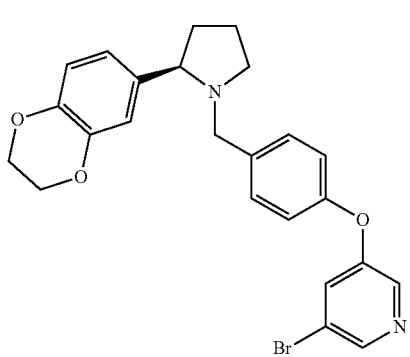
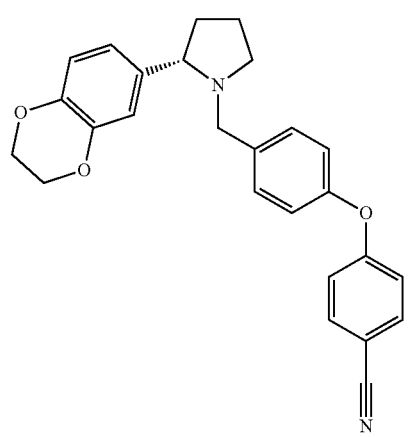
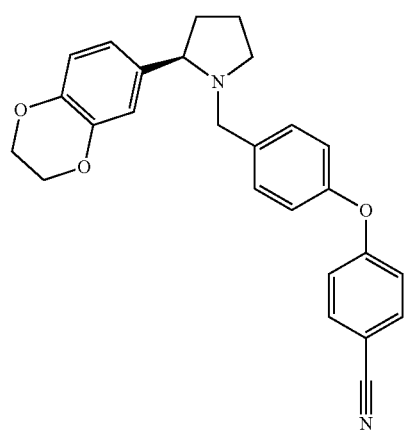
408
-continued
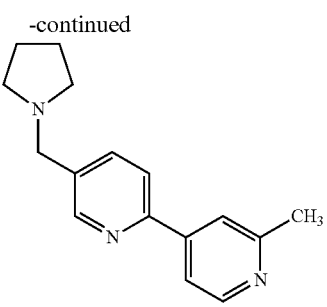
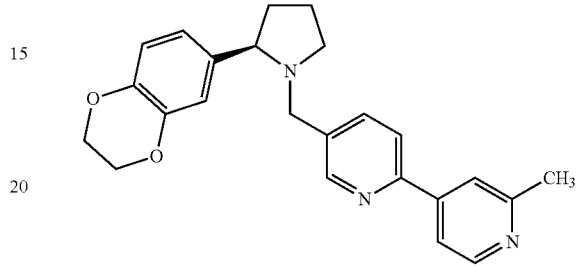
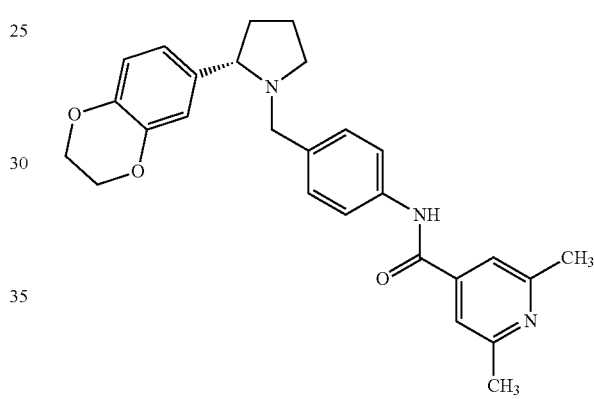
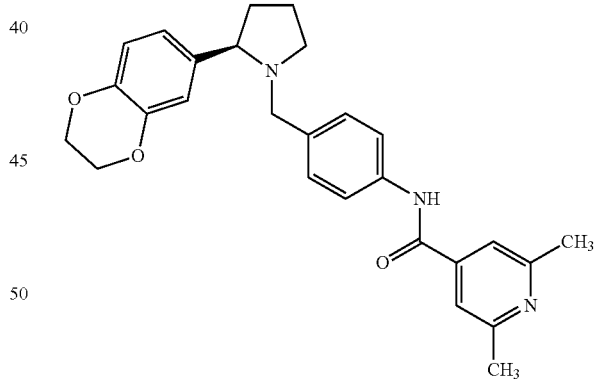
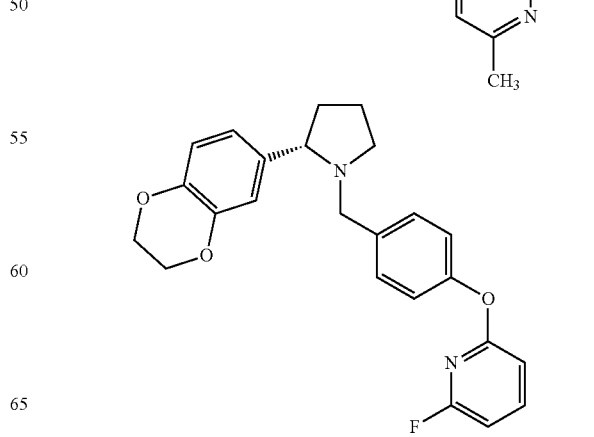

-continued

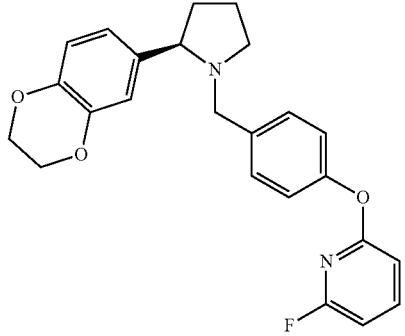

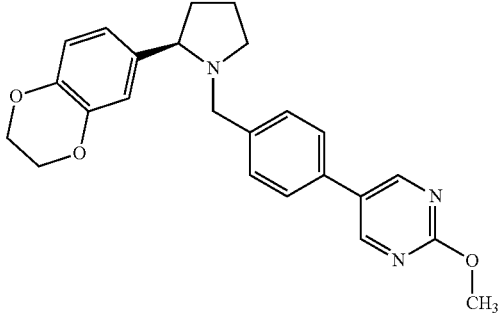

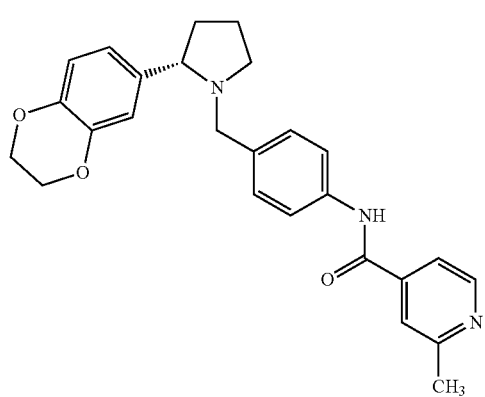

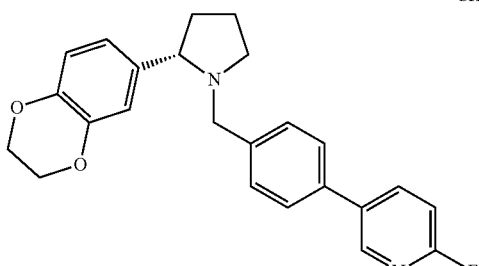

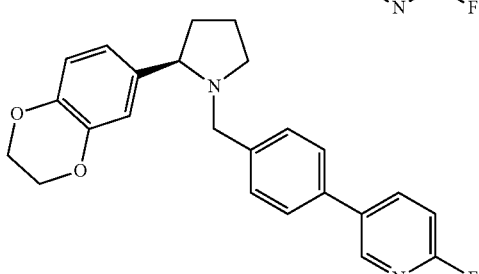

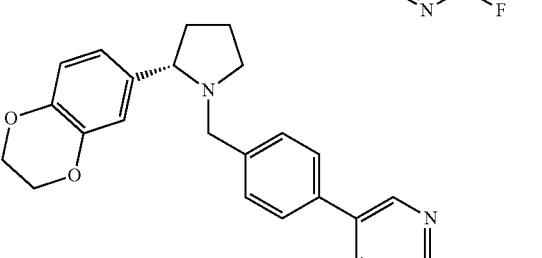, and

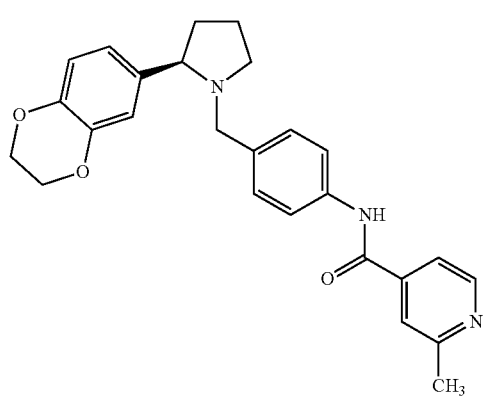

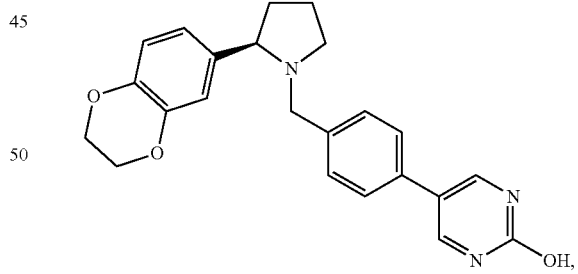, or solvate, salt or tautomer thereof.

10. A method of treating a neurodegenerative disease, diabetes, cancer, a cardiovascular disease, or stroke comprising administering a therapeutically effective amount of a compound of claim 1 to a mammal in need of such treatment.

11. The method according to claim 10, wherein the neurodegenerative disease is selected from the group consisting of one or more tauopathies, Alzheimer's disease, Dementia, Amyotrophic lateral sclerosis, Amyotrophic lateral sclerosis with cognitive impairment, Argyrophilic grain

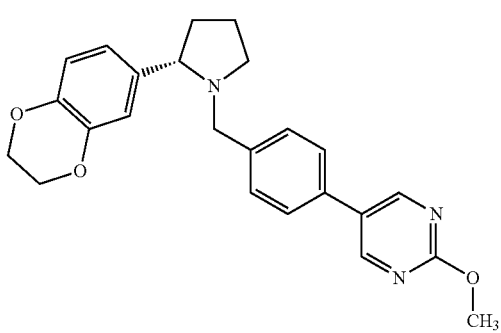

disease, Behavioural variant frontotemporal dementia, Bluit disease, Chronic traumatic encephalopathy, Corticobasal degeneration, Dementia pugilistica, Diffuse neurofibrillary tangles with calcification, Down's syndrome, Familial British dementia, Familial Danish dementia, Frontotemporal dementia with parkinsonism linked to chromosome 17, Frontotemporal lobar degeneration, Ganglioglioma, Gangliocytoma, Gerstmann-Straussler-Scheinker disease, Globular glia tauopathy, Guadeloupean parkinsonism, Hallevorden-Spatz disease (neurodegeneration with brain iron accumulation type 1), Lead encephalopathy, Lipofuscinosis, Meningioangiomatosis, Multiple system atrophy, Myotonic dystrophy, Niemann-Pick disease type C, Pallido-ponto-nigral degeneration, Parkinsonism-dementia complex of Guam, Pick's disease, Parkinson's disease dementia, Postencephalitic parkinsonism, Primary progressive aphasia, Prion diseases (including Creutzfeldt-Jakob Disease, Progressive nonfluent aphasia, Variant Creutzfeldt-Jakob Disease), Fatal Familial Insomnia, Kuru, Progressive supercortical gliosis, Progressive supranuclear palsy, Semantic dementia, Steele-Richardson-Olszewski syndrome, Subacute sclerosing panencephalitis, Tangle-only dementia, Tuberous sclerosis, Huntington's disease, and Parkinson's disease.

12. A method for treating a tauopathy, comprising administering a therapeutically effective amount of a compound of claim 1 to a mammal in need of such treatment.

13. A method for inhibiting a glycosidase, comprising contacting a system expressing the glycosidase with a compound of claim 1 under in vitro conditions such that the glycosidase is inhibited.

14. A pharmaceutical composition comprising as active ingredient a compound according to claim 1 together with pharmaceutically tolerable adjuvants and/or excipients.

15. The method of claim 11, wherein the neurodegenerative disease is selected from the group consisting of one or more tauopathies and Alzheimer's disease.

16. The pharmaceutical composition of claim 14, further comprising one or more additional active ingredients.

* * * * *

UNITED STATES PATENT AND TRADEMARK OFFICE
CERTIFICATE OF CORRECTION

| | |
|---|---|
| PATENT NO. | : 12,016,852 B2 |
| APPLICATION NO. | : 17/269814 |
| DATED | : June 25, 2024 |
| INVENTOR(S) | : Anna Quattropani et al. |

It is certified that error appears in the above-identified patent and that said Letters Patent is hereby corrected as shown below:

On the Title Page

Item (57) In the Abstract:
"for the treatment of taupathies and Alzheimer's disease."

Should read:
--for the treatment of tauopathies and Alzheimer's disease.--

In the Claims

At Column 317, Claim number 1, Line number 48:
"or R', R'''' are, independently:"

Should read:
--or R''', R'''' are, independently:--

At Column 320, Claim number 1, Line number 43:
"$Z^1$ is C, O, or $NR^3$;"

Should read:
--$Z^1$ is S, O, or $NR^3$;--

At Column 320, Claim number 1, Line number 46:
"$Z^5$ is 0, NR', $CHR^5$, $SO_2$, $S(O)(NR^{3'})$, $N(SO)R^{3''}$"

Should read:
--$Z^5$ is O, $NR^8$, $CHR^5$, $SO_2$, $S(O)(NR^{3'})$, $N(SO)R^{3'}$--

At Column 321, Claim number 1, Line number 66:
"replaced by a group selected from SO, $SO_2$, $S(O)(NR^{3'})$"

Signed and Sealed this
Twenty-seventh Day of August, 2024

*Katherine Kelly Vidal*
Katherine Kelly Vidal
*Director of the United States Patent and Trademark Office*

CERTIFICATE OF CORRECTION (continued)
U.S. Pat. No. 12,016,852 B2

Should read:
--replaced by a group selected from SO, $SO_2$, $S(O)(NR^{3'})$,--

At Column 325, Claim number 5, Line number 21:

"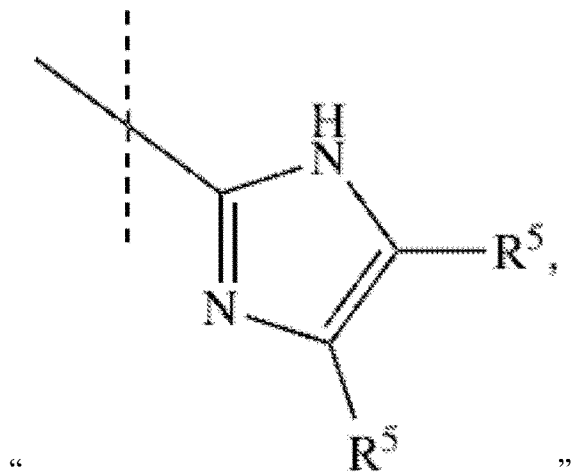"

Should read:

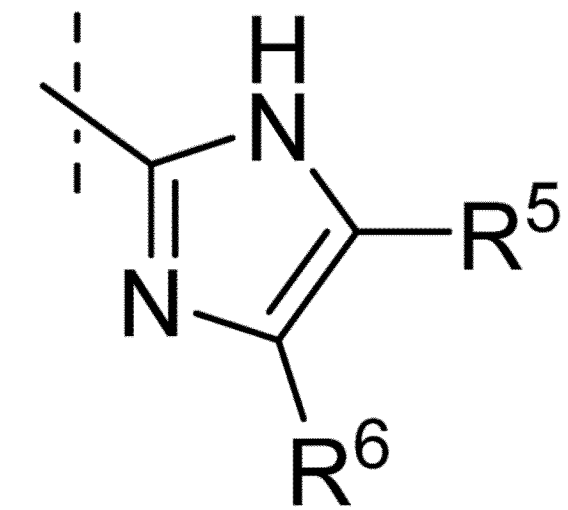

--                                    --